US011041171B2

(12) United States Patent (10) Patent No.: US 11,041,171 B2
Gao et al. (45) Date of Patent: *Jun. 22, 2021

(54) METHOD OF DETECTING AND/OR IDENTIFYING ADENO-ASSOCIATED VIRUS (AAV) SEQUENCES AND ISOLATING NOVEL SEQUENCES IDENTIFIED THEREBY

(71) Applicant: The Trustees of the University of Pennsylvania, Philadelphia, PA (US)

(72) Inventors: Guangping Gao, Westborough, MA (US); James M. Wilson, Philadelphia, PA (US); Mauricio R. Alvira, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/682,712

(22) Filed: Nov. 13, 2019

(65) Prior Publication Data

US 2020/0131534 A1 Apr. 30, 2020

Related U.S. Application Data

(60) Division of application No. 15/584,674, filed on May 2, 2017, now Pat. No. 10,508,286, which is a
(Continued)

(51) Int. Cl.
*C12N 7/00* (2006.01)
*C12N 15/86* (2006.01)
(Continued)

(52) U.S. Cl.
CPC ............ *C12N 15/86* (2013.01); *A61K 38/177* (2013.01); *A61K 38/4846* (2013.01); *C07K 14/005* (2013.01); *C12N 7/00* (2013.01); *C12Q 1/701* (2013.01); *C12Y 304/21022* (2013.01); *A61K 48/00* (2013.01); *C12N 2750/14121* (2013.01); *C12N 2750/14122* (2013.01);
(Continued)

(58) Field of Classification Search
None
See application file for complete search history.

(56) References Cited

U.S. PATENT DOCUMENTS 5,412,073 A 5/1995 Kalsheker
5,449,616 A 9/1995 Campbell
(Continued)

FOREIGN PATENT DOCUMENTS

CA 2406745 A1 1/2006
EP 1310571 A2 5/2003
(Continued)

OTHER PUBLICATIONS

Afione SA et al., In vivo model of adeno-associated virus vector persistence and rescue, Journal of Virology, vol. 70(5):3235-3241, May 1996.
(Continued)

*Primary Examiner* — M Franco G Salvoza
(74) *Attorney, Agent, or Firm* — Howson & Howson LLP; Colleen M. Schaller

(57) ABSTRACT

Adeno-associated virus rh.20 sequences, vectors containing same, and methods of use are provided.

21 Claims, 112 Drawing Sheets

Specification includes a Sequence Listing.

Related U.S. Application Data continuation of application No. 14/956,934, filed on Dec. 2, 2015, now Pat. No. 10,041,090, which is a continuation of application No. 13/633,971, filed on Oct. 3, 2012, now Pat. No. 97,970,472, which is a division of application No. 12/962,793, filed on Dec. 8, 2010, now Pat. No. 8,524,446, which is a continuation of application No. 10/291,583, filed on Nov. 12, 2002, now abandoned.

(60) Provisional application No. 60/377,066, filed on May 1, 2002, provisional application No. 60/341,117, filed on Dec. 17, 2001, provisional application No. 60/350,607, filed on Nov. 13, 2001, provisional application No. 60/386,675, filed on Jun. 5, 2002.

(51) Int. Cl.
| | | |
|---|---|---|
| *C07K 14/005* | (2006.01) | |
| *C12Q 1/70* | (2006.01) | |
| *A61K 38/17* | (2006.01) | |
| *A61K 38/48* | (2006.01) | |
| *A61K 48/00* | (2006.01) | |

(52) U.S. Cl.
CPC .............. *C12N 2750/14143* (2013.01); *C12N 2750/14151* (2013.01); *C12N 2750/14152* (2013.01); *C12N 2750/14162* (2013.01); *C12N 2750/14171* (2013.01); *C12N 2830/008* (2013.01); *C12N 2830/48* (2013.01); *C12N 2830/85* (2013.01); *C12N 2830/90* (2013.01); *C12Q 2600/158* (2013.01)

(56) References Cited

U.S. PATENT DOCUMENTS

| | | |
|---|---|---|
| 5,871,982 A | 2/1999 | Wilson et al. |
| 5,866,552 A | 5/1999 | Chiorini et al. |
| 6,039,942 A | 3/2000 | Lassen |
| 6,156,303 A | 12/2000 | Russell |
| 6,251,677 B1 | 6/2001 | Wilson et al. |
| 6,274,354 B1 | 8/2001 | Wilson et al. |
| 6,312,957 B1 | 11/2001 | Einerhand et al. |
| 6,365,394 B1 | 4/2002 | Gao et al. |
| 6,376,237 B1 | 4/2002 | Colosi |
| 6,387,368 B1 | 5/2002 | Wilson et al. |
| 6,399,385 B1 | 6/2002 | Croyle et al. |
| 6,428,988 B1 | 8/2002 | Wilson et al. |
| 6,468,524 B1 | 10/2002 | Chiorini et al. |
| 6,475,769 B1 | 11/2002 | Wilson et al. |
| 6,482,634 B1 | 11/2002 | Wilson et al. |
| 6,485,966 B2 | 11/2002 | Gao et al. |
| 6,632,670 B1 | 10/2003 | Wadsworth et al. |
| 6,759,237 B1 | 7/2004 | Wilson et al. |
| 6,821,512 B1 | 11/2004 | Gao et al. |
| 6,943,019 B2 | 9/2005 | Wilson |
| 6,953,690 B1 | 10/2005 | Gao et al. |
| 7,022,519 B2 | 4/2006 | Gao |
| 7,056,502 B2 | 6/2006 | Hildinger |
| 7,235,393 B2 | 6/2007 | Gao |
| 7,238,526 B2 | 7/2007 | Wilson |
| 7,282,199 B2 | 10/2007 | Gao |
| 7,790,449 B2 | 9/2010 | Gao |
| 9,102,949 B2 | 8/2015 | Gao |
| 2001/0006955 A1 | 7/2001 | Wilson et al. |
| 2002/0037867 A1 | 3/2002 | Wilson et al. |
| 2002/0090717 A1 | 7/2002 | Gao et al. |
| 2002/0159978 A1 | 10/2002 | Allen |
| 2003/0040101 A1 | 2/2003 | Wilson |
| 2003/0073232 A1 | 4/2003 | Wilson |
| 2003/0119191 A1 | 6/2003 | Gao |
| 2003/0138772 A1 | 7/2003 | Gao et al. |
| 2004/0052764 A1 | 3/2004 | Hildinger |
| 2005/0287122 A1 | 12/2005 | Bartlett et al. |
| 2007/0036760 A1 | 2/2007 | Wilson |
| 2008/0075737 A1 | 3/2008 | Gao et al. |
| 2008/0075740 A1 | 3/2008 | Gao |
| 2009/0054823 A1 | 2/2009 | Bridges |
| 2009/0197338 A1 | 8/2009 | Vandenberghe |
| 2009/0227030 A1 | 9/2009 | Gao |
| 2009/0275107 A1 | 11/2009 | Lock |
| 2009/0280103 A1 | 11/2009 | Flueck |
| 2011/0053221 A1 | 3/2011 | Chen |
| 2011/0070210 A1 | 3/2011 | Andrijauskas |
| 2011/0151434 A1 | 6/2011 | Gao |
| 2011/0301226 A1 | 12/2011 | Mendell |
| 2013/0195801 A1 | 8/2013 | Gao |
| 2015/0159173 A1 | 6/2015 | Vandenberghe et al. |

FOREIGN PATENT DOCUMENTS

| | | |
|---|---|---|
| EP | 3085389 A1 | 10/2016 |
| WO | WO-1996/000587 A1 | 1/1996 |
| WO | WO-1996/013598 A2 | 5/1996 |
| WO | WO-1998/009657 A2 | 3/1998 |
| WO | WO-1998/010086 A1 | 3/1998 |
| WO | WO-1998/010088 A1 | 3/1998 |
| WO | WO-1998/011244 A1 | 3/1998 |
| WO | WO-1999/014354 A1 | 3/1999 |
| WO | WO-1999/015677 A1 | 4/1999 |
| WO | WO-1999/015685 A1 | 4/1999 |
| WO | WO-1999/047691 A1 | 9/1999 |
| WO | WO-1999/061601 A2 | 12/1999 |
| WO | WO-2000/028061 A2 | 5/2000 |
| WO | WO-2000/075353 A1 | 12/2000 |
| WO | WO-2001/014539 A2 | 3/2001 |
| WO | WO-2001/023001 A2 | 4/2001 |
| WO | WO-2001/023597 A3 | 4/2001 |
| WO | WO-2001/040455 A2 | 6/2001 |
| WO | WO-2001/068888 A2 | 9/2001 |
| WO | WO-2001/070276 A2 | 9/2001 |
| WO | WO-2001/083692 A2 | 11/2001 |
| WO | WO-2002/018659 A2 | 3/2002 |
| WO | WO-2003/042397 A2 | 5/2003 |
| WO | WO-2003/104392 A2 | 12/2003 |
| WO | WO 2004/112727 A2 | 12/2004 |
| WO | WO-2013/078316 A1 | 5/2013 |
| WO | WO-2013/123503 A1 | 8/2013 |

OTHER PUBLICATIONS

Alloca M et al., Novel adeno-associated virus serotypes efficiently transduce murine photoreceptors, Journal of Virology, 81(20):11372-80, Oct. 2007. (Epub Aug. 15, 2007).

Anissimov M, "How many species of bacteria are there", accessed Sep. 23, 2011 from http://www.wisegeek.org/how-many-species-of-bacteria-are-there.htm (last modified Nov. 19, 2015).

Bantel-Schaal U et al., Human adeno-associated virus type 5 is only distantly related to other known primate helper-dependent parvoviruses, Journal of Virology, vol. 73(2):939-947, Feb. 1999.

Bevan et al., Systemic Gene Delivery in Large Species for Targeting Spinal Cord, Brain, and Peripheral Tissues for Pediatric Disorders, Mol Ther. Nov. 2011;19(11):1971-80. doi: 10.1038/mt.2011.157. Epub Aug. 2, 2011.

Black A et al., Adeno-associated virus 8-mediated gene therapy for choroideremia: preclinical studies in in vitro and in vivo models, The Journal of Gene Medicine, vol. 16:122-130, Jun. 24, 2014.

Brown KE et al., Cloning and sequencing of the simian parvovirus genome, Virology, vol. 210:314-322, May 1995.

Calcedo R et al., Serologic Characterization of Human and Non-Human Primate AAVs, Abstract 102, Molecular Therapy, vol. 7(5): S41, May 2003.

Cearley CN et al., A single injection of an adeno-associated virus vector into nuclei with divergent connections results in widespread vector distribution in the brain and global correction of a neurogenetic disease, Neurobiology of Disease, vol. 27(37):9928-40, Sep. 12, 2007.

Cearley CN et al., Transduction characteristics of adeno-associated virus vectors expressing cap serotypes 7, 8, 9, and Rh10 in the

(56) References Cited

OTHER PUBLICATIONS mouse brain, Mol Ther. Mar. 2006;13(3):528-37. Epub Jan. 18, 2006.13(3):528-37. Mar. 2006. (Epub Jan. 18, 2006).
Charan RA et al., Adeno-associated Virus Serotype 8 (AAV8) Delivery of Recombinant A20 to Skeletal Muscle Reduces Pathological Activation of Nuclear Factor (NF)-kB in Muscle of mdx Mice, Molecular Medicine, vol. 18:1527-35, Feb. 2013. (Epub Nov. 6, 2012).
Chen et al., Epidemiology of hepatitis B virus infection in the Asia-Pacific region, J Gastroenterol Hepatol. May 2000;15 Suppl:E3-6.
Chicoine LG et al., Vascular Delivery of rAAVrh741MCK. GALGT2 to the Gastrocnemius Muscle of the Rhesus Macaque Stimulates the Expression of Dystrophin and Laminin α2 Surrogates, Molecular Therapy, vol. 22(4):713-24, Apr. 2014. (Epub Oct. 22, 2013).
Childers MK et al., Gene Therapy Prolongs Survival and Restores Function in Murine and Canine Models of Myotubular Myopathy, Sci Transl Med, vol. 6(220):1-31, Jan. 22, 2014.
Chiorini JA et al., Cloning and characterization of AAV5, Journal of Virology, vol. 73(2):1309-1319, Feb. 1999.
Chirmule et al., Immune responses to adenovirus and adeno-associated virus in humans, Gene Therapy, 6:1574-1583, Sep. 1999.
Clinicaltrials.org, "AAV8 Vector Trials", Nov. 2017.
Dai X et al., Long-term retinal cone rescue using a capsid mutant AAV8 vector in a mouse model of CNGA3-achromatopsia, PLOS One, vol. 12(11):e0188032, Nov. 13, 2017.
Davidson BL et al., Recombinant adeno-associated virus type 2, 4, and 5 vectors: transduction of variant cell types and regions in the mammalian central nervous system, PNAS, vol. 97(7): 3428-3432, Mar. 28, 2000.
De BP et al. Induction of Persistent Passive Immunity Against Anthrax Toxin by an Adeno-Associated Virus Type rh10 Vector Expressing Anti-Protective Antigen Antibody [Abstract No. 611], Molecular Therapy, 13(Supp 1):S236, May 2006.
De BP et al., High levels of persistent expression of alpha1-antitrypsin mediated by the nonhuman primate serotype rh.10 adeno-associated virus despite preexisting immunity to common human adeno-associated viruses, Mol Ther., vol. 13(1):67-76, Jan. 2006. (Epub Nov. 2, 2005).
De BP et al., Therapeutic Levels for alpha1-Antitrypsin Following Intrapleural Administration of a Non-Human Primate Serotype rh10 AAV Vector Expressing alpha1-Antitrypsin, Abstract 338, $7^{th}$ Annual Meeting of the American Society of Gene Therapy [Jun. 2-6, 2004] Minneapolis, Minnesota, p. 1, e-published May 2, 2004.
Durigon EL et al., Multiple primer pairs for polymerase chain reaction (PCR) amplification of human parvovirus B19 DNA, Journal of Virological Methods, vol. 44:155-65, Feb. 1993.
Ellis et al., Virology Journal, Mar. 2013, A survey of ex vivo/in vitro transduction efficiency of mammalian primary cells and cell lines with Nine natural adeno-associated virus (AAV1-9) and one engineered adeno-associated virus serotype, 10:74.
Faria et al., The early spread and epidemic ignition of HIV-1 in human populations, Science, Oct. 2014, 346(6205):56-61.
Fischer MD et al., Codon-Optimized RPGR Improves Stability and Efficacy of AAV8 Gene Therapy in Two Mouse Models of X-Linked Retinitis Pigmentosa, Molecular Therapy, vol. 25(8):1854-65, Aug. 2, 2017. (Epub May 24, 2017).
Forslund O et al., A broad range of human papillomavirus types detected with a general PCR method suitable for analysis of cutaneous tumors and normal skin, Journal of General Virology, vol. 80(9):2437-43, XP002229850, Sep. 1999.
Gao et al., Clades of Adeno Associated Viruses Are Widely Disseminated in Human Tissues, J. Virol, Jun. 2004, 78(12) :6381-8.
Gao et al., Origin of HIV-1 in the chimpanzee Pan troglodytes troglodytes, Nature, Feb. 1999, 397 :436-440.
Gao G et al., Adeno-Associated Viruses Undergo Substantial Evolution in Primates During Natural Infections, PNAS, vol. 100(10):6081-86, May 13, 2003. (Epub Apr. 25, 2003).
Gao G et al., Autoimmune Anemia in Macaques Following Erythropoietin Gene Therapy, Abstract 341, $7^{th}$ Annual Meeting of the American Society of Gene Therapy [Jun. 2-6, 2004] Minneapolis, Minnesota, p. 1, (Epub May 2, 2004).
Gao G et al., Clades of Adeno-Associated Viruses are Widely Disseminated in human Tissues, Journal of Virology, vol. 78(12):6381-6388, Jun. 2004.
Gao G et al., Diversity of Latent AAV Genomes in Non-Human Primate and Human Tissues, Abstract 400, Molecular Therapy, vol. 7(5):S158, May 2003.
Gao G et al., Erythropoietin Gene Therapy Leads to Autoimmune Anemia in Macaques, Blood, vol. 103(9):3300-2, May 2004.
Gao GP et al., Biology of Adenovirus vectors with E1 and E4 deletions for liver-directed gene therapy, Journal of Virology, vol. 70(12):8934-8943, Dec. 1996.
Gao GP et al., Novel adeno-associated viruses from rhesus monkeys as vectors for human gene therapy, PNAS, vol. 99(18):11854-59, Sep. 2002. (Epub Aug. 21, 2002).
GenBank entry AF513851, Sep. 2002.
GenBank entry AF513852, Sep. 2002.
Giles et al., Deamidation of Amino Acids on the Surface of Adeno-Associated Virus Capsids Leads to Charge Heterogeneity and Altered Vector Function, Mol Ther, 26(12), Dec. 2018.
Gilkes JA et al., Mucopolysaccharidosis IIIB confers enhanced neonatal intracranial transduction by AAV8 but not by 5, 9 or rh10, Gene Therapy, vol. 23(3):263-271, Mar. 2016. (Epub Dec. 16, 2015).
Girod A et al. Genetic capsid modifications allow efficient re-targeting of adeno-associated virus type 2. Nat Med. 5(9):1052-6. Sep. 1999.
Girod et al., The VP1 capsid protein of adeno-associated virus type 2 is carrying a phospholipase A2 domain required for virus infectivity, J. General Virol, 2002, 83:973-978.
Green SW et al., Rhesus and pig-tailed macaque parvoviruses: identification of two new members of the erythrovirus genus in monkeys, Virology, vol. 269:105-12, Mar. 30, 2000.
Grieger et al., Surface-Exposed Adeno-Associated Virus Vpl-NLS Capsid Fusion Protein Rescues Infectivity of Noninfectious Wild-Type Vp2/Vp3 and , Vp3-Only Capsids but Not That of Fivefold Pore Mutant Virions, J. Virol, 81(15):7833-7483, Aug. 2007.
Grosse et al., Relevance of Assembly-Activating Protein for Adeno-associated Virus Vector Production and Capsid Protein Stability in Mammalian and Insect Cells, J Virol 91:e01198-17, Aug. 2017.
Halbert et al., Repeat Transduction in the Mouse Lung by Using Adeno-Associated Virus Vectors with Different Serotypes, J. Virol, 74(3):1524-1532, Feb. 2000.
Hamilton et al., Adenoviral-Mediated Gene Transfer to Murine Small Intestine Is More Efficient in Neonates Than Adults, J Pediatr Surg. Feb. 1997;32(2):373-7.
Hernandez YJ et al., Latent Adeno-associated virus infection elicits humoral but no cell-mediated immune responses in a nonhuman primate model, Journal of Virology, vol. 73(10):8549-8558, Oct. 1999.
Herzog RW et al., Stable gene transfer and expression of human blood coagulation factor IX after intramuscular injection of recombinant adeno-associated virus, Proc. Natl. Acad. Sci. USA, vol. 94:5804-5809, May 27, 1997.
Hicks MJ et al., Aav-directed persistent expression of a gene encoding anti-nicotine antibody for smoking cessation, Science Translational Medicine, vol. 4(140):140ra87, Jun. 27, 2012.
Hu C et al., AAV-based neonatal gene therapy for hemophilia A: long-term correction and avoidance of immune responses in mice, vol. 19(12):1166-76. Dec. 2012. (Epub Jan. 12, 2012).
Hu C et al., RH10 provides superior transgene expression in mice when compared with natural AAV serotypes for neonatal gene therapy, vol. 12(9):766-78. doi: 10.1002/jgm.1496, Sep. 2010.
Kapturczak MH et al. Adeno-Associated Virus (AAV) as a Vehicle for Therapeutic Gene Delivery Improvements in Vector Design and Viral Production Enhance Potential to Prolong Graft Survival in Pancreatic Islet Cell Transplantation for the Reversal of Type 1 Diabetes. Curr Mol Med. 1(2):245-58. May 2001.
Kawamura et al., HIV-2 in West Africa in 1966, The Lancet, Feb. 1989, 385.

(56) References Cited

OTHER PUBLICATIONS

Kay MA et al. Therapeutic Serum Concentrations of Human Alpha-1-Antitrypsin After Adenoviral-Mediated Gene Transfer Into Mouse Hepatocytes, Hepatology, 21(3):815-9, Mar. 1995.

Kelkar S et al., A common mechanism for cytoplasmic dynein-dependent microtubule binding shared among adeno-associated virus and adenovirus serotypes, vol. 80(15):7781-5. Aug. 2006.

Kitajima K et al, Complete Prevention of Atherosclerosis in apoE-Deficient Mice by Hepatic Human ApoE Gene Transfer with Adeno-Associated Virus Serotype 7 and 8, Arterioscler Thromb Vasc Biol, vol. 26:1852-57, Jul. 20, 2006.

Klein RL et al., AAV8, 9, Rh10, Rh43 vector gene transfer in the rat brain: effects of serotype, promoter and purification method, vol. 16(1):89-96. Jan. 2008. (Epub Oct. 23, 2007).

Kobinger GP et al., Pseudotyping HIV Vector with the Spike Envelope Protein of SARS-CoV for Studying Viral Tropism, Immunology and Gene Therapy Applications, Abstract 368, 7th Annual Meeting of the American Society of Gene Therapy [Jun. 2-6, 2004] Minneapolis, Minnesota, p. 1, e-published May 2, 2004.

Lawlor PA et al., Efficient gene delivery and selective transduction of glial cells in the mammalian brain by AAV serotypes isolated from nonhuman primates, Mol Ther, vol. 17(10):1692-702. doi: 10.1038/mt.2009.170. Oct. 2009. (Epub Jul. 28, 2009).

Le Guenno, HIV1 and HIV2: two ancient viruses for a new disease? Transactions of the Royal Society of Tropical Medicine and Hygiene, 1989, 83, 847.

Lebherz C et al., Gene Therapy with Novel Adeno-Associated Virus Vectors Substantially Diminishes Atherosclerosis in a Murine Model of Familial Hypercholesterolemia, The Journal of Gene Medicine, vol. 6(6):663-672, Jun. 2004.

Lebherz C et al., Novel AAV serotypes for improved ocular gene transfer, J. Gene Med, vol. 10(4):375-82, Apr. 2008.

Li et al., 2015, Site-Directed Mutagenesis of Surface-Exposed Lysine Residues Leads to Improved Transduction by AAV2,But Not AAV8, Vectors in Murine Hepatocytes In Vivo, Hum Gene Ther Methods. Oct. 2015;26(6):211-20.

Limberis M et al., A Novel AAV Vector for the Treatment of Cystic Fibrosis Airway Disease, Abstract 692, 7th Annual Meeting of the American Society of Gene Therapy [Jun. 2-6, 2004] Minneapolis, Minnesota, p. 1, e-published May 2, 2004.

Lin J et al., Vaccines Based on Novel Adeno-Associated Virus Vectors Elicit Aberrant CD8+ T-Cell Responses in Mice, J Virol, vol. 81(21):11840-11849, Nov. 2007. (Epub Aug. 22, 2007).

Ling et al., Human Hepatocyte Growth Factor Receptor is a Cellular Coreceptor for Adeno-Associated Virus Serotype 3, Human Gene Therapy, 21:1741-1747 (Dec. 2010).

Ling et al., Selective In Vivo Targeting of Human Liver Tumors by Optimized AAV3 Vectors in a Murine Xenograft Model, Hum Gene Ther. Dec. 2014;25(12):1023-34.

Liu et al., Neutralizing antibodies against AAV2, Aavs and AAV8 in healthy and HIV-1-infected subjects in China: implications for gene therapy using AAV vectors, Gene Therapy, 21:732-738, May 2014.

Looker et al., An estimate of the global prevalence and incidence of herpes simplex virus type 2, Bull World Health Organ. Oct. 2008;86(10):805-12, A.

Lu Y et al., Analysis of Homologous Recombination Between Different AAV Genomes in In Vitro co-Infections, Abstract 38, Molecular Therapy, vol. 7(5):S15, May 2003.

Lytle AM et al., Effects of FVIII immunity on hepatocyte and hematopoietic stem cell-directed gene therapy of murine hemophilia A, Methods & Clinical Development, vol. 3:15056, Feb. 10, 2016.

Maguire CA et al., Directed evolution of adeno-associated virus for glioma cell transduction. J Neurooncol., vol. 96(3):337-47, Feb. 2010. (Epub Jul. 19, 2009).

Mao et al. Angiotensin 1-7 Overexpression Mediated by a Capsid-optimized AAV8 Vector Leads to Significant Growth Inhibition of Hepatocellular Carcinoma In vivo, Int. J. Biol. Sci, 14, Jan. 2018.

Mao Y et al, Persistent suppression of ocular neovascularization with intravitreal administration of AAVrh.10 coding for bevacizumab, Human Gene Therapy, vol. 22(12):1525-35. doi: 10.1089/hum.2011.090. Dec. 2011. (Epub Oct. 27, 2011).

Messina et al., Adeno-Associated Viral Vectors Based on Serotype 3b Use Components of the Fibroblast Growth Factor Receptor Signaling Complex for Efficient Transduction, Hum Gene Ther. Oct. 2012; 23(10): 1031-1042.

Mimuro et al., The Prevalence of Neutralizing Antibodies Against Adeno-Associated Virus Capsids Is Reduced in Young Japanese Individuals, J. Med Virol, 86:1990-7 Oct. 2013.

Monahan PE and Semulski RJ, Adeno-Associated Virus Vectors for Gene Therapy: More Pros than Cons, Molecular Medicine Today, vol. 6(11):433-40, Nov. 2000.

Mori S et al., Two Novel Adeno-Associated Viruses from Cynomolgus Monkey: Pseudotyping Characterization of Capsid Protein, Virology, vol. 330(2):375-383, Dec. 20, 2004.

Moskaleno et al., Epitope Mapping of Human Anti-Adeno-Associated Virus Type 2 Neutralizing Antibodies: Implications for Gene Therapy and Virus Structure, J Virol, Feb. 2000, 74(4):1761-6.

Mountz JD et al., Monkey See, Monkey Do, Gene Therapy, vol. 10(3):194-6, Feb. 2003.

Nam et al., Structure of Adeno-Associated Virus Serotype 8, a Gene Therapy Vector, J Virol, 81(22) :12260-71, Nov. 2007.

Nathwani AC et al., Enhancing transduction of the liver by adeno-associated viral vectors, Gene Therapy, vol. 16(1):60-9. doi: 10.1038/gt.2008.137. Jan. 2009. (Epub Aug. 14, 2008).

Nzilambi et al., The prevalence of infection with human immunodeficiency virus over a 10-year period in rural zaire, NE J Med, 318(5):276-279, Feb. 1988.

Pacak CA et al., Long-term skeletal muscle protection after gene transfer in a mouse model of LGMD-2D, Molecular Therapy, vol. 15(10):1775-81, Oct. 2007. (Epub Jul. 24, 2007).

Pignataro D et al., Adeno-Associated Viral Vectors Serotype 8 for Cell-Specific Delivery of Therapeutic Genes in the Central Nervous System, Frontiers in Neuroanatomy, vol. 11(2):1-13, Feb. 10, 2017.

Piguet F et al., Correction of brain oligodendrocytes by AAVrh.10 intracerebral gene therapy in metachromatic leukodystrophy mice, Human Gene Therapy, vol. 23(8):903-14. doi: 10.1089/hum.2012.015. Aug. 2012. (Epub Jul. 23, 2012).

Price A et al., Targeted Gene Transfer to Lung Airway Epithelium Using Plasmid or Adenoviral Vectors Formulated with an Anti-Inflammatory Dexamathasone-Spermine conjugate, Abstract 498, 7th Annual Meeting of the American Society of Gene Therapy [Jun. 2-6, 2004] Minneapolis, Minnesota, p. 1, e-published May 2, 2004.

Quesada O et al., Production, purification and preliminary x-ray crystallographic studies of adeno-associated virus serotype 7, Acta Crystallographica, vol. F(63):1073-6, Dec. 2007. (Epub Nov. 30, 2007).

Rafi MA et al., Extended normal life after AAVrh10-mediated gene therapy in the mouse model of krabbe disease, Molecular Therapy, vol. 20(11):2031-42. doi:. 10.1038/mt.2012.153. Nov. 2012. (Epub Jul. 31, 2012).

Research Genetics, Designer PCR (advertisement), Nucleic Acids Research, vol. 22(15):2882, Aug. 11, 1994.

Rick ME et al., ASH education Book—Congenital Bleeding Disorders, Hematology/American Society of Hematology Educational Program, vol. 2003(1):559-74, Jan. 1, 2003.

Rosenberg JB et al., AAVrh.10-mediated expression of an anti-cocaine antibody mediates persistent passive immunization that suppresses cocaine-induced behavior, Human Gene Therapy, vol. 23(5):451-9. doi: 10.1089/hum.2011.178. May 2012.

Ruffing M et al., Assembly of viruslike particles by recombinant structural proteins of adeno-associated virus type 2 in insect cells, J Virol., vol. 66(12):6922-30, Dec. 1992.

Rutledge EA et al., Infectious clones and vectors derived from adeno-associated virus (AAV) serotypes other than AAV type 2, Journal of Virology, vol. 72(1):309-319, XP-002137089, Jan. 1998.

Samaranch L et al., Strong Cortical and Spinal Cord Transduction after AAV7 and AAV9 Delivery into the Cerebrospinal Fluid of Nonhuman Primates, Human Gene Therapy, vol. 24:526-53, May 2013. (Epub May 2, 2013).

Sanmiguel J et al., Real-time PCR as an Analytic Tool in Gene Therapy, Abstract 913, vol. 7(5):5352, May 2003.

(56) References Cited

OTHER PUBLICATIONS

Schnell MA et al., Activation of innate immunity in nonhuman primates following intraportal administration of adenoviral vectors, Molecular Therapy, vol. 3(5):708-722, May 2001.
Shen et al., Characterization of the Relationship of AAV Capsid Domain Swapping to Liver Transduction Efficiency, Mol Ther, Aug. 2007, 15(11):1955-62.
Skaricic D et al., Genetic delivery of an anti-RSV antibody to protect against pulmonary infection with RSV, Jour. Virol., vol. 378(1):79-85. doi: 10.1016/j.virol.2008.04.016. Aug. 2008. (Epub Jun. 16, 2008).
Sommer S and Tautz D, Minimal homology requirement for PCR primers, Nucleic Acids Research, vol. 17(16):6749. Aug. 25, 1989.
Sondhi D et al., Enhanced survival of the LINCL mouse following CLN2 gene transfer using the rh.10 rhesus macaque-derived adeno-associated virus vector, Mol Ther., vol. 15(3):481-91, Mar. 2007. (Epub Dec. 19, 2006).
Sondhi D et al., Long-term expression and safety of administration of AAVrh.10hCLN2 to the brain of rats and nonhuman primates for the treatment of late infantile neuronal ceroid lipofuscinosis, Human Gene Therapy, vol. 23(5):324-35. doi: 10.1089/hgtb.2012.120, Oct. 2012. (Epub Nov. 6, 2012).
Sondhi D et al., Survival advantage of neonatal CNS gene transfer for late infantile neuronal ceroid lipofuscinosis, Jour Exp Neurol, vol. 213(1):18-27. doi: 10.1016/j.expneurol.2008.04.022. Sep. 2008. (Epub Apr. 30, 2008).
Sonntag et al., A viral assembly factor promotes AAV2 capsid formation in the nucleolus, PNAS, 107(22):10220-5, Jun. 2010.
Suhy et al. Safe, Long-term Hepatic Expression of Anti-HCV shRNA in a Nonhuman Primate Model, Mol Ther. Sep. 2012;20(9):1737-49. doi: 10.1038/mt.2012.119. Epub Jun. 26, 2012.
Tal J, Adeno-associated virus-based vectors in gene therapy, Journal of Biomedical Science, vol. 7(4):279-291, Jul. 2000.
Tobiasch E et al., Discrimination between different types of human adeno-associated viruses clinical samples by PCR, Journal of Virology Methods, vol. 71(1):17-25, Mar. 1998.
Trempe et al., Alternate mRNA splicing is required for synthesis of adeno-associated virus VP1 capsid protein. J Virol. Sep. 1988;62(9):3356-63, Sep. 1988.
Vandenberghe LH et al., AAV Clades: Their Ability to Recombine and Cross Species-Barriers, Abstract 88, 7th Annual Meeting of the American Society of Gene Therapy [Jun. 2-6, 2004] Minneapolis, Minnesota, p. 1, e-published May 2, 2004.
Vandenberghe LH et al., AAV9 Targets Cone Photoreceptors in the Nonhuman Primate Retina, PLoS One, vol. 8(1):e53463. doi: 10.1371/journal.pone.0053463, 2013. (Epub Jan. 30, 2013).
Vandenberghe LH et al., Naturally occurring singleton residues in AAV capsid impact vector performance and illustrate structural constraints. Gene Ther., vol. 16(12):1416-28, Dec. 2009.
Vandenberghe LH et al., Structure-Function Relationship of the Novel Non-Human Primate Adeno-associated Viruses, Abstract 99, Molecular Therapy, vol. 7(5):515, May 2003.
Vercauteren, Superior In vivo Transduction of Human Hepatocytes Using Engineered AAV3 Capsid, Mol Therapy, 24(6):1042-1049, Jun. 2016.
Vincent M et al., Comparison of the efficacy of five adeno-associated virus vectors for transducing dorsal raphé nucleus cells in the mouse. J Neurosci Methods, vol. 30(235):189-92, Sep. 30, 2014. (Epub Jul. 18, 2014).
Wang et al., Comparative Study of Liver Gene Transfer With AAV Vectors Based on Natural and Engineered AAV Capsids, Molecular Therapy, Dec. 2015, 23(12):1877-87.
Wang G et al., Persistent expression of biologically active anti-HER2 antibody by AAVrh.10-mediated gene transfer, Cancer Gene Therapy, vol. 17(8):559-70. doi: 10.1038/cgt.2010.11, Aug. 2010. (Epub May 7, 2010).
Wang L et al., Enhancing Transgene Expression from Recombinant AAV8 Vectors in Different Tissues Using Woodchuck Hepatitis Virus Post-Transcriptional Regulatory Element, International Journal of Medical Sciences, vol. 13(4):286-291, Apr. 1, 2016.
Wang L et al., Production of AAV Vectors with Different Serotypes, Abstract 906, Molecular Therapy, vol. 7(5):S350, May 2003.
Wang L et al., Systematic evaluation of AAV vectors for liver directed gene transfer in murine models, Mol Ther., vol. 18(1):118-25. doi: 10.1038/mt.2009.246. Jan. 2010. (Epub Oct. 27, 2009).
Wang L et al., The pleiotropic effects of natural AAV infections on liver-directed gene transfer in macaques, Molecular Therapy, vol. 18(1):126-34, doi: 10.1038/mt.2009.245, Jan. 2010. (Epub Nov. 3, 2009).
Warrington et al., Adeno-Associated Virus Type 2 VP2 Capsid Protein Is Nonessential and Can Tolerate Large Peptide Insertions at Its N Terminus, J Virol, 78(1):6595-6609, Jun. 2004.
Watanabe M et al., AAVrh.10-mediated genetic delivery of bevacizumab to the pleura to provide local anti-VEGF to suppress growth of metastatic lung tumors. Gene Ther., vol. 17(8):1042-51. doi: 10.1038/gt.2010.87, Aug. 2010. (Epub Jul. 1, 2010).
Weitzman MD et al., Adeno-associated virus (AAV) Rep proteins mediate complex formation between AAV DNA and its integration site in human DNA, PNAS, vol. 91:5808-5812, Jun. 21, 1994.
wikipedia.com, "Fungus", accessed Jun. 3, 2013 from https://en.wikipedia.org/wiki/Fungus (last modified Nov. 17, 2015).
wikipedia.com, "List of sequenced bacterial genomes", accessed Jan. 24, 2014 from https://en.wikipedia.org/wiki/List_of_sequenced_bacterial_genomes (last modified Oct. 19, 2015).
wikipedia.com, "Mammal", accessed Sep. 22, 2011 from https://en.wikipedia.org/wiki/Mammal (last modified Nov. 19, 2015).
wikipedia.com, "Murinae", accessed Mar. 18, 2013 from https://en.wikipedia.org/wiki/Murinae (last modified Nov. 7, 2015).
wikipedia.com, "Plant", accessed Mar. 8, 2013 from https://en.wikipedia.org/wiki/Plant (last modified Oct. 5, 2015).
wikipedia.com, "Virus", accessed Nov. 24, 2012 from https://en.wikipedia.org/wiki/Virus (last modified Nov. 1, 2015).
Wobus et al., Monoclonal Antibodies against the Adeno-Associated Virus Type 2 (AAV-2) Capsid: Epitope Mapping and identification of Capsid Domains Involved in AAV-2-Cell Interaction and Neutralization of AAV-2 Infection, J Virol, Oct. 2000, 74(19):9281-93.
Wu et al., Adeno-associated Virus Serotypes: Vector Toolkit for Human Gene Therapy, Molecular Therapy, 14(3):316-327, Sep. 2006.
Wu P et al. Mutational analysis of the adeno-associated virus type 2 (AAV2) capsid gene and construction of AAV2 vectors with altered tropism. J Virol. 74(18):8635-47, Sep. 2000.
Xiao W et al., Gene therapy vectors based on adeno-associated virus type 1, Journal of Virology, 73(5):3994-4003, May 1999.
Xiao X et al., Production of High-titer Recombinant Adeno-Associated Virus Vectors in the Absence of Helper Adenovirus, Journal of Virology, 72(3):2224-32, Mar. 1998.
Xie Q et al., Towards the atomic structure of the adeno-associated virus 2 capsid, Infectious Disease Review, from the VIIIth Parvovirus Workshop, Mont Tremblant, Quebec, Canada, vol. 2(3):136, (Jun. 28-Jul. 20, 2000).
Xin KQ et al., Induction of Robust Immune Response Against Human Immunodeficiency Virus is Supported by the Inherent Tropism of Adeno-Associated Virus Type 5 for Dendritic Cells, J. Virol, vol. 80(24):11899-910, Dec. 2006. (Epub Sep. 27, 2006).
Yan Z et al., Inverted terminal repeat sequences are important for intermolecular recombination and circularization of adeno-associated virus genomes, J Virol. 79(1):364-79, Jan. 2005.
Yang B et al., Global CNS transduction of adult mice by intravenously delivered rAAVrh.8 and rAAVrh.10 and nonhuman primates by rAAVrh.10., Mol Ther., vol. 22(7):1299-309, Jul. 2014. (Epub Apr. 30, 2014).
Zadori Z et al., A viral phospholipase A2 is required for parvovirus infectivity, Developmental Cell, vol. 1:291-302, Aug. 2001.
Zhang H et al., Several rAAV vectors efficiently cross the blood-brain barrier and transduce neurons and astrocytes in the neonatal mouse central nervous system, Molecular Therapy, vol. 19(8):1440-8, Aug. 2011.
Zhou X et al., Evaluation of Novel Gene Transfer Vectors Derived from Infectious Molecular Clones of Primate AAVs, Abstract 90, 7th Annual Meeting of the American Society of Gene Therapy [Jun. 2-6, 2004] Minneapolis, Minnesota, p. 1, e-published May 2, 2004.

(56) References Cited

OTHER PUBLICATIONS

Zhou XY et al., Direct Rescue and Cloning of Infectious Novel AAV Genomes From Non-Human Primate Tissues, Abstract 907, Molecular Therapy, 7(5):5350, May 2003.
Zhu T et al., Sustained Whole-Body Functional Rescue by Systemic Delivery of AAV8 Vectors in Heart Failure and Muscular Dystrophy Hamsters, Molecular Therapy, vol. 11(suppl 1):916, May 2005.
Office Action issued in parent U.S. Appl. No. 10/291,583, dated Dec. 22, 2005.
Response to Office Action dated Dec. 22, 2005 issued in parent U.S. Appl. No. 10/291,583, dated May 15, 2006.
Office Action issued in parent U.S. Appl. No. 10/291,583, dated Feb. 16, 2007.
Response to Office Action dated Feb. 16, 2007 issued in parent U.S. Appl. No. 10/291,583, dated May 3, 2007.
Office Action issued in parent U.S. Appl. No. 10/291,583, dated Jun. 11, 2007.
Response to Office Action dated Jun. 11, 2007 issued in parent U.S. Appl. No. 10/291,583, dated Aug. 10, 2007.
Office Action dated Feb. 6, 2008 issued in parent U.S. Appl. No. 10/291,583, dated Feb. 6, 2008.
Response submitted Apr. 7, 2008 to Office Action dated Feb. 6, 2008 issued in parent U.S. Appl. No. 10/291,583, dated Apr. 7, 2008.
Office Action dated May 1, 2008 issued in parent U.S. Appl. No. 10/291,583, dated May 1, 2008.
Response submitted Sep. 29, 2008 to Office Action dated May 1, 2008 issued in parent U.S. Appl. No. 10/291,583, dated Sep. 29, 2008.
Office Action dated Apr. 15, 2009 issued in parent U.S. Appl. No. 10/291,583, dated Apr. 15, 2009.
Response submitted Jul. 15, 2009 to Office Action dated Apr. 15, 2009 issued in parent U.S. Appl. No. 10/291,583, dated Jul. 15, 2009.
Office Action dated Sep. 18, 2009 issued in parent U.S. Appl. No. 10/291,583, dated Sep. 18, 2009.
Response submitted Mar. 17, 2010 to Office Action dated Sep. 18, 2009 issued in parent U.S. Appl. No. 10/291,583, dated Mar. 17, 2010.
Office Action dated Jun. 8, 2010 issued in parent U.S. Appl. No. 10/291,583, dated Jun. 8, 2010.
Office Action issued in related U.S. Appl. No. 11/985,096, dated Dec. 12, 2011.
Response submitted to Office Action dated Dec. 12, 2011 issued in related U.S. Appl. No. 11/985,096, dated Jun. 12, 2012.
Office Action issued in related U.S. Appl. No. 11/985,096, dated Jul. 30, 2012.
Response to Office Action dated Jul. 30, 2012 issued in related U.S. Appl. No. 11/985,096, dated Jan. 30, 2013.
Advisory action issued in related U.S. Appl. No. 11/985,096, dated Mar. 1, 2013.
Response to Advisory action dated Mar. 1, 2013 issued in related U.S. Appl. No. 11/985,096, dated Mar. 18, 2013.
Office Action issued in related U.S. Appl. No. 11/985,096 and response dated Mar. 17, 2014, dated Sep. 18, 2013.
Office Action issued in related U.S. Appl. No. 11/985,096, dated Jun. 27, 2014.
Notice of Allowance and Interview Summary issued on related U.S. Appl. No. 11/985,096, dated Sep. 25, 2014.
Amendment after Notice of Allowance submitted in related U.S. Appl. No. 11/985,096, dated Oct. 14, 2014.
Amendment after Notice of Allowance submitted in related U.S. Appl. No. 11/985,096, dated Oct. 28, 2014.
Office Action issued in related U.S. Appl. No. 12/962,793, dated Dec. 19, 2011.
Response to Office Action dated Dec. 19, 2011 issued in related U.S. Appl. No. 12/962,793, dated Jun. 19, 2012.
Office Action issued in related U.S. Appl. No. 12/962,793, dated Aug. 30, 2012.
Response to Office Action dated Aug. 30, 2012 issued in related U.S. Appl. No. 12/962,793, dated Feb. 28, 2013.
Advisory Action issued in U.S. Appl. No. 12/962,793, dated Mar. 20, 2013.
Supplemental Amendment filed in U.S. Appl. No. 12/962,793, dated May 13, 2013.
Advisory Action dated issued in U.S. Appl. No. 12/962,793, dated May 24, 2013.
Notice of Allowance issued on U.S. Appl. No. 12/962,793, dated Jun. 11, 2013.
Amendment after Notice of Allowance filed in U.S. Appl. No. 12/962,793, dated Jul. 25, 2013.
Office Action issued on corresponding Chinese application No. 201310326978.2, dated Nov. 19, 2014.
Response to Office Action dated Nov. 19, 2014 issued in corresponding Chinese application No. 201310326978.2, dated Apr. 2, 2015.
Second Office Action issued on corresponding Chinese application No. 201310326978.2, dated Aug. 10, 2015.
Communication in corresponding EP Patent Application No. 10178940.2 including search report dated May 18, 2011, dated May 26, 2011.
Response to Communication dated May 26, 2011, dated Dec. 30, 2011.
Communication in corresponding EP Patent Application No. 10178940.2 pursuant to Article 94(3) and Rule 71(1), invitation to amend claims, dated Feb. 3, 2012.
Response to Communication dated Feb. 3, 2012 issued on corresponding EP Patent Application No. 10178940.2, dated Jun. 13, 2012.
Communication under Rule 71(3) EPC—Intention to Grant issued on corresponding EP Patent Application No. 10178940.2, dated Nov. 5, 2012.
Amended claims filed in response to Communication from EPO dated Nov. 5, 2012 issued on corresponding EP Patent Application No. 10178940.2, dated Mar. 15, 2013.
Communication under Rule 71(3) EPC—Intention to Grant issued on corresponding EP Patent Application No. 10178940.2, dated May 2, 2013.
Response to Communication dated May 2, 2013 issued on corresponding EP Patent Application No. 10178940.2, dated Jul. 11, 2013.
Communication under Rule 71(3) EPC—Intention to Grant issued on corresponding EP Patent Application No. 10178940.2, dated Aug. 1, 2013.
Communication under Artile 91(1) EPC—Decision to Grant issued on corresponding EP Patent Application No. 10178940.2, dated Aug. 29, 2013.
Office Action issued in corresponding Japanese Patent Application No. 2009-102988, dated Oct. 4, 2011.
Final Office Action issued in corresponding Japanese Patent Application No. 2009-102988, dated Jun. 19, 2012.
Response to Office Action dated Jun. 19, 2012 issued in corresponding Japanese Patent Application No. 2009-102988, dated Sep. 12, 2012.
Decision to Grant issued in corresponding Japanese Patent Application No. 2009-102988, dated Nov. 14, 2012.
Office Action dated Dec. 31, 2014 issued in corresponding Chinese Patent Application No. 201310326869.
Office Action dated Sep. 24, 2015 issued in corresponding Chinese Patent Application No. 201310326869.
Office Action dated Jul. 9, 2014 issued in corresponding Australian Patent Application No. 2013202568.
Applicant's response dated Aug. 20, 2015 to Office Action dated Jul. 9, 2014 issued in corresponding Australian Patent Application No. 2013202568.
Office Action dated Jul. 28, 2016 issued in related U.S. Appl. No. 13/633,971.
Office Action dated May 31, 2016 issued in corresponding Chinese Patent Application No. 201310326869.
Notice of Reasons for Rejection in Japanese Patent Application No. 2014-122390 dated Aug. 13, 2015.
Office Action issued in Canadian Patent Application No. 2,915,124, dated Aug. 15, 2016.
Office Action issued in Japanese Patent Application No. 2016-093699, dated Feb. 24, 2017 and dispatched Mar. 1, 2017.

(56) References Cited

OTHER PUBLICATIONS

Extended European Search Report issued in European Patent Application No. 16154948.0, dated Aug. 23, 2016.
Communication of a notice of opposition issued in European Patent Application No. 02795539.2 / 1453547 by the European Patent Office on Jun. 26, 2017 as well as the statement of opposition of Jun. 20, 2017 enclosed therein.
Response dated Dec. 5, 2017 in reply to the communication of a notice of opposition issued Jun. 26, 2017 in European Patent Application No. 02795539.2 / 1453547.
Examination Report issued in corresponding Australian Patent Application No. 2015258271 dated Aug. 30, 2017.
Declaration of Olivier Danos, Ph.D. dated Aug. 14, 2018, submitted in Opposition of EP Patent No. 02795539.2.
Declaration of Prof Asokan, dated Aug. 23, 2018, submitted in Opposition of EP Patent No. 02795539.2.
Declaration of Roberto Calcedo, PhD dated Sep. 24, 2018, submitted in Opposition of EP Patent No. 02795539.2.
Second declaration of Olivier Danos, Ph.D. dated Sep. 25, 2018, submitted in Opposition of EP Patent No. 02795539.2.
Proprietor's Submission pursuant to Rule 116 prior to oral proceedings dated Aug. 24, 2018 submitted in Opposition of EP Patent No. 02795539.2.
Opposer's Submission pursuant to Rule 116 prior to oral proceedings dated Aug. 24, 2018 submitted in Opposition of EP Patent No. 02795539.2.
Proprietor's Further Submission prior to oral proceedings dated Sep. 26, 2018 submitted in Opposition of EP Patent No. 02795539.2.
Opposer's Further Submission prior to oral proceedings dated Oct. 23, 2018 submitted in Opposition of EP Patent No. 02795539.2.
Summons to attend oral proceedings and Communication dated Mar. 29, 2018, issued in related European Patent No. 1453547.
Interlocutory decision in Opposition proceedings issued in related European Patent No. 1453547 on Nov. 30, 2018.
Notice of Opposition and Opponent's Brief in European Patent No. 2359869, dated Sep. 26, 2019.
Office Action dated Oct. 12, 2017 in U.S. Appl. No. 15/584,674.
Response to Office Action dated Oct. 12, 2017 in U.S. Appl. No. 15/584,674, filed Dec. 12, 2017.
Office Action dated Mar. 3, 2018 in U.S. Appl. No. 15/584,674.
Response to Office Action dated Mar. 3, 2018 in U.S. Appl. No. 15/584,674, filed Jun. 8, 2018.
Office Action dated Sep. 19, 2019 in U.S. Appl. No. 15/584,674.
Response to Office Action dated Sep. 19, 2019 in U.S. Appl. No. 15/584,674, filed Jul. 17, 2019.
Notice of Allowance dated Sep. 19, 2019 in U.S. Appl. No. 15/584,674.
Office Action dated Jul. 28, 2018 in U.S. Appl. No. 13/633,971.
International Search Report issued in corresponding International Application No. PCT/US2002/033629, dated Jul. 28, 2003.
Written Opinion issued in corresponding International Application No. PCT/US2002/033629, dated Aug. 11, 2004.

FIG. 1A

```
              1                                                                    50
      42_2    ..........  ..........  ..........  ..........  ..........
      42_8    ..........  ..........  ..........  ..........  ..........
      42_15   ..........  ..........  ..........  ..........  ..........
      42_5b   ..........  ..........  ..........  ..........  ..........
      42_1b   ..........  ..........  ..........  ..........  ..........
      42_13   ..........  ..........  ..........  ..........  ..........
      42_3a   ..........  ..........  ..........  ..........  ..........
      42_4    ..........  ..........  ..........  ..........  ..........
      42_5a   ..........  ..........  ..........  ..........  ..........
      42_10   ..........  ..........  ..........  ..........  ..........
      42_3b   ..........  ..........  ..........  ..........  ..........
      42_11   ..........  ..........  ..........  ..........  ..........
      42_6b   ..........  ..........  ..........  ..........  ..........
      43_1    ..........  ..........  ..........  ..........  ..........
      43_5    ..........  ..........  ..........  ..........  ..........
      43_12   ..........  ..........  ..........  ..........  ..........
      43_20   ..........  ..........  ..........  ..........  ..........
      43_21   ..........  ..........  ..........  ..........  ..........
      43_23   ..........  ..........  ..........  ..........  ..........
      43_25   ..........  ..........  ..........  ..........  ..........
      44_1    ..........  ..........  ..........  ..........  ..........
      44_5    ..........  ..........  ..........  ..........  ..........
      223_10  ..........  ..........  ..........  ..........  ..........
      223_2   ..........  ..........  ..........  ..........  ..........
      223_4   ..........  ..........  ..........  ..........  ..........
      223_5   ..........  ..........  ..........  ..........  ..........
      223_6   ..........  ..........  ..........  ..........  ..........
      223_7   ..........  ..........  ..........  ..........  ..........
      A3_4    ..........  ..........  ..........  ..........  ..........
      A3_5    ..........  ..........  ..........  ..........  ..........
      A3_7    ..........  ..........  ..........  ..........  ..........
      A3_3    ..........  ..........  ..........  ..........  ..........
      42_12   ..........  ..........  ..........  ..........  ..........
      AAV1    TTGCCCACTC  CCTCTCTGCG  CGCTCGCTCG  CTCGGTGGGG  CCTGCGGACC
      AAV2    TTGGCCACTC  CCTCTCTGCG  CGCTCGCTCG  CTCACTGAGG  CCGGGCGACC
      AAV3    TTGGCCACTC  CCTCTATGCG  CACTCGCTCG  CTCGGTGGGG  CCTGGCGACC
      AAV8    ..........  ..........  ..........  ..........  ..........
      AAV9    ..........  ..........  ..........  ..........  ..........
      AAV7    TTGGCCACTC  CCTCTATGCG  CGCTCGCTCG  CTCGGTGGGG  CCTGCGGACC
      44_2    ..........  ..........  ..........  ..........  ..........
```

FIG. 1C

```
Rep binding site                                                                    150
       ◄─────────────────────────┐      TRS
  42_2     ..........            |.........  ...|......  ..........  ..........
  42_8     ..........            |.........  ...|......  ..........  ..........
  42_15    ..........             ..........  ..........  ..........  ..........
  42_5b    ..........             ..........  ..........  ..........  ..........
  42_1b    ..........             ..........  ..........  ..........  ..........
  42_13    ..........             ..........  ..........  ..........  ..........
  42_3a    ..........             ..........  ..........  ..........  ..........
  42_4     ..........             ..........  ..........  ..........  ..........
  42_5a    ..........             ..........  ..........  ..........  ..........
  42_10    ..........             ..........  ..........  ..........  ..........
  42_3b    ..........             ..........  ..........  ..........  ..........
  42_11    ..........             ..........  ..........  ..........  ..........
  42_6b    ..........             ..........  ..........  ..........  ..........
  43_1     ..........             ..........  ..........  ..........  ..........
  43_5     ..........             ..........  ..........  ..........  ..........
  43_12    ..........             ..........  ..........  ..........  ..........
  43_20    ..........             ..........  ..........  ..........  ..........
  43_21    ..........             ..........  ..........  ..........  ..........
  43_23    ..........             ..........  ..........  ..........  ..........
  43_25    ..........             ..........  ..........  ..........  ..........
  44_1     ..........             ..........  ..........  ..........  ..........
  44_5     ..........             ..........  ..........  ..........  ..........
  223_10   ..........             ..........  ..........  ..........  ..........
  223_2    ..........             ..........  ..........  ..........  ..........
  223_4    ..........             ..........  ..........  ..........  ..........
  223_5    ..........             ..........  ..........  ..........  ..........
  223_6    ..........             ..........  ..........  ..........  ..........
  223_7    ..........             ..........  ..........  ..........  ..........
  A3_4     ..........             ..........  ..........  ..........  ..........
  A3_5     ..........             ..........  ..........  ..........  ..........
  A3_7     ..........             ..........  ..........  ..........  ..........
  A3_3     ..........             ..........  ..........  ..........  ..........
  42_12    ..........             ..........  ..........  ..........  ..........
  AAV1     GAGCGCGCAG             AGAGGGAGTG  GGCAACTCCA  TCACTAGGGG  TAATCGCGAA
  AAV2     GAGCGCGCAG             AGAGGGAGTG  GCCAACTCCA  TCACTAGGGG  TTC.......
  AAV3     GAGTGCGCAT             AGAGGGAGTG  GCCAACTCCA  TCACTAGAGG  T.........
  AAV8     .......CAG             AGAGGGAGTG  GCCAACTCCA  TCACTAGGGG  TAG.CGCGAA
  AAV9     .......CAG             AGAGGGAGTG  GCCAACTCCA  TCACTAGGGG  TAATCGCGAA
  AAV7     GAGCGCGCAT             AGAGGGAGTG  GCCAACTCCA  TCACTAGGGG  TA.CCGCGAA
  44_2     ..........            |.........  ...|......  ..........  ..........
◄──────────────────────────────┘               |
Rep binding site                              TRS
```

FIG. 1D

```
       151                                                           200
42_2    ..........  ..........  ..........  ..........  ..........
42_8    ..........  ..........  ..........  ..........  ..........
42_15   ..........  ..........  ..........  ..........  ..........
42_5b   ..........  ..........  ..........  ..........  ..........
42_1b   ..........  ..........  ..........  ..........  ..........
42_13   ..........  ..........  ..........  ..........  ..........
42_3a   ..........  ..........  ..........  ..........  ..........
42_4    ..........  ..........  ..........  ..........  ..........
42_5a   ..........  ..........  ..........  ..........  ..........
42_10   ..........  ..........  ..........  ..........  ..........
42_3b   ..........  ..........  ..........  ..........  ..........
42_11   ..........  ..........  ..........  ..........  ..........
42_6b   ..........  ..........  ..........  ..........  ..........
43_1    ..........  ..........  ..........  ..........  ..........
43_5    ..........  ..........  ..........  ..........  ..........
43_12   ..........  ..........  ..........  ..........  ..........
43_20   ..........  ..........  ..........  ..........  ..........
43_21   ..........  ..........  ..........  ..........  ..........
43_23   ..........  ..........  ..........  ..........  ..........
43_25   ..........  ..........  ..........  ..........  ..........
44_1    ..........  ..........  ..........  ..........  ..........
44_5    ..........  ..........  ..........  ..........  ..........
223_10  ..........  ..........  ..........  ..........  ..........
223_2   ..........  ..........  ..........  ..........  ..........
223_4   ..........  ..........  ..........  ..........  ..........
223_5   ..........  ..........  ..........  ..........  ..........
223_6   ..........  ..........  ..........  ..........  ..........
223_7   ..........  ..........  ..........  ..........  ..........
A3_4    ..........  ..........  ..........  ..........  ..........
A3_5    ..........  ..........  ..........  ..........  ..........
A3_7    ..........  ..........  ..........  ..........  ..........
A3_3    ..........  ..........  ..........  ..........  ..........
42_12   ..........  ..........  ..........  ..........  ..........
AAV1    GCGCCTCCCA  CGCTGCCGCG  TCAGCGCTGA  CGTAAATTAC  GTCATAGGGG
AAV2    .......CTG  GAGGGGTGGA  GTCGTGACGT  GAATTACGTC  ATAGGGTTAG
AAV3    .......ATG  GCAGTGACGT  AACGCGAAGC  GCGCGAAGCG  AGACCACGCC
AAV8    GCGCCTCCCA  CGCTGCCGCG  TCAGCGCTGA  CGTAAATTAC  GTCATAGGGG
AAV9    GCGCCTCCCA  CGCTGCCGCG  TCAGCGCTGA  CGTAGATTAC  GTCATAGGGG
AAV7    GCGCCTCCCA  CGCTGCCGCG  TCAGCGCTGA  CGTAAATCAC  GTCATAGGGG
44_2    ..........  ..........  ..........  ..........  ..........
```

FIG. 1H

```
         351                                                      400
42_2     ..........  ..........  ..........  ..........  ..........
42_8     ..........  ..........  ..........  ..........  ..........
42_15    ..........  ..........  ..........  ..........  ..........
42_5b    ..........  ..........  ..........  ..........  ..........
42_1b    ..........  ..........  ..........  ..........  ..........
42_13    ..........  ..........  ..........  ..........  ..........
42_3a    ..........  ..........  ..........  ..........  ..........
42_4     ..........  ..........  ..........  ..........  ..........
42_5a    ..........  ..........  ..........  ..........  ..........
42_10    ..........  ..........  ..........  ..........  ..........
42_3b    ..........  ..........  ..........  ..........  ..........
42_11    ..........  ..........  ..........  ..........  ..........
42_6b    ..........  ..........  ..........  ..........  ..........
43_1     ..........  ..........  ..........  ..........  ..........
43_5     ..........  ..........  ..........  ..........  ..........
43_12    ..........  ..........  ..........  ..........  ..........
43_20    ..........  ..........  ..........  ..........  ..........
43_21    ..........  ..........  ..........  ..........  ..........
43_23    ..........  ..........  ..........  ..........  ..........
43_25    ..........  ..........  ..........  ..........  ..........
44_1     ..........  ..........  ..........  ..........  ..........
44_5     ..........  ..........  ..........  ..........  ..........
223_10   ..........  ..........  ..........  ..........  ..........
223_2    ..........  ..........  ..........  ..........  ..........
223_4    ..........  ..........  ..........  ..........  ..........
223_5    ..........  ..........  ..........  ..........  ..........
223_6    ..........  ..........  ..........  ..........  ..........
223_7    ..........  ..........  ..........  ..........  ..........
A3_4     ..........  ..........  ..........  ..........  ..........
A3_5     ..........  ..........  ..........  ..........  ..........
A3_7     ..........  ..........  ..........  ..........  ..........
A3_3     ..........  ..........  ..........  ..........  ..........
42_12    ..........  ..........  ..........  ..........  ..........
AAV1     CGAGATCGTG  ATCAAGGTGC  CGAGCGACCT  GGACGAGCAC  CTGCCGGGCA
AAV2     CGAGATTGTG  ATTAAGGTCC  CCAGCGACCT  TGACGGGCAT  CTGCCCGGCA
AAV3     CGAGATTGTC  CTGAAGGTCC  CGAGTGACCT  GGACGAGCGC  CTGCCGGGCA
AAV8     CGAGATCGTG  ATCAAGGTGC  CGAGCGACCT  GGACGAGCAC  CTGCCGGGCA
AAV9     CGAGATTGTG  ATCAAGGTGC  CGAGCGACCT  GGACGAGCAC  CTGCCGGGCA
AAV7     CGAGATCGTG  ATCAAGGTGC  CGAGCGACCT  GGACGAGCAC  CTGCCGGGCA
44_2     ..........  ..........  ..........  ..........  ..........
```

FIG. 1I

```
        401                                                           450
 42_2    ..........   ..........   ..........   ..........   ..........
 42_8    ..........   ..........   ..........   ..........   ..........
 42_15   ..........   ..........   ..........   ..........   ..........
 42_5b   ..........   ..........   ..........   ..........   ..........
 42_1b   ..........   ..........   ..........   ..........   ..........
 42_13   ..........   ..........   ..........   ..........   ..........
 42_3a   ..........   ..........   ..........   ..........   ..........
 42_4    ..........   ..........   ..........   ..........   ..........
 42_5a   ..........   ..........   ..........   ..........   ..........
 42_10   ..........   ..........   ..........   ..........   ..........
 42_3b   ..........   ..........   ..........   ..........   ..........
 42_11   ..........   ..........   ..........   ..........   ..........
 42_6b   ..........   ..........   ..........   ..........   ..........
 43_1    ..........   ..........   ..........   ..........   ..........
 43_5    ..........   ..........   ..........   ..........   ..........
 43_12   ..........   ..........   ..........   ..........   ..........
 43_20   ..........   ..........   ..........   ..........   ..........
 43_21   ..........   ..........   ..........   ..........   ..........
 43_23   ..........   ..........   ..........   ..........   ..........
 43_25   ..........   ..........   ..........   ..........   ..........
 44_1    ..........   ..........   ..........   ..........   ..........
 44_5    ..........   ..........   ..........   ..........   ..........
223_10   ..........   ..........   ..........   ..........   ..........
223_2    ..........   ..........   ..........   ..........   ..........
223_4    ..........   ..........   ..........   ..........   ..........
223_5    ..........   ..........   ..........   ..........   ..........
223_6    ..........   ..........   ..........   ..........   ..........
223_7    ..........   ..........   ..........   ..........   ..........
 A3_4    ..........   ..........   ..........   ..........   ..........
 A3_5    ..........   ..........   ..........   ..........   ..........
 A3_7    ..........   ..........   ..........   ..........   ..........
 A3_3    ..........   ..........   ..........   ..........   ..........
 42_12   ..........   ..........   ..........   ..........   ..........
 AAV1    TTTCTGACTC   GTTTGTGAGC   TGGGTGGCCG   AGAAGGAATG   GGAGCTGCCC
 AAV2    TTTCTGACAG   CTTTGTGAAC   TGGGTGGCCG   AGAAGGAATG   GGAGTTGCCG
 AAV3    TTTCTAACTC   GTTTGTTAAC   TGGGTGGCCG   AGAAGGAATG   GGACGTGCCG
 AAV8    TTTCTGACTC   GTTTGTGAAC   TGGGTGGCCG   AGAAGGAATG   GGAGCTGCCC
 AAV9    TTTCTGACTC   TTTTGTGAAC   TGGGTGGCCG   AGAAGGAATG   GGAGCTGCCC
 AAV7    TTTCTGACTC   GTTTGTGAAC   TGGGTGGCCG   AGAAGGAATG   GGAGCTGCCC
 44_2    ..........   ..........   ..........   ..........   ..........
```

FIG. 1J

```
         451                                                              500
42_2     .......... .......... .......... .......... ..........
42_8     .......... .......... .......... .......... ..........
42_15    .......... .......... .......... .......... ..........
42_5b    .......... .......... .......... .......... ..........
42_1b    .......... .......... .......... .......... ..........
42_13    .......... .......... .......... .......... ..........
42_3a    .......... .......... .......... .......... ..........
42_4     .......... .......... .......... .......... ..........
42_5a    .......... .......... .......... .......... ..........
42_10    .......... .......... .......... .......... ..........
42_3b    .......... .......... .......... .......... ..........
42_11    .......... .......... .......... .......... ..........
42_6b    .......... .......... .......... .......... ..........
43_1     .......... .......... .......... .......... ..........
43_5     .......... .......... .......... .......... ..........
43_12    .......... .......... .......... .......... ..........
43_20    .......... .......... .......... .......... ..........
43_21    .......... .......... .......... .......... ..........
43_23    .......... .......... .......... .......... ..........
43_25    .......... .......... .......... .......... ..........
44_1     .......... .......... .......... .......... ..........
44_5     .......... .......... .......... .......... ..........
223_10   .......... .......... .......... .......... ..........
223_2    .......... .......... .......... .......... ..........
223_4    .......... .......... .......... .......... ..........
223_5    .......... .......... .......... .......... ..........
223_6    .......... .......... .......... .......... ..........
223_7    .......... .......... .......... .......... ..........
A3_4     .......... .......... .......... .......... ..........
A3_5     .......... .......... .......... .......... ..........
A3_7     .......... .......... .......... .......... ..........
A3_3     .......... .......... .......... .......... ..........
42_12    .......... .......... .......... .......... ..........
AAV1     CCGGATTCTG ACATGGATCT GAATCTGATT GAGCAGGCAC CCCTGACCGT
AAV2     CCAGATTCTG ACATGGATCT GAATCTGATT GAGCAGGCAC CCCTGACCGT
AAV3     CCGGATTCTG ACATGGATCC GAATCTGATT GAGCAGGCAC CCCTGACCGT
AAV8     CCGGATTCTG ACATGGATCG GAATCTGATC GAGCAGGCAC CCCTGACCGT
AAV9     CCGGATTCTG ACATGGATCG GAATCTGATC GAGCAGGCAC CCCTGACCGT
AAV7     CCGGATTCTG ACATGGATCT GAATCTGATC GAGCAGGCAC CCCTGACCGT
44_2     .......... .......... .......... .......... ..........
```

FIG. 1K

```
        501                                                          550
 42_2   ..........  ..........  ..........  ..........  ..........
 42_8   ..........  ..........  ..........  ..........  ..........
42_15   ..........  ..........  ..........  ..........  ..........
42_5b   ..........  ..........  ..........  ..........  ..........
42_1b   ..........  ..........  ..........  ..........  ..........
42_13   ..........  ..........  ..........  ..........  ..........
42_3a   ..........  ..........  ..........  ..........  ..........
 42_4   ..........  ..........  ..........  ..........  ..........
42_5a   ..........  ..........  ..........  ..........  ..........
42_10   ..........  ..........  ..........  ..........  ..........
42_3b   ..........  ..........  ..........  ..........  ..........
42_11   ..........  ..........  ..........  ..........  ..........
42_6b   ..........  ..........  ..........  ..........  ..........
 43_1   ..........  ..........  ..........  ..........  ..........
 43_5   ..........  ..........  ..........  ..........  ..........
43_12   ..........  ..........  ..........  ..........  ..........
43_20   ..........  ..........  ..........  ..........  ..........
43_21   ..........  ..........  ..........  ..........  ..........
43_23   ..........  ..........  ..........  ..........  ..........
43_25   ..........  ..........  ..........  ..........  ..........
 44_1   ..........  ..........  ..........  ..........  ..........
 44_5   ..........  ..........  ..........  ..........  ..........
223_10  ..........  ..........  ..........  ..........  ..........
223_2   ..........  ..........  ..........  ..........  ..........
223_4   ..........  ..........  ..........  ..........  ..........
223_5   ..........  ..........  ..........  ..........  ..........
223_6   ..........  ..........  ..........  ..........  ..........
223_7   ..........  ..........  ..........  ..........  ..........
 A3_4   ..........  ..........  ..........  ..........  ..........
 A3_5   ..........  ..........  ..........  ..........  ..........
 A3_7   ..........  ..........  ..........  ..........  ..........
 A3_3   ..........  ..........  ..........  ..........  ..........
42_12   ..........  ..........  ..........  ..........  ..........
 AAV1   GGCCGAGAAG  CTGCAGCGCG  ACTTCCTGGT  CCAATGGCGC  CGCGTGAGTA
 AAV2   GGCCGAGAAG  CTGCAGCGCG  ACTTTCTGAC  GGAATGGCGC  CGTGTGAGTA
 AAV3   GGCCGAAAAG  CTTCAGCGCG  AGTTCCTGGT  GGAGTGGCGC  CGCGTGAGTA
 AAV8   GGCCGAGAAG  CTGCAGCGCG  ACTTCCTGGT  CCAATGGCGC  CGCGTGAGTA
 AAV9   GGCCGAGAAG  CTGTAGCGCG  ACTTCCTGGT  CCAATGGCGC  CGCGTGAGTA
 AAV7   GGCCGAGAAG  CTGCAGCGCG  ACTTCCTGGT  CCAATGGCGC  CGCGTGAGTA
 44_2   ..........  ..........  ..........  ..........  ..........
```

FIG. 1L

```
         551                                                              600
  42_2   ..........  ..........  ..........  ..........  ..........
  42_8   ..........  ..........  ..........  ..........  ..........
 42_15   ..........  ..........  ..........  ..........  ..........
 42_9b   ..........  ..........  ..........  ..........  ..........
 42_1b   ..........  ..........  ..........  ..........  ..........
 42_13   ..........  ..........  ..........  ..........  ..........
 42_3a   ..........  ..........  ..........  ..........  ..........
  42_4   ..........  ..........  ..........  ..........  ..........
 42_5a   ..........  ..........  ..........  ..........  ..........
 42_10   ..........  ..........  ..........  ..........  ..........
 42_3b   ..........  ..........  ..........  ..........  ..........
 42_11   ..........  ..........  ..........  ..........  ..........
 42_6b   ..........  ..........  ..........  ..........  ..........
  43_1   ..........  ..........  ..........  ..........  ..........
  43_5   ..........  ..........  ..........  ..........  ..........
 43_12   ..........  ..........  ..........  ..........  ..........
 43_20   ..........  ..........  ..........  ..........  ..........
 43_21   ..........  ..........  ..........  ..........  ..........
 43_23   ..........  ..........  ..........  ..........  ..........
 43_25   ..........  ..........  ..........  ..........  ..........
  44_1   ..........  ..........  ..........  ..........  ..........
  44_5   ..........  ..........  ..........  ..........  ..........
 223_10  ..........  ..........  ..........  ..........  ..........
 223_2   ..........  ..........  ..........  ..........  ..........
 223_4   ..........  ..........  ..........  ..........  ..........
 223_5   ..........  ..........  ..........  ..........  ..........
 223_6   ..........  ..........  ..........  ..........  ..........
 223_7   ..........  ..........  ..........  ..........  ..........
  A3_4   ..........  ..........  ..........  ..........  ..........
  A3_5   ..........  ..........  ..........  ..........  ..........
  A3_7   ..........  ..........  ..........  ..........  ..........
  A3_3   ..........  ..........  ..........  ..........  ..........
 42_12   ..........  ..........  ..........  ..........  ..........
  AAV1   AGGCCCCGGA  GGCCCTCTTC  TTTGTTCAGT  TCGAGAAGGG  CGAGTCCTAC
  AAV2   AGGCCCCGGA  GGCCCTTTTC  TTTGTGCAAT  TTGAGAAGGG  AGAGAGCTAC
  AAV3   AGGCCCCGGA  GGCCCTCTTT  TTTGTCCAGT  TCGAAAAGGG  GGAGACCTAC
  AAV8   AGGCCCCGGA  GGCCCTCTTC  TTTGTTCAGT  TCGAGAAGGG  CGAGAGCTAC
  AAV9   AGGCCCCGGA  GGCCCTCTTC  TTTGTTCAGT  TCGAGAAGGG  CGAGAGCTAC
  AAV7   AGGCCCCGGA  GGCCCTGTTC  TTTGTTCAGT  TCGAGAAGGG  CGAGAGCTAC
  44_2   ..........  ..........  ..........  ..........  ..........
```

FIG. 1M

```
          601                                                                  650
   42_2   ..........  ..........  ..........  ..........  ..........
   42_8   ..........  ..........  ..........  ..........  ..........
  42_15   ..........  ..........  ..........  ..........  ..........
  42_5b   ..........  ..........  ..........  ..........  ..........
  42_1b   ..........  ..........  ..........  ..........  ..........
  42_13   ..........  ..........  ..........  ..........  ..........
  42_3a   ..........  ..........  ..........  ..........  ..........
   42_4   ..........  ..........  ..........  ..........  ..........
  42_5a   ..........  ..........  ..........  ..........  ..........
  42_10   ..........  ..........  ..........  ..........  ..........
  42_3b   ..........  ..........  ..........  ..........  ..........
  42_11   ..........  ..........  ..........  ..........  ..........
  42_6b   ..........  ..........  ..........  ..........  ..........
   43_1   ..........  ..........  ..........  ..........  ..........
   43_5   ..........  ..........  ..........  ..........  ..........
  43_12   ..........  ..........  ..........  ..........  ..........
  43_20   ..........  ..........  ..........  ..........  ..........
  43_21   ..........  ..........  ..........  ..........  ..........
  43_23   ..........  ..........  ..........  ..........  ..........
  43_25   ..........  ..........  ..........  ..........  ..........
   44_1   ..........  ..........  ..........  ..........  ..........
   44_5   ..........  ..........  ..........  ..........  ..........
  223_10  ..........  ..........  ..........  ..........  ..........
  223_2   ..........  ..........  ..........  ..........  ..........
  223_4   ..........  ..........  ..........  ..........  ..........
  223_5   ..........  ..........  ..........  ..........  ..........
  223_6   ..........  ..........  ..........  ..........  ..........
  223_7   ..........  ..........  ..........  ..........  ..........
   A3_4   ..........  ..........  ..........  ..........  ..........
   A3_5   ..........  ..........  ..........  ..........  ..........
   A3_7   ..........  ..........  ..........  ..........  ..........
   A3_3   ..........  ..........  ..........  ..........  ..........
  42_12   ..........  ..........  ..........  ..........  ..........
   AAV1   TTCCACCTCC  ATATTCTGGT  GGAGACCACG  GGGGTCAAAT  CCATGGTGCT
   AAV2   TTCCACATGC  ACGTGCTCGT  GGAAACCACC  GGGGTGAAAT  CCATGGTTTT
   AAV3   TTCCACCTGC  ACGTGCTGAT  TGAGACCATC  GGGGTCAAAT  CCATGGTGGT
   AAV8   TTTCACCTGC  ACGTTCTGGT  CGAGACCACG  GGGGTCAAGT  CCATGGTGCT
   AAV9   TTTCACCTGC  ACGTTCTGGT  CGAGACCACG  GGGGTCAAGT  CCATGGTGCT
   AAV7   TTCCACCTTC  ACGTTCTGGT  GGAGACCACG  GGGGTCAAGT  CCATGGTGCT
   44_2   ..........  ..........  ..........  ..........  ..........
```

FIG. 1N

```
        651                                                              700
42_2    ..........  ..........  ..........  ..........  ..........
42_8    ..........  ..........  ..........  ..........  ..........
42_15   ..........  ..........  ..........  ..........  ..........
42_5b   ..........  ..........  ..........  ..........  ..........
42_1b   ..........  ..........  ..........  ..........  ..........
42_13   ..........  ..........  ..........  ..........  ..........
42_3a   ..........  ..........  ..........  ..........  ..........
42_4    ..........  ..........  ..........  ..........  ..........
42_5a   ..........  ..........  ..........  ..........  ..........
42_10   ..........  ..........  ..........  ..........  ..........
42_3b   ..........  ..........  ..........  ..........  ..........
42_11   ..........  ..........  ..........  ..........  ..........
42_6b   ..........  ..........  ..........  ..........  ..........
43_1    ..........  ..........  ..........  ..........  ..........
43_5    ..........  ..........  ..........  ..........  ..........
43_12   ..........  ..........  ..........  ..........  ..........
43_20   ..........  ..........  ..........  ..........  ..........
43_21   ..........  ..........  ..........  ..........  ..........
43_23   ..........  ..........  ..........  ..........  ..........
43_25   ..........  ..........  ..........  ..........  ..........
44_1    ..........  ..........  ..........  ..........  ..........
44_5    ..........  ..........  ..........  ..........  ..........
223_10  ..........  ..........  ..........  ..........  ..........
223_2   ..........  ..........  ..........  ..........  ..........
223_4   ..........  ..........  ..........  ..........  ..........
223_5   ..........  ..........  ..........  ..........  ..........
223_6   ..........  ..........  ..........  ..........  ..........
223_7   ..........  ..........  ..........  ..........  ..........
A3_4    ..........  ..........  ..........  ..........  ..........
A3_5    ..........  ..........  ..........  ..........  ..........
A3_7    ..........  ..........  ..........  ..........  ..........
A3_3    ..........  ..........  ..........  ..........  ..........
42_12   ..........  ..........  ..........  ..........  ..........
AAV1    GGGCCGCTTC  CTGAGTCAGA  TTAGGGACAA  GCT.GGTGCA  GACCATCTAC
AAV2    GGGACGTTTC  CTGAGTCAGA  TTCGCGAAAA  ACT..GATTC  AGAGAATTTA
AAV3    CGGCCGCTAC  GTGAGCCAGA  TTAAAGAGAA  GCT..GGTGA  CCCGCATCTA
AAV8    AGGCCGCTTC  CTGAGTCAGA  TTCGGGAAAA  GCTTGGTCCA  GACCATCTAC
AAV9    AGGCCGCTTC  CTGAGTCAGA  TTCGGGAGAA  GCT.GGTCCA  GACCATCTAC
AAV7    AGGCCGCTTC  CTGAGTCAGA  TTCGGGAGAA  GCT....G..  GTCCAGACCA
44_2    ..........  ..........  ..........  ..........  ..........
```

FIG. 10

```
         701                                                      750
  42_2   ..........  ..........  ..........  ..........  ..........
  42_8   ..........  ..........  ..........  ..........  ..........
 42_15   ..........  ..........  ..........  ..........  ..........
 42_5b   ..........  ..........  ..........  ..........  ..........
 42_1b   ..........  ..........  ..........  ..........  ..........
 42_13   ..........  ..........  ..........  ..........  ..........
 42_3a   ..........  ..........  ..........  ..........  ..........
  42_4   ..........  ..........  ..........  ..........  ..........
 42_5a   ..........  ..........  ..........  ..........  ..........
 42_10   ..........  ..........  ..........  ..........  ..........
 42_3b   ..........  ..........  ..........  ..........  ..........
 42_11   ..........  ..........  ..........  ..........  ..........
 42_6b   ..........  ..........  ..........  ..........  ..........
  43_1   ..........  ..........  ..........  ..........  ..........
  43_5   ..........  ..........  ..........  ..........  ..........
 43_12   ..........  ..........  ..........  ..........  ..........
 43_20   ..........  ..........  ..........  ..........  ..........
 43_21   ..........  ..........  ..........  ..........  ..........
 43_23   ..........  ..........  ..........  ..........  ..........
 43_25   ..........  ..........  ..........  ..........  ..........
  44_1   ..........  ..........  ..........  ..........  ..........
  44_5   ..........  ..........  ..........  ..........  ..........
 223_10  ..........  ..........  ..........  ..........  ..........
 223_2   ..........  ..........  ..........  ..........  ..........
 223_4   ..........  ..........  ..........  ..........  ..........
 223_5   ..........  ..........  ..........  ..........  ..........
 223_6   ..........  ..........  ..........  ..........  ..........
 223_7   ..........  ..........  ..........  ..........  ..........
  A3_4   ..........  ..........  ..........  ..........  ..........
  A3_5   ..........  ..........  ..........  ..........  ..........
  A3_7   ..........  ..........  ..........  ..........  ..........
  A3_3   ..........  ..........  ..........  ..........  ..........
 42_12   ..........  ..........  ..........  ..........  ..........
  AAV1   C.GCGGGATC  GAGCCG.ACC  CTGCCCAACT  GGTTCGCGGT  GACCAA.GAC
  AAV2   CCGCGGGATC  GAGCCG.ACT  TTGCCAAACT  GGTTCGCGGT  CACAAA...G
  AAV3   CCGCGGGGTC  GAGCCG.CAG  CTTCCGAACT  GGTTCGCGGT  GACCAA...A
  AAV8   CCGCGGGGTC  GAGCCCACC   TTGCCCAACT  GGTTCGCGGT  GACCAAAGAC
  AAV9   C.GCGGGATC  GAGCCG.ACC  CTGCCCAACT  GGTTCGCGGT  GACCAA.GAC
  AAV7   TCTACCGCGG  GGTCGAGCCC  ACGCTGCCCA  ACTGGTTCGC  GGTGACCAAG
  44_2   ..........  ..........  ..........  ..........  ..........
```

FIG. 1P

```
           751                                                        800
  42_2     ..........  ..........  ..........  ..........  ..........
  42_8     ..........  ..........  ..........  ..........  ..........
  42_15    ..........  ..........  ..........  ..........  ..........
  42_5b    ..........  ..........  ..........  ..........  ..........
  42_1b    ..........  ..........  ..........  ..........  ..........
  42_13    ..........  ..........  ..........  ..........  ..........
  42_3a    ..........  ..........  ..........  ..........  ..........
  42_4     ..........  ..........  ..........  ..........  ..........
  42_5a    ..........  ..........  ..........  ..........  ..........
  42_10    ..........  ..........  ..........  ..........  ..........
  42_3b    ..........  ..........  ..........  ..........  ..........
  42_11    ..........  ..........  ..........  ..........  ..........
  42_6b    ..........  ..........  ..........  ..........  ..........
  43_1     ..........  ..........  ..........  ..........  ..........
  43_5     ..........  ..........  ..........  ..........  ..........
  43_12    ..........  ..........  ..........  ..........  ..........
  43_20    ..........  ..........  ..........  ..........  ..........
  43_21    ..........  ..........  ..........  ..........  ..........
  43_23    ..........  ..........  ..........  ..........  ..........
  43_25    ..........  ..........  ..........  ..........  ..........
  44_1     ..........  ..........  ..........  ..........  ..........
  44_5     ..........  ..........  ..........  ..........  ..........
  223_10   ..........  ..........  ..........  ..........  ..........
  223_2    ..........  ..........  ..........  ..........  ..........
  223_4    ..........  ..........  ..........  ..........  ..........
  223_5    ..........  ..........  ..........  ..........  ..........
  223_6    ..........  ..........  ..........  ..........  ..........
  223_7    ..........  ..........  ..........  ..........  ..........
  A3_4     ..........  ..........  ..........  ..........  ..........
  A3_5     ..........  ..........  ..........  ..........  ..........
  A3_7     ..........  ..........  ..........  ..........  ..........
  A3_3     ..........  ..........  ..........  ..........  ..........
  42_12    ..........  ..........  ..........  ..........  ..........
  AAV1     GCG.TAATGG  CGCCGGAGGG  GGG.AACAAG  GTGGTGGACG  AGTGCTACAT
  AAV2     ACCAGAAATG  GCGCCGGAGG  CGGAACAAG   GTGGTGGATG  AGTGCTACAT
  AAV3     ACGCGAAATG  GCGCCGGGGG  CGGAACAAG   GTGGTGGACG  ACTGCTACAT
  AAV8     GCGGTAATGG  CGCCGGCGGG  GGGAACAAG   GTGGTGGACG  AGTGCTACAT
  AAV9     GCG.TAATGG  CGCCGGCGGG  GGG.AACAAG  GTGGTGGACG  AGTGCTACAT
  AAV7     ACGCGTAATG  GCGCCGGCGG  GGGGAACAAG  GTGGTGGACG  AGTGCTACAT
  44_2     ..........  ..........  ..........  ..........  ..........
```

FIG. 1Q

```
         801                                                                      850
  42_2   .......... .......... .......... .......... ..........
  42_8   .......... .......... .......... .......... ..........
 42_15   .......... .......... .......... .......... ..........
 42_5b   .......... .......... .......... .......... ..........
 42_1b   .......... .......... .......... .......... ..........
 42_13   .......... .......... .......... .......... ..........
 42_3a   .......... .......... .......... .......... ..........
  42_4   .......... .......... .......... .......... ..........
 42_5a   .......... .......... .......... .......... ..........
 42_10   .......... .......... .......... .......... ..........
 42_3b   .......... .......... .......... .......... ..........
 42_11   .......... .......... .......... .......... ..........
 42_6b   .......... .......... .......... .......... ..........
  43_1   .......... .......... .......... .......... ..........
  43_5   .......... .......... .......... .......... ..........
 43_12   .......... .......... .......... .......... ..........
 43_20   .......... .......... .......... .......... ..........
 43_21   .......... .......... .......... .......... ..........
 43_23   .......... .......... .......... .......... ..........
 43_25   .......... .......... .......... .......... ..........
  44_1   .......... .......... .......... .......... ..........
  44_5   .......... .......... .......... .......... ..........
 223_10  .......... .......... .......... .......... ..........
 223_2   .......... .......... .......... .......... ..........
 223_4   .......... .......... .......... .......... ..........
 223_5   .......... .......... .......... .......... ..........
 223_6   .......... .......... .......... .......... ..........
 223_7   .......... .......... .......... .......... ..........
  A3_4   .......... .......... .......... .......... ..........
  A3_5   .......... .......... .......... .......... ..........
  A3_7   .......... .......... .......... .......... ..........
  A3_3   .......... .......... .......... .......... ..........
 42_12   .......... .......... .......... .......... ..........
  AAV1   CCCCAACTAC CTCCTGCCCA AGACTCAGCC CGAGCTGCAG TGGGCGTGGA
  AAV2   CCCCAATTAC TTGCTCCCCA AAACCCAGCC TGAGCTCCAG TGGGCGTGGA
  AAV3   CCCCAACTAC CTGCTCCCCA AGACCCAGCC CGAGCTCCAG TGGGCGTGGA
  AAV8   CCCCAACTAC CTCCTGCCCA AGACTCAGCC CGAGCTGCAG TGGGCGTGGA
  AAV9   CCCCAACTAC CTCCTGCCCA AGACTCAGCC CGAGCTGCAG TGGGCGTGGA
  AAV7   CCCCAACTAC CTCCTGCCCA AGACCCAGCC CGAGCTGCAG TGGGCGTGGA
  44_2   .......... .......... .......... .......... ..........
```

FIG. 1R 851                                                                                                  900

P19/TATA                              P19 RNA

```
42_2     ..........  ..........  ..........  ..........  ..........
42_8     ..........  ..........  ..........  ..........  ..........
42_15    ..........  ..........  ..........  ..........  ..........
42_5b    ..........  ..........  ..........  ..........  ..........
42_1b    ..........  ..........  ..........  ..........  ..........
42_13    ..........  ..........  ..........  ..........  ..........
42_3a    ..........  ..........  ..........  ..........  ..........
42_4     ..........  ..........  ..........  ..........  ..........
42_5a    ..........  ..........  ..........  ..........  ..........
42_10    ..........  ..........  ..........  ..........  ..........
42_3b    ..........  ..........  ..........  ..........  ..........
42_11    ..........  ..........  ..........  ..........  ..........
42_6b    ..........  ..........  ..........  ..........  ..........
43_1     ..........  ..........  ..........  ..........  ..........
43_5     ..........  ..........  ..........  ..........  ..........
43_12    ..........  ..........  ..........  ..........  ..........
43_20    ..........  ..........  ..........  ..........  ..........
43_21    ..........  ..........  ..........  ..........  ..........
43_23    ..........  ..........  ..........  ..........  ..........
43_25    ..........  ..........  ..........  ..........  ..........
44_1     ..........  ..........  ..........  ..........  ..........
44_5     ..........  ..........  ..........  ..........  ..........
223_10   ..........  ..........  ..........  ..........  ..........
223_2    ..........  ..........  ..........  ..........  ..........
223_4    ..........  ..........  ..........  ..........  ..........
223_5    ..........  ..........  ..........  ..........  ..........
223_6    ..........  ..........  ..........  ..........  ..........
223_7    ..........  ..........  ..........  ..........  ..........
A3_4     ..........  ..........  ..........  ..........  ..........
A3_5     ..........  ..........  ..........  ..........  ..........
A3_7     ..........  ..........  ..........  ..........  ..........
A3_3     ..........  ..........  ..........  ..........  ..........
42_12    ..........  ..........  ..........  ..........  ..........
AAV1     CTAACATGGA  GGAGTATATA  AGCGCCTGTT  TGAACCTGGC  CGAGCGCAAA
AAV2     CTAATATGGA  ACAGTATTTA  AGCGCCTGTT  TGAATCTCAC  GGAGCGTAAA
AAV3     CTAACATGGA  CCAGTATTTA  AGCGCCTGTT  TGAATCTCGC  GGAGCGTAAA
AAV8     CTAACATGGA  GGAGTATATA  AGCGCGTGCT  TGAACCTGGC  CGAGCGCAAA
AAV9     CTAACATGGA  GGAGTATATA  AGCGCGTGCT  TGAACCTGGC  CGAGCGCAAA
AAV7     CTAACATGGA  GGAGTATATA  AGCGCGTGTT  TGAACCTGGC  CGAACGCAAA
44_2     ..........  ..........  ..........  ..........  ..........
```

P19/TATA                              P19 RNA

FIG. 1S

```
            901                                                      950
    42_2    ..........  ..........  ..........  ..........  ..........
    42_8    ..........  ..........  ..........  ..........  ..........
   42_15    ..........  ..........  ..........  ..........  ..........
   42_5b    ..........  ..........  ..........  ..........  ..........
   42_1b    ..........  ..........  ..........  ..........  ..........
   42_13    ..........  ..........  ..........  ..........  ..........
   42_3a    ..........  ..........  ..........  ..........  ..........
    42_4    ..........  ..........  ..........  ..........  ..........
   42_5a    ..........  ..........  ..........  ..........  ..........
   42_10    ..........  ..........  ..........  ..........  ..........
   42_3b    ..........  ..........  ..........  ..........  ..........
   42_11    ..........  ..........  ..........  ..........  ..........
   42_6b    ..........  ..........  ..........  ..........  ..........
    43_1    ..........  ..........  ..........  ..........  ..........
    43_5    ..........  ..........  ..........  ..........  ..........
   43_12    ..........  ..........  ..........  ..........  ..........
   43_20    ..........  ..........  ..........  ..........  ..........
   43_21    ..........  ..........  ..........  ..........  ..........
   43_23    ..........  ..........  ..........  ..........  ..........
   43_25    ..........  ..........  ..........  ..........  ..........
    44_1    ..........  ..........  ..........  ..........  ..........
    44_5    ..........  ..........  ..........  ..........  ..........
  223_10    ..........  ..........  ..........  ..........  ..........
   223_2    ..........  ..........  ..........  ..........  ..........
   223_4    ..........  ..........  ..........  ..........  ..........
   223_5    ..........  ..........  ..........  ..........  ..........
   223_6    ..........  ..........  ..........  ..........  ..........
   223_7    ..........  ..........  ..........  ..........  ..........
    A3_4    ..........  ..........  ..........  ..........  ..........
    A3_5    ..........  ..........  ..........  ..........  ..........
    A3_7    ..........  ..........  ..........  ..........  ..........
    A3_3    ..........  ..........  ..........  ..........  ..........
   42_12    ..........  ..........  ..........  ..........  ..........
    AAV1    CGGCTCGTGG  CGCAGCACCT  GACCCACGTC  AGCCAGACCC  AGGAGCAGAA
    AAV2    CGGTTGGTGG  CGCAGCATCT  GACGCACGTG  TCGCAGACGC  AGGAGCAGAA
    AAV3    CGGCTGGTGG  CGCAGCATCT  GACGCACGTG  TCGCAGACGC  AGGAGCAGAA
    AAV8    CGGCTCGTGG  CGCAGCACCT  GACCCACGTC  AGCCAGACGC  AGGAGCAGAA
    AAV9    CGGCTCGTGG  CGCAGCACCT  GACCCACGTC  AGCCAGACGC  AGGAGCAGAA
    AAV7    CGGCTCGTGG  CGCAGCACCT  GACCCACGTC  AGCCAGACGC  AGGAGCAGAA
    44_2    ..........  ..........  ..........  ..........  ..........
```

FIG. 1T

```
              951                                                            1000
    42_2      ..........  ..........  ..........  ..........  ..........
    42_8      ..........  ..........  ..........  ..........  ..........
    42_15     ..........  ..........  ..........  ..........  ..........
    42_5b     ..........  ..........  ..........  ..........  ..........
    42_1b     ..........  ..........  ..........  ..........  ..........
    42_13     ..........  ..........  ..........  ..........  ..........
    42_3a     ..........  ..........  ..........  ..........  ..........
    42_4      ..........  ..........  ..........  ..........  ..........
    42_5a     ..........  ..........  ..........  ..........  ..........
    42_10     ..........  ..........  ..........  ..........  ..........
    42_3b     ..........  ..........  ..........  ..........  ..........
    42_11     ..........  ..........  ..........  ..........  ..........
    42_6b     ..........  ..........  ..........  ..........  ..........
    43_1      ..........  ..........  ..........  ..........  ..........
    43_5      ..........  ..........  ..........  ..........  ..........
    43_12     ..........  ..........  ..........  ..........  ..........
    43_20     ..........  ..........  ..........  ..........  ..........
    43_21     ..........  ..........  ..........  ..........  ..........
    43_23     ..........  ..........  ..........  ..........  ..........
    43_25     ..........  ..........  ..........  ..........  ..........
    44_1      ..........  ..........  ..........  ..........  ..........
    44_5      ..........  ..........  ..........  ..........  ..........
   223_10     ..........  ..........  ..........  ..........  ..........
   223_2      ..........  ..........  ..........  ..........  ..........
   223_4      ..........  ..........  ..........  ..........  ..........
   223_5      ..........  ..........  ..........  ..........  ..........
   223_6      ..........  ..........  ..........  ..........  ..........
   223_7      ..........  ..........  ..........  ..........  ..........
    A3_4      ..........  ..........  ..........  ..........  ..........
    A3_5      ..........  ..........  ..........  ..........  ..........
    A3_7      ..........  ..........  ..........  ..........  ..........
    A3_3      ..........  ..........  ..........  ..........  ..........
    42_12     ..........  ..........  ..........  ..........  ..........
    AAV1      CAAGGAGAAT  CTGAACCCCA  ATTCTGACGC  GCCTGTCATC  CGGTCAAAAA
    AAV2      CAAAGAGAAT  CAGAATCCCA  ATTCTGATGC  GCCGGTGATC  AGATCAAAAA
    AAV3      CAAAGAGAAT  CAGAACCCCA  ATTCTGACGC  GCCGGTCATC  AGGTCAAAAA
    AAV8      CAAGGAGAAT  CTGAACCCCA  ATTCTGACGC  GCCCGTGATC  AGGTCAAAAA
    AAV9      CAAGGAGAAT  CTGAACCCCA  ATTCTGACGC  GCCGTGATC   AGGTCAAAAA
    AAV7      CAAGGAGAAT  CTGAACCCCA  ATTCTGACGC  GCCCGTGATC  AGGTCAAAAA
    44_2      ..........  ..........  ..........  ..........  ..........
```

FIG. 1U

```
                                 1001                                                                         1050
                                      Rep52/40 start codon
                                                  ↓  ↓
    42_2       ..........  ..........  ..........  ..........  ..........
    42_8       ..........  ..........  ..........  ..........  ..........
    42_15      ..........  ..........  ..........  ..........  ..........
    42_5b      ..........  ..........  ..........  ..........  ..........
    42_1b      ..........  ..........  ..........  ..........  ..........
    42_13      ..........  ..........  ..........  ..........  ..........
    42_3a      ..........  ..........  ..........  ..........  ..........
    42_4       ..........  ..........  ..........  ..........  ..........
    42_5a      ..........  ..........  ..........  ..........  ..........
    42_10      ..........  ..........  ..........  ..........  ..........
    42_3b      ..........  ..........  ..........  ..........  ..........
    42_11      ..........  ..........  ..........  ..........  ..........
    42_6b      ..........  ..........  ..........  ..........  ..........
    43_1       ..........  ..........  ..........  ..........  ..........
    43_5       ..........  ..........  ..........  ..........  ..........
    43_12      ..........  ..........  ..........  ..........  ..........
    43_20      ..........  ..........  ..........  ..........  ..........
    43_21      ..........  ..........  ..........  ..........  ..........
    43_23      ..........  ..........  ..........  ..........  ..........
    43_25      ..........  ..........  ..........  ..........  ..........
    44_1       ..........  ..........  ..........  ..........  ..........
    44_5       ..........  ..........  ..........  ..........  ..........
    223_10     ..........  ..........  ..........  ..........  ..........
    223_2      ..........  ..........  ..........  ..........  ..........
    223_4      ..........  ..........  ..........  ..........  ..........
    223_5      ..........  ..........  ..........  ..........  ..........
    223_6      ..........  ..........  ..........  ..........  ..........
    223_7      ..........  ..........  ..........  ..........  ..........
    A3_4       ..........  ..........  ..........  ..........  ..........
    A3_5       ..........  ..........  ..........  ..........  ..........
    A3_7       ..........  ..........  ..........  ..........  ..........
    A3_3       ..........  ..........  ..........  ..........  ..........
    42_12      ..........  ..........  ..........  ..........  ..........
    AAV1       CCTCCGCGCG  CTACATGGAG  CTGGTCGGGT  GGCTGGTGGA  CCGGGGCATC
    AAV2       CTTCAGCCAG  GTACATGGAG  CTGGTCGGGT  GGCTCGTGGA  CAAGGGGATT
    AAV3       CCTCAGCCAG  GTACATGGAG  CTGGTCGGGT  GGCTGGTGGA  CCGCGGGATC
    AAV6       CCTCCGCGCG  CTATATGGAG  CTGGTCGGGT  GGCTGGTGGA  CCGGGGCATC
    AAV9       CCTCCGCGCG  CTACATGGAG  CTGGTCGGGT  GGCTGGTGGA  CCGGGGCATC
    AAV7       CCTCCGCGCG  CTACATGGAG  CTGGTCGGGT  GGCTGGTGGA  CCGGGGCATC
    44_2       ..........  ..........  ..........  ..........  ..........
                                 ↑  ↑
                              Rep 52/40 start
```

FIG. 1V

```
              1051                                                      1100
   42_2       ..........  ..........  ..........  ..........  ..........
   42_8       ..........  ..........  ..........  ..........  ..........
   42_15      ..........  ..........  ..........  ..........  ..........
   42_5b      ..........  ..........  ..........  ..........  ..........
   42_1b      ..........  ..........  ..........  ..........  ..........
   42_13      ..........  ..........  ..........  ..........  ..........
   42_3a      ..........  ..........  ..........  ..........  ..........
   42_4       ..........  ..........  ..........  ..........  ..........
   42_5a      ..........  ..........  ..........  ..........  ..........
   42_10      ..........  ..........  ..........  ..........  ..........
   42_3b      ..........  ..........  ..........  ..........  ..........
   42_11      ..........  ..........  ..........  ..........  ..........
   42_6b      ..........  ..........  ..........  ..........  ..........
   43_1       ..........  ..........  ..........  ..........  ..........
   43_5       ..........  ..........  ..........  ..........  ..........
   43_12      ..........  ..........  ..........  ..........  ..........
   43_20      ..........  ..........  ..........  ..........  ..........
   43_21      ..........  ..........  ..........  ..........  ..........
   43_23      ..........  ..........  ..........  ..........  ..........
   43_25      ..........  ..........  ..........  ..........  ..........
   44_1       ..........  ..........  ..........  ..........  ..........
   44_5       ..........  ..........  ..........  ..........  ..........
  223_10      ..........  ..........  ..........  ..........  ..........
  223_2       ..........  ..........  ..........  ..........  ..........
  223_4       ..........  ..........  ..........  ..........  ..........
  223_5       ..........  ..........  ..........  ..........  ..........
  223_6       ..........  ..........  ..........  ..........  ..........
  223_7       ..........  ..........  ..........  ..........  ..........
   A3_4       ..........  ..........  ..........  ..........  ..........
   A3_5       ..........  ..........  ..........  ..........  ..........
   A3_7       ..........  ..........  ..........  ..........  ..........
   A3_3       ..........  ..........  ..........  ..........  ..........
   42_12      ..........  ..........  ..........  ..........  ..........
   AAV1       ACCTCCGAGA  AGCAGTGGAT  CCAGGAGGAC  CAGGCCTCGT  ACATCTCCTT
   AAV2       ACCTCGGAGA  AGCAGTGGAT  CCAGGAGGAC  CAGGCCTCAT  ACATCTCCTT
   AAV3       ACGTCAGAAA  AGCAATGGAT  TCAGGAGGAC  CAGGCCTCGT  ACATCTCCTT
   AAV8       ACCTCCGAGA  AGCAGTGGAT  CCAGGAGGAC  CAGGCCTCGT  ACATCTCCTT
   AAV9       ACCTCCGAGA  AGCAGTGGAT  CCAGGAGGAC  CAGGCCTCGT  ACATCTCCTT
   AAV7       ACCTCCGAGA  AGCAGTGGAT  CCAGGAGGAC  CAGGCCTCGT  ACATCTCCTT
   44_2       ..........  ..........  ..........  ..........  ..........
```

FIG. 1W

```
          1101                                                              1150
  42_2    ..........  ..........  ..........  ..........  ..........
  42_8    ..........  ..........  ..........  ..........  ..........
  42_15   ..........  ..........  ..........  ..........  ..........
  42_5b   ..........  ..........  ..........  ..........  ..........
  42_1b   ..........  ..........  ..........  ..........  ..........
  42_13   ..........  ..........  ..........  ..........  ..........
  42_3a   ..........  ..........  ..........  ..........  ..........
  42_4    ..........  ..........  ..........  ..........  ..........
  42_5a   ..........  ..........  ..........  ..........  ..........
  42_10   ..........  ..........  ..........  ..........  ..........
  42_3b   ..........  ..........  ..........  ..........  ..........
  42_11   ..........  ..........  ..........  ..........  ..........
  42_6b   ..........  ..........  ..........  ..........  ..........
  43_1    ..........  ..........  ..........  ..........  ..........
  43_5    ..........  ..........  ..........  ..........  ..........
  43_12   ..........  ..........  ..........  ..........  ..........
  43_20   ..........  ..........  ..........  ..........  ..........
  43_21   ..........  ..........  ..........  ..........  ..........
  43_23   ..........  ..........  ..........  ..........  ..........
  43_25   ..........  ..........  ..........  ..........  ..........
  44_1    ..........  ..........  ..........  ..........  ..........
  44_5    ..........  ..........  ..........  ..........  ..........
  223_10  ..........  ..........  ..........  ..........  ..........
  223_2   ..........  ..........  ..........  ..........  ..........
  223_4   ..........  ..........  ..........  ..........  ..........
  223_5   ..........  ..........  ..........  ..........  ..........
  223_6   ..........  ..........  ..........  ..........  ..........
  223_7   ..........  ..........  ..........  ..........  ..........
  A3_4    ..........  ..........  ..........  ..........  ..........
  A3_5    ..........  ..........  ..........  ..........  ..........
  A3_7    ..........  ..........  ..........  ..........  ..........
  A3_3    ..........  ..........  ..........  ..........  ..........
  42_12   ..........  ..........  ..........  ..........  ..........
  AAV1    CAACGCCGCT  TCCAACTCGC  GGTCCCAGAT  CAAGGCCGCT  CTGGACAATG
  AAV2    CAATGCGGCC  TCCAACTCGC  GGTCCCAAAT  CAAGGCTGCC  TTGGACAATG
  AAV3    CAACGCCGCC  TCCAACTCGC  GGTCCCAGAT  CAAGGCCGCG  CTGGACAATG
  AAV8    CAACGCCGCC  TCCAACTCGC  GGTCCCAGAT  CAAGGCCGCG  CTGGACAATG
  AAV9    CAACGCCGCC  TCCAACTCGC  GGTCCCAGAT  CAAGGCCGCG  CTGGACAATG
  AAV7    CAACGCCGCC  TCCAACTCGC  GGTCCCAGAT  CAAGGCCGCG  CTGGACAATG
  44_2    ..........  ..........  ..........  ..........  ..........
```

FIG. 1X

```
         1151                                                              1200
  42_2   .......... .......... .......... .......... ..........
  42_8   .......... .......... .......... .......... ..........
  42_15  .......... .......... .......... .......... ..........
  42_5b  .......... .......... .......... .......... ..........
  42_1b  .......... .......... .......... .......... ..........
  42_13  .......... .......... .......... .......... ..........
  42_3a  .......... .......... .......... .......... ..........
  42_4   .......... .......... .......... .......... ..........
  42_5a  .......... .......... .......... .......... ..........
  42_10  .......... .......... .......... .......... ..........
  42_3b  .......... .......... .......... .......... ..........
  42_11  .......... .......... .......... .......... ..........
  42_6b  .......... .......... .......... .......... ..........
  43_1   .......... .......... .......... .......... ..........
  43_5   .......... .......... .......... .......... ..........
  43_12  .......... .......... .......... .......... ..........
  43_20  .......... .......... .......... .......... ..........
  43_21  .......... .......... .......... .......... ..........
  43_23  .......... .......... .......... .......... ..........
  43_25  .......... .......... .......... .......... ..........
  44_1   .......... .......... .......... .......... ..........
  44_5   .......... .......... .......... .......... ..........
 223_10  .......... .......... .......... .......... ..........
 223_2   .......... .......... .......... .......... ..........
 223_4   .......... .......... .......... .......... ..........
 223_5   .......... .......... .......... .......... ..........
 223_6   .......... .......... .......... .......... ..........
 223_7   .......... .......... .......... .......... ..........
  A3_4   .......... .......... .......... .......... ..........
  A3_5   .......... .......... .......... .......... ..........
  A3_7   .......... .......... .......... .......... ..........
  A3_3   .......... .......... .......... .......... ..........
  42_12  .......... .......... .......... .......... ..........
  AAV1   CCGGCAAGAT CATGGCGCTG ACCAAATCCG CGCCCGACTA CCTGGTAGGC
  AAV2   CGGGAAAGAT TATGAGCCTG ACTAAAACCG CCCCCGACTA CCTGGTGGGC
  AAV3   CCTCCAAGAT CATGAGCCTG ACAAAGACGG CTCCGGACTA CCTGGTGGGC
  AAV8   CCGGCAAGAT CATGGCGCTG ACCAAATCCG CGCCCGACTA CCTGGTGGGG
  AAV9   CCGGCAAGAT CATGGCGCTG ACCAAATCCG CGCCCGACTA CCTGGTAGGC
  AAV7   CCGGCAAGAT CATGGCGCTG ACCAAATCCG CGCCCGACTA CCTGGTGGGG
  44_2   .......... .......... .......... .......... ..........
```

FIG 1Y

```
              1201                                                                              1250
    42_2      ..........  ..........  ..........  ..........  ..........
    42_8      ..........  ..........  ..........  ..........  ..........
   42_15      ..........  ..........  ..........  ..........  ..........
   42_5b      ..........  ..........  ..........  ..........  ..........
   42_1b      ..........  ..........  ..........  ..........  ..........
   42_13      ..........  ..........  ..........  ..........  ..........
   42_3a      ..........  ..........  ..........  ..........  ..........
    42_4      ..........  ..........  ..........  ..........  ..........
   42_5a      ..........  ..........  ..........  ..........  ..........
   42_10      ..........  ..........  ..........  ..........  ..........
   42_3b      ..........  ..........  ..........  ..........  ..........
   42_11      ..........  ..........  ..........  ..........  ..........
   42_6b      ..........  ..........  ........GA  ATTCGCCCTT  TCTACGGCTG
    43_1      ..........  ..........  ..........  ..........  ..........
    43_5      ..........  ..........  ..........  ..........  ..........
   43_12      ..........  ..........  ..........  ..........  ..........
   43_20      ..........  ..........  ..........  ..........  ..........
   43_21      ..........  ..........  ..........  ..........  ..........
   43_23      ..........  ..........  ..........  ..........  ..........
   43_25      ..........  ..........  ..........  ..........  ..........
    44_1      ..........  ..........  ..........  ..........  ..........
    44_5      ..........  ..........  ..........  ..........  ..........
  223_10      ..........  ..........  ..........  ..........  ..........
   223_2      ..........  ..........  ..........  ..........  ..........
   223_4      ..........  ..........  ..........  ..........  ..........
   223_5      ..........  ..........  ..........  ..........  ..........
   223_6      ..........  ..........  ..........  ..........  ..........
   223_7      ..........  ..........  ..........  ..........  ..........
    A3_4      ..........  ..........  ..........  ..........  ..........
    A3_5      ..........  ..........  ..........  ..........  ..........
    A3_7      ..........  ..........  ..........  ..........  ..........
    A3_3      ..........  ..........  ..........  ..........  ..........
   42_12      ..........  ..........  ..........  ..........  ..........
    AAV1      CCCGCTCCGC  CCGCGGACAT  TAAAACCAAC  CGCATCTACC  GCATCCTGGA
    AAV2      CAGCAGCCCG  TGGAGGACAT  TTCCAGCAAT  CGGATTTATA  AAATTTTGGA
    AAV3      AGCAACCCGC  CGGAGGACAT  TACCAAAAAT  CGGATCTACC  AAATCCTGGA
    AAV8      CCCTCGCTGC  CCGCGGACAT  TACCCAGAAC  CGCATCTACC  GCATCCTCGC
    AAV9      CCTTCACTTC  CGGTGGACAT  TACGCAGAAC  CGCATCTACC  GCATCCTGCA
    AAV7      CCCTCGCTGC  CCGCGGACAT  TAAAACCAAC  CGCATCTACC  GCATCCTGGA
    44_2      ..........  ..........  ..........  ..........  ..........
```

FIG. 1Z

```
            1251                                                           1300
 42_2       ..........  ..........  ..........  ..........  ..........
 42_8       ..........  ..........  ..........  ..........  ..........
 42_15      ..........  ..........  ..........  ..........  ..........
 42_5b      ..........  ..........  ..........  ..........  ..........
 42_1b      ..........  ..........  ..........  ..........  ..........
 42_13      ..........  ..........  ..........  ..........  ..........
 42_3a      ..........  ..........  ..........  ..........  ..........
 42_4       ..........  ..........  ..........  ..........  ..........
 42_5a      ..........  ..........  ..........  ..........  ..........
 42_10      ..........  ..........  ..........  ..........  ..........
 42_3b      ..........  ..........  ..........  ..........  ..........
 42_11      ..........  ..........  ..........  ..........  ..........
 42_6b      CGTCAACTGG  ACCAATGAGA  ACTTTCCCTT  CAACGATTGC  GTCGACAAGA
 43_1       ..........  ..........  ..........  ..........  ..........
 43_5       ..........  ..........  ..........  ..........  ..........
 43_12      ..........  ..........  ..........  ..........  ..........
 43_20      ..........  ..........  ..........  ..........  ..........
 43_21      ..........  ..........  ..........  ..........  ..........
 43_23      ..........  ..........  ..........  ..........  ..........
 43_25      ..........  ..........  ..........  ..........  ..........
 44_1       ..........  ..........  ..........  ..........  ..........
 44_5       ..........  ..........  ..........  ..........  ..........
223_10      ..........  ..........  ..........  ..........  ..........
223_2       ..........  ..........  ..........  ..........  ..........
223_4       ..........  ..........  ..........  ..........  ..........
223_5       ..........  ..........  ..........  ..........  ..........
223_6       ..........  ..........  ..........  ..........  ..........
223_7       ..........  ..........  ..........  ..........  ..........
 A3_4       ..........  ..........  ..........  ..........  ..........
 A3_5       ..........  ..........  ..........  ..........  ..........
 A3_7       ..........  ..........  ..........  ..........  ..........
 A3_3       ..........  ..........  ..........  ..........  ..........
 42_12      ..........  ..........  ..........  ..........  ..........
 AAV1       GCTGAACGGC  TACGAACCTG  CCTACGCCGG  CTCCGTCTTT  CTCGGCTGGG
 AAV2       ACTAAACGGG  TACGATCCCC  AATATGCGGC  TTCCGTCTTT  CTGGGATGGG
 AAV3       GCTGAACGGG  TACGATCCGC  AGTACGCGGC  CTCCGTCTTC  CTGGGCTGGG
 AAV8       TCTCAACGGC  TACGACCCTG  CCTACGCCGG  CTCCGTCTTT  CTCGGCTGGG
 AAV9       GCTCAACGGC  TACGACCCTG  CCTACGCCGG  CTCCGTCTTT  CTCGGCTGGG
 AAV7       GCTGAACGGG  TACGATCCTG  CCTACGCCGG  CTCCGTCTTT  CTCGGCTGGG
 44_2       ..........  ..........  ..........  ..........  ..........
```

FIG. 1AA

```
          1301                                                          1350
   42_2   ..........  ..........  ..........  ..........  ..........
   42_8   ..........  ..........  ..........  ..........  ..........
  42_15   ..........  ..........  ..........  ..........  ..........
  42_5b   ..........  ..........  ..........  ..........  ..........
  42_1b   ..........  ..........  ..........  ..........  ..........
  42_13   ..........  ..........  ..........  ..........  ..........
  42_3a   ..........  ..........  ..........  ..........  ..........
   42_4   ..........  ..........  ..........  ..........  ..........
  42_5a   ..........  ..........  ..........  ..........  ..........
  42_10   ..........  ..........  ..........  ..........  ..........
  42_3b   ..........  ..........  ..........  ..........  ..........
  42_11   ..........  ..........  ..........  ..........  ..........
  42_6b   TGGTGATCTG  GTGGGAGGAG  GGCAAGATGA  CGGCCAAGGT  CGTGGAGTCC
   43_1   ..........  ..........  ..........  ..........  ..........
   43_5   ..........  ..........  ..........  ..........  ..........
  43_12   ..........  ..........  ..........  ..........  ..........
  43_20   ..........  ..........  ..........  ..........  ..........
  43_21   ..........  ..........  ..........  ..........  ..........
  43_23   ..........  ..........  ..........  ..........  ..........
  43_25   ..........  ..........  ..........  ..........  ..........
   44_1   ..........  ..........  ..........  ..........  ..........
   44_5   ..........  ..........  ..........  ..........  ..........
 223_10   ..........  ..........  ..........  ..........  ..........
  223_2   ..........  ..........  ..........  ..........  ..........
  223_4   ..........  ..........  ..........  ..........  ..........
  223_5   ..........  ..........  ..........  ..........  ..........
  223_6   ..........  ..........  ..........  ..........  ..........
  223_7   ..........  ..........  ..........  ..........  ..........
   A3_4   ..........  ..........  ..........  ..........  ..........
   A3_5   ..........  ..........  ..........  ..........  ..........
   A3_7   ..........  ..........  ..........  ..........  ..........
   A3_3   ..........  ..........  ..........  ..........  ..........
  42_12   ..........  ..........  ..........  ..........  ..........
   AAV1   CCCAGAAAAG  GTTCGGGAAG  CGCAACACCA  TCTGGCTGTT  TGGGCCGGCC
   AAV2   CCACGAAAAA  GTTCGGCAAG  AGGAACACCA  TCTGGCTGTT  TGGGCCTGCA
   AAV3   CGCAAAAGAA  GTTCGGGAAG  AGGAACACCA  TCTGGCTCTT  TGGGCCGGCC
   AAV8   CTCAGAAAAA  GTTCGGGAAA  CGCAACACCA  TCTGGCTGTT  TGGACCCGCC
   AAV9   CACAAAAGAA  GTTCGGGAAA  CGCAACACCA  TCTGGCTGTT  TGGGCCGGCC
   AAV7   CCCAGAAAAA  GTTCGGGAAG  CGCAACACCA  TCTGGCTGTT  TGGGCCCGCC
   44_2   ..........  ..........  ..........  ..........  ..........
```

42_2      ..........  ..........  ..........  .......GAA  TTCGCCCTTT
    42_8      ..........  ..........  ..........  .......GAA  TTCGCCCTTT
    42_15     ..........  ..........  ..........  .......GAA  TTCGCCCTTT
    42_5b     ..........  ..........  ..........  .......GAA  TTCGCCCTTT
    42_1b     ..........  ..........  ..........  ..........  ..........
    42_13     ..........  ..........  ..........  .......GAA  TTCGCCCTTT
    42_3a     ..........  ..........  ..........  .......GAA  TTCGCCCTTT
    42_4      ..........  ..........  ..........  ..........  ..........
    42_5a     ..........  ..........  ..........  ........GA  ATTCGCCCTT
    42_10     ..........  ..........  ..........  ..........  ..........
    42_3b     ..........  ..........  ..........  ..........  ..........
    42_11     ..........  ..........  ..........  .......GAA  TTCGCCCTTT
    42_6b     GCCAAGGCCA  TTCTCGGCGG  CAGCAAGGTG  CGCGTGGACC  AAAAGTGCAA
    43_1      ..........  ..........  ..........  .......GAA  TTCGCCCTTT
    43_5      ..........  ..........  ..........  .......GAA  TTCGCCCTTT
    43_12     ..........  ..........  ..........  .......GAA  TTCGCCCTT.
    43_20     ..........  ..........  ..........  .......GAA  TTCGCCCTTT
    43_21     ..........  ..........  ..........  .......GAA  TTCGCCCTT.
    43_23     ..........  ..........  ..........  .......GAA  TTCGCCCTT.
    43_25     ..........  ..........  ..........  .......GAA  TTCGCCCTTT
    44_1      ..........  ..........  ..........  .......GAA  TTCGCCCTTT
    44_5      ..........  ..........  ..........  .......GAA  TTCGCCCTTT
    223_10    ..........  ..........  ..........  ..........  ..........
    223_2     ..........  ..........  ..........  ..........  ..........
    223_4     ..........  ..........  ..........  ..........  ..........
    223_5     ..........  ..........  ..........  ..........  ..........
    223_6     ..........  ..........  ..........  ..........  ..........
    223_7     ..........  ..........  ..........  ..........  ..........
    A3_4      ..........  ..........  ..........  ........GA  ATTCGCCCTT
    A3_5      ..........  ..........  ..........  ........GA  ATTCGCCCTT
    A3_7      ..........  ..........  ..........  .......A    GCGGCCGCGA  ATTCGCCCTT
    A3_3      ..........  ..........  ..........  ........GA  ATTCGCCCTT
    42_12     ..........  ..........  ..........  .......GAA  TTCGCCCTTT
    AAV1      ACCACGGGCA  AGACCAACAT  CGCGGAAGCC  ATCGCCCACG  CCGTGCCCTT
    AAV2      ACTACCGGGA  AGACCAACAT  CGCGGAGGCC  ATAGCCCACA  CTGTGCCCTT
    AAV3      ACGACGGGTA  AAACCAACAT  CGCGGAAGCC  ATCGCCCACG  CCGTGCCCTT
    AAV8      ACCACCGGCA  AGACCAACAT  TGCGGAAGCC  ATCGCCCACG  CCGTGCCCTT
    AAV9      ACCACGGGAA  AGACCAACAT  CGCAGAAGCC  ATTGCCCACG  CCGTGCCCTT
    AAV7      ACCACCGGCA  AGACCAACAT  TGCGGAAGCC  ATCGCCCACG  CCGTGCCCTT
    44_2      ..........  ..........  ..........  ........GA  ATTCGCCCTT
```

FIG. 1AC

```
            1401                                                      1450
    42_2    .CTACGGCTG CGTCAACTGG ACCAATGAGA ACTTTCCCTT CAACGATTGC
    42_6    .CTACGGCTG CGTCAACTGG ACCAATGAGA ACTTTCCCTT CAACGATTGC
   42_15    .CTACGGCTG CGTCAACTGG ACCAATGAGA ACTTTCCCTT CAACGATTGC
   42_5b    .CTACGGCTG CGTCAACTGG ACCAATGAGA ACTTTCCCTT CAACGATTGC
   42_1b    .......... .......... .......... .......... ..........
   42_13    .CTACGGCTG CGTCAACTGG ACCAATGAGA ACTTTCCCTT CAACGATTGC
   42_3a    .CTACGGCTG CGTCAACTGG ACCAATGAGA ACTTTCCCTT CAACGATTGC
    42_4    .......... .......... .......... .......... ..........
   42_5a    .CTACGGCTG CGTCAACTGG ACCAATGAGA ACTTTCCCTT CAACGATTGC
   42_10    .......... .......... .......... .......... ..........
   42_3b    .......... .......... .......... .......... ..........
   42_11    .CTACGGCTG CGTCAACTGG ACCAATGAGA ACTTTCCCTT CAACGATTGC
   42_6b    .GTCTTCCGC CCAGATCGAT CCCACCCCCG TGATCGTCAC TTCCAACACC
    43_1    .CTACGGCTG CATCAACTGG ACCAATGAGA ACTTTCCCTT CAACGATTGC
    43_5    .CTACGGCTG CGTCAACTGG ACCAATGAGA ACTTTCCCTT CAACGATTGC
   43_12    .....GGCTG CGTCAACTGG ACCAATGAGA ACTTTCCCTT CAACGATTGC
   43_20    .CTACGGCTG CGTCAACTGG ACCAATGAGA ACTTTCCCTT CAACGATTGC
   43_21    .....GGCTG CGTCAACTGG ACCAATGAGA ACTTTCCCTT CAACGATTGC
   43_23    .CTACGGCTG CGTCAACTGG ACCAATGAGA ACTTTCCCTT CAACGATTGC
   43_25    .CTACGGCTG CGTCAACTGG ACCAATGAGA ACTTTCCCTT CAACGATTGC
    44_1    .CTACGGCTG CGTCAACTGG ACCAATGAGA ACTTTCCCTT CAACGATTGC
    44_5    .CTACGGCTG CGTCAACTGG ACCAATGAGA ACTTTCCCTT CAACGATTGC
   223_10   .......... .......... .......... .......... ..........
   223_2    .......... .......... .......... .......... ..........
   223_4    .......... .......... .......... .......... ..........
   223_5    .......... .......... .......... .......... ..........
   223_6    .......... .......... .......... .......... ..........
   223_7    .......... .......... .......... .......... ..........
    A3_4    TCTACGGCTG CGTCAACTGG ACCAATGAAA ACTTTCCCTT CAACGATTGC
    A3_5    TCTACGGCTG CGTCAACTGG ACCAATGAAA ACTTTCCCTT CAACGATTGC
    A3_7    TCTACGGCTG CGTCAACTGG ACCAATGAAA ACTTTCCCTT CAACGATTGC
    A3_3    TCTACGGCTG CGTCAACTGG ACCAATGAAA ACTTTCCCTT CAACGATTGC
   42_12    .CTACGGCTG CGTCAACTGG ACCAATGAGA ACTTTCCCTT CAACGATTGC
    AAV1    .CTACGGCTG CGTCAACTGG ACCAATGAGA ACTTTCCCTT CAATGATTGC
    AAV2    .CTACGGGTG CGTAAACTGG ACCAATGAGA ACTTTCCCTT CAACGACTGT
    AAV3    .CTACGGCTG CGTAAACTGG ACCAATGAGA ACTTTCCCTT CAACGATTGC
    AAV8    .CTACGGCTG CGTCAACTGG ACCAATGAGA ACTTTCCCTT CAATGATTGC
    AAV9    .CTACGGCTG CGTCAACTGG ACCAATGAGA ACTTTCCCTT CAACGATTGC
    AAV7    .CTACGGCTG CGTCAACTGG ACCAATGAGA ACTTTCCCTT CAACGATTGC
    44_2    TCTACGGCTG CGTCAACTGG ACCAATGAGA ACTTTCCCTT CAACGATTGC
```

FIG. 1AD

```
       1451                                                    1500
 42_2  GTCGACAAGA TGGTGATCTG GTGGGAGGAG GGCAAGATGA CGGCCAAGGT
 42_8  GTCGACAAGA TGGTGATCTG GTGGGAGGAG GGCAAGATGA CGGCCAAGGT
42_15  GTCGACAAGA TGGTGATCTG GTGGGAGGAG GGCAAGATGA CGGCCAAGGT
42_5b  GTCGACAAGA TGGTGATCTG GTGGGAGGAG GGCAAGATGA CGGCCAAGGT
42_1b  .......... .......... .......... .......... ..........
42_13  GTCGACAAGA TGGTGATCTG GTGGGAGGAG GGCAAGATGA CGGCCAAGGT
42_3a  GTCGACAAGA TGGTGATCTG GTGGGAGGAG GGCAAGATGA CGGCCAAGGT
 42_4  .......... .......... .......... .......... ..........
42_5a  GTCGACAAGA TGGTGATCTG GTGGGAGGAG GGCAAGATGA CGGCCAAGGT
42_10  .......... .......... .......... .......... ..........
42_3b  .......... .......... .......... .......... ..........
42_11  GTCGACAAGA TGGTGATCTG GTGGGAGGAG GGCAAGATGA CGGCCAAGGT
42_6b  AACATGTGCG CCGTGATTGA CGGGAACAGC ACCACCTTCG AGCACCAGCA
 43_1  GTCGACAAGA TGGTGATCTG GTGGGAGGAG GGCAAGATGA CGGCCAAGGT
 43_5  GTCGACAAGA TGGTGATCTG GTGGGAGGAG GGCAACATGA CGGCCAAGGT
43_12  GTCGACAAGA TGGTGATCTG GTGGGAGGAG GGCAAGATGA CGGCCAAGGT
43_20  GTCGACAAGA TGGTGATCTG GTGGGAGGAG GGCAAGATGA CGGCCAAGGT
43_21  GTCGACAAGA TGGTGATCTG GTGGGAGGAG GGCAAGATGA CGGCCAAGGT
43_23  GTCGACAAGA TGGTGATCTG GTGGGAGGAG GGCAAGATGA CGGCCAAGGT
43_25  GTCGACAAGA TGGTGATCTG GTGGGAGGAG GGCAAGATGA CGGCCAAGGT
 44_1  GTCGACAAGA TGTTGATCTG GTGGGAGGAG GGCAAGATGA CGGCCAAGGT
 44_5  GTCGACAAGA TGGTGATCTG GTGGGAGGAG GGCAAGATGA CGGCCAAGGT
223_10 .......... .......... .......... .......... ..........
223_2  .......... .......... .......... .......... ..........
223_4  .......... .......... .......... .......... ..........
223_5  .......... .......... .......... .......... ..........
223_6  .......... .......... .......... .......... ..........
223_7  .......... .......... .......... .......... ..........
 A3_4  GTCGACAAGA TGGTGATCTG GTGGGAGGAG GGAAAGATGA CCGCCAAGGT
 A3_5  GTCGACAAGA TGGTGATCTG GTGGGAGGAG GGAAAGATGA CCGCCAAGGT
 A3_7  GTCGACAAGA TGGTGATCTG GTGGGAGGAG GGAAAGATGA CCGCCAAGGT
 A3_3  GTCGACAAGA TGGTGATCTG GTGGGAGGAG GGAAAGATGA CCGCCAAGGT
42_12  GTCGACAAGA TGGTGATCTG GTGGGAGGAG GGCAAGATGA CGGCCAAGGT
 AAV1  GTCGACAAGA TGGTGATCTG GTGGGAGGAG GGCAAGATGA CGGCCAAGGT
 AAV2  GTCGACAAGA TGGTGATCTG GTGGGAGGAG GGGAAGATGA CCGCCAAGGT
 AAV3  GTCGACAAGA TGGTGATCTG GTGGGAGGAG GGCAAGATGA CGGCCAAGGT
 AAV8  GTCGACAAGA TGGTGATCTG GTGGGAGGAG GGCAAGATGA CGGCCAAGGT
 AAV9  GTCGACAAGA TGGTGATCTG GTGGGAGGAG GGCAAGATGA CGGCCAAGGT
 AAV7  GTCGACAAGA TGGTGATCTG GTGGGAGGAG GGCAAGATGA CGGCCAAGGT
 44_2  GTCGACAAGA TGGTGATCTG GTGGGAGGAG GGCAAGATGA CGGCCAAGGT
```

FIG. 1AE

```
           1501                                                        1550
   42_2    CGTGGAGTCC GCCAAGGCCA TTCTCGGCGG CAGCAAGGTG CGCGTGGACC
   42_8    CGTGGAGTCC GCCAAGGCCA TTCTCGGCGG CAGCAAGGTG CGCGTGGACC
  42_15    CGTGGAGTCC GCCAAGGCCA TTCTCGGCGG CAGCAAGGTG CGCGTGGACC
  42_5b    CGTGGAGTCC GCCAAGGCCA TTCTCGGCGG CAGCAAGGTG CGCGTGGACC
  42_1b    .......... .......... .......... .......... ..........
  42_13    CGTGGAGTCC GCCAAGGCCA TTCTCGGCGG CAGCAAGGTG CGCGTGGACC
  42_3a    CGTGGAGTCC GCCAAGGCCA TTCTCGGCGG CAGCAAGGTG CGCGTGGACC
   42_4    .......... .......... .......... .......... ..........
  42_5a    CGTGGAGTCC GCCAAGGCCA TTCTCGGCGG CAGCAAGGTG CGCGTGGACC
  42_10    .......... .......... .......... .......... ..........
  42_3b    .......... .......... .......... .......... ..........
  42_11    CGTGGAGTCC GCCAAGGCCA TTCTCGGCGG CAGCAAGGTG CGCGTGGACC
  42_6b    GCCGTTGCAG GACCGGATGT TCAAATTTGA ACTCACCCGC CGTCTGGAGC
   43_1    CGTGGAGTCC GCCAAGGCCA TTCTCGGCGG CAGCAAGGTG CGCGTGGACC
   43_5    CGTGGAGTCC GCCAAGGCCA TTCTCGGCGG CAGCAAGGTG CGCGTGGACC
  43_12    CGTGGAGTCC GCCAAGGCCA TTCTCGGCGG CAGCAAGGTG CGCGTGGACC
  43_20    CGTGGAGTCC GCCAAGGCCA TTCTCGGCGG CAGCAAGGTG CGTGTGGACC
  43_21    CGTGGAGTCC GCCAAGGCCA TTCTCGGCGG CAGCAAGGTG CGTGTGGACC
  43_23    CGTGGAGTCC GCCAAGGCCA TTCTCGGCGG CAGCAAGGTG CGTGTGGACC
  43_25    CGTGGAGTCC GCCAAGGCCA TTCTCGGCGG CAGCAAGGTG CGTGTGGACC
   44_1    CGTGGAGTCC GCCAAGGCCA TTCTCGGCGG CAGCAAAGTG CGCGTGGACC
   44_5    CGTGGAGTCC GCCAAGGCCA TTCTCGGCGG CAGCAAAGTG CGCGTGGACC
  223_10   .......... .......... .......... .......... ..........
  223_2    .......... .......... .......... .......... ..........
  223_4    .......... .......... .......... .......... ..........
  223_5    .......... .......... .......... .......... ..........
  223_6    .......... .......... .......... .......... ..........
  223_7    .......... .......... .......... .......... ..........
   A3_4    CGTGGAATCT GCCAAAGCCA TTCTGGGTGG AAGCAAGGTT CGTGTGGACC
   A3_5    CGTGGAATCT GCCAAAGCCA TTCTGGGTGG AAGCAAGGTT CGTGTGGACC
   A3_7    CGTGGAATCT GCCAAAGCCA TTCTGGGTGG AAGCAAGGTT CGTGTGGACC
   A3_3    CGTGGAATCT GCCAAAGCCA TTCTGGGTGG AGGCAAGGTT CGTGTGGACC
  42_12    CGTGGAGTCC GCCAAGGCCA TTCTCGGCGG CAGCAAGGTG CGCGTGGACC
   AAV1    CGTGGAGTCC GCCAAGGCCA TTCTCGGCGG CAGCAAGGTG CGCGTGGACC
   AAV2    CGTGGAGTCG GCCAAAGCCA TTCTCGGAGG AAGCAAGGTG CGCGTGGACC
   AAV3    CGTGGAGAGC GCCAAGGCCA TTCTGGGCGG AAGCAAGGTG CGCGTGGACC
   AAV8    CGTGGAGTCC GCCAAGGCCA TTCTCGGCGG CAGCAAGGTG CGCGTGGACC
   AAV9    CGTGGAGTCC GCCAAGGCCA TTCTCGGCGG CAGCAAGGTG CGCGTGGACC
   AAV7    CGTGGAGTCC GCCAAGGCCA TTCTCGGCGG CAGCAAGGTG CGCGTGGACC
   44_2    CGTGGAGTCC GCCAAGGCCA TTCTCGGCGG CAGCAAAGTG CGCGTGGACC
```

FIG. 1AF

```
          1551                                                              1600
  42_2    AAAAGTGCAA  GTCTTCCGCC  CAGATCGATC  CCACCCCCGT  GATCGTCACT
  42_8    AAAAGTGCAA  GTCTTCCGCC  CAGATCGATC  CCACCCCCGT  GATCGTCACT
  42_15   AAAAGTGCAA  GTCGTCCGCC  CAGATCGACC  CCACCCCCGT  GATCGTCACC
  42_5b   AAAAGTGCAA  GTCGTCCGCC  CAGATCGACC  CCACCCCCGT  GATCGTCACC
  42_1b   ..........  ..........  ..........  ..........  ..........
  42_13   AAAAGTGCAA  GTCGTCCGCC  CAGATCGATC  CCACCCCCGT  GATCGTCACT
  42_3a   AAAAGTGCAA  GTCGTCCGCC  CAGATCGATC  CCACCCCCGT  GATCGTCACT
  42_4    ..........  ..........  ..........  ..........  ..........
  42_5a   AAAAGTGCAA  GTCGTCCGCC  CAGATCGACC  CCACCCCCGT  GATCGTCACC
  42_10   ..........  ..........  ..........  ..........  ..........
  42_3b   ..........  ..........  ..........  ..........  ..........
  42_11   AAAAGTGCAA  GTCTTCCGCC  CAGATCGATC  CCACCCCCGT  GATCGTCACT
  42_6b   ATGACTTTGG  CAAGGTGACA  AAGCAGGAAG  TCAAAGAGTT  CTTCCGCTGG
  43_1    AAAAGTGCAA  GTCGTCCGCC  CAGATCGACC  CCACCCCCGT  GATCGTCACC
  43_5    AAAAGTGCAA  GTCGTCCGCC  CAGATCGACC  CCACCCCCGT  GATCGTCACC
  43_12   AAAAGTGCAA  GTCGTCCGCC  CAGATCGACC  CCACCCCCGT  GATCGTCACC
  43_20   AAAAGTGCAA  GTCTTCCGCC  CAGATCGATC  CCACCCCCGT  GATCGTCACC
  43_21   AAAAGTGCAA  GTCTTCCGCC  CAGATCGATC  CCACCCCCGT  GATCGTCACC
  43_23   AAAAGTGCAA  GTCTTCCGCC  CAGATCGATC  CCACCCCCGT  GATCGTCACC
  43_25   AAAAGTGCAA  GTCTTCCGCC  CAGATCGATC  CCACCCCCGT  GATCGTCACC
  44_1    AAAAGTGCAA  GCCGTCCGCC  CAGATCGACC  CCACCCCCGT  GATCGTCACC
  44_5    AAAAGTGCAA  GTCGTCCGCC  CAGATCGACC  CCACCCCCGT  GATCGTCACC
  223_10  ..........  ..........  ..........  ..........  ..........
  223_2   ..........  ..........  ..........  ..........  ..........
  223_4   ..........  ..........  ..........  ..........  ..........
  223_5   ..........  ..........  ..........  ..........  ..........
  223_6   ..........  ..........  ..........  ..........  ..........
  223_7   ..........  ..........  ..........  ..........  ..........
  A3_4    AGAAATGCAA  GTCTTCGGCC  CAGATCGACC  CGACTCCGGT  GATTGTCACC
  A3_5    AGAAATGCAA  GTCTTCGGCC  CAGATCGACC  CGACTCCGGT  GATTGTCACC
  A3_7    AGAAATGCAG  GTCTTCGGCC  CAGATCGACC  CGACTCCGGT  GATTGTCACC
  A3_3    AGAAATGCAA  GTCTTCGGCC  CAGATCGACC  CGACTCCGGT  GATTGTCACC
  42_12   AAAAGTGCAA  GTCGTCCGCC  CAGATCGACC  CCACCCCCGT  GATCGTCACC
  AAV1    AAAAGTGCAA  GTCGTCCGCC  CAGATCGACC  CCACCCCCGT  GATCGTCACC
  AAV2    AGAAATGCAA  GTCCTCGGCC  CAGATAGACC  CGACTCCCGT  GATCGTCACC
  AAV3    AAAAGTGCAA  GTCATCGGCC  CAGATCGAAC  CCACTCCCGT  GATCGTCACC
  AAV8    AAAAGTGCAA  GTCGTCCGCC  CAGATCGACC  CCACCCCCGT  GATCGTCACC
  AAV9    AAAAGTGCAA  GTCGTCCGCC  CAGATCGACC  CCACTCCCGT  GATCGTCACC
  AAV7    AAAAGTGCAA  GTCGTCCGCC  CAGATCGACC  CCACCCCCGT  GATCGTCACC
  44_2    AAAAGTGCAA  GTCGTCCGCC  CAGATCGACC  CCACCCCCGT  GATCGTCACC
```

FIG. 1AG

```
         1601                                                    1650
42_2     TCCAACACCA ACATGTGCGC TGTGATTGAC GGGAACAGCA CCACCTTCGA
42_8     TCCAACACCA ACATGTGCGC CGTGATTGAC GGGAACAGCA CCACCTTCGA
42_15    TCCAACACCA ACATGTGCGC CGTGATTGAC GGGAACAGCA CCACCTTCGA
42_5b    TCCAACACCA ACATGTGCGC CGTGATTGAC GGGAACAGCA CCACCTTCGA
42_1b    .......... .......... .......... .......... ..........
42_13    TCCAACACCA ACATGTGCGC CGTGATTGAC GGGAACAGCA CCACCTTCGA
42_3a    TCCAACACCA ACATGTGCGC CGTGATTGAC GGGAACAGCA CCACCTTCGA
42_4     .......... .......... .......... .......... ..........
42_5a    TCCAACACCA ACATGTGCGC CGTGATTGAC GGGAACAGCA CCACCTTCGA
42_10    .......... .......... .......... .......... ..........
42_3b    .......... .......... .......... .......... ..........
42_11    TCCAACACCA ACATGTGCGC CGTGATTGAC GGGAACAGCA CCACCTTCGA
42_6b    GCGCAGGATC ACGTGACCGA GGTGGCGCAT GAGTTCTACG TCAGAAAGGG
43_1     TCCAACACCA ACATGTGCGC CGTGATTGAC GGGAACAGCA CCACCTTCGA
43_5     TCCAACACCA ACATGTGCGC CGTGATTGAC GGGAACAGCA CCACCTTCGA
43_12    TCCAACACCA ACATGTGCGC CGTGATTGAC GGGAACAGCA CCACCTTCGA
43_20    TCCAACACCA ACATGTGCGC CGTGATTGAC GGGAACAGCG CCACCTTCGA
43_21    TCCAACACCA ACATGTGCGC CGTGATTGAC GGGAACAGCA CCACCTTCGA
43_23    TCCAACACCA ACATGTGCGC CGTGATTGAC GGGAACAGCA CCACCTTCGA
43_25    TCCAACACCA ACATGTGCGC CGTGATTGAC GGGAACAGCA CCACCTTCGA
44_1     TCCAACACCA ACATGTGCGC CGTGATTGAC GGGAACAGCA CCACCTTCGA
44_5     TCCAACACCA ACATGTGCGC CGTGATTGAC GGGAACAGCA CCACCTTCGA
223_10   .......... .......... .......... .......... ..........
223_2    .......... .......... .......... .......... ..........
223_4    .......... .......... .......... .......... ..........
223_5    .......... .......... .......... .......... ..........
223_6    .......... .......... .......... .......... ..........
223_7    .......... .......... .......... .......... ..........
A3_4     TCTAACACCA ACATGTGCGC CGTGATTGAC GGAAACTCGA CCACCTTCGA
A3_5     TCTAACACCA ACATGTGCGC CGTGATTGAC GGAAACTCGA CCACCTTCGA
A3_7     TCTAACACCA ACATGTGCGC CGTGATTGAC GGAAACTCGA CCACCTTCGA
A3_3     TCTAACACCA ACATGTGCGC CGTGATTGAC GGAAACTCGA CCACCTTCGA
42_12    TCCAACACCA ACATGTGCGC CGTGATTGAC GGGAACAGCA CCACCTTCGA
AAV1     TCCAACACCA ACATGTGCGC CGTGATTGAC GGGAACAGCA CCACCTTCGA
AAV2     TCCAACACCA ACATGTGCGC CGTGATTGAC GGGAACTCAA CGACCTTCGA
AAV3     TCCAACACCA ACATGTGCGC CGTGATTGAC GGGAACAGCA CCACCTTCGA
AAV8     TCCAACACCA ACATGTGCGC CGTGATTGAC GGGAACAGCA CCACCTTCGA
AAV9     TCCAACACCA ACATGTGCGC CGTGATTGAC GGGAACAGCA CCACCTTCGA
AAV7     TCCAACACCA ACATGTGCGC CGTGATTGAC GGGAACAGCA CCACCTTCGA
44_2     TCCAACACCA ACATGTGCGC CGTGATTGAC GGGAACAGCA CCACCTTCGA
```

FIG. 1AH

```
         1651                                                              1700
  42_2   GCACCAGCAG  CCGTTACAAG  ACCGGATGTT  CAAATTTGAA  CTCACCCGCC
  42_8   GCACCAGCAG  CCGTTACAAG  ACCGGATGTT  CAAATTTGAA  CTCACCCGCC
 42_15   GCACCAGCAG  CCGTTGCAGG  ACCGGATGTT  CAAATTTGAA  CTCACCCGCC
 42_5b   GCACCAGCAG  CCGTTACAAG  ACCGGATGTT  CAAATTTGAA  CTCACCCGCC
 42_1b   ..........  ..........  ..........  ..........  ..........
 42_13   GCACCAGCAG  CCGTTACAAG  ACCGGATGTT  CAAATTTGAA  CTCACCCGCC
 42_3a   GCACCAGCAG  CCGTTACAAG  ACCGGATGTT  CAAATTTGAA  CTCACCCGCC
  42_4   ..........  ..........  ..........  ..........  ..........
 42_5a   GCACCAGCAG  CCGTTGCAGG  ACCGGATGTT  CAAATTTGAA  CTCACCCGCC
 42_10   ..........  ..........  ..........  ..........  ..........
 42_3b   ..........  ..........  ..........  ..........  ..........
 42_11   GCACCAGCAG  CCGTTACAAG  ACCGGATGTT  CAAATTTGAA  CTCACCCGCC
 42_6b   TGGAGCCAAC  AAGAGACCCG  CCCCCGATGA  CGCGGATAAA  AGCGAGCCCA
  43_1   GCACCAGCAG  CCGTTGCAGG  ACCGGATGTT  CAAGTTCGAA  CTCACCCGCC
  43_5   GCACCAGCAG  CCGTTGCAGG  ACCGGATGTT  CAAGTTCGAA  CTCACCCGCC
 43_12   GCACCAGCAG  CCGTTGCAGG  ACCGGATGTT  CAAGTTCGAA  CTCACCCGCC
 43_20   GCACCAGCAG  CCGTTGCAGG  ACCGGATGTT  CAAATTTGAA  CTCACCCGCC
 43_21   GCACCAGCAG  CCGTTGCAGG  ACCGGATGTT  CAAATTTGAA  CTCACCCGCC
 43_23   GCACCAGCAG  CCGTTGCAGG  ACCGGATGTT  CAAATTTGAA  CTCACCCGCC
 43_25   GCACCAGCAG  CCGTTGCAGG  ACCGGATGTT  CAAATTTGAA  CTCACCCGCC
  44_1   GCACCAGCAG  CCGTTGCGGG  ACCGGATGTT  CAAGTTTGAA  CTCACCCGCC
  44_5   GCACCAGCAG  CCGTTGCAGG  ACCGGATGTT  CAAGTTTGAA  CTCACCCGCC
 223_10  ..........  ..........  ..........  ..........  ..........
 223_2   ..........  ..........  ..........  ..........  ..........
 223_4   ..........  ..........  ..........  ..........  ..........
 223_5   ..........  ..........  ..........  ..........  ..........
 223_6   ..........  ..........  ..........  ..........  ..........
 223_7   ..........  ..........  ..........  ..........  ..........
  A3_4   GCACCAGCAG  CCGTTGCAAG  ACCGGATGTT  CAAATTTGAA  CTTACCCGCC
  A3_5   GCACCAGCAG  CCGTTGCAAG  ACCGGATGTT  CAAATTTGAA  CTTACCCGCC
  A3_7   GCACCAGCAG  CCGTTGCAAG  ACCGGATGTT  CAAATTTGAA  CTTACCCGCC
  A3_3   GCACCAGCAG  CCGTTGCAAG  ACCGGATGTT  CAAATTTGAA  CTTACCCGCC
 42_12   GCACCAGCAG  CCGTTACAAG  ACCGGATGTT  CAAATTTGAA  CTCACCCGCC
  AAV1   GCACCAGCAG  CCGTTGCAGG  ACCGGATGTT  CAAATTTGAA  CTCACCCGCC
  AAV2   ACACCAGCAG  CCGTTGCAAG  ACCGGATGTT  CAAATTTGAA  CTCACCCGCC
  AAV3   GCATCAGCAG  CCGCTGCAGG  ACCGGATGTT  TGAATTTGAA  CTTACCCGCC
  AAV8   GCACCAGCAG  CCTCTCCAGG  ACCGGATGTT  TAAGTTCGAA  CTCACCCGCC
  AAV9   GCACCAGCAG  CCTCTCCAGG  ACCGGATGTT  TAAGTTCGAA  CTCACCCGCC
  AAV7   GCACCAGCAG  CCGTTGCAGG  ACCGGATGTT  CAAATTTGAA  CTCACCCGCC
  44_2   GCACCAGCAG  CCGTTGCAGG  ACCGGATGTT  CAAGTTTGAA  CTCACCCGCC
```

FIG. 1AI

```
          1701                                                          1750
 42_2     GTCTGGAGCA CGACTTTGGC AAGGTGACAA AGCAGGAAGT CAAAGAGTTC
 42_8     GTCTGGAGCA CGACTTTGGC AAGGTGACAA AGCAGGAAGT CAAAGAGTTC
 42_15    GTCTGGAGCA TGACTTTGGC AAGGTGACAA AGCAGGAAGT CAAAGAGTTC
 42_5b    GTCTGGAGCA CGACTTTGCC AAGGTGACAA AGCAGGAAGT CAAAGAGTTC
 42_1b    .......... .......... .......... .......... ..........
 42_13    GTCTGGAGCA TGACTTTGGC AAGGTGACAA AGCAGGAAGT CAAAGAGTTC
 42_3a    GTCTGGAGCA TGACTTTGGC AAGGTGACAA AGCAGGAAGT CAAAGAGTTC
 42_4     .......... .......... .......... .......... ..........
 42_5a    GTCTGGAGCA TGACTTTGGC AAGGCGACAA AGCAGGAAGT CAAAGAGTTC
 42_10    .......... .......... .......... .......... ..........
 42_3b    .......... .......... .......... .......... ..........
 42_11    GTCTGGAGCA CGACTTTGGC AAGGTGACAA AGCAGGAAGT CAAAGAGTTC
 42_6b    AGCGGGCCTG CCCCTCAGTC GCGGATCCAT CGACGTCAGA CGCGGAAGGA
 43_1     GTCTGGAGCA CGACTTTGGC AAGGTGACCA AGCAGGAAGT CAAAGAGTTC
 43_5     GTCTGGAGCA CGACTTTGGC AAGGTGACCA AGCAGGAAGT CAAAGAGTTC
 43_12    GTCTGGAGCA CGACTTTGGC AAGGTGACCA AGCAGGAAGT CAAAGAGTTC
 43_20    GTCTGGAGCA TGACTTTGGC AAGGTGACGA AGCAGGAAGT CAAAGAGTTC
 43_21    GTCTGGAGCA TGACTTTGGC AAGGTGACGA AGCAGGAAGT CAAAGAGTTC
 43_23    GTCTGGAGCA TGACTTTGGC AAGGTGACGA AGCAGGAAGT CAAAGAGTTC
 43_25    GTCTGGAGCA TGACTTTGGC AAGGTGACGA AGCAGGAAGT CAAAGGGTTC
 44_1     GTCTGGAGCA CGACTTTGGC AAGGTGACAA AGCAGGAAGT CAGAGAGTTC
 44_5     GTCTGGAGCA CGACTTTGGC AAGGTGACAA AGCAGGAAGT CAGAGAGTTC
223_10    .......... .......... .......... .......... ..........
223_2     .......... .......... .......... .......... ..........
223_4     .......... .......... .......... .......... ..........
223_5     .......... .......... .......... .......... ..........
223_6     .......... .......... .......... .......... ..........
223_7     .......... .......... .......... .......... ..........
 A3_4     GTTTGGATCA TGACTTTGGG AAGGTCACCA AGCAGGAAGT CAAAGACTTT
 A3_5     GTTTGGATCA TGACTTTGGG AAGGTCACCA AGCAGGAAGT CAAAGACTTT
 A3_7     GTTTGGATCA TGACTTTGGG AAGGTCACCA AGCAGGAAGT CAAAGACTTT
 A3_3     GTTTGGATCA TGACTTTGGG AAGGTCACCA AGCAGGAAGT CAAAGACTTT
 42_12    GTCTGGAGCA CGACTTTGGC AAGGTGACAA AGCAGGAAGT CAAAGAGTTC
 AAV1     GTCTGGAGCA TGACTTTGGC AAGGTGACAA AGCAGGAAGT CAAAGAGTTC
 AAV2     GTCTGGATCA TGACTTTGGG AAGGTCACCA AGCAGGAAGT CAAAGACTTT
 AAV3     GTTTGGACCA TGACTTTGGG AAGGTCACCA AACAGGAAGT AAAGGACTTT
 AAV8     GTCTGGAGCA CGACTTTGGC AAGGTGACAA AGCAGGAAGT CAAAGAGTTC
 AAV9     GTCTGGAGCA CGACTTTGGC AAGGTGACAA AGCAGGAAGT CAAAGAGTTC
 AAV7     GTCTGGAGCA CGACTTTGGC AAGGTGACGA AGCAGGAAGT CAAAGAGTTC
 44_2     GTCTGGAGCA CGACTTTGGC AAGGTGACAA AGCAGGAAGT CAGAGAGTTC
```

FIG. 1AJ

```
          1751                                                              1800
  42_2    TTCCGCTGGG CGCAGGATCA CGTGACCGAG GTGGCGCATG AGTTCTACGT
  42_8    TTCCGCTGGG CGCAGGATCA CGTGACCGAG GTGGCGCATG AGTTCTACGT
  42_15   TTCCGCTGGG CGCAGGATCA CGTGACCGAG GTGGCGCATG AGTTCTACGT
  42_5b   TTCCGCTGGG CGCAGGATCA CGTGACCGAG GTGGCGCATG AGTTCTACGT
  42_1b   .......... .......... .......... .......... ..........
  42_13   TTCCGCTGGG CGCAGGATCA CGTGACCGAG GTGGCGCATG AGTTCTACGT
  42_3a   TTCCGCTGGG CGCAGGATCA CGTGACCGAG GTGGCGCATG AGTTCTACGT
  42_4    .......... .......... .......... .......... ..........
  42_5a   TTCCGCTGGG CGCAGGATCA CGTGACCGAG GTGGCGCATG AGTTCTACGT
  42_10   .......... .......... .......... .......... ..........
  42_3b   .......... .......... .......... .......... ..........
  42_11   TTCCGCTGGG CGCAGGATCA CGTGACCGAG GTGGCGCATG AGTTCTACGT
  42_6b   GCTCCGGTGG ACTTTGCCGA CAGGTACCAA AACAAATGTT CTCGTCACGC
  43_1    TTCCGCTGGG CGCAGGATCA CGTGACCGAG GTGGCGCATG AGTTCTACGT
  43_5    TTCCGCTGGG CGCAGGATCA CGTGACCGAG GTGGCGCATG AGTTCTACGT
  43_12   TTCCGCTGGG CGCAGGATCA CGTGACCGAG GTGGCGCATG AGTTCTACGT
  43_20   TTCCGCTGGG CGCAGGATCA CGTGACCGAG GTGGCGCATG AGTTCCACGT
  43_21   TTCCGCTGGG CGCAGGATCA CGTGACCGAG GTGGCGCATG AGTTCCACGT
  43_23   TTCCGCTGGG CGCAGGATCA CGTGACCGAG GTGGCGCATG AGTTCCACGT
  43_25   TTCCGCTGGG CGCAGGATCA CGTGACCGAG GTGGCGCATG AGTTCCACGT
  44_1    TTCCGCTGGG CGCAGGATCA CGTGACCGAG GTGGCGCACG AGTTCTACGT
  44_5    TTCCGCTGGG CGCAGGATCA CGTGACCGAG GTGGCGCACG AGTTCTACGT
  223_10  .......... .......... .......... .......... ..........
  223_2   .......... .......... .......... .......... ..........
  223_4   .......... .......... .......... .......... ..........
  223_5   .......... .......... .......... .......... ..........
  223_6   .......... .......... .......... .......... ..........
  223_7   .......... .......... .......... .......... ..........
  A3_4    TTCCGGTGGG CTCAAGATCA CGTGACTGAG GTGGAGCATG AGTTCTACGT
  A3_5    TTCCGGTGGG CTCAAGATCA CGTGACTGAG GTGGAGCATG AGTTCTACGT
  A3_7    TTCCGGTGGG CTCAAGATCA CGTGACTGAG GTGGAGCATG AGTTCTACGT
  A3_3    TTCCGGTGGG CTCAAGATCA CGTGACTGAG GTGGAGCATG AGTTCTACGT
  42_12   TTCCGCTGGG CGCAGGATCA CGTGACCGAG GTGGCGCATG AGTTCTACGT
  AAV1    TTCCGCTGGG CGCAGGATCA CGTGACCGAG GTGGCGCATG AGTTCTACGT
  AAV2    TTCCGGTGGG CAAAGGATCA CGTGGTTGAG GTGGAGCATG AATTCTACGT
  AAV3    TTCCGGTGGG CTTCCGATCA CGTGACTGAC GTGGCTCATG AGTTCTACGT
  AAV8    TTCCGCTGGG CCAGTGATCA CGTGACCGAG GTGGCGCATG AGTTTTACGT
  AAV9    TTCCGCTGGG CCAGTGATCA CGTGACCGAG GTGGCGCATG AGTTTTACGT
  AAV7    TTCCGCTGGG CCAGTGATCA CGTGACCGAG GTGGCGCATG AGTTTTACGT
  44_2    TTCCGCTGGG CGCAGGATCA CGTGACCGAG GTGGCGCACG AGTTCTACGT
```

FIG. 1AK

```
          1801                                                        1850
                                                                  P40/TATA
  42_2    CAGAAAGGGT  GGAGCCAACA  AGAGACCCGC  CCCCGATGAC  GCGGATAAAA
  42_8    CAGAAAGGGT  GGAGCCAACA  AGAGACCCGC  CCCCGATGAC  GCGGATAAAA
  42_15   CAGAAAGGGT  GGAGCCAACA  AGAGACCCGC  CCCCGATGAC  GCGGATAAAA
  42_5b   CAGAAAGGGT  GGAGCCAACA  AGAGACCCGC  CCCCGATGAC  GCGGATAAAA
  42_1b   ..........  ..........  ..........  ..........  ..........
  42_13   CAGAAAGGGT  GGAGCCAACA  AGAGACCCGC  CCCCGATGAC  GCGGATAAAA
  42_3a   CAGAAAGGGT  GGAGCCAACA  AGAGACCCGC  CCCCGATGAC  GCGGATAAAA
  42_4    ..........  ..........  ..........  ..........  ..........
  42_5a   CAGAAAGGGT  GGAGCCAACA  AGAGACCCGC  CCCCGATGAC  GCGGATAAAA
  42_10   ..........  ..........  ..........  ..........  ..........
  42_3b   ..........  ..........  ..........  ..........  ..........
  42_11   CAGAAAGGGT  GGAGCCAACA  AGAGACCCGC  CCCCGATGAC  GCGGATAAAA
  42_6b   GGGCATAGCG  CTGACGTAAA  TCACGTCATA  GGGGAGTGGT  CCTGTATTAG
  43_1    CAGAAAGGGC  GGAGCCAGCA  AAAGACCCGC  CCCCGATGAC  GCGGATATAA
  43_5    CAGAAAGGGC  GGAGCCAGCA  AAAGACCCGC  CCCCGATGAC  GCGGATATAA
  43_12   CAGAAAGGGC  GGAGCCAGCA  AAAGACCCGC  CCCCGATGAC  GCGGATATAA
  43_20   CAGAAAGGGT  GGAGCCAACA  AGAGACCCGC  CCCCGATGAC  GCGGATATAA
  43_21   CAGAAAGGGT  GGAGCCAACA  AGAGACCCGC  CCCCGATGAC  GCGGATATAA
  43_23   CAGAAAGGGT  GGCGCCAACA  AGAGACCCGC  CCCCGATGAC  GCGGATATAA
  43_25   CAGAAAGGGT  GGAGCCAACA  AGAGACCCGC  CCCCGATGAC  GCGGATATAA
  44_1    CAGAAAGGGT  GGAGCCAACA  AGAGACCCGC  CCCCGATGAC  GCGGATAAAA
  44_5    CAGAAAGGGT  GGAGCCAACA  AGAGACCCGC  CCCCGATGAC  GCGGATAAAA
  223_10  ..........  ..........  ..........  ..........  ..........
  223_2   ..........  ..........  ..........  ..........  ..........
  223_4   ..........  ..........  ..........  ..........  ..........
  223_5   ..........  ..........  ..........  ..........  ..........
  223_6   ..........  ..........  ..........  ..........  ..........
  223_7   ..........  ..........  ..........  ..........  ..........
  A3_4    CAAAAAGGGT  GGAGCCAAGA  AAAGGCCCGC  CCCCGATGAT  GTATATATAA
  A3_5    CAAAAAGGGT  GGAGCCAAGA  AAAGGCCCGC  CCCCGATGAT  GTATATATAA
  A3_7    CAAAAAGGGT  GGAGCCAAGA  AAAGGCCCGC  CCCCGATGAT  GTATATATAA
  A3_3    CAAAAAGGGT  GGAGCCAAGA  AAAGGCCCGC  CCCCGATGAT  GTATATATAA
  42_12   CAGAAAGGGT  GGAGCCAACA  AGAGACCCGC  CCCCGATGAC  GCGGATAAAA
  AAV1    CAGAAAGGGT  GGAGCCAACA  AAAGACCCGC  CCCCGATGAC  GCGGATAAAA
  AAV2    CAAAAAGGGT  GGAGCCAAGA  AAAGACCCGC  CCCCAGTGAC  GCAGATATAA
  AAV3    CAGAAAGGGT  GGAGCTAAGA  AACGCCCCGC  CTCCAATGAC  GCGGATGTAA
  AAV8    CAGAAAGGGC  GGAGCCAGCA  AAAGACCCGC  CCCCGATGAC  GCGGATAAAA
  AAV9    CAGAAAGGGC  GGAGCCAGCA  AAAGACCCGC  CCCCGATGAC  GCGGATAAAA
  AAV7    CAGAAAGGGC  GGAGCCAGCA  AAAGACCCGC  CCCCGATGAC  GCGGATATAA
  44_2    CAGAAAGGGT  GGAGCCAACA  AGAGACCCGC  CCCCGATGAC  GCGGATAAAA
                                                                  P40/TATA
```

FIG. 1AL

```
        1851                                                              1900
                                                    P40 RNA
 42_2    GCGAGCCCAA GCGGGCCTGC CCCTCAGTCG CGGATCCATC GACGTCAGAC
 42_8    GCGAGCCCAA GCGGGCCTGC CCCTCAGTCG CGGATCCATC GACGTCAGAC
 42_15   GCGAGCCCAA GCGGGCCTGC CCCTCAGTCG CGGATCCATC GACGTCAGAC
 42_5b   GCGAGCCCAA GCGGGCCTGC CCCTCAGTCG CGGATCCATC GACGTCAGAC
 42_1b   .......... .......... .......... .......... ..........
 42_13   GCGAGCCCAA GCGGGCCTGC CCCTCAGTCG CGGATCCATC GACGTCAGAC
 42_3a   GCGAGCCCAA GCGGGCCTGC CCCTCAGTCG CGGATCCATC GACGTCAGAC
 42_4    .......... .......... .......... .......... ..........
 42_5a   GCGAGCCCAA GCGGGCCCGC CCCTCAGTCG CGGATCCATC GACGTCAGAC
 42_10   .......... .......... .......... .......... ..........
 42_3b   .......... .......... .......... .......... ..........
 42_11   GCGAGCCCAA GCGGGCCTGC CCCTCAGTCG CGGATCCATC GACGTCAGAC
 42_6b   CTGTCACGTG AGTGCTTTTG CGACATTTG  C..ATCCATC GACGTCAGAC
 43_1    GCGAGCCCAA GCGGGCCTGC CCCTCAGTCG CGGATCCATC GACGTCAGAC
 43_5    GCGAGCCCAA GCGGGCCTGC CCCTCAGTCG CGGATCCATC GACGTCAGAC
 43_12   GCGAGCCCAA GCGGGCCTGC CCCTCAGTCG CGGATCCATC GACGTCAGAC
 43_20   GCGAGCCCAA GCGGGCCTGC CCCTCAGTCG CGGATCCATC GACGTCAGAC
 43_21   GCGAGCCCAA GCGGGCCTGC CCCTCAGTCG CGGATCCATC GACGTCAGAC
 43_23   GCGAGCCCAA GCGGGCCTGC CCCTCAGTCG CGGATCCATC GACGTCAGAC
 43_25   GCGAGCCCAA GCGGGCCTGC CCCTCAGTCG CGGATCCATC GACGTCAGAC
 44_1    GCGAGCCCAA GCGGGCCTGC CCCTCAGTCG CGGATCCATC GACGTCAGAC
 44_5    GCGAGCCCAA GCGGGCCTGC CCCTCAGTCG CGGATCCATC GACGTCAGAC
223_10   .......... .......... .......... .......... ..........
223_2    .......... .......... .......... .......... ..........
223_4    .......... .......... .......... .......... ..........
223_5    .......... .......... .......... .......... ..........
223_6    .......... .......... .......... .......... ..........
223_7    .......... .......... .......... .......... ..........
 A3_4    ATGAGCCCAA GCGGGCGCGC GAGTCAGTTG CGCAGCCATC GACGTCAGAC
 A3_5    ATGAGCCCAA GCGGGCGCGC GAGTCAGTTG CGCAGCCATC GACGTCAGAC
 A3_7    ATGAGCCCAA GCGGGCGCGC GAGTCAGTTG CGCAGCCATC GACGTCAGAC
 A3_3    ATGAGCCCAA GCGGGCGCGC GAGTCAGTTG CGCAGCCATC GACGTCAGAC
 42_12   GCGAGCCCAA GCGGGCCTGC CCCTCAGTCG CGGATCCATC GACGTCAGAC
 AAV1    GCGAGCCCAA GCGGGCCTGC CCCTCAGTCG CGGATCCATC GACGTCAGAC
 AAV2    GTGAGCCCAA ACGGGTGCGC GAGTCAGTTG CGCAGCCATC GACGTCAGAC
 AAV3    GCGAGCCAAA ACGGGAGTGC ACGTCACTTG CGCAGCCGAC AACGTCAGAC
 AAV8    GCGAGCCCAA GCGGGCCTGC CCCTCAGTCG CGGATCCATC GACGTCAGAC
 AAV9    GCGAGCCCAA GCGGGCCTGC CCCTCAGTCG CGGATCCATC GACGTCAGAC
 AAV7    GCGAGCCCAA GCGGGCCTGC CCCTCAGTCG CGGATCCATC GACGTCAGAC
 44_2    GCGAGCCCAA GCGGGCCTGC CCCTCAGTCG CGGATCCATC GACGTCAGAC
                                                    P40 RNA
```

FIG. 1AM

```
           1901                                                      1950
   42_2    GCGGAAGGAG CTCCGGTGGA CTTTGCCGAC AGGTACCAAA ACAAATGTTC
   42_8    GCGGAAGGAG CTCCGGTGGA CTTTGCCGAC AGGTACCAAA ACAAATGTTC
  42_15    GCGGAAGGAG CTCCGGTGGA CTTTGCCGAC AGGTACCAAA ACAAATGTTC
  42_5b    GCGGAAGGAG CTCCGGTGGA CTTTGCCGAC AGGTACCAAA ACAAATGTTC
  42_1b    .......... .......... .......... .......... ..........
  42_13    GCGGAAGGAG CTCCGGTGGA CTTTGCCGAC AGGTACCAAA ACAAATGTTC
  42_3a    GCGGAAGGAG CTCCGGTGGA CTTTGCCGAC AGGTACCAAA ACAAATGTTC
   42_4    .......... .......... .......... .......... ..........
  42_5a    GCGGAAGGAG CTCCGGTGGA CTTTGCCGAC AGGTACCAAA ACAAATGTTC
  42_10    .......... .......... .......... .......... ..........
  42_3b    .......... .......... .......... .......... ..........
  42_11    GCGGAAGGAG CTCCGGTGGA CTTTGCCGAC AGGTACCAAA ACAAATGTTC
  42_6b    GCGGAAGGAG CTCCGGTGGA CTTTGCCGAC AGGTACCAAA ACAAGTGTTC
   43_1    GCGGAAGGAG CTCCGGTGGA CTTTGCCGAC AGGTACCAAA ACAAATGTTC
   43_5    GCGGAAGGAG CTCCGGTGGA CTTTGCCGAC AGGTACCAAA ACAAATGTTC
  43_12    GCGGAAGGAG CTCCGGTGGA CTTTGCCGAC AGGTACCAAA ACAAATGTTC
  43_20    GCGGAAGGAG CTCCGGTGGA CTTTGCCGAC AGGTACCAAA ACAAATGTTC
  43_21    GCGGAAGGAG CTCCGGTGGA CTTTGCCGAC AGGTACCAAA ACAAATGTTC
  43_23    GCGGAAGGAG CTCCGGTGGA CTTTGCCGAC AGGTACCAAA ACAAATGTTC
  43_25    GCGGAAGGAG CTCCGGTGGA CTTTGCCGAC AGGTACCAAA ACAAATGTTC
   44_1    GCGGAAGGAG CTCCGGTGGA CTTTGCCGAC AGGTACCAAA ACAAATGTTC
   44_5    GCGGAAGGAG CTCCGGTGGA CTTTGCCGAC AGGTACCAAA ACAAATGTTC
  223_10   .......... .......... .......... .......... ..........
  223_2    .......... .......... .......... .......... ..........
  223_4    .......... .......... .......... .......... ..........
  223_5    .......... .......... .......... .......... ..........
  223_6    .......... .......... .......... .......... ..........
  223_7    .......... .......... .......... .......... ..........
   A3_4    GCGGA...AG CTTCGATAAA CTACGCGGGC AGGTACCAAA ACAAATGTTC
   A3_5    GCGGA...AG CTTCGATAAA CTACGCGGAC AGGTACCAAA ACAAATGTTC
   A3_7    GCGGA...AG CTTCGATAAA CTACGCGGAC AGGTACCAAA ACAAATGTTC
   A3_3    GCGGA...AG CTTCGATAAA CTACGCGGAC AGGTACCAAA ACAAATGTTC
  42_12    GCGGAAGGAG CTCCGGTGGA CTTTGCCGAC AGGTACCAAA ACAAATGTTC
   AAV1    GCGGAAGGAG CTCCGGTGGA CTTTGCCGAC AGGTACCAAA ACAAATGTTC
   AAV2    GCGGA...AG CTTCGATCAA CTACGCAGAC AGGTACCAAA ACAAATGTTC
   AAV3    GCGGA...AG CACCGGCGGA CTACGCGGAC AGGTACCAAA ACAAATGTTC
   AAV8    GCGGAAGGAG CTCCGGTGGA CTTTGCCGAC AGGTACCAAA ACAAATGTTC
   AAV9    GCGGAAGGAG CTCCGGTGGA CTTTGCCGAC AGGTACCAAA ACAAATGTTC
   AAV7    GCGGAAGGAG CTCCGGTGGA CTTTGCCGAC AGGTACCAAA ACAAATGTTC
   44_2    GCGGAAGGAG CTCCGGTGGA CTTTGCCGAC AGGTACCAAA ACAAATGTTC
```

FIG. 1AN

```
            1951                                                          2000
  42_2     TCGTCACGCG  GGCATGCTTC  AGATGCTGTT  TCCCTG.CAA  GACATGCGAG
  42_8     TCGTCACGCG  GGCATGCTTC  AGATGCTGTT  TCCCTG.CAA  GACATGCGAG
  42_15    TCGTCACGCG  GGCATGCTTC  AGATGCTGTT  TCCCTG.CAA  GACATGCGAG
  42_5b    TCGTCACGCG  GGCATGCTTC  AGATGCTGTT  TCCCTG.CAA  GACATGCGAG
  42_1b    ..........  ..........  ....GAATTC  GCCCTT....  .GGCTGCGTC
  42_13    TCGTCACGCG  GGCATGCTTC  AGATGCTGTT  TCCCTG.CAA  GACATGCGAG
  42_3a    TCGTCACGCG  GGCATGCTTC  AGATGCTGCT  TCCCTG.CAA  GACATGCGAG
  42_4     ..........  ..........  ....GAATTC  GCCCTTCTA   CGGCTGCGTC
  42_5a    TCGTCACGCG  GGCATGCTTC  AGATGCTGTT  TCCCTG.CAA  AACATGCGAG
  42_10    ..........  ..........  ....GAATTC  GCCCTTCTA   CGGCTGCGTC
  42_3b    ..........  ..........  ....GAATTC  GCCCTTCTA   CGGCTGCGTC
  42_11    TCGTCACGCG  GGCATGCTTC  AGATGCTGTT  TCCCTG.CAA  GACATGCGAG
  42_6b    TCGTCACGCG  GGCATGCTTC  AGATGCTGTT  TCCCTG.CAA  GACATGCGAG
  43_1     TCGTCACGCG  GGCATGCTTC  AGATGCTGTT  TCCCTG.CAA  AACGTGCGAG
  43_5     TCGTCACGCG  GGCATGCTTC  AGACGCTGTT  TCCCTG.CAA  AACGTGCGAG
  43_12    TCGTCACGCG  GGCATGCTCC  AGATGCTGTT  TCCCTG.CAA  AACGTGCGAG
  43_20    TCGTCACGCG  GGCATGCTTC  AGATGCTGTT  TCCCTG.CAA  GACATGCGAG
  43_21    TCGTCACGCG  GGCATGCTTC  AGATGCTGTT  TCCCTG.CAA  GACATGCGAG
  43_23    TCGTCACGCG  GGCATGCTTC  AGATGCTGTT  TCCCTG.CAA  GACATGCGAG
  43_25    TCGTCACGCG  GGCATGCTTC  AGATGCTGTT  TCCCTG.CAA  GACATGCGAG
  44_1     TCGTCACGCG  GGCATGCTTC  AGATGCTGTT  TCCCTG.CAA  AACATGCGAG
  44_5     TCGTCACGCG  GGCATGCTTC  AGATGCTGTT  TCCCTG.CAA  AACATGCGAG
  223_10   ..........  ..........  ..........  ..........  ..........
  223_2    ..........  ..........  ..........  ..........  ..........
  223_4    ..........  ..........  ..........  ..........  ..........
  223_5    ..........  ..........  ..........  ..........  ..........
  223_6    ..........  ..........  ..........  ..........  ..........
  223_7    ..........  ..........  ..........  ..........  ..........
  A3_4     TCGTCACGTG  GGCATGAATC  TGATGCTGTT  TCCCTG.TCG  ACAATGCGAA
  A3_5     TCGTCACGTG  GGCATGAATC  TGATGCTGTT  TCCCTG.TCG  ACAATGCGAA
  A3_7     TCGTCACGTG  GGCATGAATC  TGATGCTGTT  TCCCTG.TCG  ACAATGCGAA
  A3_3     TCGTCACGTG  GGCATGAATC  TGATGCTGTT  TCCCTG.TCG  ACAATGCGAA
  42_12    TCGTCACGCG  GGCATGCTTC  AGATGCTGTT  TCCCTG.CAA  GACATGCGAG
  AAV1     TCGTCACGCG  GGCATGCTTC  AGATGCTGTT  TCCCTG.CAA  GACATGCGAG
  AAV2     TCGTCACGTG  GGCATGAATC  TGATGCTGTT  TCCCTG.CAG  ACAATGCGAG
  AAV3     TCGTCACGTG  GGCATGAATC  TGATGCTTTT  TCCCTG.TAA  AACATGCGAG
  AAV8     TCGTCACGCG  GGCATGCTTC  AGATGCTGTT  TCCCTG.CAA  AACGTGCGAG
  AAV9     TCGTCACGCG  GGCATGCTTC  AGATGCTGCT  TCCCTG.CAA  AACGTGCGAG
  AAV7     TCGTCACGCG  GGCATGATTC  AGATGCTGTT  TCCCTG.CAA  AACGTGCGAG
  44_2     TCGTCACGCG  GGCATGCTTC  AGATGCTGTT  TCCCTG.CAA  AACATGCGAG
```

FIG. 1AO

```
         2001                                                      2050
  42_2   AGAATGAATC AGAATTTCAA CATTTGCTTC ACGCACGGGA CCAGAGACTG
  42_8   AGAATGAATC AGAATTTCAA CATTTGCTTC ACGCACGGGA CCAGAGACTG
  42_15  AGAATGAATC AGAATTTCAA CATTTGCTTC ACGCGCGGGA CCAGAGACTG
  42_5b  AGAATGAATC AGAATTTCAA CATTTGCTTC ACGCACGGGA CCAGAGACTG
  42_1b  A.ACTGGACC A..ATGAGAA CTTTCCCTTC A........A CGATTGCGTC
  42_13  AGAATGAATC AGAATTTCAA CATTTGCTTC ACGCACGGGA CCAGAGACTG
  42_3a  AGAATGAATC AGAATTTCAG CATTTGCTTC ACGCACGGGA CCAGAGACTG
  42_4   A.ACTGGACC A..ATGAGAA CTTTCCCTTC A........A CGATTGCGTC
  42_5a  AGAATGAATC AGAATTTCAA CATTTGCTTC ACGCACGGGA CCAGAGACTG
  42_10  A.ACTGGACC A..ATGAGAA CTTTCCCTTC A........A CGATTGCGTC
  42_3b  A.ACTAGACC A..ATGAGAA CTTTCCCTTC A........A CGATTGCGTC
  42_11  AGAATGAATC AGAATTTCAA CATTTGCTTC ACGCACGGGA CCGGAGACTG
  42_6b  AGAATGAATC AGAATTTCAA CATTTGCTTC ACGCACGGGA CCAGAGACTG
  43_1   AAAATGAATC AGAATTTCAA CATTTGCTTC ACGCACGGGG TCAGAGACTG
  43_5   AGAATGAATC AGAATTTCAA CATTTGCTTC ACGCACGGGG TCAGAGACTG
  43_12  AGAATGAATC AGAATTTCAA CATTTGCTTC ACGCACGGGG TCAGAGACTG
  43_20  AGAATGAATC AGAATTTCAA CATTTGCTTC ACGCACGGGA CCAGAGACTG
  43_21  AGAATGAATC AGAATTTCAA CATTTGCTTC ACGCACGGGA CCAGAGACTG
  43_23  AGAATGAATC AGAATTTCAA CATTTGCTTC ACGCACGGGA CCAGAGACTG
  43_25  AGAATGAATC AGAATTTCAA CATTTGCTTC ACGCACGGGA CCAGAGACTG
  44_1   AGAATGAATC AGAATTTCAA CATTTGCTTC ACGCACGGGA CCAGAGACTG
  44_5   AGAATGAATC AGAATTTCAA CATTTGCTTC ACGCACGGGA CCAGAGACTG
 223_10  .......... .......... .......... .......... ..........
 223_2   .......... .......... .......... .......... ..........
 223_4   .......... .......... .......... .......... ..........
 223_5   .......... .......... .......... .......... ..........
 223_6   .......... .......... .......... .......... ..........
 223_7   .......... .......... .......... .......... ..........
  A3_4   AGAATGAATC AGAATTCAAA TATCTGCTTC ACACACGGGC AAAAAGACTG
  A3_5   AGAATGAATC AGAATTCAAA TATCTGCTTC ACACACGGGC AAAAAGACTG
  A3_7   AGAATGAATC AGAATTCAAA TATCTGCTTC ACACACGGGC AAAAAGACTG
  A3_3   AGAATGAATC AGAATTCAAA TATCTGCTTC ACACACGGGC AAAAAGACTG
  42_12  AGAATGAATC AGAATTTCAA CATTTGCTTC ACGCACGGGA CCAGAGACTG
  AAV1   AGAATGAATC AGAATTTCAA CATTTGCTTC ACGCACGGGA CGAGAGACTG
  AAV2   AGAATGAATC AGAATTCAAA TATCTGCTTC ACTCACGGAC AGAAAGACTG
  AAV3   AGAATGAATC AAATTTCCAA TGTCTGTTTT ACGCATGGTC AAAGAGACTG
  AAV8   AGAATGAATC AGAATTTCAA CATTTGCTTC ACACACGGGG TCAGAGACTG
  AAV9   AGAATGAATC AGAATTTCAA CATTTGCTTC ACACACGGGG TCAGAGACTG
  AAV7   AGAATGAATC AGAATTTCAA CATTTGCTTC ACACACGGGG TCAGAGACTG
  44_2   AGAATGAATC AGAATTTCAA CATTTGCTTC ACGCACGGGA CCAGAGACTG
```

FIG. 1AP

```
          2051                                                    2100
 42_2    TTCAGAATGT TTCCCCGGCG TGTCAGAATC TCAACC.... ..GGTCGTCA

42_8    TTCAGAATGT TTCCCCGGCG TGTCAGAATC TCAACC.... ..GGTCGTCA
 42_15   TTCAGAATGT TTCCCGGGCG TGTCAGAATC TCAACC.... ..GGTCGTCA
 42_5b   TTCAGAATGT TTCCCCGGCG TGTCAGAATC TCAACC.... ..GGTCGTCA
 42_1b   GACAAGATGG TGATCTGGTG GG..AGGAGG GCAAGA.... ..TGACGGCC
 42_13   TTCAGAATGT TTCCCCGGCG TGTCAGAATC TCAACC.... ..GGTCGTCA
 42_3a   TTCAGAATGT TTCCCCGGCG TGTCAGAATC TCAACC.... ..GGTCGTCA
 42_4    GACAAGATGG TGATCTGGTG GG..AGGAGG GCAAGA.... ..TGACGGCC
 42_5a   TTCAGAATGT TTCCCCGGCG TGTCAGAATC TCAACC.... ..GGTCGTCA
 42_10   GACAAGATGG TGATCTGGTG GG..AGGAGG GCAAGA.... ..TGACGGCC
 42_3b   GACAAGATGG TGATCTGGTG GG..AGGAGG GCAAGA.... ..TGACGGCC
 42_11   TTCAGAATGT TTCCCCGGCG TGTCAGAATC TCAACC.... ..GGTCGTCA
 42_6b   TTCAGAATGT TTCCCCGGCG TGTCAGAATC TCAACC.... ..GGTCGTCA
 43_1    CTCAGAATGT TTCCCCGGTG CATCAGAATC TCAACC.... ..GGTCGTCA
 43_5    CTCAGAATGT TTCCCCGGTG CATCAGAATC TCAACC.... ..GGTCGTCA
 43_12   CTCAGAATGT TTCCCCGGTG CATCAGAATC TCAACC.... ..GGTCGTCA
 43_20   TTCAGAATGT TTCCCCGGCG TGTCAGAATC TCAACC.... ..GGTCGTCA
 43_21   TTCAGAATGT TTCCCCGGCG TGTCAGAATC TCAACC.... ..GCTCGTCA
 43_23   TTCAGAATGT TTCCCCGGCG TGTCAGAATC TCAACC.... ..GGTCGTCA
 43_25   TTCAGAATGT TTCCCCGGCG TGTCAGAATC TCAACC.... ..GGTCGTCA
 44_1    TTCAGAATGT TTCCCCGGCG TGTCAGAATC TCAACC.... ..GGTCGTCA
 44_5    TTCAGAATGT TTCCCCGGCG TGTCAGAATC TCAACC.... ..GGTTGTCA
223_10   .......... .......... .......... .......... ..........
223_2    .......... .......... .......... .......... ..........
223_4    .......... .......... .......... .......... ..........
223_5    .......... .......... .......... .......... ..........
223_6    .......... .......... .......... .......... ..........
223_7    .......... .......... .......... .......... ..........
 A3_4    TTTGGAATGC TTTCCCG... TGTCAGAATC TCAACCCGTT TCTGTCGTCA
 A3_5    TTTGGAATGC TTTCCCG... TGTCAGAATC TCAACCCGTT CCTGTCGTCA
 A3_7    TTTGGAATGC TTTCCCG... TGTCAGAATC TCAACCCGTT TCTGTCGTCA
 A3_3    TTTGGAATGC TTTCCCG... TGTCAGAATC TCAACCCGTT TCTGTCGTCA
 42_12   TTCAGAATGT TTCCCCGGCG TGTCAGAATC TCAACC.... ..GGTCGTCA
 AAV1    TTCAGAGTGC TTCCCCGGCG TGTCAGAATC TCAACC.... ..GGTCGTCA
 AAV2    TTTAGAGTGC TTTCCCG... TGTCAGAATC TCAACCCGTT TCTGTCGTCA
 AAV3    TGGGGAATGC TTCCCTGGAA TGTCAGAATC TCAACCCGTT TCTGTCGTCA
 AAV8    CTCAGAGTGT TTCCCCGGCG TGTCAGAATC TCAACC.... ..GGTCGTCA
 AAV9    CTCAGAGTGT TTCCCCGGCG TGTCAGAATC TCAACC.... ..GGTCGTCA
 AAV7    TTTAGAGTGT TTCCCCGGCG TGTCAGAATC TCAACC.... ..GGTCGTCA
 44_2    TTCAGAATGT TTCCCCGGCG TGTCAGAATC TCAACC.... ..GGTCGTCA
```

FIG. 1AQ

```
         2101                                                      2150
 42_2    GAAAGAGGAC GTATCGGAAA CTCTGTGCCA TTCATCATCT GCTGGGG.CG

42_8    GAAAGAGGAC GTATCGGAAA CTCTGTGCCA TTCATCATCT GCTAGGG.CG
 42_15   GAAAGAGGAC GTATCGGAAA CTCTGTGCCA TTCATCATCT GCTGGGG.CG
 42_5b   GAAAGAGGAC GTATCGGAAA CTCTGTGCCA TTCATCATCT GCTGGGG.CG
 42_1b   .AAGGTCGTG GAGTCCGCCA AG....GCCA TTCATCATCT GCTGGGG.CG
 42_13   GAAAGAGGAC GTATCGGAAA CTCTGTGCCA TTCATCATCT GCTGGGG.CG
 42_3a   GAAAGAGGAC GTATCGGAAA CTCTGTGCCA TTCATCATCT GCTGGGG.CG
 42_4    .AAGGTCGTG GAGTCCGCCA AG....GCCA TTCATCATCT GCTGGGG.CG
 42_5a   GAAAGAGGAC GTATCGGAAA CTCTGTGCCA TTCATCATCT GCTGGGG.CG
 42_10   AA....GGTC GTGAAGTCCG CCAAG.GCCA TTCATCATCT GCTGGGG.CG
 42_3b   AA....GGTC GTGGAGTCCG CCAAG.GCCA TTCATCATCT GCTGGGG.CG
 42_11   GAAAGAGGAC GTATCGGAAA CTCTGTGCCA TTCATCATCT GCTGGGG.CG
 42_6b   GAAAGAGGAC GTATCGGAAA CTCTGTGCCA TTCATCATCT GCTGGGG.CG
 43_1    GAAAAAAAAC GTATCAGAAA CTGTGTGCCA TTCATCATCT GCTGGGG.CG
 43_5    GAAAAAAAAC GTATCAGAAA CTGTGTGCCA TTCATCATCT GCTGGGG.CG
 43_12   GAAAAAAAAC GTATCAGAAA CTGTGTGCCA TTCATCATCT GCTGGGG.CG
 43_20   GAAAGAGGAC GTATCGGAAA CTCTGTGCGA TTCATCATCT GCTGGGG.CG
 43_21   GAAAGAGGAC GTATCGGAAA CTCTGTGCGA TTCATCATCT GCTGGGG.CG
 43_23   GAAAGAGGAC GTATCGGAAA CTCTGTGCGA TTCATCATCT GCTGGGG.CG
 43_25   GAAAGAGGAC GTATCGGAAA CTCTGTGCGA TTCATCATCT GCTGGGG.CG
 44_1    GAAAAAAGAC GTATCGGAAA CTCTGTGCGA TTCATCATCT GCTGGGG.CG
 44_5    GAAAAAAGAC GTATCGGAAA CTCTGTGCGA TTCATCATCT GCTGGGG.CG
 223_10  .......... .......... .......... .......... ..........
 223_2   .......... .......... .......... .......... ..........
 223_4   .......... .......... .......... .......... ..........
 223_5   .......... .......... .......... .......... ..........
 223_6   .......... .......... .......... .......... ..........
 223_7   .......... .......... .......... .......... ..........
 A3_4    GAAAAACG.. .TATCAGAAA CTTTGTTACA TTCATCATAT CATGGGA.AA
 A3_5    GAAAAACG.. .TATCAGAAA CTTTGTTACA TTCATCATAT CATGGGA.AA
 A3_7    GAAAAACG.. .TATCAGAAA CTTTGTTACA TTCATCATAT CATGGGA.AA
 A3_3    GAAAAACG.. .TATCAGAAA CTTTGTTACA TTCATCATAT CATGGGA.AA
 42_12   GAAAGAGGAC GTATCGGAAA CTCTGTGCCA TTCATCATCT GCTGGGG.CG
 AAV1    GAAAGAGGAC GTATCGGAAA CTCTGTGCCA TTCATCATCT GCTGGGG.CG
 AAV2    AAAAGGCG.. .TATCAGAAA CTGTGCTACA TTCATCATAT CATGGGA.AA
 AAV3    AAAAGAAGAC TTATCAGAAA CTGTGTCCAA TTCATCATAT CCTGGGA.AG
 AAV8    GAAAGAGGAC GTATCGGAAA CTCTGTGCGA TTCATCATCT GCTGGGG.CG
 AAV9    GAAAGAGGAC GTATCGGAAA CTCTGTGCGA TTCATCATCT GCTGGGG.CG
 AAV7    GAAAAAGAC GTATCGGAAA CTCTGCGCGA TTCATCATCT GCTGGGG.CG
 44_2    GAAAAAAGAC GTATCGGAAA CTCTGTGCGA TTCATCATCT GCTGGGGGCG
```

FIG. 1AR

```
       2151                                                      2200
 42_2   GGCTCCCGAG ATTGCTTGCT CGGCCTGCGA TCTGGTCAAC GTGGACCTGG
 42_8   GGCTCCCGAG ATTGCTTGCT CGGCCTGCGA TCTGGTCAAC GTGGACCTGG
 42_15  GGCTCCCGAG ATTGCTTGCT CGGCCTGCGA TCTGGTCAAC GTGGACCTGG
 42_5b  CGCTCCCGAG ATTGCTTGCT CGGCCTGCGA TCTGGTCAAC GTGGACCTGG
 42_1b  GGCTCCCGAG ATTGCTTGCT CGGCCTGCGA TCTGGTCAAC GTGGACCTGG
 42_13  GGCTCCCGAG ATTGCTTGCT CGGCCTGCGA TCTGGTCAAC GTGGACCTGG
 42_3a  GGCTCCCGAG ATTGCTTGCT CGGCCTGCGA TCTGGTCAAC GTGGACCTGG
 42_4   GGCTCCCGAG ATTGCTTGCT CGGCCTGCGA TCTGGTCAAC GTGGACCTGG
 42_5a  GGCTCCCGAG ATTGCTTGCT CGGCCTGCGA TCTGGTCAAC GTGGACCTGG
 42_10  GGCTCCCGAG ATTGCTTGCT CGGCCTGCGA TCTGGTCAAC GTGGACCTGG
 42_3b  GGCTCCCGAG ATTGCTTGCT CGGCCTGCGA TCTGGTCAAC GTGGACCTGG
 42_11  GGCTCCCGAG ATTGCTTGCT CGGCCTGCGA TCTGGTCAAC GTGGACCTGG
 42_6b  GGCTCCCGAG ATTGCTTGCT CGGCCTGCGA TCTGGTCAAC GTGGACCTGG
 43_1   GGCACCCGAG ATTGCTTGCT CGGCCTGCGA TCTGGTCAAC GTGGACCTGG
 43_5   GGCACCCGAG ATTGCTTGCT CGGCCTGCGA TCTGGTCAAC GTGGACCTGG
 43_12  GGCACCCGAG ATTGCTTGCT CGGCCTGCGA TCTGGTCAAC GTGGACCTGG
 43_20  GGCTCCCGAG ATTGCTTGCT CGGCCTGCGA TCTGGTCAAC GTGGACCTGG
 43_21  GGCTCCCGAG ATTGCTTGCT CGGCCTGCGA TCTGGTCAAC GTGGACCTGG
 43_23  GGCTCCCGAG ATTGCTTGCT CGGCCTGCGA TCTGGTCAAC GTGGACCTGG
 43_25  GGCTCCCGAG ATTGCTTGCT CGGCCTGCGA TCTGGTCAAC GTGGACCTGG
 44_1   GGCACCCGAG ATTGCTTGCT CGGCCTGCGA TCTGGTCAAC GTGGACCTAG
 44_5   GGCACCCGAG ATTGCTTGCT CGGCCTGCGA TCTGGTCAAC GTGGACCTAG
 223_10 .......... .......... .......... .......... ..........
 223_2  .......... .......... .......... .......... ..........
 223_4  .......... .......... .......... .......... ..........
 223_5  .......... .......... .......... .......... ..........
 223_6  .......... .......... .......... .......... ..........
 223_7  .......... .......... .......... .......... ..........
 A3_4   AGAACCAGAC ...GCCTGCA CTGCCTGCGA CCTGGTAAAT GTGGACTTGG
 A3_5   AGTACCAGAC ...GCCTGCA CTGCCTGCGA CCTGGTAAAT GTGGACTTGG
 A3_7   AGTACCAGAC ...GCCTGCA CTGCCTGCGA CCTGGTAAAT GTGGACTTGG
 A3_3   AGTACCAGAC ...GCCTGCA CTGCCTGCGA CCTGGTAAAT GTGGACTTGG
 42_12  GGCTCCCGAG ATTGCTTGCT CGGCCTGCGA TCTGGTCAAC GTGGACCTGG
 AAV1   GGCTCCCGAG ATTGCTTGCT CGGCCTGCGA TCTGGTCAAC GTGGACCTGG
 AAV2   GGTGCCAGAC ...GCTTGCA CTGCCTGCGA TCTGGTCAAT GTGGATTTGG
 AAV3   GGCACCCGAG ATTGCCTGTT CGGCCTGCGA TTTGGCCAAT GTGGACTTGG
 AAV8   GGCTCCCGAG ATTGCTTGCT CGGCCTGCGA TCTGGTCAAC GTGGACCTGG
 AAV9   GGCTCCCGAG ATTGCTTGCT CGGCCTGCGA TCTGGTCAAC GTGGACCTGG
 AAV7   GGCGCCCGAG ATTGCTTGCT CGGCCTGCGA CCTGGTCAAC GTGGACCTGG
 44_2   GGCACCCGAG ATTGCTTGCT CGGCCTGCGA TCTGGTCAAC GTGGACCTAG
```

FIG. 1AS

```
                                                              2201                                                                           2250
                                                                            Rep 78 stop        vp1 start
        42_2    ATGACCGTGT  TTCTGAGCAA  TAAATGACTT  AAACCAGGTA  TGGCTGCCGA
        42_8    ATGACTGTGT  TTCTGAGCAA  TAAATGACTT  AAACCAGGTA  TGGCTGCCGA
        42_15   ATGACTGTGT  TTCTGAGCAA  TAAATGACTT  AAACCAGGTA  TGGCTGCCGA
        42_5b   ATGACTGTGT  TTCTGAGCAA  TAAATGACTT  AAACCAGGTA  TGGCTGCCGA
        42_1b   ATGACTGTGT  TTCTGAGCAA  TAAATGACTT  AAACCAGGTA  TGGCTGCCGA
        42_13   ATGACTGTGT  TTCTGAGCAA  TAAATGACTT  AAACCAGGTA  TGGCTGCCGA
        42_3a   ATGACTGTGT  TTCTGAGCAA  TAAATGACTT  AAACCAGGTA  TGGCTGCCGA
        42_4    ATGACTGTGT  TTCTGAGCAA  TAAATGACTT  AAACCAGGTA  TGGCTGCCGA
        42_5a   ATGACTGTGT  TTCTGAGCAA  TAAATGACTT  AAACCAGGTA  TGGCTGCCGA
        42_10   ATGACTGTGT  TTCTGAGCAA  TAAATGACTT  AAACCAGGTA  TGGCTGCCGA
        42_3b   ATGACTGTGT  TTCTGAGCAA  TAAATGACTT  AAACCAGGTA  TGGCTGCCGA
        42_11   ATGACTGTGT  TTCTGAGCAA  TAAATGACTT  AAACCAGGTA  TGGCTGCCGA
        42_6b   ATGACTGTGT  TTCTGAGCAA  TAAATGACTT  AAACCAGGTA  TGGCTGCCGA
        43_1    ACGACTGTGT  TTCTGAGCAA  TAAATGACTT  AAACCAGGTA  TGGCTGCCGA
        43_5    ACGACTGTGT  TTCTGAGCAA  TAAATGACTT  AAACCAGGTA  TGGCTGCCGA
        43_12   ACGACTGTGT  TTCTGAGCAA  TAAATGACTT  AAACCAGGTA  TGGCTGCCGA
        43_20   ATGACTGTGT  TTCTGAGCAA  TAAATGACTT  AAACCAGGTA  TGGCTGCCGA
        43_21   ATGACTGTGT  TTCTGAGCAA  TAAATGACTT  AAACCAGGTA  TGGCTGCCGA
        43_23   ATGACTGTGT  TTCTGAGCAA  TAAATGACTT  AAACCAGGTA  TGGCTGCCGA
        43_25   ATGACTGTGT  TTCTGAGCAA  TAAATGACTT  AAACCAGGTA  TGGCTGCCGA
        44_1    ATGACTGTGT  TTCTGAGCAA  TAAATGACTT  AAACCAGGTA  TGGCTGCCGA
        44_5    ATGACTGTGT  TTCTGAGCAA  TAAATGACTT  AAACCAGGTA  TGGCTGCCGA
        223_10  ..........  ..........  ..........  ..........  ..........
        223_2   ..........  ..........  ..........  ..........  ..........
        223_4   ..........  ..........  ..........  ..........  ..........
        223_5   ..........  ..........  ..........  ..........  ..........
        223_6   ..........  ..........  ..........  ..........  ..........
        223_7   ..........  ..........  ..........  ..........  ..........
        A3_4    ATGACTGTAT  TTCTGAGCAA  TAAATGACTT  AAATCAGGTA  TGGCTGCTGA
        A3_5    ATGACTGTAT  TTCTGAGCAA  TAAATGACTT  AAATCAGGTA  TGGCTGCTGA
        A3_7    ATGACTGTAT  TTCTGAGCAA  TAAATGACTT  AAATCAGGTA  TGGCTGCTGA
        A3_3    ATGACTGTAT  TTCTGAGCAA  TAAATGACTT  AAATCAGGTA  TGGCTGCTGA
        42_12   ATGACTGTGT  TTCTGAGCAA  TAAATGACTT  AAACCAGGTA  TGGCTGCCGA
        AAV1    ATGACTGTGT  TTCTGAGCAA  TAAATGACTT  AAACCAGGTA  TGGCTGCCGA
        AAV2    ATGACTGCAT  CTTTGAACAA  TAAATGATTT  AAATCAGGTA  TGGCTGCCGA
        AAV3    ATGACTGTGT  TTCTGAGCAA  TAAATGACTT  AAACCAGGTA  TGGCTGCTGA
        AAV8    ATGACTGTGT  TTCTGAGCAA  TAAATGACTT  AAACCAGGTA  TGGCTGCCGA
        AAV9    ATGACTGTGT  TTCTGAGCAA  TAAATGACTT  AAACCAGGTA  TGGCTGCCGA
        AAV7    ACGACTGCGT  TTCTGAGCAA  TAAATGACTT  AAACCAGGTA  TGGCTGCCGA
        44_2    ATGACTGTGT  TTCTGAGCAA  TAAATGACTT  AAACCAGGTA  TGGCTGCCGA
                                                         Rep78 stop          vp1 start
```

FIG. 1AT

```
        2251                                                              2300
                                                    Rep68 stop
   42_2   TGGTTATCTT CCAGATTGGC TCGAGGACAA CCTCTCTGAG GGCATTCGCG
   42_8   TGGTTATCTT CCAGATTGGC TCGAGGACAA CCTCTCTGAG GGCATTCGCG
  42_15   TGGTTATCTT CCAGATTGGC TCGAGGACAA CCTCTCTGAG GGCATTCGCG
  42_5b   TGGTTATCTT CCAGATTGGC TCGAGGACAA CCTCTCTGAG GGCATTCGCG
  42_1b   TGGTTATCTT CCAGATTGGC TCGAGGACAA CCTCTCTGAG GGCATTCGCG
  42_13   TGGTTATCTT CCAGATTGGC TCGAGGACAA CCTCTCTGAG GGCATTCGCG
  42_3a   TGGTCATCTT CCAGATTGGC TCGAGGACAA CCTCTCTGAG GGCATTCGCG
   42_4   TGGTTATCTT CCAGATTGGC TCGAGGACAA CCTCTCTGAG GGCATTCGCG
  42_5a   TGGTTATCTT CCAGATTGGC TCGAGGACAA CCTCTCTGAG GGCATTCGCG
  42_10   TGGTTATCTT CCAGATTGGC TCGAGGACAA CCTCTCTGAG GGCATTCGCG
  42_3b   TGGTTATCTT CCAGATTGGC TCGAGGACAA CCTCTCTGAG GGCATTCGCG
  42_11   TGGTTATCTT CCAGATTGGC TCGAGGACAA CCTCTCTGAG GGCATTCGCG
  42_6b   TGGTTATCTT CCAGATTGGC TCGAGGACAA CCTCTCTGAG GGCATTCGCG
   43_1   TGGTTATCTT CCAGATTGGC TTGAGGACAA CCTCTCTGAG GGCATTCGCG
   43_5   TGGTTATCTT CCAGATTGGC TTGAGGACAA CCTCTCTGAG GGCATTCGCG
  43_12   TGGTTATCTT CCAGATTGGC TTGAGGACAA CCTCTCTGAG GGCATTCGCG
  43_20   TGGTTATCTT CCAGATTGGC TCGAGGACAA CCTCTCTGAG GGCATTCGCG
  43_21   TGGTTATCTT CCAGATTGGC TCGAGGACAA CCTCTCTGAG GGCATTCGCG
  43_23   TGGTTATCTT CCAGATTGGC TCGAGGACAA CCTCTCTGAG GGCATTCGCG
  43_25   TGGTTATCTT CCAGATTGGC TCGAGGACAA CCTCTCTGAG GGCATTCGCG
   44_1   TGGTTATCTT CCAGATTGGC TCGAGGACAA CCTCTCTGAG GGCATTCGCG
   44_5   TGGTTATCTT CCAGATTGGC TCGAGGACAA CCTCTCTGAG GGCATTCGCG
 223_10   .......... .......... .......... .......... ..........
  223_2   .......... .......... .......... .......... ..........
  223_4   .......... .......... .......... .......... ..........
  223_5   .......... .......... .......... .......... ..........
  223_6   .......... .......... .......... .......... ..........
  223_7   .......... .......... .......... .......... ..........
   A3_4   CGGTTATCTT CCAGATTGGC TCGAGGACAC TCTCTCTGAA GGAATCAGAC
   A3_5   CGGTTATCTT CCAGATTGGC TCGAGGACAC TCTCTCTGAA GGAATCAGAC
   A3_7   CGGTTATCTT CCAGATTGGC TCGAGGACAC TCTCTCTGAA GGAATCAGAC
   A3_3   CGGTTATCTT CCAGATTGGC TCGAGGACAC TCTCTCTGAA GGAATCAGAC
  42_12   TGGTTATCTT CCAGATTGGC TCGAGGACAA CCTCTCTGAG GGCATCCGCG
   AAV1   TGGTTATCTT CCAGATTGGC TCGAGGACAA CCTCTCTGAG GGCATTCGCG
   AAV2   TGGTTATCTT CCAGATTGGC TCGAGGACAC TCTCTCTGAA GGAATAAGAC
   AAV3   CGGTTATCTT CCAGATTGGC TCGAGGACAA CCTTTCTGAA GGCATTCGTG
   AAV8   TGGTTATCTT CCAGATTGGC TCGAGGACAA CCTCTCTGAG GGCATTCGCG
   AAV9   TGGTTATCTT CCAGATTGGC TCGAGGACAA CCTCTCTGAG GGCATTCGCG
   AAV7   TGGTTATCTT CCAGATTGGC TCGAGGACAA CCTCTCTGAG GGCATTCGCG
   44_2   TGGTTATCTT CCAGATTGGC TCGAGGACAA CCTCTCTGAG GGCATTCGCG
                                                    Rep 68 stop
```

FIG. 1AU

```
          2301                                                    2350
   42_2   AGTGGTGGGA CTTGAAACCT GGAGCCCCGA AACCCAAAGC CAACCAGCAA

42_8   AGTGGTGGGA CTTGAAACCT GGAGCCCCGA AACCCAAAGC CAACCAGCAA
  42_15   AGTGGTGGGA CTTGAAACCT GGAGCCCCGA AACCCAAAGC CAACCAGCAA
  42_5b   AGTGGTGGGA CTTGAAACCT GGAGCCCCGA AACCCAAAGC CAACCAGCAA
  42_1b   AGTGGTGGGA CTTGAGACCT GGAGCCCCGA AACCCAAAGC CAACCAGCAA
  42_13   AGTGGTGGGA CTTGAAACCT GGAGCCCCGA AACCCAAAGC CAACCAGCAA
  42_3a   AGTGGTGGGA CTTGAAACCT GGAGCCCCGA AACCCAAAGC CAACCAGCAA
   42_4   AGTGGTGGGA CTTGAAACCT GGAGCCCCGA AACCCAAAGC CAACCAGCAA
  42_5a   AGTGGTGGGA CTTGAAACCT GGAGCCCCGA AACCCAAAGC CAACCAGCAA
  42_10   AGTGGTGGGA CTTGAAACCT GGAGCCCCGA AACCCAAAGC CAACCAGCAA
  42_3b   AGTGGTGGGA CTTGAAACCT GGAGCCCCGA AACCCAAAGC CAACCAGCAA
  42_11   AGTGGTGGGA CTTGAAACCT GGAGCCCCGA AACCCAAAGC CAACCAGCAA
  42_6b   AGTGGTGGGA CTTGAAACCT GGAGCCCCGA AACCCAAAGC CAACCAGCAA
   43_1   AGTGGTGGGA CCTGAAACCT GGAGCCCCGA AACCCAAAGC CAACCAGCAA
   43_5   AGTGGTGGGA CCTGAAACCT GGAGCCCCGA AACCCAAAGC CAACCAGCAA
  43_12   AGTGGTGGGA CCTGAAACCT GGAGCCCCGA AACCCAAAGC CAACCAGCAA
  43_20   AGTGGTGGGA CTTGAAACCT GGAGCCCCGA AACCCAAAGC CAACCAGCAA
  43_21   AGTGGTGGGA CTTGAAACCT GGAGCCCCGA AACCCAAAGC CAACCAGCAA
  43_23   AGTGGTGGGA CTTGAAACCT GGAGCCCCGA AACCCAAAGC CAACCAGCAA
  43_25   AGTGGTGGGA CTTGAAACCT GGAGCCCCGA AACCCAAAGC CAACCAGCAA
   44_1   AGTGGTGGGA CTTGAAACCT GGAGCCCCGA AACCCAAAGC CAACCAGCAA
   44_5   AGTGGTGGGA CTTGAAACCT GGAGCCCCGA AACCCAAAGC CAACCAGCAA
 223_10   .......... .......... .......... .......... ..........
  223_2   .......... .......... .......... .......... ..........
  223_4   .......... .......... .......... .......... ..........
  223_5   .......... .......... .......... .......... ..........
  223_6   .......... .......... .......... .......... ..........
  223_7   .......... .......... .......... .......... ..........
   A3_4   AGTGGTGGAA GCTCAAACCT GGCCCACCAC CGCCGAAACC TAACCAACAA
   A3_5   AGTGGTGGAA GCTCAAACCT GGCCCACCAC CGCCGAAACC TAACCAACAA
   A3_7   AGTGGTGGAA GCTCAAACCT GGCCCACCAC CGCCGAAACC TAACCAACAA
   A3_3   AGTGGTGGAA GCTCAAACCT GGCCCACCAC CGCCGAAACC TAACCAACAA
  42_12   AGTGGTGGGA CTTGAAACCT GGAGCCCCGA AACCCAAAGC CAACCAGCAA
   AAV1   AGTGGTGGGA CTTGAAACCT GGAGCCCCGA AGCCCAAAGC CAACCAGCAA
   AAV2   AGTGGTGGAA GCTCAAACCT GGCCCACCAC CACCAAAGCC CGCAGAGCGG
   AAV3   AGTGGTGGGC TCTGAAACCT GGAGTCCCTC AACCCAAAGC GAACCAACAA
   AAV8   AGTGGTGGGC GCTGAAACCT GGAGCCCCGA AGCCCAAAGC CAACCAGCAA
   AAV9   AGTGGTGGGC GCTGAAACCT GGAGCCCCGA AGCCCAAAGC CAACCAGCAA
   AAV7   AGTGGTGGGA CCTGAAACCT GGAGCCCCGA AACCCAAAGC CAACCAGCAA
   44_2   AGTGGTGGGA CTTGAAACCT GGAGCCCCGA AACCCAAAGC CAACCAGCAA
```

FIG. 1AV

|       | 2351 | | | | 2400 |
|---|---|---|---|---|---|
| 42_2  | AAGCAGGACG | ACGGCCGGGG | TCTGGTGCTT | CCTGGCTACA | AGTACCTCGG |
| 42_8  | AAGCAGGACG | ACGGCCGGGG | TCTGGTGCTT | CCTGGCTACA | AGTACCTCGG |
| 42_15 | AAGCAGGACG | ACGGCCGGGG | TCTGGTGCTT | CCTGGCTACA | AGTACCTCGG |
| 42_5b | AAGCAGGACG | ACGGCCGGGG | TCTGGTGCTT | CCTGGCTACA | AGTACCTCGG |
| 42_1b | AAGCAGGACG | ACGGCCGGGG | TCTGGTGCTT | CCTGGCTACA | AGTACCTCGG |
| 42_13 | AAGCAGGACG | ACGGCCGGGG | TCTGGTGCTT | CCTGGCTACA | AGTACCTCGG |
| 42_3a | AAGCAGGACG | ACGGCCGGGG | TCTGGTGCTT | CCTGGCTACA | AGTACCTCGG |
| 42_4  | AAGCAGGACG | ACGGCCGGGG | TCTGGTGCTT | CCTGGCTACA | AGTACCTCGG |
| 42_5a | AAGCAGGACG | ACGGCCGGGG | TCTGGTGCTT | CCTGGCTACA | AGTACCTCGG |
| 42_10 | AAGCAGGACG | ACGGCCGGGG | TCTGGTGCTT | CCTGGCTACA | AGTACCTCGG |
| 42_3b | AAGCAGGACG | ACGGCCGGGG | TCTGGTGCTT | CCTGGCTACA | AGTACCTCGG |
| 42_11 | AAGCAGGACG | ACGGCCGGGG | TCTGGTGCTT | CCTGGCTACA | AGTACCTCGG |
| 42_6b | AAGCAGGACG | ACGGCCGGGG | TCTGGTGCTT | CCTGGCTACA | AGTACCTCGG |
| 43_1  | AAGCAGGACG | ACGGCCGGGG | TCTGGTGCTT | CCTGGCTACA | AGTACCTCGG |
| 43_5  | AAGCAGGACG | ACGGCCGGGG | TCTGGTGCTT | CCTGGCTACA | AGTACCTCGG |
| 43_12 | AAGCAGGACG | ACGGCCGGGG | TCTGGTGCTT | CCTGGCTACA | AGTACCTCGG |
| 43_20 | AAGCAGGACG | ACGGCCGGGG | TCTGGTGCTT | CCTGGCTACA | AGTACCTCGG |
| 43_21 | AAGCAGGACG | ACGGCCGGGG | TCTGGTGCTT | CCTGGCTACA | AGTACCTCGG |
| 43_23 | AAGCAGGACG | ACGGCCGGGG | TCTGGTGCTT | CCTGGCTACA | AGTACCTCGG |
| 43_25 | AAGCAGGACG | ACGGCCGGGG | TCTGGTGCTT | CCTGGCTACA | AGTACCTCGG |
| 44_1  | AAGCAGGACG | ACGGCCGGGG | TCTGGTGCTT | CCTGGCTACA | AGTACCTCGG |
| 44_5  | AAGCAGGACG | ACGGCCGGGG | TCTGGTGCTT | CCTGGCTACA | AGTACCTCGG |
| 223_10 | .......... | .......... | .......... | .......... | .......... |
| 223_2  | .......... | .......... | .......... | .......... | .......... |
| 223_4  | .......... | .......... | .......... | .......... | .......... |
| 223_5  | .......... | .......... | .......... | .......... | .......... |
| 223_6  | .......... | .......... | .......... | .......... | .......... |
| 223_7  | .......... | .......... | .......... | .......... | .......... |
| A3_4  | CACCGGGACG | ACAGTAGGGG | TCTTGTGCTT | CCTGGGTACA | AGTACCTCGG |
| A3_5  | CACCGGGACG | ACAGTAGGGG | TCTTGTGCTT | CCTGGGTACA | AGTACCTCGG |
| A3_7  | CACCGGGACG | ACAGTAGGGG | TCTTGTGCTT | CCTGGGTACA | AGTACCTCGG |
| A3_3  | CACCGGGACG | ACAGTAGGGG | TCTTGTGCTT | CCTGGGTACA | AGTACCTCGG |
| 42_12 | AAGCAGGACG | ACGGCCGGGG | TCTGGTGCTT | CCTGGCTACA | AGTACCTCGG |
| AAV1  | AAGCAGGACG | ACGGCCGGGG | TCTGGTGCTT | CCTGGCTACA | AGTACCTCGG |
| AAV2  | CATAAGGACG | ACAGCAGGGG | TCTTGTGCTT | CCTGGGTACA | AGTACCTCGG |
| AAV3  | CACCAGGACA | ACCGTCGGGG | TCTTGTGCTT | CCGGGTTACA | AATACCTCGG |
| AAV8  | AAGCAGGACG | ACGGCCGGGG | TCTGGTGCTT | CCTGGCTACA | AGTACCTCGG |
| AAV9  | AAGCAGGACG | ACGGCCGGGG | TCTGGTGCTT | CCTGGCTACA | AGTACCTCGG |
| AAV7  | AAGCAGGACA | ACGGCCGGGG | TCTGGTGCTT | CCTGGCTACA | AGTACCTCGG |
| 44_2  | AAGCAGGACG | ACGGCCGGGG | TCTGGTGCTT | CCTGGCTACA | AGTACCTCGG |

FIG. 1AW

```
           2401                                                              2450
   42_2    ACCCTTCAAC GGACTCGACA AGGGAGAGCC GGTCAACGAG GCAGACGCCG
   42_8    ACCCTTCAAC GGACTCGACA AGGGGGAGCC CGTCAACGCG GCGGACGCAG
   42_15   ACCCTTCAAC GGACTCGACA AGGGGGAGCC CGTCAACGCG GCGGACGCAG
   42_5b   ACCCTTCAAC GGACTCGACA AGGGAGAGCC GGTCAACGAG GCAGACGCCG
   42_1b   ACCCTTCAAC GGACTCGACA AGGGAGAGCC GGTCAACGAG GCAGACGCCG
   42_13   ACCCTTCAAC GGACTCGACA AGGGGGAGCC CGTCAACGCG GCGGACGCAG
   42_3a   ACCCTTCAAC GGACTCGACA AGGGGGAGCC CGTCAACGCG GCGGACGCAG
   42_4    ACCCTTCAAC GGACTCGACA AGGGAGAGCC GGTCAACGAG GCAGACGCCG
   42_5a   ACCCTTCAAC GGACTCGACA AGGGAGAGCC GGTCAACGAG GCAGACGCCG
   42_10   ACCCTTCAAC GGACTCGACA AGGGAGAGCC GGTCAACGAG GCAGACGCCG
   42_3b   ACCCTTCAAC GGACTCGACA AGGGAGAGCC GGTCAACGAG GCAGACGCCG
   42_11   ACCCTTCAAC GGACTCGACA AGGGAGAGCC GGTCAACGCG GCGGACGCAG
   42_6b   ACCCTTCAAC GGACTCGACA AGGGAGAGCC GGTCAACGAG GCAGACGCCG
   43_1    ACCCTTCAAC GGACTCGACA AGGGGGAGCC CGTCAACGCG GCGGACGCAG
   43_5    ACCCTTCAAC GGACTCGACA AGGGGGAGCC CGTCAACGCG GCGGACGCAG
   43_12   ACCCTTCAAC GGACTCGACA AGGGGGAGCC CGTCAACGCG GCGGACGCAG
   43_20   ACCCTTCAAC GGACTCGACA AGGGGGAGCC CGTCAACGCG GCGGACGCAG
   43_21   ACCCTTCAAC GGACTCGACA AGGGGGAGCC CGTCAACGCG GCGGACGCAG
   43_23   ACCCTTCAAC GGACTCGACA AGGGGGAGCC CGTCAACGCG GCGGACGCAG
   43_25   ACCCTTCAAC GGACTCGACA AGGGGGAGCC CGTCAACGCG GCGGACGCAG
   44_1    ACCCTTCAAC GGACTCGACA AGGGGGAGCC CGTCAACGCG GCGGACGCAG
   44_5    ACCCTTCAAC GGACTCGACA AGGGGGAGCC CGTCAACGCG GCGGACGCAG
  223_10   .......... .......... .......... .......... ..........
  223_2    .......... .......... .......... .......... ..........
  223_4    .......... .......... .......... .......... ..........
  223_5    .......... .......... .......... .......... ..........
  223_6    .......... .......... .......... .......... ..........
  223_7    .......... .......... .......... .......... ..........
   A3_4    ACCCTTCAAC GGACTCGACA AAGGAGAGCC GGTCAACGAG GCAGACGCCG
   A3_5    ACCCTTCAAC GGACTCGACA AAGGAGAGCC GGTCAACGAG GCAGACGCCG
   A3_7    ACCCTTCAAC GGACTCGACA AAGGAGAGCC GGTCAACGAG GCAGACGCCG
   A3_3    ACCCTTCAAC GGACTCGACA AAGGAGAGCC GGTCAACGAG GCAGACGCCG
   42_12   ACCCTTCAAC GGACTCGACA AGGGAGAGCC GGTCAACGAG GCAGACGCCG
   AAV1    ACCCTTCAAC GGACTCGACA AGGGGGAGCC CGTCAACGCG GCGGACGCAG
   AAV2    ACCCTTCAAC GGACTCGACA AGGGAGAGCC GGTCAACGAG GCAGACGCCG
   AAV3    ACCCGGTAAC GGACTCGACA AAGGAGAGCC GGTCAACGAG GCGGACGCGG
   AAV8    ACCCTTCAAC GGACTCGACA AGGGGGAGCC CGTCAACGCG GCGGACGCAG
   AAV9    ACCCTTCAAC GGACTCGACA AGGGGGAGCC CGTCAACGCG GCGGACGCAG
   AAV7    ACCCTTCAAC GGACTCGACA AGGGGGAGCC CGTCAACGCG GCGGACGCAG
   44_2    ACCCTTCAAC GGACTCGACA AGGGGGAGCC CGTCAACGCG GCGGACGCAG
```

FIG. 1AX

```
             2451                                                              2500
   42_2    CGGCCCTCGA GCACG.ACAA GGCCTACGAC AAGCAGCTCG AGCAGGGGGA
   42_8    CGGCCCTCGA GCACG.ACAA GGCCTACGAC CAGCAGCTCA AAGCGGGTGA
  42_15    CGGCCCTCGA GCACG.ACAA GGCCTACGAC CAGCAGCTCA AAGCGGGTGA
  42_5b    CGGCCCTCGA GCACG.ACAA GGCCTACGAC AAGCAGCTCG AGCAGGGGGA
  42_1b    CGGCCCTCGA GCACG.ACAA GGCCTACGAC AAGCAGCTCG AGCAGGGGGA
  42_13    CGGCCCTCGA GCACG.ACAA GGCCTACGAC CAGCAGCTCA AAGCGGGTGA
  42_3a    CGGCCCTCGA GCACG.ACAA GGCCTACGAC CAGCAGCTCA AAGCGGGTGA
   42_4    CGGCCCTCGA GCACG.ACAA GGCCTACGAC AAGCAGCTCG AGCAGGGGGA
  42_5a    CGGCCCTCGA GCACG.ACAA GGCCTACGAC AAGCAGCTCG AGCAGGGGGA
  42_10    CGGCCCTCGA GCACG.ACAA GGCCTACGAC AAGCAGCTCG AGCAGGGGGA
  42_3b    CGGCCCTCGA GCACG.ACAA GGCCTACGAC AAGCAGCTCG AGCAGGGGGA
  42_11    CGGCCCTCGA GCACG.ACAA GGCCTACGAC CAGCAGCTCA AAGCGGGTGA
  42_6b    CGGCCCTCGA GCACG.ACAA GGCCTACGAC AAGCAGCTCG AGCAGGGGGA
   43_1    CGGCCCTCGA GCACG.ACAA GGCCTACGAC CAGCAGCTCA AAGCGGGTGA
   43_5    CGGCCCTCGA GCACG.ACAA GGCCTACGAC CAGCAGCTCA AAGCGGGTGA
  43_12    CGGCCCTCGA GCACG.ACAA GGCCTACGAC CAGCAGCTCA AAGCGGGTGA
  43_20    CGGCCCTCGA GCACG.ACAA AGCCTACGAC CAGCAGCTCA AAGCGGGTGA
  43_21    CGGCCCTCGA GCACG.ACAA AGCCTACGAC CAGCAGCTCA AAGCGGGTGA
  43_23    CGGCCCTCGA GCACG.ACAA AGCCTACGAC CAGCAGCTCA AAGCGGGTGA
  43_25    CGGCCCTCGA GCACG.ACAA AGCCTACGAC CAGCAGCTCA AAGCGGGTGA
   44_1    CGGCCCTCGA GCACG.ACAA GGCCTACGAC CAGCAGCTCA AAGCGGGTGA
   44_5    CGGCCCTCGA GCACG.ACAA GGCCTACGAC CAGCAGCTCA AAGCGGGTGA
 223_10    .......... .......CAA GGCCTACGAC CAGCAGCTCA AAGCGGGTGA
  223_2    .......... .......CAA GGCCTACGAC CAGCAGCTCA AAGCGGGTGA
  223_4    .......... .......CAA GGCCTACGAC CAGCAGCTCA AAGCGGGTGA
  223_5    .......... .......CAA GGCCTACGAC CAGCAGCTCA AAGCGGGTGA
  223_6    .......... .......CAA GGCCTACGAC CAGCAGCTCA AAGCGGGTGA
  223_7    .......... .......CAA GGCCTACGAC CAGCAGCTCA AAGCGGGTGA
   A3_4    CGGCCCTCGA GCACG.ACAA AGCCTACGAC CACCAGCTCA AGCAAGGGGA
   A3_5    CGGCCCTCGA GCACG.ACAA AGCCTACGAC CACCAGCTCA AGCAAGGGGA
   A3_7    CGGCCCTCGA GCACG.ACAA AGCCTACGAC CACCAGCTCA AGCAAGGGGA
   A3_3    CGGCCCTCGA GCACG.ACAA AGCCTACGAC CACCAGCTCA AGCAAGGGGA
  42_12    CGGCCCTCGA GCACG.ACAA GGCCTACGAC AAGCAGCTCG AGCAGGGGGA
   AAV1    CGGCCCTCGA GCACG.ACAA GGCCTACGAC CAGCAGCTCA AAGCGGGTGA
   AAV2    CGGCCCTCGA GCACGTACAA AGCCTACGAC CGGCAGCTCG ACAGCGGAGA
   AAV3    CAGCCCTCGA ACACG.ACAA AGCTTACGAC CAGCAGCTCA AGGCCGGTGA
   AAV8    CGGCCCTCGA GCACG.ACAA GGCCTACGAC CAGCAGCTGC AGGCGGGTGA
   AAV9    CGGCCCTCGA GCACG.GCAA GGCCTACGAC CAGCAGCTGC AGGCGGGTGA
   AAV7    CGGCCCTCGA GCACG.ACAA GGCCTACGAC CAGCAGCTCA AAGCGGGTGA
   44_2    CGGCCCTCGA GCACG.ACAA GGCCTACGAC CAGCAGCTCA AAGCGGGTGA
```

FIG. 1AY

```
         2501                                                          2550
 42_2    CAACCCGTAC CTCAAGTACA ACCACGCCGA CGCCGAGTTT CAGGAGCGTC
 42_8    CAATCCGTAC CTGCGGTATA ACCACGCCGA CGCCGAGTTT CAGGAGCGTC
 42_15   CAATCCGTAC CTGCGGTATA ACCACGCCGA CGCCGAGTTT CAGGAGCGTC
 42_5b   CAACCCGTAC CTCAAGTACA ACCACGCCGA CGCCGAGTTT CAGGAGCGTC
 42_1b   CAACCCGTAC CTCAAGTACA ACCACGCCGA CGCCGAGTTT CAGGAGCGTC
 42_13   CAATCCGTAC CTGCGGTATA ACCACGCCGA CGCCGAGTTT CAGGAGCGTC
 42_3a   CAATCCGTAC CTGCGGTATA ACCACGCCGA CGCCGAGTTT CAGGAGCGTC
 42_4    CAACCCGTAC CTCAAGTACA ACCACGCCGA CGCCGAGTTT CAGGAGCGTC
 42_5a   CAACCCGTAC CTCAAGTACA ACCACGCCGA CGCCGAGTTT CAGGAGCGTC
 42_10   CAACCCGTAC CTCAAGTACA ACCACGCCGA CGCCGAGTTT CAGGAGCGTC
 42_3b   CAACCCGTAC CTCAAGTACA ACCACGCCGA CGCCGAGTTT CAGGAGCGTC
 42_11   CAATCCGTAC CTGCGGTATA ACCACGCCGA CGCCGAGTTT CAGGAGCGTC
 42_6b   CAACCCGTAC CTCAAGTACA ACCACGCCGA CGCCGAGTTT CAGGAGCGTC
 43_1    CAATCCGTAC CTGCGGTATA ACCACGCCGA CGCCGAGTTT CAGGAGCGTC
 43_5    CAATCCGTAC CTGCGGTATA ACCACGCCGA CGCCGAGTTT CAGGAGCGTC
 43_12   CAATCCGTAC CTGCGGTATA ACCACGCCGA CGCCGAGTTT CAGGAGCGTC
 43_20   CAATCCGTAC CTGCGGTATA ATCACGCCGA CGCCGAGTTT CAGGAGCGTC
 43_21   CAATCCGTAC CTGCGGTATA ATCACGCCGA CGCCGAGTTT CAGGAGCGTC
 43_23   CAATCCGTAC CTGCGGTATA ATCACGCCGA CGCCGAGTTT CAGGAGCGTC
 43_25   CAATCCGTAC CTGCGGTATA ATCACGCCGA CGCCGAGTTT CAGGAGCGTC
 44_1    CAATCCGTAC CTGCGGTATA ACCACGCCGA CGCCGAGTTT CAGGAGCGTC
 44_5    CAATCCGTAC CTGCGGTATA ACCACGCCGA CGCCGAGTTT CAGGAGCGTC
223_10   CAATCCGTAC CTGCGGTATA ACCACGCCGA CGCCGAGTTT CAGGAGCGTC
223_2    CAATCCGTAC CTGCGGTATA ACCACGCCGA CGCCGAGTTT CAGGAGTGTC
223_4    CAATCCGTAC CTGCGGTATA ACCACGCCGA CGCCGAGTTT CAGGAGCGTC
223_5    CAATCCGTAC CTGCGGTATA ACCACGCCGA CGCCGAGTTT CAGGAGCGTC
223_6    CAATCCGTAC CTGCGGTATA ACCACGCCGA CGCCGAGTTT CAGGAGCGTC
223_7    CAATCCGTAC CTGCGGTATA ACCACGCCGA CGCCGAGTTT CAGGAGCGTC
 A3_4    CAACCCGTAC CTCAAATACA ACCACGCGGA CGCTGAATTT CAGGAGCGTC
 A3_5    CAACCCGTAC CTCAAATACA ACCACGCGGA CGCTGAATTT CAGGAGCGTC
 A3_7    CAACCCGTAC CTCAAATACA ACCACGCGGA CGCTGAATTT CAGGAGCGTC
 A3_3    CAACCCGTAC CTCAAATACA ACCACGCGGA CGCTGAATTT CAGGAGCGTC
 42_12   CAACCCGTAC CTCAAGTACA ACCACGCCGA CGCCGAGTTT CAGGAGCGTC
 AAV1    CAATCCGTAC CTGCGGTATA ACCACGCCGA CGCCGAGTTT CAGGAGCGTC
 AAV2    CAACCCGTAC CTCAAGTACA ACCACGCCGA CGCGGAGTTT CAGGAGCGCC
 AAV3    CAACCCGTAC CTCAAGTACA ACCACGCCGA CGCCGAGTTT CAGGAGCGTC
 AAV8    CAATCCGTAC CTGCGGTATA ACCACGCCGA CGCCGAGTTT CAGGAGCGTC
 AAV9    CAATCCGTAC CTGCGGTATA ACCACGCCGA CGCCGAGTTT CAGGAGCGTC
 AAV7    CAATCCGTAC CTGCGGTATA ACCACGCCGA CGCCGAGTTT CAGGAGCGTC
 44_2    CAATCCGTAC CTGCGGTATA ACCACGCCGA CGCCGAGTTT CAGGAGCGTC
```

FIG. 1AZ

```
        2551                                                      2600
 42_2   TTCAAGAAGA TACGTCTTTT GGGGGCAACC TCGGGCGAGC AGTCTTCCAG
 42_8   TGCAAGAAGA TACGTCTTTT GGGGGCAACC TCGGGCGAGC AGTCTTCCAG
 42_15  TGCAAGAAGA TACGTCTTTT GGGGGCAACC TCGGGCGAGC AGTCTTCCAG
 42_5b  TTCAAGAAGA TACGTCTTTT GGGGGCAACC TCGGGCGAGC AGTCTTCCAG
 42_1b  TTCAAGAAGA TACGTCTTTT GGGGGCAACC TCGGGCGAGC AGTCTTCCAG
 42_13  TTCAAGAAGA TACGTCTTTT GGGGGCAACC TCGGGCGAGC AGTCTTCCAG
 42_3a  TTCAAGAAGA TACGTCTTTT GGGGGCAACC TCGGGCGAGC AGTCTTCCAG
 42_4   TTCAAGAAGA TACGTCTTTT GGGGGCAACC TCGGGCGAGC AGTCTTCCAG
 42_5a  TTCAAGAAGA TACGTCTTTT GGGGGCAACC TCGGGCGAGC AGTCTTCCGG
 42_10  TTCAAGAAGA TACGTCTTTT GGGGGCAACC TCGGGCGAGC AGTCTTCCAG
 42_3b  TTCAAGAAGA TACGTCTTTT GGGGGCAACC TCGGGCGAGC AGTCTTCCAG
 42_11  TTCAAGAAGA TACGTCTTTT GGGGGCAACC TCGGGCGAGC AGTCTTCCAG
 42_6b  TTCAAGAAGA TACGTCTTTT GGGGGCAACC TCGGGCGAGC AGTCTTCCAG
 43_1   TGCAAGAAGA TACGTCTTTT GGGGGCAACC TCGGGCGAGC AGTCTTCCAG
 43_5   TGCAAGAAGA TACGTCTTTT GGGGGCAACC TCGGGCGAGC AGTCTTCCAG
 43_12  TGCAAGAAGA TACGTCTTTT GGGGGCAACC TCGGGCGAGC AGTCTTCCAG
 43_20  TGCAAGAAGA TACGTCTTTT GGGGGCAACC TCGGGCGAGC AGTCTTCCAG
 43_21  TGCAAGAAGA TACGTCTTTT GGGGGCAACC TCGGGCGAGC AGTCTTCCAG
 43_23  TGCAAGAAGA TACGTCCTTT GGGGGCAACC TCGGGCGAGC AGTCTTCCAG
 43_25  TGCAAGAAGA TACGTCTTTT GGGGGCAACC TCGGGCGAGC AGTCTTCCAG
 44_1   TGCAAGAAGA TACGTCTTTT GGGGGCAACC TCGGGCGAGC AGTCTTCCAG
 44_5   TGCAAGAAGA TACGTCTTTT GGGGGCAACC TCGGGCGAGC AGTCTTCCAG
223_10  TTCAAGAAGA TACGTCTTTT GGGGGCAACC TCGGGCGAGC AGTCTTCCAG
223_2   TTCAAGAAGA TACGTCTTTT GGGGGCAACC TCGGGCGAGC AGTCTTCCAG
223_4   TTCAAGAAGA TACGTCTTTT GGGGGCAACC TCGGGCGAGC AGTCTTCCAG
223_5   TTCAAGAAGA TACGTCTTTT GGGGGCAACC TCGGGCGAGC AGTCTTCCAG
223_6   TTCAAGAAGA TACGTCTTTT GGGGGCAACC TCGGGCGAGC AGTCTTCCAG
223_7   TTCAAGAAGA TACGTCTTTT GGGGGCAACC TCGGGCGAGC AGTCTTCCAG
 A3_4   TTCAAGAAGA TACGTCTTTC GGGGGCAACC TCGGGCGAGC AGTCTTCCAG
 A3_5   TTCAAGAAGA TACGTCTTTC GGGGGCAACC TCGGGCGAGC AGTCTTCCAG
 A3_7   TTCAAGAAGA TACGTCTTTC GGGGGCAACC TCGGGCGAGC AGTCTTCCAG
 A3_3   TTCAAGAAGA TACGTCTTTC GGGGGCAACC TCGGGCGAGC AGTCTTCCAG
 42_12  TTCAAGAAGA TACGTCTTTT GGGGGCAACC TCGGGCGAGC AGTCTTCCAG
 AAV1   TGCAAGAAGA TACGTCTTTT GGGGGCAACC TCGGGCGAGC AGTCTTCCAG
 AAV2   TTAAAGAAGA TACGTCTTTT GGGGGCAACC TCGGACGAGC AGTCTTCCAG
 AAV3   TTCAAGAAGA TACGTCTTTT GGGGGCAACC TTGGCAGAGC AGTCTTCCAG
 AAV8   TGCAAGAAGA TACGTCTTTT GGGGGCAACC TCGGGCGAGC AGTCTTCCAG
 AAV9   TGCAAGAAGA TACGTCTTTT GGGGGCAACC TCGGGCGAGC AGTCTTCCAG
 AAV7   TGCAAGAAGA TACGTCATTT GGGGGCAACC TCGGGCGAGC AGTCTTCCAG
 44_2   TGCAAGAAGA TACGTCTTTT GGGGGCAACC TCGGGCGAGC AGTCTTCCAG
```

FIG. 1AAA

```
         2601                                                         2650
42_2     GCCAAGAAGC GGGTTCTCGA ACCTCTCGGT CTGGTTGAGG AAGGCGCTAA
42_8     GCCAAGAAGC GGGTTCTCGA ACCTCTCGGT CTGGTTGAGG AAGGCGCTAA
42_15    GCCAAGAAGC GGGTTCTCGA ACCTCTCGGT CTGGTTGAGG AAGGCGCTAA
42_5b    GCCAAGAAGC GGGTTCTCGA ACCTCTCGGT CTGGTTGAGG AAGGCGCTAA
42_1b    GCCAAGAAGC GGGTTCTCGA ACCTCTCGGT CTGGTTGAGG AAGGCGCTAA
42_13    GCCAAGAAGC GGGTTCTCGA ACCTCTCGGT CTGGTTGAGG AAGGCGCTAA
42_3a    GCCAAGAAGC GGGTTCTCGA ACCTCTCGGT CTGGTTGAGG AAGGCGCTAA
42_4     GCCAAGAAGC GGGTTCTCGA ACCTCTCGGT CTGGTTGAGG AAGGCGCTAA
42_5a    GCCAAGAAGC GGGTTCTCGA ACCTCTCGGT CTGGTTGAGG AAGGCGCTAA
42_10    GCCAAGAAGC GGGTTCTCGA ACCTCTCGGT CTGGTTGAGG AAGGCGCTAA
42_3b    GCCAAGAAGC GGGTTCTCGA ACCTCTCGGT CTGGTTGAGG AAGGCGCTAA
42_11    GCCAAGAAGC GGGTTCTCGA ACCTCTCGGT CTGGTTGAGG AAGGCGCTAA
42_6b    GCCAAGAAGC GGGTTCTCGA ACCTCTCGGT CTGGTTGAGG AAGGCGCTAA
43_1     GCCAAGAAGC GGGTTCTCGA ACCTCTCGGT CTGGTTGAGG AAGGCGCTAA
43_5     GCCAAGAAGC GGGTTCTCGA ACCTCTCGGT CTGGTTGAGG AAGGCGCTAA
43_12    GCCAAGAAGC GGGTTCTCGA ACCTCTCGGT CTGGTTGAGG AAGGCGCTAA
43_20    GCCAAGAAGC GGGTTCTCGA ACCTCTCGGT CTGGTTGAGG AAGGCGCTAA
43_21    GCCAAGAAGC GGGTTCTCGA ACCTCTCGGT CTGGTTGAGG AAGGCGCTAA
43_23    GCCAAGAAGC GGGTTCTCGA ACCTCTCGGT CTGGTTGAGG AAGGCGCTAA
43_25    GCCAAGAAGC GGGTTCTCGA ACCTCTCGGT CTGGTTGAGG AAGGCGCTAA
44_1     GCCAAGAAGC GGGTTCTCGA ACCTCTCGGT CTGGTTGAGG AAGGCGCTAA
44_5     GCCAAGAAGC GGGTTCTCGA ACCTCTCGGT CTGGTTGAGG AAGGCGCTAA
223_10   GCCAAAAAGC GGGTTCTCGA ACCTCTTGGT CTGGTTGAGA CGCCAGCTAA
223_2    GCCAAAAAGC GGGTTCTCGA ACCTCTTGGT CTGGTTGAGA CGCCAGCTAA
223_4    GCCAAAAAGC GGGTTCTCGA ACCTCTTGGT CTGGTTGAGA CGCCAGCTAA
223_5    GCCAAAAAGC GGGTTCTCGA ACCTCTTGGT CTGGTTGAGA CGCCAGCTAA
223_6    GCCAAAAAGC GGGTTCTCGA ACCTCTTGGT CTGGTTGAGA CGCCAGCTAA
223_7    GCCAAAAAGC GGGTTCTCGA ACCTCTTGGT CTGGTTGAGA CGCCAGCTAA
A3_4     GCCAAAAAGA GGGTACTCGA GCCTCTTGGT CTGGTTGAGG AAGCTGTTAA
A3_5     GCCAAAAAGA GGGTACTCGA GCCTCTTGGT CTGGTTGAGG AAGCTGTTAA
A3_7     GCCAAAAAGA GGGTACTCGA GCCTCTTGGT CTGGTTGAGG AAGCTGTTAA
A3_3     GCCAAAAAGA GGGTACTCGA GCCTCTTGGT CTGGTTGAGG AAGCTGTTAA
42_12    GCCAAGAAGC GGGTTCTCGA ACCTCTCGGT CTGGTTGAGG AAGGCGCTAA
AAV1     GCCAAGAAGC GGGTTCTCGA ACCTCTCGGT CTGGTTGAGG AAGGCGCTAA
AAV2     GCGAAAAAGA GGGTTCTTGA ACCTCTGGGC CTGGTTGAGG AACCTGTTAA
AAV3     GCCAAAAAGA GGATCCTTGA GCCTCTTGGT CTGGTTGAGG AAGCAGCTAA
AAV8     GCCAAGAAGC GGGTTCTCGA ACCTCTCGGT CTGGTTGAGG AAGGCGCTAA
AAV9     GCCAAGAAGC GGGTTCTCGA ACCTCTCGGT CTGGTTGAGG AAGGCGCTAA
AAV7     GCCAAGAAGC GGGTTCTCGA ACCTCTCGGT CTGGTTGAGG AAGGCGCTAA
44_2     GCCAAGAAGC GGGTTCTCGA ACCTCTCGGT CTGGTTGAGG AAGGCGCTAA
```

FIG. 1AAB

```
                                                                   2651                                                      2700
          vp2 start
 42_2    GACGGCTCCT GGAAAGAAGA GACCCATAGA ...ATCCCCC ..........
 42_8    GACGGCTCCT GGAAAGAAGA GACCGGTAGA GCCATCACCC CAGCGTTCTC
 42_15   GACGGCTCCT GGAAAGAAGA GACCGGTAGA GCCATCACCC CAGCGTTCTC
 42_5b   GACGGCTCCT GGAAAGAAGA GACCGGTAGA GCCATCACCC CAGCGTTCTC
 42_1b   GACGGCTCCT GGAAAGAAGA GACCCATAGA ...ATCCCCC ..........
 42_13   GACGGCTCCT GGAAAGAAGA GACCCATAGA ...ATCCCCC ..........
 42_3a   GACGGCTCCT GGAAAGAAGA GACCCATAGA ...ATCCCCC ..........
 42_4    GACGGCTCCT GGAAAGAAGA GACCCATAGA ...ATCCCCC ..........
 42_5a   GACGGCTCCT GGAAAGAAGA GACCCATAGA ...ATCCCCC ..........
 42_10   GACGGCTCCT GGAAAGAAGA GACCCATAGA ...ATCCCCC ..........
 42_3b   GACGGCTCCT GGAAAGAAGA GACCCATAGA ...ATCCCCC ..........
 42_11   GACGGCTCCT GGAAAGAAGA GACCCATAGA ...ATCCCCC ..........
 42_6b   GACGGCTCCT GGAAAGAAGA GACCGGTAGA GCCATCACCC CAGCGTTCTC
 43_1    GACGGCTCCT GGAAAGAAGA GACCGGTAGA GCCATCACCT CAGCGTTCCC
 43_5    GACGGCTCCT GGAAAGAAGA GACCGGTAGA GCCATCACCT CAGCGTTCCC
 43_12   GACGGCTCCT GGAAAGAAGA GACCGGTAGA GCCATCACCT CAGCGTTCCC
 43_20   GACGGCTCCT GGAAAGAAGA GACTGGTAGA GCAGTCGCCA CAAGAG...C
 43_21   GACGGCTCCT GGAAAGAAGA GACCGGTAGA GCAGTCGCCA CAAGAG...C
 43_23   GACGGCTCCT GGAAAGAAGA GACCGGTAGA GCAGTCGCCA CAAGAG...C
 43_25   GACGGCTCCT GGAAAGAAGA GACCGGTAGA GCAGTCGCCA CAAGAG...C
 44_1    GACGGCTCCT GGAAAGAAGA GACCGGTAGA GCCATCACCC CAGCGTTCTC
 44_5    GACGGCTCCT GGAAAGAAGA GACCGGTAGA GCCATCACCC CAGCGTTCTC
223_10   GACGGCACCT GGAAAGAAGC GACCGGTAGA CTCGCCA... ..........
223_2    GACGGCACCT GGAAAGAAGC GACCGGTAGA CTCGCCA... ..........
223_4    GACGGCACCT GGAAAGAAGC GACCGGTAGA CTCGCCA... ..........
223_5    GACGGCACCT GGAAAGAAGC GACCGGTAGA CTCGCCA... ..........
223_6    GACGGCACCT GGAAAGAAGC GACCGGTAGA CTCGCCA... ..........
223_7    GACGGCACCT GGAAAGAAGC GACCGGTAGA CTCGCCA... ..........
 A3_4    GACGGCTCCT GGAAAAAAGA GACCTATAGA GCAGTCTCCT GCAGAA...C
 A3_5    GACGGCTCCT GGAAAAAAGA GACCTATAGA GCAGTCTCCT GCAGAA...C
 A3_7    GACGGCTCCT GGAAAAAAGA GACCTATAGA GCAGTCTCCT GCAGAA...C
 A3_3    GACGGCTCCT GGAAAAAAGA GACCTATAGA GCAGTCTCCT GCAGAA...C
 42_12   GACGGCTCCT GGAAAGAAGA GACCGGTAGA GCCATCACCC CAGCGTTCTC
 AAV1    GACGGCTCCT GGAAAGAAAC GTCCGGTAGA GCAGTCGCCA CAAGAG...C
 AAV2    GACGGCTCCG GGAAAAAAGA GGCCGGTAGA GCACTCTCCT GTGGAG...C
 AAV3    AACGGCTCCT GGAAGAAGG GGGCTGTAGA TCAGTCTCCT CAGGAA...C
 AAV8    GACGGCTCCT GGAAAGAAGA GACCGGTAGA GCCATCACCC CAGCGTTCTC
 AAV9    GACGGCTCCT GGAAAGAAGA GACCGGTAGA GCCATCACCC CAGCGTTCTC
 AAV7    GACGGCTCCT GCAAAGAAGA GACCGGTAGA GCCGTCACCT CAGCGTTCCC
 44_2    GACGGCTCCT GGAAAGAAGA GACCGGTAGA GCCATCACCC CAGCGTTCTC
          vp2 start
```

FIG. 1AAC

```
          2701                                                         2750
  42_2    ..GACTCCTC CACGGGCATC GGCAAGAAAG GCCAGCAGCC CGCTAAAAAG
  42_8    CAGACTCCTC TACGGGCATC GGCAAGACAG GCCAGCAGCC CGCGAAAAAG
  42_15   CAGACTCCTC TACGGGCATC GGCAAGACAG GCCAGCAGCC CGCGAAAAAG
  42_5b   CAGACTCCTC TACGGGCATC GGCAAGACAG GCCAGCAGCC CGCGAAAAAG
  42_1b   ..GACTCCTC CACGGGCATC GGCAAGAAAG GCCAGCAGCC CGCTAAAAAG
  42_13   ..GACTCCTC CACGGGCATC GGCAAGAAAG GCCAGCAGCC CGCTAAAAAG
  42_3a   ..GACTCCTC CACGGGCATC GGCAAGAAAG GCCAGCAGCC CGCTAAAAAG
  42_4    ..GACTCCTC CACGGGCATC GGCAAGAAAG GCCAGCAGCC CGCTAAAAAG
  42_5a   ..GACTCCTC CACGGGCATC GGCAAGAAAG GCCAGCAGCC CGCTAAAAAG
  42_10   ..GACTCCTC CACGGGCATC GGCAGGAAAG GCCAGCAGCC CGCTAAAAAG
  42_3b   ..GACTCCTC CACGGGCATC GGCAAGAAAG GCCAGCAGCC CGCTAAAAAG
  42_11   ..GACTCCTC CACGGGCATC GGCAAGAAAG GCCAGCAGCC CGCTAAAAAG
  42_6b   CAGACTCCTC TACGGGCATC GGCAAGACAG GCCAGCAGCC CGCGAAAAAG
  43_1    CCGACTCCTC CACGGGCATC GGCAAGAAAG GCCACCAGCC CGCGAGAAAG
  43_5    CCGACTCCTC CACGGGCATC GGCAAGAAAG GCCACCAGCC CGCGAGAAAG
  43_12   CCGACTCCTC CACGGGCATC GGCAAGAAAG GCCACCAGCC CGCGAGAAAG
  43_20   CAGACTCCTC CTCGGGCATC GGCAAGACAG GCCAGCAGCC CGCTAAAAAG
  43_21   CAGACTCCTC CTCGGGCATC GGCAAGACAG GCCAGCAGCC CGCTAAAAAG
  43_23   CAGACTCCTC CTCGGGCATC GGCAAGACAG GCCAGCAGCC CGCTAAAAAG
  43_25   CAGACTCCTC CTCGGGCATC GGCAAGACAG GCCAGCAGCC CGCTAAAAAG
  44_1    CAGACTCCTC TACGGGCATC GGCAAGAAAG GCCAGCAGCC CGCGAAAAAG
  44_5    CAGACTCCTC TACGGGCATC GGCAAGAAAG GCCAGCAGCC CGCGAAAAAG
 223_10   ..GACTCCAC CTCGGGCATC GGCAAGAAAG GCCAGCAGCC CGCGAAAAAG
 223_2    ..GACTCCAC CTCGGGCATC GGCAAGAAAG GCCAGCAGCC CGCGAAAAAG
 223_4    ..GACTCCAC CTCGGGCATC GGCAAGAAAG GCCAGCAGCC CGCGAAAAAG
 223_5    ..GACTCCAC CTCGGGCATC GGCAAGAAAG GCCAGCAGCC CGCGAAAAAG
 223_6    ..GACTCCAC CTCGGGCATC GGCAAGAAAG GCCAGCAGCC CGCGAAAAAG
 223_7    ..GACTCCAC CTCGGGCATC GGCAAGAAAG GCCAGCAGCC CGCGAAAAAG
  A3_4    CGGACTCTTC CTCGGGCATC GGCGAATCAG GCCAGCAGCC CGCTAAGAAA
  A3_5    CGGACTCTTC CTCGGGCATC GGCAAATCAG GCCAGCAGCC CGCTAAGAAA
  A3_7    CGGACTCTTC CTCGGGCATC GGCAAATCAG GCCAGCAGCC CGCTAAGAAA
  A3_3    CGGACTCTTC CTCGGGCATC GGCAAATCAG GCCAGCAGCC CGCTAAGAAA
  42_12   CAGACTCCTC TACGGGCATC GGCAAGACAG GCCAGCAGCC CGCGAAAAAG
  AAV1    CAGACTCCTC CTCGGGCATC GGCAAGACAG GCCAGCAGCC CGCTAAAAAG
  AAV2    CAGACTCCTC CTCGGGAACC GGAAAGGCGG GCCAGCAGCC TGCAAGAAAA
  AAV3    CGGACTCATC ATCTGGTGTT GGCAAATCGG GCAACAGCC TGCCAGAAAA
  AAV8    CAGACTCCTC TACGGGCATC GGCAAGAAAG GCCAACAGCC CGCCAGAAAA
  AAV9    CAGACTCCTC TACGGGCATC GGCAAGAAAG GCCAACAGCC CGCCAGAAAA
  AAV7    CCGACTCCTC CACGGGCATC GGCAAGAAAG GCCAGCAGCC CGCCAGAAAG
  44_2    CAGACTCCTC TACGGGCATC GGCAAGAAAG GCCAGCAGCC CGCGAAAAAG
```

FIG. 1AAD

```
         2751                                                       2800
 42_2    AAGCTCAACT TTGGGCAGAC TGGCGACTCA GAGTCAGTGC CCGACCCCCA
 42_8    AGACTCAACT TTGGGCAGAC TGGCGACTCA GAGTCAGTGC CCGACCCTCA
 42_15   AGACTCAACT TTGGGCAGAC TGGCGACTCA GAGTCAGTGC CCGACCCTCA
 42_5b   AGACTCAACT TTGGGCAGAC TGGCGACTCA GAGTCAGTGC CCGACCCTCA
 42_1b   AGACTCAACT TTGGGCAGAC TGGCGACTCA GAGTCAGTGC CCGACCCTCA
 42_13   AAGCTCAACT TTGGGCAGAC TGGCGACTCA GAGTCAGTGC CCGACCCTCA
 42_3a   AAGCTCAACT TTGGGCAGAC TGGCGACTCA GAGTCAGTGC CCGACCCTCA
 42_4    AAGCTCAACT TTGGGCAGAC TGGCGACTCA GAGTCAGTGC CCGACCCTCA
 42_5a   AAGCTCAACT TTGGGCAGAC TGGCGACTCA GAGTCAGTGC CCGACCCCCA
 42_10   AAGCTCAACT TTGGGCAGAC TGGCGACTCA GAGTCAGTGC CCGACCCTCA
 42_3b   AAGCTCAACT TTGGGCAGAC TGGCGACTCA GAGTCAGTGC CCGACCCTCA
 42_11   AAGCTCAACT TTGGGCAGAC TGGCGACTCA GAGTCAGTGC CCGACCCTCA
 42_6b   AGACTCAACT TTGGGCAGAC TGGCGACTCA GAGTCAGTGC CCGACCCTCA
 43_1    AGACTGAACT TTGGGCAGAC TGGCGACTCG GAGTCAGTCC CCGACCCTCA
 43_5    AGACTGAACT TTGGGCAGAC TGGCGACTCG GAGTCAGTCC CCGACCCTCA
 43_12   AGACTGAACT TTGGGCAGAC TGGCGACTCG GAGTCAGTCC CCGACCCTCA
 43_20   AGACTCAATT TTGGTCAGAC TGGCGACTCA GAGTCAGTCC CCGACCCACA
 43_21   AGACTCAATT TTGGTCAGAC TGGCGACTCA GAGTCAGTCC CCGACCCACA
 43_23   AGACTCAATT TTGGTCAGAC TGGCGACTCA GAGTCAGTCC CCGACCCACA
 43_25   AGACTCAATT TTGGTCAGAC TGGCGACTCA GAGTCAGTCC CCGACCCACA
 44_1    AGACTCAACT TTGGGCAGAC TGGCGACTCA GAGTCAGTGC CCGACCCTCA
 44_5    AGACTCAACT TTGGGCAGAC TGGCGACTCA GAGTCAGTGC CCGACCCTCA
 223_10  AGACTCAACT TTGGGCAGAC TGGCGACTCA GAGTCAGTCC CCGACCCTCA
 223_2   AGACTCAACT TTGGGCAGAC TGGCGACTCA GAGTCAGTCC CCGACCCTCA
 223_4   AGACTCAACT TTGGGCAGAC TGGCGACTCA GAGCCAGTCC CCGACCCTCA
 223_5   AGACTCAACT TTGGGCAGAC TGGCGACTCA GAGCCAGTCC CCGACCCTCA
 223_6   AGACTCAACT TTGGGCAGAC TGGCGACTCA GAGTCAGTCC CCGACCCTCA
 223_7   AGACTCAACT TTGGGCAGAC TGGCGACTCA GAGTCAGTCC CCGACCCTCA
 A3_4    AGACTCAATT TTGGTCAGAC TGGCGACACA GAGTCAGTCC CAGACCCTCA
 A3_5    AGACTCAATT TTGGTCAGAC TGGCGACACA GAGTCAGTCC CAGACCCTCA
 A3_7    AGACTCAATT TTGGTCAGAC TGGCGACACA GAGTCAGTCC CAGACCCTCA
 A3_3    AGACTCAATT TTGGTCAGAC TGGCGACACA GAGTCAGTCC CAGGCCCTCA
 42_12   AGACTCAACT TTGGGCAGAC TGGCGACTCA GAGTCAGTGC CCGACCCTCA
 AAV1    AGACTCAATT TTGGTCAGAC TGGCGACTCA GAGTCAGTCC CCGATCCACA
 AAV2    AGATTGAATT TTGGTCAGAC TGGAGACGCA GACTCAGTAC CTGACCCCCA
 AAV3    AGACTAAATT TCGGTCAGAC TGGAGACTCA GAGTCAGTCC CAGACCCTCA
 AAV8    AGACTCAATT TTGGTCAGAC TGGCGACTCA GAGTCAGTTC CAGACCCTCA
 AAV9    AGACTCAATT TTGGTCAGAC TGGCGACTCA GAGTCAGTTC CAGACCCTCA
 AAV7    AGACTCAATT TCGGTCAGAC TGGCGACTCA GAGTCAGTCC CCGACCCTCA
 44_2    AGACTCAACT TTGGGCAGAC TGGCGACTCA GAGTCAGTGC CCGACCCTCA
```

FIG. 1AAE

```
          2801                                                              2850
                                                                            vp3 start
   42_2   ACCTCTCGGA GAACCTCCCG CCGCGCCCTC AGGTCTGGGA TCTGGTACAA
   42_8   ACCAATCGGA GAACCCCCCG CAGGCCCCTC TGGTCTGGGA TCTGGTACAA
  42_15   ACCAATCGGA GAACCCCCCG CAGGCCCCTC TGGTCTGGGA TCTGGTACAA
  42_5b   ACCAATCGGA GAACCCCCCG CAGGCCCCTC TGGTCTGGGA TCTGGTACAA
  42_1b   ACCAATCGGA GAACCCCCCG CAGGCCCCTC TGGTCTGGGA TCTGGCACAA
  42_13   ACCAATCGGA GAACCCCCCG CAGGCCCCTC TGGTCTGGGA TCTGGTACAA
  42_3a   ACCAATCGGA GAACCCCCCG CAGGCCCCTC TGGTCTGGGA TCTGGTACAA
   42_4   ACCAATCGGA GAACCCCCCG CAGGCCCCTC TGGTCTGGGA TCTGGTACAA
  42_5a   ACCTCTCGGA GAACCTCCCG CCGCGCCCTC AGGTCTGGGA TCTGGTACAA
  42_10   ACCAATCGGA GAACCCCCCG CAGGCCCCTC TGGTCTGGGA TCTGGTACAA
  42_3b   ACCAATCGGA GAACCCCCCG CAGGCCCCTC TGGTCTGGGA TCTGGTACAA
  42_11   ACCAATCGGA GAACCCCCCG CAGGCCCCTC TGGTCTGGGA TCTGGTACAA
  42_6b   ACCAATCGGA GAACCCCCCG CAGGCCCCTC TGGTCTGGGA TCTGGTACAA
   43_1   ACCAATCGGA GAACCACCAG CAGGCCCCTC TGGTCTGGGA TCTGGTACAA
   43_5   ACCAATCGGA GAACCACCAG CAGGCCCCTC TGGTCTGGGA TCTGGTACAA
  43_12   ACCAATCGGA GAACCACCAG CAGGCCCCTC TGGTCTGGGA TCTGGTACAA
  43_20   ACCTCTCGGA GAACCTCCAG CAGCCCCCTC AGGTCTGGGA CCTAATACAA
  43_21   ACCTCTCGGA GAACCTCCAG CAGCCCCCTC AGGTCTGGGA CCTAATACAA
  43_23   ACCTCTCGGA GAACCTCCAG CAGCCCCCTC AGGTCTGGGA CCTAATACAA
  43_25   ACCTCTCGGA GAACCTCCAG CAGCCCCCTC AGGTCTGGGA CCTAATACAA
   44_1   ACCAATCGGA GAACCCCCCG CAGGCCCCTC TGGTCTGGGA TCTGGTACAA
   44_5   ACCAATCGGA GAACCCCCCG CAGGCCCCTC TGGTCTGGGA TCTGGTACAA
  223_10  ACCAATCGGA GAACCACCAG CAGGCCCCTC TGGTCTGGGA TCTGGTACAA
  223_2   ACCAATCGGA GAACCACCAG CAGGCCCCTC TGGTCTGGGA TCTGGTACAA
  223_4   ACCAATCGGA GAACCACCAG CAGGCCCCTC TGGTCTGGGA TCTGGTACAA
  223_5   ACCAATCGGA GAACCACCAG CAGGCCCCTC TGGTCTGGGA TCTGGTACAA
  223_6   ACCAATCGGA GAACCACCAG CAGGCCCCTC TGGTCTGGGA TCTGGTACAA
  223_7   ACCAATCGGA GAACCACCAG CAGGCCCCTC TGGTCTGGGA TCTGGTACAA
   A3_4   ACCAATCGGA GAACCCCCCG CAGCCCCCTC TGGTGTGGGA TCTAATACAA
   A3_5   ACCAATCGGA GAACCCCCCG CAGCCCCCTC TGGTGTGGGA TCTAATACAA
   A3_7   ACCAATCGGA GAACCCCCCG CAGCCCCCTC TGGTGTGGGA TCTAATACAA
   A3_3   ACCAATCGGA GAACCCCCCG CAGCCCCCTC TGGTGTGGGA TCTAATACAA
  42_12   ACCAATCGGA GAACCCCCCG CAGGCCCCTC TGGTCTGGGA TCTGGTACAA
   AAV1   ACCTCTCGGA GAACCTCCAG CAACCCCCGC TGCTGTGGGA CCTACTACAA
   AAV2   GCCTCTCGGA CAGCCACCAG CAGCCCCCTC TGGTCTGGGA ACTAATACGA
   AAV3   ACCTCTCGGA GAACCACCAG CAGCCCCCAC AAGTTTGGGA TCTAATACAA
   AAV8   ACCTCTCGGA GAACCTCCAG CAGCGCCCTC TGGTGTGGGA CCTAATACAA
   AAV9   ACCTCTCGGA GAACCTCCAG CAGCGCCCTC TGGTGTGGGA CCTAATACAA
   AAV7   ACCTCTCGGA GAACCTCCAG CAGCGCCCTC TAGTGTGGGA TCTGGTACAG
   44_2   ACCAATCGGA GAACCCCCCG CAGGCCCCTC TGGTCTGGGA TCTGGTACAA
                                                                            vp3 start
```

FIG. 1AAF

```
         2851                                                                    2900
         vp3 start codon
   42_2  TGGCTGCAGG CGGTGGCGCA CCAATGGCAG ACAATAACGA AGGCGCCGAC
   42_8  TGGCTGCAGG CGGTGGCGCT CCAATGGCAG ACAATAACGA AGGCGCCGAC
  42_15  TGGCTGCAGG CGGTGGCGCT CCAATGGCAG ACAATAACGA AGGCGCCGAC
  42_5b  TGGCTGCAGG CGGTGGCGCT CCAATGGCAG ACAATAACGA AGGCGCCGAC
  42_1b  TGGCTGCAGG CGGTGGCGCT CCAATGGCAG ACAATAACGA AGGCGCCGAC
  42_13  TGGCTGCAGG CGGTGGCGCT CCAATGGCAG ACAATAACGA AGGCGCCGAC
  42_3a  TGGCTGCAGG CGGTGGCGCT CCAATGGCAG ACAATAACGA AGGCGCCGAC
   42_4  TGGCTGCAGG CGGTGGCGCT CCAATGGCAG ACAATAACGA AGGCGCCGAC
  42_5a  TGGCTGCAGG CGGTGGCGCA CCAATGGCAG ACAATAACGA AGGCGCCGAC
  42_10  TGGCTGCAGG CGGTGGCGCT CCAATGGCAG ACAATAACGA AGGCGCCGAC
  42_3b  TGGCTGCAGG CGGTGGCGCT CCAATGGCAG ACAATAACGA AGGCGCCGAC
  42_11  TGGCTGCAGG CGGTGGCGCT CCAATGGCAG ACAATAACGA AGGCGCCGAC
  42_6b  TGGCTGCAGG CGGTGGCGCT CCAATGGCAG ACAATAACGA AGGCGCCGAC
   43_1  TGGCTGCAGG CGGTGGCGCT CCAATGGCAG ACAATAACGA AGGCGCCGAC
   43_5  TGGCTGCAGG CGGTGGCGCT CCAATGGCAG ACAATAACGA AGGCGCCGAC
  43_12  TGGCTGCAGG CGGTGGCGCT CCAATGGCAG ACAATAACGA AGGCGCCGAC
  43_20  TGGCTTCAGG CGGTGGCGCT CCAATGGCAG ACAATAACGA AGGCGCCGAC
  43_21  TGGCTTCAGG CGGTGGCGCT CCAATGGCAG ACAATAACGA AGGCGCCGAC
  43_23  TGGCTTCAGG CGGTGGCGCT CCAATGGCAG ACAATAACGA AGGCGCCGAC
  43_25  TGGCTTCAGG CGGTGGCGCT CCAATGGCAG ACAATAACGA AGGCGCCGAC
   44_1  TGGCTGCAGG CGGTGGCGCT CCAATGGCAG ACAATAACGA AGGCGCCGAC
   44_5  TGGCTGCAGG CGGTGGCGCT CCAATGGCAG ACAATAACGA AGGCGCCGAC
 223_10  TGGCTGCAGG CGGTGGCGCA CCAATGGCTG ACAATAACGA GGGCGCCGAC
  223_2  TGGTTGCAGG CGGTGGCGCA CCAATGGCTG ACAATAACGA GGGCGCCGAC
  223_4  TGGCTGCAGG CGGTGGCGCA CCAATGGCTG ACAATAACGA GGGCGCCGAC
  223_5  TGGCTGCAGG CGGTGGCGCA CCAATGGCTG ACAATAACGA GGGCGCCGAC
  223_6  TGGCTGCAGG CGGTGGCGCA CCAATGGCTG ACAATAGCGA GGGCGCCGAC
  223_7  TGGCTGCAGG CGGTGGCGCA CCAATGGCTG ACAATAACGA GGGCGCCGAC
   A3_4  TGGCTTCAGG CGGTGGGGCA CCAATGGCAG ACGATAACGA AGGCGCCGAC
   A3_5  TGGCTTCAGG CGGTGGGGCA CCAATGGCAG ACAATAACGA AGGCGCCGAC
   A3_7  TGGCTTCAGG CGGTGGGGCA CCAATGGCAG ACAATAACGA AGGCGCCGAC
   A3_3  TGGCTTCAGG CGGTGGGGCA CCAATGGCAG ACAATAACGA AGGCGCCGAC
  42_12  TGGCTGCAGG CGGTGGCGCT CCAATGGCAG ACAATAACGA AGGCGCCGAC
   AAV1  TGGCTTCAGG CGGTGGCGCA CCAATGGCAG ACAATAACGA AGGCGCCGAC
   AAV2  TGGCTACAGG CAGTGGCGCA CCAATGGCAG ACAATAACGA GGGCGCCGAC
   AAV3  TGGCTTCAGG CGGTGGCGCA CCAATGGCAG ACAATAACGA GGGTGCCGAT
   AAV8  TGGCTGCAGG CGGTGGCGCA CCAATGGCAG ACAATAACGA AGGCGCCGAC
   AAV9  TGGCTGCAGG CGGTGGCGCA CCAATGGCAG ACAATAACGA AGGCGCCGAC
   AAV7  TGGCTGCAGG CGGTGGCGCA CCAATGGCAG ACAATAACGA AGGTGCCGAC
   44_2  TGGCTGCAGG CGGTGGCGCT CCAATGGCAG ACAATAACGA AGGCGCCGAC
         vp3 start codon (cont'd)
```

FIG. 1AAG

```
        2901                                                                      2950
 42_2   GGAGTGGGTA ATGCCTCCGG AAATTGGCAT TGCGATTCCA CATGGCTGGG
 42_8   GGAGTGGGTA GTTCCTCAGG AAATTGGCAT TGCGATTCCA CATGGCTGGG
 42_15  GGAGTGGGTA GTTCCTCAGG AAATTGGCAT TGCGATTCCA CATGGCTGGG
 42_5b  GGAGTGGGTA GTTCCTCAGG AAATTGGCAT TGCGATTCCA CATGGCTGGG
 42_1b  GGAGTGGGTA GTTCCTCAGG AAATTGGCAT TGCGATTCCA CATGGCTGGG
 42_13  GGAGTGGGTA GTTCCTCAGG AAATTGGCAT TGCGATTCCA CATGGCTGGG
 42_3a  GGAGTGGGTA GTTCCTCAGG AAATTGGCAT TGCGATTCCA CATAGCTGGG
 42_4   GGAGTGGGTA ATGCCTCCGG AAATTGGCAT TGCGATTCCA CATGGCTGGG
 42_5a  GGAGTGGGTA ATGCCTCCGG AAATTGGCAT TGCGATTCCA CATGGCTGGG
 42_10  GGAGTGGGTA ATGCCTCCGG AAATTGGCAT TGCGATTCCA CATGGCTGGG
 42_3b  GGAGTGGGTA ATGCCTCCGG AAATTGGCAT TGCGATTCCA CATGGCTGGG
 42_11  GGAGTGGGTA ATGCCTCCGG AAATTGGCAT TGCGATTCCA CATGGCTGGG
 42_6b  GGAGTGGGTA GTTCCTCAGG AAATTGGCAT TGCGATTCCA CATGGCTGGG
 43_1   GGAGTGGGTA GTTCCTCAGG AAATTGGCAT TGCGATTCCA CATGGCTGGG
 43_5   GGAGTGGGTA GTTCCTCAGG AAATTGGCAT TGCGATTCCA CATGGCTGGG
 43_12  GGAGTGGGTA GTTCCTCAGG AAATTGGCAT TGCGATTCCA CATGGCTGGG
 43_20  GGAGTGGGTA ATTCCTCGGG AAATTGGCAT TGCGATTCCA CATGGCTGGG
 43_21  GGAGTGGGTA ATTCCTCGGG AAATTGGCAT TGCGATTCCA CATGGCTGGG
 43_23  GGAGTGGGTA ATTCCTCGGG AAATTGGCAT TGCGATTCCA CATGGCTGGG
 43_25  GGAGTGGGTA ATTCCTCGGG AAATTGGCAT TGCGATTCCA CATGGCTGGG
 44_1   GGAGTGGGTA GTTCCTCAGG AAATTGGCAT TGCGATTCCA CATGGCTGGG
 44_5   GGAGTGGGTA GTTCCTCAGG AAATTGGCAT TGCGATTCCA CATGGCTGGG
223_10  GGAGTGGGTA ATGCCTCAGG AAATTGGCAT TGCGATTCCA CATGGCTGGG
223_2   GGAGTGGGTA ATGCCTCAGG AAATTGGCAT TGCGATTCCA CATGGCTGGG
223_4   GGAGTGGGTA ATGCCTCAGG AAATTGGCAT TGCGATTCCA CACGGCTGGG
223_5   GGAGTGGGTA ATGCCTCAGG AAATTGGCAT TGCGATTCCA CACGGCTGGG
223_6   GGAGTGGGTA ATGCCTCAGG AAATTGGCAT TGCGATTCCA CATGGCTGGG
223_7   GGAGTGGGTA ATGCCTCAGG AAATTGGCAT TGCGATTCCA CATGGCTGGG
 A3_4   GGAGTGGGTA ATTCCTCGGG AAATTGGCAT TGCGATTCCA CATGGATGGG
 A3_5   GGAGTGGGTA ATTCCTCGGG AAATTGGCAT TGCGATTCCA CATGGATGGG
 A3_7   GGAGTGGGTA ATTCCTCGGG AAATTGGCAT TGCGATTCCA CATGGATGGG
 A3_3   GGAGTGGGTA ATTCCTCGGG AAATTGGCAT TGCGATTCCA CATGGATGGG
 42_12  GGAGTGGGTA GTTCCTCAGG AAATTGGCAT TGCGATTCCA CATGGCTGGG
 AAV1   GGAGTGGGTA ATGCCTCAGG AAATTGGCAT TGCGATTCCA CATGGCTGGG
 AAV2   GGAGTGGGTA ATTCCTCCGG AAATTGGCAT TGCGATTCCA CATGGATGGG
 AAV3   GGAGTGGGTA ATTCCTCAGG AAATTGGCAT TGCGATTCCC AATGGCTGGG
 AAV8   GGAGTGGGTA GTTCCTCGGG AAATTGGCAT TGCGATTCCA CATGGCTGGG
 AAV9   GGAGTGGGTA ATTCCTCGGG AAATTGGCAT TGCGATTCCA CATGGCTGGG
 AAV7   GGAGTGGGTA ATGCCTCAGG AAATTGGCAT TGCGATTCCA CATGGCTGGG
 AAV10             GGTA ATTCCTCCGG AAATTGGCAT TGCGATTCCA CATGGCTGGG
 AAV11             GGTA ATTCCTCCGG AAATTGGCAT TGCGATTCCA CATGGCTGGG
 AAV12             GGTA ATTCCTCCGG AAATTGGCAT TGCGATTCCA CATGGCTGGG
 44_2   GGAGTGGGTA GTTCCTCAGG AAATTGGCAT TGCGATTCCA CATGGCTGGG
```

FIG. 1AAH

```
        2951                                                      3000
 42_2   CGACAGAGTC  ATCACCACCA  GCACCCGCAC  CTGGGCCCTG  CCCACCTACA
 42_8   CGACAGAGTC  ATCACCACCA  GCACCCGAAC  CTGGGCCCTC  CCCACCTACA
 42_15  CGACAGAGTC  ATCACCACCA  GCACCCGAAC  CTGGGCCCTC  CCCACCTACA
 42_5b  CGACAGAGTC  ATCACCACCA  GCACCCGAAC  CTGGGCCCTC  CCCACCTACA
 42_1b  CGACAGAGTC  ATCACCACCA  GCACCCGAAC  CTGGGCCCTC  CCCACCTACA
 42_13  CGACAGAGTC  ATCACCACCA  GCACCCGAAC  CTGGGCCCTC  CCCACCTACA
 42_3a  CGACAGAGTC  ATCACCACCA  GCACCCGAAC  CTGGGCCCTC  CCCACCTACA
 42_4   CGACAGAGTC  ATCACCACCA  GCACCCGCAC  CTGGGCCCTG  CCCACCTACA
 42_5a  CGACAGAGTC  ATCACCACCA  GCACCCGCAC  CTGGGCCCTG  CCCACCTACA
 42_10  CGACAGAGTC  ATCACCACCA  GCACCCGCAC  CTGGGCCCTG  CCCACCTACA
 42_3b  CGACAGAGTC  ATCACCACCA  GCACCCGCAC  CTGGGCCCTG  CCCACCTACA
 42_11  CGACAGAGTC  ATCACCACCA  GCACCCGCAC  CTGGGCCCTG  CCCACCTACA
 42_6b  CGACAGAGTC  ATCACCACCA  GCACCCGAAC  CTGGGCCCTC  CCCACCTACA
 43_1   CGACAGAGTC  ATCACCACCA  GCACCCGAAC  CTGGGCCCTG  CCCACCTACA
 43_5   CGACAGAGTC  ATCACCACCA  GCACCCGAAC  CTGGGCCCTG  CCCACCTACA
 43_12  CGACAGAGTC  ATCACCACCA  GCACCCGAAC  CTGGGCCCTG  CCCACCTACA
 43_20  GGACAGAGTC  ATCACCACCA  GCACCCGAAC  CTGGGCCCTG  CCCACCTACA
 43_21  GGACAGAGTC  ATCACCACCA  GCACCCGAAC  CTGGGCCCTG  CCCACCTACA
 43_23  GGACAGAGTC  ATCACCACCA  GCACCCGAAC  CTGGGCCCTG  CCCACCTACA
 43_25  GGACAGAGTC  ATCACCACCA  GCACCCGAAC  CTGGGCCCTG  CCCACCTACA
 44_1   CGACAGAGTC  ATCACCACCA  GCACCCGAAC  CTGGGCCCTC  CCCACCTACA
 44_5   CGACAGAGTC  ATCACCACCA  GCACCCGAAC  CTGGGCCCTC  CCCACCTACA
223_10  CGACAGAGTC  ATCACCACCA  GCACCCGAAC  CTGGGCCCTG  CCCACCTACA
223_2   CGACAGAGTC  ATCACCACCA  GCACCCGAAC  CTGGGCCCTG  CCCACCTACA
223_4   CGACAGAGTC  ATCACCACCA  GCACCCGAAC  CTGGGCCCTG  CCCACCTACA
223_5   CGACAGAGTC  ATCACCACCA  GCACCCGAAC  CTGGGCCCTG  CCCACCTACA
223_6   CGACAGAGTC  ATCACCACCA  GCACCCGAAC  CTGGGCCCTG  CCCACCTACA
223_7   CGACAGAGTC  ATCACCACCA  GCACCCGAAC  CTGGGCCCTG  CCCACCTACA
 A3_4   CGACAGAGTT  ATCACCACCA  GCACAAGAAC  CTGGGCCCTC  CCCACCTACA
 A3_5   CGACAGAGTT  ATCACCACCA  GCACAAGAAC  CTGGGCCCTC  CCCACCTACA
 A3_7   CGACAGAGTT  ATCACCACCA  GCACAAGAAC  CTGGGCCCTC  CCCACCTACA
 A3_3   CGACAGAGTT  ATCACCACCA  GCACAAGAAC  CTGGGCCCTC  CCCACCTACA
 42_12  CGACAGAGTC  ATCACCACCA  GCACCCGAAC  CTGGGCCCTC  CCCACCTACA
 AAV1   CGACAGAGTC  ATCACCACCA  GCACCCGCAC  CTGGGCCTTG  CCCACCTACA
 AAV2   CGACAGAGTC  ATCACCACCA  GCACCCGAAC  CTGGGCCCTG  CCCACCTACA
 AAV3   CGACAGAGTC  ATCACCACCA  GCACCAGAAC  CTGGGCCCTG  CCCACTTACA
 AAV8   CGACAGAGTC  ATCACCACCA  GCACCCGAAC  CTGGGCCCTG  CCCACCTACA
 AAV9   GGACAGAGTC  ATCACCACCA  GCACCCGAAC  CTGGGCATTG  CCCACCTACA
 AAV7   CGACAGAGTC  ATTACCACCA  GCACCCGAAC  CTGGGCCCTG  CCCACCTACA
 AAV10  CGACAGAGTC  ATCACCACCA  GCACCCGAAC  CTGGGTCCTG  CCCACCTACA
 AAV11  CGACAGAGTC  ATCACCACCA  GCACCCGAAC  CTGGGCCCTG  CCAACCTACA
 AAV12  CGACCGAGTC  ATTACCACCA  GCACCCGGAC  TTGGGCCCTG  CCCACCTACA
 44_2   CGACAGAGTC  ATCACCACCA  GCACCCGAAC  CTGGGCCCTC  CCCACCTACA
```

FIG. 1AAI

```
           3001                                                    3050
  42_2    ACAACCACCT CTACAAGCAG ATATCAA..G TCAGAGCGGG GCT....ACC
  42_8    ACAACCACCT CTACAAGCAA ATCTCCAACG GGACATCGGG AGGAAGCACC
  42_15   ACAACCACCT CTACAAGCAA ATCTCCAACG GGACATCGGG AGGAAGCACC
  42_5b   ACAACCACCT CTACAAGCAA ATCTCCAACG GGACATCGGG AGGAAGCACC
  42_1b   ACAACCACCT CTACAAGCAA ATCTCCAACG GGACATCGGG AGGAAGCACC
  42_13   ACAACCACCT CTACAAGCAA ATCTCCAACG GGACATCGGG AGGAAGCACC
  42_3a   ACAACCACCT CTACAAGCAA ATCTCCAACG GGACATCGGG AGGAAGCACC
  42_4    ACAACCACCT CTACAAGCAG ATATCAA... .GTCAGAGCG GGGC..TACC
  42_5a   ACAACCACCT CTACAAGCAG ATATCAA... .GTCAGAGCG GGGC..TACC
  42_10   ACAACCACCT CTACAAGCAG ATATCAA..G TCAGAGCGGG GCTA....CC
  42_3b   ACAACCACCT CTACAAGCAG ATATCAA..G TCAGAGCGGG GCTA....CC
  42_11   ACAACCACCT CTACAAGCAG ATATCAA..G TCAGAGCGGG GCTA....CC
  42_6b   ACAACCACCT CTACAAGCAA ATCTCCAACG GGACATCGGG AGGAAGCACC
  43_1    ACAACCATCT CTACAAGCAA ATCTCCAACG GGACATCGGG AGGAAGCACT
  43_5    ACAACCATCT CTACAAGCAA ATCTCCAACG GGACATCGGG AGGAAGCACT
  43_12   ACAACCATCT CTACAAGCAA ATCTCCAACG GGACATCGGG AGGAAGCACT
  43_20   ACAACCACCT CTACAAGCAA ATCTCCAACG GCACCTCGGG AGGAAGCACC
  43_21   ACAACCACCT CTACAAGCAA ATCTCCAACG GCACCTCGGG AGGAAGCACC
  43_23   ACAACCACCT CTACAAGCAA ATCTCCAACG GCACCTCGGG AGGAAGCACC
  43_25   ACAACCACCT CTACAAGCAA ATCTCCAACG GCACCTCGGG AGGAAGCACC
  44_1    ACAACCACCT CTACAAGCAA ATCTCCAACG GGACTTCGGG AGGAAGCACC
  44_5    ACAACCACCT CTACAAGCAA ATCTCCAACG GGACTTCGGG AGGAAGCACC
 223_10   ACAACCACCT CTACAAGCAA ATCTCCAGTC AGTCAGCAGG GAG...CACC
 223_2    ACAACCACCT CTACAAGCAA ATCTCCAGTC AGTCAGCAGG GAG...CACC
 223_4    ACAACCACCT CTACAAGCAA ATCTCCAGTC AGTCAGCAGG GAG...CACC
 223_5    ACAACCACCT CTACAAGCAA ATCTCCAGTC AGTCAGCAGG GAG...CACC
 223_6    ACAACCACCT CTACAAGCAA ATCTCCAGTC AGTCAGCAGG GAG...CACC
 223_7    ACAACCACCT CTACAAGCAA ATCTCCAGTC AGTCAGCAGG GAG...CACC
  A3_4    ATAATCACCT CTACAAGCAA ATCTCCA... GCGAATCGGG AGC...CACC
  A3_5    ATAATCACCT CTACAAGCAA ATCTCCA... GCGAATCGGG AGC...CACC
  A3_7    ATAATCGCCT CTACAAGCAA ATCTCCA... GCGAATCGGG AGC...CACC
  A3_3    ATAATCACCT CTACAAGCAA ATCTCCA... GCGAATCGGG AGC...CACC
  42_12   ACAACCACCT CTACAAGCAA ATCTCCAACG GGACATCGGG AGGAAGCACC
  AAV1    ATAACCACCT CTACAAGCAA ATCTCCAGTG CTTCAACGGG .GG..CCAGC
  AAV2    ACAACCACCT CTACAAACAA ATTTCCA... GCCAATCAGG AGC...CTCG
  AAV3    ACAACCATCT CTACAAGCAA ATCTCCA... GCCAATCAGG AGC...TTCA
  AAV8    ACAACCACCT CTACAAGCAA ATCTCCAACG GGACATCGGG AGGAGCACC
  AAV9    ACAACCACCT CTACAAGCAA ATCTCCAATG GAACATCGGG AGGAAGCACC
  AAV7    ACAACCACCT CTACAAGCAA ATCTCCAGTG AAACTGCAGG TAG...TACC
  AAV10   ACAACCACAT CTACAAGCAA ATCTCCAGCG AGACAGGAGC CACCAACGAC
  AAV11   ACAACCACCT CTACAAACAA ATCTCCAGCG CTTCAACGGG GGCCAGCAAC
  AAV12   ACAACCACCT CTACAAGCAA ATCTCCAGCC AATCGGGTGC CACCAACGAC
  44_2    ACAACCACCT CTACAAGCAA ATCTCCAACG GGACTTCGGG AGGAAGCACC
```

FIG. 1AAJ

```
         3051                                                    3100
  42_2   AACGACAACC ACTTCTTCGG CTACAGCACC CCCTGGGGCT ATTTTGACTT
  42_8   AACGACAACA CCTACTTCGG CTACAGCACC CCCTGGGGGT ATTTTGACTT
 42_15   AACGACAACA CCTACTTCGG CTACAGCACC CCCTGGGGGT ATTTTGACTT
 42_5b   AACGACAACA CCTACTTCGG CTACAGCACC CCCTGGGGGT ATTTTGACTT
 42_1b   AACGACAACA CCTACTTCGG CTACAGCACC CCCTGGGGGT ATTTTGACTT
 42_13   AACGACAACA CCTACTTCGG CTACAGCACC CCCTGGGGGT ATTTTGACTT
 42_3a   AACGACAACA CCTACTTCGG CTACAGCACC CCCTGGGGGT ATTTTGACTT
  42_4   AACGACAACC ACTTCTTCGG CTACAGCACC CCCTGGGGCT ATTTTGACTT
 42_5a   AACGACAACC ACTTCTTCGG CTACAGCACC CCCTGGGGCT ATTTTGACTT
 42_10   AACGACAACC ACTTCTTCGG CTACAGCACC CCCTGGGGCT ATTTTGACTT
 42_3b   AACGACAACC ACTTCTTCGG CTACAGCACC CCCTGGGGCT ATTTTGACTT
 42_11   AACGACAACC ACTTCTTCGG CTACAGCACC CCCTGGGGCT ATTTTGACTT
 42_6b   AACGACAACA CCTACTTCGG CTACAGCACC CCCTGGGGGT ATTTTGACTT
  43_1   AACGACAACA CCTACTTTGG CTACAGCACC CCCTGGGGGT ATTTTGACTT
  43_5   AACGACAACA CCTACTTTGG CTACAGCACC CCCTGGGGGT ATTTTGACTT
 43_12   AACGACAACA CCTACTTTGG CTACAGCACC CCCTGGGGGT ATTTTGACTT
 43_20   AACGACAACA CCTATTTTGG CTACAGCACC CCCTGGGGGT ATTTTGACTT
 43_21   AACGACAACA CCTATTTTGG CTACAGCACC CCCTGGGGGT ATTTTGACTT
 43_23   AACGACAACA CCTATTTTGG CTACAGCACC CCCTGGGGGT ATTTTGACTT
 43_25   AACGACAACA CCTATTTTGG CTACAGCACC CCCTGGGGGT ATTTTGACTT
  44_1   AACGACAACA CCTACTTCGG CTACAGCACC CCCTGGGGGT ATTTTGACTT
  44_5   AACGACAACA CCTACTTCGG CTACAGCACC CCCTGGGGGT ATTTTGACTT
 223_10  AACGATAACG TCTATTTCGG CTACAGCACC CCCTGGGGGT ATTTTGACTT
 223_2   AACGATAACG TCTATTTCGG CTACAGCACC CCCTGGGGGT ATTTTGACTT
 223_4   AACGATAACG TCTATTTCGG CTACAGCACC CCCTGGGGGT ATTTTGACTT
 223_5   AACGATAACG TCTATTTCGG CTACAGCACC CCCTGGGGGT ATTTTGACTT
 223_6   AACGATAACG TCTATTTCGG CTACAGCACC CCCTGGGGGT ATTTTGACTT
 223_7   AACGATAACG TCTATTTCGG CTACAGCACC CCCTGGGGGT ATTTTGACTT
   A3_4  AACGACAACC ACTACTTCGG CTACAGCACC CCCTGGGGGT ATTTTGACTT
   A3_5  AACGACAACC ACTACTTCGG CTACAGCACC CCCTGGGGGT ATTTTGACTT
   A3_7  AACGACAACC ACTACTTCGG CTACAGCACC CCCTGGGGGT ATTTTGACTT
   A3_3  AACGACAACC ACTACTTCGG CTACAGCACC CCCTGGGGGT ATTTTGACTT
 42_12   AACGACAACA CCTACTTCGG CTACAGCACC CCCTGGGGGT ATTTTGACTT
  AAV1   AACGACAACC ACTACTTCGG CTACAGCACC CCCTGGGGGT ATTTTGATTT
  AAV2   AACGACAATC ACTACTTTGG CTACAGCACC CCTTGGGGGT ATTTTGACTT
  AAV3   AACGACAACC ACTACTTTGG CTACAGCACC CCTTGGGGGT ATTTTGACTT
  AAV8   AACGACAACA CCTACTTCGG CTACAGCACC CCCTGGGGGT ATTTTGACTT
  AAV9   AACGACAACA CCTACTTTGG CTACAGCACC CCCTGGGGGT ATTTTGACTT
  AAV7   AACGACAACA CCTACTTCGG CTACAGCACC CCCTGGGGGT ATTTTGACTT
 AAV10   AACCACTACT TCGGCTACAG C......ACC CCCTGGGGGT ATTTTGACTT
 AAV11   ...GACAACC ACTACTTTGG CTACAGCACC CCCTGGGGGT ATTTTGACTT
 AAV12   AACCACTACT TCGGCTA... ...CAGCACC CCTTGGGGGT ATTTTGATTT
  44_2   AACGACAACA CCTACTTCGG CTACAGCACC CCCTGGGGGT ATTTTGACTT
```

FIG. 1AAK

```
         3101                                                           3150
  42_2   TAACAGATTC CACTGCCACT TCTCACCACG TGACTGGCAG CGACTCATCA
  42_8   TAACAGATTC CACTGCCACT TCTCACCACG TGACTGGCAG CGACTCATCA
  42_15  TAACAGATTC CACTGCCACT TCTCACCACG TGACTGGCAG CGACTCATCA
  42_5b  TAACAGATTC CACTGCCACT TCTCACCACG TGACTGGCAG CGACTCATCA
  42_1b  TAACAGATTC CACTGCCACT TCTCACCACG TGACTGGCAG CGACTCATCA
  42_13  TAACAGATTC CACTGCCACT TCTCACCACG TGACTGGCAG CGACTCATCA
  42_3a  TAACAGATTC CACTGCCACT TCTCACCACG TGACTGGCAG CGACTCATCA
  42_4   CAACAGATTC CACTGCCACT TCTCATCACG TGACTGGCAG CGACTCATCA
  42_5a  CAACAGATTC CACTGCCACT TCTCACCACG TGACTGGCAG CGACTCATCA
  42_10  CAACAGATTC CACTGCCACT TCTCACCACG TGACTGGCAG CGACTCATCA
  42_3b  CAACAGATTC CACTGCCACT TCTCACCACG TGACTGGCAG CGACTCATCA
  42_11  CAACAGATTC CACTGCCACT TCTCACCACG TGACTGGCAG CGACTCATCA
  42_6b  TAACAGATTC CACTGCCACT TCTCACCACG TGACTGGCAG CGACTCATCA
  43_1   CAACAGATTC CACTGCCACT TCTCACCACG TGACTGGCAG CGACTCATCA
  43_5   CAACAGATTC CACTGCCACT TCTCACCACG TGACTGGCAG CGACTCATCA
  43_12  CAACAGATTC CACTGCCACT TCTCACCACG TGACTGGCAG CGACTCATCA
  43_20  CAACAGATTC CACTGTCACT TTTCACCACG TGACTGGCAA CGACTCATCA
  43_21  CAACAGATTC CACTGTCACT TTTCACCACG TGACTGGCAA CGACTCATCA
  43_23  CAACAGATTC CACTGTCACT TTTCACCACG TGACTGGCAA CGACTCATCA
  43_25  CAACAGATTC CACTGTCACT TTTCACCACG TGACTGGCAA CGACTCATCA
  44_1   TAACAGATTC CACTGCCACT TCTCACCACG TGACTGGCAG CGACTCATCA
  44_5   TAACAGATTC CACTGCCACT TCTCACCACG TGACTGGCAG CGACTCATCA
  223_10 CAACAGATTC CATTGCCACT TCTCACCACG TGACTGGCAG CGACTTATCA
  223_2  CAACAGATTC CATTGCCACT TCTCACCACG TGACTGGCAG CGACTTATCA
  223_4  CAACAGATTC CATTGCCACT TCTCACCACG TGACTGGCAG CGACTTATCA
  223_5  CAACAGATTC CATTGCCACT TCTCACCACG TGACTGGCAG CGACTTATCA
  223_6  CAACAGATTC CATTGCCACT TCTCACCACG TGACTGGCAG CGACTTATCA
  223_7  CAACAGATTC CATTGCCACT TCTCACCACG TGACTGGCAG CGACTTATCA
  A3_4   TAACAGATTC CACTGTCACT TCTCACCACG TGACTGGCAG CGACTCATCA
  A3_5   TAACAGATTC CACTGTCACT TCTCACCACG TGACTGGCAG CGACTCATCA
  A3_7   TAACAGATTC CACTGTCACT TCTCACCACG TGACTGGCAG CGACTCATCA
  A3_3   TAACAGATTC CACTGTCACT TCTCACCACG TGACTGGCAG CGACTCATCA
  42_12  TAACAGATTC CACTGCCACT TCTCACCACG TGACTGGCAG CGACTCATCA
  AAV1   CAACAGATTC CACTGCCACT TTTCACCACG TGACTGGCAG CGACTCATCA
  AAV2   CAACAGATTC CACTGCCACT TTTCACCACG TGACTGGCAA AGACTCATCA
  AAV3   TAACAGATTC CACTGCCACT TCTCACCACG TGACTGGCAG CGACTCATTA
  AAV8   TAACAGATTC CACTGCCACT TTTCACCACG TGACTGGCAG CGACTCATCA
  AAV9   CAACAGATTC CACTGCCACT TCTCACCACG TGACTGGCAG CGACTCATCA
  AAV7   TAACAGATTC CACTGCCACT TCTCACCACG TGACTGGCAG CGACTCATCA
  AAV10  TAACAGATTC CACTGCCACT TTTCACCACG TGACTGGCAG CGACTCATCA
  AAV11  TAACAGATTC CACTGCCACT TCTCACCACG TGACTGGCAG CGACTCATCA
  AAV12  CAACAGATTC CACTGCCATT TCTCACCACG TGACTGGCAG CGACTCATCA
  44_2   TAACAGATTC CACTGCCACT TCTCACCACG TGACTGGCAG CGACTCATCA
```

FIG. 1AAL

```
            3151                                                          3200
    42_2    ACAACAACTG GGGATTCCGG CCCAGAAAGC TGCGGTTCAA GTTGTTCAAC
    42_8    ACAACAACTG GGGATTCCGG CCCAAGAGAC TCAACTTCAA GCTCTTCAAC
    42_15   ACAACAACTG GGGATTCCGG CCCAAGAGAC TCAACTTCAA GCTCTTCAAC
    42_5b   ACAACAACTG GGGATTCCGG CCCAAGAGAC TCAACTTCAA GCTCTTCAAC
    42_1b   ACAACAACTG GGGATTCCGG CCCAAGAGAC TCAACTTCAA GCTCTTCAAC
    42_13   ACAACAACTG GGGATTCCGG CCCAAGAGAC TCAACTTCAA GCTCTTCAAC
    42_3a   ACAACAGCTG GGGATTCCGG CCCAAGAGAC TCAACTTCAA GCTCTTCAAC
    42_4    ACAACAACTG GGGATTCCGG CCCAAGAGAC TCAACTTCAA GCTCTTCAAC
    42_5a   ACAACAACCG GGGATTCCGG CCCAGAAAGC TGCGGTTCAA GTTGTTCAAC
    42_10   ACAACAACTG GGGATTCCGG CCCAGAAAGC TGCGGTTCAA GTTGTTCAAC
    42_3b   ACAACAACTG GGGATTCCGG CCCAGAAAGC TGCGGTTCAA GTTGTTCAAC
    42_11   ACAACAACTG GGGATTCCGG CCCAGAAAGC TGCGGTTCAA GTTGTTCAAC
    42_6b   ACAACAACTG GGGATTCCGG CCCAGAAAGC TGCGGTTCAA GTTGTTCAAC
    43_1    ACAATAACTG GGGATTCCGG CCCAAGAGAC TCAACTTCAA GCTCTTCAAC
    43_5    ACAATAACTG GGGATTCCGG CCCAAGAGAC TCAACTTCAA GCTCTTCAAC
    43_12   ACAATAACTG GGGATTCCGG CCCAAGAGAC TCAACTTCAA GCTCTTCAAC
    43_20   ACAACAATTG GGGATTCCGG CCCAAAAGAC TCAACTTCAA GCTGTTCAAC
    43_21   ACAACAATTG GGGATTCCGG CCCAAAAGAC TCAACTTCAA GCTGTTCAAC
    43_23   ACAACAATTG GGGATTCCGG CCCAAAAGAC TCAACTTCAA GCTGTTCAAC
    43_25   ACAACAATTG GGGATTCCGG CCCAAAAGAC TCAACTTCAA GCTGTTCAAC
    44_1    ACAACAACTG GGGATTCCGG CCCAAGAGAC TCAACTTCAA GCTCTTCAAC
    44_5    ACAACAACTG GGGATTCCGG CCCAAGAGAC CCAACTTCAA GCTCTTCAAC
   223_10   ACAACAACTG GGGATTCCGG CCCAAGAAGC TCAACTTCAA GCTCTTCAAC
   223_2    ACAACAACTG GGGATTCCGG CCCAAGAAGC TCAACTTCAA GCTCTTCAAC
   223_4    ACAACAACTG GGGATTCCGG CCCAAGAAGC TCAACTTCAA GCTCTTCAAC
   223_5    ACAACAACTG GGGATTCCGG CCCAAGAAGC TCAACTTCAA GCTCTTCAAC
   223_6    ACAACAACTG GGGATTCCGG CCCAAGAAGC TCAACTTCAA GCTCTTCAAC
   223_7    ACAACAACTG GGGATTCCGG CCCAAGAAGC TCAACTTCAA GCTCTTCAAC
    A3_4    ACAACAACTG GGGATTTAGA CCCAAGAAAC TCAATTTCAA GCTCTTCAAC
    A3_5    ATAACAACTG GGGATTTAGA CCCAAGAAAC TCAATTTCAA GCTCTTCAAC
    A3_7    ACAACAACTG GGGATTTAGA CCCAAGAAAC TCAATTTCAA GCTCTTCAAC
    A3_3    ACAACAACTG GGGATTTAGA CCCAAGAAAC TCAATTTCAA GCTCTTCAAC
    42_12   ACAACAACTG GGGATTCCGG CCCAAGAGAC TCAACTTCAA GCTCTTCAAC
    AAV1    ACAACAATTG GGGATTCCGG CCCAAGAGAC TCAACTTCAA ACTCTTCAAC
    AAV2    ACAACAACTG GGGATTCCGA CCCAAGAGAC TCAACTTCAA GCTCTTTAAC
    AAV3    ACAACAACTG GGGATTCCGG CCCAAGAAAC TCAGCTTCAA GCTCTTCAAC
    AAV8    ACAACAACTG GGGATTCCGG CCCAAGAGAC TCAGCTTCAA GCTCTTCAAC
    AAV9    ACAACAACTG GGGATTCCGG CCAAAGAGAC TCAACTTCAA GCTGTTCAAC
    AAV7    ACAACAACTG GGGATTCCGG CCCAAGAAGC TGCGGTTCAA GCTCTTCAAC
    AAV10   ACAACAACTG GGGATTC
    AAV11   ACAACAACTG GGGATTC
    AAV12   ACAACAACTG GGGATTC
    44_2    ACAACAACTG GGGATTCCGG CCCAAGAGAC TCAACTTCAA GCTCTTCAAC
```

FIG. 1AAM

```
         3201                                                    3250
 42_2    ATCCAGGTCA AGGAGGTCAC GACGAACGAC GGCGTTACGA CCATCGCTAA
 42_8    ATCCAGGTCA AGGAGGTCAC GCAGAATGAA GGCACCAAGA CCATCGCCAA
 42_15   ATCCAGGTCA AGGAGGTCAC GCAGAATGAA GGCACCAAGA CCATCGCCAA
 42_5b   ATCCAGGTCA AGGAGGTCAC GCAGAATGAA GGCACCAAGA CCATCGCCAA
 42_1b   ATCCAGGTCA AGGAGGTCAC GCAGAATGAA GGCACCAAGA CCATCGCCAA
 42_13   ATCCAGGTCA AGGAGGTCAC GCAGAATGAA GGCACCAAGA CCATCGCCAA
 42_3a   ATCCAGGTCA AGGAGGTCAC GCAGAATGAA GGCACCAAGA CCATCGCCAA
 42_4    ATCCAGGTCA AGGAGGTCAC GCAGAATGAA GGCACCAAGA CCATCGCCAA
 42_5a   ATCCAGGTCA AGGAGGTCAC GACGAACGAC GGCGTTACGA CCATCGCTAA
 42_10   ATCCAGGTCA AGGAGGTCAC GACGAACGAC GGCGTTACGA CCATCGCCAA
 42_3b   ATCCAGGTCA AGGAGGTCAC GACGAACGAC GGCGTTACGA CCATCGCTAA
 42_11   ATCCAGGTCA AGGAGGTCAC GACGAACGAC GGCGTTACGA CCATCGCTAA
 42_6b   ATCCAGGTCA AGGAGGTCAC GACGGACGAC GGCGTTACGA CCATCGCTAA
 43_1    ATCCAGGTCA AGGAGGTCAC GCAGAATGAA GGCACCAAGA CCATCGCCAA
 43_5    ATCCAGGTCA AGGAGGTCAC GCAGAATGAA GGCACCAAGA CCATCGCCAA
 43_12   ATCCAGGTCA AGGAGGTCAC GCAGAATGAA GGCACCAAGA CCATCGCCAA
 43_20   ATCCAGGTCA AGGAAGTCAC GACGAACGAA GGCACCAAGA CCATCGCCAA
 43_21   ATCCAGGTCA AGGAAGTCAC GACGAACGAA GGCACCAAGA CCATCGCCAA
 43_23   ATCCAGGTCA AGGAAGTCAC GACGAACGAA GGCACCAAGA CCATCGCCAA
 43_25   ATCCAGGTCA AGGAAGTCAC GACGAACGAA GGCACCAAGA CCATCGCCAA
 44_1    ATCCAGGTCA AGGAGGTCAC GCAGAATGAA GGCACCAAGA CCATCGCCAA
 44_5    ATCCAGGTCA AGGAGGTCAC GCAGAATGAA GGCACCAAGA CCATCGCCAA
 223_10  ATCCAGGTCA AGGAGGTCAC GACGAATGAC GGTGTCACAA CCATCGCTAA
 223_2   ATCCAGGTCA AGGAGGTCAC GACGAATGAC GGTGTCACAA CCATCGCTAA
 223_4   ATCCAGGTCA AGGAGGTCAC GACGAATGAC GGCGTCACAA CCATCGCTAA
 223_5   ATCCAGGTCA AGGAGGTCAC GACGAATGAC GGCGTCACAA CCATCGCTAA
 223_6   ATCCAGGTCA AGGAGGTCAC GACGAATGAC GGTGTCACAA CCATCGCTAA
 223_7   ATCCAGGTCA AGGAGGTCAC GACGAATGAC GGCGTCACAA CCATCGCTAA
 A3_4    ATCCAAGTCA AGGAGGTCAC GCAGAATGAT GGAACCACGA CCATCGCCAA
 A3_5    ATCCAAGTCA AGGAGGTCAC GCAGAATGAT GGAACCACGA CCATCGCCAA
 A3_7    ATCCAAGTCA AGGAGGTCAC GCAGAATGAT GGAACCACGA CCATCGCCAA
 A3_3    ATCCAAGTCA AGGAGGTCAC GCAGAATGAT GGAACCACGA CCATCGCCAA
 42_12   ATCCAGGTCA AGGAGGTCAC GCAGAATGAA GGCACCAAGA CCATCGCCAA
 AAV1    ATCCAAGTCA AGGAGGTCAC GACGAATGAT GGCGTCACAA CCATCGCTAA
 AAV2    ATTCAAGTCA AAGAGGTCAC GCAGAATGAC GGTACGACGA CGATTGCCAA
 AAV3    ATCCAAGTTA GAGGGGTCAC GCAGAACGAT GGCACGACGA CTATTGCCAA
 AAV8    ATCCAGGTCA AGGAGGTCAC GCAGAATGAA GGCACCAAGA CCATCGCCAA
 AAV9    ATCCAGGTCA AGGAGGTTAC GACGAACGAA GGCACCAAGA CCATCGCCAA
 AAV7    ATCCAGGTCA AGGAGGTCAC GACGAATGAC GGCGTTACGA CCATCGCTAA
 44_2    ATCCAGGTCA AGGAGGTCAC GCAGAATGAA GGCACCAAGA CCATCGCCAA
```

FIG. 1AAN

```
            3251                                                      3300
   42_2   TAACCTTACC AGCACGATTC AGGTCTTCTC GGACTCGGAG TACCAACTGC
   42_8   TAACCTTACC AGCACGATTC AGGTCTTTAC GGACTCGGAA TACCAGCTCC
  42_15   TAACCTTACC AGCACGATTC AGGTCTTTAC GGACTCGGAA TACCAGCTCC
  42_5b   TAACCTTACC AGCACGATTC AGGTCTTTAC GGACTCGGAA TACCAGCTCC
  42_1b   TAACCTTACC AGCACGATTC AGGTCTTTAC GGACTCGGAA TACCAGCTCC
  42_13   TAACCTTACC AGCACGATTC AGGTCTTTAC GGACTCGGAA TACCAGCTCC
  42_3a   TAACCTTACC AGCACGATTC AGGTCTTTAC GGACTCGGAA TACCAGCTCC
   42_4   TAACCTTACC AGCACGATTC AGGTCTTTAC GGACTCGGAA TACCGGCTCC
  42_5a   TAACCTTACC AGCACGATTC AGGTCTTCTC GGACTCGGAG TACCAACTGC
  42_10   TAACCTTACC AGCACGATTC AGGTCTTCTC GGACTCGGAG TACCAACTGC
  42_3b   TAACCTTACC AGCACGATTC AGGTCTTCTC GGACTCGGAG TACCAACTGC
  42_11   TAACCTTACC AGCACGATTC AGGTCTTCTC GGACTCGGAG TACCAACTGC
  42_6b   TAACCTTACC AGCACGATTC AGGTCTTCTC GGACTCGGAG TACCAACTGC
   43_1   TAACCTTACC AGCACGATTC AGGTGTTTAC GGACTCGGAA TACCAGCTCC
   43_5   TAACCTTACC AGCACGATTC AGGTGTTTAC GGACTCGGAA TACCAGCTCC
  43_12   TAACCTTACC AGCACGATTC AGGTGTTTAC GGACTCGGAA TACCAGCTCC
  43_20   TAATCTCACC AGCACCGTGC AGGTCTTTAC GGACTCGGAG TACCAGTTAC
  43_21   TAATCTCACC AGCACCGTGC GGGTCTTTAC GGACTCGGAG TACCAGTTAC
  43_23   TAATCTCACC AGCACCGTGC AGGTCTTTAC GGACTTGGAG TACCAGTTAC
  43_25   TAATCTCACC AGCACCGTGC AGGTCTTTAC GGACTCGGAG TACCAGTTAC
   44_1   TAACCTTACC AGCACGATTC AGGTCTTTAC GGACTCGGAA TACCAGCTCC
   44_5   TAACCTTACC AGCACGATTC AGGTCTTTAC GGACTCGGAA TACCAGCTCC
  223_10  TAACCTTACC AGCACGGTTC AGGTCTTTTC GGACTCGGAA TATCAACTGC
  223_2   TAACCTTACC AGCACGGTTC AGGTCTTTTC GGACTCGGAA TATCAACTGC
  223_4   TAACCTTACC AGCACGGTTC AGGTCTTTTC GGACTCGGAA TATCAACTGC
  223_5   TAACCTTACC AGCACGGTTC AGGTCTTTTC GGACTCGGAA TATCAACTGC
  223_6   TAACCTTACC AGCACGGTTC AGGTCTTTTC GGACTCGGAA TATCAACTGC
  223_7   TAACCTTACC AGCACGGTTC AGGTCTTTTC GGACCCGGAA TATCAACTGC
   A3_4   TAACCTTACC AGCACGGTGC AGGTCTTCAC AGACTCTGAG TACCAGCTGC
   A3_5   TAACCTTACC AGCACGGTGC AGGTCTTCAC AGACTCTGAG TACCAGCTGC
   A3_7   TAACCTTACC AGCACGGTGC AGGTCTTCAC AGACTCTGAG TACCAGCTGC
   A3_3   TAACCTTACC AGCGCGGTGC AGGTCTTCAC AGACTCTGAG TACCAGCTGC
  42_12   TAACCTTACC AGCACGATTC AGGTCTTTAC GGACTCGGAA TACCAGCTCC
   AAV1   TAACCTTACC AGCACGGTTC AAGTCTTCTC GGACTCGGAG TACCAGCTTC
   AAV2   TAACCTTACC AGCACGGTTC AGGTGTTTAC TGACTCGGAG TACCAGCTCC
   AAV3   TAACCTTACC AGCACGGTTC AAGTGTTTAC GGACTCGGAG TATCAGCTCC
   AAV8   TAACCTCACC AGCACCATCC AGGTGTTTAC GGACTCGGAG TACCAGCTGC
   AAV9   TAACCTTACC AGCACCGTCC AGGTCTTTAC GGACTCGGAG TACCAGCTAC
   AAV7   TAACCTTACC AGCACGATTC AGGTATTCTC GGACTCGGAA TACCAGCTGC
   44_2   TAACCTTACC AGCACGATTC AGGTCTTTAC GGACTCGGAA TACCAGCTCC
```

FIG. 1AAO

```
         3301                                                              3350
 42_2    CGTACGTCCT  CGGCTCTGCG  CACCAGGGCT  GCCTCCCTCC  GTTCCCTGCG
 42_8    CGTACGTCCT  CGGCTCTGCG  CACCAGGGCT  GCCTGCCTCC  GTTCCCGGCG
 42_15   CGTACGTCCT  CGGCTCTGCG  CACCAGGGCT  GCCCGCCTCC  GTTCCCGGCG
 42_5b   CGTACGTCCT  CGGCTCTGCG  CACCAGGGCT  GCCTGCCTCC  GTTCCCGGCG
 42_1b   CGTACGTCCT  CGGCTCTGCG  CACCAGGGCT  GCCTGCCTCC  GTTCCCGGCG
 42_13   CGTACGTCCT  CGGCTCTGCG  CACCAGGGCT  GCCTGCCTCC  GTTCCCGGCG
 42_3a   CGTACGTCCT  CGGCTCTGCG  CACCAGGGCT  GCCTGCCTCC  GTTCCCGGCG
 42_4    CGTACGTCCT  CGGCTCTGCG  CACCAGGGCT  GCCTGCCTCC  GTTCCCGGCG
 42_5a   CGTACGTCCT  CGGCTCTGCG  CACCAGGGCT  GCCTCCCTCC  GTTCCCTGCG
 42_10   CGTACGTCCT  CGGCTCTGCG  CACCAGGGCT  GCCTCCCTCC  GTTCCCTGCG
 42_3b   CGTACGTCCT  CGGCTCTGCG  CACCAGGGCT  GCCTCCCTCC  GTTCCCTGCG
 42_1    CGTACGTCCT  CGGCTCTGCG  CACCAGGGCT  GCCTCCCTCC  GTTCCCTGCG
 42_6b   CGTACGTCCT  CGGCTCTGCG  CACCAGGGCT  GCCTCCCTCC  GTTCCCTGCG
 43_1    CGTACGTCCC  CGGCTCTGCG  CACCAGGGCT  GCCTCCCTCC  GTTCCCGGCG
 43_5    CGTACGTCCT  CGGCTCTGCG  CACCAGGGCT  GCCTCCCTCC  GTTCCCGGCG
 43_12   CGTACGTCCT  CGGCTCTGCG  CACCAGGGCT  GCCTCCCTCC  GTTCCCGGCG
 43_20   CGTACGTGCT  AGGATCCGCT  CACCAGGGAT  GTCTGCCTCC  GTTCCCGGCG
 43_21   CGTACGTGCT  AGGATCCGCT  CACCAGGGAT  GTCTGCCTCC  GTTCCCGGCG
 43_23   CGTACGTGCT  AGGATCCGCT  CACCAGGGAT  GTCTGCCTCC  GTTCCCGGCG
 43_25   CGTACGTGCT  AGGATCCGCT  CACCAGGGAT  GTCTGCCTCC  GTTCCCGGCG
 44_1    CGTACGTCCT  CGGCTCTGCG  CACCAGGGCT  GCCTGCCTCC  GTTCCCGGCG
 44_5    CGTACGTCCT  CGGCTCTGCG  CACCAGGGCT  GCCTGCCTCC  GTTCCCGGCG
223_10   CGTACGTCCT  CGGCTCCGCG  CACCAGGGCT  GCCTGCCTCC  GTTCCCGGCA
223_2    CGTACGTCCT  CGGCTCCGCG  CACCAGGGCT  GCCTGCCTCC  GTTCCCGGCA
223_4    CGTACGTCCT  CGGCTCCGCG  CACCAGGGCT  GCCTGCCTCC  GTTCCCGGCA
223_5    CGTACGTCCT  CGGCTCCGCG  CACCAGGGCT  GCCTGCCTCC  GTTCCCGGCA
223_6    CGTACGTCCT  CGGCTCCGCG  CACCAGGGCT  GCCTGCCTCC  GTTCCCGGCA
223_7    CGTACGTCCT  CGGCTCCGCG  CACCAGGGCT  GCCTGCCTCC  GTTCCCGGCA
 A3_4    CCTACGTCCT  CGGTTCGGCT  CACCAGGGCT  GCCTTCCGCC  GTTCCCAGCA
 A3_5    CCTACGTCCT  CGGTTCGGCT  CACCAGGGCT  GCCTTCCGCC  GTTCCCAGCA
 A3_7    CCTACGTCCT  CGGTTCGGCT  CACCAGGGCT  GCCTTCCGCC  GTTCCCAGCA
 A3_3    CCTACGTCCT  CGGTTCGGCT  CACCAGGGCT  GCCTTCCGCC  GTTCCCAGCA
 42_12   CGTACGTCCT  CGGCTCTGCG  CACCAGGGCT  GCCTGCCTCC  GTTCCCGGCG
 AAV1    CGTACGTCCT  CGGCTCTGCG  CACCAGGGCT  GCCTCCCTCC  GTTCCCGGCG
 AAV2    CGTACGTCCT  CGGCTCGGCG  CATCAAGGAT  GCCTCCCGCC  GTTCCCAGCA
 AAV3    CGTACGTGCT  CGGGTCGGCG  CACCAAGGCT  GTCTCCCGCC  GTTTCCAGCG
 AAV8    CGTACGTTCT  CGGCTCTGCC  CACCAGGGCT  GCCTGCCTCC  GTTCCCGGCG
 AAV9    CGTACGTCCT  AGGCTCTGCC  CACCAAGGAT  GCCTGCCACC  GTTTCCTGCA
 AAV7    CGTACGTCCT  CGGCTCTGCG  CACCAGGGCT  GCCTGCCTCC  GTTCCCGGCG
 44_2    CGTACGTCCT  CGGCTCTGCG  CACCAGGGCT  GCCTGCCTCC  GTTCCCGGCG
```

FIG. 1AAP

```
         3351                                                              3400
  42_2   GACGTGTTCA TGATTCCTCA GTACGGATAT CTGACTCTAA ACAACGGCAG
  42_8   GACGTCTTCA TGATTCCTCA GTACGGGTAC CTGACTCTGA ACAACGGCAG
  42_15  GACGTCTTCA TGATTCCTCA GTACGGGTAC CTGACTCTGA ACAACGGCAG
  42_5b  GACGTCTTCA TGATTCCTCA GTACGGGTAC CTGACTCTGA ACAACGGCAG
  42_1b  GACGTCTTCA TGATTCCTCA GTACGGGTAC CTGACTCTGA ACAACGGCAG
  42_13  GACGTCTTCA TGATTCCTCA GTACGGGTAC CTGACTCTGA ACAACGGCAG
  42_3a  GACGTCTTCA TGATTCCTCA GTACGGGTAC CTGACTCTGA ACAACGGCAG
  42_4   GACGTCTTCA TGATTCCTCA GTACGGGTAC CTGACTCTGA ACAACGGCAG
  42_5a  GACGTGTTCA TGATTCCTCA GTACGGATAT CTGACTCTAA ACAACGGCAG
  42_10  GACGTGTTCA TGATTCCTCA GTACGGATAT CTGACTCTAA ACAACGGCAG
  42_3b  GACGTGTTCA TGATTCCTCA GTACGGATAT CTGACTCTAA ACAACGGCAG
  42_1   GACGTGTTCA TGATTCCTCA GTACGGATAT CTGACTCTAA ACAACGGCAG
  42_6b  GACGTGTTCA TGATTCCTCA GTACGGATAT CTGACTCTAA ACAACGGCAG
  43_1   GACGTCTTCA TGATTCCTCA GTACGGGTAT CTGACCCTAA ACAATGGCAG
  43_5   GACGTCTTCA TGATTCCTCA GTACGGGTAT CTGACCCTAA ACAATGGCAG
  43_12  GACGTCTTCA TGATTCCTCA GTACGGGTAT CTGACCCTAA ACAATGGCAG
  43_20  GACGTCTTCA CGGTTCCTCA GTACGGCTAT TTAACTTTAA ACAATGGAAG
  43_21  GACGTCTTCA TGGTTCCTCA GTACGGCTAT TTAACTTTAA ACAATGGAAG
  43_23  GACGTCTTCA TGGTTCCTCA GTACGGCTAT TTAACTTTAA ACAATGGAAG
  43_25  GACGTCTTCA TGGTTCCTCA GTACGGCTAT TTAACTTTAA ACAATGGAAG
  44_1   GACGTCTTCA TGATTCCTCA GTACGGGTAC CTGACTCTGA ACAATGGCAG
  44_5   GACGTCTTCA TGATTCCTCA GTACGGGTAC CTGACTCTGA ACAATGGCAG
 223_10  GACGTGTTCA TGATTCCGCA GTACGGATAC CTGACTCTGA ACAATGGCAG
 223_2   GACGTGTTCA TGATTCCGCA GTACGGATAC CTGACTCTGA ACAATGGCAG
 223_4   GACGTGTTCA TGATTCCGCA GTACGGATAC CTGACTCTGA ACAATGGCAG
 223_5   GACGTGTTCA TGATTCCGCA GTACGGATAC CTGACTCTGA ACAATGGCAG
 223_6   GACGTGTTCA TGATTCCGCA GTACGGATAC CTGACTCTGA ACAATGGCAG
 223_7   GACGTGTTCA TGATTCCGCA GTACGGATAC CTGACTCTGA ACAATGGCAG
  A3_4   GACGTCTTCA TGATTCCTCA GTACGGCTAC TTGACTCTGA ACAATGGCAG
  A3_5   GACGTCTTCA TGATTCCTCA GTACGGCTAC TTGACTCTGA ACAATGGCAG
  A3_7   GACGTCTTCA TGATTCCTCA GTACGGCTAC TTGACTCTGA ACAATGGCAG
  A3_3   GACGTCTTCA TGATTCCTCA GTACGGCTAC TTGACTCTGA ACAATGGCAG
  42_12  GACGTCTTCA TGATTCCTCA GTACGGGTAC CTGACTCTGA ACAACGGCAG
  AAV1   GACGTGTTCA TGATTCCGCA ATACGGCTAC CTGACGCTCA ACAATGGCAG
  AAV2   GACGTCTTCA TGGTGCCACA GTATGGATAC CTCACCCTGA ACAACGGGAG
  AAV3   GACGTCTTCA TGGTCCCTCA GTATGGATAC CTCACCCTGA ACAACGGAAG
  AAV8   GACGTGTTCA TGATTCCCCA GTACGGCTAC CTAACACTCA ACAACGGTAG
  AAV9   GACGTCTTCA TGGTTCCTCA GTACGGCTAC CTGACGCTCA ACAATGGAAG
  AAV7   GACGTCTTCA TGATTCCTCA GTACGGCTAC CTGACTCTCA ACAATGGCAG
  44_2   GACGTCTTCA TGATTCCTCA GTACGGGTAC CTGACTCTGA ACAATGGCAG
```

FIG. 1AAQ

```
          3401                                                        3450
  42_2    TCAGTCTGTG GGACGTTCCT CCTTCTACTG CCTGGAGTAC TTTCCTTCTC
  42_8    TCAGGCCGTG GGCCGTTCCT CCTTCTACTG CCTGGAGTAC TTTCCTTCTC
  42_15   TCAGGCCGTG GGCCGTTCCT CCTTCTACTG CCTGGAGTAC TTTCCTTCTC
  42_5b   TCAGGCCGTG GGCCGTTCCT CCTTCTACTG CCTGGAGTAC TTTCCTTCTC
  42_1b   TCAGGCCGTG GGCCGTTCCT CCTTCTACTG CCTGGAGTAC TTTCCTTCTC
  42_13   TCAGGCCGTG GGCCGTTCCT CCTTCTACTG CCTGGAGTAC TTTCCTTCTC
  42_3a   TCAGGCCGTG GGCCGTTCCT CCTTCTACTG CCTGGAGTAC TTTCCTTCTC
  42_4    TCAGGCCGTG GGCCGTTCCT CCTTCTACTG CCTGGAGTAC TTTCCTTCTC
  42_5a   TCAGTCTGTG GGACGTTCCT CCTTCTACTG CCTGGAGTAC TTTCCTTCTC
  42_10   TCAGTCTGTG GGACGTTCCT CCTTCTACTG CCTGGAGTAC TTTCCTTCTC
  42_3b   TCAGTCTGTG GGACGTTCCT CCTTCTACTG CCTGGAGTAC TTTCCTTCTC
  42_11   TCAGTCTGTG GGACGTTCCT CCTTCTACTG CCTGGAGTAC TTTCCTTCTC
  42_6b   TCAGTCTGTG GGACGTTCCT CCTTCTACTG CCTGGAGTAC TTTCCTTCTC
  43_1    TCAGGCTGTG GGCCGTTCCT CCTTCTACTG CCTGGAATAC TTCCCTTCTC
  43_5    TCAGGCTGTG GGCCGTTCCT CCTTCTACTG CCTGGAATAC TTCCCTTCTC
  43_12   TCAGGCTGTG GGCCGTTCCT CCTTCTACTG CCTGGAATAC TTCCCTTCTC
  43_20   CCAAGCCCTG GGACGTTCCT CCTTCTACTG TCTGGAGTAT TTCCCATCGC
  43_21   CCAAGCCCTG GGACGTTCCT CCTTCTACTG TCTGGAGTAT TTCCCATCGC
  43_23   CCAAGCCCTG GGACGTTCCT CCTTCTACTG TCTGGAGTAT TTCCCATCGC
  43_25   CCAAGCCCTG GGACGTTCCT CCTTCTACTG TCTGGAGTAT TTCCCATCGC
  44_1    TCAGGCCGTG GGCCGTTCCT CCTTCTACTG CCTGGAGTAC TTTCCTTCTC
  44_5    TCAGGCCGTG GGCCGTTCCT CCTTCTACTG CCTGGAGTAC TTTCCTTCTC
 223_10   CCAATCGGTA GGCCGTTCCT CCTTCTACTG CCTGGAGTAC TTTCCTTCTC
 223_2    CCAATCGGTA GGCCGTTCCT CCTTCTACTG CCTGGAGTAC TTTCCTTCTC
 223_4    CCAATCGGTA GGCCGTTCCT CCTTCTACTG CCTGGAGTAC TTTCCTTCTC
 223_5    CCAATCGGTA GGCCGTTCCT CCTTCTACTG CCTGGAGTAC TTTCCTTCTC
 223_6    CCAATCGGTA GGCCGTTCCT CCTTCTACTG CCTGGAGTAC TTTCCTTCTC
 223_7    CCAATCGGTA GGCCGTTCCT CCTTCTACTG CCTGGAGTAC TTTCCTTCTC
  A3_4    CCAAGCGGTA GGACGTTCTT CATTCTACTG TCTAGAGTAT TTTCCCTCTC
  A3_5    CCAAGCGGTA GGACGTTCTT CATTCTACTG TCTAGAGTAT TTTCCCTCTC
  A3_7    CCAAGCGGTA GGACGTTCTT CATTCTACTG TCTAGAGTAT TTTCCCTCTC
  A3_3    CCAAGCGGTA GGACGTTCTT CATTCTACTG TCTAGAGTAT TTTCCCTCTC
  42_12   TCAGGCCGTG GGCCGTTCCT CCTTCTACTG CCTGGAGTAC TTTCCTTCTC
  AAV1    CCAAGCCGTG GGACGTTCAT CCTTTTACTG CCTGGAATAT TTCCCTTCTC
  AAV2    TCAGGCAGTA GGACGCTCTT CATTTTACTG CCTGGAGTAC TTTCCTTCTC
  AAV3    TCAAGCGGTG GGACGCTCAT CCTTTTACTG CCTGGAGTAC TTCCCTTCGC
  AAV8    TCAGGCCGTG GGACGCTCCT CCTTCTACTG CCTGGAATAC TTCCCTTCGC
  AAV9    TCAAGCGTTA GGACGTTCTT CTTTCTACTG TCTGGAATAC TTCCCTTCTC
  AAV7    TCAGTCTGTG GGACGTTCCT CCTTCTACTG CCTGGAGTAC TTCCCCTCTC
  44_2    TCAGGCCGTG GGCCGTTCCT CCTTCTACTG CCTGGAGTAC TTTCCTTCTC
```

FIG. 1AAR

```
          3451                                                    3500
  42_2    AGATGCTGAG AACGGGCAAT AACTTTGAAT TCAGCTACAC CTTTGAGGAA
  42_8    AAATGCTGAG AACGGGCAAC AACTTTGAGT TCAGCTACCA GTTTGAGGAC
  42_15   AAATGCGGAG AACGGGCAAC AACTTTGAGT TCAGCTACCA GTTTGAGGAC
  42_5b   AAATGCTGAG AACGGGCAAC AACTTTGAGT TCAGCTACCA GTTTGAGGAC
  42_1b   AAATGCTGAG AACGGGCAAC AACTTTGAGT TCAGCTACCA GTTTGAGGAC
  42_13   AAATGCTGAG AACGGGCAAC AACTTTGAGT TCAGCTACCA GTTTGAGGAC
  42_3a   AAATGCTGAG AACGGGCAAC AACTTTGAGT TCAGCTACCA GTTTGAGGAC
  42_4    AAATGCTGAG AACGGGCAAC AACTTTGAGT TCAGCTACCA GTTTGAGGAC
  42_5a   AGATGCTGAG AACGGGCAAT AACTTTGAAT TCAGCTACCA GTTTGAGGAC
  42_10   AGATGCTGAG AACGGGCAAT AACTTTGAAT TCAGCTACAC CTTTGAGGAA
  42_3b   AGATGCTGAG AACGGGCAAT AACTTTGAAT TCAGCTACAC CTTTGAGGAA
  42_11   AGATGCTGAG AACGGGCAAT AACTTTGAAT TCAGCTACAC CTTTGAGGAA
  42_6b   AGATGCTGAG AACGGGCAAT AACTTTGAAT TCAGCTACAC CTTTGAGGAA
  43_1    AAATGCTGAG GACGGGCAAC AACTTTGAAT TCAGCTACAC CTTCGAGGAC
  43_5    AAATGCTGAG GACGGGCAAC AACTTTGAAT TCAGCTACAC CTTCGAGGAC
  43_12   AAATGCTGAG GACGGGCAAC AACTTTGAAT TCAGCTACAC CTTCGAGGAC
  43_20   AGATGCTGAG AACCGGCAAC AACTTTCAGT TCAGCTACAC CTTCGAGGAC
  43_21   AGATGCTGAG AACCGGCAAC AACTTTCAGT TCAGCTACAC CTTCGAGGAC
  43_23   AGATGCCGAG AACCGGCAAC AACTTTCAGT TCAGCTACAC CTTCGAGGAC
  43_25   AGATGCTGAG AACCGGCAAC AACTTTCAGT TCAGCTACAC CTTCGAGGAC
  44_1    AAATGCTGAG AACGGGCAAC AACTTTGAGT TCAGCTACCA GTTTGAGGAC
  44_5    AAATGCTGAG AACGGGCAAC AACTTTGAGT TCAGCTACCA GTTTGAGGAC
  223_10  AGATGCTGAG AACGGGCAAC AACTTCACCT TTAGCTACAC CTTCGAGGAC
  223_2   AGATGCTGAG AACGGGCAAC AACTTCACCT TTAGCTACAC CTTCGAGGAC
  223_4   AGATGCTGAG AACGGGCAAC AACTTCACCT TTAGCTACAC CTTCGAGGAC
  223_5   AGATGCTGAG AACGGGCAAC AACTTCACCT TTAGCTACAC CTTCGAGGAC
  223_6   AGATGCTGAG AACGGGCAAC AACTTCACCT TTAGCTACAC CTTCGAGGAC
  223_7   AGATGCTGAG AACGGGCAAC AACTTCACCT TTAGCTACAC CTTCGAGGAC
  A3_4    AGATGCTGAG GACGGGAAAC AACTTCACCT TCAGCTACAC TTTTGAAGAC
  A3_5    AGATGCTGAG GACGGGAAAC AACTTCACCT TCAGCTACAC TTTTGAAGAC
  A3_7    AGATGCTGAG GACGGGAAAC AACTTCACCT TCAGCTACAC TTTTGAAGAC
  A3_3    AGATGCTGAG GACGGGAAAC AACTTCACCT TCAGCTACAC TTTTGAAGAC
  42_12   AAATGCTGAG AACGGGCAAC AACTTTGAGT TCAGCTACCA GTTTGAGGAC
  AAV1    AGATGCTGAG AACGGGCAAC AACTTTACCT TCAGCTACAC CTTTGAGGAA
  AAV2    AGATGCTGCG TACCGGAAAC AACTTTACCT TCAGCTACAC TTTTGAGGAC
  AAV3    AGATGCTAAG GACTGGAAAT AACTTCCAAT TCAGCTATAC CTTCGAGGAT
  AAV8    AGATGCTGAG AACCGGCAAC AACTTCCAGT TTACTTACAC CTTCGAGGAC
  AAV9    AGATGCTGAG AACCGGCAAC AACTTTCAGT TCAGCTACAC TTTCGAGGAC
  AAV7    AGATGCTGAG AACGGGCAAC AACTTTGAGT TCAGCTACAG CTTCGAGGAC
  44_2    AAATGCTGAG AACGGGCAAC AACTTTGAGT TCAGCTACCA GTTTGAGGAC
```

FIG. 1AAS

```
              3501                                                              3550
    42_2      GTGCCTTTCC ACAGCAGCTA TGCGCACAGC CAGAGCCTGG ACCGGCTGAT
    42_8      GTGCCTTTTC ACAGCAGCTA CGCGCACAGC CAAAGCCTGG ACCGGCTGAT
    42_15     GTGCCTTTTC ACAGCAGCTA CGCGCATAGC CAAAGCCTGG ACCGGCTGAT
    42_5b     GTGCCTTTTC ACAGCAGCTA CGCGCACAGC CAAAGCCTGG ACCGGCTGAT
    42_1b     GTGCCTTTTC ACAGCAGCTA TGCGCACAGC CAAAGCCTGG ACCGGCTGAT
    42_13     GTGCCTTTTC ACAGCAGCTA TGCGCACAGC CAAAGCCTGG ACCGGCTGAT
    42_3a     GTGCCTTTTC ACAGCAGCTA CGCGCACAGC CAAAGCCTGG ACCGGCTGAT
    42_4      GTGCCTTTTC ACAGCAGCTA CGCGCACAGC CAAAGCCTGG ACCGGCTGAT
    42_5a     GTGCCCTTTC ACAGCAGCTA CGCGCACAGC CAAAGCCTGG ACCGGCTGAT
    42_10     GTGCCTTTCC ACAGCAGCTA TGCGCACAGC CAGAGCCTGG ACCGGCTGAT
    42_3b     GTGCCTTTCC ACAGCAGCTA TGCGCACAGC CAGAGCCTGG ACCGGCTGAT
    42_11     GTGCCTTTCC ACAGCAGCTA TGCGCACAGC CAGAGCCTGG ACCGGCTGAT
    42_6b     GTGCCTTTCC ACAGCAGCTA TGCGCATAGC CAGAGCCTGG ACCGGCTGAT
    43_1      GTGCCTTTCC ACAGCAGCTA CGCGCACAGC CAGAGCCTGG ACCGGCTGAT
    43_5      GTGCCTTTCC ACAGCAGCTA CGCGCACAGC CAGAGCCTGG ACCGGCTGAT
    43_12     GTGCCTTTCC ACAGCAGCTA CGCGCACAGC CAGAGCCTGG ACCGGCTGAT
    43_20     GTGCCTTTCC ACAGCAGCTA CGCGCACAGC CAGAGCCTGG ACAGGCTGAT
    43_21     GTGCCTTTCC ACAGCAGCTA CGCGCACAGC CAGAGCCTGG ACAGGCTGAT
    43_23     GTGCCTTTCC ACAGCAGCTA CGCGCACAGC CAGAGCCTGG ACAGGCTGAT
    43_25     GTGCCTTTCC ACAGCAGCTA CGCGCACAGC CAGAGCCTGG ACAGGCTGAT
    44_1      GTGCCTTTTC ACAGCAGCTA CGCGCACAGC CAAAGCCTGG ACCGGCTGAT
    44_5      GTGCCTTTTC ACAGCAGCTA CGCGCACAGC CAAAGCCTGG ACCGGCTGAT
    223_10    GTGCCTTTCC ACAGCAGCTA CGCGCACAGC CAGAGTCTGG ACCGGCTGAT
    223_2     GTGCCTTTCC ACAGCAGCTA CGCGCACAGC CAGAGTCTGG ACCGGCTGAT
    223_4     GTGCCTTTCC ACAGCAGCTA CGCGCACAGC CAGAGTCTGG GCCGGCTGAT
    223_5     GTGCCTTTCC ACAGCAGCTA CGCGCACAGC CAGAGTCTGG GCCGGCTGAT
    223_6     GTGCCTTTCC ACAGCAGCTA CGCGCACAGC CAGAGTCTGG ACCGGCTGAT
    223_7     GTGCCTTTCC ACAGCAGCTA CGCGCACAGC CAGAGTCTGG ACCGGCTGAT
    A3_4      GTGCCTTTCC ACAGCAGCTA CGCGCACAGC CAGAGTCTGG ATCGGCTGAT
    A3_5      GTGCCTTTCC ACAGCAGCTA CGCGCACAGC CAGAGTCTGG ATCGGCTGAT
    A3_7      GTGCCTTTCC ACAGCAGCTA CGCGCACAGC CAGAGTCTGG ATCGGCTGAT
    A3_3      GTGCCTTTCC ACAGCAGCTA CGCGCACAGC CAGAGTCTGG ATCGGCTGAT
    42_12     GTGCCTTTTC ACAGCAGCTA CGCGCACAGC CAAAGCCTGG ACCGGCTGAC
    AAV1      GTGCCTTTCC ACAGCAGCTA CGCGCACAGC CAGAGCCTGG ACCGGCTGAT
    AAV2      GTTCCTTTCC ACAGCAGCTA CGCTCACAGC CAGAGTCTGG ACCGTCTCAT
    AAV3      GTACCTTTTC ACAGCAGCTA CGCTCACAGC CAGAGTTTGG ATCGCTTGAT
    AAV8      GTGCCTTTCC ACAGCAGCTA CGCCCACAGC CAGAGCTTGG ACCGGCTGAT
    AAV9      GTGCCTTTCC ACAGCAGCTA CGCACACAGC CAGAGTCTAG ATCGACTGAT
    AAV7      GTGCCTTTCC ACAGCAGCTA CGCACACAGC CAGAGCCTGG ACCGGCTGAT
    44_2      GTGCCTTTTC ACAGCAGCTA CGCGCACAGC CAAAGCCTGG ACCGGCTGAT
```

FIG. 1AAT

```
            3551                                                              3600
   42_2     GAATCCCCTC  ATCGACCAGT  ACCTGTACTA  CCTGGCCCGG  ACCCAGAGCA
   42_8     GAACCCCCTC  ATCGACCAGT  ACCTGTACTA  CCTGTCTCGG  ACTCAGTCCA
   42_15    GAACCCCCTC  ATCGACCAGT  ACCTGTACTA  CCTGTCTCGG  ACTCAGTCCA
   42_5b    GAACCCCCTC  ATCGACCAGT  ACCTGTACTA  CCTGTCTCGG  ACTCAGTCCA
   42_1b    GAACCCCCTC  ATCGACCAGT  ACCTGTACTA  CCTGTCTCGG  ACTCAGTCCA
   42_13    GAACCCCCTC  ATCGACCAGT  ACCTGTACTA  CCTGTCTCGG  ACTCAGTCCA
   42_3a    GAACCCCCTC  ATCGACCAGT  ACCTGTACTA  CCTGTCTCGG  ACTCAGTCCA
   42_4     GAACCCCCTC  ATCGACCAGT  ACCTGTACTA  CCTGTCTCGG  ACTCAGTCCA
   42_5a    GAACCCCCTC  ATCGACCAGT  ACCTGTACTA  CCTGTCTCGG  ACTCAGTCCA
   42_10    GAATCCCCTC  ATCGACCAGT  ACCTGTACTA  CCTGGCCCGG  ACCCAGAGCA
   42_3b    GAATCCCCTC  ATCGACCAGT  ACCTGTACTA  CCTGGCCCGG  ACCCAGAGCA
   42_11    GAATCCCCTC  ATCGACCAGT  ACCTGTACTA  CCTGGCCCGG  ACCCAGAGCA
   42_6b    GAATCCCCTC  ATCGACCAGT  ACCTGTACTA  CCTGGCCCGG  ACCCAGAGCA
   43_1     GAACCCTCTC  ATCGACCAGT  ACCTGTATTA  CTTATCCAGA  ACTCAGTCCA
   43_5     GAACCCTCTC  ATCGACCAGT  ACCTGTATTA  CTTATCCAGA  ACTCAGTCCA
   43_12    GAACCCTCTC  ATCGACCAGT  ACCTGTATTA  CTTATCCAGA  ACTCAGTCCA
   43_20    GAATCCCCTC  ATCGACCAGT  ACCTGTACTA  CCTGGTCAGA  ACGCAAACGA
   43_21    GAATCCCCTC  ATCGACCAGT  ACCTGTACTA  CCTGGTCAGA  ACGCAAACGA
   43_23    GAATCCCCTC  ATCGACCAGT  ACCTGTACTA  CCTGGTCAGA  ACGCAAACGA
   43_25    GAATCCCCTC  ATCGACCAGT  ACCTGTACTA  CCTGGTCAGA  ACGCAAACGA
   44_1     GAACCCCCTC  ATCGACCAGT  ACCTGTACTA  CCTGTCTCGG  ACTCAGTCCA
   44_5     GAACCCCCTC  ATCGACCAGT  ACCTGTACTA  CCTGTCTCGG  ACTCAGTCCA
   223_10   GAATCCCCTC  ATCGACCAGT  ACCTGTACTA  CTTGGCCAGA  ACACAGAGCA
   223_2    GAATCCCCTC  ATCGACCAGT  ACCTGTACTA  CTTGGCCAGA  ACACAGAGCA
   223_4    GAATCCCCTC  ATCGACCAGT  ACCTGTACTA  CTTGGCCAGA  ACACAGAGCA
   223_5    GAATCCCCTC  ATCGACCAGT  ACCTGTACTA  CTTGGCCAGA  ACACAGAGCA
   223_6    GAATCCCCTC  ATCGACCAGT  ACCTGTACTA  CTTGGCCAGA  ACACAGAGCA
   223_7    GAATCCCCTC  ATCGACCAGT  ACCTGTACTA  CTTGGCCAGA  ACACAGAGCA
   A3_4     GAATCCTCTC  ATTGACCAGT  ACCTGTATTA  CCTGAGCAAA  ACTCAGGGTA
   A3_5     GAATCCTCTC  ATTGACCAGT  ACCTGTATTA  CCTGAGCAAA  ACTCAGGGTA
   A3_7     GAATCCTCTC  ATTGACCAGT  ACCTGTATTA  CCTGAGCAAA  ACTCAGGGTA
   A3_3     GAATCCTCTC  ATTGACCAGT  ACCTGTATTA  CCTGAGCAAA  ACTCAGGGTA
   42_12    GAACCCCCTC  ATCGACCAGT  ACCTGTACTA  CCTGGCCCGG  ACCCAGAGCA
   AAV1     GAATCCTCTC  ATCGACCAAT  ACCTGTATTA  CCTGAACAGA  ACTCAAA.AT
   AAV2     GAATCCTCTC  ATCGACCAGT  ACCTGTATTA  CTTGAGCAGA  ACAAACACTC
   AAV3     GAATCCTCTT  ATTGATCAGT  ATCTGTACTA  CCTGAACAGA  ACGCAAGGAA
   AAV8     GAATCCTCTG  ATTGACCAGT  ACCTGTACTA  CTTGTCTCGG  ACTCAAACAA
   AAV9     GAACCCCCTC  ATCGACCAGT  ACCTATACTA  CCTGGTCAGA  ACACAGACAA
   AAV7     GAATCCCCTC  ATCGACCAGT  ACTTGTACTA  CCTGGCCAGA  ACACAGAGTA
   44_2     GAACCCCCTC  ATCGACCAGT  ACCTGTACTA  CCTGTCTCGG  ACTCAGTCCA
```

FIG. 1AAU

```
        3601                                                    3650
42_2    CTACGG..GG TCCACAAGGG AGCTGCA.GT TCCA.. ... TCAGGCTGGG
42_8    CGGGA...GG TACCGCAGGA ACTCAGCAGT TGCTATTTTC TCAGGCCGGG
42_15   CGGGA...GG TACCGCAGGA ACTCAGCAGT TGCTATTTTC TCAGGCCGGG
42_5b   CGGGA...GG TACCGCAGGA ACTCAGCAGT TGCTATTTTC TCAGGCCGGG
42_1b   CGGGA...GG TACCGCAGGA ACTCAGCAGT TGCTATTTTC TCAGGCCGGG
42_13   CGGGA...GG TACCGCAGGA ACTCAGCAGT TGCTATTTTC TCAGGCCGGG
42_3a   CGGGA...GG TACCGCAGGA ACTCAGCAGT TGCTATTTTC TCAGGCCGGG
42_4    CGGGA...GG TACCGCAGGA ACTCAGCAGT TGCTATTTTC TCAGGCCGGG
42_5a   CGGGA...GG TACCGCAGGA ACTCAGCAGT TGCTATTTTC TCAGGCCGGG
42_10   CTACG...GG GTCCACAAGG GAGCTGCAGT TCCA...... TCAGGCTGGG
42_3b   CTACG...GG GTCCACAAGG GAGCTGCAGT TCCA...... TCAGGCTGGG
42_11   CTACG...GG GTCCACAAGG GAGCTGCAGT TCCA...... TCAGGCTGGG
42_6b   CTACG...GG GTCCACAAGG GAGCTGCAGT TCCA...... TCAGGCTGGG
43_1    CAGGA...GG AACTCAAGGT ACTCAGCAAT TGTTATTTTC TCAAGCCGGG
43_5    CAGGA...GG AACTCAAGGT ACTCAGCAAT TGTTATTTTC TCAAGCCGGG
43_12   CAGGA...GG AACTCAAGGT ACTCAGCAAT TGTTATTTTC TCAAGCCGGG
43_20   CT......GG AACTGGAGGG ACGCAGACTC TGGCATTCAG CCAAGCGGGT
43_21   CT......GG AACTGGAGGG ACGCAGACTC TGGCATTCAG CCAAGCGGGT
43_23   CT......GG AACTGGAGGG ACGCAGACTC TGGCATTCAG CCAAGCGGGT
43_25   CT......GG AACTGGAGGG ACGCAGACTC TGGCATTCAG CCAAGCGGGT
44_1    CGGGA...GG TACCGCAGGA ACTCAGCAGT TGCTATTTTC TCAGGCCGGG
44_5    CGGGA...GG TACCGCAGGA ACTCAGCAGT TGCTATTTTC TCAGGCCGGG
223_10  ACGCAGGAGG TACTGCTGGC AATCGGGAAC TGCAGTTTTA TCAGGGCGGA
223_2   ACGCAGGAGG TACTGCTGGC AATCGGGAAC TGCAGTTTTA TCAGGGCGGA
223_4   ACGCAGGAGG TACTGCTGGC AATCGGGAAC TGCAGTTTTA TCAGGGCGGA
223_5   ACGCAGGAGG TACTGCTGGC AATCGGGAAC TGCAGTTTTA TCAGGGCGGA
223_6   ACGCAGGAGG TACTGCTGGC AATCGGGAAC TGCAGTTTTA TCAGGGCGGA
223_7   ACGCAGGAGG TACTGCTGGC AATCGGGAAC TGCAGTTTTA TCAGGGCGGA
A3_4    CAAG...TGG AACAACGCAG CAATCGAGAC TGCAGTTCAG CCAAGCTGGG
A3_5    CAAG...TGG AACAACGCAG CAATCGAGAC TGCAGTTCAA CCAAGCTGGG
A3_7    CAAG...TGG AACAACGCAG CAATCGAGAC TGCAGTTCAG CCAAGCTGGG
A3_3    CAAG...TGG AACAACGCAG CAATCGAGAC TGCAGTTCAG CCAAGCTGGG
42_12   CTACG...GG GTCCACAAGG GGGCTGCAGT TCCA...... TCAGGCTGGG
AAV1    CAGTCC..GG AAGTGCCCAA AACAAGGACT TGCTGTTTAG CCGTGGGTCT
AAV2    CAAG...TGG AACCACCACG CAGTCAAGGC TTCAGTTTTC TCAGGCCGGA
AAV3    CAACCTCTGG AACAACCAAC CAATCACGGC TGCTTTTTAG CCAGGCTGGG
AAV8    CAGGAG..GC .ACGGCAAAT ACGCAGACTC TGGGCTTCAG CCAAGGTGGG
AAV9    CTGGA..... .ACTGGGGGA ACTCAAACTT TGGCATTCAG CCAAGCAGGC
AAV7    ACCCAGGAGG CACAGCTGGC AATCGGGAAC TGCAGTTTTA CCAGGGCGGG
44_2    CGGGA...GG TACCGCAGGA ACTCAGCAGT TGCTATTTTC TCAGGCCGGG
```

FIG. 1AAV

```
          3651                                                              3700
  42_2    CCCAACACCA TGGCCGAGCA ATCAAAGAAC TGGCTGCCCG GACCCTGTTA
  42_8    CCTAATAACA TGTCGGCTCA GGCCAAAAAC TGGCTACCCG GGCCCTGCTA
  42_15   CCTAATAACA TGTCGGCTCA GGCCAAAAAC TGGCTACCCG GGCCCTGCTA
  42_5b   CCTAATAACA TGTCGGCTCA GGCCAAAAAC TGGCTACCCG GGCCCTGCTA
  42_1b   CCTAATAACA TGTCGGCTCA GGCCAAAAAC TGGCTACCCG GGCCCTGCTA
  42_13   CCTAATAACA TGTCGGCTCA GGCCAAAAAC TGGCTACCCG GGCCCTGCTA
  42_3a   CCTAATAACA TGTCGGCTCA GGCCAAAAAC TGGCTACCCG GGCCCTGCTA
  42_4    CCTAATAACA TGTCGGCTCA GGCCAAAAAC TGGCTACCCG GGCCCTGCTA
  42_5a   CCTAATAACA TGTCGGCTCA GGCCAAAAAC TGGCTACCCG GGCCCTGCTA
  42_10   CCCAACACCA TGGCCGAGCA ATCAAAGAAC TGGCTGCCCG GACCCTGTTA
  42_3b   CCCAACACCA TGGCCGAGCA ATCAAAGAAC TGGCTGCCCG GACCCTGTTA
  42_11   CCCAACACCA TGGCCGAGCA ATCAAAGAAC TGGCTGCCCG GACCCTGTTA
  42_6b   CCCAACACCA TGGCCGAGCA ATCAAAGAAC TGGCTGCCCG GACCCTGTTA
  43_1    CCCGCAAACA TGTCGGCTCA GGCCAAGAAC TGGCTACCTG GACCGTGTTA
  43_5    CCCGCAAACA TGTCGGCTCA GGCCAAGAAC TGGCTACCTG GACCGTGTTA
  43_12   CCCGCAAACA TGTCGGCTCA GGCCAAGAAC TGGCTACCTG GACCGTGTTA
  43_20   CCTAGCTCAA TGGCCAACCA GGCTAGAAAT TGGGTGCCCG GACCTTGCTA
  43_21   CCTAGCTCAA TGGCCAACCA GGCTAGAAAT TGGGTGCCCG GACCTTGCTA
  43_23   CCTAGCTCAA TGGCCAACCA GGCTAGAAAT TGGGTGCCCG GACCTTGCTA
  43_25   CCTAGCTCAA TGGCCAACCA GGCTAGAAAT TGGGTGCCCG GACCTTGCTA
  44_1    CCTAATAACA TGTCGGCTCA GGCCAAAAAC TGGCTACCCG GGCCCTGCTA
  44_5    CCTAATAACA TGTCGGCTCA GGCCAAAAAC TGGCTACCCG GGCCCTGCTA
  223_10  CCTACCACCA TGGCCGAACA AGCAAAGAAC TGGCTGCCCG GACCTTGCTT
  223_2   CCTACCACCA TGGCCGAACA AGCAAAGAAC TGGCTGCCCG GACCTTGCTT
  223_4   CCTACCACCA TGGCCGAACA AGCAAAGAAC TGGCTGCCCG GACCTTGCTT
  223_5   CCTACCACCA TGGCCGAACA AGCAAAGAAC TGGCTGCCCG GACCTTGCTT
  223_6   CCTACCACCA TGGCCGAACA AGCAAAGAAC TGGCTGCCCG GACCTTGCTT
  223_7   CCTACCACCA TGGCCGAACA AGCAAAGAAC TGGCTGCCCG GACCTTGCTT
  A3_4    CCTAGCTCCA TGGCTCAGCA GGCCAAAAAC TGGCTACCGG GACCCAGCTA
  A3_5    CCTAGCTCCA TGGCTCAGCA GGCCAAAAAC TGGCTACCGG GACCCAGCTA
  A3_7    CCTAGCTCCA TGGCTCAGCA GGCCAAAAAC TGGCTACCGG GACCCAGCTA
  A3_3    CCTAGCTCCA TGGCTCAGCA GGCCAAAAAC TGGCTACCGG GACCCAGCTA
  42_12   CCCAACACCA TGGCCGAGCA ATCAAAGAAC TGGCTGCCCG GACCCTGTTA
  AAV1    CCAGCTGGCA TGTCTGTTCA GCCCAAAAAC TGGCTACCTG GACCCTGTTA
  AAV2    GCGAGTGACA TTCGGGACCA GTCTAGGAAC TGGCTTCCTG GACCCTGTTA
  AAV3    CCTCAGTCTA TGTCTTTGCA GGCCAGAAAT TGGCTACCTG GCCCTGCTA
  AAV8    CCTAATACAA TGGCCAATCA GGCAAAGAAC TGGCTGCCAG GACCCTGTTA
  AAV9    CCTAGCTCAA TGGCCAATCA GGCTAGAAAC TGGGTACCCG GGCCTTGCTA
  AAV7    CCTTCAACTA TGGCCGAACA AGCCAAGAAT TGGTTACCTG GACCTTGCTT
  44_2    CCTAATAACA TGTCGGCTCA GGCCAAAAAC TGGCTACCCG GGCCCTGCTA
```

FIG. 1AAW

```
          3701                                                          3750
   42_2   TCGGCAGCAG AGACTGTCAA AAAACATAGA CAGCAACAAC AACAGTAACT
   42_8   CCGGCAGCAA CGCGTCTCCA CGACACTGTC GCAAAATAAC AACAGCAACT
  42_15   CCGGCAGCAA CGCGTCTCCA CGACACTGTC GCAAAATAAC AACAGCAACT
  42_5b   CCGGCAGCAA CGCGTCTCCA CGACACTGTC GCAAAATAAC AACAGCAACT
  42_1b   CCGGCAGCAA CGCGTCTCCA CGACAGTGTC GCAAAATAAC AACAGCAACT
  42_13   CCGGCAGCAA CGCGTCTCCA CGACAGTGTC GCAAAATAAC AACAGCAACT
  42_3a   CCGGCAGCAA CGCGTCTCCA CGACACTGTC GCAAAATAAC AACAGCAACT
   42_4   CCGGCAGCAA CGCGTCTCCA CGACACTGTC GCAAAATAAC AACAGCAACT
  42_5a   CCGGCAGCAA CGCGTCTCCA CGACACTGTC GCAAAATAAC AACAGCAACT
  42_10   TCGGCAGCAG AGACTGTCAA AAAACATAGA CAGCAACAAC AACAGTAACT
  42_3b   TCGGCAGCAG AGACTGTCAA AAAACATAGA CAGCAACAAC ACCAGTAACT
  42_11   TCGGCGGCAG AGACTGTCAA AAGACATAGA CAGCAACAAC AACAGTAACT
  42_6b   TCGGCAGCAG AGACTGTCAA AAAACATAGA CAGCAACAAC AACAGTAACT
   43_1   CCGTCAGCAA CGAGTTTCCA CGACACTGTC GCAAAACAAC AACAGCAATT
   43_5   CCGTCAGCAA CGAGTTTCCA CGACACTGTC GCAAAACAAC AACAGCAATT
  43_12   CCGTCAGCAA CGAGTTTCCA CGACACTGTC GCAAAACAAC AACAGCAATT
  43_20   CCGGCAGCAG CGCGTCTCCA CGACAACCAA CCAGAACAAC AACAGCAACT
  43_21   CCGGCAGCAG CGCGTCTCCA CGACAACCAA CCAGAGCAAC AACAGCAACT
  43_23   CCGGCAGCAG CGCGTCTCCA CGACAACCAA CCAGAACAAC AACAGCAACT
  43_25   CCGGCAGCAG CGCGTCTCCA CGACAACCAA CCAGAACAAC AACAGCAACT
   44_1   CCGGCAGCAA CGCGTCTCCA CGACACTGTC GCAAAATAAC AACAGCAACT
   44_5   CCGGCAGCAA CGCGTCTCCA CGACACTGTC GCAAAATAAC AACAGCAACT
  223_10  CCGGCAACAG AGAGTATCCA AGACGCTGGA TCAAAATAAC AACAGCAACT
  223_2   CCGGCAACAG AGAGTATCCA AGACGCTGGA TCAAAATAAC AACAGCAACT
  223_4   CCGGCAACAG AGAGTATCCA AGACGCTGGA TCAAAATAAC AACAGCAACT
  223_5   CCGGCAACAG AGAGTATCCA AGACGCTGGA TCAAAATAAC AACAGCAACT
  223_6   CCGGCAACAG AGAGTATCCA AGACGCTGGA TCAAAATAAC AACAGCAACT
  223_7   CCGGCAACAG AGAGTATCCA AGACGCTGGA TCAAAATAAC AACAGCAACT
   A3_4   CCGACAGCAG CGAATGTCTA AGACGGCTAA TGACAACAAC AACAGTGAAT
   A3_5   CCGACAGCAG CGAATGTCTA AGACGGCTAA TGACAACAAC AACAGTGAAT
   A3_7   CCGACAGCAG CGAATGTCTA AGACGGCTAA TGACAACAAC AACAGTGAAT
   A3_3   CCGACAGCAG CGAATGTCTA AGACGGCTAA TGACAACAAC AACAGTGAAT
  42_12   TCGGCAGCAG AGACTGTCAA AAAACATAGA CAGCAACAAC AACAGTAACT
   AAV1   TCGGCAGCAG CGCGTTTCTA AAACAAAAAC AGACAACAAC AACAGCAATT
   AAV2   CCGCCAGCAG CGAGTATCAA AGACATCTGC GGATAACAAC AACAGTGAAT
   AAV3   CCGGCAACAG AGACTTTCAA AGACTGCTAA CGACAACAAC AACAGTAACT
   AAV8   CCGCCAACAA CGCGTCTCAA CGACAACCGG GCAAACAAC  AATAGCAACT
   AAV9   CCGTCAGCAG CGCGTCTCCA CAACCACCAA CCAAAATAAC AACAGCAACT
   AAV7   CCGGCAACAA AGAGTCTCCA AAACGCTGGA TCAAAACAAC AACAGCAACT
   44_2   CCGGCAGCAA CGCGTCTCCA CGACACTGTC GCAAAATAAC AACAGCAACT
```

FIG. 1AAX

```
            3751                                                              3800
  42_2    TTGCCTGGAC CGGGGCCACT AAATACCATC TGAATGGTAG AAATTCATTA
  42_8    TTGCTTGGAC CGGTGCCACC AAGTATCATC TGAATGGCAG AGACTCTCTG
  42_15   TTGCTTGGAC CGGTGCCACC AAGTATCATC TGAATGGCAG AGACTCTCTG
  42_5b   TTGCTTGGAC CGGTGCCACC AAGTATCATC TGAATGGCAG AGACTCTCTG
  42_1b   TTGCTTGGAC CGGTGCCACC AAGTATCATC TGAATGGCAG AGACTCTCTG
  42_13   TTGCTTGGAC CGGTGCCACC AAGTATCATC TGAATGGCAG AGACTCTCTG
  42_3a   TTGCTTGGAC CGGTGCCACC AAGTATCATC TGAATGGCAG AGACTCTCTG
  42_4    TTGCTTGGAC CGGTGCCACC AAGTATCATC TGAATGGCAG AGACTCTCTG
  42_5a   TTGCTTGGAC CGGTGCCACC AAGTATCATC TGAATGGCAG AGACTCTCTG
  42_10   TTGCCTGGAC CGGGGCCACT AAATACCATC TGAATGGTAG AAATTCATTA
  42_3b   TTGCCTGGAC CGGGGCCACT AAATACCATC TGAATGGTAG AAATTCATTA
  42_11   TTGCCTGGAC CGGGGCCACT AAATACCATC TGAATGGTAG AAATTCATTA
  42_6b   TTGCCTGGAC CGGGGCCACT AAATACCATC TGAATGGTAG AAATTCATTA
  43_1    TTGCTTGGAC CGGTGCCACC AAGTATCACC TGAATGGCAG AGACTCCCTG
  43_5    TTGCTTGGAC CGGTGCCACC AAGTATCACC TGAATGGCAG AGACTCCCTG
  43_12   TTGCTTGGAC CGGTGCCACC AAGTATCACC TGAATGGCAG AGACTCCCTG
  43_20   TTGCCTGGAC GGGAGCTGCC AAGTTTAAGC TGAACGGCCG AGACTCTCTA
  43_21   TTGCCTGGAC GGGAGCTGCC AAGTTTAAGC TGAACGGCCG AGACTCTCTA
  43_23   TTGCCTGGAC GGGAGCTGCC AAGTTTAAGC TGAACGGCCG AGACTCTCTA
  43_25   TTGCCTGGAC GGGAGCTGCC AAGTTTAAGC TGAACGGCCG AGACTCTCTA
  44_1    TTGCCTGGAC CGGTGCCACC AAGTATCATC TGAATGGCAG AGACTCTCTG
  44_5    TTGCCTGGAC CGGTGCCACC AAGTATCATC TGAATGGCAG AGACTCTCTG
 223_10   TTGCCTGGAC TGGTGCCACA AAATACCATT TAAATGNAAG AAATTCATTG
 223_2    TTGCCTGGAC TGGTGCCACA AAATACCATT TAAATGGAAG AAATTCATTG
 223_4    TTGCCTGGAC TGGTGCCACA AAATACCATT TAAATGGAAG AAATTCATTG
 223_5    TTGCCTGGAC TGGTGCCACA AAATACCATT TAAATGGAAG AAATTCATTG
 223_6    TTGCCTGGAC TGGTGCCACA AAATACCATT TAAATGGAAG AAATTCATTG
 223_7    TTGCCTGGAC TGGTGCCACA AAATACCATT TAAATGGAAG AAATTCATTG
  A3_4    TTGCTTGGAC TGCAGCCACC AAATATTACC TGAATGGAAG AAATTCTCTG
  A3_5    TTGCTTGGAC TGCAGCCACC AAATATTACC CGAATGGAAG AAATTCTCTG
  A3_7    TTGCTTGGAC TGCAGCCACC AAATATTACC TGAATGGAAG AAATTCTCTG
  A3_3    TTGCTTGGAC TGCAGCCACC AAATATTACC TGAATGGAAG AAATTCTCTG
  42_12   TTGCCTGGAC CGGGGCCACT AAATACCATC TGAATGGTAG AAATTCATTA
  AAV1    TTACCTGGAC TGGTGCTTCA AAATATAACC TCAATGGGCG TGAATCCATC
  AAV2    ACTCGTGGAC TGGAGCTACC AAGTACCACC TCAATGGCAG AGACTCTCTG
  AAV3    TTCTTGGAC  AGCGGCCAGC AAATATCATC TCAATGGCCG CGACTCGCTG
  AAV8    TTGCCTGGAC TGCTGGGACC AAATACCATC TGAATGGAAG AAATTCATTG
  AAV9    TTGCGTGGAC GGGAGCTGCT AAATTCAAGC TGAACGGGAG AGACTCGCTA
  AAV7    TTGCTTGGAC TGGTGCCACC AAATATCACC TGAACGGCAG AAACTCGTTG
  44_2    TTGCCTGGAC CGGTGCCACC AAGTATCATC TGAATGGCAG AGACTCTCTG
```

FIG. 1AAY

```
         3801                                                      3850
  42_2   ACCAACCCGG GCGTAGCCAT GGCCACCAAC AAGGACGACG AGGACCAGTT
  42_8   GTAAATCCCG GTGTCGCTAT GGCAACGCAC AAGGACGACG AAGAGCGATT
 42_15   GTAAATCCCG GTGTCGCTAT GGCAACGCAC AAGGACGACG AAGAGCGATT
 42_5b   GTAAATCCCG GTGTCGCTAT GGCAACGCAC AAGGACGACG AAGAGCGATT
 42_1b   GTAAATCCCG GTGTCGCTAT GGCAACGCAC AAGGGCGACG AAGAGCGATT
 42_13   GTAAATCCCG GTGTCGCTAT GGCAACGCAC AAGGGCGACG AAGAGCGATT
 42_3a   GTAAATCCCG GTGTCGCTAT GGCAACGCAC AAGGACGACG AAGAGCGATT
  42_4   GTAAATCCCG GTGTCGCTAT GGCAACGCAC AAGGACGACG AAGAGCGATT
 42_5a   GTAAATCCCG GTGTCGCTAT GGCAACGCAC AAGGACGACG AAGAGCGATT
 42_10   ACCAACCCGG GCGTAGCCAT GGCCACCAAC AAGGACGACG AGGACCAGTT
 42_3b   ACCAACCCGG GCGTAGCCAT GGCCACCAAC AAGGACGACG AGGACCAGTT
 42_11   ACCAACCCGG GCGTAGCCAT GGCCACCAAC AAGGACGACG AGGACCAGTT
 42_6b   ACCAACCCGG GCGTAGCCAT GGCCACCAAC AAGGACGACG AGGACCAGTT
  43_1   GTTAATCCCG GCGTTGCCAT GGCTACCCAC AAGGACGACG AGGAGCGCTT
  43_5   GTTAATCCCG GCGTTGCCAT GGCTACCCAC AAGGACGACG AGGAGCGCTT
 43_12   GTTAATCCCG GCGTTGCCAT GGCTACCCAC AAGGACGACG AGGAGCGCTT
 43_20   ATGAATCCGG GCGTGGCAAT GGCTTCCCAC AAGGATGACG ACGACCGCTT
 43_21   ATGAATCCGG GCGTGGCAAT GGCTTCCCAC AAGGATGACG ACGACCGCTT
 43_23   ATGAATCCGG GCGTGGCAAT GGCTTCCCAC AAGGATGACG ACGACCGCTT
 43_25   ATGAATCCGG GCGTGGCAAT GGCTTCCCAC AAGGATGACG ACGACCGCTT
  44_1   GTAAATCCCG GTGTCGCTAT GGCAACCCAC AAGGACGACG AAGAGCGATT
  44_5   GTAAATCCCG GTGTCGCTAT GGCAACCCAC AAGGACGACG AAGAGCGATT
 223_10  GTTAATCCCG GTGTCGCCAT GGCAACCCAC AAGGACGACG AGGAACGCTT
 223_2   GTTAATCCCG GTGTCGCCAT GGCAACCCAC AAGGACGACG AGGAACGCTT
 223_4   GTTAATCCCG GTGTCGCCAT GGCAACCCAC AAGGACGACG AGGAACGCTT
 223_5   GTTAATCCCG GTGTCGCCAT GGCAACCCAC AAGGACGACG AGGAACGCTT
 223_6   GTTAATCCCG GTGTCGCCAT GGCAACCCAC AAGGACGACG AGGAACGCTT
 223_7   GTTAATCCCG GTGTCGCCAT GGCAACCCAC AAGGACGACG AGGAACGCTT
  A3_4   GTCAATCCCG GGCCCCAAT  GGCCAGTCAC AAGGACGATG AGGAAAAGTA
  A3_5   GTCAATCCCG GGCCCCAAT  GGCCAGTCAC AAGGACGATG AGGAAAAGTA
  A3_7   GTCAATCCCG GGCCCCAAT  GGCCAGTCAC AAGGACGATG AGGAAAAGTA
  A3_3   GTCAATCCCG GGCCCCAGT  GGCCAGTCAC AAGGACGATG AGGAAAAGTA
 42_12   ACCAACCCGG GCGTAGCCAT GGCCACCAAC AAGGACGACG AGGACCAGTT
  AAV1   ATCAACCCTG GCACTGCTAT GGCCTCACAC AAAGACGACG AAGACAAGTT
  AAV2   GTGAATCC.. GGCC....AT GGCAAGCCAC AAGGACGATG AAGAAAAGTT
  AAV3   GTGAATCCAG GACCAGCTAT GGCCAGTCAC AAGGACGATG AAGAAAAATT
  AAV8   GCTAATCCTG GCATCGCTAT GGCAACACAC AAAGACGACG AGGAGCGTTT
  AAV9   ATGAATCCTG GCGTGGCTAT GGCATCGCAC AAAGACGACG AGGACCGCTT
  AAV7   GTTAATCCCG GCGTCGCCAT GGCAACTCAC AAGGACGACG AGGACCGCTT
  44_2   GTAAATCCCG GTGTCGCTAT GGCAACCCAC AAGGACGACG AAGAGCGATT
```

FIG. 1AAZ

```
           3851                                                           3900
   42_2    CTTTCCCATC AACGGAGTGC TGGTTTTTGG CGAAACGGGG GCTGCCAACA
   42_8    TTTTCCATCC AGCGGAGTCT TGATGTTTGG GAAACAGGGA GCTGGAAA..
   42_15   TTTTCCATCC AGCGGAGTCT TGATGTTTGG GAAACAGGGA GCTGGAAA..
   42_5b   TTTTCCATCC AGCGGAGTCT TGATGTTTGG GAAACAGGGA GCTGGAAA..
   42_1b   TTTTCCATCC AGCGGAGTCT TGATGTTTGG GAAACAGGGA GCTGGAAA..
   42_13   TTTTCCATCC AGCGGAGTCT TGATGTTTGG GAAACAGGGA GCTGGAAA..
   42_3a   TTTTCCATCC AGCGGAGTCT TGATGTTTGG GAAACAGGGA GCTGGAAA..
   42_4    TTTTCCATCC AGCGGAGTCT TGATGTTTGG GAAACAGGGA GCTGGAAA..
   42_5a   TTTTCCATCC AGCGGAGTCT TGATGTTTGG GAAACAGGGA GCTGGAAA..
   42_10   CTTTCCCATC AACGGAGTGC TGGTTTTTGG CAAAACGGGG GCTGCCAACA
   42_3b   CTTTCCCATC AACGGAGTGC TGGTTTTTGG CAAAACGGGG GCTGCCAACA
   42_11   CTTTCCCATC AACGGAGTGC TGGTTTTTGG CAAAACGGGG GCTGCCAACA
   42_6b   CTTTCCCATC AACGGAGTGC TGGTTTTTGG CAAAACGGGG GCTGCCAACA
   43_1    CTTCCCGTCA AGCGGAGTTC TAATGTTTGG CAAGCAGGGG GCTGGAAA..
   43_5    CTTCCCGTCA AGCGGAGTTC TAATGTTTGG CAAGCAGGGG GCTGGAAA..
   43_12   CTTCCCGTCA AGCGGAGTTC TAATGTTTGG CAAGCAGGGG GCTGGAAA..
   43_20   CTTCCCTTCG AGCGGGGTCC TGATTTTTGG CAAGCAAGGA GCCGGGAA..
   43_21   CTTCCCTTCG AGCGGGGTCC TGATTTTTGG CAAGCAAGGA GCCGGGAA..
   43_23   CTTCCCTTCG AGCGGGGTCC TGATTTTTGG CAAGCAAGGA GCCGGGAA..
   43_25   CTTCCCTTCG AGCGGGGTCC TGATTTTTGG CAAGCAAGGA GCCGGGAA..
   44_1    TTTTCCGTCC AGCGGAGTCT TAATGTTTGG GAAACAGGGA GCTGGAAA..
   44_5    TTTTCCGTCC AGCGGAGTCT TAATGTTTGG GAAACAGGGA GCTGGAAA..
  223_10   CTTCCCTTCG AGCGGAGTTC TAATTTTTGG CAAAACTGGA GCAGCTAATA
  223_2    CTCCCCTTCG AGCGGAGTTC TAATTTTTGG CAAAACTGGA GCAGCTAATA
  223_4    CTTCCCTTCG AGCGGAGTTC TAATTTTTGG CAAAACTGGA GCAGCTAATA
  223_5    CTTCCCTTCG AGCGGAGTTC TAATTTTTGG CAAAACTGGA GCAGCTAATA
  223_6    CTTCCCTTCG AGCGGAGTTC TAATTTTTGG CAAAACTGGA GCAGCTAATA
  223_7    CTTCCCTTCG AGCGGAGTTC TAATTTTTGG CAAAACTGGA GCAGCTAATA
   A3_4    TTTCCCCATG CACGGAAATC TCATCTTTGG AAAACAAGGC ACAGGAAC..
   A3_5    TTTCCCCATG CACGGAAATC TCATCTTTGG AAAACAAGGC ACAGGAAC..
   A3_7    TTTCCCCATG CACGGAAATC TCATCTTTGG AAAACAAGGC ACAGGAAC..
   A3_3    TTTCCCCATG CACGGAAATC TCATCTTTGG AAAACAAGGC ACAGGAAC..
   42_12   CTTTCCCATC AACGGAGTGC TGGTTTTTGG CAAAACGGGG GCTGCCAACA
   AAV1    CTTTCCCATG AGCGGTGTCA TGATTTTTGG AAAAGAGAGC GCCGGAGC..
   AAV2    TTTTCCTCAG AGCGGGGTTC TCATCTTTGG GAAGCAAGGC TCAGAGAA..
   AAV3    TTTCCCTATG CACGGCAATC TAATATTTGG CAAAGAAGGG ACAACGGC..
   AAV8    TTTTCCAGT  AACGGATCC  TGATTTTTGG CAAACAAAAT GCTGCCAG..
   AAV9    CTTTCCATCA AGTGGCGTTC TCATATTTGG CAAGCAAGGA GCCGGGAA..
   AAV7    TTTCCCATCC AGCGGAGTCC TGATTTTTGG AAAAACTGGA GCAACTAACA
   44_2    TTTTCCGTCC AGCGGAGTCT TAATGTTTGG GAAACAGGGA GCTGGAAA..
```

FIG. 1AAAA

```
          3901                                                                    3950
  42_2    AGACAACGCT  GGAA......  AACGTGCTAA  TGACCAGCGA  GGAGGAGATC
  42_8    AGACAACG.T  GGACTATAGC  AGCGTTATGC  TAACCAGTGA  GGAAGAAATC
  42_15   AGACAACG.T  GGACTATAGC  AGCGTTATGC  TAACCAGTGA  GGAAGAAATC
  42_5b   AGACAACG.T  GGACTATAGC  AGCGTTATGC  TAACCAGTGA  GGAAGAAATC
  42_1b   AGACAACG.T  AGACTATAGC  AGCGTTATGC  TAACCAGTGA  GGAAGAAATC
  42_13   AGACAACG.T  GGACTATAGC  AGCGTTATGC  TAACCAGTGA  GGAAGAAATC
  42_3a   AGACAACG.T  GGACTATAGC  AGCGTTATGC  TAACCAGTGA  GGAAGAAATC
  42_4    AGACAACG.T  GGACTATAGC  AGCGTTATGC  TAACCAGTGA  GGAAGAAATC
  42_5a   AGACAACG.T  GGACTATAGC  AGCGTTATGC  TAACCAGTGA  GGAAGAAATC
  42_10   AGACAACGCT  GGAA......  AACGTGCTAA  TGACCAGCGA  GGAGGAGATC
  42_3b   AGACAACGCT  GGAA......  AACGTGCTAA  TGACCAGCGA  GGAGGAGATC
  42_11   AGACAACGCT  GGAA......  AACGTGCTAA  TGACCAGCGA  GGAGGAGATC
  42_6b   AGACAACGCT  GGAA......  AACGTGCTAA  TGACCAGCGA  GGAGGAGATC
  43_1    AGACAATG.T  GGACTACAGC  AGCGTGATGC  TCACCAGCGA  AGAAGAAATT
  43_5    AGACAATG.T  GGACTACAGC  AGCGTGATGC  TCACCAGCGA  AGAAGAAATT
  43_12   AGACAATG.T  GGACTACAGC  AGCGTGATGC  TCACCAGCGA  AGAAGAAATT
  43_20   CGATGGAG.T  GGATTACAGC  CAAGTGCTGA  TTACAGATGA  GGAAGAAATC
  43_21   CGATGGAG.T  GGATTACAGC  CAAGTGCTGA  TTACAGATGA  GGAAGAAATC
  43_23   CGATGGAG.T  GGATTACAGC  CAAGTGCTGA  TTACAGATGA  GGAAGAAATC
  43_25   CGATGGAG.T  GGATTACAGC  CAAGTGCTGA  TTACAGATGA  GGAAGAAATC
  44_1    AGACAACG.T  GGACTATAGC  AGCGTTATGC  TAACCAGTGA  GGAAGAAATT
  44_5    AGACAACG.T  GGACTATAGC  AGCGTTATGC  TAACCAGTGA  GGAAGAAATT
  223_10  AAACTACATT  AGAA......  AACGTGCTCA  TGACAAATGA  AGAAGAAATT
  223_2   AAACTACATT  AGAA......  AACGTGCTCA  TGACAAATGA  AGAAGAAATT
  223_4   AAACTACATT  AGAA......  AACGTGCTCA  TGACAAATGA  AGAAGAAATT
  223_5   AAACTACATT  AGAA......  AACGTGCTCA  TGACAAATGA  AGAAGAAATT
  223_6   AAACTACATT  AGAA......  AACGTGCTCA  TGACAAATGA  AGAAGAAATT
  223_7   AAACTACATT  AGAA......  AACGTGCTCA  TGACAAATGA  AGAAGAAATT
  A3_4    TACCAATG.T  GGACATTGAA  TCAGTGCTTA  TTACAGACGA  AGAAGAAATC
  A3_5    TACCAATG.T  GGACATTGAA  TCAGTGCTTA  TTACAGACGA  AGAAGAAATC
  A3_7    TACCAATG.T  GGACATTGAA  TCAGTGCTTA  TTACAGACGA  AGAAGAAATC
  A3_3    TACCAATG.T  GGACATTGAA  TCAGTGCTTA  TTACAGACGA  AGAAGAAATC
  42_12   AGACAACGCT  GGAA......  AACGTGCTAA  TGACCAGCGA  GGAGGAGATC
  AAV1    TTCAAACA.C  TGCATTGGAC  AATGTCATGA  TTACAGACGA  AGAGGAAATT
  AAV2    AACAAATG.T  GAACATTGAA  AAGGTCATGA  TTACAGACGA  AGAGGAAATC
  AAV3    AAGTAACG.C  AGAATTAGAT  AATGTAATGA  TTACGGATGA  AGAAGAGATT
  AAV8    AGACAATG.C  GGATTACAGC  GATGTCATGC  TCACCAGCGA  GGAAGAAATC
  AAV9    CGATGGAG.T  CGACTACAGC  CAGGTGCTGA  TTACAGATGA  GGAAGAAATT
  AAV7    AAACTACATT  GGAA......  AATGTGTTAA  TGACAAATGA  AGAAGAAATT
  44_2    AGACAACG.T  GGACTATAGC  AGCGTTATGC  TAACCAGTGA  GGAAGAAATT
```

FIG. 1AAAB

```
          3951                                                              4000
  42_2    AAAACCACCA ATCCCGTGGC TACAGAAGAA TACGGTGTGG TCTCCAGCAA
  42_8    AAAACCACCA ACCCAGTGGC CACAGAACAG TACGGCGTGG TGGCCGATAA
  42_15   AAAACCACCA ACCCAGTGGC CACAGAACAG TACGGCGTGG TGGCCGATAA
  42_5b   AAAACCACCA ACCCAGTGGC CACAGAACAG TACGGCGTGG TGGCCGATAA
  42_1b   AAAACCACCA ACCCAGTGGC CACAGAACAG TACGGCGTGG TGGCCGATAA
  42_13   AAAACCACCA ACCCAGTGGC CACAGAACAG TACGGCGTGG TGGCCGATAA
  42_3a   AAAACCACCA ACCCAGTGGC CACAGAACAG TACGGCGTGG TGGCCGATAA
  42_4    AAAACCACCA ACCCAGTGGC CACAGAACAG TACGGCGTGG TGGCCGATAA
  42_5a   AAAACCACCA ACCCAGTGGC CACAGAACAG TACGGCGTGG TGGCCGATAA
  42_10   AAAACCACCA ATCCCGTGGC TACAGAAGAA TACGGTGTGG TCTCCAGCAA
  42_3b   AAAACCACCA ATCCCGTGGC TACAGAACAG TACGGTGTGG TCTCCAGCAA
  42_11   AAAACCACCA ATCCCGTGGC TACAGAAGAA TACGGTGTGG TCTCCAGCAA
  42_6b   AAAACCACCA ATCCCGTGGC TACAGAAGAA TACGGTGTGG TCTCCAGCAA
  43_1    AAAACTACTA ACCCAGTGGC TACAGAGCAG TATGGTGTGG TGGCAGACAA
  43_5    AAAACTACTA ACCCAGTGGC TACAGAGCAG TATGGTGTGG TGGCAGACAA
  43_12   AAAACTACTA ACCCAGTGGC TACAGAGCAG TATGGTGTGG TGGCAGACAA
  43_20   AAGGCTACCA ACCCCGTGGC CACAGAAGAA TATGGAGCAG TGGCCATCAA
  43_21   AAGGCTACCA ACCCCGTGGC CACAGAAGAA TATGGAGCAG TGGCCATCAA
  43_23   AAGGCTACCA ACCCCGTGGC CACAGAAGAA TATGGAGCAG TGGCCATCAA
  43_25   AAGGCTACCA ACCCCGTGGC CACAGAAGAA TATGGAGCAG TGGCCATCAA
  44_1    AAAACCACCA ACCCAGTGGC CACGGAACAG TACGGCGTGG TGGCCGATAA
  44_5    AAAACCACCA ACCCAGTGGC CACAGAACAG TACGGCGTGG TGGCCGATAA
  223_10  CGTCCTACCA ACCCGGTAGC TACCGAGGAA TACGGGATTG TAAGCAGCAA
  223_2   CGTCCTACCA ACCCGGTAGC TACCGAGGAA TACGGGATTG TAAGCAGCAA
  223_4   CGTCCTACCA ACCCGGTAGC TACCGAGGAA TACGGGATTG TAAGCAGCAA
  223_5   CGTCCTACCA ACCCGGTAGC TACCGAGGAA TACGGGATTG TAAGCAGCAA
  223_6   CGTCCTACCA ACCCGGTAGC TACCGAGGAA TACGGGATTG TAAGCAGCAA
  223_7   CGTCCTACCA ACCCGGTAGC TACCGAGGAA TACGGGATTG TAAGCAGCAA
  A3_4    AGAACAACTA ATCCTGTGGC TACAGAACAA TACGGACAGG TTGCCACCAA
  A3_5    AGAACGACTA ATCCTGTGGC TACAGAACAA TACGGACAGG TTGCCACCAA
  A3_7    AGAACAACTA ATCCTGTGGC TACAGAACAA TACGGACAGG TTGCCACCAA
  A3_3    AGAACAACTA ATCCTGTGGC TACAGAACAA TACGGACAGG TTGCCACCAA
  42_12   AAAACCACCA ATCCCGTGGC TACAGAAGAA TACGGTGTGG TCTCCAGCAA
  AAV1    AAAGCCACTA ACCCTGTGGC CACCGAAAGA TTTGGGACCG TGGCAGTCAA
  AAV2    GGAACAACCA ATCCCGTGGC TACGGAGCAG TATGGTTCTG TATCTACCAA
  AAV3    CGTACCACCA ATCCTGTGGC AACAGAGCAG TATGGAACTG TGGCAAATAA
  AAV8    AAAACCACTA ACCCTGTGGC TACAGAGGAA TACGGTATCG TGGCAGATAA
  AAV9    AAAGCCACCA ACCCTGTAGC CACAGAGGAA TACGGAGCAG TGGCCATCAA
  AAV7    CGTCCTACTA ATCCTGTAGC CACGGAAGAA TACGGGATAG TCAGCAGCAA
  44_2    AAAACCACCA ACCCAGTGGC CACAGAACAG TACGGCGTGG TGGCCGATAA
```

FIG. 1AAAC

```
       4001                                                    4050
 42_2   CCTGCAATCG TCTACGGCCG GACCCCAGAC ACAGACTGTC AACAGCCAGG
 42_8   CCTGCAACAG CAAAACGCCG CTCCTATTGT AGGGGCCGTC AACAGTCAAG
 42_15  CCTGCAACAG CAAAACGCCG CTCCTATTGT AGGGGCCGTC AACAGTCAAG
 42_5b  CCTGCAACAG CAAAACGCCG CTCCTATTGT AGGGGCCGTC AACAGTCAAG
 42_1b  CCTGCAACAG CAAAACGCCG CTCCTATTGT AGGGGCCGTC AACAGTCAAG
 42_13  CCTGCAACAG CAAAACGCCG CTCCTATTGT AGGGGCCGTC AACAGTCAAG
 42_3a  CCTGCAACAG CAAAACGCCG CTCCTATTGT AGGGGCCGTC AACAGTCAAG
 42_4   CCTGCAACAG CAAAACGCCG CTCCTATTGT AGGGGCCGTC AACAGTCAAG
 42_5a  CCTGCAACAG CAAAACGCCG CTCCTATTGT AGGGGCCGTC AACAGTCAAG
 42_10  CCTGCAATCG TCTACGGCCG GACCCCAGAC ACAGACTGTC AACAGCCAGG
 42_3b  CCTGCAATCG TCTACGGCCG GACCCCAGAC ACAGACTGTC AACAGCCAGG
 42_11  CCTGCAATCG TCTACGGCCG GACCCCAGAC ACAGACTGTC AACAGCCAGG
 42_6b  CCTGCAATCG TCTACGGCCG GACCCCAGAC ACAGACTGTC AACAGCCAGG
 43_1   CCTGCAGCAG ACCAACGGAG CTCCCATTGT GGGAACTGTC AACAGCCAGG
 43_5   CCTGCAGCAG ACCAACGGAG CTCCCATTGT GGGAACTGTC AACAGCCAGG
 43_12  CCTGCAGCAG ACCAACGGAG CTCCCATTGT GGGAACTGTC AACAGCCAGG
 43_20  CAACCAGGCC GCCAATACGC AGGCGCAGAC CGGACTCGTG CACAACCAGG
 43_21  CAACCAGGCC GCCAATACGC AGGCGCAGAC CGGACTCGTG CACAACCAGG
 43_23  CAACCAGGCC GCCAATACGC AGGCGCAGAC CGGACTCGTG CACAACCAGG
 43_25  CAACCAGGCC GCCAATACGC AGGCGCAGAC CGGACTCGTG CACAACCAGG
 44_1   CCTGCAACAG CAAAACGCCG CTCCTATTGT AGGGGCCGTC AACAGTCAAG
 44_5   CCTGCAACAG CAAAACGCCG CTCCTATTGT AGGGGCCGTC AACAGTCAAG
223_10  CTTGCAGGCG GCTAGCACCG CAGCCCAGAC ACAAGTTGTT AACAACCAGG
223_2   CTTGCAGGCG GCTAGCACCG CAGCCCAGAC ACAAGTTGTT AACAACCAGG
223_4   CTTGCAGGCG GCTAGCACCG CAGCCCAGAC ACAAGTTGTT AACAACCAGG
223_5   CTTGCAGGCG GCTAGCACCG CAGCCCAGAC ACAAGTTGTT AACAACCAGG
223_6   CTTGCAGGCG GCTAGCACCG CAGCCCAGAC ACAAGTTGTT AACAACCAGG
223_7   CTTGCAGGCG GCTAGCACCG CAGCCCAGAC ACAAGTTGTT AACAACCAGG
 A3_4   CCATCAGAGT CAGGACACCA CAGCTTCCTA TGGAAGTGTG GACAGCCAGG
 A3_5   CCGTCAGAGT CAGAACACCA CAGCTTCCTA TGGAAGTGTG GACAGCCAGG
 A3_7   CCATCAGAGT CAGAACACCA CAGCTTCCTA TGGAAGTGTG GACAGCCAGG
 A3_3   CCATCAGAGT CAGAACACCA CAGCTTCCTA TGGAAGTGTG GACAGCCAGG
 42_12  CCTGCAATCG TCTACGGCCG GACCCCAGAC ACAGACTGTC AACAGCCAGG
 AAV1   TTTCCAGAGC AGCAGCACAG ACCTGCGAC CGGAGATGTG CATGCTATGG
 AAV2   CCTCCAGAGA GGCAACAGAC AAGCAGCTAC CGCAGATGTC AACACACAAG
 AAV3   CTTGCAGAGC TCAAATACAG CTCCACGAC TGGAACTGTC AATCATCAGG
 AAV8   CTTGCAGCAG CAAAACACGG CTCCTCAAAT TGGAACTGTC AACAGCCAGG
 AAV9   CAACCAGGCC GCTAACACGC AGGCGCAAAC TGGACTTGTG CATAACCAGG
 AAV7   CTTACAAGCG GCTAATACTG CAGCCCAGAC ACAAGTTGTC AACAACCAGG
 44_2   CCTGCAACAG CAAAACGCCG CTCCTATTGT AGGGGCCGTC AACAGTCAAG
```

FIG. 1AAAD

```
         4051                                                          4100
 42_2    GGGCTCTGCC CGGCATGGTC TGGCAGAACC GGGACGTGTA CCTGCAGGGT
 42_8    GAGCCTTACC TGGCATGGTC TGGCAGAACC GGGACGTGTA CCTGCAGGGT
 42_15   GAGCCTTACC TGGCATGGTC TGGCAGAACC GGGACGTGTA CCTGCAGGGT
 42_5b   GAGCCTTACC TGGCATGGTC TGGCAGAACC GGGACGTGTA CCTGCAGGGT
 42_1b   GAGCCTTACC TGGCATGGTC TGGCAGAACC GGGACGTGTA CCTGCAGGGT
 42_13   GAGCCTTACC TGGCATGGTC TGGCAGAACC GGGACGTGTA CCTGCAGGGT
 42_3a   GAGCCTTACC TGGCATGGTC TGGCAGAACC GGGACGTGTA CCTGCAGGGT
 42_4    GAGCCTTACC TGGCATGGTC TGGCAGAACC GGGACGTGTA CCTGCAGGGT
 42_5a   GAGCCTTACC TGGCATGGCC TGGCAGAACC GGGACGTGTA CCTGCAGGGT
 42_10   GGGCTCTGCC CGGCATGGTC TGGCAGAACC GGGACGTGTA CCTGCAGGGT
 42_3b   GGGCTCTGCC CGGCATGGTC TGGCAGAACC GGGACGTGTA CCTGCAGGGT
 42_11   GGGCTCTGCC CGGCATGGTC TGGCAGAACC GGGACGTGTA CCTGCAGGGT
 42_6b   GGGCTCTGCC CGGCATGGTC TGGCAGAACC GGGACGTGTA CCTGCAGGGT
 43_1    GGGCCTTACC TGGTATGGTC TGGCAAAACC GGGACGTGTA CCTGCAGGGC
 43_5    GGGCCTTACC TGGTATGGTC TGGCAAAACC GGGACGTGTA CCTGCAGGGC
 43_12   GGGCCTTACC TGGTATGGTC TGGCAAAACC GGGACGTGTA CCTGCAGGGC
 43_20   GGGTGATTCC CGGCATGGTG TGGCAGAATA GAGACGTGTA CCTGCAGGGT
 43_21   GGGTGATTCC CGGCATGGTG TGGCAGAATA GAGACGTGTA CCTGCAGGGT
 43_23   GGGTGATTCC CGGCATGGTG TGGCAGAATA GAGACGTGTA CCTGCAGGGT
 43_25   GGGTGATTCC CGGCATGGTG TGGCAGAATA GAGACGTGTA CCTGCAGGGT
 44_1    GAGCCTTACC TGGCATGGTC TGGCAGAACC GGGACGTGTA CCTGCAGGGT
 44_5    GAGCCTTACC TGGCATGGTC TGGCAGAACC GGGACGTGTA CCTGCAGGGT
 223_10  GAGCCTTACC TGGCATGGTC TGGCAGAACC GGGACGTGTA CCTGCAAGGT
 223_2   GAGCCTTACC TGGCATGGTC TGGCAGAACC GGGACGTGTA CCTGCAAGGT
 223_4   GAGCCTTACC TGGCATGGTC TGGCAGAACC GGGACGTGTA CCTGCAAGGT
 223_5   GAGCCTTACC TGGCATGGTC TGGCAGAACC GGGACGTGTA CCTGCAAGGT
 223_6   GAGCCTTACC TGGCATGGTC TGGCAGAACC GGGACGTGTA CCTGCAAGGT
 223_7   GAGCCTTACC TGGCATGGTC TGGCAGAACC GGGACGTGTA CCTGCAAGGT
 A3_4    GAATCTTACC TGGAATGGTG TGGCAGGACC GCGATGTCTA TCTTCAAGGT
 A3_5    GAATCTTACC TGGAATGGTG TGGCAGGACC GCGATGTCTA TCTTCAAGGT
 A3_7    GAATCTTACC TGGAATGGTG TGGCAGGACC GCGATGTCTA TCTTCAAGGT
 A3_3    GAATCTTACC TGGAATGGTG TGGCAGGACC GCGATGTCTA TCTTCAAGGT
 42_12   GGGCTCTGCC CGGCATGGTC TGGCAGAACC GGGACGTGTA CCTGCAGGGT
 AAV1    GAGCATTACC TGGCATGGTG TGGCAAGATA GAGACGTGTA CCTGCAGGGT
 AAV2    GCGTTCTTCC AGGCATGGTC TGGCAGGACA GAGATGTGTA CCTTCAGGGG
 AAV3    GGGCCTTACC TGGCATGGTG TGGCAAGATC GTGACGTGTA CCTTCAAGGA
 AAV8    GGGCCTTACC CGGTATGGTC TGGCAGAACC GGGACGTGTA CCTGCAGGGT
 AAV9    GAGTTATTCC TGGTATGGTC TGGCAGAACC GGGACGTGTA CCTGCAGGGC
 AAV7    GAGCCTTACC TGGCATGGTC TGGCAGAACC GGGACGTGTA CCTGCAGGGT
 44_2    GAGCCTTACC TGGCATGGTC TGGCAGAACC GGGACGTGTA CCTGCAGGGT
```

FIG. 1AAAE

```
           4101                                                4150
  42_2    CCC.ATCTGG  GCCAAAATTC  CTCACACGGA  CGGCAACTTT  CACCCGTCTC
  42_8    CCT.ATCTGG  GCCAAGATTC  CTCACACGGA  CGGCAACTTT  CATCCTTCGC
  42_15   CCT.ATCTGG  GCCAAGATTC  CTCACACGGA  CGGCAACTTT  CATCCTTCGC
  42_5b   CCT.ATCTGG  GCCAAGATTC  CTCACACGGA  CGGCAACTTT  CATCCTTCGC
  42_1b   CCT.ATCTGG  GCCAAGATTC  CTCACACGGA  CGGCAACTTT  CATCCTTCGC
  42_13   CCT.ATCTGG  GCCAAGATTC  CTCACACGGA  CGGCAACTTT  CATCCTTCGC
  42_3a   CCT.ATCTGG  GCCAAGATTC  CTCACACGGA  CGGCAACTTT  CATCCTTCGC
  42_4    CCT.ATCTGG  GCCAAGATTC  CTCACACGGA  CGGCAACTTT  CATCCTTCGC
  42_5a   CCT.ATCTGG  GCCAAGATTC  CTCACACGGA  CGGCAACTTT  CATCCTTCGC
  42_10   CCC.ATCTGG  GCCAAAATTC  CTCACACGGA  CGGCAACTTT  CACCCGTCTC
  42_3b   CCC.ATCTGG  GCCAAAATTC  CTCACACGGA  CGGCAACTTT  CACCCGTCTC
  42_11   CCC.ATCTGG  GCCAAAATTC  CTCACACGGA  CGGCAACTTT  CACCCGTCTC
  42_6b   CCC.ATCTGG  GCCAAAATTC  CTCACACGGA  CGGCAACTTT  CACCCGTCTC
  43_1    CCC.ATCTGG  GCCAAAATTC  CTCACACGGA  CGGCAACTTT  CATCCTTCGC
  43_5    CCC.ATCTGG  GCCAAAATTC  CTCACACGGA  CGGCAACTTT  CATCCTTCGC
  43_12   CCC.ATCTGG  GCCAAAATTC  CTCACACGGA  CGGCAACTTT  CATCCTTCGC
  43_20   CCC.ATCTGG  GCCAAAATTC  CTCACACGGA  CGGCAACTTT  CACCCGTCTC
  43_21   CCC.ATCTGG  GCCAAAATTC  CTCACACGGA  CGGCAACTTT  CACCCGTCTC
  43_23   CCC.ATCTGG  GCCAAAATTC  CTCACACGGA  CGGCAACTTT  CACCCGTCTC
  43_25   CCC.ATCTGG  GCCAAAATTC  CTCACACGGA  CGGCAACTTT  CACCCGTCTC
  44_1    CCT.ATCTGG  GCCAAGATTC  CTCACACGGA  CGGAAACTTT  CATCCCTCGC
  44_5    CCT.ATCTGG  GCCAAGATTC  CTCACACGGA  CGGAAACTTT  CATCCCTCGC
 223_10   CCC.ATTTGG  GCCAAGATTC  CTCACACGGA  CGGCAACTTT  CACCCGTCTC
 223_2    CCC.ATTTGG  GCCAAGATTC  CTCACACGGA  CGGCAACTTT  CACCCGTCTC
 223_4    CCC.ATTTGG  GCCAAGATTC  CTCACACGGA  CGGCAACTTT  CACCCGTCTC
 223_5    CCC.ATTTGG  GCCAAGATTC  CTCACACGGA  CGGCAACTTT  CACCCGTCTC
 223_6    CCC.ATTTGG  GCCAAGATTC  CTCACACGGA  CGGCAACTTT  CACCCGTCTC
 223_7    CCC.ATTTGG  GCCAAGATTC  CTCACACGGA  CGGCAACTTT  CACCCGTCTC
  A3_4    CCC.ATTTGG  GCCAAAACTC  CTCACACGGA  CGGACACTTT  CATCCTTCTC
  A3_5    CCC.ATTTGG  GCCAAAACTC  CTCACACGGA  CGGACACTTT  CATCCTTCTC
  A3_7    CCC.ATTTGG  GCCAAAACTC  CTCACACGGA  CGGACACTTT  CATCCTTCTC
  A3_3    CCC.ATTTGG  GCCAAAACTC  CTCACACGGA  CGGACACTTT  CATCCTTCTC
  42_12   CCC.ATCTGG  GCCAAAATTC  CTCACACGGA  CGGCAACTTT  CACCCGTCTC
  AAV1    CCC.ATTTGG  GCCAAAATTC  CTCACACAGA  TGGACACTTT  CACCCGTCTC
  AAV2    CCC.ATCTGG  GCAAGATTC   CACACACGGA  CGGACATTTT  CACCCCTCTC
  AAV3    CCT.ATCTGG  GCAAAGATTC  CTCACACGGA  TGGACACTTT  CATCCTTCTC
  AAV8    CCC.ATCTGG  GCCAAGATTC  CTCACACGGA  CGGCAACTTC  CACCCGTCTC
  AAV9    CCCTATTTGG  GCTAAAATAC  CTCACACAGA  TGGCAACTTT  CACCCGTCTC
  AAV7    CCC.ATCTGG  GCCAAGATTC  CTCACACGGA  TGGCAACTTT  CACCCGTCTC
  44_2    CCT.ATCTGG  GCCAAGATTC  CTCACACGGA  CGGAAACTTT  CATCCCTCGC
```

FIG. 1AAAF

```
         4151                                                            4200
 42_2    CCCTGATGGG CGGATTTGGA CTCAAACACC CGCCTCCTCA AATTCTCATC
 42_8    CGCTGATGGG AGGCTTTGGA CTGAAACACC CGCCTCCTCA GATCCTGATT
 42_15   CGCTGATGGG AGGCTTTGGA CTGAAACACC CGCCTCCTCA GATCCTGATT
 42_5b   CGCTGATGGG AGGCTTTGGA CTGAAACACC CGCCTCCTCA GATCCTGATT
 42_1b   CGCTGATGGG AGGCTTTGGA CTGAAACACC CGCCTCCTCA GATCCTGATT
 42_13   CGCTGATGGG AGGCTTTGGA CTGAAACACC CGCCTCCTCA GATCCTGATT
 42_3a   CGCTGATGGG AGGCTTTGGA CTGAAACACC CGCCTCCTCA GATCCTGATT
 42_4    CGCTGATGGG AGGCTTTGGA CTGAAACACC CGCCTCCTCA GATCCTGATT
 42_5a   CGCTGATGGG AGGCTTTGGA CTGAAACACC CGCCTCCTCA GATCCTGATT
 42_10   CCCTGATGGG CGGATTTGGA CTCAAACACC CGCCTCCTCA AATTCTCATC
 42_3b   CCCTGATGGG CGGATTTGGA CTCAAACACC CGCCTCCTCA AATTCTCATC
 42_11   CCCTGATGGG CGGATTTGGA CTCAAACACC CGCCTCCTCA AATTCTCATC
 42_6b   CCCTGATGGA CGGATTTGGA CTCAAACACC CGCCTCCTCA AATTCTCATC
 43_1    CGCTGATGGG AGGCTTTGGA CTGAAACACC CGCCTCCTCA GATCCTGGTG
 43_5    CGCTGATGGG AGGCTTTGGA CTGAAACACC CGCCTCCTCA GATCCTGGTG
 43_12   CGCTGATGGG AGGCTTTGGA CTGAAACACC CGCCTCCTCA GATCCTGGTG
 43_20   CCCTGATGGG CGGCTTTGGA CTGAAGCACC CGCCTCCTCA AATTCTCATC
 43_21   CCCTGATGGG CGGCTTTGGA CTGAAGCACC CGCCTCCTCA AATTCTCATC
 43_23   CCCTGATGGG CGGCTTTGGA CTGAAGCACC CGCCTCCTCA AATTCTCATC
 43_25   CCCTGATGGG CGGCTTTGGA CTGAAGCACC CGCCTCCTCA AATTCTCATC
 44_1    CGCTGATGGG AGGCTTTGGA CTGAAACACC CGCCTCCTCA GATCCTGATT
 44_5    CGCTGATGGG AGGCTTTGGA CTGAAACACC CGCCTCCTCA GATCCTGATT
223_10   CTCTAATGGG TGGCTTTGGA CTGAAACACC CGCCTCCCCA GATCCTGATC
223_2    CTCTAATGGG TGGCTTTGGA CTGAAACACC CGCCTCCCCA GATCCTGATC
223_4    CTCTAATGGG TGGCTTTGGA CTGAAACACC CGCCTCCCCA GATCCTGATC
223_5    CTCTAATGGG TGGCTTTGGA CTGAAACACC CGCCTCCCCA GATCCTGATC
223_6    CTCTAATGGG TGGCTTTGGA CTGAAACACC CGCCTCCCCA GATCCTGATC
223_7    CTCTAATGGG TGGCTTTGGA CTGAAACACC CGCCTCCCCA GATCCTGATC
 A3_4    CGCTCATGGG AGGCTTTGGA CTGAAACACC CTCCTCCCCA GATCCTGATC
 A3_5    CGCTCATGGG AGGCTTTGGA CTGAAACACC CTCCTCCCCA GATCCTGATC
 A3_7    CGCTCATGGG AGGCTTTGGA CTGAAACACC CTCCTCCCCA GATCCTGATC
 A3_3    CGCTCATGGG AGGCTTTGGA CTGAAACACC CTCCTCCCCA GATCCTGATC
 42_12   CCCTGATGGG CGGATTTGGA CTCAAACACC CGCCTCCTCA AATTCTCATC
 AAV1    CTCTTATGGG CGGCTTTGGA CTCAAGAACC CGCCTCCTCA GATCCTCATC
 AAV2    CCCTCATGGG TGGATTCGGA CTTAAACACC CTCCTCCACA GATTCTCATC
 AAV3    CTCTGATGGG AGGCTTTGGA CTGAAACATC CGCCTCCTCA AATCATGATC
 AAV8    CGCTGATGGG CGGCTTTGGC CTGAAACATC CTCCGCCTCA GATCCTGATC
 AAV9    CTCTGATGGG TGGATTTGGA CTGAAACACC CACCTCCACA GATTCTAATT
 AAV7    CTTTGATGGG CGGCTTTGGA CTTAAACATC CGCCTCCTCA GATCCTGATC
 44_2    CGCTGATGGG AGGCTTTGGA CTGAAACACC CGCCTCCTCA GATCCTGATT
```

FIG. 1AAAG

```
         4201                                                          4250
  42_2   AAAAACACCC CGGTACCTGC TAATCCTCCA GAGGTGTTTA CTCCTGCCAA
  42_8   AAGAATACAC CTGTTCCCGC GGATCCTCCA ACTACCTTCA GTCAAGCCAA
 42_15   AAGAATACAC CTGTTCCCGC GGATCCTCCA ACTACCTTCA GTCAAGCCAA
 42_5b   AAGAATACAC CTGTTCCCGC GGATCCTCCA ACTACCTTCA GTCAAGCCAA
 42_1b   AAGAATACAC CTGTTCCCGC GGATCCTCCA ACTACCTTCA GTCAAGCCAA
 42_13   AAGAATACAC CTGTTCCCGC GGATCCTCCA ACTACCTTCA GTCAAGCCAA
 42_3a   AAGAATACAC CTGTTCCCGC GGATCCTCCA ACTACCTTCA GTCAAGCCAA
  42_4   AAGAATACAC CTGTTCCCGC GGATCCTCCA ACTACCTTCA GTCAAGCCAA
 42_5a   AAGAATACAC CTGTTCCCGC GGATCCTCCA ACTACCTTCA GTCAAGCCAA
 42_10   AAAAACACCC CGGTACCTGC TAATCCTCCA GAGGTGTTTA CTCCTGCCAA
 42_3b   AAAAACACCC CGGTACCTGC TAATCCTCCA GAGGTGTTTA CTCCTGCCAA
 42_11   AAAAACACCC CGGTACCTGC TAATCCTCCA GAGGTGTTTA CTCCTGCCAA
 42_6b   AAAAACACCC CGGTACCTGC TAATCCTCCA GAGGTGTTTA CTCCTGCCAA
  43_1   AAAAACACTC CTGTTCCTGC GGATCCTCCG ACCACCTTCA GCCAGGCCAA
  43_5   AAAAACACTC CTGTTCCTGC GGATCCTCCG ACCACCTTCA GCCAGGCCAA
 43_12   AAAAACACTC CTGTTCCTGC GGATCCTCCG ACCACCTTCA GCCAGGCCAA
 43_20   AAGAACACAC CGGTTCCAGC GGACCCGCCG CTTACCTTCA ACCAGGCCAA
 43_21   AAGAACACAC CGGTTCCAGC GGACCCGCCG CTTACCTTCA ACCAGGCCAA
 43_23   AAGAACACAC CGGTTCCAGC GGACCCGCCG CTTACCTTCA ACCAGGCCAA
 43_25   AAGAACACAC CGGTTCCAGC GGACCCGCCG CTTACCTTCA ACCAGGCCAA
  44_1   AAGAATACAC CTGTTCCCGC GGATCCTCCA ACTACCTTCA GTCAAGCTAA
  44_5   AAGAATACAC CTGTTCCCGC GGATCCTCCA ACTACCTTCA GTCAAGCTAA
 223_10  AAAAACACAC CGGTACCTGC TAATCCTCCA GAAGTGTTTA CTCCTGCCAA
 223_2   AAAAACACGC CGGTACCTGC TAATCCTCCA GAAGTGTTTA CTCCTGCCAA
 223_4   AAAAACACAC CGGTACCTGC TAATCCTCCA GAAGTGTTTA CTCCTGCCAA
 223_5   AAAAACACAC CGGTACCTGC TAATCCTCCA GAAGTGTTTA CTCCTGCCAA
 223_6   AAAAACACAC CGGTACCTGC TAATCCTCCA GAAGTGTTTA CTCCTGCCAA
 223_7   AAAAACACAC CGGTACCTGC TAATCCTCCA GAAGTGTTTA CTCCTGCCAA
  A3_4   AAAAACACAC CTGTGCCAGC GAATCCCGCG ACCACTTTCA CTCCTGGAAA
  A3_5   AAAAACACAC CTGTGCCAGC GAATCCCGCG ACCACTTTCA CTCCTGGAAA
  A3_7   AAAAACACAC CTGTGCCAGC GAATCCCGCG ACCACTTTCA CTCCTGGAAA
  A3_3   AAAAACACAC CTGTGCCAGC GAATCCCGCG ACCACTTTCA CTCCTGGAAA
 42_12   A...A..... .......... .......... .......... ..........
  AAV1   AAAAACACGC CTGTTCCTGC GAATCCTCCG GCGGAGTTTT CAGCTACAAA
  AAV2   AAGAACACCC CGGTACCTGC GAATCCTTCG ACCACCTTCA GTGCGGCAAA
  AAV3   AAAAATACTC CGGTACCGGC AAATCCTCCG ACGACTTTCA GCCGGCCAA
  AAV8   AAGAACACGC CTGTACCTGC GGATCCTCCG ACCACCTTCA ACCAGTCAAA
  AAV9   AAAAATACAC CAGTGCCGGC AGATCCTCCT CTTACCTTCA ATCAAGCCAA
  AAV7   AAGAACACTC CCGTTCCCGC TAATCCTCCG GAGGTGTTTA CTCCTGCCAA
  44_2   AAGAATACAC CTGTTCCCGC GGATCCTCCA ACTACCTTCA GTCAAGCTAA
```

FIG. 1AAAH

```
             4251                                                                          4300
   42_2     GTTTGCCTCA  TTTATCACGC  AGTACAGCAC  CGGCCA.GGT  CAGCGTGGAG
   42_8     GCTGGCGTCG  TTCATCACGC  AGTACAGCAC  CGGACA.GGT  CAGCGTGGAA
   42_15    GCTGGCGTCG  TTCATCACGC  AGTACAGCAC  CGGACA.GGT  CAGCGTGGAA
   42_5b    GCTGGCGTCG  TTCATCACGC  AGTACAGCAC  CGGACA.GGT  CAGCGTGGAA
   42_1b    GCTGGCGTCG  TTCATCACGC  AGTACAGCAC  CGGACA.GGT  CAGCGTGGAA
   42_13    GCTGGCGTCG  TTCATCACGC  AGTACAGCAC  CGGACA.GGT  CAGCGTGGAA
   42_3a    GCTGGCGTCG  TTCATCACGC  AGTACAGCAC  CGGACA.GGT  CAGCGTGGAA
   42_4     GCCGGCGTCG  TTCATCACGC  AGTACAGCAC  CGGACA.GGT  CAGCGTGGAA
   42_5a    GCTGGCGTCG  TTCATCACGC  AGTACAGCAC  CGGACA.GGT  CAGCGTGGAA
   42_10    GTTTGCCTCA  TTTATCACGC  AGTACAGCAC  CGGCCA.GGT  CAGCGTGGAG
   42_3b    GTTTGCCTCA  TTTATCACGC  AGTACAGCAC  CGGCCA.GGT  CAGCGTGGAG
   42_11    GTTTGCCTCA  TTTATCACGC  AGTACAGCAC  CGGCCA.GGT  CAGCGTGGAG
   42_6b    GTTTGCCTCA  TTTATCACGC  AGTACAGCAC  CGGCCA.GGT  CAGCGTGGAG
   43_1     GCTGGCTTCT  TTTATCACGC  AGTACAGCAC  CGGACA.GGT  CAGCGTGGAA
   43_5     GCTGGCTTCT  TTTATCACGC  AGTACAGCAC  CGGACA.GGT  CAGCGTGGAA
   43_12    GCTGGCTTCT  TTTATCACGC  AGTACAGCAC  CGGACA.GGT  CAGCGTGGAA
   43_20    GCTGAACTCT  TTCATCACGC  AGTACAGCAC  CGGACA.GGT  CAGCGTGGAA
   43_21    GCTGAACTCT  TTCATCACGC  AGTACAGCAC  CGGACA.GGT  CAGCGTGGAA
   43_23    GCTGAACTCT  TTCATCACGC  AGTACAGCAC  CGGACA.GGT  CAGCGTGGAA
   43_25    GCTGAACTCT  TTCATCACGC  AGTACAGCAC  CGGACA.GGT  CAGCGTGGAA
   44_1     GCTGGCGTCG  TTCATCACGC  AGTACAGCAC  CGGACA.GGT  CAGCGTGGAA
   44_5     GCTGGCGTCG  TTCATCACGC  AGTACAGCAC  CGGACA.GGT  CAGCGTGGAA
  223_10    GTTTGCTTCC  TTCATCACGC  AGTACAGCAC  CGGGCA.AGT  CAGCGTTGAG
  223_2     GTTTGCTTCC  TTCATCACGC  AGTACAGCAC  CGGGCA.AGT  CAGCGTTGAG
  223_4     GTTTGCTTCC  TTCATCACGC  AGTACAGCAC  CGGGCA.AGT  CAGCGTTGAG
  223_5     GTTTGCTTCC  TTCATCACGC  AGTACAGCAC  CGGGCA.AGT  CAGCGTTGAG
  223_6     GCTTGCTTCC  TTCATCACGC  AGTACAGCAC  CGGGCA.AGT  CAGCGTTGAG
  223_7     GATTGCTTCC  TTCATCACGC  AGTACAGCAC  CGGGCA.AGT  CAGCGTTGAG
   A3_4     GTTTGCTTCG  TTCATTACCC  AGTATTCCAC  CGGACA.GGT  CAGCGTGGAA
   A3_5     GTTTGCTTCG  TTCATTACCC  AGTATTCCAC  CGGACA.GGT  CAGCGTGGAA
   A3_7     GTTTGCTTCG  TTCATTACCC  AGTATTCCAC  CGGACA.GGT  CAGCGTGGAA
   A3_3     GTTTGCTTCG  TTCATTACCC  AGTATTCCAC  CGGACA.GGT  CAGCGTGGAA
   42_12    ..........  ..........  ..........  ..........  ..........
   AAV1     GTTTGCTTCA  TTCATCACCC  AATACTCCAC  AGGACA.AGT  GAGTGTGGAA
   AAV2     GTTTGCTTCC  TTCATCACAC  AGTACTCCAC  GGGACACGGT  CAGCGTGGAG
   AAV3     GTTTGCTTCA  TTTATCACTC  AGTACTCCAC  TGGACA.GGT  CAGCGTGGAA
   AAV8     GCTGAACTCT  TTCATCACGC  AATACAGCAC  CGGACA.GGT  CAGCGTGGAA
   AAV9     GCTGAACTCT  TTCATCACGC  AGTACAGCAC  GGGACA.AGT  CAGCGTGGAA
   AAV7     GTTTGCTTCG  TTCATCACAC  AGTACAGCAC  CGGACA.AGT  CAGCGTGGAA
   44_2     GCTGGCGTCG  TTCATCACGC  AGTACAGCAC  CGGACA.GGT  CAGCGTGGAA
```

FIG. 1AAAl

```
        4301                                                              4350
 42_2   ATCGAGTGGG AACTGCAGAA AGAAAACAGC AAACGCTGGA ATCCAGAGAT
 42_8   ATTGAATGGG AGCTGCAGAA AGAGAACAGC AAGCGCTGGA ACCCAGAGAT
 42_15  ATTGAATGGG AGCTGCAGAA AGAGAACAGC AAGCGCTGGA ACCCAGAGAT
 42_5b  ATTGAATGGG AGCTGCAGAA AGAGAACAGC AAGCGCTGGA ACCCAGAGAT
 42_1b  ATTGAATGGG AGCTGCAGAA AGAGAACAGC AAGCGCTGGA ACCCAGAGAT
 42_13  ATTGAATGGG AGCTGCAGAA AGAGAACAGC AAGCGCTGGA ACCCAGAGAT
 42_3a  ATTGAATGGG AGCTGCAGAA AGAGAACAGC AAGCGCTGGA ACCCAGAGAT
 42_4   ATTGAATGGG AGCTGCAGAA AGAGAACAGC AAGCGCTGGA ACCCAGAGAT
 42_5a  ATTGAATGGG AGCTGCAGAA AGAGAACAGC AAGCGCTGGA ACCCAGAGAT
 42_10  ATCGAGTGGG AACTGCAGAA AGAAAACAGC AAACGCTGGA ATCCAGAGAT
 42_3b  ATCGAGTGGG AACTGCAGAA AGAAAACAGC AAACGCTGGA ATCCAGAGAT
 42_11  ATCGAGTGGG AACTGCAGAA AGAGAACAGC AAACGCTGGA ATCCAGAGAT
 42_6b  ATCGAGTGGG AACTGCAGAA AGAAAACAGC AAACGCTGGA ATCCAGAGAT
 43_1   ATCGAATGGG AGCTGCAGAA AGAAAACAGC AAGCGCTGGA ACCCAGAGAT
 43_5   ATCGAATGGG AGCTGCAGAA AGAAAACAGC AAGCGCTGGA ACCCAGAGAT
 43_12  ATCGAATGGG AGCTGCAGAA AGAAAACAGC AAGCGCTGGA ACCCAGAGAT
 43_20  ATCGAGTGGG AGCTGCAGAA AGAAAACAGC AAACGCTGGA ATCCAGAGAT
 43_21  ATCGAGTGGG AGCTGCAGAA AGAAAACAGC AAACGCTGGA ATCCAGAGAT
 43_23  ATCGAGTGGG AGCTGCAGAA AGAAAACAGC AAACGCTGGA ATCCAGAGAT
 43_25  ATCGAGTGGG AGCTGCAGAA AGAAAACAGC AAACGCTGGA ATCCAGAGAT
 44_1   ATTGAATGGG AGCTGCAGAA AGAAAACAGC AAACGCTGGA ACCCAGAGAT
 44_5   ATTGAATGGG AGCTGCAGAA AGAAAACAGC AAACGCTGGA ACCCAGAGAT
223_10  ATCGAGTGGG AGCTGCAGAA AGAGAACAGC AAGCGCTGGA ACCCAGAGAT
223_2   ATCGAGTGGG AGCTGCAGAA AGAGAACAGC AAGCGCTGGA ACCCAGAGAT
223_4   ATCGAATGGG AGCTGCAGAA AGAGAACAGC AAGCGCTGGA ACCCAGAGAT
223_5   ATCGAATGGG AGCTGCAGAA AGAGAACAGC AAGCGCTGGA ACCCAGAGAT
223_6   ATCGAGTGGG AGCTGCAGAA AGAGAACAGC AAGCGCTGGA ACCCAGAGAT
223_7   ATCGAGTGGG AGCTGCAGAA AGAGAACAGC AAGCGCTGGA ACCCAGAGAT
 A3_4   ATAGAGTGGG AGCTGCAGAA AGAAAACAGC AAACGCTGGA ACCCAGAAAT
 A3_5   ATAGAGTGGG AGCTGCAGAA AGAAAACAGC AAACGCTGGA ACCCGGAAAT
 A3_7   ATAGAGTGGG AGCTGCAGAA AGAAAACAGC AAACGCTGGA ACCCAGAAAT
 A3_3   ATAGAGTGGG AGCTGCAGAA AGAAAACAGC AAACGCTGGA ACCCAGAAAT
 42_12  .......... .......... .......... .......... ..........
 AAV1   ATTGAATGGG AGCTGCAGAA AGAAAACAGC AAGCGCTGGA ATCCCGAAGT
 AAV2   ATCGAGTGGG AGCTGCAGAA GGAAAACAGC AAACGCTGGA ATCCCGAAAT
 AAV3   ATTGAGTGGG AGCTACAGAA AGAAAACAGC AAACGTTGGA ATCCAGAGAT
 AAV8   ATTGAATGGG AGCTGCAGAA GGAAAACAGC AAGCGCTGGA ACCCCGAGAT
 AAV9   ATCGAGTGGG AGCTGCAGAA AGAAAACAGC AAGCGCTGGA ATCCAGAGAT
 AAV7   ATCGAGTGGG AGCTGCAGAA GGAAAACAGC AAGCGCTGGA ACCCGGAGAT
 44_2   ATTGAATGGG AGCTGCAGAA AGAAAACAGC AAACGCTGGA ACCCAGAGAT
```

FIG. 1AAAJ

```
           4351                                                      4400
  42_2     TCAGTACACC TCAAATTATG CCAAGTCTAA TAAT.GTGGA ATTTGCTGTC
  42_8     TCAGTATACT TCCAACTACT ACAAATCTAC AAAT.GTGGA CTTTGCTGTC
  42_15    TCAGTATACT TCCAACTACT ACAAATCTAC AAAT.GTGGA CTTTGCTGTC
  42_5b    TCAGTATACT TCCAACTACT ACAAATCTAC AAAT.GTGGA CTTTGCTGTC
  42_1b    TCAGTATACT TCCAACTACT ACAAATCTAC AAAT.GTGGA CTTTGCTGTC
  42_13    TCAGTATACT TCCAACTACT ACAAATCTAC AAAT.GTGGA CTTTGCTGTC
  42_3a    TCAGTATACT TCCAACTACT ACAAATCTAC AAAT.GTGGA CTTTGCTGTC
  42_4     TCAGTATACT TCCAACTACT ACAAATCTAC AAAT.GTGGA CTTTGCTGTC
  42_5a    TCAGTATACT TCCAACTACT ACAAATCTAC AAAT.GTGGA CTTTGCTGTC
  42_10    TCAGTACACC TCAAATTATG CCAAGTCTAA TAAT.GTGGA ATTTGCTGTC
  42_3b    TCAGTACACC TCAAATTATG CCAAGTCTAA TAAT.GTGGA ATTTGCTGTC
  42_11    TCAGTACACC TCAAATTATG CCAAGTCTAA TAAT.GTGGA ATTTGCTGTC
  42_6b    TCAGTACACC TCAAATTATG CCAAGTCTAA TAAT.GTGGA ATTTGCTGTC
  43_1     TCAGTATACT TCCAACTACT ACAAATCTAC AAAT.GTGGA CTTTGCTGTC
  43_5     TCAGTATACT TCCAACTACT ACAAATCTAC AAAT.GTGGA CTTTGCTGTC
  43_12    TCAGTATACT TCCAACTACT ACAAATCTAC AAAT.GTGGA CTTTGCTGTC
  43_20    TCAATACACT TCCAACTACT ACAAATCTAC AAAT.GTGGA CTTTGCTGTC
  43_21    TCAATACACT TCCAACTACT ACAAATCTAC AAAT.GTGGA CTTTGCTGTC
  43_23    TCAATACACT TCCAACTACT ACAAATCTAC AAAT.GTGGA CTTTGCTGTC
  43_25    TCAATACACT TCCAACTACT ACAAATCTAC AAAT.GTGGA CTTTGCTGTC
  44_1     TCAATACACT TCCAACTACT ACAAATCTAC AAAT.GTGGA CTTCGCTGTT
  44_5     TCAATACACT TCCAACTACT ACAAATCTAC AAAT.GTGGA CTTTGCTGTT
  223_10   TCAGTACACC TCCAACTTTG ACAAACAGAC TGGA.GTGGA CTTTGCTGTT
  223_2    TCAGTACACC TCCAACTTTG ACAAACAGAC TGGA.GTGGA CTTTGCTGTT
  223_4    TCAGTACACC TCCAACTTTG ACAAACAGAC TGGA.GTGGA CTTTGCTGTT
  223_5    TCAGTACACC TCCAACTTTG ACAAACAGAC TGGA.GTGGA CTTTGCTGTT
  223_6    TCAGTACACC TCCAACTTTG ACAAACAGAC TGGA.GTGGA CTTTGCTGTT
  223_7    TCAGTACACC TCCAACTTTG ACAAACAGAC TGGA.GTGGA CTTTGCTGTT
  A3_4     TCAGTACACC TCCAACTACA ACAAGTCGGT GAAT.GTGGA GTTACCGTG
  A3_5     TCAGTACACC TCCAACTACA ACAAGTCGGT GAAT.GTGGA GTTACCGTG
  A3_7     TCAGTACACC TCCAACTACA ACAAGTCGGT GAAT.GTGGA GTTACCGTG
  A3_3     TCAGTACACC TCCAACTACA ACAAGTCGGT GAAT.GTGGA GTTACCGTG
  42_12    ...GTATACT TCCAACTACT ACAAATCTAC AAAT.GTGGA CTTTGCTGTC
  AAV1     GCAGTACACA TCCAATTATG CAAAATCTGC CAAC.GTTGA TTTTACTGTG
  AAV2     TCAGTACACT TCCAACTACA ACAAGTCTGT TAATCGTGGA CTT.ACCGTG
  AAV3     TCAGTACACT TCCAACTACA ACAAGTCTGT TAAT.GTGGA CTTTACTGTA
  AAV8     CCAGTACACC TCCAACTACT ACAAATCTAC AAGT.GTGGA CTTTGCTGTT
  AAV9     CCAGTATACT TCAAACTACT ACAAATCTAC AAAT.GTGGA CTTTGCTGTC
  AAV7     TCAGTACACC TCCAACTTTG AAAAGCAGAC TGGT.GTGGA CTTTGCCGTT
  44_2     TCAATACACT TCCAACTACT ACAAATCTAC AAAT.GTGGA CTTTGCTGTT
```

FIG. 1AAAK

```
          4401                                                                    4450
 42_2     AACAACGAAG  GGGTTTATAC  TGAGCCTCGC  CCCATTGGCA  CCCGTTACCT
 42_8     AATACTGAGG  GTACTTATTC  AGAGCCTCGC  CCCATTGGCA  CCCGTTACCT
 42_15    AATACTGAGG  GTACTTATTC  AGAGCCTCGC  CCCATTGGCA  CCCGTTACCT
 42_5b    AATACTGAGG  GTACTTATTC  AGAGCCTCGC  CCCATTGGCA  CCCGTTACCT
 42_1b    AATACTGAGG  GTACTTATTC  AGAGCCTCGC  CCCATTGGCA  CCCGTTACCT
 42_13    AATACTGAGG  GTACTTATTC  AGAGCCTCGC  CCCATTGGCA  CCCGTTACCT
 42_3a    AATACTGAGG  GTACTTATTC  AGAGCCTCGC  CCCATTGGCA  CCCGTTACCT
 42_4     AATACTGAGG  GTACTTATTC  AGAGCCTCGC  CCCATTGGCA  CCCGTTACCT
 42_5a    AATACTGAGG  GTACTTATTC  AGAGCCTCGC  CCCATTGGCA  CCCGTTACCT
 42_10    AACAACGAAG  GGGTTTATAC  TGAGCCTCGC  CCCATTGGCA  CCCGTTACCT
 42_3b    AACAACGAAG  GGGTTTATAC  TGAGCCTCGC  CCCATTGGCA  CCCGTTACCT
 42_11    AACAACGAAG  GGGTTTATAC  TGAGCCTCGC  CCCATTGGCA  CCCGTTACCT
 42_6b    AACAACGAAG  GGGTTTATAC  TGAGCCTCGC  CCCATTGGCA  CCCGTTACCT
 43_1     AATACTGAGG  GTACTTATTC  AGAGCCTCGC  CCCATTGGCA  CTCGTTATCT
 43_5     AATACCGAGG  GTACTTATTC  AGAGCCTCGC  CCCATTGGCA  CTCGTTATCT
 43_12    AATACTGAGG  GTACTTATTC  AGAGCCTCGC  CCCATTGGCA  CTCGTTATCT
 43_20    AACACGGAAG  GAGTTTATAG  CGAGCCTCGC  CCCATTGGCA  CCCGTTACCT
 43_21    AACACGGAAG  GAGTTTATAG  CGAGCCTCGC  CCCATTGGCA  CCCGTTACCT
 43_23    AACACGGAAG  GAGTTTATAG  CGAGCCTCGC  CCCATTGGCA  CCCGTTACCT
 43_25    AACACGGAGG  GGGTTTATAG  CGAGCCTCGC  CCCATTGGCA  CCCGTTACCT
 44_1     AACACAGATG  GCACTTATTC  TGAGCCTCGC  CCCATTGGCA  CCCGTTACCT
 44_5     AACACAGATG  GCACTTATTC  TGAGCCTCGC  CCCATTGGCA  CCCGTTACCT
223_10    GACAGCCAGG  GTGTTTACTC  TGAGCCT...  ..........  ..........
223_2     GACAGCCAGG  GTGTTTACTC  TGAGCCT...  ..........  ..........
223_4     GACAGCCAGG  GTGTTTACTC  TGAGCCT...  ..........  ..........
223_5     GACAGCCAGG  GTGTTTACTC  TGAGCCT...  ..........  ..........
223_6     GACAGCCAGG  GTGTTTACTC  TGAGCCT...  ..........  ..........
223_7     GACAGCCAGG  GTGTTTACTC  TGAGCCT...  ..........  ..........
A3_4      GACGCAAACG  GTGTTTATTC  TGAACCCCGC  CCTATTGGCA  CTCGTTACCT
A3_5      GACGCAAACG  GTGTTTATTC  TGAACCCCGC  CCTATTGGCA  CTCGTTACCT
A3_7      GACGCAAACG  GTGTTTATTC  TGAACCCCGC  CCTATTGGCA  CTCGTTACCT
A3_3      GACGCAAACG  GTGTTTATTC  TGAACCCCGC  CCTATTGGCA  CTCGTTACCT
 42_12    AATACTGAGG  GTACTTATTC  AGAGCCTCGC  CCCATTGGCA  CCCGTTACCT
AAV1      GACAACAATG  GACTTTATAC  TGAGCCTCGC  CCCATTGGCA  CCCGTTACCT
AAV2      GATACTAATG  GCGTGTATTC  AGAGCCTCGC  CCCATTGGCA  CCAGATACCT
AAV3      GACACTAATG  GTGTTTATAG  TGAACCTCGC  CCTATTGGAA  CCCGGTATCT
AAV8      AATACAGAAG  GCGTGTACTC  TGAACCCCGC  CCCATTGGCA  CCCGTTACCT
AAV9      AATACCGAAG  GTGTTTACTC  TGAGCCTCGC  CCCATTGGTA  CTCGTTACCT
AAV7      GACAGCCAGG  GTGTTTACTC  TGAGCCTCGC  CCTATTGGCA  CTCGTTACCT
 44_2     AACACAGATG  GCACTTATTC  TGAGCCTCGC  CCCATCGGCA  CCCGTTACCT
```

FIG. 1AAAL

```
         4451                                                        4500
                    VP1-3 stop      Poly A signal
  42_2   CACCCGTAAC CTGTAATTGC CTGTTAATCA ATAAACCGGT TAATTCGTTT
  42_8   CACCCGTAAC CTGTAATTGC CTGTTAATCA ATAAACCGGC TAATTCGTTT
  42_15  CACCCGTAAC CTGTAATTGC CTGTTAATCA ATAAACCGGT TAATTCGTTT
  42_5b  CACCCGTAAC CTGTAATTGC CTGTTAATCA ATAAACCGGT TAATTCGTTT
  42_1b  CACCCGTAAC CTGTAATTGC CTGTTAATCA ATAAACCGGT TGATTCGTTT
  42_13  CACCCGTAGC CTGTAATTGC CTGTTAATCA ATAAACCGGT TGATTCGTTT
  42_3a  CACCCGTAAC CTGTAATTGC CTGTTAATCA ATAAACCGGT TAATTCGTTT
  42_4   CACCCGTAAC CTGTAATTGC CTGTTAATCA ATAAACCGGT TAATTCGTTT
  42_5a  CACCCGTAAC CTGTAATTGC CTGTTAATCA ATAAACCGGT TAATTCGTTT
  42_10  CACCCGTAAC CTGTAATTGC CTGTTAATCA ATAAACCGGT TAATTCGTTT
  42_3b  CACCCGTAAC CTGTAATTGC CTGTTAATCA ATAAACCGGT TAATTCGTTT
  42_11  CACCCGTAAC CTGTAATTAC TTGTTAATCA ATAAACCGGT TGATTCGTTT
  42_6b  CACCCGTAAC CTGTAATTGC CTGTTAATCA ATAAACCGGT TAATTCGTTT
  43_1   CACCCGTAAT CTGTAATTGC TTGTTAATCA ATAAACCGGT ..........
  43_5   CACCCGTAAT CTGTAATTGC TTGTTAATCA ATAAACCGGT TAATTCGTTT
  43_12  CACCCGTAAT CTGTAATTGC TTGTTAATCA ATAAACCGGT TAATTCGTTT
  43_20  CACCCGCAAC CTGTAATTAC ATGTTAATCA ATAAACCGGT TAATTCGTTT
  43_21  CACCCGCAAC CTGTAATTAC ATGTTAATCA ATAAACCGGT TAATTCGTTT
  43_23  CACCCGCAAC CTGTAATTAC ATGTTAATCA ATAAACCGGT TAATTCGTTT
  43_25  CACCCGCAAC CTGTAATTAC ATGTTAATCA ATAAACCGGT TAATTCGTTT
  44_1   CACCCGTAAT CTGTAATTGC TCGTTAATCA ATAAACCGGT TGATTCGTTT
  44_5   CACCCGTAAT CTGTAATTGC TTGTTAATCA ATAAACCGGT TGATTCGTTT
  223_10 .......... .......... .......... .......... ..........
  223_2  .......... .......... .......... .......... ..........
  223_4  .......... .......... .......... .......... ..........
  223_5  .......... .......... .......... .......... ..........
  223_6  .......... .......... .......... .......... ..........
  223_7  .......... .......... .......... .......... ..........
  A3_4   TACCCGGAAC TTGTAATTTC CTGTTAATGA ATAAACCGAT TTATGCGTTT
  A3_5   TACCCGGAAC TTGTAATTTC CTGTTAATGA ATAAACCGAT TTATGCGTTT
  A3_7   TACCCGGAAC TTGTAATTTC CTGTTAATGA ATAAACCGAT TTATGCGTTT
  A3_3   TACCCGGAAC TTGTAATTTC CTGTTAATGA ATAAGCCGAT TTATGCGTTT
  42_12  CACCCGTAAC CTGTAATTGC CTGTTAATCA ATAAACCGGT TAATTCGTTT
  AAV1   TACCCGTCCC CTGTAATTAC GTGTTAATCA ATAAACCGGT TGATTCGTTT
  AAV2   GACTCGTAAT CTGTAATTGC TTGTTAATCA ATAAACCGTT TAATTCGTTT
  AAV3   CACACGAAAC TTGTGAATCC TGGTTAATCA ATAAACCGTT TAATTCGTTT
  AAV8   CACCCGTAAT CTGTAATTGC CTGTTAATCA ATAAACCGGT TGATTCGTTT
  AAV9   CACCCGTAAT TTGTAATTGC CTGTTAATCA ATAAACCGGT TAATTCGTTT
  AAV7   CACCCGTAAT CTGTAATTGC ATGTTAATCA ATAAACCGGT TGATTCGTTT
  44_2   CACCCGTAAT CTGTAATTGC TTGTTAATCA ATAAACCGGT TGATTCGTTT
                    vp1-3 stop       PolyA signal
```

FIG. 1AAAM

```
          4501                                                              4550
 42_2    CAGTTGAACT TTGGTCTC.T GCGAAGGGCG AATTC..... ..........
 42_8    CAGTTGAACT TTGGTCTC.T GCGAAGGGCG AATTC..... ..........
 42_15   CAGTTGAACT TTGGTCTC.T GCGAAGGGCG AATTC..... ..........
 42_5b   CAGTTGAACT TTGGTCTC.T GCGAAGGGCG AATTCGTTTA AACCTGCAGG
 42_1b   CAGTTGAACT TTGGTCTC.. ...AAGGGCG AATTC..... ..........
 42_13   CAGTTGAACT TTGGTCTC.T GCGAAGGGCG AATTC..... ..........
 42_3a   CAGTTGAACT TTGGTCTC.T GCGAAGGGCG AATTC..... ..........
 42_4    CAGTTGAACT TTGGTCTC.T GCGAAGGGCG AATTC..... ..........
 42_5a   CAGTTGAACT TTGGTCTC.T GCGAAGGGCG AATTC..... ..........
 42_10   CAGTTGAACT TTGGTC.... ...AAGGGCG AATTC..... ..........
 42_3b   CAGTTGAACT TTGGTCTC.T GCGAAGGGCG AATTC..... ..........
 42_11   CAGTTGAACT TTGGTCTC.T GCGAAGGGCG AATTC..... ..........
 42_6b   CAGTTGAACT TTGGTCTC.T GCGAAGGGCG AATTC..... ..........
 43_1    .......... .......... .......... .......... ..........
 43_5    CAGTTGAACT TTGGTCTC.T GCGAAGGGCG AATTCGTTTA AACCTGCAGG
 43_12   CAGTTGAACT TTGGTCTC.T GCGAAGGGCG AATTC..... ..........
 43_20   CAGTTGAACT TTGGTCTC.T GCGAAGGGCG AATTC..... ..........
 43_21   CAGTTGAACT TTGGTCTC.T GCGAAGGGCG AATTC..... ..........
 43_23   CAGTTGAACT TTGGTCTC.T GCGAAGGGCG AATTC..... ..........
 43_25   CAGTTGAACT TTGGTCTC.T GCGAAGGGCG AATTC..... ..........
 44_1    CAGTTGAACT TTGGTCTC.T GCGAAGGGCG AATTC..... ..........
 44_5    CAGTTGAACT TTGGTCTC.T GCGAAGGGCG AATTC..... ..........
223_10   .......... .......... .......... .......... ..........
223_2    .......... .......... .......... .......... ..........
223_4    .......... .......... .......... .......... ..........
223_5    .......... .......... .......... .......... ..........
223_6    .......... .......... .......... .......... ..........
223_7    .......... .......... .......... .......... ..........
 A3_4    CAGTTGAACT TTGGTCTC.T GCGAAGGGCG AATTCGC.GG CCGCTA....
 A3_5    CAGTTGAACT TTGGTCTC.T GCGAAGGGCG AATTC..... ..........
 A3_7    CAGTTGAACT TTGGTCTC.T GCGAAGGGCG AATTC..... ..........
 A3_3    CAGTTGAACT TTGGTCTC.T GCGAAGGGCG AATTCGT.TT AAACCT....
 42_12   CAGTTGAACT TTGGTCTC.T GCGAAGGGCG AATTC..... ..........
 AAV1    CAGTTGAACT TTGGTCTCCT GTCCTTCTTA TCTTATCGGT TACCATGGTT
 AAV2    CAGTTGAACT TTGGTCTC.T GCGTATTTCT ..TTCTT.AT CTAGTTTCCA
 AAV3    CAGTTGAACT TTGGCTCT.T GTGCACTTCT TTATCTTTAT CTTGTTTCCA
 AAV8    CAGTTGAACT TTGGTCTC.T GCG....... .......... ..........
 AAV9    CAGTTGAACT TTGGTCTC.T GCG....... .......... ..........
 AAV7    CAGTTGAACT TTGGTCTCCT GTGCTTCTTA TCTTATCGGT TTCCATAGCA
 44_2    CAGTTGAACT TTGGTCTC.T GCGAAGGGCG AATTC..... ..........
```

FIG. 1AAAN

```
           4551                                                          4600
  42_2     ..........  ..........  ..........  ..........  ..........
  42_8     ..........  ..........  ..........  ..........  ..........
  42_15    ..........  ..........  ..........  ..........  ..........
  42_5b    ACTAGTCCCT  TTAGTGAGGG  TTAATTCTGA  G.........  ..........
  42_1b    ..........  ..........  ..........  ..........  ..........
  42_13    ..........  ..........  ..........  ..........  ..........
  42_3a    ..........  ..........  ..........  ..........  ..........
  42_4     ..........  ..........  ..........  ..........  ..........
  42_5a    ..........  ..........  ..........  ..........  ..........
  42_10    ..........  ..........  ..........  ..........  ..........
  42_3b    ..........  ..........  ..........  ..........  ..........
  42_11    ..........  ..........  ..........  ..........  ..........
  42_6b    ..........  ..........  ..........  ..........  ..........
  43_1     ..........  ..........  ..........  ..........  ..........
  43_5     AC........  ..........  ..........  ..........  ..........
  43_12    ..........  ..........  ..........  ..........  ..........
  43_20    ..........  ..........  ..........  ..........  ..........
  43_21    ..........  ..........  ..........  ..........  ..........
  43_23    ..........  ..........  ..........  ..........  ..........
  43_25    ..........  ..........  ..........  ..........  ..........
  44_1     ..........  ..........  ..........  ..........  ..........
  44_5     ..........  ..........  ..........  ..........  ..........
  223_10   ..........  ..........  ..........  ..........  ..........
  223_2    ..........  ..........  ..........  ..........  ..........
  223_4    ..........  ..........  ..........  ..........  ..........
  223_5    ..........  ..........  ..........  ..........  ..........
  223_6    ..........  ..........  ..........  ..........  ..........
  223_7    ..........  ..........  ..........  ..........  ..........
  A3_4     ..........  ..........  ..........  ..........  ..........
  A3_5     ..........  ..........  ..........  ..........  ..........
  A3_7     ..........  ..........  ..........  ..........  ..........
  A3_3     ..........  ..........  ..........  ..........  ..........
  42_12    ..........  ..........  ..........  ..........  ..........
  AAV1     ATAGCTTACA  CATTAACTGC  TTGGTTGCGC  T.........  ..........
  AAV2     TGGCTAC...  GTAGATAAGT  AGC.......  ..........  ..........
  AAV3     TGGCTACTGC  GTAGATAAGC  AGCGGCCTGC  GGCGCTTGCG  CTTCGCGGTT
  AAV8     ..........  ..........  ..........  ..........  ..........
  AAV9     ..........  ..........  ..........  ..........  ..........
  AAV7     ACTGGTTACA  CATTAACTGC  TTGGGTGCGC  TTCACGATAA  GAACACTGAC
  44_2     ..........  ..........  ..........  ..........  ..........
```

FIG. 1AAAO

```
         4601                                                    4650
42_2     ..........  ..........  ..........  ..........  ..........
42_8     ..........  ..........  ..........  ..........  ..........
42_15    ..........  ..........  ..........  ..........  ..........
42_5b    ....CTTGGC  GTAATCATGG  GTCATAG...  ..........  ..........
42_1b    ..........  ..........  ..........  ..........  ..........
42_13    ..........  ..........  ..........  ..........  ..........
42_3a    ..........  ..........  ..........  ..........  ..........
42_4     ..........  ..........  ..........  ..........  ..........
42_5a    ..........  ..........  ..........  ..........  ..........
42_10    ..........  ..........  ..........  ..........  ..........
42_3b    ..........  ..........  ..........  ..........  ..........
42_11    ..........  ..........  ..........  ..........  ..........
42_6b    ..........  ..........  ..........  ..........  ..........
43_1     ..........  ..........  ..........  ..........  ..........
43_5     ..........  ..........  ..........  ..........  ..........
43_12    ..........  ..........  ..........  ..........  ..........
43_20    ..........  ..........  ..........  ..........  ..........
43_21    ..........  ..........  ..........  ..........  ..........
43_23    ..........  ..........  ..........  ..........  ..........
43_25    ..........  ..........  ..........  ..........  ..........
44_1     ..........  ..........  ..........  ..........  ..........
44_5     ..........  ..........  ..........  ..........  ..........
223_10   ..........  ..........  ..........  ..........  ..........
223_2    ..........  ..........  ..........  ..........  ..........
223_4    ..........  ..........  ..........  ..........  ..........
223_5    ..........  ..........  ..........  ..........  ..........
223_6    ..........  ..........  ..........  ..........  ..........
223_7    ..........  ..........  ..........  ..........  ..........
A3_4     ..........  ..........  ..........  ..........  ..........
A3_5     ..........  ..........  ..........  ..........  ..........
A3_7     ..........  ..........  ..........  ..........  ..........
A3_3     ..........  ..........  ..........  ..........  ..........
42_12    ..........  ..........  ..........  ..........  ..........
AAV1     ....TCGCGA  TAAAAGACTT  ACGTCATCGG  GTTACCCCTA  GTGATGGAGT
AAV2     ....ATGGCG  GGTTAATCAT  TAACTACAAG  GA.ACCCCTA  GTGATGGAGT
AAV3     TACAACTGCT  GGTTAATATT  TAACTCTCGC  CATACCTCTA  GTGATGGAGT
AAV8     ..........  ..........  ..........  ..........  ..........
AAV9     ..........  ..........  ..........  ..........  ..........
AAV7     ..........  ..........  ..GTCACCGC  GGTACCCCTA  GTGATGGAGT
44_2     ..........  ..........  ..........  ..........  ..........
```

FIG. 1AAAP

```
           4651                                                              4700
   42_2    ..........  ..........  ..........  ..........  ..........
   42_8    ..........  ..........  ..........  ..........  ..........
  42_15    ..........  ..........  ..........  ..........  ..........
  42_5b    ..........  ..........  ..........  ..........  ..........
  42_1b    ..........  ..........  ..........  ..........  ..........
  42_13    ..........  ..........  ..........  ..........  ..........
  42_3a    ..........  ..........  ..........  ..........  ..........
   42_4    ..........  ..........  ..........  ..........  ..........
  42_5a    ..........  ..........  ..........  ..........  ..........
  42_10    ..........  ..........  ..........  ..........  ..........
  42_3b    ..........  ..........  ..........  ..........  ..........
  42_11    ..........  ..........  ..........  ..........  ..........
  42_6b    ..........  ..........  ..........  ..........  ..........
   43_1    ..........  ..........  ..........  ..........  ..........
   43_5    ..........  ..........  ..........  ..........  ..........
  43_12    ..........  ..........  ..........  ..........  ..........
  43_20    ..........  ..........  ..........  ..........  ..........
  43_21    ..........  ..........  ..........  ..........  ..........
  43_23    ..........  ..........  ..........  ..........  ..........
  43_25    ..........  ..........  ..........  ..........  ..........
   44_1    ..........  ..........  ..........  ..........  ..........
   44_5    ..........  ..........  ..........  ..........  ..........
  223_10   ..........  ..........  ..........  ..........  ..........
  223_2    ..........  ..........  ..........  ..........  ..........
  223_4    ..........  ..........  ..........  ..........  ..........
  223_5    ..........  ..........  ..........  ..........  ..........
  223_6    ..........  ..........  ..........  ..........  ..........
  223_7    ..........  ..........  ..........  ..........  ..........
   A3_4    ..........  ..........  ..........  ..........  ..........
   A3_5    ..........  ..........  ..........  ..........  ..........
   A3_7    ..........  ..........  ..........  ..........  ..........
   A3_3    ..........  ..........  ..........  ..........  ..........
  42_12    ..........  ..........  ..........  ..........  ..........
   AAV1    TGCCCACTCC  CTCTCTGCGC  GCTCGCTCGC  TCGGTGGGGC  CTGCGGACCA
   AAV2    TGGCCACTCC  CTCTCTGCGC  GCTCGCTCGC  TCACTGAGGC  CGGGCGACCA
   AAV3    TGGCCACTCC  CTCTATGCGC  ACTCGCTCGC  TCGGTGGGGC  CTGGCGACCA
   AAV8    ..........  ..........  ..........  ..........  ..........
   AAV9    ..........  ..........  ..........  ..........  ..........
   AAV7    TGGCCACTCC  CTCTATGCGC  GCTCGCTCGC  TCGGTGGGGC  CTGCGGACCA
   44_2    ..........  ..........  ..........  ..........  ..........
```

FIG. 1AAAQ

```
       4701                                                              4750
 42_2   ..........  ..........  ..........  ..........  ..........
 42_8   ..........  ..........  ..........  ..........  ..........
42_15   ..........  ..........  ..........  ..........  ..........
42_5b   ..........  ..........  ..........  ..........  ..........
42_1b   ..........  ..........  ..........  ..........  ..........
42_13   ..........  ..........  ..........  ..........  ..........
42_3a   ..........  ..........  ..........  ..........  ..........
 42_4   ..........  ..........  ..........  ..........  ..........
42_5a   ..........  ..........  ..........  ..........  ..........
42_10   ..........  ..........  ..........  ..........  ..........
42_3b   ..........  ..........  ..........  ..........  ..........
42_11   ..........  ..........  ..........  ..........  ..........
42_6b   ..........  ..........  ..........  ..........  ..........
 43_1   ..........  ..........  ..........  ..........  ..........
 43_5   ..........  ..........  ..........  ..........  ..........
43_12   ..........  ..........  ..........  ..........  ..........
43_20   ..........  ..........  ..........  ..........  ..........
43_21   ..........  ..........  ..........  ..........  ..........
43_23   ..........  ..........  ..........  ..........  ..........
43_25   ..........  ..........  ..........  ..........  ..........
 44_1   ..........  ..........  ..........  ..........  ..........
 44_5   ..........  ..........  ..........  ..........  ..........
223_10  ..........  ..........  ..........  ..........  ..........
223_2   ..........  ..........  ..........  ..........  ..........
223_4   ..........  ..........  ..........  ..........  ..........
223_5   ..........  ..........  ..........  ..........  ..........
223_6   ..........  ..........  ..........  ..........  ..........
223_7   ..........  ..........  ..........  ..........  ..........
 A3_4   ..........  ..........  ..........  ..........  ..........
 A3_5   ..........  ..........  ..........  ..........  ..........
 A3_7   ..........  ..........  ..........  ..........  ..........
 A3_3   ..........  ..........  ..........  ..........  ..........
42_12   ..........  ..........  ..........  ..........  ..........
 AAV1   AAGGTCCGCA  GACGGCAGAG  CTCTGCTCTG  CCGGCCCCAC  CGAGCGAGCG
 AAV2   AAGGTCGCCC  GACGCCCGGG  CTTTGCCCGG  GCGGCCTCAG  TGAGCGAGCG
 AAV3   AAGGTCGCCA  GACGGACGTG  CTTTGCACGT  CCGGCCCCAC  CGAGCGAGCG
 AAV8   ..........  ..........  ..........  ..........  ..........
 AAV9   ..........  ..........  ..........  ..........  ..........
 AAV7   AAGGTCCGCA  GACGGCAGAG  CTCTGCTCTG  CCGGCCCCAC  CGAGCGAGCG
 44_2   ..........  ..........  ..........  ..........  ..........
```

FIG. 1AAAR

```
              4751                            4774
    42_2      ..........  ..........  ....
    42_8      ..........  ..........  ....
    42_15     ..........  ..........  ....
    42_5b     ..........  ..........  ....
    42_1b     ..........  ..........  ....
    42_13     ..........  ..........  ....
    42_3a     ..........  ..........  ....
    42_4      ..........  ..........  ....
    42_5a     ..........  ..........  ....
    42_10     ..........  ..........  ....
    42_3b     ..........  ..........  ....
    42_11     ..........  ..........  ....
    42_6b     ..........  ..........  ....
    43_1      ..........  ..........  ....
    43_5      ..........  ..........  ....
    43_12     ..........  ..........  ....
    43_20     ..........  ..........  ....
    43_21     ..........  ..........  ....
    43_23     ..........  ..........  ....
    43_25     ..........  ..........  ....
    44_1      ..........  ..........  ....
    44_5      ..........  ..........  ....
    223_10    ..........  ..........  ....
    223_2     ..........  ..........  ....
    223_4     ..........  ..........  ....
    223_5     ..........  ..........  ....
    223_6     ..........  ..........  ....
    223_7     ..........  ..........  ....
    A3_4      ..........  ..........  ....
    A3_5      ..........  ..........  ....
    A3_7      ..........  ..........  ....
    A3_3      ..........  ..........  ....
    42_12     ..........  ..........  ....
    AAV1      AGCGCGCAGA  GAGGGAGTGG  GCAA
    AAV2      AGCGCGCAGA  GAGGGAGTGG  CCAA
    AAV3      AGTGCGCATA  GAGGGAGTGG  CCAA
    AAV8      ..........  ..........  ....
    AAV9      ..........  ..........  ....
    AAV7      AGCGCGCATA  GAGGGAGTGG  CCAA
    44_2      ..........  ..........  ....
```

```
                      10         20         30         40         50         60
                ....|....|....|....|....|....|....|....|....|....|....|....|
C1\VP1          MAADGYLPDWLEDNLSEGIREWWDLKPGAPKPKANQQKQDDGRGLVLPGYKYLGPFNGLD
C2\VP1          MAADGYLPDWLEDNLSEGIREWWDLKPGAPKLKANQQKQDDGRGLVLPGYKYLGPFHGLD
C5\VP1@2        MAADGYLPDWLEDNLSEGIREWWDLKPGAPKPKANQQKQDDGRGLVLPGYEYLGPFNGLD
AAV4\VP1        -MTDGYLPDWLEDNLSEGVREWWALQPGAPKPKANQQHQDNARGLVLPGYKYLGPGNGLD
AAV1            MAADGYLPDWLEDNLSEGIREWWDLKPGAPKPKANQQKQDDGRGLVLPGYKYLGPFNGLD
AAV6\VP1        MAADGYLPDWLEDNLSEGIREWWDLKPGAPKPKANQQKQDDGRGLVLPGYKYLGPFNGLD
A3_3            MAADGYLPDWLEDTLSEGIRQWWKLKPGPPPPKPNQQHRDDSRGLVLPGYKYLGPFNGLD
A3_7            MAADGYLPDWLEDTLSEGIRQWWKLKPGPPPPKPNQQHRDDSRGLVLPGYKYLGPFNGLD
A3_4            MAADGYLPDWLEDTLSEGIRQWWKLKPGPPPPKPNQQHRDDSRGLVLPGYKYLGPFNGLD
A3_5            MAADGYLPDWLEDTLSEGIRQWWKLKPGPPPPKPNQQHRDDSRGLVLPGYKYLGPFNGLD
AAV2            MAADGYLPDWLEDTLSEGIRQWWKLKPGPPPPKPAERHKDDSRGLVLPGYKYLGPFNGLD
AAV3            MAADGYLPDWLEDNLSEGIREWWALKPGVPQPKANQQHQDNRRGLVLPGYKYLGPGNGLD
13.3b\VP1       MAADGYLPDWLEDNLSEGIREWWDLKPGAPKPKANQQKQDNGRGLVLPGYKYLGPFNGLD
AAV7            MAADGYLPDWLEDNLSEGIREWWDLKPGAPKPKANQQKQDNGRGLVLPGYKYLGPFNGLD
223_4           ------------------------------------------------------------
223_5           ------------------------------------------------------------
223_10          ------------------------------------------------------------
223_2           ------------------------------------------------------------
223_7           ------------------------------------------------------------
223_6           ------------------------------------------------------------
44_1            MAADGYLPDWLEDNLSEGIREWWDLKPGAPKPKANQQKQDDGRGLVLPGYKYLGPFNGLD
44_5            MAADGYLPDWLEDNLSEGIREWWDLKPGAPKPKANQQKQDDGRGLVLPGYKYLGPFNGLD
44_2            MAADGYLPDWLEDNLSEGIREWWDLKPGAPKPKANQQKQDDGRGLVLPGYKYLGPFNGLD
29.3\VP1        MAADGYLPDWLEDNLSEGIREWWALKPGAPKPKANQQKQDDGRGLVLPGYKYLGPFNGLD
29.5\VP1        MAADGYLPDWLEDNLSEGIREWWALKPGAPKPKANQQKQDDGRGLVLPGYKYLGPFNGLD
42_15           MAADGYLPDWLEDNLSEGIREWWDLKPGAPKPKANQQKQDDGRGLVLPGYKYLGPFNGLD
42_8            MAADGYLPDWLEDNLSEGIREWWDLKPGAPKPKANQQKQDDGRGLVLPGYKYLGPFNGLD
42_13           MAADGYLPDWLEDNLSEGIREWWDLKPGAPKPKANQQKQDDGRGLVLPGYKYLGPFNGLD
42_3A           MAADGHLPDWLEDNLSEGIREWWDLKPGAPKPKANQQKQDDGRGLVLPGYKYLGPFNGLD
42_4            MAADGYLPDWLEDNLSEGIREWWDLKPGAPKPKANQQKQDDGRGLVLPGYKYLGPFNGLD
42_5A           MAADGYLPDWLEDNLSEGIREWWDLKPGAPKPKANQQKQDDGRGLVLPGYKYLGPFNGLD
42_1B           MAADGYLPDWLEDNLSEGIREWWDLRPGAPKPKANQQKQDDGRGLVLPGYKYLGPFNGLD
42_5B           MAADGYLPDWLEDNLSEGIREWWDLKPGAPKPKANQQKQDDGRGLVLPGYKYLGPFNGLD
43_1            MAADGYLPDWLEDNLSEGIREWWDLKPGAPKPKANQQKQDDGRGLVLPGYKYLGPFNGLD
43_12           MAADGYLPDWLEDNLSEGIREWWDLKPGAPKPKANQQKQDDGRGLVLPGYKYLGPFNGLD
43_5            MAADGYLPDWLEDNLSEGIREWWDLKPGAPKPKANQQKQDDGRGLVLPGYKYLGPFNGLD
AAV8            MAADGYLPDWLEDNLSEGIREWWALKPGAPKPKANQQKQDDGRGLVLPGYKYLGPFNGLD
43_21           MAADGYLPDWLEDNLSEGIREWWDLKPGAPKPKANQQKQDDGRGLVLPGYKYLGPFNGLD
43_25           MAADGYLPDWLEDNLSEGIREWWDLKPGAPKPKANQQKQDDGRGLVLPGYKYLGPFNGLD
43_23           MAADGYLPDWLEDNLSEGIREWWDLKPGAPKPKANQQKQDDGRGLVLPGYKYLGPFNGLD
43_20           MAADGYLPDWLEDNLSEGIREWWDLKPGAPKPKANQQKQDDGRGLVLPGYKYLGPFNGLD
AAV_9           MAADGYLPDWLEDNLSEGIREWWDLKPGAPKPKANQQKQDDGRGLVLPGYKYLGPFNGLD
24.1            MAADGYLPDWLEDNLSEGIREWWDLKPGAPKPKANQQKQDDGRGLVLPGYKYLRPFNGLD
42.2REAL        MAADGYLPDWLEDNLSEGIREWWDLKPGAPKPKANQQKQDDGRGLVLPGYKYLGPFNGLD
7.2\VP1         MAADGYLPDWLEGNLSEGIREWWDLKPGAPKPKANQQKQDDGRGLVLPGYRYLGPFNGLD
27.3\VP1        MAADGYLPDWLEDNLSEGIREWWDLKPGAPKPKANQQKQDDGRGLVLPGYKYLGPFNGLD
16.3\VP1        MAADGYLPDWLEDNLSEGIREWWDLKPGAPKPKANQQKQDDGRGLVLPGYKYLGPFNGLD
42_10           MAADGYLPDWLEDNLSEGIREWWDLKPGAPKPKANQQKQDDGRGLVLPGYKYLGPFNGLD
42_3B           MAADGYLPDWLEDNLSEGIREWWDLKPGAPKPKANQQKQDDGRGLVLPGYKYLGPFNGLD
42_11           MAADGYLPDWLEDNLSEGIREWWDLKPGAPKPKANQQKQDDGRGLVLPGYKYLGPFNGLD
F1\VP1          MAADGYLPDWLEDNLSEGIREWWDLKPGAPKPKANQQKQDDGRGLVLPGYKYLGPFNGLD
F5\VP1@3        MAADGYLPDWLEDNLSEGIREWWDLKPGAPKPKANQQKQDDGRGLVLPGYKYLGPFNGLD
F3\VP1          MAADGYLPDWLEDNLSEGIREWWDLKPGAPKPKANQQKQDDGRGLVLPGYKYLGPFNGLD
42_6B           MAADGYLPDWLEDNLSEGIREWWDLKPGAPKPKANQQKQDDGRGLVLPGYKYLGPFNGLD
42_12           MAADGYLPDWLEDNLSEGIREWWDLKPGAPKPKANQQKQDDGRGLVLPGYKYLGPFNGLD
AAV5\CAP        MSFVDHPPDWLEE-VGEGLREFLGLEAGPPKPKPNQQHQDQARGLVLPGYNYLGPGNGLD
```

FIG. 2A

```
                       70        80        90        100       110       120
                ....|....|....|....|....|....|....|....|....|....|....|....|....|
C1\VP1          KGEPVNAADAAALEHDKAYDQQLKAGDNPYLRYNHADAEFQERLQEDTSFGGNLGRAVFQ
C2\VP1          KGEPVNAADAAALEHDKAYDQQLKAGDNPYLRYNHADAEFQERLQEDTSFGGNLGRAVFQ
C5\VP1@2        KGEPVNAADAAALEHDKAYDQQLKAGDNPYLRYNHADAEFQERLQEDTSFGGNLGRAVFQ
AAV4\VP1        KGEPVNAADAAALEHDKAYDQQLKAGDNPYLKYNHADAEFQQRLQGDTSFGGNLGRAVFQ
AAV1            KGEPVNAADAAALEHDKAYDQQLKAGDNPYLRYNHADAEFQERLQEDTSFGGNLGRAVFQ
AAV6\VP1        KGEPVNAADAAALEHDKAYDQQLKAGDNPYLRYNHADAEFQERLQEDTSFGGNLGRAVFQ
A3_3            KGEPVNEADAAALEHDKAYDHQLKQGDNPYLKYNHADAEFQERLQEDTSFGGNLGRAVFQ
A3_7            KGEPVNEADAAALEHDKAYDHQLKQGDNPYLKYNHADAEFQERLQEDTSFGGNLGRAVFQ
A3_4            KGEPVNEADAAALEHDKAYDHQLKQGDNPYLKYNHADAEFQERLQEDTSFGGNLGRAVFQ
A3_5            KGEPVNEADAAALEHDKAYDHQLKQGDNPYLKYNHADAEFQERLQEDTSFGGNLGRAVFQ
AAV2            KGEPVNEADAAALEHDKAYDRQLDSGDNPYLKYNHADAEFQERLKEDTSFGGNLGRAVFQ
AAV3            KGEPVNEADAAALEHDKAYDQQLKAGDNPYLKYNHADAEFQERLQEDTSFGGNLGRAVFQ
13.3b\VP1       KGEPVNAADAAALEHDKAYDQQLNAGDNPYLRYNHADAEFQERLQEDTSFGGNLGRAVFQ
AAV7            KGEPVNAADAAALEHDKAYDQQLKAGDNPYLRYNHADAEFQERLQEDTSFGGNLGRAVFQ
223_4           ------------------KAYDQQLKAGDNPYLRYNHADAEFQERLQEDTSFGGNLGRAVFQ
223_5           ------------------KAYDQQLKAGDNPYLRYNHADAEFQERLQEDTSFGGNLGRAVFQ
223_10          ------------------KAYDQQLKAGDNPYLRYNHADAEFQERLQEDTSFGGNLGRAVFQ
223_2           ------------------KAYDQQLKAGDNPYLRYNHADAEFQECLQEDTSFGGNLGRAVFQ
223_7           ------------------KAYDQQLKAGDNPYLRYNHADAEFQERLQEDTSFGGNLGRAVFQ
223_6           ------------------KAYDQQLKAGDNPYLRYNHADAEFQERLQEDTSFGGNLGRAVFQ
44_1            KGEPVNAADAAALEHDKAYDQQLKAGDNPYLRYNHADAEFQERLQEDTSFGGNLGRAVFQ
44_5            KGEPVNAADAAALEHDKAYDQQLKAGDNPYLRYNHADAEFQERLQEDTSFGGNLGRAVFQ
44_2            KGEPVNAADAAALEHDKAYDQQLKAGDNPYLRYNHADAEFQERLQEDTSFGGNLGRAVFQ
29.3\VP1        KGEPVNAADAAALEHDKAYDQQLKAGDNPYLRYNHADAEFQERLQEDTSFGGNLGRAVFQ
29.5\VP1        KGEPVNAADAAALEHDKAYDQQLKAGDNPYLRYNHADAEFQERLQEDTSFGGNLGRAVFQ
42_15           KGEPVNAADAAALEHDKAYDQQLKAGDNPYLRYNHADAEFQERLQEDTSFGGNLGRAVFQ
42_8            KGEPVNAADAAALEHDKAYDQQLKAGDNPYLRYNHADAEFQERLQEDTSFGGNLGRAVFQ
42_13           KGEPVNAADAAALEHDKAYDQQLKAGDNPYLRYNHADAEFQERLQEDTSFGGNLGRAVFQ
42_3A           KGEPVNAADAAALEHDKAYDQQLKAGDNPYLRYNHADAEFQERLQEDTSFGGNLGRAVFQ
42_4            KGEPVNEADAAALEHDKAYDKQLEQGDNPYLKYNHADAEFQERLQEDTSFGGNLGRAVFQ
42_5A           KGEPVNEADAAALEHDKAYDKQLEQGDNPYLKYNHADAEFQERLQEDTSFGGNLGRAVFR
42_1B           KGEPVNEADAAALEHDKAYDKQLEQGDNPYLKYNHADAEFQERLQEDTSFGGNLGRAVFQ
42_5B           KGEPVNEADAAALEHDKAYDKQLEQGDNPYLKYNHADAEFQERLQEDTSFGGNLGRAVFQ
43_1            KGEPVNAADAAALEHDKAYDQQLKAGDNPYLRYNHADAEFQERLQEDTSFGGNLGRAVFQ
43_12           KGEPVNAADAAALEHDKAYDQQLKAGDNPYLRYNHADAEFQERLQEDTSFGGNLGRAVFQ
43_5            KGEPVNAADAAALEHDKAYDQQLKAGDNPYLRYNHADAEFQERLQEDTSFGGNLGRAVFQ
AAV8            KGEPVNAADAAALEHDKAYDQQLQAGDNPYLRYNHADAEFQERLQEDTSFGGNLGRAVFQ
43_21           KGEPVNAADAAALEHDKAYDQQLKAGDNPYLRYNHADAEFQERLQEDTSFGGNLGRAVFQ
43_25           KGEPVNAADAAALEHDKAYDQQLKAGDNPYLRYNHADAEFQERLQEDTSFGGNLGRAVFQ
43_23           KGEPVNAADAAALEHDKAYDQQLKAGDNPYLRYNHADAEFQERLQEDTSFGGNLGRAVFQ
43_20           KGEPVNAADAAALEHDKAYDQQLKAGDNPYLRYNHADAEFQERLQEDTSFGGNLGRAVFQ
AAV_9           KGEPVNAADAAALEHDKAYDQQLKAGDNPYLRYNHADAEFQERLQEDTSFGGNLGRAVFQ
24.1            KGEPVNEADAAALEHDKAYDKQLEQGDNPYLKYNHADAEFQERLQEDTSFGGNLGRAVFQ
42.2REAL        KGEPVNEADAAALEHDKAYDKQLEQGDNPYLKYNHADAEFQERLQEDTSFGGNLGRAVFQ
7.2\VP1         KGEPVNEADAAALEHDKAYDKQLEQGDNPYLKYNHADAEFQERLQEDTSFGGNLGRAVFQ
27.3\VP1        KGEPVNEADAAALEHDKAYDKQLEQGDNPYLKYNHADAEFQERLQEDTSFGGNLGRAVFQ
16.3\VP1        KGEPVNEADAAALEHDKAYDKQLEQGDNPYLKYNHADAEFQERLQEDTSFGGNLGRAVFQ
42_10           KGEPVNEADAAALEHDKAYDKQLEQGDNPYLKYNHADAEFQERLQEDTSFGGNLGRAVFQ
42_3B           KGEPVNEADAAALEHDKAYDKQLEQGDNPYLKYNHADAEFQERLQEDTSFGGNLGRAVFQ
42_11           KGEPVNAADAAALEHDKAYDQQLKAGDNPYLRYNHADAEFQERLQEDTSFGGNLGRAVFQ
F1\VP1          KGEPVNAADAAALEHDKAYDQQLKAGDNPYLRYNHADAEFQERLQEDTSFGGNLGRAVFQ
F5\VP1@3        KGEPVNAADAAALEHDKAYDQQLKAGDNPYLRYNHADAEFQERLQEDTSFGGNLGRAVFQ
F3\VP1          KGEPVNAADAAALEHDKAYDQQLKAGDNPYLRYNHADAEFQERLQEDTSFGGNLGRAVFQ
42_6B           KGEPVNEADAAALEHDKAYDKQLEQGDNPYLKYNHADAEFQERLQEDTSFGGNLGRAVFQ
42_12           KGEPVNEADAAALEHDKAYDKQLEQGDNPYLKYNHADAEFQERLQEDTSFGGNLGRAVFQ
AAV5\CAP        RGEPVNRADEVAREHDISYNEQLEAGDNPYLKYNHADAEFQEKLADDTSFGGNLGKAVFQ
```

FIG. 2B

```
                    130        140        150        160        170        180
                    ....|....|....|....|....|....|....|....|....|....|....|....|
C1\VP1              AKKRVLEPLGLVEEGAKTAPGKKRP-LESPQ-EPDSSSGIGKKGKQPAKKRLNFEEDTGA
C2\VP1              AKKRVLEPLGLVEEGAKTAPGKKRP-LESPQ-EPDSSSGIGKKGKQPAKKRLNFEEDTGA
C5\VP1@2            AKKRVLEPLGLVEEGAKTAPGKKRP-LESPQ-EPDSSSGIGKKGKQPAKKRLNFEEDTGA
AAV4\VP1            AKKRVLEPLGLVEQAGETAPGKKRPLIESPQ-QPDSSTGIGKKGKQPAKKKLVFEDETGA
AAV1                AKKRVLEPLGLVEEGAKTAPGKKRPVEQSPQ-EPDSSSGIGKTGQQPAKKRLNFGQTGDS
AAV6\VP1            AKKRVLEPFGLVEEGAKTAPGKKRPVEQSPQ-EPDSSSGIGKTGQQPAKKRLNFGQTGDS
A3_3                AKKRVLEPLGLVEEAVKTAPGKKRPIEQSPA-EPDSSSGIGKSGQQPAKKRLNFGQTGDT
A3_7                AKKRVLEPLGLVEEAVKTAPGKKRPIEQSPA-EPDSSSGIGKSGQQPAKKRLNFGQTGDT
A3_4                AKKRVLEPLGLVEEAVKTAPGKKRPIEQSPA-EPDSSSGIGESGQQPAKKRLNFGQTGDT
A3_5                AKKRVLEPLGLVEEAVKTAPGKKRPIEQSPA-EPDSSSGIGKSGQQPAKKRLNFGQTGDT
AAV2                AKKRVLEPLGLVEEPVKTAPGKKRPVEHSPV-EPDSSSGTGKAGQQPARKRLNFGQTGDA
AAV3                AKKRILEPLGLVEEAAKTAPGKKGAVDQSPQ-EPDSSSGVGKSGKQPARKRLNFGQTGDS
13.3b\VP1           AKKRVLEPLGLVEEGAKTAPAKKRPVEPSPQRSPDSSTGIGKKGQQPARKRLNFGQTGDS
AAV7                AKKRVLEPLGLVEEGAKTAPAKKRPVEPSPQRSPDSSTGIGKKGQQPARKRLNFGQTGDS
223_4               AKKRVLEPLGLVETPAKTAPGKKRPVD-----SPDSTSGIGKKGQQPAKKRLNFGQTGDS
223_5               AKKRVLEPLGLVETPAKTAPGKKRPVD-----SPDSTSGIGKKGQQPAKKRLNFGQTGDS
223_10              AKKRVLEPLGLVETPAKTAPGKKRPVD-----SPDSTSGIGKKGQQPAKKRLNFGQTGDS
223_2               AKKRVLEPLGLVETPAKTAPGKKRPVD-----SPDSTSGIGKKGQQPAKKRLNFGQTGDS
223_7               AKKRVLEPLGLVETPAKTAPGKKRPVD-----SPDSTSGIGKKGQQPAKKRLNFGQTGDS
223_6               AKKRVLEPLGLVETPAKTAPGKKRPVD-----SPDSTSGIGKKGQQPAKKRLNFGQTGDS
44_1                AKKRVLEPLGLVEEGAKTAPGKKRPVEPSPQRSPDSSTGIGKKGQQPAKKRLNFGQTGDS
44_5                AKKRVLEPLGLVEEGAKTAPGKKRPVEPSPQRSPDSSTGIGKKGQQPAKKRLNFGQTGDS
44_2                AKKRVLEPLGLVEEGAKTAPGKKRPVEPSPQRSPDSSTGIGKKGQQPAKKRLNFGQTGDS
29.3\VP1            AKKRVLEPLGLVEEGAKTAPGKKRPVEPSPQRSPDSTTGIGKKGQQPAKKRLNFGQTGDS
29.5\VP1            AKKRVLEPLGLVEEGAKTAPGKKRPVEPSPQRSPDSSTGIGKKGQQPAKKRLNFGQTGDS
42_15               AKKRVLEPLGLVEEGAKTAPGKKRPVEPSPQRSPDSSTGIGKTGQQPAKKRLNFGQTGDS
42_8                AKKRVLEPLGLVEEGAKTAPGKKRPVEPSPQRSPDSSTGIGKTGQQPAKKRLNFGQTGDS
42_13               AKKRVLEPLGLVEEGAKTAPGKKRPIE-----SPDSSTGIGKKGQQPAKKKLNFGQTGDS
42_3A               AKKRVLEPLGLVEEGAKTAPGKKRPIE-----SPDSSTGIGKKGQQPAKKKLNFGQTGDS
42_4                AKKRVLEPLGLVEEGAKTAPGKKRPIE-----SPDSSTGIGKKGQQPAKKKLNFGQTGDS
42_5A               AKKRVLEPLGLVEEGAKTAPGKKRPIE-----SPDSSTGIGKKGQQPAKKKLNFGQTGDS
42_1B               AKKRVLEPLGLVEEGAKTAPGKKRPIE-----SPDSSTGIGKKGQQPAKKKLNFGQTGDS
42_5B               AKKRVLEPLGLVEEGAKTAPGKKRPVEPSPQRSPDSSTGIGKTGQQPAKKRLNFGQTGDS
43_1                AKKRVLEPLGLVEEGAKTAPGKKRPVEPSPQRSPDSSTGIGKKGHQPARKRLNFGQTGDS
43_12               AKKRVLEPLGLVEEGAKTAPGKKRPVEPSPQRSPDSSTGIGKKGHQPARKRLNFGQTGDS
43_5                AKKRVLEPLGLVEEGAKTAPGKKRPVEPSPQRSPDSSTGIGKKGHQPARKRLNFGQTGDS
AAV8                AKKRVLEPLGLVEEGAKTAPGKKRPVEPSPQRSPDSSTGIGKKGQQPARKRLNFGQTGDS
43_21               AKKRVLEPLGLVEEGAKTAPGKKRPVEQSPQ-EPDSSSGIGKTGQQPAKKRLNFGQTGDS
43_25               AKKRVLEPLGLVEEGAKTAPGKKRPVEQSPQ-EPDSSSGIGKTGQQPAKKRLNFGQTGDS
43_23               AKKRVLEPLGLVEEGAKTAPGKKRPVEQSPQ-EPDSSSGIGKTGQQPAKKRLNFGQTGDS
43_20               AKKRVLEPLGLVEEGAKTAPGKKRLVEQSPQ-EPDSSSGIGKTGQQPAKKRLNFGQTGDS
AAV_9               AKKRVLEPLGLVEEGAKTAPGKKRPVEQSPQ-EPDSSSGIGKSGQQPAKKRLNFGQTGDS
24.1                AKKRVLEPLGLVEEVAKTAPGKKRPIE-----SPDSSTGIGKKGQQPAKKKLNFGQTGDS
42.2REAL            AKKRVLEPLGLVEEGAKTAPGKKRPIE-----SPDSSTGIGKKGQQPAKKKLNFGQTGDS
7.2\VP1             AKKRVLEPLGLVEEGAKTAPGKKRPIE-----SPDSSTGIGKNGQPPAKKKLNFGQTGDS
27.3\VP1            AKKRVLEPLGLVEEGAKTASGKKRPIE-----SPDSSTGIGKKGQQPAKKKLNFGQTGDS
16.3\VP1            AKKRVLEPLGLVEEGAKTAPGKKRPIE-----SPDSSTGIGKKGQQPAKKKLNFGQTGDS
42_10               AKKRVLEPLGLVEEGAKTAPGKKRPIE-----SPDSSTGIGRKGQQPAKKKLNFGQTGDS
42_3B               AKKRVLEPLGLVEEGAKTAPGKKRPIE-----SPDSSTGIGKKGQQPAKKKLNFGQTGDS
42_11               AKKRVLEPLGLVEEGAKTAPGKKRPIE-----SPDSSTGIGKKGQQPAKKKLNFGQTGDS
F1\VP1              AKKRVLEPLGLVEEGAKTAPGKKRPID-----SPDSSTGIGKKGQQPAKKKLNFGQTGDS
F5\VP1@3            AKKRVLEPLGLVEEGAKTAPGKKRPID-----SPDSSTGIGKKGQQPAKKKLNFGQTGDS
F3\VP1              AKKRVLEPLGLVEEGAKTAPGKKRPIG-----SPDSSTGIGKKGQQPAKKKLNFGQTGDS
42_6B               AKKRVLEPLGLVEEGAKTAPGKKRPVEPSPQRSPDSSTGIGKTGQQPAKKRLNFGQTGDS
42_12               AKKRVLEPLGLVEEGAKTAPGKKRPVEPSPQRSPDSSTGIGKTGQQPAKKRLNFGQTGDS
AAV5\CAP            AKKRVLEPFGLVEEGAKTAPTGKR---------IDDHFPKRKKARTEEDSKP--STSSDA
```

FIG. 2C

```
                         190       200       210       220       230       240
                    ....|....|....|....|....|....|....|....|....|....|....|....|
C1\VP1              GDGP----PEGSDTSAMS--SDIEMRAAPGGNAVDAGQGSDGVGNASGDWHCDSTWSEGK
C2\VP1              GDGP----PEGSDTSAMS--SDIEMRAAPGGNAVDAGQGSDGVGNASGDWHCDSTWSEGK
C5\VP1@2            GDGP----PEGSDTSAMS--SDIEMRAAPGGNAVDAGQGSDGVGNASGDWHCDSTWSEGK
AAV4\VP1            GDGP----PEGSTSGAMS--DDSEMRAAAGGAAVEGGQGADGVGNASGDWHCDSTWSEGH
AAV1                ESVPD-PQPLGEPPATPAAVGPTTMASGGGAPMADNNEGADGVGNASGNWHCDSTWLGDR
AAV6\VP1            ESVPD-PQPLGEPPATPAAVGPTTMASGGGAPMADNNEGADGVGNASGNWHCDSTWLGDR
A3_3                ESVPG-PQPIGEPPAAPSGVGSNTMASGGGAPMADNNEGADGVGNSSGNWHCDSTWMGDR
A3_7                ESVPD-PQPIGEPPAAPSGVGSNTMASGGGAPMADNNEGADGVGNSSGNWHCDSTWMGDR
A3_4                ESVPD-PQPIGEPPAAPSGVGSNTMASGGGAPMADDNEGADGVGNSSGNWHCDSTWMGDR
A3_5                ESVPD-PQPIGEPPAAPSGVGSNTMASGGGAPMADNNEGADGVGNSSGNWHCDSTWMGDR
AAV2                DSVPD-PQPLGQPPAAPSGLGTNTMATGSGAPMADNNEGADGVGNSSGNWHCDSTWMGDR
AAV3                ESVPD-PQPLGEPPAAPTSLGSNTMASGGGAPMADNNEGADGVGNSSGNWHCDSQWLGDR
13.3b\VP1           ESVPD-PQPLGEPPAAPSSVGSGTVAAGGGAPMADNNEGADGVGNASGNWHCDSTWLGDR
AAV7                ESVPD-PQPLGEPPAAPSSVGSGTVAAGGGAPMADNNEGADGVGNASGNWHCDSTWLGDR
223_4               EPVPD-PQPIGEPPAGPSGLGSGTMAAGGGAPMADNNEGADGVGNASGNWHCDSTRLGDR
223_5               EPVPD-PQPIGEPPAGPSGLGSGTMAAGGGAPMADNNEGADGVGNASGNWHCDSTRLGDR
223_10              ESVPD-PQPIGEPPAGPSGLGSGTMAAGGGAPMADNNEGADGVGNASGNWHCDSTWLGDR
223_2               ESVPD-PQPIGEPPAGPSGLGSGTMVAGGGAPMADNNEGADGVGNASGNWHCDSTWLGDR
223_7               ESVPD-PQPIGEPPAGPSGLGSGTMAAGGGAPMADNNEGADGVGNASGNWHCDSTWLGDR
223_6               ESVPD-PQPIGEPPAGPSGLGSGTMAAGGGAPMADNSEGADGVGNASGNWHCDSTWLGDR
44_1                ESVPD-PQPIGEPPAGPSGLGSGTMAAGGGAPMADNNEGADGVGSSSGNWHCDSTWLGDR
44_5                ESVPD-PQPIGEPPAGPSGLGSGTMAAGGGAPMADNNEGADGVGSSSGNWHCDSTWLGDR
44_2                ESVPD-PQPIGEPPAGPSGLGSGTMAAGGGAPMADNNEGADGVGSSSGNWHCDSTWLGDR
29.3\VP1            ESVPD-PQPIGEPPAGPSGLGSGTMAAGGGAPMADNNEGADGVGSSSGNWHCDSTWLGDR
29.5\VP1            ESVPD-PQPIGEPPAGPSGLGSGTMAAGGGAPMADNNEGADGVGSSSGNWHCDSTWLGDG
42_15               ESVPD-PQPIGEPPAGPSGLGSGTMAAGGGAPMADNNEGADGVGSSSGNWHCDSTWLGDR
42_8                ESVPD-PQPIGEPPAGPSGLGSGTMAAGGGAPMADNNEGADGVGSSSGNWHCDSTWLGDR
42_13               ESVPD-PQPIGEPPAGPSGLGSGTMAAGGGAPMADNNEGADGVGSSSGNWHCDSTWLGDR
42_3A               ESVPD-PQPIGEPPAGPSGLGSGTMAAGGGAPMADNNEGADGVGSSSGNWHCDSTWLGDR
42_4                ESVPD-PQPIGEPPAGPSGLGSGTMAAGGGAPMADNNEGADGVGNASGNWHCDSTWLGDR
42_5A               ESVPD-PQPLGEPPAAPSGLGSGTMAAGGGAPMADNNEGADGVGNASGNWHCDSTWLGDR
42_1B               ESVPD-PQPIGEPPAGPSGLGSGTMAAGGGAPMADNNEGADGVGSSSGNWHCDSTWLGDR
42_5B               ESVPD-PQPIGEPPAGPSGLGSGTMAAGGGAPMADNNEGADGVGSSSGNWHCDSTWLGDR
43_1                ESVPD-PQPIGEPPAGPSGLGSGTMAAGGGAPMADNNEGADGVGSSSGNWHCDSTWLGDR
43_12               ESVPD-PQPIGEPPAGPSGLGSGTMAAGGGAPMADNNEGADGVGSSSGNWHCDSTWLGDR
43_5                ESVPD-PQPIGEPPAGPSGLGSGTMAAGGGAPMADNNEGADGVGSSSGNWHCDSTWLGDR
AAV8                ESVPD-PQPLGEPPAAPSGVGPNTMAAGGGAPMADNNEGADGVGSSSGNWHCDSTWLGDR
43_21               ESVPD-PQPLGEPPAAPSGLGPNTMASGGGAPMADNNEGADGVGNSSGNWHCDSTWLGDR
43_25               ESVPD-PQPLGEPPAAPSGLGPNTMASGGGAPMADNNEGADGVGNSSGNWHCDSTWLGDR
43_23               ESVPD-PQPLGEPPAAPSGLGPNTMASGGGAPMADNNEGADGVGNSSGNWHCDSTWLGDR
43_20               ESVPD-PQPLGEPPAAPSGLGPNTMASGGGAPMADNNEGADGVGNSSGNWHCDSTWLGDR
AAV_9               ESVPD-PQPLGEPPEAPSGLGPNTMASGGGAPMADNNEGADGVGNSSGNWHCDSTWLGDR
24.1                ESVPD-PQPLGEPPAAPSGLGSGTMAAGGGAPMADNNEGADGVGNASGNWHCDSTWLGDR
42.2REAL            ESVPD-PQPLGEPPAAPSGLGSGTMAAGGGAPMADNNEGADGVGNASGNWHCDSTWLGDR
7.2\VP1             ESVPD-PQPLGEPPAAPSGLGSGTMAAGGGAPMADNNEGADGVGNASGNWHCDSTWLGDR
27.3\VP1            ESVPD-PQPLGEPPAAPSGLGSGTMAAGGGAPMADNNEGADGVGNASGNWHCDSTWLGDR
16.3\VP1            ESVPD-PQPLGEPPAAPSGLGSGTMAAGGGAPMADNNEGADGVGNASGNWHCDSTWLGDR
42_10               ESVPD-PQPIGEPPAGPSGLGSGTMAAGGGAPMADNNEGADGVGNASGNWHCDSTWLGDR
42_3B               ESVPD-PQPIGEPPAGPSGLGSGTMAAGGGAPMADNNEGADGVGNASGNWHCDSTWLGDR
42_11               ESVPD-PQPIGEPPAGPSGLGSGTMAAGGGAPMADNNEGADGVGNASGNWHCDSTWLGDR
F1\VP1              ESVPD-PQPLGEPPAAPSSVGSGTMAAGGGAPMADNNEGADGVGNASGNWHCDSTWLGDR
F5\VP1@3            ESVPD-PQPLGEPPAAPSSVGSGTMAAGGGAPTADNNEGADGVGNASGNWHCDSTWLGDR
F3\VP1              ESVPD-PQPLGEPPAAPSSVGSGTMAAGGGAPMADNNEGADGVGNASGNWHCDSTWLGDR
42_6B               ESVPD-PQPIGEPPAGPSGLGSGTMAAGGGAPMADNNEGADGVGNASGNWHCDSTWLGDR
42_12               ESVPD-PQPIGEPPAGPSGLGSGTMAAGGGAPMADNNEGADGVGSSSGNWHCDSTWLGDR
AAV5\CAP            EAGPSGSQQLQIPAQPASSLGADTMSAGGGGPLGDNNQGADGVGNASGDWHCDSTWMGDR
```

FIG. 2D

```
                    250       260       270       280       290       300
                    ....|....|....|....|....|....|....|....|....|....|....|....|
C1\VP1              VTTTSTRTWVLPTYNNHLYLRLG-----TTSNSNTYNGFSTPWGYFDFNRFHCHFSPRDW
C2\VP1              VTTTSTRTWVLPTYNNHLYLRLG-----TTSNSNTYNGFSTPWGYFDFNRFHCHFSPRDW
C5\VP1@2            VTTTSTRTWVLPTYNNHLYLRLG-----TTSNSNTYNGFSTPWGYFDFNRFHCHFSPRDW
AAV4\VP1            VTTTSTRTWVLPTYNNHLYKRLG-----ESLQSNTYNGFSTPWGYFDFNRFHCHFSPRDW
AAV1                VITTSTRTWALPTYNNHLYKQIS-SASTGASNDNHYFGYSTPWGYFDFNRFHCHFSPRDW
AAV6\VP1            VITTSTRTWALPTYNNHLYKQIS-SASTGASNDNHYFGYSTPWGYFDFNRFHCHFSPRDW
A3_3                VITTSTRTWALPTYNNHLYKQIS--SESGATNDNHYFGYSTPWGYFDFNRFHCHFSPRDW
A3_7                VITTSTRTWALPTYNNRLYKQIS--SESGATNDNHYFGYSTPWGYFDFNRFHCHFSPRDW
A3_4                VITTSTRTWALPTYNNHLYKQIS--SESGATNDNHYFGYSTPWGYFDFNRFHCHFSPRDW
A3_5                VITTSTRTWALPTYNNHLYKQIS--SESGATNDNHYFGYSTPWGYFDFNRFHCHFSPRDW
AAV2                VITTSTRTWALPTYNNHLYKQIS--SQSGASNDNHYFGYSTPWGYFDFNRFHCHFSPRDW
AAV3                VITTSTRTWALPTYNNHLYKQIS--SQSGASNDNHYFGYSTPWGYFDFNRFHCHFSPRDW
13.3b\VP1           VITTSTRTWALPTYNNHLYEQIS-SETAGSTNDNTYFGYSTPWGYFDFNRFHCHFSPRDW
AAV7                VITTSTRTWALPTYNNHLYKQIS-SETAGSTNDNTYFGYSTPWGYFDFNRFHCHFSPRDW
223_4               VITTSTRTWALPTYNNHLYKQIS-SQSAGSTNDNVYFGYSTPWGYFDFNRFHCHFSPRDW
223_5               VITTSTRTWALPTYNNHLYKQIS-SQSAGSTNDNVYFGYSTPWGYFDFNRFHCHFSPRDW
223_10              VITTSTRTWALPTYNNHLYKQIS-SQSAGSTNDNVYFGYSTPWGYFDFNRFHCHFSPRDW
223_2               VITTSTRTWALPTYNNHLYKQIS-SQSAGSTNDNVYFGYSTPWGYFDFNRFHCHFSPRDW
223_7               VITTSTRTWALPTYNNHLYKQIS-SQSAGSTNDNVYFGYSTPWGYFDFNRFHCHFSPRDW
223_6               VITTSTRTWALPTYNNHLYKQIS-SQSAGSTNDNVYFGYSTPWGYFDFNRFHCHFSPRDW
44_1                VITTSTRTWALPTYNNHLYKQISNGTSGGSTNDNTYFGYSTPWGYFDFNRFHCHFSPRDW
44_5                VITTSTRTWALPTYNNHLYKQISNGTSGGSTNDNTYFGYSTPWGYFDFNRFHCHFSPRDW
44_2                VITTSTRTWALPTYNNHLYKQISNGTSGGSTNDNTYFGYSTPWGYFDFNRFHCHFSPRDW
29.3\VP1            VITTSTRTWALPTYNNHLYKQISNGTSGGSTNDNTYFGYSTPWGYFDFNRFHCHFSPRDW
29.5\VP1            VITTSTRTWALPTYNNHLYKQISNGTSGGSTNDNTYFGYSTPWGYFDFNRFHCHFSPRDW
42_15               VITTSTRTWALPTYNNHLYKQISNGTSGGSTNDNTYFGYSTPWGYFDFNRFHCHFSPRDW
42_8                VITTSTRTWALPTYNNHLYKQISNGTSGGSTNDNTYFGYSTPWGYFDFNRFHCHFSPRDW
42_13               VITTSTRTWALPTYNNHLYKQISNGTSGGSTNDNTYFGYSTPWGYFDFNRFHCHFSPRDW
42_3A               VITTSTRTWALPTYNNHLYKQISNGTSGGSTNDNTYFGYSTPWGYFDFNRFHCHFSPRDW
42_4                VITTSTRTWALPTYNNHLYKQIS--SQSGATNDNHFFGYSTPWGYFDFNRFHCHFSSRDW
42_5A               VITTSTRTWALPTYNNHLYKQIS--SQSGATNDNHFFGYSTPWGYFDFNRFHCHFSPRDW
42_1B               VITTSTRTWALPTYNNHLYKQISNGTSGGSTNDNTYFGYSTPWGYFDFNRFHCHFSPRDW
42_5B               VITTSTRTWALPTYNNHLYKQISNGTSGGSTNDNTYFGYSTPWGYFDFNRFHCHFSPRDW
43_1                VITTSTRTWALPTYNNHLYKQISNGTSGGSTNDNTYFGYSTPWGYFDFNRFHCHFSPRDW
43_12               VITTSTRTWALPTYNNHLYKQISNGTSGGSTNDNTYFGYSTPWGYFDFNRFHCHFSPRDW
43_5                VITTSTRTWALPTYNNHLYKQISNGTSGGSTNDNTYFGYSTPWGYFDFNRFHCHFSPRDW
AAV8                VITTSTRTWALPTYNNHLYKQISNGTSGGATNDNTYFGYSTPWGYFDFNRFHCHFSPRDW
43_21               VITTSTRTWALPTYNNHLYKQISNGTSGGSTNDNTYFGYSTPWGYFDFNRFHCHFSPRDW
43_25               VITTSTRTWALPTYNNHLYKQISNGTSGGSTNDNTYFGYSTPWGYFDFNRFHCHFSPRDW
43_23               VITTSTRTWALPTYNNHLYKQISNGTSGGSTNDNTYFGYSTPWGYFDFNRFHCHFSPRDW
43_20               VITTSTRTWALPTYNNHLYKQISNGTSGGSTNDNTYFGYSTPWGYFDFNRFHCHFSPRDW
AAV_9               VITTSTRTWALPTYNNHLYKQISNGTSGGSTNDNTYFGYSTPWGYFDFNRFHCHFSPRDW
24.1                VITTSTRTWALPTYNNHLYKQIS-SQS-GATNDNHFFSYSTPWGYFDFNRFHCHFSPRDW
42.2REAL            VITTSTRTWALPTYNNHLYKQIS-SQS-GATNDNHFFGYSTPWGYFDFNRFHCHFSPRDW
7.2\VP1             VITTSTRTWALPTYNNHLYKQIS-SQS-GATNDNHFFGYSTPWGYFDFNRFHCHFSPRDW
27.3\VP1            VITTSTRTWALPTYNNHLYKQIS-SQS-GATNDNHFFGYSTPWGYFDFNRFHCHFSPRDW
16.3\VP1            VITTSTRTWALPTYNNHLYKQIS-SQS-GATNDNHFFGYSTPWGYFDFNRFHCHFSPRDW
42_10               VITTSTRTWALPTYNNHLYKQIS-SQS-GATNDNHFFGYSTPWGYFDFNRFHCHFSPRDW
42_3B               VITTSTRTWALPTYNNHLYKQIS-SQS-GATNDNHFFGYSTPWGYFDFNRFHCHFSPRDW
42_11               VITTSTRTWALPTYNNHLYKQIS-SQS-GATNDNHFFGYSTPWGYFDFNRFHCHFSPRDW
F1\VP1              VITTSTRTWALPTYNNHLYKQIS-SSSSGATNDNHYFGYSTPWGYFDFNRFHCHFSPRDW
F5\VP1@3            VITTSTRTWALPTYNNHLYKQIS-SSSSGATNDNHYFGYSTPWGYFDFNRFHCHFSPRDW
F3\VP1              VITTSTRTWALPTYNNHLYKQIS-SSSSGATNDNHYFGYSTPWGYFDFNRFHCHFSPRDW
42_6B               VITTSTRTWALPTYNNHLYKQISNGTSGGSTNDNTYFGYSTPWGYFDFNRFHCHFSPRDW
42_12               VITTSTRTWALPTYNNHLYKQISNGTSGGSTNDNTYFGYSTPWGYFDFNRFHCHFSPRDW
AAV5\CAP            VVTKSTRTWVLPSYNNHQYREIK-SGSVDGSNANAYFGYSTPWGYFDFNRFHSHWSPRDW
```

FIG. 2E

```
                      310        320        330        340        350        360
            ....|....|....|....|....|....|....|....|....|....|....|....|....|
C1\VP1      QRLINNNWGLRPKAMRVKIFNIQVKEVTTSNGETTVANNLTSTVQIFADSSYELPYVMDA
C2\VP1      QRLINNNWGLRPKAMRVKIFNIQVKEVTTSNGETTVANNLTSTVQIFADSSYELPYVMDA
C5\VP1@2    QRLINNNWGLRPKAMRVKIFNIQVKEVTTSNGETTVANNLTSTVQIFADSSYELPYVMDA
AAV4\VP1    QRLINNNWGMRPKAMRVKIFNIQVKEVTTSNGETTVANNLTSTVQIFADSSYELPYVMDA
AAV1        QRLINNNWGFRPKRLNFKLFNIQVKEVTTNDGVTTIANNLTSTVQVFSDSEYQLPYVLGS
AAV6\VP1    QRLINNNWGFRPKRLNFKLFNIQVKEVTTNDGVTTIANNLTSTVQVFSDSEYQLPYVLGS
A3_3        QRLINNNWGFRPKKLNFKLFNIQVKEVTQNDGTTTIANNLTSAVQVFTDSEYQLPYVLGS
A3_7        QRLINNNWGFRPKKLNFKLFNIQVKEVTQNDGTTTIANNLTSTVQVFTDSEYQLPYVLGS
A3_4        QRLINNNWGFRPKKLNFKLFNIQVKEVTQNDGTTTIANNLTSTVQVFTDSEYQLPYVLGS
A3_5        QRLINNNWGFRPKKLNFKLFNIQVKEVTQNDGTTTIANNLTSTVQVFTDSEYQLPYVLGS
AAV2        QRLINNNWGFRPKRLNFKLFNIQVKEVTQNDGTTTIANNLTSTVQVFTDSEYQLPYVLGS
AAV3        QRLINNNWGFRPKKLSFKLFNIQVRGVTQNDGTTTIANNLTSTVQVFTDSEYQLPYVLGS
13.3b\VP1   QRLINNNWGFRPKKLRFKLFNIQVKEVTTNDGVTTIANNLTSTIQVFSDSEYQLPYVLGS
AAV7        QRLINNNWGFRPKKLRFKLFNIQVKEVTTNDGVTTIANNLTSTIQVFSDSEYQLPYVLGS
223_4       QRLINNNWGFRPKKLNFKLFNIQVKEVTTNDGVTTIANNLTSTVQVFSDSEYQLPYVLGS
223_5       QRLINNNWGFRPKKLNFKLFNIQVKEVTTNDGVTTIANNLTSTVQVFSDSEYQLPYVLGS
223_10      QRLINNNWGFRPKKLNFKLFNIQVKEVTTNDGVTTIANNLTSTVQVFSDSEYQLPYVLGS
223_2       QRLINNNWGFRPKKLNFKLFNIQVKEVTTNDGVTTIANNLTSTVQVFSDSEYQLPYVLGS
223_7       QRLINNNWGFRPKKLNFKLFNIQVKEVTTNDGVTTIANNLTSTVQVFSDPEYQLPYVLGS
223_6       QRLINNNWGFRPKKLNFKLFNIQVKEVTTNDGVTTIANNLTSTVQVFSDSEYQLPYVLGS
44_1        QRLINNNWGFRPKRLNFKLFNIQVKEVTQNEGTKTIANNLTSTIQVFTDSEYQLPYVLGS
44_5        QRLINNNWGFRPKRPNFKLFNIQVKEVTQNEGTKTIANNLTSTIQVFTDSEYQLPYVLGS
44_2        QRLINNNWGFRPKRLNFKLFNIQVKEVTQNEGTKTIANNLTSTIQVFTDSEYQLPYVLGS
29.3\VP1    QRLINNNWGFRPKRLNFKLFNIQVKEVTQNEGTKTIANNLTSTIQVFTDSEYQLPYVLGS
29.5\VP1    QRLINNNWGFRPKSLNFKLFNIQVKEVTQNEGTKTIANNLTSTIQVFTDSEYQLPYVLGS
42_15       QRLINNNWGFRPKRLNFKLFNIQVKEVTQNEGTKTIANNLTSTIQVFTDSEYQLPYVLGS
42_8        QRLINNNWGFRPKRLNFKLFNIQVKEVTQNEGTKTIANNLTSTIQVFTDSEYQLPYVLGS
42_13       QRLINNNWGFRPKRLNFKLFNIQVKEVTQNEGTKTIANNLTSTIQVFTDSEYQLPYVLGS
42_3A       QRLINNSWGFRPKRLNFKLFNIQVKEVTQNEGTKTIANNLTSTIQVFTDSEYQLPYVLGS
42_4        QRLINNNWGFRPKRLNFKLFNIQVKEVTQNEGTKTIANNLTSTIQVFTDSEYRLPYVLGS
42_5A       QRLINNNRGFRPRKLRFKLFNIQVKEVTTNDGVTTIANNLTSTIQVFSDSEYQLPYVLGS
42_1B       QRLINNNWGFRPKRLNFKLFNIQVKEVTQNEGTKTIANNLTSTIQVFTDSEYQLPYVLGS
42_5B       QRLINNNWGFRPKRLNFKLFNIQVKEVTQNEGTKTIANNLTSTIQVFTDSEYQLPYVLGS
43_1        QRLINNNWGFRPKRLNFKLFNIQVKEVTQNEGTKTIANNLTSTIQVFTDSEYQLPYVPGS
43_12       QRLINNNWGFRPKRLNFKLFNIQVKEVTQNEGTKTIANNLTSTIQVFTDSEYQLPYVLGS
43_5        QRLINNNWGFRPKRLNFKLFNIQVKEVTQNEGTKTIANNLTSTIQVFTDSEYQLPYVLGS
AAV8        QRLINNNWGFRPKRLSFKLFNIQVKEVTQNEGTKTIANNLTSTIQVFTDSEYQLPYVLGS
43_21       QRLINNNWGFRPKRLNFKLFNIQVKEVTTNEGTKTIANNLTSTVRVFTDSEYQLPYVLGS
43_25       QRLINNNWGFRPKRLNFKLFNIQVKEVTTNEGTKTIANNLTSTVQVFTDSEYQLPYVLGS
43_23       QRLINNNWGFRPKRLNFKLFNIQVKEVTTNEGTKTIANNLTSTVQVFTDLEYQLPYVLGS
43_20       QRLINNNWGFRPKRLNFKLFNIQVKEVTTNEGTKTIANNLTSTVQVFTDSEYQLPYVLGS
AAV_9       QRLINNNWGFRPKRLNFKLFNIQVKEVTTNEGTKTIANNLTSTVQVFTDSEYQLPYVLGS
24.1        QRLINNNWGFRPRKLRFKLFNIQVKEVTTNDGVTTIANNLTSTIQVFSDSEYQLPYVLGS
42.2REAL    QRLINNNWGFRPRKLRFKLFNIQVKEVTTNDGVTTIANNLTSTIQVFSDSEYQLPYVLGS
7.2\VP1     QRLINNNWGFRPRKLRFKLFNIQVKEVTTNDGVTTIANNLTSTIQVFSDSEYQLPYVLGS
27.3\VP1    QRLINNNWGFRPRKLRFKLFNIQVKEVTTNDGVTTIANNLTSTIQVFSDSEYQLPYVLGS
16.3\VP1    QRLINNNWGFRPRKLRFKLFNIQVKEVTTNDGVTTIANNLTSTIQVFSDSEYQLPYVLGS
42_10       QRLINNNWGFRPRKLRFKLFNIQVKEVTTNDGVTTIANNLTSTIQVFSDSEYQLPYVLGS
42_3B       QRLINNNWGFRPRKLRFKLFNIQVKEVTTNDGVTTIANNLTSTIQVFSDSEYQLPYVLGS
42_11       QRLINNNWGFRPRKLRFKLFNIQVKEVTTNDGVTTIANNLTSTIQVFSDSEYQLPYVLGS
F1\VP1      QRLINNNWGFRPKKLRFKLFNIQVKEVTTNDGVTTIANNLTSTVQVFSDSEYQLPYVLGS
F5\VP1@3    QRLINNNWGFRPKKLRFKLFNIQVKEVTTNDGVTTIANNLTSTVQVFSDSEYQLPYVLGS
F3\VP1      QRLINNNWGFRPKKLRFKLLNIQVKEVTTNDGVTTIANNLTSTVQVFSDSEYQLPYVLGS
42_6B       QRLINNNWGFRPRKLRFKLFNIQVKEVTTDDGVTTIANNLTSTIQVFSDSEYQLPYVLGS
42_12       QRLINNNWGFRPKRLNFKLFNIQVKEVTQNEGTKTIANNLTSTIQVFTDSEYQLPYVLGS
AAV5\CAP    QRLINNYWGFRPRSLRVKIFNIQVKEVTVQDSTTTIANNLTSTVQVFTDDDYQLPYVVGN
```

FIG. 2F

```
                        370       380       390       400       410       420
                        ....|....|....|....|....|....|....|....|....|....|....|....|
C1\VP1         GQEGSLSPFPNDVFMVPQYGYCGIVTG-ENQNQTDRNAFYCLEYFPSQMLRTGNNFEMAY
C2\VP1         GQEGSLPPFPNDVFMVPQYGYCGIVTG-ENQNQTDRNAFYCLEYFPSQMLRTGNNFEMAY
C5\VP1@2       GQEGSLPPFPNDVFMVPQYGYCGIVTG-ENQNQTDRNAFYCLEYFPSQMLRTGNNFETAY
AAV4\VP1       GQEGSLPPFPNDVFMVPQYGYCGLVTGNTSQQQTDRNAFYCLEYFPSQMLRTGNNFEITY
AAV1           AHQGCLPPFPADVFMIPQYGYLTLNNG---SQAVGRSSFYCLEYFPSQMLRTGNNFTFSY
AAV6\VP1       AHQGCLPPFPADVFMIPQYGYLTLNNG---SQAVGRSSFYCLEYFPSQMLRTGNNFTFSY
A3_3           AHQGCLPPFPADVFMIPQYGYLTLNNG---SQAVGRSSFYCLEYFPSQMLRTGNNFTFSY
A3_7           AHQGCLPPFPADVFMIPQYGYLTLNNG---SQAVGRSSFYCLEYFPSQMLRTGNNFTFSY
A3_4           AHQGCLPPFPADVFMIPQYGYLTLNNG---SQAVGRSSFYCLEYFPSQMLRTGNNFTFSY
A3_5           AHQGCLPPFPADVFMIPQYGYLTLNNG---SQAVGRSSFYCLEYFPSQMLRTGNNFTFSY
AAV2           AHQGCLPPFPADVFMVPQYGYLTLNNG---SQAVGRSSFYCLEYFPSQMLRTGNNFTFSY
AAV3           AHQGCLPPFPADVFMVPQYGYLTLNNG---SQAVGRSSFYCLEYFPSQMLRTGNNFQFSY
13.3b\VP1      AHQGCLPPFPADVFMIPQYGYLTLNNG---SQSVGRSSFYCLEYFPSQMLRTGNNFEFSY
AAV7           AHQGCLPPFPADVFMIPQYGYLTLNNG---SQSVGRSSFYCLEYFPSQMLRTGNNFEFSY
223_4          AHQGCLPPFPADVFMIPQYGYLTLNNG---SQSVGRSSFYCLEYFPSQMLRTGNNFTFSY
223_5          AHQGCLPPFPADVFMIPQYGYLTLNNG---SQSVGRSSFYCLEYFPSQMLRTGNNFTFSY
223_10         AHQGCLPPFPADVFMIPQYGYLTLNNG---SQSVGRSSFYCLEYFPSQMLRTGNNFTFSY
223_2          AHQGCLPPFPADVFMIPQYGYLTLNNG---SQSVGRSSFYCLEYFPSQMLRTGNNFTFSY
223_7          AHQGCLPPFPADVFMIPQYGYLTLNNG---SQSVGRSSFYCLEYFPSQMLRTGNNFTFSY
223_6          AHQGCLPPFPADVFMIPQYGYLTLNNG---SQSVGRSSFYCLEYFPSQMLRTGNNFTFSY
44_1           AHQGCLPPFPADVFMIPQYGYLTLNNG---SQAVGRSSFYCLEYFPSQMLRTGNNFEFSY
44_5           AHQGCLPPFPADVFMIPQYGYLTLNNG---SQAVGRSSFYCLEYFPSQMLRTGNNFEFSY
44_2           AHQGCLPPFPADVFMIPQYGYLTLNNG---SQAVGRSSFYCLEYFPSQMLRTGNNFEFSY
29.3\VP1       ARQGCLPPFPADVFMIPQYGYLTLNNG---SQAVGRSSFYCLEYFPSQMLRTGNNFEFSY
29.5\VP1       AHQGCLPPFPADVFMIPQYGYLTLNNG---SQAVGRSSFYCLEYFPSQMLRTGNNFEFSY
42_15          AHQGCPPPFPADVFMIPQYGYLTLNNG---SQAVGRSSFYCLEYFPSQMRRTGNNFEFSY
42_8           AHQGCLPPFPADVFMIPQYGYLTLNNG---SQAVGRSSFYCLEYFPSQMLRTGNNFEFSY
42_13          AHQGCLPPFPADVFMIPQYGYLTLNNG---SQAVGRSSFYCLEYFPSQMLRTGNNFEFSY
42_3A          AHQGCLPPFPADVFMIPQYGYLTLNNG---SQAVGRSSFYCLEYFPSQMLRTGNNFEFSY
42_4           AHQGCLPPFPADVFMIPQYGYLTLNNG---SQAVGRSSFYCLEYFPSQMLRTGNNFEFSY
42_5A          AHQGCLPPFPADVFMIPQYGYLTLNNG---SQSVGRSSFYCLEYFPSQMLRTGNNFEFSY
42_1B          AHQGCLPPFPADVFMIPQYGYLTLNNG---SQAVGRSSFYCLEYFPSQMLRTGNNFEFSY
42_5B          AHQGCLPPFPADVFMIPQYGYLTLNNG---SQAVGRSSFYCLEYFPSQMLRTGNNFEFSY
43_1           AHQGCLPPFPADVFMIPQYGYLTLNNG---SQAVGRSSFYCLEYFPSQMLRTGNNFEFSY
43_12          AHQGCLPPFPADVFMIPQYGYLTLNNG---SQAVGRSSFYCLEYFPSQMLRTGNNFEFSY
43_5           AHQGCLPPFPADVFMIPQYGYLTLNNG---SQAVGRSSFYCLEYFPSQMLRTGNNFEFSY
AAV8           AHQGCLPPFPADVFMIPQYGYLTLNNG---SQAVGRSSFYCLEYFPSQMLRTGNNFQFTY
43_21          AHQGCLPPFPADVFMVPQYGYLTLNNG---SQALGRSSFYCLEYFPSQMLRTGNNFQFSY
43_25          AHQGCLPPFPADVFMVPQYGYLTLNNG---SQALGRSSFYCLEYFPSQMLRTGNNFQFSY
43_23          AHQGCLPPFPADVFMVPQYGYLTLNNG---SQALGRSSFYCLEYFPSQMPRTGNNFQFSY
43_20          AHQGCLPPFPADVFTVPQYGYLTLNNG---SQALGRSSFYCLEYFPSQMLRTGNNFQFSY
AAV_9          AHQGCLPPFPADVFMIPQYGYLTLNNG---SQALGRSSFYCLEYFPSQMLRTGNNFQFSY
24.1           AHQGCLPPFPADVFMIPQYGYLTLNNG---SQSVGRSSFYCLEYFPSQMLRTGNNFEFSY
42.2REAL       AHQGCLPPFPADVFMIPQYGYLTLNNG---SQSVGRSSFYCLEYFPSQMLRTGNNFEFSY
7.2\VP1        AHQGCLPPFPADVFMIPQYGYLTLNNG---SQSVGRSSFYCLEYFPSQMLRTGDNFEFSY
27.3\VP1       AHQGCLPPFPADVFMIPQYGYLTLNNG---SQSVGRSSFCCLEYFPSQMLRTGNNFEFSY
16.3\VP1       AHQGCLPPFPADVFMIPQYGYLTLNNG---SQSMGRSSFYCLEYFPSQMLRTGNNFEFSY
42_10          AHQGCLPPFPADVFMIPQYGYLTLNNG---SQSVGRSSFYCLEYFPSQMLRTGNNFEFSY
42_3B          AHQGCLPPFPADVFMIPQYGYLTLNNG---SQSVGRSSFYCLEYFPSQMLRTGNNFEFSY
42_11          AHQGCLPPFPADVFMIPQYGYLTLNNG---SQSVGRSSFYCLEYFPSQMLRTGNNFEFSY
F1\VP1         AHQGCLPPFPADVFMIPQYGYLTLNNG---SQSVGRSSFYCLEYFPSQMLRTGNNFEFSY
F5\VP1@3       AHQGCLPPFPADVFMIPQYGYLTLNNG---SQSVGRSSFYCLEYFPSQMLRTGNNFEFSY
F3\VP1         AHQGCLPPFPADVFMIPQYGYLTLDNG---SQSVGRSSFYCLEYFPSQMLRTGNNFEFSY
42_6B          AHQGCLPPFPADVFMIPQYGYLTLNNG---SQSVGRSSFYCLEYFPSQMLRTGNNFEFSY
42_12          AHQGCLPPFPADVFMIPQYGYLTLNNG---SQAVGRSSFYCLEYFPSQMLRTGNNFEFSY
AAV5\CAP       GTEGCLPAFPPQVFTLPQYGYATLNRD-NTENPTERSSFFCLEYFPSKMLRTGNNFEFTY
```

FIG. 2G

```
                       430        440        450        460        470        480
                  ....|....|....|....|....|....|....|....|....|....|....|....|
C1\VP1            NFGKVPFHSMYAYSQSPDRLMNPLLDQYLWHLQSTTSGETLNQGNAATTFGKIRSGDFAF
C2\VP1            NFEKVPFHSMYAHSQSLDRLMNPLLDQYLWHLQSTTSGETLNQGNAATTFGKIRSGDFAF
C5\VP1@2          NFEKVPFHSMYAHSQSLDGLMNPLLDQYLWHLQSTTSGETLNQGNAATTFGKIRSGDFAF
AAV4\VP1          SFEKVPFHSMYAHSQSLDRLMNPLIDQYLWGLQSTTTGTTLNAGTATTNFTKLRPTNFSN
AAV1              TFEEVPFHSSYAHSQSLDRLMNPLIDQYLYYLNRTQNQSG-SAQNKDLLFSRGSPAGMSV
AAV6\VP1          TFEDVPFHSSYAHSQSLDRLMNPLIDQYLYYLNRTQNQSG-SAQNKDLLFSRGSPAGMSV
A3_3              TFEDVPFHSSYAHSQSLDRLMNPLIDQYLYYLSKTQ-GTSGTTQQSRLQFSQAGPSSMAQ
A3_7              TFEDVPFHSSYAHSQSLDRLMNPLIDQYLYYLSKTQ-GTSGTTQQSRLQFSQAGPSSMAQ
A3_4              TFEDVPFHSSYAHSQSLDRLMNPLIDQYLYYLSKTQ-GTSGTTQQSRLQFSQAGPSSMAQ
A3_5              TFEDVPFHSSYAHSQSLDRLMNPLIDQYLYYLSKTQ-GTSGTTQQSRLQFNQAGPSSMAQ
AAV2              TFEDVPFHSSYAHSQSLDRLMNPLIDQYLYYLSRTN-TPSGTTTQSRLQFSQAGASDIRD
AAV3              TFEDVPFHSSYAHSQSLDRLMNPLIDQYLYYLNRTQGTTSGTTNQSRLLFSQAGPQSMSL
13.3b\VP1         SFEDVPFHSSYAHSQSLDRLMNPLIDQYLYYLARTQSDPGGTAGNRELQFYQGGPSTMAE
AAV7              SFEDVPFHSSYAHSQSLDRLMNPLIDQYLYYLARTQSNPGGTAGNRELQFYQGGPSTMAE
223_4             TFEDVPFHSSYAHSQSLGRLMNPLIDQYLYYLARTQSNAGGTAGNRELQFYQGGPTTMAE
223_5             TFEDVPFHSSYAHSQSLGRLMNPLIDQYLYYLARTQSNAGGTAGNRELQFYQGGPTTMAE
223_10            TFEDVPFHSSYAHSQSLGRLMNPLIDQYLYYLARTQSNAGGTAGNRELQFYQGGPTTMAE
223_2             TFEDVPFHSSYAHSQSLGRLMNPLIDQYLYYLARTQSNAGGTAGNRELQFYQGGPTTMAE
223_7             TFEDVPFHSSYAHSQSLGRLMNPLIDQYLYYLARTQSNAGGTAGNRELQFYQGGPTTMAE
223_6             TFEDVPFHSSYAHSQSLGRLMNPLIDQYLYYLARTQSNAGGTAGNRELQFYQGGPTTMAE
44_1              QFEDVPFHSSYAHSQSLDRLMNPLIDQYLYYLSRTQSTGG-TAGTQQLLFSQAGPNNMSA
44_5              QFEDVPFHSSYAHSQSLDRLMNPLIDQYLYYLSRTQSTGG-TAGTQQLLFSQAGPNNMSA
44_2              QFEDVPFHSSYAHSQSLDRLMNPLIDQYLYYLSRTQSTGG-TAGTQQLLFSQAGPNNMSA
29.3\VP1          QFEDVPFHSSYAHSQSLDRLMNPLIDQYLYYLSRTQSTGG-TAGTQQLLFSQAGPNNMSA
29.5\VP1          QFEDVPFHSSYAHSQSLDRLMNPLIDQYLYYLSRTQSTGG-TAGTQQLLFSQAGPNNMSA
42_15             QFEDVPFHSSYAHSQSLDRLMNPLIDQYLYYLSRTQSTGG-TAGTQQLLFSQAGPNNMSA
42_8              QFEDVPFHSSYAHSQSLDRLMNPLIDQYLYYLSRTQSTGG-TAGTQQLLFSQAGPNNMSA
42_13             QFEDVPFHSSYAHSQSLDRLMNPLIDQYLYYLSRTQSTGG-TAGTQQLLFSQAGPNNMSA
42_3A             QFEDVPFHSSYAHSQSLDRLMNPLIDQYLYYLSRTQSTGG-TAGTQQLLFSQAGPNNMSA
42_4              QFEDVPFHSSYAHSQSLDRLMNPLIDQYLYYLSRTQSTGG-TAGTQQLLFSQAGPNNMSA
42_5A             QFEDVPFHSSYAHSQSLDRLMNPLIDQYLYYLSRTQSTGG-TAGTQQLLFSQAGPNNMSA
42_1B             QFEDVPFHSSYAHSQSLDRLMNPLIDQYLYYLSRTQSTGG-TAGTQQLLFSQAGPNNMSA
42_5B             QFEDVPFHSSYAHSQSLDRLMNPLIDQYLYYLSRTQSTGG-TAGTQQLLFSQAGPNNMSA
43_1              TFEDVPFHSSYAHSQSLDRLMNPLIDQYLYYLSRTQSTGG-TQGTQQLLFSQAGPANMSA
43_12             TFEDVPFHSSYAHSQSLDRLMNPLIDQYLYYLSRTQSTGG-TQGTQQLLFSQAGPANMSA
43_5              TFEDVPFHSSYAHSQSLDRLMNPLIDQYLYYLSRTQSTGG-TQGTQQLLFSQAGPANMSA
AAV8              TFEDVPFHSSYAHSQSLDRLMNPLIDQYLYYLSRTQTTGG-TANTQTLGFSQGGPNTMAN
43_21             TFEDVPFHSSYAHSQSLDRLMNPLIDQYLYYLVRTQTTG--TGGTQTLAFSQAGPSSMAN
43_25             TFEDVPFHSSYAHSQSLDRLMNPLIDQYLYYLVRTQTTG--TGGTQTLAFSQAGPSSMAN
43_23             TFEDVPFHSSYAHSQSLDRLMNPLIDQYLYYLVRTQTTG--TGGTQTLAFSQAGPSSMAN
43_20             TFEDVPFHSSYAHSQSLDRLMNPLIDQYLYYLVRTQTTG--TGGTQTLAFSQAGPSSMAN
AAV_9             TFEDVPFHSSYAHSQSLDRLMNPLIDQYLYYLVRTQTTG--TGGTQTLAFSQAGPSSMAN
24.1              TFEEVPFHSSYVHSQSLDRLMNPLIDQYLYYLARTQST---TGSTRELQFHQAGPNTMAE
42.2REAL          TFEEVPFHSSYAHSQSLDRLMNPLIDQYLYYLARTQST---TGSTRELQFHQAGPNTMAE
7.2\VP1           TFEEVPFHSSYAHSQSLDRLMNPLIDQYLYYLARTQST---TGSTRELQFHQAGPNTMAE
27.3\VP1          TFEEVPFHSSYAHSQSLDRLMNPLIDQYLYYLARTQST---TGSTRELQFHQAGPNTVAE
16.3\VP1          TFEEVPFHSSYAHSQSLDRLMNPLIDQYLYYLARTQST---TGSTRELQFHQAGPNTMAE
42_10             TFEEVPFHSSYAHSQSLDRLMNPLIDQYLYYLARTQST---TGSTRELQFHQAGPNTMAE
42_3B             TFEEVPFHSSYAHSQSLDRLMNPLIDQYLYYLARTQST---TGSTRELQFHQAGPNTMAE
42_11             TFEEVPFHSSYAHSQSLDRLMNPLIDQYLYYLARTQST---TGSTRELQFHQAGPNTMAE
F1\VP1            SFEDVPFHSSYAHSQSLDRLMNPLIDQYLYYLARTQST---TGSTRELQFHQAGPNTMAE
F5\VP1@3          SFEDVPFHSSYAHSQSLDRLMNPLIDQYLYYLARTQST---TGSTRELQFHQAGPNTMAE
F3\VP1            SFEDVPFHSSYAHSQSLDRLMNPLIDQYLYYLARTQST---TGSTRELQFHQAGPNTMAE
42_6B             TFEEVPFHSSYAHSQSLDRLMNPLIDQYLYYLARTQST---TGSTRELQFHQAGPNTMAE
42_12             QFEDVPFHSSYAHSQSLDRLTNPLIDQYLYYLARTQST---TGSTRGLQFHQAGPNTMAE
AAV5\CAP          NFEEVPFHSSFAPSQNLFKLANPLVDQYLYRFVSTNNTGG-------VQFNKNLAGRYAN
```

FIG. 2H

```
              490        500        510        520        530        540
            ....|....|....|....|....|....|....|....|....|....|....|....|
C1\VP1      YRKNWLPGPCVKQQRLSKTASQNYKIPASGGNALLKYDTHYTLNNRWSNIAPGPPMATAG
C2\VP1      YRKNWLPGPCVKQQRFSKTASQNYKIPASGGNALLKYDTHYTLNNRWSNIAPGPPMATAG
C5\VP1@2    YRKNWLPGPCVKQQRFSKTASQNYKIPASGGNALLKYDTHYTLNNRWSNIAPGPPMATAG
AAV4\VP1    FKKNWLPGPSIKQQGFSKTANQNYKIPATGSDSLIKYETHSTLDGRWSALTPGPPMATAG
AAV1        QPKNWLPGPCYRQQRVSKTKTDN-----NNSNFTWTGASKYNLNGRESIINPGTAMASHK
AAV6\VP1    QPKNWLPGPCYRQQRVSKTKTDN-----NNSNFTWTGASKYNLNGRESIINPGTAMASHK
A3_3        QAKNWLPGPSYRQQRMSKTANDN-----NNSEFAWTAATKYYLNGRNSLVNPGPPVASHK
A3_7        QAKNWLPGPSYRQQRMSKTANDN-----NNSEFAWTAATKYYLNGRNSLVNPGPPMASHK
A3_4        QAKNWLPGPSYRQQRMSKTANDN-----NNSEFAWTAATKYYLNGRNSLVNPGPPMASHK
A3_5        QAKNWLPGPSYRQQRMSKTANDN-----NNSEFAWTAATKYYPNGRNSLVNPGPPMASHK
AAV2        QSRNWLPGPCYRQQRVSKTSADN-----NNSEYSWTGATKYHLNGRDSLVNPGPAMASHK
AAV3        QARNWLPGPCYRQQRLSKTANDN-----NNSNFPWTAASKYHLNGRDSLVNPGPAMASHK
13.3b\VP1   QAKNWLPGPCFRQQRVSKTLDQN-----NNSNFAWTGATKYHLNGRNSLVNPGVAMATHK
AAV7        QAKNWLPGPCFRQQRVSKTLDQN-----NNSNFAWTGATKYHLNGRNSLVNPGVAMATHK
223_4       QAKNWLPGPCFRQQRVSKTLDQN-----NNSNFAWTGATKYHLNGRNSLVNPGVAMATHK
223_5       QAKNWLPGPCFRQQRVSKTLDQN-----NNSNFAWTGATKYHLNGRNSLVNPGVAMATHK
223_10      QAKNWLPGPCFRQQRVSKTLDQN-----NNSNFAWTGATKYHLNXRNSLVNPGVAMATHK
223_2       QAKNWLPGPCFRQQRVSKTLDQN-----NNSNFAWTGATKYHLNGRNSLVNPGVAMATHK
223_7       QAKNWLPGPCFRQQRVSKTLDQN-----NNSNFAWTGATKYHLNGRNSLVNPGVAMATHK
223_6       QAKNWLPGPCFRQQRVSKTLDQN-----NNSNFAWTGATKYHLNGRNSLVNPGVAMATHK
44_1        QAKNWLPGPCYRQQRVSTTLSQN-----NNSNFAWTGATKYHLNGRDSLVNPGVAMATHK
44_5        QAKNWLPGPCYRQQRVSTTLSQN-----NNSNFAWTGATKYHLNGRDSLVNPGVAMATHK
44_2        QAKNWLPGPCYRQQRVSTTLSQN-----NNSNFAWTGATKYHLNGRDSLVNPGVAMATHK
29.3\VP1    QAKNWLPGPCYRQQRVSTTLSQN-----NNSNFAWTGATKYHLNGRDSLVNPGVAMATHK
29.5\VP1    QAKNWLPGPCYRQQRVSTTLSQN-----DNSNFAWTGATKYHLNGRDSLVNPGVAMATHK
42_15       QAKNWLPGPCYRQQRVSTTLSQN-----NNSNFAWTGATKYHLNGRDSLVNPGVAMATHK
42_8        QAKNWLPGPCYRQQRVSTTLSQN-----NNSNFAWTGATKYHLNGRDSLVNPGVAMATHK
42_13       QAKNWLPGPCYRQQRVSTTVSQN-----NNSNFAWTGATKYHLNGRDSLVNPGVAMATHK
42_3A       QAKNWLPGPCYRQQRVSTTLSQN-----NNSNFAWTGATKYHLNGRDSLVNPGVAMATEK
42_4        QAKNWLPGPCYRQQRVSTTLSQN-----NNSNFAWTGATKYHLNGRDSLVNPGVAMATHK
42_5A       QAKNWLPGPCYRQQRVSTTLSQN-----NNSNFAWTGATKYHLNGRDSLVNPGVAMATHK
42_1B       QAKNWLPGPCYRQQRVSTTVSQN-----NNSNFAWTGATKYHLNGRDSLVNPGVAMATHK
42_5B       QAKNWLPGPCYRQQRVSTTLSQN-----NNSNFAWTGATKYHLNGRDSLVNPGVAMATHK
43_1        QAKNWLPGPCYRQQRVSTTLSQN-----NNSNFAWTGATKYHLNGRDSLVNPGVAMATHK
43_12       QAKNWLPGPCYRQQRVSTTLSQN-----NNSNFAWTGATKYHLNGRDSLVNPGVAMATHK
43_5        QAKNWLPGPCYRQQRVSTTLSQN-----NNSNFAWTGATKYHLNGRDSLVNPGVAMATHK
AAV8        QAKNWLPGPCYRQQRVSTTTGQN-----NNSNFAWTAGTKYHLNGRNSLANPGIAMATHK
43_21       QARNWVPGPCYRQQRVSTTTNQS-----NNSNFAWTGAAKFKLNGRDSLMNPGVAMASHK
43_25       QARNWVPGPCYRQQRVSTTTNQN-----NNSNFAWTGAAKFKLNGRDSLMNPGVAMASHK
43_23       QARNWVPGPCYRQQRVSTTTNQN-----NNSNFAWTGAAKFKLNGRDSLMNPGVAMASHK
43_20       QARNWVPGPCYRQQRVSTTTNQN-----NNSNFAWTGAAKFKLNGRDSLMNPGVAMASHK
AAV_9       QARNWVPGPCYRQQRVSTTTNQN-----NNSNFAWTGAAKFKLNGRDSLMNPGVAMASHK
24.1        QSKNWLPGPCYRQQRLSKNIDSN-----NNSNFAWTGATKYHLNGRNSLTNPGVAMATNK
42.2REAL    QSKNWLPGPCYRQQRLSKNIDSN-----NNSNFAWTGATKYHLNGRNSLTNPGVAMATNK
7.2\VP1     QSKNWLPGPCYRQQRLSKNIDSN-----NNSNFAWTGATKYHLNGRNSLTNPGVAMATNK
27.3\VP1    QSKNWLPGPCYRQQRLSKNIDSN-----NNSNFAWTGATKYHLNGRNSLTNPGVAMATNK
16.3\VP1    QSKNWLPGPCYRQQRLSKNIDSN-----NNSNFAWTGATKYHLNGRNSLTNPGVAMATNK
42_10       QSKNWLPGPCYRQQRLSKNIDSN-----NNSNFAWTGATKYHLNGRNSLTNPGVAMATNK
42_3B       QSKNWLPGPCYRQQRLSKNIDSN-----NTSNFAWTGATKYHLNGRNSLTNPGVAMATNK
42_11       QSKNWLPGPCYRRQRLSKDIDSN-----NNSNFAWTGATKYHLNGRNSLTNPGVAMATNK
F1\VP1      QSKNWLPGPCYRQQGLSKNLDFN-----NNSNFAWTAATKYHLNGRNSLTNPGIPMATNK
F5\VP1@3    QSKNWLPGPCYRQQRLSKNLDFN-----NNSNFAWTAATKYHLNGRNSLTNPGIPMATNK
F3\VP1      QSKNWLPGPCYRQQRLSKNLDFN-----NNSNFAWTAATKYHLNGRNSLTNPGIPMATNK
42_6B       QSKNWLPGPCYRQQRLSKNIDSN-----NNSNFAWTGATKYHLNGRNSLTNPGVAMATNK
42_12       QSKNWLPGPCYRQQRLSKNIDSN-----NNSNFAWTGATKYHLNGRNSLTNPGVAMATNK
AAV5\CAP    TYKNWFPGPMGRTQGWNLGSGVN-----RASVSAFATTNRMELEGASYQVPPQPNGMTNN
```

FIG. 2I

```
                        550        560        570        580        590        600
                    ....|....|....|....|....|....|....|....|....|....|....|....|
         C1\VP1     PSDGDFS-NAQLIFPGPS--VTGNTTTSAN-NLLFTSEEEIAATNPRDTDMFGQIADNNQ
         C2\VP1     PSDGDFS-NAQLIFPGPS--VTGNTTTSAN-NLLFTSEGEIAATNPRDTDMFGQIADNNQ
         C5\VP1@2   PSDGDFS-NAQLIFPGPS--VTGNTTTSAN-NLLFTSEEEIAATNPRDTDMFGQIADNNQ
         AAV4\VP1   PADSKFS-NSQLIFAGPK--QNGNTATVPG-TLIFTSEEELAATNATDTDMWGNLPGGDQ
         AAV1       DDEDKFFPMSGVMIFGKE--SAGASNTALD-NVMITDEEEIKATNPVATERFGTVAVNFQ
         AAV6\VP1   DDKDKFFPMSGVMIFGKE--SAGASNTALD-NVMITDEEEIKATNPVATERFGTVAVNLQ
         A3_3       DDEEKYFPMHGNLIFGKQ--GTGTTNVDIE-SVLITDEEEIRTTNPVATEQYGQVATNHQ
         A3_7       DDEEKYFPMHGNLIFGKQ--GTGTTNVDIE-SVLITDEEEIRTTNPVATEQYGQVATNHQ
         A3_4       DDEEKYFPMHGNLIFGKQ--GTGTTNVDIE-SVLITDEEEIRTTNPVATEQYGQVATNHQ
         A3_5       DDEEKYFPMHGNLIFGKQ--GTGTTNVDIE-SVLITDEEEIRTTNPVATEQYGQVATNRQ
         AAV2       DDEEKFFPQSGVLIFGKQ--GSEKTNVDIE-KVMITDEEEIRTTNPVATEQYGSVSTNLQ
         AAV3       DDEEKFFPMHGNLIFGKE--GTTASNAELD-NVMITDEEEIRTTNPVATEQYGTVANNLQ
         13.3b\VP1  DDEDRFFPSSGVLIFGKT--GATN-KTTLE-NVLMTNEEEIRPTNPVATEEYGIVSSNLQ
         AAV7       DDEDRFFPSSGVLIFGKT--GATN-KTTLE-NVLMTNEEEIRPTNPVATEEYGIVSSNLQ
         223_4      DDEERFFPSSGVLIFGKT--GAAN-KTTLE-NVLMTNEEEIRPTNPVATEEYGIVSSNLQ
         223_5      DDEERFFPSSGVLIFGKT--GAAN-KTTLE-NVLMTNEEEIRPTNPVATEEYGIVSSNLQ
         223_10     DDEERFFPSSGVLIFGKT--GAAN-KTTLE-NVLMTNEEEIRPTNPVATEEYGIVSSNLQ
         223_2      DDEERFSPSSGVLIFGKT--GAAN-KTTLE-NVLMTNEEEIRPTNPVATEEYGIVSSNLQ
         223_7      DDEERFFPSSGVLIFGKT--GAAN-KTTLE-NVLMTNEEEIRPTNPVATEEYGIVSSNLQ
         223_6      DDEERFFPSSGVLIFGKT--GAAN-KTTLE-NVLMTNEEEIRPTNPVATEEYGIVSSNLQ
         44_1       DDEERFFPSSGVLMFGKQ--GAGKDNVDYS-SVMLTSEEEIKTTNPVATEQYGVVADNLQ
         44_5       DDEERFFPSSGVLMFGKQ--GAGKDNVDYS-SVMLTSEEEIKTTNPVATEQYGVVADNLQ
         44_2       DDEERFFPSSGVLMFGKQ--GAGKDNVDYS-SVMLTSEEEIKTTNPVATEQYGVVADNLQ
         29.3\VP1   DDEERFFPSSGVLMFGKQ--GAGKGNVDYS-SVMLTSEEEIKTTNPVATEQYGVVADNLQ
         29.5\VP1   DDEERFFPSSGVLMFGKQ--GAGKDNVDYS-SVMLTSEEEIKTTNPVATEQYGVVADNLQ
         42_15      DDEERFFPSSGVLMFGKQ--GAGKDNVDYS-SVMLTSEEEIKTTNPVATEQYGVVADNLQ
         42_8       DDEERFFPSSGVLMFGKQ--GAGKDNVDYS-SVMLTSEGEIKTTNPVATEQYGVVADNLQ
         42_13      GDEERFFPSSGVLMFGKQ--GAGKDNVDYS-SVMLTSEEEIKTTNPVATEQYGVVADNLQ
         42_3A      DDEERFFPSSGVLMFGKQ--GAGKDNVDYS-SVMLTSEEEIKTTNPVATEQYGVVADNLQ
         42_4       DDEERFFPSSGVLMFGKQ--GAGKDNVDYS-SVMLTSEEEIKTTNPVATEQYGVVADNLQ
         42_5A      DDEERFFPSSGVLMFGKQ--GAGKDNVDYS-SVMLTSEEEIKTTNPVATEQYGVVADNLQ
         42_1B      GDEERFFPSSGVLMFGKQ--GAGKDNVDYS-SVMLTSEEEIKTTNPVATEQYGVVADNLQ
         42_5B      DDEERFFPSSGVLMFGKQ--GAGKDNVDYS-SVMLTSEEEIKTTNPVATEQYGVVADNLQ
         43_1       DDEERFFPSSGVLMFGKQ--GAGKDNVDYS-SVMLTSEEEIKTTNPVATEQYGVVADNLQ
         43_12      DDEERFFPSSGVLMFGKQ--GAGKDNVDYS-SVMLTSEEEIKTTNPVATEQYGVVADNLQ
         43_5       DDEERFFPSSGVLMFGKQ--GAGKDNVDYS-SVMLTSEEEIKTTNPVATEQYGVVADNLQ
         AAV8       DDEERFFPSNGILIFGKQ--NAARDNADYS-DVMLTSEEEIKTTNPVATEEYGIVADNLQ
         43_21      DDDDRFFPSSGVLIFGKQ--GAGNDGVDYS-QVLITDEEEIKATNPVATEEYGAVAINNQ
         43_25      DDDDRFFPSSGVLIFGKQ--GAGNDGVDYS-QVLITDEEEIKATNPVATEEYGAVAINNQ
         43_23      DDDDRFFPSSGVLIFGKQ--GAGNDGVDYS-QVLITDEEEIKATNPVATEEYGAVAINNQ
         43_20      DDDDRFFPSSGVLIFGKQ--GAGNDGVDYS-QVLITDEEEIKATNPVATEEYGAVAINNQ
         AAV_9      DDEDRFFPSSGVLIFGKQ--GAGNDGVDYS-QVLITDEEEIKATNPVATEEYGAVAINNQ
         24.1       DDEDQFFPINGVLVFGKT--GAAN-KTTLE-NVLMTSEEEIKTTNPVATEEYGVVSSNLQ
         42.2REAL   DDEDQFFPINGVLVFGET--GAAN-KTTLE-NVLMTSEEEIKTTNPVATEEYGVVSSNLQ
         7.2\VP1    DDEDQFFPINGVLVFGKT--GAAN-KTTLE-NVLMTSEEEIKTTNPVATEEYGVVSSNLQ
         27.3\VP1   DDEDQFLPINGVLVFGKT--GAAN-KTTLE-NVLMTSEEEIKTTNPVATEEYGVVSSNLQ
         16.3\VP1   DDEGQFFPINGVLVFGKT--GAAN-KTTLE-NVLMTSEEEIKTTNPVATEEYGVVSSNLQ
         42_10      DDEDQFFPINGVLVFGKT--GAAN-KTTLE-NVLMTSEEEIKTTNPVATEEYGVVSSNLQ
         42_3B      DDEDQFFPINGVLVFGKT--GAAN-KTTLE-NVLMTSEEEIKTTNPVATEQYGVVSSNLQ
         42_11      DDEDQFFPINGVLVFGKT--GAAN-KTTLE-NVLMTSEEEIKTTNPVATEEYGVVSSNLQ
         F1\VP1     DDEDQFFPINGVLVFGKT--GAAN-KTTLE-NVLMTSEEEIKTTNPVATEEYGVVSSNLQ
         F5\VP1@3   DDEDQFFPINGVLVFGKT--GAAN-KTTLE-NVLMTSEEEIKTTNPVATEEYGVVSSNLQ
         F3\VP1     DDEDQFFPINGVLVFGKT--GAAN-KTTLE-NVLMTSEEEIKTTNPVATEEYGVVSSNLQ
         42_6B      DDEDQFFPINGVLVFGKT--GAAN-KTTLE-NVLMTSEEEIKTTNPVATEEYGVVSSNLQ
         42_12      DDEDQFFPINGVLVFGKT--GAAN-KTTLE-NVLMTSEEEIKTTNPVATEEYGVVSSNLQ
         AAV5\CAP   LQGSNTYALENTMIFNSQPANPGTTATYLEGNMLITSESETQPVNRVAYNVGGQMATNNQ
```

FIG. 2J

```
                    610       620       630       640       650       660
                    ....|....|....|....|....|....|....|....|....|....|....|....|
        C1\VP1      NATTAPITGNVTAMGVLPGMVWQNRDIYYQGPIWAKIPHADGHFHPSPLIGGFGLKHPPP
        C2\VP1      NATTAPITGNVTAMGVLPGMVWQNRDIYYQGPIWAKIPHADGHFHPSPLIGGFGLKHPPP
        C5\VP1@2    NATTAPITGNVTAMGVLPGMVWQNRDIYYQGPIWAKIPHADGHFHPSPLIGGFGLKHPPP
        AAV4\VP1    SNSNLPTVDRLTALGAVPGMVWQNRDIYYQGPIWAKIPHTDGHFHPSPLIGGFGLKHPPP
        AAV1        SSSTDPATGDVHAMGALPGMVWQDRDVYLQGPIWAKIPHTDGHFHPSPLMGGFGLKNPPP
        AAV6\VP1    SSSTDPATGDVHVMGALPGMVWQDRDVYLQGPIWAKIPHTDGHFHPSPLMGGFGLKHPPP
        A3_3        SQNTTASYGSVDSQGILPGMVWQDRDVYLQGPIWAKTPHTDGHFHPSPLMGGFGLKHPPP
        A3_7        SQNTTASYGSVDSQGILPGMVWQDRDVYLQGPIWAKTPHTDGHFHPSPLMGGFGLKHPPP
        A3_4        SQDTTASYGSVDSQGILPGMVWQDRDVYLQGPIWAKTPHTDGHFHPSPLMGGFGLKHPPP
        A3_5        SQNTTASYGSVDSQGILPGMVWQDRDVYLQGPIWAKTPHTDGHFHPSPLMGGFGLKHPPP
        AAV2        RGNRQAATADVNTQGVLPGMVWQDRDVYLQGPIWAKIPHTDGHFHPSPLMGGFGLKHPPP
        AAV3        SSNTAPTTGTVNHQGALPGMVWQDRDVYLQGPIWAKIPHTDGHFHPSPLMGGFGLKHPPP
        13.3b\VP1   AANTAAQTQVVNNQGALPGMVWQNRDVYLQGPIWAKIPHTDGNFHPSPLMGGFGLKHPPP
        AAV7        AANTAAQTQVVNNQGALPGMVWQNRDVYLQGPIWAKIPHTDGNFHPSPLMGGFGLKHPPP
        223_4       AASTAAQTQVVNNQGALPGMVWQNRDVYLQGPIWAKIPHTDGNFHPSPLMGGFGLKHPPP
        223_5       AASTAAQTQVVNNQGALPGMVWQNRDVYLQGPIWAKIPHTDGNFHPSPLMGGFGLKHPPP
        223_10      AASTAAQTQVVNNQGALPGMVWQNRDVYLQGPIWAKIPHTDGNFHPSPLMGGFGLKHPPP
        223_2       AASTAAQTQVVNNQGALPGMVWQNRDVYLQGPIWAKIPHTDGNFHPSPLMGGFGLKHPPP
        223_7       AASTAAQTQVVNNQGALPGMVWQNRDVYLQGPIWAKIPHTDGNFHPSPLMGGFGLKHPPP
        223_6       AASTAAQTQVVNNQGALPGMVWQNRDVYLQGPIWAKIPHTDGNFHPSPLMGGFGLKHPPP
        44_1        QQNAAPIVGAVNSQGALPGMVWQNRDVYLQGPIWAKIPHTDGNFHPSPLMGGFGLKHPPP
        44_5        QQNAAPIVGAVNSQGALPGMVWQNRDVYLQGPIWAKIPHTDGNFHPSPLMGGFGLKHPPP
        44_2        QQNAAPIVGAVNSQGALPGMVWQNRDVYLQGPIWAKIPHTDGNFHPSPLMGGFGLKHPPP
        29.3\VP1    QQNAAPIVGAVNSQGALPGMVWQNRDVYLQGPIWAKIPHTDGNFHPSPLMGGFGLKHPPP
        29.5\VP1    QQNAAPIVGAVNSQGALPGMVWQNRDVYLQGPIWAKIPHTDGNFHPSPLMGGFGLKHPPP
        42_15       QQNAAPIVGAVNSQGALPGMVWQNRDVYLQGPIWAKIPHTDGNFHPSPLMGGFGLKHPPP
        42_8        QQNAAPIVGAVNSQGALPGMVWQNRDVYLQGPIWAKIPHTDGNFHPSPLMGGFGLKHPPP
        42_13       QQNAAPIVGAVNSQGALPGMVWQNRDVYLQGPIWAKIPHTDGNFHPSPLMGGFGLKHPPP
        42_3A       QQNAAPIVGAVNSQGALPGMVWQNRDVYLQGPIWAKIPHTDGNFHPSPLMGGFGLKHPPP
        42_4        QQNAAPIVGAVNSQGALPGMVWQNRDVYLQGPIWAKIPHTDGNFHPSPLMGGFGLKHPPP
        42_5A       QQNAAPIVGAVNSQGALPGMAWQNRDVYLQGPIWAKIPHTDGNFHPSPLMGGFGLKHPPP
        42_1B       QQNAAPIVGAVNSQGALPGMVWQNRDVYLQGPIWAKIPHTDGNFHPSPLMGGFGLKHPPP
        42_5B       QQNAAPIVGAVNSQGALPGMVWQNRDVYLQGPIWAKIPHTDGNFHPSPLMGGFGLKHPPP
        43_1        QTNGAPIVGTVNSQGALPGMVWQNRDVYLQGPIWAKIPHTDGNFHPSPLMGGFGLKHPPP
        43_12       QTNGAPIVGTVNSQGALPGMVWQNRDVYLQGPIWAKIPHTDGNFHPSPLMGGFGLKHPPP
        43_5        QTNGAPIVGTVNSQGALPGMVWQNRDVYLQGPIWAKIPHTDGNFHPSPLMGGFGLKHPPP
        AAV8        QQNTAPQIGTVNSQGALPGMVWQNRDVYLQGPIWAKIPHTDGNFHPSPLMGGFGLKHPPP
        43_21       AANTQAQTGLVHNQGVIPGMVWQNRDVYLQGPIWAKIPHTDGNFHPSPLMGGFGLKHPPP
        43_25       AANTQAQTGLVHNQGVIPGMVWQNRDVYLQGPIWAKIPHTDGNFHPSPLMGGFGLKHPPP
        43_23       AANTQAQTGLVHNQGVIPGMVWQNRDVYLQGPIWAKIPHTDGNFHPSPLMGGFGLKHPPP
        43_20       AANTQAQTGLVHNQGVIPGMVWQNRDVYLQGPIWAKIPHTDGNFHPSPLMGGFGLKHPPP
        AAV_9       AANTQAQTGLVHNQGVIPGMVWQNRDVYLQGPIWAKIPHTDGNFHPSPLMGGFGLKHPPP
        24.1        SSTAGPQTQTVNSQGALPGMVWQNRDVCLQGPIWAKIPHTDGNFHPSPLMGGFGLKHPPP
        42.2REAL    SSTAGPQTQTVNSQGALPGMVWQNRDVYLQGPIWAKIPHTDGNFHPSPLMGGFGLKHPPP
        7.2\VP1     SSTAGPQTQTVNSQGALPGMVWQNRDVYLQGPIWAKIPHTDGNFHPSPLMGGFGLKHPPP
        27.3\VP1    SSTAGPRTQTVNSQGALPGMVWQNRDVYLQGPIWAEIPHTDGNFHPSPLMGGFGLKHPPP
        16.3\VP1    SSTAGPQTQTVNSQGALPGMVWQNRDVYLQGPIWAKIPHTDGNFHPSPLMGGFGLKHPPP
        42_10       SSTAGPQTQTVNSQGALPGMVWQNRDVYLQGPIWAKIPHTDGNFHPSPLMGGFGLKHPPP
        42_3B       SSTAGPQTQTVNSQGALPGMVWQNRDVYLQGPIWAKIPHTDGNFHPSPLMGGFGLKHPPP
        42_11       SSTAGPQTQTVNSQGALPGMVWQNRDVYLQGPIWAKIPHTDGNFHPSPLMGGFGLKHPPP
        F1\VP1      PSTAGPQSQTINSQGALPGMVWQNRDVYLQGPIWAKIPHTDGNFHPSPLMGGFGLKHPPP
        F5\VP1@3    SSTAGPQSQTINSQGALPGMVWQNRDVYLQGPIWAKIPHTDGNFHPSPLMGGFGLEHPPP
        F3\VP1      SSTAGPQSQTINSQGALPGMVWQNRDVYLQGPIWAKIPHTDGNFHPSPLMGGFGLKHPPP
        42_6B       SSTAGPQTQTVNSQGALPGMVWQNRDVYLQGPIWAKIPHTDGNFHPSPLMDGFGLKHPPP
        42_12       SSTAGPQTQTVNSQGALPGMVWQNRDVYLQGPIWAKIPHTDGNFHPSPLMGGFGLKHPPP
        AAV5\CAP    SSTTAPATGTYNLQEIVPGSVWMERDVYLQGPIWAKIPETGAHFHPSPAMGGFGLKHPPP
```

FIG. 2K

```
                  670        680        690        700        710        720
             ....|....|....|....|....|....|....|....|....|....|....|....|
C1\VP1       QIFIKNTPVPANPATTFTAARVDSFITQYSTGQVAVQIEWEIEKERSKRWNPEVQFTSNY
C2\VP1       QIFIKNTPVPANPATTFTAARVDSFITQYSTGQVAVQIEWEIEKERSKRRNPEVQFTSNY
C5\VP1@2     QIFIKNTPVPAYPATTFTAARVDSFITQYSTGQVAVQIEWEIEKERSKRWNPEVQFTSNC
AAV4\VP1     QIFIKNTPVPANPATTFSSTPVNSFITQYSTGQVSVQIDWEIQKERSKRWNPEVQFTSNY
AAV1         QILIKNTPVPANPPAEFSATKFASFITQYSTGQVSVEIEWELQKENSKRWNPEVQYTSNY
AAV6\VP1     QILIKNTPVPANPPAEFSATKFASFITQYSTGQVSVEIEWELQKENSKRWNPEVQYTSNY
A3_3         QILIKNTPVPANPATTFTPGKFASFITQYSTGQVSVEIEWELQKENSKRWNPEIQYTSNY
A3_7         QILIKNTPVPANPATTFTPGKFASFITQYSTGQVSVEIEWELQKENSKRWNPEIQYTSNY
A3_4         QILIKNTPVPANPATTFTPGKFASFITQYSTGQVSVEIEWELQKENSKRWNPEIQYTSNY
A3_5         QILIKNTPVPANPATTFTPGKFASFITQYSTGQVSVEIEWELQKENSKRWNPEIQYTSNY
AAV2         QILIKNTPVPANPSTTFSAAKFASFITQYSTGQVSVEIEWELQKENSKRWNPEIQYTSNY
AAV3         QIMIKNTPVPANPPTTFSPAKFASFITQYSTGQVSVEIEWELQKENSKRWNPEIQYTSNY
13.3b\VP1    QILIKNTPVPANPPEVFTPAKFASFITQYSTGQVSVEIEWELQKENSKRWDPEIQYTSNF
AAV7         QILIKNTPVPANPPEVFTPAKFASFITQYSTGQVSVEIEWELQKENSKRWNPEIQYTSNF
223_4        QILIKNTPVPANPPEVFTPAKFASFITQYSTGQVSVEIEWELQKENSKRWNPEIQYTSNF
223_5        QILIKNTPVPANPPEVFTPAKFASFITQYSTGQVSVEIEWELQKENSKRWNPEIQYTSNF
223_10       QILIKNTPVPANPPEVFTPAKFASFITQYSTGQVSVEIEWELQKENSKRWNPEIQYTSNF
223_2        QILIKNTPVPANPPEVFTPAKFASFITQYSTGQVSVEIEWELQKENSKRWNPEIQYTSNF
223_7        QILIKNTPVPANPPEVFTPAKIASFITQYSTGQVSVEIEWELQKENSKRWNPEIQYTSNF
223_6        QILIKNTPVPANPPEVFTPAKLASFITQYSTGQVSVEIEWELQKENSKRWNPEIQYTSNF
44_1         QILIKNTPVPADPPTTFSQAKLASFITQYSTGQVSVEIEWELQKENSKRWNPEIQYTSNY
44_5         QILIKNTPVPADPPTTFSQAKLASFITQYSTGQVSVEIEWELQKENSKRWNPEIQYTSNY
44_2         QILIKNTPVPADPPTTFSQAKLASFITQYSTGQVSVEIEWELQKENSKRWNPEIQYTSNY
29.3\VP1     QILIKNTPVPADPPTTFSQAKLASFITQYSTGQVSVEIEWELQKENSKRWNPEIQYTSNY
29.5\VP1     QILIKNTPVPADPPTTFSQAKLASFITQYSTGQVSVEIEWELQKENSKRWNPEIQYTSNY
42_15        QILIKNTPVPADPPTTFSQAKLASFITQYSTGQVSVEIEWELQKENSKRWNPEIQYTSNY
42_8         QILIKNTPVPADPPTTFSQAKLASFITQYSTGQVSVEIEWELQKENSKRWNPEIQYTSNY
42_13        QILIKNTPVPADPPTTFSQAKLASFITQYSTGQVSVEIEWELQKENSKRWNPEIQYTSNY
42_3A        QILIKNTPVPADPPTTFSQAKLASFITQYSTGQVSVEIEWELQKENSKRWNPEIQYTSNY
42_4         QILIKNTPVPADPPTTFSQAKPASFITQYSTGQVSVEIEWELQKENSKRWNPEIQYTSNY
42_5A        QILIKNTPVPADPPTTFSQAKLASFITQYSTGQVSVEIEWELQKENSKRWNPEIQYTSNY
42_1B        QILIKNTPVPADPPTTFSQAKLASFITQYSTGQVSVEIEWELQKENSKRWNPEIQYTSNY
42_5B        QILIKNTPVPADPPTTFSQAKLASFITQYSTGQVSVEIEWELQKENSKRWNPEIQYTSNY
43_1         QILVKNTPVPADPPTTFSQAKLASFITQYSTGQVSVEIEWELQKENSKRWNPEIQYTSNY
43_12        QILVKNTPVPADPPTTFSQAKLASFITQYSTGQVSVEIEWELQKENSKRWNPEIQYTSNY
43_5         QILVKNTPVPADPPTTFSQAKLASFITQYSTGQVSVEIEWELQKENSKRWNPEIQYTSNY
AAV8         QILIKNTPVPADPPTTFNQSKLNSFITQYSTGQVSVEIEWELQKENSKRWNPEIQYTSNY
43_21        QILIKNTPVPADPPLTFNQAKLNSFITQYSTGQVSVEIEWELQKENSKRWNPEIQYTSNY
43_25        QILIKNTPVPADPPLTFNQAKLNSFITQYSTGQVSVEIEWELQKENSKRWNPEIQYTSNY
43_23        QILIKNTPVPADPPLTFNQAKLNSFITQYSTGQVSVEIEWELQKENSKRWNPEIQYTSNY
43_20        QILIKNTPVPADPPLTFNQAKLNSFITQYSTGQVSVEIEWELQKENSKRWNPEIQYTSNY
AAV_9        QILIKNTPVPADPPLTFNQAKLNSFITQYSTGQVSVEIEWELQKENSKRWNPEIQYTSNY
24.1         QILIKNTPVPANPPEVFTPAKFASFITQYSTGQVSVEIEWELQKENSKRWNPEIQYTSNY
42.2REAL     QILIKNTPVPANPPEVFTPAKFASFITQYSTGQVSVEIEWELQKENSKRWNPEIQYTSNY
7.2\VP1      QILIKNTPVPANPPEVFTPAKFASFITQYSTGQVSVEIEWELQKENSKRWNPEIQYTSNY
27.3\VP1     QILIKNTPVPANPPEVFTPAKFASFITQYSTGQVSVEIEWELQKENSKRWNPEIQYTSNY
16.3\VP1     QILIKNTPVPANPPGVFTPALFASFITQYSTGQVSVEIEWELQKENSKRWNPEIQYTSNY
42_10        QILIKNTPVPANPPEVFTPAKFASFITQYSTGQVSVEIEWELQKENSKRWNPEIQYTSNY
42_3B        QILIKNTPVPANPPEVFTPAKFASFITQYSTGQVSVEIEWELQKENSKRWNPEIQYTSNY
42_11        QILIKNTPVPANPPEVFTPAKFASFITQYSTGQVSVEIEWELQKENSKRWNPEIQYTSNY
F1\VP1       QILIKNTPVPANPPEVFTPAKFASFITQYSTGQVSVEIEWELQKENSKRWNPEIQYTSNY
F5\VP1@3     QILIKNTPVPANPPEVFTPAKFASFITQYSTGQVSVEIEWELQKENSKRWNPEIQYTSNY
F3\VP1       QILIKNTPVPANPPEVFTPAKFASFITQYSTGQVSVEIEWELQKENSKRWNPEIQYTSNY
42_6B        QILIKNTPVPANPPEVFTPAKFASFITQYSTGQVSVEIEWELQKENSKRWNPEIQYTSNY
42_12        QILIK-------------------------------------------------YTSNY
AAV5\CAP     MMLIKNTPVPGN-ITSFSDVPVSSFITQYSTGQVTVEMEWELKKENSKRWNPEIQYTNNY
```

FIG. 2L

```
                        730       740       750
                        ....|....|....|....|....|....|.
C1\VP1         GNQSSMLWAPDTTGKYTEPRVIGSRYLTNHL
C2\VP1         GNQSSMLWAPDTTGKYTEPRVIGSRYLTNHL
C5\VP1@2       GNQSSMLWAPDTTGKYTEPRVIGSRYLTNHL
AAV4\VP1       GQQNSLLWAPDAAGKYTEPRAIGTRYLTHHL
AAV1           AKSANVDFTVDNNGLYTEPRPIGTRYLTRPL
AAV6\VP1       AKSANVDFTVDNNGLYTEPRPIGTRYLTRPL
A3_3           NKSVNVEFTVDANGVYSEPRPIGTRYLTRNL
A3_7           NKSVNVEFTVDANGVYSEPRPIGTRYLTRNL
A3_4           NKSVNVEFTVDANGVYSEPRPIGTRYLTRNL
A3_5           NKSVNVEFTVDANGVYSEPRPIGTRYLTRNL
AAV2           NKSVNVDFTVDTNGVYSEPRPIGTRYLTRNL
AAV3           NKSVNVDFTVDTNGVYSEPRPIGTRYLTRNL
13.3b\VP1      EKQTGVDFAVDSQGVYSEPRPIGTRYLTRNL
AAV7           EKQTGVDFAVDSQGVYSEPRPIGTRYLTRNL
223_4          DKQTGVDFAVDSQGVYSEP------------
223_5          DKQTGVDFAVDSQGVYSEP------------
223_10         DKQTGVDFAVDSQGVYSEP------------
223_2          DKQTGVDFAVDSQGVYSEP------------
223_7          DKQTGVDFAVDSQGVYSEP------------
223_6          DKQTGVDFAVDSQGVYSEP------------
44_1           YKSTNVDFAVNTDGTYSEPRPIGTRYLTRNL
44_5           YKSTNVDFAVNTDGTYSEPRPIGTRYLTRNL
44_2           YKSTNVDFAVNTDGTYSEPRPIGTRYLTRNL
29.3\VP1       YKSTNVDFAVNTDGTYSEPRPIGTRYLTRNL
29.5\VP1       YKSTNVDFAVNTDGTYSEPRPIGTRYLTRNL
42_15          YKSTNVDFAVNTEGTYSEPRPIGTRYLTRNL
42_8           YKSTNVDFAVNTEGTYSEPRPIGTRYLTRNL
42_13          YKSTNVDFAVNTEGTYSEPRPIGTRYLTRSL
42_3A          YKSTNVDFAVNTEGTYSEPRPIGTRYLTRNL
42_4           YKSTNVDFAVNTEGTYSEPRPIGTRYLTRNL
42_5A          YKSTNVDFAVNTEGTYSEPRPIGTRYLTRNL
42_1B          YKSTNVDFAVNTEGTYSEPRPIGTRYLTRNL
42_5B          YKSTNVDFAVNTEGTYSEPRPIGTRYLTRNL
43_1           YKSTNVDFAVNTEGTYSEPRPIGTRYLTRNL
43_12          YKSTNVDFAVNTEGTYSEPRPIGTRYLTRNL
43_5           YKSTNVDFAVNTEGTYSEPRPIGTRYLTRNL
AAV8           YKSTSVDFAVNTEGVYSEPRPIGTRYLTRNL
43_21          YKSTNVDFAVNTEGVYSEPRPIGTRYLTRNL
43_25          YKSTNVDFAVNTEGVYSEPRPIGTRYLTRNL
43_23          YKSTNVDFAVNTEGVYSEPRPIGTRYLTRNL
43_20          YKSTNVDFAVNTEGVYSEPRPIGTRYLTRNL
AAV_9          YKSTNVDFAVNTEGVYSEPRPIGTRYLTRNL
24.1           AKSNNVEFAVNNEGVYTEPRPIGTRYLTRNL
42.2REAL       AKSNNVEFAVNNEGVYTEPRPIGTRYLTRNL
7.2\VP1        AKSNNVEFAVNNEGVYTEPRPIGTRYLTRNL
27.3\VP1       AKSNNVEFAVNNEGVYTEPRPIGTRYLTRNL
16.3\VP1       AKSNNVEFAVNNEGVYTEPRPIGTRYLTRNL
42_10          AKSNNVEFAVNNEGVYTEPRPIGTRYLTRNL
42_3B          AKSNNVEFAVNNEGVYTEPRPIGTRYLTRNL
42_11          AKSNNVEFAVNNEGVYTEPRPIGTRYLTRNL
F1\VP1         AKSNNVEFAVNPDGVYTEPRPIGTRYLPRNL
F5\VP1@3       AKSNNVEFAVNPDGVYTEPRPIGTRYLTRNL
F3\VP1         AKSNNVEFAVNPDGVYTEPRPIGTRYLTRNL
42_6B          AKSNNVEFAVNNEGVYTEPRPIGTRYLTRNL
42_12          YKSTNVDFAVNTEGTYSEPRPIGTRYLTRNL
AAV5\CAP       NDPQFVDFAPDSTGEYRTTRPIGTRYLTRPL
```

```
Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
                20                  25                  30

Lys Glu Trp Glu Leu Pro Pro Asp Ser Asp Met Asp Leu Asn Leu Ile
                35                  40                  45

Glu Gln Ala Pro Leu Thr Val Ala Glu Lys Leu Gln Arg Asp Phe Leu
                50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Val Leu Val Glu
                85                  90                  95

Thr Thr Gly Val Lys Ser Met Val Leu Gly Arg Phe Leu Ser Gln Ile
                100                 105                 110

Arg Glu Lys Leu Val Gln Thr Ile Tyr Arg Gly Val Glu Pro Thr Leu
                115                 120                 125

Pro Asn Trp Phe Ala Val Thr Lys Thr Arg Asn Gly Ala Gly Gly Gly
                130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala Gln His
                180                 185                 190

Leu Thr His Val Ser Gln Thr Gln Glu Gln Asn Lys Glu Asn Leu Asn
                195                 200                 205

Pro Asn Ser Asp Ala Pro Val Ile Arg Ser Lys Thr Ser Ala Arg Tyr
                210                 215                 220
```

Fig. 3B

```
Met Glu Leu Val Gly Trp Leu Val Asp Arg Gly Ile Thr Ser Glu Lys
225             230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
                260                 265                 270

Ile Met Ala Leu Thr Lys Ser Ala Pro Asp Tyr Leu Val Gly Pro Ser
                275                 280                 285

Leu Pro Ala Asp Ile Lys Thr Asn Arg Ile Tyr Arg Ile Leu Glu Leu
    290                 295                 300

Asn Gly Tyr Asp Pro Ala Tyr Ala Gly Ser Val Phe Leu Gly Trp Ala
305             310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
                340                 345                 350

Phe Tyr Gly Cys Val Asn Trp Thr Asn Glu Asn Phe Pro Phe Asn Asp
                355                 360                 365

Cys Val Asp Lys Met Val Ile Trp Trp Glu Glu Gly Lys Met Thr Ala
                370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
                420                 425                 430

Thr Thr Phe Glu His Gln Gln Pro Leu Gln Asp Arg Met Phe Lys Phe
                435                 440                 445
```

Fig. 3C

Glu Leu Thr Arg Arg Leu Glu His Asp Phe Gly Lys Val Thr Lys Gln
    450             455             460

Glu Val Lys Glu Phe Phe Arg Trp Ala Ser Asp His Val Thr Glu Val
465             470             475                         480

Ala His Glu Phe Tyr Val Arg Lys Gly Gly Ala Ser Lys Arg Pro Ala
                485             490             495

Pro Asp Asp Ala Asp Ile Ser Glu Pro Lys Arg Ala Cys Pro Ser Val
            500             505             510

Ala Asp Pro Ser Thr Ser Asp Ala Glu Gly Ala Pro Val Asp Phe Ala
            515             520             525

Asp Arg Tyr Gln Asn Lys Cys Ser Arg His Ala Gly Met Ile Gln Met
        530             535             540

Leu Phe Pro Cys Lys Thr Cys Glu Arg Met Asn Gln Asn Phe Asn Ile
545             550             555                         560

Cys Phe Thr His Gly Val Arg Asp Cys Leu Glu Cys Phe Pro Gly Val
                565             570             575

Ser Glu Ser Gln Pro Val Val Arg Lys Lys Thr Tyr Arg Lys Leu Cys
            580             585             590

Ala Ile His His Leu Leu Gly Arg Ala Pro Glu Ile Ala Cys Ser Ala
        595             600             605

Cys Asp Leu Val Asn Val Asp Leu Asp Asp Cys Val Ser Glu Gln
    610             615             620

METHOD OF DETECTING AND/OR IDENTIFYING ADENO-ASSOCIATED VIRUS (AAV) SEQUENCES AND ISOLATING NOVEL SEQUENCES IDENTIFIED THEREBY

CROSS-REFERENCE TO RELATED APPLICATIONS

This application is a divisional of U.S. patent application Ser. No. 15/584,674, filed May 5, 2017, which is a continuation of U.S. patent application Ser. No. 14/956,934, filed Dec. 2, 2015, now U.S. Pat. No. 10,041,090, issued Aug. 7, 2018, which is a continuation of U.S. patent application Ser. No. 13/633,971, filed Oct. 3, 2012, now U.S. Pat. No. 9,790,472, issued Oct. 17, 2017, which is a divisional of U.S. patent application Ser. No. 12/962,793, filed Dec. 8, 2010, now U.S. Pat. No. 8,524,446, issued Sep. 3, 2013, which is a continuation of U.S. patent application Ser. No. 10/291,583, filed Nov. 12, 2002, now abandoned, which claims the benefit under 35 USC 119(e) of U.S. Provisional Patent Application No. 60/386,675, filed Jun. 5, 2002, U.S. Provisional Patent Application No. 60/377,066, filed May 1, 2002, U.S. Provisional Patent Application No. 60/341,117, filed Dec. 17, 2001, and U.S. Provisional Patent Application No. 60/350,607, filed Nov. 13, 2001. These applications are incorporated by reference herein.

BACKGROUND OF THE INVENTION

Adeno-associated virus (AAV), a member of the Parvovirus family, is a small nonenveloped, icosahedral virus with single-stranded linear DNA genomes of 4.7 kilobases (kb) to 6 kb. AAV is assigned to the genus, Dependovirus, because the virus was discovered as a contaminant in purified adenovirus stocks. AAV's life cycle includes a latent phase at which AAV genomes, after infection, are site specifically integrated into host chromosomes and an infectious phase in which, following either adenovirus or herpes simplex virus infection, the integrated genomes are subsequently rescued, replicated, and packaged into infectious viruses. The properties of non-pathogenicity, broad host range of infectivity, including non-dividing cells, and potential site-specific chromosomal integration make AAV an attractive tool for gene transfer.

Recent studies suggest that AAV vectors may be the preferred vehicle for gene therapy. To date, there have been 6 different serotypes of AAVs isolated from human or non-human primates (NHP) and well characterized. Among them, human serotype 2 is the first AAV that was developed as a gene transfer vector; it has been widely used for efficient gene transfer experiments in different target tissues and animal models. Clinical trials of the experimental application of AAV2 based vectors to some human disease models are in progress, and include such diseases as cystic fibrosis and hemophilia B.

What are desirable are AAV-based constructs for gene delivery.

SUMMARY OF THE INVENTION

In one aspect, the invention provides a novel method of detecting and identifying AAV sequences from cellular DNAs of various human and non-human primate (NHP) tissues using bioinformatics analysis, PCR based gene amplification and cloning technology, based on the nature of latency and integration of AAVs in the absence of helper virus co-infection.

In another aspect, the invention provides method of isolating novel AAV sequences detected using the above described method of the invention. The invention further comprises methods of generating vectors based upon these novel AAV serotypes, for serology and gene transfer studies solely based on availability of capsid gene sequences and structure of rep/cap gene junctions.

In still another aspect, the invention provides a novel method for performing studies of serology, epidemiology, biodistribution and mode of transmission, using reagents according to the invention, which include generic sets of primers/probes and quantitative real time PCR.

In yet another aspect, the invention provides a method of isolating complete and infectious genomes of novel AAV serotypes from cellular DNA of different origins using RACE and other molecular techniques.

In a further aspect, the invention provides a method of rescuing novel serotypes of AAV genomes from human and NHP cell lines using adenovirus helpers of different origins.

In still a further aspect, the invention provides novel AAV serotypes, vectors containing same, and methods of using same.

These and other aspects of the invention will be readily apparent from the following detailed description of the invention.

BRIEF DESCRIPTION OF THE DRAWINGS

FIGS. 2A through 2M are an alignment of the amino acid sequences of the proteins of the vp1 capsid proteins of previously published AAV serotypes 1 [SEQ ID NO:64], AAV2 [SEQ ID NO:70], AAV3 [SEQ ID NO: 71], AAV4 [SEQ ID NO:63], AAV5 [SEQ ID NO:114], and AAV6 [SEQ ID NO:65] and novel AAV sequences of the invention, including: C1 [SEQ ID NO:60], C2 [SEQ ID NO:61], C5 [SEQ ID NO:62], A3-3 [SEQ ID NO:66], A3-7 [SEQ ID NO:67], A3-4 [SEQ ID NO:68], A3-5 [SEQ ID NO: 69], 3.3b [SEQ ID NO: 62], 223.4 [SEQ ID NO: 73], 223-5 [SEQ ID NO:74], 223-10 [SEQ ID NO:75], 223-2 [SEQ ID NO:76], 223-7 [SEQ ID NO: 77], 223-6 [SEQ ID NO: 78], 44-1 [SEQ ID NO: 79], 44-5 [SEQ ID NO:80], 44-2 [SEQ ID NO:81], 42-15 [SEQ ID NO: 84], 42-8 [SEQ ID NO: 85], 42-13 [SEQ ID NO:86], 42-3A [SEQ ID NO:87], 42-4 [SEQ ID NO:88], 42-5A [SEQ ID NO:89], 42-1B [SEQ ID NO:90], 42-5B [SEQ ID NO:91], 43-1 [SEQ ID NO: 92], 43-12 [SEQ ID NO: 93], 43-5 [SEQ ID NO:94], 43-21 [SEQ ID NO:96], 43-25 [SEQ ID NO: 97], 43-20 [SEQ ID NO:99], 24.1 [SEQ ID NO: 101], 42.2 [SEQ ID NO:102], 7.2 [SEQ ID NO: 103], 27.3 [SEQ ID NO: 104], 16.3 [SEQ ID NO: 105], 42.10 [SEQ ID NO: 106], 42-3B [SEQ ID NO: 107], 42-11 [SEQ ID NO: 108], F1 [SEQ ID NO: 109], F5 [SEQ ID NO: 110], F3 [SEQ ID NO:111], 42-6B [SEQ ID NO: 112], 42-12 [SEQ ID NO: 113]. Novel serotypes AAV8 [SEQ ID NO:95] and AAV9 [SEQ ID NO:100] are the subject of co-filed patent applications.

FIGS. 3A through 3C provide the amino acid sequences of the AAV7 rep proteins [SEQ ID NO:3].

DETAILED DESCRIPTION OF THE INVENTION

Figure 1B:
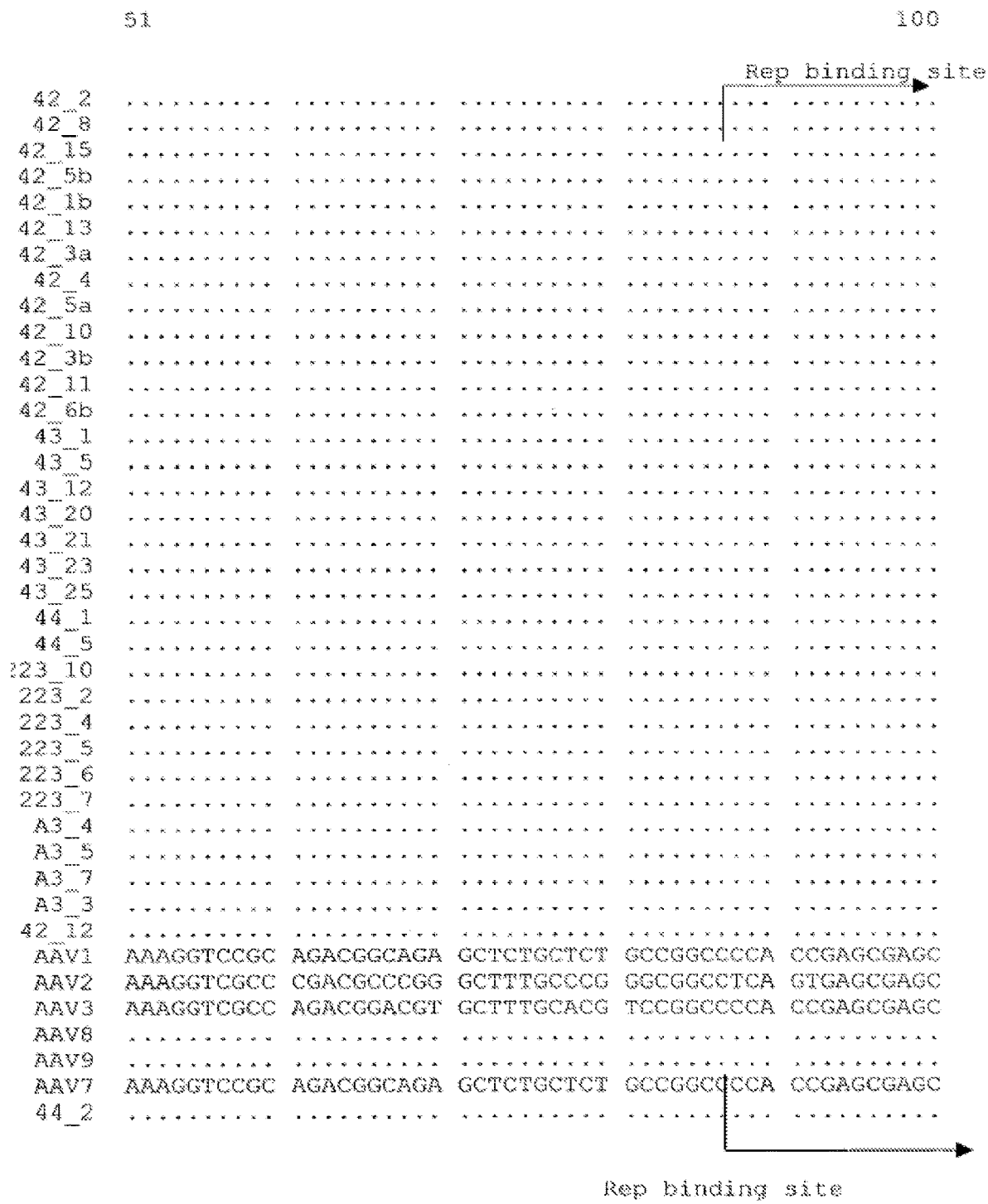
FIGS. 1A through 1AAAR provide an alignment of the nucleic acid sequences encoding at least the cap proteins for the AAV serotypes. The full-length sequences including the ITRs, the rep region, and the capsid region are provided for novel AAV serotype 7 [SEQ ID NO:1], and for previously published AAV1 [SEQ IN NO:6], AAV2 [SEQ ID NO:7]; and AAV3 [SEQ ID NO:8]. Novel AAV serotypes AAV8 [SEQ ID NO:4] and AAV9 [SEQ ID NO:5] are the subject of co-filed applications. The other novel clones of the invention provided in this alignment include: 42-2 [SEQ ID NO:9], 42-8 [SEQ ID NO:27], 42-15 [SEQ ID NO:28], 42-5b [SEQ ID NO: 29], 42-1b [SEQ ID NO:30]; 42-13 [SEQ ID NO: 31], 42-3a [SEQ ID NO: 32], 42-4 [SEQ ID NO:33], 42-5a [SEQ ID NO: 34], 42-10 [SEQ ID NO:35], 42-3b [SEQ ID NO: 36], 42-11 [SEQ ID NO: 37], 42-6b [SEQ ID NO:38], 43-1 [SEQ ID NO: 39], 43-5 [SEQ ID NO: 40], 43-12 [SEQ ID NO:41], 43-20 [SEQ ID NO:42], 43-21 [SEQ ID NO: 43], 43-23 [SEQ ID NO:44], 43-25 [SEQ ID NO: 45], 44.1 [SEQ ID NO:47], 44.5 [SEQ ID NO:47], 223.10 [SEQ ID NO:48], 223.2 [SEQ ID NO:49], 223.4 [SEQ ID NO:50], 223.5 [SEQ ID NO: 51], 223.6 [SEQ ID NO: 52], 223.7 [SEQ ID NO: 53], A3.4 [SEQ ID NO: 54], A3.5 [SEQ ID NO:55], A3.7 [SEQ ID NO: 56], A3.3 [SEQ ID NO:57], 42.12 [SEQ ID NO: 58], 44.2 [SEQ ID NO: 59]. The nucleotide sequences of the signature regions of AAV10 [SEQ ID NO: 117], AAV11 [SEQ ID NO: 118] and AAV12 [SEQ ID NO:119] are provided in this figure. Critical landmarks in the structures of AAV genomes are shown. Gaps are demonstrated by dots. The 3' ITR of AAV1 [SEQ ID NO:6] is shown in the same configuration as in the published sequences. TRS represents terminal resolution site. Notice that AAV7 is the only AAV reported that uses GTG as the initiation codon for VP3.

In the present invention, the inventors have found a method which takes advantage of the ability of adeno-associated virus (AAV) to penetrate the nucleus, and, in the absence of a helper virus co-infection, to integrate into cellular DNA and establish a latent infection. This method utilizes a polymerase chain reaction (PCR)-based strategy for detection, identification and/or isolation of sequences of AAVs from DNAs from tissues of human and non-human primate origin as well as from other sources. Advantageously, this method is also suitable for detection, identification and/or isolation of other integrated viral and non-viral sequences, as described below.

The invention further provides nucleic acid sequences identified according to the methods of the invention. One such adeno-associated virus is of a novel serotype, termed herein serotype 7 (AAV7). Other novel adeno-associated virus serotypes provided herein include AAV10, AAV11, and AAV12. Still other novel AAV serotypes identified according to the methods of the invention are provided in the present specification. See, Figures and Sequence Listing, which is incorporated by reference.

Also provided are fragments of these AAV sequences. Among particularly desirable AAV fragments are the cap proteins, including the vp1, vp2, vp3, the hypervariable regions, the rep proteins, including rep 78, rep 68, rep 52, and rep 40, and the sequences encoding these proteins. Each of these fragments may be readily utilized in a variety of vector systems and host cells. Such fragments may be used alone, in combination with other AAV sequences or fragments, or in combination with elements from other AAV or non-AAV viral sequences. In one particularly desirable embodiment, a vector contains the AAV cap and/or rep sequences of the invention.

As described herein, alignments are performed using any of a variety of publicly or commercially available Multiple Sequence Alignment Programs, such as AClustal accessible through Web Servers on the internet. Alternatively, Vector NTI utilities are also used. There are also a number of algorithms known in the art which can be used to measure nucleotide sequence identity, including those contained in the programs described above. As another example, polynucleotide sequences can be compared using Fasta, a program in GCG Version 6.1. Fasta provides alignments and percent sequence identity of the regions of the best overlap between the query and search sequences. For instance, percent sequence identity between nucleic acid sequences can be determined using Fasta with its default parameters (a word size of 6 and the NOPAM factor for the scoring matrix) as provided in GCG Version 6.1, herein incorporated by reference. Similar programs are available for amino acid sequences, e.g., the "Clustal X" program. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs.

The term "substantial homology" or "substantial similarity," when referring to a nucleic acid, or fragment thereof, indicates that, when optimally aligned with appropriate nucleotide insertions or deletions with another nucleic acid (or its complementary strand), there is nucleotide sequence identity in at least about 95 to 99% of the aligned sequences. Preferably, the homology is over full-length sequence, or an open reading frame thereof, or another suitable fragment which is at least 15 nucleotides in length. Examples of suitable fragments are described herein.

The term "substantial homology" or "substantial similarity," when referring to amino acids or fragments thereof, indicates that, when optimally aligned with appropriate amino acid insertions or deletions with another amino acid, there is amino acid sequence identity in at least about 95 to 99% of the aligned sequences. Preferably, the homology is over full-length sequence, or a protein thereof, e.g., a cap protein, a rep protein, or a fragment thereof which is at least 8 amino acids, or more desirably, at least 15 amino acids in length. Examples of suitable fragments are described herein.

By the term "highly conserved" is meant at least 80% identity, preferably at least 90% identity, and more preferably, over 97% identity. Identity is readily determined by one of skill in the art by resort to algorithms and computer programs known by those of skill in the art.

The term "percent sequence identity" or "identical" in the context of nucleic acid sequences refers to the residues in the two sequences which are the same when aligned for maximum correspondence. The length of sequence identity comparison may be over the full-length of the genome, the full-length of a gene coding sequence, or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired. Similarly, "percent sequence identity" may be readily determined for amino acid sequences, over the full-length of a protein, or a fragment thereof. Suitably, a fragment is at least about 8 amino acids in length, and may be up to about 700 amino acids. Examples of suitable fragments are described herein.

The AAV sequences and fragments thereof are useful in production of rAAV, and are also useful as antisense delivery vectors, gene therapy vectors, or vaccine vectors. The invention further provides nucleic acid molecules, gene delivery vectors, and host cells which contain the AAV sequences of the invention.

As described herein, the vectors of the invention containing the AAV capsid proteins of the invention are particularly well suited for use in applications in which the neutralizing antibodies diminish the effectiveness of other AAV serotype based vectors, as well as other viral vectors. The rAAV vectors of the invention are particularly advantageous in rAAV readministration and repeat gene therapy.

These and other embodiments and advantages of the invention are described in more detail below. As used throughout this specification and the claims, the terms Acomprising≅ and "including" and their variants are inclusive of other components, elements, integers, steps and the like. Conversely, the term "consisting" and its variants is exclusive of other components, elements, integers, steps and the like.

I. Methods of the Invention

A. Detection of Sequences Via Molecular Cloning

In one aspect, the invention provides a method of detecting and/or identifying target nucleic acid sequences in a sample. This method is particularly well suited for detection of viral sequences which are integrated into the chromosome of a cell, e.g., adeno-associated viruses (AAV) and retroviruses, among others. The specification makes reference to AAV, which is exemplified herein. However, based on this information, one of skill in the art may readily perform the methods of the invention on retroviruses [e.g., feline leukemia virus (FeLV), HTLVI and HTLVII], and lentivirinae [e.g., human immunodeficiency virus (HIV), simian immunodeficiency virus (SIV), feline immunodeficiency virus (FIV), equine infectious anemia virus, and spumavirinal)], among others. Further, the method of the invention may also be used for detection of other viral and non-viral sequences, whether integrated or non-integrated into the genome of the host cell.

As used herein, a sample is any source containing nucleic acids, e.g., tissue, tissue culture, cells, cell culture, and biological fluids including, without limitation, urine and blood. These nucleic acid sequences may be DNA or RNA from plasmids, natural DNA or RNA from any source, including bacteria, yeast, viruses, and higher organisms such as plants or animals. DNA or RNA is extracted from the sample by a variety of techniques known to those of skill in the art, such as those described by Sambrook, Molecular Cloning: A Laboratory Manual (New York: Cold Spring Harbor Laboratory). The origin of the sample and the method by which the nucleic acids are obtained for application of the method of the invention is not a limitation of the present invention. Optionally, the method of the invention can be performed directly on the source of DNA, or on nucleic acids obtained (e.g., extracted) from a source.

The method of the invention involves subjecting a sample containing DNA to amplification via polymerase chain reaction (PCR) using a first set of primers specific for a first region of double-stranded nucleic acid sequences, thereby obtaining amplified sequences.

As used herein, each of the Aregions≅ is predetermined based upon the alignment of the nucleic acid sequences of at least two serotypes (e.g., AAV) or strains (e.g., lentiviruses), and wherein each of said regions is composed of sequences having a 5' end which is highly conserved, a middle which is preferably, but necessarily, variable, and a 3' end which is highly conserved, each of these being conserved or variable relative to the sequences of the at least two aligned AAV serotypes. Preferably, the 5' and/or 3' end is highly conserved over at least about 9, and more preferably, at least 18 base pairs (bp). However, one or both of the sequences at the 5= or 3=end may be conserved over more than 18 bp, more than 25 bp, more than 30 bp, or more than 50 bp at the 5' end. With respect to the variable region, there is no requirement for conserved sequences, these sequences may be relatively conserved, or may have less than 90, 80, or 70% identity among the aligned serotypes or strains.

Each of the regions may span about 100 bp to about 10 kilobase pairs in length. However, it is particularly desirable that one of the regions is a Asignature≅ i.e., a region which is sufficiently unique to positively identify the amplified sequence as being from the target source. For example, in one embodiment, the first region is about 250 bp in length, and is sufficiently unique among known AAV sequences, that it positively identifies the amplified region as being of AAV origin. Further, the variable sequences within this region are sufficiently unique that can be used to identify the serotype from which the amplified sequences originate. Once amplified (and thereby detected), the sequences can be identified by performing conventional restriction digestion and comparison to restriction digestion patterns for this region in any of AAV1, AAV2, AAV3, AAV4, AAV5, or AAV6, or that of AAV7, AAV10, AAV11, AAV12, or any of the other novel serotypes identified by the invention, which is predetermined and provided by the present invention.

Given the guidance provided herein, one of skill in the art can readily identify such regions among other integrated viruses to permit ready detection and identification of these sequences. Thereafter, an optimal set of generic primers located within the highly conserved ends can be designed and tested for efficient amplification of the selected region from samples. This aspect of the invention is readily adapted to a diagnostic kit for detecting the presence of the target sequence (e.g., AAV) and for identifying the AAV serotype, using standards which include the restriction patterns for the AAV serotypes described herein or isolated using the techniques described herein. For example, quick identification or molecular serotyping of PCR products can be accomplished by digesting the PCR products and comparing restriction patterns.

Figure 1E:
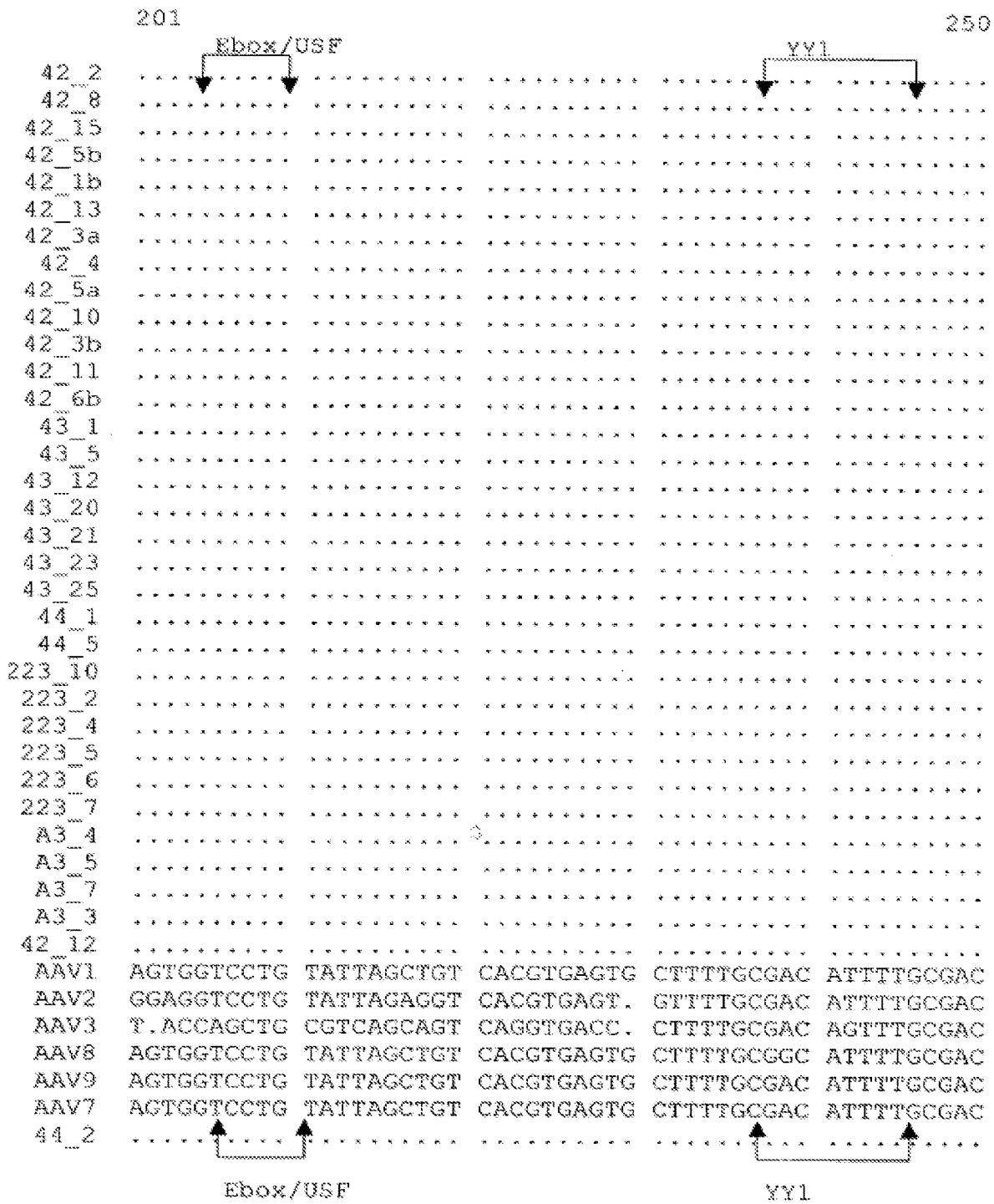
Figure 1F:
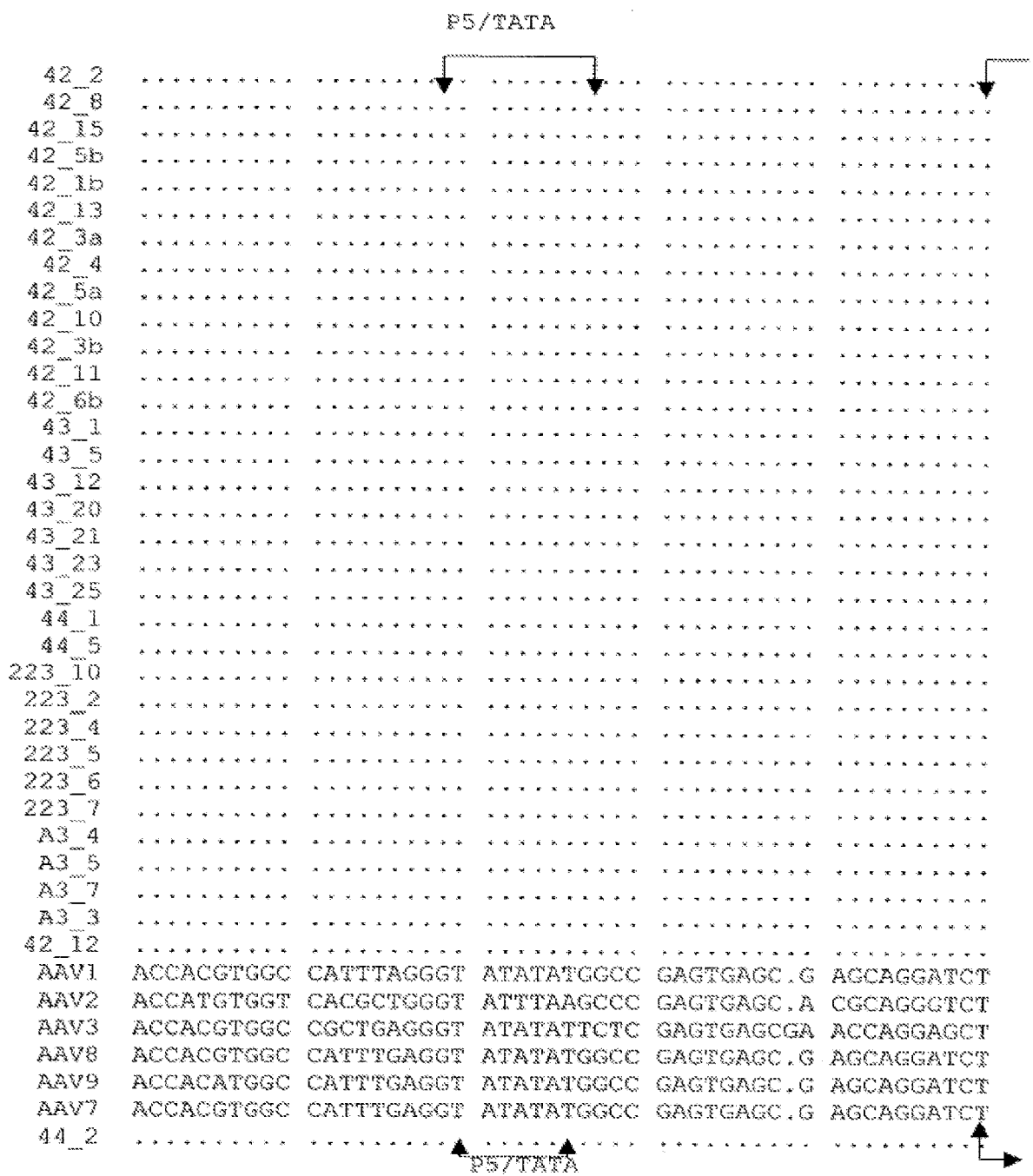
Figure 1G:
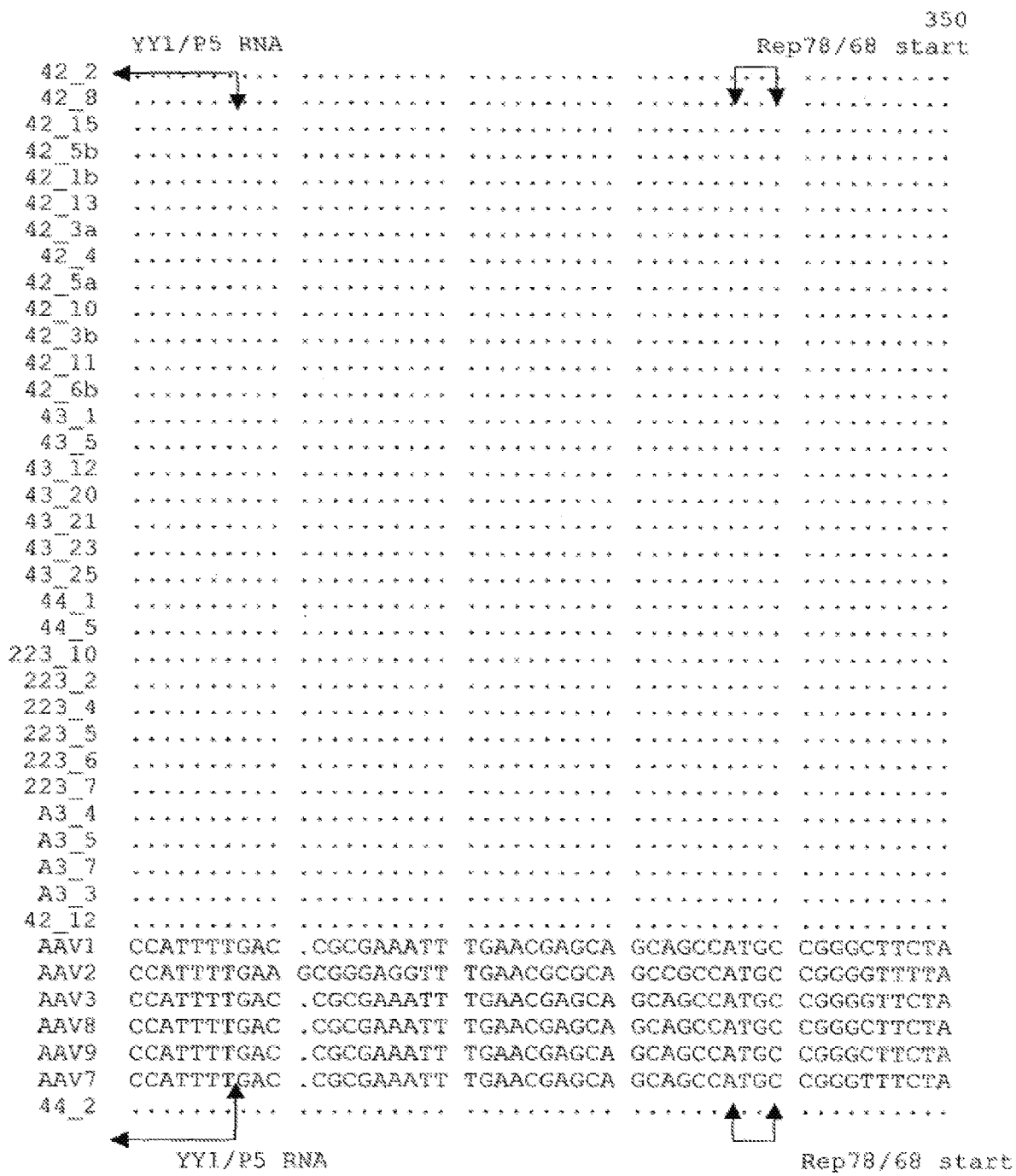

Thus, in one embodiment, the "signature region" for AAV spans about bp 2800 to about 3200 of AAV 1 [SEQ ID NO:6], and corresponding base pairs in AAV 2, AAV3, AAV4, AAV5, and AAV6. More desirably, the region is about 250 bp, located within bp 2886 to about 3143 bp of AAV 1 [SEQ ID NO:6], and corresponding base pairs in AAV 2 [SEQ ID NO:7], AAV3 [SEQ ID NO8], and other AAV serotypes. See, FIG. 1. To permit rapid detection of AAV in the sample, primers which specifically amplify this signature region are utilized. However, the present invention is not limited to the exact sequences identified herein for the AAV signature region, as one of skill in the art may readily alter this region to encompass a shorter fragment, or a larger fragment of this signature region.

The PCR primers are generated using techniques known to those of skill in the art. Each of the PCR primer sets is composed of a 5' primer and a 3' primer. See, e.g., Sambrook et al, cited herein. The term "primer" refers to an oligonucleotide which acts as a point of initiation of synthesis when placed under conditions in which synthesis of a primer extension product which is complementary to a nucleic acid strand is induced. The primer is preferably single stranded. However, if a double stranded primer is utilized, it is treated to separate its strands before being used to prepare extension products. The primers may be about 15 to 25 or more nucleotides, and preferably at least 18 nucleotides. However, for certain applications shorter nucleotides, e.g., 7 to 15 nucleotides are utilized.

The primers are selected to be sufficiently complementary to the different strands of each specific sequence to be amplified to hybridize with their respective strands. Therefore, the primer sequence need not reflect the exact sequence of the region being amplified. For example, a non-complementary nucleotide fragment may be attached to the 5' end of the primer, with the remainder of the primer sequence being completely complementary to the strand. Alternatively, non-complementary bases or longer sequences can be interspersed into the primer, provided that the primer sequence has sufficient complementarity with the sequence of the strand to be amplified to hybridize therewith and form a template for synthesis of the extension product of the other primer.

The PCR primers for the signature region according to the invention are based upon the highly conserved sequences of two or more aligned sequences (e.g., two or more AAV serotypes). The primers can accommodate less than exact identity among the two or more aligned AAV serotypes at the 5' end or in the middle. However, the sequences at the 3' end of the primers correspond to a region of two or more aligned AAV serotypes in which there is exact identity over at least five, preferably, over at least nine base pairs, and more preferably, over at least 18 base pairs at the 3' end of the primers. Thus, the 3' end of the primers is composed of sequences with 100% identity to the aligned sequences over at least five nucleotides. However, one can optionally utilize one, two, or more degenerate nucleotides at the 3' end of the primer.

For example, the primer set for the signature region of AAV was designed based upon a unique region within the AAV capsid, as follows. The 5' primer was based upon nt 2867-2891 of AAV2 [SEQ ID NO:7], 5'-GGTAAT-TCCTCCGGAAATTGGCATT3'. See, FIG. 1. The 3' primer was designed based upon nt 3096-3122 of AAV2 [SEQ ID NO:7], 5'-GACTCATCAACAACAACTGGGGATTC-3'. However, one of skill in the art may have readily designed the primer set based upon the corresponding regions of AAV 1, AAV3, AAV4, AAV5, AAV6, or based upon the information provided herein, AAV7, AAV10, AAV11, AAV12, or another novel AAV of the invention. In addition, still other primer sets can be readily designed to amplify this signature region, using techniques known to those of skill in the art.

B. Isolation of Target Sequences

As described herein, the present invention provides a first primer set which specifically amplifies the signature region of the target sequence, e.g., an AAV serotype, in order to permit detection of the target. In a situation in which further sequences are desired, e.g., if a novel AAV serotype is identified, the signature region may be extended. Thus, the invention may further utilize one or more additional primer sets.

Suitably, these primer sets are designed to include either the 5' or 3' primer of the first primer set and a second primer unique to the primer set, such that the primer set amplifies a region 5' or 3' to the signature region which anneals to either the 5' end or the 3' end of the signature region. For example, a first primer set is composed of a 5' primer, P1 and a 3' primer P2 to amplify the signature region. In order to extend the signature region on its 3' end, a second primer set is composed of primer P1 and a 3' primer P4, which amplifies the signature region and contiguous sequences downstream of the signature region. In order to extend the signature region on its 5' end, a third primer set is composed of a 5' primer, P5, and primer P2, such that the signature region and contiguous sequences upstream of the signature region are amplified. These extension steps are repeated (or performed at the same time), as needed or desired. Thereafter, the products results from these amplification steps are fused using conventional steps to produce an isolated sequence of the desired length.

The second and third primer sets are designed, as with the primer set for the signature region, to amplify a region having highly conserved sequences among the aligned sequences. Reference herein to the term "second" or "third" primer set is for each of discussion only, and without regard to the order in which these primers are added to the reaction mixture, or used for amplification. The region amplified by the second primer set is selected so that upon amplification it anneals at its 5' end to the 3' end of the signature region. Similarly, the region amplified by the third primer set is selected so that upon amplification it anneals at its 3' end anneals to the 5' end of the signature region. Additional primer sets can be designed such that the regions which they amplify anneal to the either the 5' end or the 3' end of the extension products formed by the second or third primer sets, or by subsequent primer sets.

For example, where AAV is the target sequence, a first set of primers (P1 and P2) are used to amplify the signature region from the sample. In one desirable embodiment, this signature region is located within the AAV capsid. A second set of primers (P1 and P4) is used to extend the 3' end of the signature region to a location in the AAV sequence which is just before the AAV 3' ITR, i.e., providing an extension product containing the entire 3' end of the AAV capsid when using the signature region as an anchor. In one embodiment, the P4 primer corresponds to nt 4435 to 4462 of AAV2 [SEQ ID NO:7], and corresponding sequences in the other AAV serotypes. This results in amplification of a region of about 1.6 kb, which contains the 0.25 kb signature region. A third set of primers (P3 and P2) is used to extend the 5' end of signature region to a location in the AAV sequences which is in the 3' end of the rep genes, i.e., providing an extension product containing the entire 5' end of the AAV capsid when using the signature region as an anchor. In one embodiment, the P3 primer corresponds to nt 1384 to 1409 of AAV2 [SEQ ID NO:7], and corresponding sequences in the other AAV serotypes. This results in amplification of a region of about 1.7 kb, which contains the 0.25 kb signature region. Optionally, a fourth set of primers are used to further extend the 5' extension product containing the entire 5' end of the AAV capsid to also include the rep sequences. In one embodiment, the primer designated P5 corresponds to nt 108 to 133 of AAV2 [SEQ ID NO:7], and corresponding sequences in the other AAV serotypes and is used in conjunction with the P2 primer.

Following completion of the desired number of extension steps, the various extension products are fused, making use of the signature region as an anchor or marker, to construct an intact sequence. In the example provided herein, AAV sequences containing, at a minimum, an intact AAV cap gene are obtained. Larger sequences may be obtained, depending upon the number of extension steps performed.

Suitably, the extension products are assembled into an intact AAV sequence using methods known to those of skill in the art. For example, the extension products may be digested with DraIII, which cleaves at the DraIII site located within the signature region, to provide restriction fragments which are re-ligated to provide products containing (at a minimum) an intact AAV cap gene. However, other suitable techniques for assembling the extension products into an intact sequence may be utilized. See, generally, Sambrook et al, cited herein.

As an alternative to the multiple extension steps described above, another embodiment of the invention provides for direct amplification of a 3.1 kb fragment which allows isolation of full-length cap sequences. To directly amplify a 3.1 kb full-length cap fragment from NHP tissue and blood DNAs, two other highly conserved regions were identified in AAV genomes for use in PCR amplification of large fragments. A primer within a conserved region located in the middle of the rep gene is utilized (AV1ns: 5' GCTGCGT-CAACTGGACCAATGAGAAC 3', nt of SEQ ID NO:6) in combination with the 3' primer located in another conserved region downstream of the Cap gene (AV2cas: 5' CGCAGA-GACCAAAGTTCAACTGAAACGA 3', SEQ ID NO: 7) for amplification of AAV sequences including the full-length AAV cap. Typically, following amplification, the products are cloned and sequence analysis is performed with an accuracy of 99.9%. Using this method, the inventors have isolated at least 50 capsid clones which have subsequently been characterized. Among them, 37 clones were derived from Rhesus macaque tissues (rh.1-rh.37), 6 clones from cynomologous macaques (cy.1-cy.6), 2 clones from Baboons (bb.1 and bb.2) and 5 clones from Chimps (ch.1-ch.5). These clones are identified elsewhere in the specification, together with the species of animal from which they were identified and the tissues in that animal these novel sequences have been located.

C. Alternative Method for Isolating Novel AAV

In another aspect, the invention provides an alternative method for isolating novel AAV from a cell. This method involves infecting the cell with a vector which provides helper functions to the AAV; isolating infectious clones containing AAV; sequencing the isolated AAV; and comparing the sequences of the isolated AAV to known AAV serotypes, whereby differences in the sequences of the isolated AAV and known AAV serotypes indicates the presence of a novel AAV.

In one embodiment, the vector providing helper functions provides essential adenovirus functions, including, e.g., E1a, E1b, E2a, E4ORF6. In one embodiment, the helper functions are provided by an adenovirus. The adenovirus may be a wild-type adenovirus, and may be of human or non-human origin, preferably non-human primate (NHP) origin. The DNA sequences of a number of adenovirus types are available from Genbank, including type Ad5 [Genbank Accession No. M73260]. The adenovirus sequences may be obtained from any known adenovirus serotype, such as serotypes 2, 3, 4, 7, 12 and 40, and further including any of the presently identified human types [see, e.g., Horwitz, cited above]. Similarly adenoviruses known to infect non-human animals (e.g., chimpanzees) may also be employed in the vector constructs of this invention. See, e.g., U.S. Pat. No. 6,083,716. In addition to wild-type adenoviruses, recombinant viruses or non-viral vectors (e.g., plasmids, episomes, etc.) carrying the necessary helper functions may be utilized. Such recombinant viruses are known in the art and may be prepared according to published techniques. See, e.g., U.S. Pat. Nos. 5,871,982 and 6,251,677, which describe a hybrid Ad/AAV virus. The selection of the adenovirus type is not anticipated to limit the following invention. A variety of adenovirus strains are available from the American Type Culture Collection, Manassas, Va., or available by request from a variety of commercial and institutional sources. Further, the sequences of many such strains are available from a variety of databases including, e.g., PubMed and GenBank.

In another alternative, infectious AAV may be isolated using genome walking technology (Siebert et al., 1995, *Nucleic Acid Research,* 23:1087-1088, Friezner-Degen et al., 1986, *J. Biol. Chem.* 261:6972-6985, BD Biosciences Clontech, Palo Alto, Calif.). Genome walking is particularly well suited for identifying and isolating the sequences adjacent to the novel sequences identified according to the method of the invention. For example, this technique may be useful for isolating inverted terminal repeat (ITRs) of the novel AAV serotype, based upon the novel AAV capsid and/or rep sequences identified using the methods of the invention. This technique is also useful for isolating sequences adjacent to other AAV and non-AAV sequences identified and isolated according to the present invention. See, Examples 3 and 4.

The methods of the invention may be readily used for a variety of epidemiology studies, studies of biodistribution, monitoring of gene therapy via AAV vectors and vector derived from other integrated viruses. Thus, the methods are well suited for use in pre-packaged kits for use by clinicians, researchers, and epidemiologists.

II. Diagnostic Kit

In another aspect, the invention provides a diagnostic kit for detecting the presence of a known or unknown adeno-associated virus (AAV) in a sample. Such a kit may contain a first set of 5' and 3' PCR primers specific for a signature region of the AAV nucleic acid sequence. Alternatively, or additionally, such a kit can contain a first set of 5' and 3' PCR primers specific for the 3.1 kb fragment which includes the full-length AAV capsid nucleic acid sequence identified herein (e.g., the AV1ns and AV2cas primers.) Optionally, a kit of the invention may further contain two or more additional sets of 5' and 3' primers, as described herein, and/or PCR probes. These primers and probes are used according to the present invention amplify signature regions of each AAV serotype, e.g., using quantitative PCR.

The invention further provides a kit useful for identifying an AAV serotype detected according to the method of the invention and/or for distinguishing novel AAV from known AAV. Such a kit may further include one or more restriction enzymes, standards for AAV serotypes providing their "signature restriction enzyme digestions analyses", and/or other means for determining the serotype of the AAV detected.

In addition, kits of the invention may include, instructions, a negative and/or positive control, containers, diluents and buffers for the sample, indicator charts for signature comparisons, disposable gloves, decontamination instructions, applicator sticks or containers, and sample preparator cups, as well as any desired reagents, including media, wash reagents and concentration reagents. Such reagents may be readily selected from among the reagents described herein, and from among conventional concentration reagents. In one desirable embodiment, the wash reagent is an isotonic saline solution which has been buffered to physiologic pH, such as phosphate buffered saline (PBS); the elution reagent is PBS containing 0.4 M NaCl, and the concentration reagents and devices. For example, one of skill in the art will recognize that reagents such as polyethylene glycol (PEG), or $NH_4SO_4$ may be useful, or that devices such as filter devices. For example, a filter device with a 100 K membrane would concentrate rAAV.

The kits provided by the present invention are useful for performing the methods described herein, and for study of biodistribution, epidemiology, mode of transmission of novel AAV serotypes in human and NHPs.

Thus, the methods and kits of the invention permit detection, identification, and isolation of target viral sequences, particularly integrated viral sequences. The methods and kits are particularly well suited for use in detection, identification and isolation of AAV sequences, which may include novel AAV serotypes.

In one notable example, the method of the invention facilitated analysis of cloned AAV sequences by the inventors, which revealed heterogeneity of proviral sequences between cloned fragments from different animals, all of which were distinct from the known six AAV serotypes, with the majority of the variation localized to hypervariable regions of the capsid protein. Surprising divergence of AAV sequences was noted in clones isolated from single tissue sources, such as lymph node, from an individual rhesus monkey. This heterogeneity is best explained by apparent evolution of AAV sequence within individual animals due, in part, to extensive homologous recombination between a limited number of co-infecting parenteral viruses. These studies suggest sequence evolution of widely disseminated virus during the course of a natural AAV infection that presumably leads to the formation of swarms of quasispecies which differ from one another in the array of capsid hypervariable regions. This is the first example of rapid molecular evolution of a DNA virus in a way that formerly was thought to be restricted to RNA viruses.

Sequences of several novel AAV serotypes identified by the method of the invention and characterization of these serotypes is provided.

III. Novel AAV Serotypes

A. Nucleic Acid Sequences

Nucleic acid sequences of novel AAV serotypes identified by the methods of the invention are provided. See, SEQ ID NO:1, 9-59, and 117-120, which are incorporated by reference herein. See also, FIG. 1 and the sequence listing.

For novel serotype AAV7, the full-length sequences, including the AAV 5' ITRs, capsid, rep, and AAV 3' ITRs are provided in SEQ ID NO:1.

For other novel AAV serotypes of the invention, the approximately 3.1 kb fragment isolated according to the method of the invention is provided. This fragment contains sequences encoding full-length capsid protein and all or part of the sequences encoding the rep protein. These sequences include the clones identified below.

For still other novel AAV serotypes, the signature region encoding the capsid protein is provided. For example, the AAV10 nucleic acid sequences of the invention include those illustrated in FIG. 1 [See, SEQ ID NO:117, which spans 255 bases]. The AAV11 nucleic acid sequences of the invention include the DNA sequences illustrated in FIG. 1 [See, SEQ ID NO:118 which spans 258 bases]. The AAV12 nucleic acid sequences of the invention include the DNA sequences illustrated in FIG. 1 [See, SEQ ID NO:119, which consists of 255 bases]. Using the methodology described above, further AAV10, AAV11 and AAV12 sequences can be readily identified and used for a variety of purposes, including those described for AAV7 and the other novel serotypes herein.

FIG. 1 provides the non-human primate (NHP) AAV nucleic acid sequences of the invention in an alignment with the previously published AAV serotypes, AAV 1 [SEQ ID NO:6], AAV2 [SEQ ID NO:7], and AAV3 [SEQ ID NO:8]. These novel NHP sequences include those provided in the following Table I, which are identified by clone number:

TABLE 1

| AAV Cap Sequence | Clone Number | Source Species | Tissue | SEQ ID NO (DNA) |
|---|---|---|---|---|
| Rh. 1 | Clone 9 (AAV9) | Rhesus | Heart | 5 |
| Rh. 2 | Clone 43.1 | Rhesus | MLN | 39 |
| Rh. 3 | Clone 43.5 | Rhesus | MLN | 40 |
| Rh. 4 | Clone 43.12 | Rhesus | MLN | 41 |
| Rh. 5 | Clone 43.20 | Rhesus | MLN | 42 |
| Rh. 6 | Clone 43.21 | Rhesus | MLN | 43 |
| Rh. 7 | Clone 43.23 | Rhesus | MLN | 44 |
| Rh. 8 | Clone 43.25 | Rhesus | MLN | 45 |
| Rh. 9 | Clone 44.1 | Rhesus | Liver | 46 |
| Rh. 10 | Clone 44.2 | Rhesus | Liver | 59 |
| Rh. 11 | Clone 44.5 | Rhesus | Liver | 47 |
| Rh. 12 | Clone 42.1B | Rhesus | MLN | 30 |
| Rh. 13 | 42.2 | Rhesus | MLN | 9 |
| Rh. 14 | Clone 42.3A | Rhesus | MLN | 32 |
| Rh. 15 | Clone 42.3B | Rhesus | MLN | 36 |
| Rh. 16 | Clone 42.4 | Rhesus | MLN | 33 |
| Rh. 17 | Clone 42.5A | Rhesus | MLN | 34 |
| Rh. 18 | Clone 42.5B | Rhesus | MLN | 29 |
| Rh. 19 | Clone 42.6B | Rhesus | MLN | 38 |
| Rh. 20 | Clone 42.8 | Rhesus | MLN | 27 |
| Rh. 21 | Clone 42.10 | Rhesus | MLN | 35 |
| Rh. 22 | Clone 42.11 | Rhesus | MLN | 37 |
| Rh. 23 | Clone 42.12 | Rhesus | MLN | 58 |
| Rh. 24 | Clone 42.13 | Rhesus | MLN | 31 |
| Rh. 25 | Clone 42.15 | Rhesus | MLN | 28 |
| Rh. 26 | Clone 223.2 | Rhesus | Liver | 49 |
| Rh. 27 | Clone 223.4 | Rhesus | Liver | 50 |
| Rh. 28 | Clone 223.5 | Rhesus | Liver | 51 |
| Rh. 29 | Clone 223.6 | Rhesus | Liver | 52 |
| Rh. 30 | Clone 223.7 | Rhesus | Liver | 53 |
| Rh. 31 | Clone 223.10 | Rhesus | Liver | 48 |
| Rh. 32 | Clone C1 | Rhesus | Spleen, Duo, Kid & Liver | 19 |
| Rh. 33 | Clone C3 | Rhesus | | 20 |
| Rh. 34 | Clone C5 | Rhesus | | 21 |
| Rh. 35 | Clone F1 | Rhesus | Liver | 22 |
| Rh. 36 | Clone F3 | Rhesus | | 23 |
| Rh. 37 | Clone F5 | Rhesus | | 24 |
| Cy. 1 | Clone 1.3 | Cyno | Blood | 14 |
| Cy. 2 | Clone 13.3B | Cyno | Blood | 15 |
| Cy. 3 | Clone 24.1 | Cyno | Blood | 16 |
| Cy. 4 | Clone 27.3 | Cyno | Blood | 17 |
| Cy. 5 | Clone 7.2 | Cyno | Blood | 18 |
| Cy. 6 | Clone 16.3 | Cyno | Blood | 10 |
| bb. 1 | Clone 29.3 | Baboon | Blood | 11 |
| bb. 2 | Clone 29.5 | Baboon | Blood | 13 |
| Ch. 1 | Clone A3.3 | Chimp | Blood | 57 |
| Ch. 2 | Clone A3.4 | Chimp | Blood | 54 |
| Ch. 3 | Clone A3.5 | Chimp | Blood | 55 |
| Ch. 4 | Clone A3.7 | Chimp | Blood | 56 |

A novel NHP clone was made by splicing capsids fragments of two chimp adenoviruses into an AAV2 rep construct. This new clone, A3.1, is also termed Ch.5 [SEQ ID NO:20]. Additionally, the present invention includes two human AAV sequences, termed H6 [SEQ ID NO:25] and H2 [SEQ ID NO:26].

The AAV nucleic acid sequences of the invention further encompass the strand which is complementary to the strands provided in the sequences provided in FIG. 1 and the Sequence Listing [SEQ ID NO:1, 9-59, 117-120], nucleic acid sequences, as well as the RNA and cDNA sequences corresponding to the sequences provided in FIG. 1 and the Sequence Listing [SEQ ID NO:1, 9-59, 117-120], and their complementary strands. Also included in the nucleic acid sequences of the invention are natural variants and engineered modifications of the sequences of FIG. 1 and the Sequence Listing [SEQ ID NO:1, 9-59, 117-120], and their complementary strands. Such modifications include, for example, labels which are known in the art, methylation, and substitution of one or more of the naturally occurring nucleotides with a degenerate nucleotide.

Further included in this invention are nucleic acid sequences which are greater than 85%, preferably at least about 90%, more preferably at least about 95%, and most preferably at least about 98 to 99% identical or homologous to the sequences of the invention, including FIG. 1 and the Sequence Listing [SEQ ID NO:1, 9-59, 117-120]. These terms are as defined herein.

Also included within the invention are fragments of the novel AAV sequences identified by the method described herein. Suitable fragments are at least 15 nucleotides in length, and encompass functional fragments, i.e., fragments which are of biological interest. In one embodiment, these fragments are fragments of the novel sequences of FIG. 1 and the Sequence Listing [SEQ ID NO:1, 9-59, 117-120], their complementary strands, cDNA and RNA complementary thereto.

Examples of suitable fragments are provided with respect to the location of these fragments on AAV1, AAV2, or AAV7. However, using the alignment provided herein (obtained using the Clustal W program at default settings), or similar techniques for generating an alignment with other novel serotypes of the invention, one of skill in the art can readily identify the precise nucleotide start and stop codons for desired fragments.

Examples of suitable fragments include the sequences encoding the three variable proteins (vp) of the AAV capsid which are alternative splice variants: vp1 [e.g., nt 825 to 3049 of AAV7, SEQ ID NO: 1]; vp2 [e.g., nt 1234-3049 of AAV7, SEQ ID NO: 1]; and vp 3 [e.g., nt 1434-3049 of AAV7, SEQ ID NO:1]. It is notable that AAV7 has an unusual GTG start codon. With the exception of a few house-keeping genes, such a start codon has not previously been reported in DNA viruses. The start codons for vp1, vp2 and vp3 for other AAV serotypes have been believed to be such that they permit the cellular mechanism of the host cell in which they reside to produce vp1, vp2 and vp3 in a ratio of 10%:10%:80%, respectively, in order to permit efficient assembly of the virion. However, the AAV7 virion has been found to assemble efficiently even with this rare GTG start codon. Thus, the inventors anticipate this it is desirable to alter the start codon of the vp3 of other AAV serotypes to contain this rare GTG start codon, in order to improve packaging efficiency, to alter the virion structure and/or to alter location of epitopes (e.g., neutralizing antibody epitopes) of other AAV serotypes. The start codons may be altered using conventional techniques including, e.g., site directed mutagenesis. Thus, the present invention encompasses altered AAV virions of any selected serotype, composed of a vp 3, and/or optionally, vp 1 and/or vp2 having start codons altered to GTG.

Other suitable fragments of AAV, include a fragment containing the start codon for the AAV capsid protein [e.g., nt 468 to 3090 of AAV7, SEQ ID NO:1, nt 725 to 3090 of AAV7, SEQ ID NO: 1, and corresponding regions of the other AAV serotypes]. Still other fragments of AAV7 and the other novel AAV serotypes identified using the methods described herein include those encoding the rep proteins, including rep 78 [e.g., initiation codon 334 of FIG. 1 for AAV7], rep 68 [initiation codon nt 334 of FIG. 1 for AAV7], rep 52 [initiation codon 1006 of FIG. 1 for AAV7], and rep 40 [initiation codon 1006 of FIG. 1 for AAV7] Other fragments of interest may include the AAV 5' inverted terminal repeats ITRs, [nt 1 to 107 of FIG. 1 for AAV7]; the AAV 3' ITRs [nt 4704 to 4721 of FIG. 1 for AAV7], P19 sequences, AAV P40 sequences, the rep binding site, and the terminal resolute site (TRS). Still other suitable fragments will be readily apparent to those of skill in the art. The corresponding regions in the other novel serotypes of the invention can be readily determined by reference to FIG. 1, or by utilizing conventional alignment techniques with the sequences provided herein.

In addition to including the nucleic acid sequences provided in the figures and Sequence Listing, the present invention includes nucleic acid molecules and sequences which are designed to express the amino acid sequences, proteins and peptides of the AAV serotypes of the invention. Thus, the invention includes nucleic acid sequences which encode the following novel AAV amino acid sequences: C1 [SEQ ID NO:60], C2 [SEQ ID NO:61], C5 [SEQ ID NO:62], A3-3 [SEQ ID NO:66], A3-7 [SEQ ID NO:67], A3-4 [SEQ ID NO:68], A3-5 [SEQ ID NO: 69], 3.3b [SEQ ID NO: 62], 223.4 [SEQ ID NO: 73], 223-5 [SEQ ID NO:74], 223-10 [SEQ ID NO:75], 223-2 [SEQ ID NO:76], 223-7 [SEQ ID NO: 77], 223-6 [SEQ ID NO: 78], 44-1 [SEQ ID NO: 79], 44-5 [SEQ ID NO:80], 44-2 [SEQ ID NO:81], 42-15 [SEQ ID NO: 84], 42-8 [SEQ ID NO: 85], 42-13 [SEQ ID NO:86], 42-3A [SEQ ID NO:87], 42-4 [SEQ ID NO:88], 42-5A [SEQ ID NO:89], 42-1B [SEQ ID NO:90], 42-5B [SEQ ID NO:91], 43-1 [SEQ ID NO: 92], 43-12 [SEQ ID NO: 93], 43-5 [SEQ ID NO:94], 43-21 [SEQ ID NO:96], 43-25 [SEQ ID NO: 97], 43-20 [SEQ ID NO:99], 24.1 [SEQ ID NO: 101], 42.2 [SEQ ID NO:102], 7.2 [SEQ ID NO: 103], 27.3 [SEQ ID NO: 104], 16.3 [SEQ ID NO: 105], 42.10 [SEQ ID NO: 106], 42-3B [SEQ ID NO: 107], 42-11 [SEQ ID NO: 108], F1 [SEQ ID NO: 109], F5 [SEQ ID NO: 110], F3 [SEQ ID NO:111], 42-6B [SEQ ID NO: 112], and/or 42-12 [SEQ ID NO: 113], and artificial AAV serotypes generated using these sequences and/or unique fragments thereof.

As used herein, artificial AAV serotypes include, without limitation, AAV with a non-naturally occurring capsid protein. Such an artificial capsid may be generated by any suitable technique, using a novel AAV sequence of the invention (e.g., a fragment of a vp1 capsid protein) in combination with heterologous sequences which may be obtained from another AAV serotype (known or novel), non-contiguous portions of the same AAV serotype, from a non-AAV viral source, or from a non-viral source. An artificial AAV serotype may be, without limitation, a chimeric AAV capsid, a recombinant AAV capsid, or a "humanized" AAV capsid.

B. AAV Amino Acid Sequences, Proteins and Peptides

The invention provides proteins and fragments thereof which are encoded by the nucleic acid sequences of the novel AAV serotypes identified herein, including, e.g., AAV7 [nt 825 to 3049 of AAV7, SEQ ID NO: 1] the other novel serotypes provided herein. Thus, the capsid proteins of the novel serotypes of the invention, including: H6 [SEQ ID NO: 25], H2 [SEQ ID NO: 26], 42-2 [SEQ ID NO:9], 42-8 [SEQ ID NO:27], 42-15 [SEQ ID NO:28], 42-5b [SEQ ID NO: 29], 42-1b [SEQ ID NO:30]; 42-13 [SEQ ID NO: 31], 42-3a [SEQ ID NO: 32], 42-4 [SEQ ID NO:33], 42-5a [SEQ ID NO: 34], 42-10 [SEQ ID NO:35], 42-3b [SEQ ID NO: 36], 42-11 [SEQ ID NO: 37], 42-6b [SEQ ID NO:38], 43-1 [SEQ ID NO: 39], 43-5 [SEQ ID NO: 40], 43-12 [SEQ ID NO:41], 43-20 [SEQ ID NO: 42], 43-21 [SEQ ID NO: 43], 43-23 [SEQ ID NO:44], 43-25 [SEQ ID NO: 45], 44.1 [SEQ ID NO:47], 44.5 [SEQ ID NO:47], 223.10 [SEQ ID NO:48], 223.2 [SEQ ID NO:49], 223.4 [SEQ ID NO:50], 223.5 [SEQ ID NO: 51], 223.6 [SEQ ID NO: 52], 223.7 [SEQ ID NO: 53], A3.4 [SEQ ID NO: 54], A3.5 [SEQ ID NO:55], A3.7 [SEQ ID NO: 56], A3.3 [SEQ ID NO:57], 42.12 [SEQ ID NO: 58], and 44.2 [SEQ ID NO: 59], can be readily generated using conventional techniques from the open reading frames provided for the above-listed clones.

The invention further encompasses AAV serotypes generated using sequences of the novel AAV serotypes of the invention, which are generated using synthetic, recombinant or other techniques known to those of skill in the art. The invention is not limited to novel AAV amino acid sequences, peptides and proteins expressed from the novel AAV nucleic acid sequences of the invention and encompasses amino acid sequences, peptides and proteins generated by other methods known in the art, including, e.g., by chemical synthesis, by other synthetic techniques, or by other methods. For example, the sequences of any of C1 [SEQ ID NO:60], C2 [SEQ ID NO:61], C5 [SEQ ID NO:62], A3-3 [SEQ ID NO:66], A3-7 [SEQ ID NO:67], A3-4 [SEQ ID NO:68], A3-5 [SEQ ID NO: 69], 3.3b [SEQ ID NO: 62], 223.4 [SEQ ID NO: 73], 223-5 [SEQ ID NO:74], 223-10 [SEQ ID NO:75], 223-2 [SEQ ID NO:76], 223-7 [SEQ ID NO: 77], 223-6 [SEQ ID NO: 78], 44-1 [SEQ ID NO: 79], 44-5 [SEQ ID NO:80], 44-2 [SEQ ID NO:81], 42-15 [SEQ ID NO: 84], 42-8 [SEQ ID NO: 85], 42-13 [SEQ ID NO:86], 42-3A [SEQ ID NO:87], 42-4 [SEQ ID NO:88], 42-5A [SEQ ID NO:89], 42-1B [SEQ ID NO:90], 42-5B [SEQ ID NO:91], 43-1 [SEQ ID NO: 92], 43-12 [SEQ ID NO: 93], 43-5 [SEQ ID NO:94], 43-21 [SEQ ID NO:96], 43-25 [SEQ ID NO: 97], 43-20 [SEQ ID NO:99], 24.1 [SEQ ID NO: 101], 42.2 [SEQ ID NO:102], 7.2 [SEQ ID NO: 103], 27.3 [SEQ ID NO: 104], 16.3 [SEQ ID NO: 105], 42.10 [SEQ ID NO: 106], 42-3B [SEQ ID NO: 107], 42-11 [SEQ ID NO: 108], F1 [SEQ ID NO: 109], F5 [SEQ ID NO: 110], F3 [SEQ ID NO:111], 42-6B [SEQ ID NO: 112], and/or 42-12 [SEQ ID NO: 113] by be readily generated using a variety of techniques.

Suitable production techniques are well known to those of skill in the art. See, e.g., Sambrook et al, Molecular Cloning: A Laboratory Manual, Cold Spring Harbor Press (Cold Spring Harbor, N.Y.). Alternatively, peptides can also be synthesized by the well known solid phase peptide synthesis methods (Merrifield, J. Am. Chem. Soc., 85:2149 (1962); Stewart and Young, Solid Phase Peptide Synthesis (Freeman, San Francisco, 1969) pp. 27-62). These and other suitable production methods are within the knowledge of those of skill in the art and are not a limitation of the present invention.

Particularly desirable proteins include the AAV capsid proteins, which are encoded by the nucleotide sequences identified above. The sequences of many of the capsid proteins of the invention are provided in an alignment in FIG. 2 and/or in the Sequence Listing, SEQ ID NO: 2 and 60 to 115, which is incorporated by reference herein. The AAV capsid is composed of three proteins, vp1, vp2 and vp3, which are alternative splice variants. The full-length sequence provided in these figures is that of vp1. Based on the numbering of the AAV7 capsid [SEQ ID NO:2], the sequences of vp2 span amino acid 138-737 of AAV7 and the sequences of vp3 span amino acids 203-737 of AAV7. With this information, one of skill in the art can readily determine the location of the vp2 and vp3 proteins for the other novel serotypes of the invention.

Other desirable proteins and fragments of the capsid protein include the constant and variable regions, located between hypervariable regions (HPV) and the sequences of the HPV regions themselves. An algorithm developed to determine areas of sequence divergence in AAV2 has yielded 12 hypervariable regions (HVR) of which 5 overlap or are part of the four previously described variable regions. [Chiorini et al, J. Virol, 73:1309-19 (1999); Rutledge et al, J. Virol., 72:309-319] Using this algorithm and/or the alignment techniques described herein, the HVR of the novel AAV serotypes are determined. For example, with respect to the number of the AAV2 vp1 [SEQ ID NO:70], the HVR are located as follows: HVR1, aa 146-152; HVR2, aa 182-186; HVR3, aa 262-264; HVR4, aa 381-383; HVR5, aa 450-474; HVR6, aa 490-495; HVR7, aa500-504; HVR5, aa 514-522; HVR9, aa 534-555; HVR10, aa 581-594; HVR11, aa 658-667; and HVR12, aa 705-719. Utilizing an alignment prepared in accordance with conventional methods and the novel sequences provided herein [See, e.g., FIG. 2], one can readily determine the location of the HVR in the novel AAV serotypes of the invention. For example, utilizing FIG. 2, one can readily determine that for AAV7 [SEQ ID NO:2]. HVR1 is located at aa 146-152; HVR2 is located at 182-187; HVR3 is located at aa 263-266, HVR4 is located at aa 383-385, HVR5 is located at aa 451-475; HVR6 is located at aa 491-496 of AAV7; HVR7 is located at aa 501-505; HVR8 is located at aa 513-521; HVR9 is located at 533-554; HVR10 is located at aa 583-596; HVR11 is located at aa 660-669; HVR12 is located at aa 707-721. Using the information provided herein, the HVRs for the other novel serotypes of the invention can be readily determined.

In addition, within the capsid, amino acid cassettes of identity have been identified. These cassettes are of particular interest, as they are useful in constructing artificial serotypes, e.g., by replacing a HVR1 cassette of a selected serotype with an HVR1 cassette of another serotype. Certain of these cassettes of identity are noted in FIG. 2. See, FIG. 2, providing the Clustal X alignment, which has a ruler is displayed below the sequences, starting at 1 for the first residue position. The line above the ruler is used to mark strongly conserved positions. Three characters (*, :, .) are used. "*" indicates positions which have a single, fully conserved residue. ":" indicates that a "strong" group is fully conserved "." Indicates that a "weaker" group is fully conserved. These are all the positively scoring groups that occur in the Gonnet Pam250 matrix. The strong groups are defined as a strong score >0.5 and the weak groups are defined as weak score <0.5.

Additionally, examples of other suitable fragments of AAV capsids include, with respect to the numbering of AAV2 [SEQ ID NO:70], aa 24-42, aa 25-28; aa 81-85; aa133-165; aa 134-165; aa 137-143; aa 154-156; aa 194-208; aa 261-274; aa 262-274; aa 171-173; aa 413-417; aa 449-478; aa 494-525; aa 534-571; aa 581-601; aa 660-671; aa 709-723. Still other desirable fragments include, for example, in AAV7, amino acids 1 to 184 of SEQ ID NO:2, amino acids 199 to 259; amino acids 274 to 446; amino acids 603 to 659; amino acids 670 to 706; amino acids 724 to 736; aa 185 to 198; aa 260 to 273; aa447 to 477; aa495 to 602; aa660 to 669; and aa707 to 723. Still other desirable regions, based on the numbering of AAV7 [SEQ ID NO:2], are selected from among the group consisting of aa 185 to 198; aa 260 to 273; aa447 to 477; aa495 to 602; aa660 to 669; and aa707 to 723. Using the alignment provided herein performed using the Clustal X program at default settings, or using other commercially or publicly available alignment programs at default settings, one of skill in the art can readily determine corresponding fragments of the novel AAV capsids of the invention.

Other desirable proteins are the AAV rep proteins [aa 1 to 623 of SEQ ID NO:3 for AAV7] and functional fragments thereof, including, e.g., aa 1 to 171, aa 172 to 372, aa 373 to 444, aa 445 to 623 of SEQ ID NO:3, among others. Suitably, such fragments are at least 8 amino acids in length. See, FIG. 3. Comparable regions can be identified in the proteins of the other novel AAV of the invention, using the techniques described herein and those which are known in the art. In addition, fragments of other desired lengths may be readily utilized. Such fragments may be produced recombinantly or by other suitable means, e.g., chemical synthesis.

The sequences, proteins, and fragments of the invention may be produced by any suitable means, including recombinant production, chemical synthesis, or other synthetic means. Such production methods are within the knowledge of those of skill in the art and are not a limitation of the present invention.

IV. Production of rAAV with Novel AAV Capsids

The invention encompasses novel, wild-type AAV serotypes identified by the invention, the sequences of which wild-type AAV serotypes are free of DNA and/or cellular material with these viruses are associated in nature. In another aspect, the present invention provides molecules which utilize the novel AAV sequences of the invention, including fragments thereof, for production of molecules useful in delivery of a heterologous gene or other nucleic acid sequences to a target cell.

The molecules of the invention which contain sequences of a novel AAV serotype of the invention include any genetic element (vector) which may be delivered to a host cell, e.g., naked DNA, a plasmid, phage, transposon, cosmid, episome, a protein in a non-viral delivery vehicle (e.g., a lipid-based carrier), virus, etc. which transfer the sequences carried thereon. The selected vector may be delivered by any suitable method, including transfection, electroporation, liposome delivery, membrane fusion techniques, high velocity DNA-coated pellets, viral infection and protoplast fusion. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y.

In one embodiment, the vectors of the invention contain sequences encoding a novel AAV capsid of the invention (e.g., AAV7 capsid, AAV 44-2 (rh.10), an AAV10 capsid, an AAV11 capsid, an AAV12 capsid), or a fragment of one or more of these AAV capsids. Alternatively, the vectors may contain the capsid protein, or a fragment thereof, itself.

Optionally, vectors of the invention may contain sequences encoding AAV rep proteins. Such rep sequences may be from the same AAV serotype which is providing the cap sequences. Alternatively, the present invention provides vectors in which the rep sequences are from an AAV serotype which differs from that which is providing the cap sequences. In one embodiment, the rep and cap sequences are expressed from separate sources (e.g., separate vectors, or a host cell and a vector). In another embodiment, these rep sequences are expressed from the same source as the cap sequences. In this embodiment, the rep sequences may be fused in frame to cap sequences of a different AAV serotype to form a chimeric AAV vector. Optionally, the vectors of the invention further contain a minigene comprising a selected transgene which is flanked by AAV 5' ITR and AAV 3' ITR.

Thus, in one embodiment, the vectors described herein contain nucleic acid sequences encoding an intact AAV capsid which may be from a single AAV serotype (e.g., AAV7 or another novel AAV). Alternatively, these vectors contain sequences encoding artificial capsids which contain one or more fragments of the AAV7 (or another novel AAV) capsid fused to heterologous AAV or non-AAV capsid proteins (or fragments thereof). These artificial capsid proteins are selected from non-contiguous portions of the AAV7 (or another novel AAV) capsid or from capsids of other AAV serotypes. For example, it may be desirable to modify the coding regions of one or more of the AAV vp1, e.g., in one or more of the hypervariable regions (i.e., HPV1-12), or vp2, and/or vp3. In another example, it may be desirable to alter the start codon of the vp3 protein to GTG. These modifications may be to increase expression, yield, and/or to improve purification in the selected expression systems, or for another desired purpose (e.g., to change tropism or alter neutralizing antibody epitopes).

The vectors described herein, e.g., a plasmid, are useful for a variety of purposes, but are particularly well suited for use in production of a rAAV containing a capsid comprising AAV sequences or a fragment thereof. These vectors, including rAAV, their elements, construction, and uses are described in detail herein.

In one aspect, the invention provides a method of generating a recombinant adeno-associated virus (AAV) having an AAV serotype 7 (or another novel AAV) capsid, or a portion thereof. Such a method involves culturing a host cell which contains a nucleic acid sequence encoding an adeno-associated virus (AAV) serotype 7 (or another novel AAV) capsid protein, or fragment thereof, as defined herein; a functional rep gene; a minigene composed of, at a minimum, AAV inverted terminal repeats (ITRs) and a transgene; and sufficient helper functions to permit packaging of the minigene into the AAV7 (or another novel AAV) capsid protein.

The components required to be cultured in the host cell to package an AAV minigene in an AAV capsid may be provided to the host cell in trans. Alternatively, any one or more of the required components (e.g., minigene, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

The minigene, rep sequences, cap sequences, and helper functions required for producing the rAAV of the invention may be delivered to the packaging host cell in the form of any genetic element which transfer the sequences carried thereon. The selected genetic element may be delivered by any suitable method, including those described herein. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. See, e.g., K. Fisher et al, *J. Virol.,* 70:520-532 (1993) and U.S. Pat. No. 5,478,745.

A. The Minigene

The minigene is composed of, at a minimum, a transgene and its regulatory sequences, and 5= and 3=AAV inverted terminal repeats (ITRs). It is this minigene which is packaged into a capsid protein and delivered to a selected host cell.

1. The Transgene

The transgene is a nucleic acid sequence, heterologous to the vector sequences flanking the transgene, which encodes a polypeptide, protein, or other product, of interest. The nucleic acid coding sequence is operatively linked to regulatory components in a manner which permits transgene transcription, translation, and/or expression in a host cell.

The composition of the transgene sequence will depend upon the use to which the resulting vector will be put. For example, one type of transgene sequence includes a reporter sequence, which upon expression produces a detectable signal. Such reporter sequences include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc.

These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for beta-galactosidase activity. Where the transgene is green fluorescent protein or luciferase, the vector carrying the signal may be measured visually by color or light production in a luminometer.

However, desirably, the transgene is a non-marker sequence encoding a product which is useful in biology and medicine, such as proteins, peptides, RNA, enzymes, or catalytic RNAs. Desirable RNA molecules include tRNA, dsRNA, ribosomal RNA, catalytic RNAs, and antisense RNAs. One example of a useful RNA sequence is a sequence which extinguishes expression of a targeted nucleic acid sequence in the treated animal.

The transgene may be used to correct or ameliorate gene deficiencies, which may include deficiencies in which normal genes are expressed at less than normal levels or deficiencies in which the functional gene product is not expressed. A preferred type of transgene sequence encodes a therapeutic protein or polypeptide which is expressed in a host cell. The invention further includes using multiple transgenes, e.g., to correct or ameliorate a gene defect caused by a multi-subunit protein. In certain situations, a different transgene may be used to encode each subunit of a protein, or to encode different peptides or proteins. This is desirable when the size of the DNA encoding the protein subunit is large, e.g., for an immunoglobulin, the platelet-derived growth factor, or a dystrophin protein. In order for the cell to produce the multi-subunit protein, a cell is infected with the recombinant virus containing each of the different subunits. Alternatively, different subunits of a protein may be encoded by the same transgene. In this case, a single transgene includes the DNA encoding each of the subunits, with the DNA for each subunit separated by an internal ribozyme entry site (IRES). This is desirable when the size of the DNA encoding each of the subunits is small, e.g., the total size of the DNA encoding the subunits and the IRES is less than five kilobases. As an alternative to an IRES, the DNA may be separated by sequences encoding a 2A peptide, which self-cleaves in a post-translational event. See, e.g., M. L. Donnelly, et al, *J. Gen. Vivol.,* 78(Pt 1):13-21 (January 1997); Furler, S., et al, *Gene Ther.,* 8(11):864-873 (June 2001); Klump H., et al., *Gene Ther.,* 8(10):811-817 (May 2001). This 2A peptide is significantly smaller than an IRES, making it well suited for use when space is a limiting factor. However, the selected transgene may encode any biologically active product or other product, e.g., a product desirable for study.

Suitable transgenes may be readily selected by one of skill in the art. The selection of the transgene is not considered to be a limitation of this invention.

2. Regulatory Elements

In addition to the major elements identified above for the minigene, the vector also includes conventional control elements necessary which are operably linked to the transgene in a manner which permits its transcription, translation and/or expression in a cell transfected with the plasmid vector or infected with the virus produced by the invention. As used herein, Aoperably linked≅ sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, *Cell,* 41:521-530 (1985)], the SV40 promoter, the dihydrofolate reductase promoter, the β-actin promoter, the phosphoglycerol kinase (PGK) promoter, and the EF1α promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system [WO 98/10088]; the ecdysone insect promoter [No et al, *Proc. Natl. Acad. Sci. USA*, 93:3346-3351 (1996)], the tetracycline-repressible system [Gossen et al, *Proc. Natl. Acad. Sci. USA*, 89:5547-5551 (1992)], the tetracycline-inducible system [Gossen et al, *Science*, 268:1766-1769 (1995), see also Harvey et al, *Curr. Opin. Chem. Biol.*, 2:512-518 (1998)], the RU486-inducible system [Wang et al, *Nat. Biotech.*, 15:239-243 (1997) and Wang et al, *Gene Ther.*, 4:432-441 (1997)] and the rapamycin-inducible system [Magari et al, *J. Clin. Invest.*, 100:2865-2872 (1997)]. Still other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Another embodiment of the transgene includes a transgene operably linked to a tissue-specific promoter. For instance, if expression in skeletal muscle is desired, a promoter active in muscle should be used. These include the promoters from genes encoding skeletal β-actin, myosin light chain 2A, dystrophin, muscle creatine kinase, as well as synthetic muscle promoters with activities higher than naturally-occurring promoters (see Li et al., *Nat. Biotech.*, 17:241-245 (1999)). Examples of promoters that are tissue-specific are known for liver (albumin, Miyatake et al., *J. Vivol.*, 71:5124-32 (1997); hepatitis B virus core promoter, Sandig et al., *Gene Ther.*, 3:1002-9 (1996); alpha-fetoprotein (AFP), Arbuthnot et al., *Hum. Gene Ther.*, 7:1503-14 (1996)), bone osteocalcin (Stein et al., *Mol. Biol. Rep.*, 24:185-96 (1997)); bone sialoprotein (Chen et al., *J. Bone Miner. Res.*, 11:654-64 (1996)), lymphocytes (CD2, Hansal et al., *J. Immunol.*, 161:1063-8 (1998); immunoglobulin heavy chain; T cell receptor a chain), neuronal such as neuron-specific enolase (NSE) promoter (Andersen et al., *Cell. Mol. Neurobiol.*, 13:503-15 (1993)), neurofilament light-chain gene (Piccioli et al., *Proc. Natl. Acad. Sci. USA*, 88:5611-5 (1991)), and the neuron-specific vgf gene (Piccioli et al., *Neuron*, 15:373-84 (1995)), among others.

Optionally, plasmids carrying therapeutically useful transgenes may also include selectable markers or reporter genes may include sequences encoding geneticin, hygromicin or purimycin resistance, among others. Such selectable reporters or marker genes (preferably located outside the viral genome to be rescued by the method of the invention) can be used to signal the presence of the plasmids in bacterial cells, such as ampicillin resistance. Other components of the plasmid may include an origin of replication. Selection of these and other promoters and vector elements are conventional and many such sequences are available [see, e.g., Sambrook et al, and references cited therein].

The combination of the transgene, promoter/enhancer, and 5= and 3=ITRs is referred to as a "minigene" for ease of reference herein. Provided with the teachings of this invention, the design of such a minigene can be made by resort to conventional techniques.

3. Delivery of the Minigene to a Packaging Host Cell

The minigene can be carried on any suitable vector, e.g., a plasmid, which is delivered to a host cell. The plasmids useful in this invention may be engineered such that they are suitable for replication and, optionally, integration in prokaryotic cells, mammalian cells, or both. These plasmids (or other vectors carrying the 5' AAV ITR-heterologous molecule-3'ITR) contain sequences permitting replication of the minigene in eukaryotes and/or prokaryotes and selection markers for these systems. Selectable markers or reporter genes may include sequences encoding geneticin, hygromicin or purimycin resistance, among others. The plasmids may also contain certain selectable reporters or marker genes that can be used to signal the presence of the vector in bacterial cells, such as ampicillin resistance. Other components of the plasmid may include an origin of replication and an amplicon, such as the amplicon system employing the Epstein Barr virus nuclear antigen. This amplicon system, or other similar amplicon components permit high copy episomal replication in the cells. Preferably, the molecule carrying the minigene is transfected into the cell, where it may exist transiently. Alternatively, the minigene (carrying the 5' AAV ITR-heterologous molecule-3' ITR) may be stably integrated into the genome of the host cell, either chromosomally or as an episome. In certain embodiments, the minigene may be present in multiple copies, optionally in head-to-head, head-to-tail, or tail-to-tail concatamers. Suitable transfection techniques are known and may readily be utilized to deliver the minigene to the host cell.

Generally, when delivering the vector comprising the minigene by transfection, the vector is delivered in an amount from about 5 μg to about 100 μg DNA, and preferably about 10 to about 50 μg DNA to about $1\times10^4$ cells to about $1\times10^{13}$ cells, and preferably about $10^5$ cells. However, the relative amounts of vector DNA to host cells may be adjusted, taking into consideration such factors as the selected vector, the delivery method and the host cells selected.

B. Rep and Cap Sequences

In addition to the minigene, the host cell contains the sequences which drive expression of the novel AAV capsid protein (e.g., AAV7 or other novel AAV capsid or an artificial capsid protein comprising a fragment of one or more of these capsids) in the host cell and rep sequences of the same serotype as the serotype of the AAV ITRs found in the minigene. The AAV cap and rep sequences may be independently obtained from an AAV source as described above and may be introduced into the host cell in any manner known to one in the art as described above. Additionally, when pseudotyping a novel AAV capsid of the invention, the sequences encoding each of the essential rep proteins may be supplied by the same AAV serotype, or the sequences encoding the rep proteins may be supplied by different AAV serotypes (e.g., AAV1, AAV2, AAV3, AAV4, AAV5, AAV6, or one of the novel serotypes identified herein). For example, the rep78/68 sequences may be from AAV2, whereas the rep52/40 sequences may from AAV1.

In one embodiment, the host cell stably contains the capsid protein under the control of a suitable promoter, such as those described above. Most desirably, in this embodiment, the capsid protein is expressed under the control of an inducible promoter. In another embodiment, the capsid protein is supplied to the host cell in trans. When delivered to the host cell in trans, the capsid protein may be delivered via a plasmid which contains the sequences necessary to direct expression of the selected capsid protein in the host cell. Most desirably, when delivered to the host cell in trans, the plasmid carrying the capsid protein also carries other sequences required for packaging the rAAV, e.g., the rep sequences.

In another embodiment, the host cell stably contains the rep sequences under the control of a suitable promoter, such as those described above. Most desirably, in this embodiment, the essential rep proteins are expressed under the control of an inducible promoter. In another embodiment, the rep proteins are supplied to the host cell in trans. When delivered to the host cell in trans, the rep proteins may be delivered via a plasmid which contains the sequences necessary to direct expression of the selected rep proteins in the host cell. Most desirably, when delivered to the host cell in trans, the plasmid carrying the capsid protein also carries other sequences required for packaging the rAAV, e.g., the rep and cap sequences.

Thus, in one embodiment, the rep and cap sequences may be transfected into the host cell on a single nucleic acid molecule and exist stably in the cell as an episome. In another embodiment, the rep and cap sequences are stably integrated into the genome of the cell. Another embodiment has the rep and cap sequences transiently expressed in the host cell. For example, a useful nucleic acid molecule for such transfection comprises, from 5' to 3', a promoter, an optional spacer interposed between the promoter and the start site of the rep gene sequence, an AAV rep gene sequence, and an AAV cap gene sequence.

Optionally, the rep and/or cap sequences may be supplied on a vector that contains other DNA sequences that are to be introduced into the host cells. For instance, the vector may contain the rAAV construct comprising the minigene. The vector may comprise one or more of the genes encoding the helper functions, e.g., the adenoviral proteins E1, E2a, and E4ORF6, and the gene for VAI RNA.

Preferably, the promoter used in this construct may be any of the constitutive, inducible or native promoters known to one of skill in the art or as discussed above. In one embodiment, an AAV P5 promoter sequence is employed. The selection of the AAV to provide any of these sequences does not limit the invention.

In another preferred embodiment, the promoter for rep is an inducible promoter, as are discussed above in connection with the transgene regulatory elements. One preferred promoter for rep expression is the T7 promoter. The vector comprising the rep gene regulated by the T7 promoter and the cap gene, is transfected or transformed into a cell which either constitutively or inducibly expresses the T7 polymerase. See WO 98/10088, published Mar. 12, 1998.

The spacer is an optional element in the design of the vector. The spacer is a DNA sequence interposed between the promoter and the rep gene ATG start site. The spacer may have any desired design; that is, it may be a random sequence of nucleotides, or alternatively, it may encode a gene product, such as a marker gene. The spacer may contain genes which typically incorporate start/stop and polyA sites. The spacer may be a non-coding DNA sequence from a prokaryote or eukaryote, a repetitive non-coding sequence, a coding sequence without transcriptional controls or a coding sequence with transcriptional controls. Two exemplary sources of spacer sequences are the phage ladder sequences or yeast ladder sequences, which are available commercially, e.g., from Gibco or Invitrogen, among others. The spacer may be of any size sufficient to reduce expression of the rep78 and rep68 gene products, leaving the rep52, rep40 and cap gene products expressed at normal levels. The length of the spacer may therefore range from about 10 bp to about 10.0 kbp, preferably in the range of about 100 bp to about 8.0 kbp. To reduce the possibility of recombination, the spacer is preferably less than 2 kbp in length; however, the invention is not so limited.

Although the molecule(s) providing rep and cap may exist in the host cell transiently (i.e., through transfection), it is preferred that one or both of the rep and cap proteins and the promoter(s) controlling their expression be stably expressed in the host cell, e.g., as an episome or by integration into the chromosome of the host cell. The methods employed for constructing embodiments of this invention are conventional genetic engineering or recombinant engineering techniques such as those described in the references above. While this specification provides illustrative examples of specific constructs, using the information provided herein, one of skill in the art may select and design other suitable constructs, using a choice of spacers, P5 promoters, and other elements, including at least one translational start and stop signal, and the optional addition of polyadenylation sites.

In another embodiment of this invention, the rep or cap protein may be provided stably by a host cell.

C. The Helper Functions

The packaging host cell also requires helper functions in order to package the rAAV of the invention. Optionally, these functions may be supplied by a herpesvirus. Most desirably, the necessary helper functions are each provided from a human or non-human primate adenovirus source, such as those described above and/or are available from a variety of sources, including the American Type Culture Collection (ATCC), Manassas, Va. (US). In one currently preferred embodiment, the host cell is provided with and/or contains an E1a gene product, an E1b gene product, an E2a gene product, and/or an E4 ORF6 gene product. The host cell may contain other adenoviral genes such as VAI RNA, but these genes are not required. In a preferred embodiment, no other adenovirus genes or gene functions are present in the host cell.

By Aadenoviral DNA which expresses the E1a gene product≡, it is meant any adenovirus sequence encoding E1a or any functional E1a portion. Adenoviral DNA which expresses the E2a gene product and adenoviral DNA which expresses the E4 ORF6 gene products are defined similarly. Also included are any alleles or other modifications of the adenoviral gene or functional portion thereof. Such modifications may be deliberately introduced by resort to conventional genetic engineering or mutagenic techniques to enhance the adenoviral function in some manner, as well as naturally occurring allelic variants thereof. Such modifications and methods for manipulating DNA to achieve these adenovirus gene functions are known to those of skill in the art.

The adenovirus E1a, E1b, E2a, and/or E4ORF6 gene products, as well as any other desired helper functions, can be provided using any means that allows their expression in a cell. Each of the sequences encoding these products may be on a separate vector, or one or more genes may be on the same vector. The vector may be any vector known in the art or disclosed above, including plasmids, cosmids and viruses. Introduction into the host cell of the vector may be achieved by any means known in the art or as disclosed above, including transfection, infection, electroporation, liposome delivery, membrane fusion techniques, high velocity DNA-coated pellets, viral infection and protoplast fusion, among others. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently. Furthermore, the promoters for each of the adenoviral genes may be selected independently from a constitutive promoter, an inducible promoter or a native adenoviral promoter. The promoters may be regulated by a specific physiological state of the organism or cell (i.e., by the differentiation state or in replicating or quiescent cells) or by exogenously-added factors, for example.

D. Host Cells and Packaging Cell Lines

The host cell itself may be selected from any biological organism, including prokaryotic (e.g., bacterial) cells, and eukaryotic cells, including, insect cells, yeast cells and mammalian cells. Particularly desirable host cells are selected from among any mammalian species, including, without limitation, cells such as A549, WEHI, 3T3, 10T1/2, BHK, MDCK, COS 1, COS 7, BSC 1, BSC 40, BMT 10, VERO, WI38, HeLa, 293 cells (which express functional adenoviral E1), Saos, C2C12, L cells, HT1080, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc. The most desirable cells do not carry any adenovirus gene other than E1, E2a and/or E4 ORF6; nor do they contain any other virus gene which could result in homologous recombination of a contaminating virus during the production of rAAV; and it is capable of infection or transfection of DNA and expression of the transfected DNA. In a preferred embodiment, the host cell is one that has rep and cap stably transfected in the cell.

One host cell useful in the present invention is a host cell stably transformed with the sequences encoding rep and cap, and which is transfected with the adenovirus E1, E2a, and E4ORF6 DNA and a construct carrying the minigene as described above. Stable rep and/or cap expressing cell lines, such as B-50 (PCT/US98/19463), or those described in U.S. Pat. No. 5,658,785, may also be similarly employed. Another desirable host cell contains the minimum adenoviral DNA which is sufficient to express E4 ORF6. Yet other cell lines can be constructed using the novel AAV rep and/or novel AAV cap sequences of the invention.

The preparation of a host cell according to this invention involves techniques such as assembly of selected DNA sequences. This assembly may be accomplished utilizing conventional techniques. Such techniques include cDNA and genomic cloning, which are well known and are described in Sambrook et al., cited above, use of overlapping oligonucleotide sequences of the adenovirus and AAV genomes, combined with polymerase chain reaction, synthetic methods, and any other suitable methods which provide the desired nucleotide sequence.

Introduction of the molecules (as plasmids or viruses) into the host cell may also be accomplished using techniques known to the skilled artisan and as discussed throughout the specification. In preferred embodiment, standard transfection techniques are used, e.g., $CaPO_4$ transfection or electroporation, and/or infection by hybrid adenovirus/AAV vectors into cell lines such as the human embryonic kidney cell line HEK 293 (a human kidney cell line containing functional adenovirus E1 genes which provides trans-acting E1 proteins).

These novel AAV-based vectors which are generated by one of skill in the art are beneficial for gene delivery to selected host cells and gene therapy patients since no neutralization antibodies to AAV7 have been found in the human population. Further, early studies show no neutralizing antibodies in cyno monkey and chimpanzee populations, and less than 15% cross-reactivity of AAV 7 in rhesus monkeys, the species from which the serotype was isolated. One of skill in the art may readily prepare other rAAV viral vectors containing the AAV7 capsid proteins provided herein using a variety of techniques known to those of skill in the art. One may similarly prepare still other rAAV viral vectors containing AAV7 sequence and AAV capsids of another serotype. Similar advantages are conferred by the vectors based on the other novel AAV of the invention.

Thus, one of skill in the art will readily understand that the AAV7 sequences of the invention can be readily adapted for use in these and other viral vector systems for in vitro, ex vivo or in vivo gene delivery. Similarly, one of skill in the art can readily select other fragments of the novel AAV genome of the invention for use in a variety of rAAV and non-rAAV vector systems. Such vectors systems may include, e.g., lentiviruses, retroviruses, poxviruses, vaccinia viruses, and adenoviral systems, among others. Selection of these vector systems is not a limitation of the present invention.

Thus, the invention further provides vectors generated using the nucleic acid and amino acid sequences of the novel AAV of the invention. Such vectors are useful for a variety of purposes, including for delivery of therapeutic molecules and for use in vaccine regimens. Particularly desirable for delivery of therapeutic molecules are recombinant AAV containing capsids of the novel AAV of the invention. These, or other vector constructs containing novel AAV sequences of the invention may be used in vaccine regimens, e.g., for co-delivery of a cytokine, or for delivery of the immunogen itself.

V. Recombinant Viruses and Uses Thereof

Using the techniques described herein, one of skill in the art may generate a rAAV having a capsid of a novel serotype of the invention, or a novel capsid containing one or more novel fragments of an AAV serotype identified by the method of the invention. In one embodiment, a full-length capsid from a single serotype, e.g., AAV7 [SEQ ID NO: 2] can be utilized. In another embodiment, a full-length capsid may be generated which contains one or more fragments of a novel serotype of the invention fused in frame with sequences from another selected AAV serotype. For example, a rAAV may contain one or more of the novel hypervariable region sequences of an AAV serotype of the invention. Alternatively, the unique AAV serotypes of the invention may be used in constructs containing other viral or non-viral sequences.

It will be readily apparent to one of skill in the art one embodiment, that certain serotypes of the invention will be particularly well suited for certain uses. For example, vectors based on AAV7 capsids of the invention are particularly well suited for use in muscle; whereas vectors based on rh.10 (44-2) capsids of the invention are particularly well suited for use in lung. Uses of such vectors are not so limited and one of skill in the art may utilize these vectors for delivery to other cell types, tissues or organs. Further, vectors based upon other capsids of the invention may be used for delivery to these or other cells, tissues or organs.

A. Delivery of Trans gene

In another aspect, the present invention provides a method for delivery of a transgene to a host which involves transfecting or infecting a selected host cell with a vector generated with the sequences of the AAV of the invention.

Methods for delivery are well known to those of skill in the art and are not a limitation of the present invention.

In one desirable embodiment, the invention provides a method for AAV-mediated delivery of a transgene to a host. This method involves transfecting or infecting a selected host cell with a recombinant viral vector containing a selected transgene under the control of sequences which direct expression thereof and AAV capsid proteins.

Optionally, a sample from the host may be first assayed for the presence of antibodies to a selected AAV serotype. A variety of assay formats for detecting neutralizing antibodies are well known to those of skill in the art. The selection of such an assay is not a limitation of the present invention. See, e.g., Fisher et al, *Nature Med*, 3(3):306-312 (March 1997) and W C Manning et al, *Human Gene Therapy*, 9:477-485 (Mar. 1, 1998). The results of this assay may be used to determine which AAV vector containing capsid proteins of a particular serotype are preferred for delivery, e.g., by the absence of neutralizing antibodies specific for that capsid serotype.

In one aspect of this method, the delivery of vector with a selected AAV capsid proteins may precede or follow delivery of a gene via a vector with a different serotype AAV capsid protein. Similarly, the delivery of vector with other novel AAV capsid proteins of the invention may precede or follow delivery of a gene via a vector with a different serotype AAV capsid protein. Thus, gene delivery via rAAV vectors may be used for repeat gene delivery to a selected host cell. Desirably, subsequently administered rAAV vectors carry the same transgene as the first rAAV vector, but the subsequently administered vectors contain capsid proteins of serotypes which differ from the first vector. For example, if a first vector has AAV7 capsid proteins [SEQ ID NO:2], subsequently administered vectors may have capsid proteins selected from among the other serotypes, including AAV1, AAV2, AAV3A, AAV3B, AAV4, AAV6, AAV10, AAV11, and AAV12, or any of the other novel AAV capsids identified herein including, without limitation: A3.1, H2, H6, C1, C2, C5, A3-3, A3-7, A3-4, A3-5, 3.3b, 223.4, 223-5, 223-10, 223-2, 223-7, 223-6, 44-1, 44-5, 44-2, 42-15, 42-8, 42-13, 42-3A, 42-4, 42-5A, 42-1B, 42-5B, 43-1, 43-12, 43-5, 43-21, 43-25, 43-20, 24.1, 42.2, 7.2, 27.3, 16.3, 42.10, 42-3B, 42-11, F1, F5, F3, 42-6B, and/or 42-12.

The above-described recombinant vectors may be delivered to host cells according to published methods. The rAAV, preferably suspended in a physiologically compatible carrier, may be administered to a human or non-human mammalian patient. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present invention.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The viral vectors are administered in sufficient amounts to transfect the cells and to provide sufficient levels of gene transfer and expression to provide a therapeutic benefit without undue adverse effects, or with medically acceptable physiological effects, which can be determined by those skilled in the medical arts. Conventional and pharmaceutically acceptable routes of administration include, but are not limited to, direct delivery to the selected organ (e.g., intraportal delivery to the liver), oral, inhalation (including intranasal and intratracheal delivery), intraocular, intravenous, intramuscular, subcutaneous, intradermal, and other parental routes of administration. Routes of administration may be combined, if desired.

Dosages of the viral vector will depend primarily on factors such as the condition being treated, the age, weight and health of the patient, and may thus vary among patients. For example, a therapeutically effective human dosage of the viral vector is generally in the range of from about 1 ml to about 100 ml of solution containing concentrations of from about $1 \times 10^9$ to $1 \times 10^{16}$ genomes virus vector. A preferred human dosage may be about $1 \times 10^{13}$ to $1 \times 10^{16}$ AAV genomes. The dosage will be adjusted to balance the therapeutic benefit against any side effects and such dosages may vary depending upon the therapeutic application for which the recombinant vector is employed. The levels of expression of the transgene can be monitored to determine the frequency of dosage resulting in viral vectors, preferably AAV vectors containing the minigene. Optionally, dosage regimens similar to those described for therapeutic purposes may be utilized for immunization using the compositions of the invention.

Examples of therapeutic products and immunogenic products for delivery by the AAV-containing vectors of the invention are provided below. These vectors may be used for a variety of therapeutic or vaccinal regimens, as described herein. Additionally, these vectors may be delivered in combination with one or more other vectors or active ingredients in a desired therapeutic and/or vaccinal regimen.

B. Therapeutic Transgenes

Useful therapeutic products encoded by the transgene include hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), transforming growth factor α (TGFα), platelet-derived growth factor (PDGF), insulin growth factors I and II (IGF-I and IGF-II), any one of the transforming growth factor β superfamily, including TGF β, activins, inhibins, or any of the bone morphogenic proteins (BMP) BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful transgene products include proteins that regulate the immune system including, without limitation, cytokines and lymphokines such as thrombopoietin (TPO), interleukins (IL) IL-1 through IL-25 (including, IL-2, IL-4, IL-12, and IL-18), monocyte chemoattractant protein, leukemia inhibitory factor, granulocyte-macrophage colony stimulating factor, Fas ligand, tumor necrosis factors α and β, interferons α, β, and γ, stem cell factor, flk-2/flt3 ligand. Gene products produced by the immune system are also useful in the invention. These include, without limitations, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered immunoglobulins and MHC molecules. Useful gene products also include complement regulatory proteins such as complement regulatory proteins, membrane cofactor protein (MCP), decay accelerating factor (DAF), CR1, CF2 and CD59.

Still other useful gene products include any one of the receptors for the hormones, growth factors, cytokines, lymphokines, regulatory proteins and immune system proteins. The invention encompasses receptors for cholesterol regulation, including the low density lipoprotein (LDL) receptor, high density lipoprotein (HDL) receptor, the very low density lipoprotein (VLDL) receptor, and the scavenger receptor. The invention also encompasses gene products such as members of the steroid hormone receptor superfamily including glucocorticoid receptors and estrogen receptors, Vitamin D receptors and other nuclear receptors. In addition, useful gene products include transcription factors such as jun, fos, max, mad, serum response factor (SRF), AP-1, AP2, myb, MyoD and myogenin, ETS-box containing proteins, TFE3, E2F, ATF1, ATF2, ATF3, ATF4, ZF5, NFAT, CREB, HNF-4, C/EBP, SP1, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

Other useful gene products include, carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, factor VIII, factor IX, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin cDNA sequence. Still other useful gene products include enzymes such as may be useful in enzyme replacement therapy, which is useful in a variety of conditions resulting from deficient activity of enzyme. For example, enzymes that contain mannose-6-phosphate may be utilized in therapies for lysosomal storage diseases (e.g., a suitable gene includes that encoding β-glucuronidase (GUSB)).

Other useful gene products include non-naturally occurring polypeptides, such as chimeric or hybrid polypeptides having a non-naturally occurring amino acid sequence containing insertions, deletions or amino acid substitutions. For example, single-chain engineered immunoglobulins could be useful in certain immunocompromised patients. Other types of non-naturally occurring gene sequences include antisense molecules and catalytic nucleic acids, such as ribozymes, which could be used to reduce overexpression of a target.

Reduction and/or modulation of expression of a gene is particularly desirable for treatment of hyperproliferative conditions characterized by hyperproliferating cells, as are cancers and psoriasis. Target polypeptides include those polypeptides which are produced exclusively or at higher levels in hyperproliferative cells as compared to normal cells. Target antigens include polypeptides encoded by oncogenes such as myb, myc, fyn, and the translocation gene bcr/abl, ras, src, P53, neu, trk and EGRF. In addition to oncogene products as target antigens, target polypeptides for anti-cancer treatments and protective regimens include variable regions of antibodies made by B cell lymphomas and variable regions of T cell receptors of T cell lymphomas which, in some embodiments, are also used as target antigens for autoimmune disease. Other tumor-associated polypeptides can be used as target polypeptides such as polypeptides which are found at higher levels in tumor cells including the polypeptide recognized by monoclonal antibody 17-1A and folate binding polypeptides.

Other suitable therapeutic polypeptides and proteins include those which may be useful for treating individuals suffering from autoimmune diseases and disorders by conferring a broad based protective immune response against targets that are associated with autoimmunity including cell receptors and cells which produce Aself-directed antibodies. T cell mediated autoimmune diseases include Rheumatoid arthritis (RA), multiple sclerosis (MS), Sjögren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors (TCRs) that bind to endogenous antigens and initiate the inflammatory cascade associated with autoimmune diseases.

C. Immunogenic Transgenes

Alternatively, or in addition, the vectors of the invention may contain AAV sequences of the invention and a transgene encoding a peptide, polypeptide or protein which induces an immune response to a selected immunogen. For example, immunogens may be selected from a variety of viral families. Example of desirable viral families against which an immune response would be desirable include, the picornavirus family, which includes the genera rhinoviruses, which are responsible for about 50% of cases of the common cold; the genera enteroviruses, which include polioviruses, coxsackieviruses, echoviruses, and human enteroviruses such as hepatitis A virus; and the genera apthoviruses, which are responsible for foot and mouth diseases, primarily in non-human animals. Within the picornavirus family of viruses, target antigens include the VP1, VP2, VP3, VP4, and VPG. Another viral family includes the calcivirus family, which encompasses the Norwalk group of viruses, which are an important causative agent of epidemic gastroenteritis. Still another viral family desirable for use in targeting antigens for inducing immune responses in humans and non-human animals is the togavirus family, which includes the genera alphavirus, which include Sindbis viruses, RossRiver virus, and Venezuelan, Eastern & Western Equine encephalitis, and rubivirus, including Rubella virus. The flaviviridae family includes dengue, yellow fever, Japanese encephalitis, St. Louis encephalitis and tick borne encephalitis viruses. Other target antigens may be generated from the Hepatitis C or the coronavirus family, which includes a number of non-human viruses such as infectious bronchitis virus (poultry), porcine transmissible gastroenteric virus (pig), porcine hemagglutinating encephalomyelitis virus (pig), feline infectious peritonitis virus (cats), feline enteric coronavirus (cat), canine coronavirus (dog), and human respiratory coronaviruses, which may cause the common cold and/or non-A, B or C hepatitis. Within the coronavirus family, target antigens include the E1 (also called M or matrix protein), E2 (also called S or Spike protein), E3 (also called HE or hemagglutin-elterose) glycoprotein (not present in all coronaviruses), or N (nucleocapsid). Still other antigens may be targeted against the rhabdovirus family, which includes the genera vesiculovirus (e.g., Vesicular Stomatitis Virus), and the general lyssavirus (e.g., rabies). Within the rhabdovirus family, suitable antigens may be derived from the G protein or the N protein. The family filoviridae, which includes hemorrhagic fever viruses such as Marburg and Ebola virus may be a suitable source of antigens. The paramyxovirus family includes parainfluenza Virus Type 1, parainfluenza Virus Type 3, bovine parainfluenza Virus Type 3, rubulavirus (mumps virus, parainfluenza Virus Type 2, parainfluenza virus Type 4, Newcastle disease virus (chickens), rinderpest, morbillivirus, which includes measles and canine distemper, and pneumovirus, which includes respiratory syncytial virus. The influenza virus is classified within the family orthomyxovirus and is a suitable source of antigen (e.g., the HA protein, the N1 protein). The bunyavirus family includes the genera bunyavirus (California encephalitis, La Crosse), phlebovirus (Rift Valley Fever), hantavirus (puremala is a hemahagin fever virus), nairovirus (Nairobi sheep disease) and various unassigned bungaviruses. The arenavirus family provides a source of antigens against LCM and Lassa fever virus. The reovirus family includes the genera reovirus, rotavirus (which causes acute gastroenteritis in children), orbiviruses, and cultivirus (Colorado Tick fever, Lebombo (humans), equine encephalosis, blue tongue).

The retrovirus family includes the sub-family oncoriviriral which encompasses such human and veterinary diseases as feline leukemia virus, HTLVI and HTLVII, lentivirinal (which includes human immunodeficiency virus (HIV), simian immunodeficiency virus (SIV), feline immunodeficiency virus (FIV), equine infectious anemia virus, and spumaviriral). Between the HIV and SIV, many suitable antigens have been described and can readily be selected. Examples of suitable HIV and SIV antigens include, without limitation the gag, pol, Vif, Vpx, VPR, Env, Tat and Rev proteins, as well as various fragments thereof. In addition, a variety of modifications to these antigens have been described. Suitable antigens for this purpose are known to those of skill in the art. For example, one may select a sequence encoding the gag, pol, Vif, and Vpr, Env, Tat and Rev, amongst other proteins. See, e.g., the modified gag protein which is described in U.S. Pat. No. 5,972,596. See, also, the HIV and SIV proteins described in D. H. Barouch et al, J. Virol., 75(5):2462-2467 (March 2001), and R. R. Amara, et al, Science, 292:69-74 (6 Apr. 2001). These proteins or subunits thereof may be delivered alone, or in combination via separate vectors or from a single vector.

The papovavirus family includes the sub-family polyomaviruses (BKU and JCU viruses) and the sub-family papillomavirus (associated with cancers or malignant progression of papilloma). The adenovirus family includes viruses (EX, AD7, ARD, O.B.) which cause respiratory disease and/or enteritis. The parvovirus family feline parvovirus (feline enteritis), feline panleucopeniavirus, canine parvovirus, and porcine parvovirus. The herpesvirus family includes the sub-family alphaherpesvirinae, which encompasses the genera simplexvirus (HSVI, HSVII), varicellovirus (pseudorabies, varicella zoster) and the sub-family betaherpesvirinae, which includes the genera cytomegalovirus (HCMV, muromegalovirus) and the sub-family gammaherpesvirinae, which includes the genera lymphocryptovirus, EBV (Burkitts lymphoma), infectious rhinotracheitis, Marek=s disease virus, and rhadinovirus. The poxvirus family includes the sub-family chordopoxvirinae, which encompasses the genera orthopoxvirus (Variola (Smallpox) and Vaccinia (Cowpox)), parapoxvirus, avipoxvirus, capripoxvirus, leporipoxvirus, suipoxvirus, and the sub-family entomopoxvirinae. The hepadnavirus family includes the Hepatitis B virus. One unclassified virus which may be suitable source of antigens is the Hepatitis delta virus. Still other viral sources may include avian infectious bursal disease virus and porcine respiratory and reproductive syndrome virus. The alphavirus family includes equine arteritis virus and various Encephalitis viruses.

The present invention may also encompass immunogens which are useful to immunize a human or non-human animal against other pathogens including bacteria, fungi, parasitic microorganisms or multicellular parasites which infect human and non-human vertebrates, or from a cancer cell or tumor cell. Examples of bacterial pathogens include pathogenic gram-positive cocci include pneumococci; staphylococci; and streptococci. Pathogenic gram-negative cocci include meningococcus; gonococcus. Pathogenic enteric gram-negative bacilli include enterobacteriaceae; pseudomonas, acinetobacteria and eikenella; melioidosis; salmonella; shigella; haemophilus; moraxella; H. ducreyi (which causes chancroid); brucella; Franisella tularensis (which causes tularemia); yersinia (pasteurella); streptobacillus moniliformis and spirillum; Gram-positive bacilli include Listeria monocytogenes; erysipelothrix rhusiopathiae; Corynebacterium diphtheria (diphtheria); cholera; B. anthracis (anthrax); donovanosis (granuloma inguinale); and bartonellosis. Diseases caused by pathogenic anaerobic bacteria include tetanus; botulism; other clostridia; tuberculosis; leprosy; and other mycobacteria. Pathogenic spirochetal diseases include syphilis; treponematoses: yaws, pinta and endemic syphilis; and leptospirosis. Other infections caused by higher pathogen bacteria and pathogenic fungi include actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. Rickettsial infections include Typhus fever, Rocky Mountain spotted fever, Q fever, and Rickettsialpox. Examples of mycoplasma and chlamydial infections include: Mycoplasma pneumoniae; lymphogranuloma venereum; psittacosis; and perinatal chlamydial infections. Pathogenic eukaryotes encompass pathogenic protozoans and helminths and infections produced thereby include: amebiasis; malaria; leishmaniasis; trypanosomiasis; toxoplasmosis; Pneumocystis carinii; Trichans; Toxoplasma gondii; babesiosis; giardiasis; trichinosis; filariasis; schistosomiasis; nematodes; trematodes or flukes; and cestode (tapeworm) infections.

Many of these organisms and/or toxins produced thereby have been identified by the Centers for Disease Control [(CDC), Department of Heath and Human Services, USA], as agents which have potential for use in biological attacks. For example, some of these biological agents, include, Bacillus anthracis (anthrax), Clostridium botulinum and its toxin (botulism), Yersinia pestis (plague), variola major (smallpox), Francisella tularensis (tularemia), and viral hemorrhagic fever, all of which are currently classified as Category A agents; Coxiella burnetti (Q fever); Brucella species (brucellosis), Burkholderia mallei (glanders), Ricinus communis and its toxin (ricin toxin), Clostridium perfringens and its toxin (epsilon toxin), Staphylococcus species and their toxins (enterotoxin B), all of which are currently classified as Category B agents; and Nipan virus and hantaviruses, which are currently classified as Category C agents. In addition, other organisms, which are so classified or differently classified, may be identified and/or used for such a purpose in the future. It will be readily understood that the viral vectors and other constructs described herein are useful to deliver antigens from these organisms, viruses, their toxins or other by-products, which will prevent and/or treat infection or other adverse reactions with these biological agents.

Administration of the vectors of the invention to deliver immunogens against the variable region of the T cells elicit an immune response including CTLs to eliminate those T cells. In rheumatoid arthritis (RA), several specific variable regions of T cell receptors (TCRs) which are involved in the disease have been characterized. These TCRs include V-3, V-14, V-17 and Vα-17. Thus, delivery of a nucleic acid sequence that encodes at least one of these polypeptides will elicit an immune response that will target T cells involved in RA. In multiple sclerosis (MS), several specific variable regions of TCRs which are involved in the disease have been characterized. These TCRs include V-7 and Vα-10. Thus, delivery of a nucleic acid sequence that encodes at least one of these polypeptides will elicit an immune response that will target T cells involved in MS. In scleroderma, several specific variable regions of TCRs which are involved in the disease have been characterized. These TCRs include V-6, V-8, V-14 and Vα-16, Vα-3C, Vα-7, Vα-14, Vα-15, Vα-16, Vα-28 and Vα-12. Thus, delivery of a nucleic acid molecule that encodes at least one of these polypeptides will elicit an immune response that will target T cells involved in scleroderma.

Optionally, vectors containing AAV sequences of the invention may be delivered using a prime-boost regimen. A variety of such regimens have been described in the art and may be readily selected. See, e.g., WO 00/11140, published Mar. 2, 2000, incorporated by reference.

Such prime-boost regimens typically involve the administration of a DNA (e.g., plasmid) based vector to prime the immune system to second, booster, administration with a traditional antigen, such as a protein or a recombinant virus carrying the sequences encoding such an antigen. In one embodiment, the invention provides a method of priming and boosting an immune response to a selected antigen by delivering a plasmid DNA vector carrying said antigen, followed by boosting, e.g., with a vector containing AAV sequences of the invention.

In one embodiment, the prime-boost regimen involves the expression of multiproteins from the prime and/or the boost vehicle. See, e.g., R. R. Amara, Science, 292:69-74 (6 Apr. 2001) which describes a multiprotein regimen for expression of protein subunits useful for generating an immune response against HIV and SIV. For example, a DNA prime may deliver the Gag, Pol, Vif, VPX and Vpr and Env, Tat, and Rev from a single transcript. Alternatively, the SIV Gag, Pol and HIV-1 Env is delivered.

However, the prime-boost regimens are not limited to immunization for HIV or to delivery of these antigens. For example, priming may involve delivering with a first chimp vector of the invention followed by boosting with a second chimp vector, or with a composition containing the antigen itself in protein form. In one or example, the prime-boost regimen can provide a protective immune response to the virus, bacteria or other organism from which the antigen is derived. In another desired embodiment, the prime-boost regimen provides a therapeutic effect that can be measured using convention assays for detection of the presence of the condition for which therapy is being administered.

The priming vaccine may be administered at various sites in the body in a dose dependent manner, which depends on the antigen to which the desired immune response is being targeted. The invention is not limited to the amount or situs of injection(s) or to the pharmaceutical carrier. Rather, the priming step encompasses treatment regimens which include a single dose or dosage which is administered hourly, daily, weekly or monthly, or yearly. As an example, the mammals may receive one or two priming injection containing between about 10 μg to about 50 μg of plasmid in carrier. A desirable priming amount or dosage of the priming DNA vaccine composition ranges between about 1 μg to about 10,000 μg of the DNA vaccine. Dosages may vary from about 1 μg to 1000 μs DNA per kg of subject body weight. The amount or site of injection is desirably selected based upon the identity and condition of the mammal being vaccinated.

The dosage unit of the DNA vaccine suitable for delivery of the antigen to the mammal is described herein. The DNA vaccine is prepared for administration by being suspended or dissolved in a pharmaceutically or physiologically acceptable carrier such as isotonic saline, isotonic salts solution or other formulations which will be apparent to those skilled in such administration. The appropriate carrier will be evident to those skilled in the art and will depend in large part upon the route of administration. The compositions of the invention may be administered to a mammal according to the routes described above, in a sustained release formulation using a biodegradable biocompatible polymer, or by on-site delivery using micelles, gels and liposomes.

Optionally, the priming step of this invention also includes administering with the priming DNA vaccine composition, a suitable amount of an adjuvant, such as are defined herein.

Preferably, a boosting composition is administered about 2 to about 27 weeks after administering the priming DNA vaccine to the mammalian subject. The administration of the boosting composition is accomplished using an effective amount of a boosting vaccine composition containing or capable of delivering the same antigen as administered by the priming DNA vaccine. The boosting composition may be composed of a recombinant viral vector derived from the same viral source or from another source. Alternatively, the "boosting composition" can be a composition containing the same antigen as encoded in the priming DNA vaccine, but in the form of a protein or peptide, which composition induces an immune response in the host. In another embodiment, the boosting vaccine composition includes a composition containing a DNA sequence encoding the antigen under the control of a regulatory sequence directing its expression in a mammalian cell, e.g., vectors such as well-known bacterial or viral vectors. The primary requirements of the boosting vaccine composition are that the antigen of the vaccine composition is the same antigen, or a cross-reactive antigen, as that encoded by the DNA vaccine.

Suitably, the vectors of the invention are also well suited for use in regimens which use non-AAV vectors as well as proteins, peptides, and/or other biologically useful therapeutic or immunogenic compounds. These regimens are particularly well suited to gene delivery for therapeutic poses and for immunization, including inducing protective immunity. Such uses will be readily apparent to one of skill in the art.

Further, a vector of the invention provides an efficient gene transfer vehicle which can deliver a selected transgene to a selected host cell in vivo or ex vivo even where the organism has neutralizing antibodies to one or more AAV serotypes. In one embodiment, the vector (e.g., an rAAV) and the cells are mixed ex vivo; the infected cells are cultured using conventional methodologies; and the transduced cells are re-infused into the patient. Further, the vectors of the invention may also be used for production of a desired gene product in vitro. For in vitro production, a desired product (e.g., a protein) may be obtained from a desired culture following transfection of host cells with a rAAV containing the molecule encoding the desired product and culturing the cell culture under conditions which permit expression. The expressed product may then be purified and isolated, as desired. Suitable techniques for transfection, cell culturing, purification, and isolation are known to those of skill in the art.

The following examples illustrate several aspects and embodiments of the invention.

EXAMPLES

Example 1: PCR Amplification, Cloning and Characterization of Novel AAV Sequences Tissues from nonhuman primates were screened for AAV sequences using a PCR method based on oligonucleotides to highly conserved regions of known AAVs. A stretch of AAV sequence spanning 2886 to 3143 bp of AAV1 [SEQ ID NO:6] was selected as a PCR amplicon in which a hypervariable region of the capsid protein (Cap) that is unique to each known AAV serotype, which is termed herein a "signature region," is flanked by conserved sequences. In later analysis, this signature region was shown to be located between conserved residues spanning hypervariable region 3.

An initial survey of peripheral blood of a number of nonhuman primate species revealed detectable AAV in a subset of animals from species such as rhesus macaques, cynomologous macaques, chimpanzees and baboons. However, there were no AAV sequences detected in some other species tested, including Japanese macaques, pig-tailed macaques and squirrel monkeys. A more extensive analysis of vector distribution was conducted in tissues of rhesus monkeys of the University of Pennsylvania and Tulane colonies recovered at necropsy. This revealed AAV sequence throughout a wide array of tissues.

A. Amplification of an AAV Signature Region

DNA sequences of AAV1-6 and AAVs isolated from Goose and Duck were aligned to each other using "Clustal W" at default settings. The alignment for AAV1-6, and including the information for the novel AAV7, is provided in FIG. 1. Sequence similarities among AAVs were compared.

In the line of study, a 257 bp region spanning 2886 bp to 3143 bp of AAV 1 [SEQ ID NO: 6], and the corresponding region in the genomes of AAV 2-6 genomes [See, FIG. 1], was identified by the inventors. This region is located with the AAV capsid gene and has highly conserved sequences among at both 5' and 3' ends and is relatively variable sequence in the middle. In addition, this region contains a DraIII restriction enzyme site (CACCACGTC, SEQ ID NO:15). The inventors have found that this region serves as specific signature for each known type of AAV DNA. In other words, following PCR reactions, digestion with endonucleases that are specific to each known serotypes and gel electrophoresis analysis, this regions can be used to definitively identify amplified DNA as being from serotype 1, 2, 3, 4, 5, 6, or another serotype.

The primers were designed, validated and PCR conditions optimized with AAV1, 2 and 5 DNA controls. The primers were based upon the sequences of AAV2: 5' primer, 1S: bp 2867-2891 of AAV2 (SEQ ID NO:7) and 3' primer, 18as, bp 3095-3121 of AAV2 (SEQ ID NO:7).

Cellular DNAs from different tissues including blood, brain, liver, lung, testis, etc. of different rhesus monkeys were studied utilizing the strategy described above. The results revealed that DNAs from different tissues of these monkeys gave rise to strong PCR amplifications. Further restriction analyses of PCR products indicated that they were amplified from AAV sequences different from any published AAV sequences.

PCR products (about 255 bp in size) from DNAs of a variety of monkey tissues have been cloned and sequenced. Bioinformatics study of these novel AAV sequences indicated that they are novel AAV sequences of capsid gene and distinct from each other. FIG. 1 includes in the alignment the novel AAV signature regions for AAV10-12 [SEQ ID NO:117, 118 and 119, respectively]. Multiple sequence alignment analysis was performed using the Clustal W (1.81) program. The percentage of sequence identity between the signature regions of AAV 1-7 and AAV 10-12 genomes is provided below.

TABLE 2

| Sequences for Analysis | | |
|---|---|---|
| Sequence # | AAV Serotype | Size (bp) |
| 1 | AAV1 | 258 |
| 2 | AAV2 | 255 |
| 3 | AAV3 | 255 |
| 4 | AAV4 | 246 |
| 5 | AAV5 | 258 |
| 6 | AAV6 | 258 |
| 7 | AAV7 | 258 |
| 10 | AAV10 | 255 |
| 11 | AAV11 | 258 |
| 12 | AAV12 | 255 |

TABLE 3

| Pairwise Alignment (Percentage of Identity) | | | | | | | | | |
|---|---|---|---|---|---|---|---|---|---|
| | AAV2 | AAV3 | AAV4 | AAV5 | AAV6 | AAV7 | AAV10 | AAV11 | AAV12 |
| AAV1 | 90 | 90 | 81 | 76 | 97 | 91 | 93 | 94 | 93 |
| AAV2 | | 93 | 79 | 78 | 90 | 90 | 93 | 93 | 92 |
| AAV3 | | | 80 | 76 | 90 | 92 | 92 | 92 | 92 |
| AAV4 | | | | 76 | 81 | 84 | 82 | 81 | 79 |
| AAV5 | | | | | 75 | 78 | 79 | 79 | 76 |
| AAV6 | | | | | | 91 | 92 | 94 | 94 |
| AAV7 | | | | | | | 94 | 92 | 92 |
| AAV10 | | | | | | | | 95 | 93 |
| AAV11 | | | | | | | | | 94 |

Over 300 clones containing novel AAV serotype sequences that span the selected 257 bp region were isolated and sequenced. Bioinformatics analysis of these 300+ clones suggests that this 257 bp region is critical in serving as a good land marker or signature sequence for quick isolation and identification of novel AAV serotype.

B. Use of the Signature Region for PCR Amplification.

The 257 bp signature region was used as a PCR anchor to extend PCR amplifications to 5' of the genome to cover the junction region of rep and cap genes (1398 bp-3143 bp, SEQ ID NO:6) and 3' of the genome to obtain the entire cap gene sequence (2866 bp-4600 bp, SEQ ID NO:6). PCR amplifications were carried out using the standard conditions, including denaturing at 95° C. for 0.5-1 min, annealing at 60-65° C. for 0.5-1 min and extension at 72° C. for 1 min per kb with a total number of amplification cycles ranging from 28 to 42.

Using the aligned sequences as described in "A", two other relative conserved regions were identified in the sequence located in 3' end of rep genes and 5' to the 257 bp region and in the sequence down stream of the 257 bp fragment but before the AAV' 3 ITR. Two sets of new primers were designed and PCR conditions optimized for recovery of entire capsid and a part of rep sequences of novel AAV serotypes. More specifically, for the 5' amplification, the 5' primer, AV1Ns, was GCTGCGT-CAACTGGACCAATGAGAAC [nt 1398-1423 of AAV1, SEQ ID NO:6] and the 3' primer was 18as, identified above. For the 3' amplification, the 5' primer was 1s, identified above, and the 3' primer was AV2Las, TCGTTTCAGTT-GAACTTTGGTCTCTGCG [nt 4435-4462 of AAV2, SEQ ID NO:7].

In these PCR amplifications, the 257 bp region was used as a PCR anchor and land marker to generate overlapping fragments to construct a complete capsid gene by fusion at the DraIII site in the signature region following amplification of the 5' and 3' extension fragments obtained as described herein. More particularly, to generate the intact AAV7 cap gene, the three amplification products (a) the sequences of the signature region; (b) the sequences of the 5' extension; and (c) the sequences of the 3' extension were cloned into a pCR4-Topo [Invitrogen] plasmid backbone according to manufacturer's instructions. Thereafter, the plasmids were digested with DraIII and recombined to form an intact cap gene.

In this line of work, about 80% of capsid sequences of AAV7 and AAV 8 were isolated and analyzed. Another novel serotype, AAV9, was also discovered from Monkey #2.

Using the PCR conditions described above, the remaining portion of the rep gene sequence for AAV7 is isolated and cloned using the primers that amplify 108 bp to 1461 bp of AAV genome (calculated based on the numbering of AAV2, SEQ ID NO:7). This clone is sequenced for construction of a complete AAV7 genome without ITRs.

C. Direct Amplification of 3.1 kb Cap Fragment

To directly amplify a 3.1 kb full-length Cap fragment from NHP tissue and blood DNAs, two other highly conserved regions were identified in AAV genomes for use in PCR amplification of large fragments. A primer within a conserved region located in the middle of the rep gene was selected (AV1ns: 5' GCTGCGTCAACTGGACCAAT-GAGAAC 3', nt 1398-1423 of SEQ ID NO:6) in combination with the 3' primer located in another conserved region downstream of the Cap gene (AV2cas: 5' CGCAGAGAC-CAAAGTTCAACTGAAACGA 3', SEQ ID NO:7) for amplification of full-length cap fragments. The PCR products were Topo-cloned according to manufacturer's directions (Invitrogen) and sequence analysis was performed by Qiagengenomics (Qiagengenomics, Seattle, Wash.) with an accuracy of 99.9%. A total of 50 capsid clones were isolated and characterized. Among them, 37 clones were derived from Rhesus macaque tissues (rh.1-rh.37), 6 clones from cynomologous macaques (cy.1-cy.6), 2 clones from Baboons (bb.1 and bb.2) and 5 clones from Chimps (ch.1-ch.5).

To rule out the possibility that sequence diversity within the novel AAV family was not an artifact of the PCR, such as PCR-mediated gene splicing by overlap extension between different partial DNA templates with homologous sequences, or the result of recombination process in bacteria, a series of experiments were performed under identical conditions for VP1 amplification using total cellular DNAs. First, intact AAV7 and AAV8 plasmids were mixed at an equal molar ratio followed by serial dilutions. The serially diluted mixtures were used as templates for PCR amplification of 3.1 kb VP1 fragments using universal primers and identical PCR conditions to that were used for DNA amplifications to see whether any hybrid PCR products were generated. The mixture was transformed into bacteria and isolated transformants to look for hybrid clones possibly derived from recombination process in bacterial cells. In a different experiment, we restricted AAV7 and AAV8 plasmids with Msp I, Ava I and HaeI, all of which cut both genomes multiple times at different positions, mixed the digestions in different combinations and used them for PCR amplification of VP1 fragments under the same conditions to test whether any PCR products could be generated through overlap sequence extension of partial AAV sequences. In another experiment, a mixture of gel purified 5' 1.5 kb AAV7 VP1 fragment and 3' 1.7 kb AAV8 VP1 fragment with overlap in the signature region was serially diluted and used for PCR amplification in the presence and absence of 200 ng cellular DNA extracted from a monkey cell line that was free of AAV sequences by TaqMan analysis. None of these experiments demonstrated efficient PCR-mediated overlap sequence production under the conditions of the genomic DNA Cap amplification (data not shown). As a further confirmation, 3 pairs of primers were designed, which were located at different HVRs, and were sequence specific to the variants of clone 42s from Rhesus macaque F953, in different combinations to amplify shorter fragments from mesenteric lymph node (MLN) DNA from F953 from which clone 42s were isolated. All sequence variations identified in full-length Cap clones were found in these short fragments (data not shown).

Example 2: Adeno-Associated Viruses Undergo Substantial Evolution in Primates During Natural Infections Sequence analysis of selected AAV isolates revealed divergence throughout the genome that is most concentrated in hypervariable regions of the capsid proteins. Epidemiologic data indicate that all known serotypes are endemic to primates, although isolation of clinical isolates has been restricted to AAV2 and AAV3 from anal and throat swabs of human infants and AAV5 from a human condylomatous wart. No known clinical sequalae have been associated with AAV infection.

In an attempt to better understand the biology of AAV, nonhuman primates were used as models to characterize the sequlae of natural infections. Tissues from nonhuman primates were screened for AAV sequences using the PCR method of the invention based on oligonucleotides to highly conserved regions of known AAVs (see Example 1). A stretch of AAV sequence spanning 2886 to 3143 bp of AAV1 [SEQ ID NO:6] was selected as a PCR amplicon in which conserved sequences are flanked by a hypervariable region that is unique to each known AAV serotype, termed herein a "signature region."

An initial survey of peripheral blood of a number of nonhuman primate species including rhesus monkeys, cynomologous monkeys, chimpanzees, and baboons revealed detectable AAV in a subset of animals from all species. A more extensive analysis of vector distribution was conducted in tissues of rhesus monkeys of the University of Pennsylvania and Tulane colonies recovered at necropsy. This revealed AAV sequence throughout a wide array of tissues.

The amplified signature sequences were subcloned into plasmids and individual transformants were subjected to sequence analysis. This revealed substantial variation in nucleotide sequence of clones derived from different animals. Variation in the signature sequence was also noted in clones obtained within individual animals. Tissues harvested from two animals in which unique signature sequences were identified (i.e., colon from 98E044 and heart from 98E056) were further characterized by expanding the sequence amplified by PCR using oligonucleotides to highly conserved sequences. In this way, complete proviral structures were reconstructed for viral genomes from both tissues as described herein. These proviruses differ from the other known AAVs with the greatest sequence divergence noted in regions of the Cap gene.

Additional experiments were performed to confirm that AAV sequences resident to the nonhuman primate tissue represented proviral genomes of infectious virus that is capable of being rescued and form virions. Genomic DNA from liver tissue of animal 98E056, from which AAV8 signature sequence was detected, was digested with an endonuclease that does not have a site within the AAV sequence and transfected into 293 cells with a plasmid containing an E1 deleted genome of human adenovirus serotype 5 as a source of helper functions. The resulting lysate was passaged on 293 cells once and the lysate was recovered and analyzed for the presence of AAV Cap proteins using a broadly reacting polyclonal antibody to Cap proteins and for the presence and abundance of DNA sequences from the PCR amplified AAV provirus from which AAV8 was derived. Transfection of endonuclease restricted heart DNA and the adenovirus helper plasmid yielded high quantities of AAV8 virus as demonstrated by the detection of Cap proteins by Western blot analysis and the presence of $10^4$ AAV8 vector genomes per 293 cell. Lysates were generated from a large-scale preparation and the AAV was purified by cesium sedimentation. The purified preparation demonstrated 26 nm icosohedral structures that look identical to those of AAV serotype 2. Transfection with the adenovirus helper alone did not yield AAV proteins or genomes, ruling out contamination as a source of the rescued AAV.

To further characterize the inter and intra animal variation of AAV signature sequence, selected tissues were subjected to extended PCR to amplify entire Cap open reading frames.

The resulting fragments were cloned into bacterial plasmids and individual transformants were isolated and fully sequenced. This analysis involved mesenteric lymph nodes from three rhesus monkeys (Tulane/V223—6 clones; Tulane/T612—7 clones; Tulane/F953—14 clones), liver from two rhesus monkeys (Tulane/V251—3 clones; Penn/00E033—3 clones), spleen from one rhesus monkey (Penn/97E043—3 clones), heart from one rhesus monkey (IHGT/98E046—1 clone) and peripheral blood from one chimpanzee (New Iberia/X133—5 clones), six cynomologous macaques (Charles River/A1378, A3099, A3388, A3442, A2821, A3242—6 clones total) and one Baboon (SFRB/8644—2 clones). Of the 50 clones that were sequenced from 15 different animals, 30 were considered non-redundant based on the finding of at least 7 amino acid differences from one another. The non-redundant VP1 clones are numbered sequentially as they were isolated, with a prefix indicating the species of non-human primate from which they were derived. The structural relationships between these 30 non-redundant clones and the previously described 8 AAV serotypes were determined using the SplitsTree program [Huson, D. H. SplitsTree: analyzing and visualizing evolutionary data. *Bioinformatics* 14, 68-73 (1998)] with implementation of the method of split decomposition. The analysis depicts homoplasy between a set of sequences in a tree-like network rather than a bifurcating tree. The advantage is to enable detection of groupings that are the result of convergence and to exhibit phylogenetic relationships even when they are distorted by parallel events. Extensive phylogenetic research will be required in order to elucidate the AAV evolution, whereas the intention here only is to group the different clones as to their sequence similarity.

To confirm that the novel VP1 sequences were derived from infectious viral genomes, cellular DNA from tissues with high abundance of viral DNA was restricted with an endonuclease that should not cleave within AAV and transfected into 293 cells, followed by infection with adenovirus. This resulted in rescue and amplification of AAV genomes from DNA of tissues from two different animals (data not shown).

VP1 sequences of the novel AAVs were further characterized with respect to the nature and location of amino acid sequence variation. All 30 VP1 clones that were shown to differ from one another by greater than 1% amino acid sequence were aligned and scored for variation at each residue. An algorithm developed to determine areas of sequence divergence yielded 12 hypervariable regions (HVR) of which 5 overlap or are part of the 4 previously described variable regions [Kotin, cited above; Rutledge, cited above]. The three-fold-proximal peaks contain most of the variability (HVR5-10). Interestingly the loops located at the 2 and 5 fold axis show intense variation as well. The HVRs 1 and 2 occur in the N-terminal portion of the capsid protein that is not resolved in the X-ray structure suggesting that the N-terminus of the VP1 protein is exposed on the surface of the virion.

Real-time PCR was used to quantify AAV sequences from tissues of 21 rhesus monkeys using primers and probes to highly conserved regions of Rep (one set) and Cap (two sets) of known AAVs. Each data point represents analysis from tissue DNA from an individual animal. This confirmed the wide distribution of AAV sequences, although the quantitative distribution differed between individual animals. The source of animals and previous history or treatments did not appear to influence distribution of AAV sequences in rhesus macaques. The three different sets of primers and probes used to quantify AAV yielded consistent results. The highest levels of AAV were found consistently in mesenteric lymph nodes at an average of 0.01 copies per diploid genome for 13 animals that were positive. Liver and spleen also contained high abundance of virus DNA. There were examples of very high AAV, such as in heart of rhesus macaque 98E056, spleen of rhesus macaque 97E043 and liver of rhesus macaque RQ4407, which demonstrated 1.5, 3 and 20 copies of AAV sequence per diploid genome respectively. Relatively low levels of virus DNA were noted in peripheral blood mononuclear cells, suggesting the data in tissue are not due to resident blood components (data not shown). It should be noted that this method would not necessarily capture all AAVs resident to the nonhuman primates since detection requires high homology to both the oligonucleotides and the real time PCR probe. Tissues from animals with high abundance AAV DNA was further analyzed for the molecular state of the DNA, by DNA hybridization techniques, and its cellular distribution, by in situ hybridization.

The kind of sequence variation revealed in AAV proviral fragments isolated from different animals and within tissues of the same animals is reminiscent of the evolution that occurs for many RNA viruses during pandemics or even within the infection of an individual. In some situations the notion of a wild-type virus has been replaced by the existence of swarms of quasispecies that evolve as a result of rapid replication and mutations in the presence of selective pressure. One example is infection by HIV, which evolves in response to immunologic and pharmacologic pressure. Several mechanisms contribute to the high rate of mutations in RNA viruses, including low fidelity and lack of proof reading capacity of reverse transcriptase and non-homologous and homologous recombination.

Evidence for the formation of quasispecies of AAV was illustrated in this study by the systematic sequencing of multiple cloned proviral fragments. In fact, identical sequences could not be found within any extended clones isolated between or within animals. An important mechanism for this evolution of sequence appears to be a high rate of homologous recombination between a more limited number of parenteral viruses. The net result is extensive swapping of hypervariable regions of the Cap protein leading to an array of chimeras that could have different tropisms and serologic specificities (i.e., the ability to escape immunologic responses especially as it relates to neutralizing antibodies). Mechanisms by which homologous recombination could occur are unclear. One possibility is that + and − strands of different single stranded AAV genomes anneal during replication as has been described during high multiplicity of infections with AAV recombinants. It is unclear if other mechanisms contribute to sequence evolution in AAV infections. The overall rate of mutation that occurs during AAV replication appears to be relatively low and the data do not suggest high frequencies of replication errors. However, substantial rearrangements of the AAV genome have been described during lytic infection leading to the formation of defective interfering particles. Irrespective of the mechanisms that lead to sequence divergence, with few exceptions, vp1 structures of the quasispecies remained intact without frameshifts or nonsense mutations suggesting that competitive selection of viruses with the most favorable profile of fitness contribute to the population dynamics.

These studies have implications in several areas of biology and medicine. The concept of rapid virus evolution, formerly thought to be a property restricted to RNA viruses, should be considered in DNA viruses, which classically have been characterized by serologic assays. It will be important in terms of parvoviruses to develop a new method for describing virus isolates that captures the complexity of its structure and biology, such as with HIV, which are categorized as general families of similar structure and function called Clades. An alternative strategy is to continue to categorize isolates with respect to serologic specificity and develop criteria for describing variants within serologic groups.

Example 3: Vectorology of Recombinant AAV Genomes Equipped with AAV2 ITRs is Using Chimeric Plasmids Containing AAV2 Rep and Novel AAV Cap Genes for Serological and Gene Transfer Studies in Different Animal Models Chimeric packaging constructs are generated by fusing AAV2 rep with cap sequences of novel AAV serotypes. These chimeric packaging constructs are used, initially, for pseudotyping recombinant AAV genomes carrying AAV2 ITRs by triple transfection in 293 cell using Ad5 helper plasmid. These pseudotyped vectors are used to evaluate performance in transduction-based serological studies and evaluate gene transfer efficiency of novel AAV serotypes in different animal models including NHP and rodents, before intact and infectious viruses of these novel serotypes are isolated.

A. pAAV2GFP

The AAV2 plasmid which contains the AAV2 ITRs and green fluorescent protein expressed under the control of a constitutitive promoter. This plasmid contains the following elements: the AAV2 ITRs, a CMV promoter, and the GFP coding sequences.

B. Cloning of Trans Plasmid

To construct the chimeric trans-plasmid for production of recombinant pseudotyped AAV7 vectors, p5E18 plasmid (Xiao et al., 1999, *J. Virol* 73:3994-4003) was partially digested with Xho I to linearize the plasmid at the Xho I site at the position of 3169 bp only. The Xho I cut ends were then filled in and ligated back. This modified p5E18 plasmid was restricted with Xba I and Xho I in a complete digestion to remove the AAV2 cap gene sequence and replaced with a 2267 bp Spe I/Xho I fragment containing the AAV7 cap gene which was isolated from pCRAAV7 6-5+15-4 plasmid.

The resulting plasmid contains the AAV2 rep sequences for Rep78/68 under the control of the AAV2 P5 promoter, and the AAV2 rep sequences for Rep52/40 under the control of the AAV2 P19 promoter. The AAV7 capsid sequences are under the control of the AAV2 P40 promoter, which is located within the Rep sequences. This plasmid further contains a spacer 5' of the rep ORF.

C. Production of Pseudotyped rAAV

The rAAV particles (AAV2 vector in AAV7 capsid) are generated using an adenovirus-free method. Briefly, the cis plasmid (pAAV2.1 lacZ plasmid containing AAV2 ITRs), and the trans plasmid pCRAAV7 6-5+15-4 (containing the AAV2 rep and AAV7 cap) and a helper plasmid, respectively, were simultaneously co-transfected into 293 cells in a ratio of 1:1:2 by calcium phosphate precipitation.

For the construction of the pAd helper plasmids, pBG10 plasmid was purchased from Microbix (Canada). A RsrII fragment containing L2 and L3 was deleted from pBHG10, resulting in the first helper plasmid, pAdΔF13. Plasmid AdA F1 was constructed by cloning Asp700/SalI fragment with a PmeI/SgfI deletion, isolating from pBHG10, into Bluescript. MLP, L2, L2 and L3 were deleted in the pAdΔF1. Further deletions of a 2.3 kb NruI fragment and, subsequently, a 0.5 kb RsrII/NruI fragment generated helper plasmids pAdΔF5 and pAdΔF6, respectively. The helper plasmid, termed pΔF6, provides the essential helper functions of E2a and E4 ORF6 not provided by the E1-expressing helper cell, but is deleted of adenoviral capsid proteins and functional E1 regions).

Typically, 50 µg of DNA (cis:trans:helper) was transfected onto a 150 mm tissue culture dish. The 293 cells were harvested 72 hours post-transfection, sonicated and treated with 0.5% sodium deoxycholate (37EC for 10 min) Cell lysates were then subjected to two rounds of a CsCl gradient. Peak fractions containing rAAV vector are collected, pooled and dialyzed against PBS.

Example 4: Creation of Infectious Clones Carrying Intact Novel AAV Serotypes for Study of Basic Virology in Human and NHP Derived Cell Lines and Evaluation of Pathogenesis of Novel AAV Serotypes in NHP and Other Animal Models To achieve this goal, the genome walker system is employed to obtain 5' and 3' terminal sequences (ITRs) and complete construction of clones containing intact novel AAV serotype genomes.

Briefly, utilizing a commercially available Universal Genome Walker Kit [Clontech], genomic DNAs from monkey tissues or cell lines that are identified as positive for the presence of AAV7 sequence are digested with Dra I, EcoR V, Pvu II and Stu I to endonucleases and ligated to Genome Walker Adaptor to generate 4 individual Genome Walker Libraries (GWLs). Using DNAs from GWLs as templates, AAV7 and adjacent genomic sequences will be PCR-amplified by the adaptor primer 1 (AP', provided in the kit) and an AAV7 specific primer 1, followed by a nested PCR using the adaptor primer 2 (AP2) and another AAV7 specific primer 2, both of which are internal to the first set of primers. The major PCR products from the nested PCR are cloned and characterized by sequencing analysis.

In this experiment, the primers covering the 257 bp or other signature fragment of a generic AAV genome are used for PCR amplification of cellular DNAs extracted from Human and NHP derived cell lines to identify and characterize latent AAV sequences. The identified latent AAV genomes are rescued from the positive cell lines using adenovirus helpers of different species and strains.

To isolate infectious AAV clones from NHP derived cell lines, a desired cell line is obtained from ATCC and screened by PCR to identify the 257 bp amplicon, i.e., signature region of the invention. The 257 bp PCR product is cloned and serotyped by sequencing analysis. For these cell lines containing the AAV7 sequence, the cells are infected with SV-15, a simian adenovirus purchased from ATCC, human Ad5 or transfected with plasmid construct housing the human Ad genes that are responsible for AAV helper functions. At 48 hour post infection or transfection, the cells are harvested and Hirt DNA is prepared for cloning of AAV7 genome following Xiao et al., 1999, J. Virol, 73:3994-4003.

Example 5—Production of AAV Vectors

A pseudotyping strategy similar to that of Example 3 for AAV1/7 was employed to produce AAV2 vectors packaged with AAV1, AAV5 and AAV8 capsid proteins. Briefly, recombinant AAV genomes equipped with AAV2 ITRs were packaged by triple transfection of 293 cells with cis-plasmid, adenovirus helper plasmid and a chimeric packaging construct where the AAV2 rep gene is fused with cap genes of novel AAV serotypes. To create the chimeric packaging constructs, the Xho I site of p5E18 plasmid at 3169 bp was ablated and the modified plasmid was restricted with Xba I and Xho I in a complete digestion to remove the AAV2 cap gene and replace it with a 2267 bp Spe I/Xho I fragment containing the AAV8 cap gene [Xiao, W., et al., (1999) J Virol 73, 3994-4003]. A similar cloning strategy was used for creation of chimeric packaging plasmids of AAV2/1 and AAV2/5. All recombinant vectors were purified by the standard $CsCl_2$ sedimentation method except for AAV2/2, which was purified by single step heparin chromatography.

Genome copy (GC) titers of AAV vectors were determined by TaqMan analysis using probes and primers targeting SV40 poly A region as described previously [Gao, G., et al., (2000) Hum Gene Ther 11, 2079-91].

Vectors were constructed for each serotype for a number of in vitro and in vivo studies. Eight different transgene cassettes were incorporated into the vectors and recombinant virions were produced for each serotype. The recovery of virus, based on genome copies, is summarized in Table 4 below. The yields of vector were high for each serotype with no consistent differences between serotypes. Data presented in the table are average genome copy yields with standard deviation×$10^{13}$ of multiple production lots of 50 plate (150 mm) transfections.

TABLE 4

Production of Recombinant Vectors

|  | AAV2/1 | AAV2/2 | AAV2/5 | AAV2/7 | AAV2/8 |
|---|---|---|---|---|---|
| CMV | 7.30 ± 4.33 | 4.49 ± 2.89 | 5.19 ± 5.19 | 3.42 | 0.87 |
| LacZ | (n = 9) | (n = 6) | (n = 8) | (n = 1) | (n = 1) |
| CMV | 6.43 ± 2.42 | 3.39 ± 2.42 | 5.55 ± 6.49 | 2.98 ± 2.66 | 3.74 ± 3.88 |
| EGFP | (n = 2) | (n = 2) | (n = 4) | (n = 2) | (n = 2) |
| TBG | 4.18 | 0.23 | 0.704 ± 0.43 | 2.16 | 0.532 |
| LacZ | (n = 1) | (n = 1) | (n = 2) | (n = 1) | (n = 1) |
| Alb | 4.67 ± 0.75 | 4.77 | 4.09 | 5.04 | 2.02 |
| A1AT | (n = 2) | (n = 1) | (n = 1) | (n = 1) | (n = 1) |
| CB | 0.567 | 0.438 | 2.82 | 2.78 | 0.816 ± |
| A1AT | (n = 1) | (n = 1) | (n = 1) | (n = 1) | 0.679 (n = 2) |
| TBG | 8.51 ± 6.65 | 3.47 ± 2.09 | 5.26 ± 3.85 | 6.52 ± 3.08 | 1.83 ± 0.98 |
| rhCG | (n = 6) | (n = 5) | (n = 4) | (n = 4) | (n = 5) |
| TBG | 1.24 ± 1.29 | 0.63 ± 0.394 | 3.74 ± 2.48 | 4.05 | 15.8 ± 15.0 |
| cFIX | (n = 3) | (n = 6) | (n = 7) | (n = 1) | (n = 5) |

Example 6—Serologic Analysis of Pseudotyped Vectors

C57BL/6 mice were injected with vectors of different serotypes of AAVCBA1AT vectors intramuscularly (5×$10^{11}$ GC) and serum samples were collected 34 days later. To test neutralizing and cross-neutralizing activity of sera to each serotype of AAV, sera was analyzed in a transduction based neutralizing antibody assay [Gao, G. P., et al., (1996) J Virol 70, 8934-43]. More specifically, the presence of neutralizing antibodies was determined by assessing the ability of serum to inhibit transduction of 84-31 cells by reporter viruses (AAVCMVEGFP) of different serotypes. Specifically, the reporter virus AAVCMVEGFP of each serotype [at multiplicity of infection (MOI) that led to a transduction of 90% of indicator cells] was pre-incubated with heat-inactivated serum from animals that received different serotypes of AAV or from naïve mice. After 1-hour incubation at 37° C., viruses were added to 84-31 cells in 96 well plates for 48 or 72-hour, depending on the virus serotype. Expression of GFP was measured by FluoroImagin (Molecular Dynamics) and quantified by Image Quant Software. Neutralizing antibody titers were reported as the highest serum dilution that inhibited transduction to less than 50%.

The availability of GFP expressing vectors simplified the development of an assay for neutralizing antibodies that was based on inhibition of transduction in a permissive cell line (i.e., 293 cells stably expressing E4 from Ad5). Sera to selected AAV serotypes were generated by intramuscular injection of the recombinant viruses. Neutralization of AAV transduction by 1:20 and 1:80 dilutions of the antisera was evaluated (See Table 5 below). Antisera to AAV1, AAV2, AAV5 and AAV8 neutralized transduction of the serotype to which the antiserum was generated (AAV5 and AAV8 to a lesser extent than AAV1 and AAV2) but not to the other serotype (i.e., there was no evidence of cross neutralization suggesting that AAV 8 is a truly unique serotype).

chemical staining from animals that received the lacZ vectors. For the re-administration experiment, C56BL/6 mice initially received AAV2/1, 2/2, 2/5, 2/7 and 2/8CBA1AT vectors intramuscularly and followed for A1AT gene expression for 7 weeks. Animals were then treated with AAV2/8TBGcFIX intraportally and studied for cFIX gene expression.

ELISA based assays were performed to quantify serum levels of hA1AT, rhCG and cFIX proteins as described

TABLE 5

Serological Analysis of New AAV Serotypes.

| | | % Infection on 84-31 cells with AAVCMVEGFP virus: | | | | | | | | |
|---|---|---|---|---|---|---|---|---|---|---|
| | | AAV2/1 Serum dilution: | | AAV2/2 Serum dilution: | | AAV2/5 Serum dilution: | | AAV2/7 Serum dilution: | | AAV2/8 Serum dilution: | |
| Sera: | Immunization Vector | 1/20 | 1/80 | 1/20 | 1/80 | 1/20 | 1/80 | 1/20 | 1/80 | 1/20 | 1/80 |
| Group 1 | AAV2/1 | 0 | 0 | 100 | 100 | 100 | 100 | 100 | 100 | 100 | 100 |
| Group 2 | AAV2/2 | 100 | 100 | 0 | 0 | 100 | 100 | 100 | 100 | 100 | 100 |
| Group 3 | AAV2/5 | 100 | 100 | 100 | 100 | 16.5 | 16.5 | 100 | 100 | 100 | 100 |
| Group 4 | AAV2/7 | 100 | 100 | 100 | 100 | 100 | 100 | 61.5 | 100 | 100 | 100 |
| Group 5 | AAV2/8 | 100 | 100 | 100 | 100 | 100 | 100 | 100 | 100 | 26.3 | 60 |

Human sera from 52 normal subjects were screened for neutralization against selected serotypes. No serum sample was found to neutralize AAV2/7 and AAV2/8 while AAV2/2 and AAV2/1 vectors were neutralized in 20% and 10% of sera, respectively. A fraction of human pooled IgG representing a collection of 60,000 individual samples did not neutralize AAV2/7 and AAV2/8, whereas AAV2/2 and AAV2/1 vectors were neutralized at titers of serum equal to $\frac{1}{1280}$ and $\frac{1}{640}$, respectively.

Example 7—In Vivo Evaluation of Different Serotypes of AAV Vectors

In this study, 7 recombinant AAV genomes, AAV2CBhA1AT, AAV2AlbhA1AT, AAV2CMVrhCG, AAV2TBGrhCG, AAV2TBGcFIX, AAV2CMVLacZ and AAV2TBGLacZ were packaged with capsid proteins of different serotypes. In all 7 constructs, minigene cassettes were flanked with AAV2 ITRs. cDNAs of human α-antitrypsin (A1AT) [Xiao, W., et al., (1999) J Virol 73, 3994-4003] β-subunit of rhesus monkey choriogonadotropic hormone (CG) [Zoltick, P. W. & Wilson, J. M. (2000)Mol Ther 2, 657-9] canine factor IX [Wang, L., et al., (1997) Proc Natl Acad Sci USA 94, 11563-6] and bacterial β-glactosidase (i.e., Lac Z) genes were used as reporter genes. For liver-directed gene transfer, either mouse albumin gene promoter (Alb) [Xiao, W. (1999), cited above] or human thyroid hormone binding globulin gene promoter (TBG) [Wang (1997), cited above] was used to drive liver specific expression of reporter genes. In muscle-directed gene transfer experiments, either cytomegalovirus early promoter (CMV) or chicken β-actin promoter with CMV enhancer (CB) was employed to direct expression of reporters.

For muscle-directed gene transfer, vectors were injected into the right tibialis anterior of 4-6 week old NCR nude or C57BL/6 mice (Taconic, Germantown, N.Y.). In liver-directed gene transfer studies, vectors were infused intraportally into 7-9 week old NCR nude or C57BL/6 mice (Taconic, Germantown, N.Y.). Serum samples were collected intraorbitally at different time points after vector administration. Muscle and liver tissues were harvested at different time points for cryosectioning and Xgal histopreviously [Gao, G. P., et al., (1996) J Vivol 70, 8934-43; Zoltick, P. W. & Wilson, J. M. (2000) Mol Ther 2, 657-9; Wang, L., et al., Proc Natl Acad Sci USA 94, 11563-6]. The experiments were completed when animals were sacrificed for harvest of muscle and liver tissues for DNA extraction and quantitative analysis of genome copies of vectors present in target tissues by TaqMan using the same set of primers and probe as in titration of vector preparations [Zhang, Y., et al., (2001) Mol Ther 3, 697-707].

The performance of vectors base on the new serotypes were evaluated in murine models of muscle and liver-directed gene transfer and compared to vectors based on the known serotypes AAV1, AAV2 and AAV5. Vectors expressing secreted proteins (alpha-antitrypsin (A1AT) and chorionic gonadotropin (CG)) were used to quantitate relative transduction efficiencies between different serotypes through ELISA analysis of sera. The cellular distribution of transduction within the target organ was evaluated using lacZ expressing vectors and X-gal histochemistry.

The performance of AAV vectors in skeletal muscle was analyzed following direct injection into the tibialis anterior muscles. Vectors contained the same AAV2 based genome with the immediate early gene of CMV or a CMV enhanced β-actin promoter driving expression of the transgene. Previous studies indicated that immune competent C57BL/6 mice elicit limited humoral responses to the human A1AT protein when expressed from AAV vectors [Xiao, W., et al., (1999) J Virol 73, 3994-4003].

In each strain, AAV2/1 vector produced the highest levels of A1AT and AAV2/2 vector the lowest, with AAV2/7 and AAV2/8 vectors showing intermediate levels of expression. Peak levels of CG at 28 days following injection of nu/nu NCR mice showed the highest levels from AAV2/7 and the lowest from AAV2/2 with AAV2/8 and AAV2/1 in between. Injection of AAV2/1 and AAV2/7 lacZ vectors yielded gene expression at the injection sites in all muscle fibers with substantially fewer lacZ positive fibers observed with AAV2/2 and AAV 2/8 vectors. These data indicate that the efficiency of transduction with AAV2/7 vectors in skeletal muscle is similar to that obtained with AAV2/1, which is the most efficient in skeletal muscle of the previously described serotypes [Xiao, W. (1999), cited above; Chao, H., et al., (2001) Mol Ther 4, 217-22; Chao, H., et al., (2000) Mol Ther 2, 619-23].

Similar murine models were used to evaluate liver-directed gene transfer. Identical doses of vector based on genome copies were infused into the portal veins of mice that were analyzed subsequently for expression of the transgene. Each vector contained an AAV2 based genome using previously described liver-specific promoters (i.e., albumin or thyroid hormone binding globulin) to drive expression of the transgene. More particularly, CMVCG and TBGCG minigene cassettes were used for muscle and liver-directed gene transfer, respectively. Levels of rhCG were defined as relative units (RUs×$10^3$). The data were from assaying serum samples collected at day 28, post vector administration (4 animals per group). As shown in Table 3, the impact of capsid proteins on the efficiency of transduction of A1AT vectors in nu/nu and C57BL/6 mice and CG vectors in C57BL/6 mice was consistent (See Table 6).

TABLE 6

Expression of β-unit of Rhesus Monkey Chorionic Gonadotropin (rhCG)

| Vector | Muscle | Liver |
|---|---|---|
| AAV2/1 | 4.5 ± 2.1 | 1.6 ± 1.0 |
| AAV2 | 0.5 ± 0.1 | 0.7 ± 0.3 |
| AAV2/5 | ND* | 4.8 ± 0.8 |
| AAV2/7 | 14.2 ± 2.4 | 8.2 ± 4.3 |
| AAV2/8 | 4.0 ± 0.7 | 76.0 ± 22.8 |

*Not determined in this experiment.

In all cases, AAV2/8 vectors yielded the highest levels of transgene expression that ranged from 16 to 110 greater than what was obtained with AAV2/2 vectors; expression from AAV2/5 and AAV2/7 vectors was intermediate with AAV2/7 higher than AAV2/5. Analysis of X-Gal stained liver sections of animals that received the corresponding lacZ vectors showed a correlation between the number of transduced cells and overall levels of transgene expression. DNAs extracted from livers of C57BL/6 mice who received the A1AT vectors were analyzed for abundance of vector DNA using real time PCR technology.

The amount of vector DNA found in liver 56 days after injection correlated with the levels of transgene expression (See Table 7). For this experiment, a set of probe and primers targeting the SV40 polyA region of the vector genome was used for TaqMan PCR. Values shown are means of three individual animals with standard deviations. The animals were sacrificed at day 56 to harvest liver tissues for DNA extraction. These studies indicate that AAV8 is the most efficient vector for liver-directed gene transfer due to increased numbers of transduced hepatocytes.

TABLE 7

Real Time PCR Analysis for Abundance of AAV Vectors in nu/nu Mouse Liver Following Injection of 1 × $10^{11}$ Genome Copies of Vector.

| AAV vectors/Dose | Genome Copies per Cell |
|---|---|
| AAV2/1AlbA1AT | 0.6 ± 0.36 |
| AAV2AlbA1AT | 0.003 ± 0.001 |
| AAV2/5AlbA1AT | 0.83 ± 0.64 |
| AAV2/7AlbA1AT | 2.2 ± 1.7 |
| AAV2/8AlbA1AT | 18 ± 11 |

The serologic data described above suggest that AAV2/8 vector should not be neutralized in vivo following immunization with the other serotypes. C57BL/6 mice received intraportal injections of AAV2/8 vector expressing canine factor IX ($10^{11}$ genome copies) 56 days after they received intramuscular injections of A1AT vectors of different serotypes. High levels of factor IX expression were obtained 14 days following infusion of AAV2/8 into naïve animals (17+2 µg/ml, n=4) which were not significantly different that what was observed in animals immunized with AAV2/1 (31+23 µg/ml, n=4), AAV2/2 (16 µg/ml, n=2), and AAV2/7 (12 µg/ml, n=2). This contrasts to what was observed in AAV2/8 immunized animals that were infused with the AAV2/8 factor IX vector in which no detectable factor IX was observed (<0.1 µg/ml, n=4).

Oligonucleotides to conserved regions of the cap gene did amplify sequences from rhesus monkeys that represented unique AAVs. Identical cap signature sequences were found in multiple tissues from rhesus monkeys derived from at least two different colonies. Full-length rep and cap open reading frames were isolated and sequenced from single sources. Only the cap open reading frames of the novel AAVs were necessary to evaluate their potential as vectors because vectors with the AAV7 or AAV8 capsids were generated using the ITRs and rep from AAV2. This also simplified the comparison of different vectors since the actual vector genome is identical between different vector serotypes. In fact, the yields of recombinant vectors generated using this approach did not differ between serotypes.

Vectors based on AAV7 and AAV8 appear to be immunologically distinct (i.e., they are not neutralized by antibodies generated against other serotypes). Furthermore, sera from humans do not neutralize transduction by AAV7 and AAV8 vectors, which is a substantial advantage over the human derived AAVs currently under development for which a significant proportion of the human population has pre-existing immunity that is neutralizing [Chirmule, N., et al., (1999) Gene Ther 6, 1574-83].

The tropism of each new vector is favorable for in vivo applications. AAV2/7 vectors appear to transduce skeletal muscle as efficiently as AAV2/1, which is the serotype that confers the highest level of transduction in skeletal muscle of the primate AAVs tested to date [Xiao, W., cited above; Chou (2001), cited above, and Chou (2000), cited above]. Importantly, AAV2/8 provides a substantial advantage over the other serotypes in terms of efficiency of gene transfer to liver that until now has been relatively disappointing in terms of the numbers of hepatocytes stably transduced. AAV2/8 consistently achieved a 10 to 100-fold improvement in gene transfer efficiency as compared to the other vectors. The basis for the improved efficiency of AAV2/8 is unclear, although it presumably is due to uptake via a different receptor that is more active on the basolateral surface of hepatocytes. This improved efficiency will be quite useful in the development of liver-directed gene transfer where the number of transduced cells is critical, such as in urea cycle disorders and familial hypercholesterolemia.

Thus, the present invention provides a novel approach for isolating new AAVs based on PCR retrieval of genomic sequences. The amplified sequences were easily incorporated into vectors and tested in animals. The lack of pre-existing immunity to AAV7 and the favorable tropism of the vectors for muscle indicates that AAV7 is suitable for use as a vector in human gene therapy and other in vivo applications. Similarly, the lack of pre-existing immunity to the AAV serotypes of the invention, and their tropisms, renders them useful in delivery of therapeutic molecules and other useful molecules.

Example 9—Tissue Tropism Studies

In the design of a high throughput functional screening scheme for novel AAV constructs, a non-tissue specific and highly active promoter, CB promoter (CMV enhanced chicken β actin promoter) was selected to drive an easily detectable and quantifiable reporter gene, human α antitrypsin gene. Thus only one vector for each new AAV clone needs to be made for gene transfer studies targeting 3 different tissues, liver, lung and muscle to screen for tissue tropism of a particular AAV construct. The following table summarizes data generated from 4 novel AAV vectors in the tissue tropism studies (AAVCBA1AT), from which a novel AAV capsid clone, 44.2, was found to be a very potent gene transfer vehicle in all 3 tissues with a big lead in the lung tissue particularly. Table 8 reports data obtained (inn A1AT/mL serum) at day 14 of the study.

TABLE 8

| Vector | Target Tissue | | |
|---|---|---|---|
| | Lung | Liver | Muscle |
| AAV2/1 | ND | ND | 45 ± 11 |
| AAV2/5 | 0.6 ± 0.2 | ND | ND |
| AAV2/8 | ND | 84 ± 30 | ND |
| AAV2/rh. 2 (43.1) | 14 ± 7 | 25 ± 7.4 | 35 ± 14 |
| AAV2/rh. 10 (44.2) | 23 ± 6 | 53 ± 19 | 46 ± 11 |
| AAV2/rh. 13 (42.2) | 3.5 ± 2 | 2 ± 0.8 | 3.5 ± 1.7 |
| AAV2/rh. 21 (42.10) | 3.1 ± 2 | 2 ± 1.4 | 4.3 ± 2 |

A couple of other experiments were then performed to confirm the superior tropism of AAV 44.2 in lung tissue. First, AAV vector carried CC10hA1AT minigene for lung specific expression were pseudotyped with capsids of novel AAVs were given to Immune deficient animals (NCR nude) in equal volume (50 µl each of the original preps without dilution) via intratracheal injections as provided in the following table. In Table 9, 50 µl of each original prep per mouse, NCR Nude, detection limit ≥0.033 µg/ml, Day 28

TABLE 9

| Vector | Total GC in 50 µl vector | µg of A1AT/ml with 50 µl vector | µg of A1AT/ml with $1 \times 10^{11}$ vector | Relative Gene transfer as compared to rh. 10 (clone 44.2) |
|---|---|---|---|---|
| 2/1 | $3 \times 10^{12}$ | 2.6 ± 0.5 | 0.09 ± 0.02 | 2.2 |
| 2/2 | $5.5 \times 10^{11}$ | <0.03 | <0.005 | <0.1 |
| 2/5 | $3.6 \times 10^{12}$ | 0.65 ± 0.16 | 0.02 ± 0.004 | 0.5 |
| 2/7 | $4.2 \times 10^{12}$ | 1 ± 0.53 | 0.02 ± 0.01 | 0.5 |
| 2/8 | $7.5 \times 10^{11}$ | 0.9 ± 0.7 | 0.12 ± 0.09 | 2.9 |
| 2/ch. 5 (A.3.1) | $9 \times 10^{12}$ | 1 ± 0.7 | 0.01 ± 0.008 | 0.24 |
| 2/rh. 8 (43.25) | $4.6 \times 10^{12}$ | 26 ± 21 | 0.56 ± 0.46 | 13.7 |
| 2/rh. 10 (44.2) | $2.8 \times 10^{12}$ | 115 ± 38 | 4.1 ± 1.4 | 100 |
| 2/rh. 13 (42.2) | $6 \times 10^{12}$ | 7.3 ± 0.8 | 0.12 ± 0.01 | 2.9 |
| 2/rh. 21 (42.10) | $2.4 \times 10^{12}$ | 9 ± 0.9 | 0.38 ± 0.04 | 9.3 |
| 2/rh. 22 (42.11) | $2.6 \times 10^{12}$ | 6 ± 0.4 | 0.23 ± 0.02 | 5.6 |
| 2/rh. 24 (42.13) | $1.1 \times 10^{11}$ | 0.4 ± 0.3 | 0.4 ± 0.3 | 1 |

The vectors were also administered to immune competent animals (C57BL/6) in equal genome copies ($1 \times 10^{11}$ GC) as shown in the Table 10. ($1 \times 10^{11}$ GC per animal, C57BL/6, day 14, detection limit ≥0.033 µg/ml)

TABLE 10

| AAV Vector | µg of A1AT/ml with $1 \times 10^{11}$ vector | Relative Gene transfer as compared to rh. 10 (clone 44.2) |
|---|---|---|
| 2/1 | 0.076 ± 0.031 | 2.6 |
| 2/2 | 0.1 ± 0.09 | 3.4 |
| 2/5 | 0.0840.033 | 2.9 |
| 2/7 | 0.33 ± 0.01 | 11 |
| 2/8 | 1.92 ± 1.3 | 2.9 |
| 2/ch. 5 (A.3.1) | 0.048 ± 0.004 | 1.6 |
| 2/rh. 8 (43.25) | 1.7 ± 0.7 | 58 |
| 2/rh. 10 (44.2) | 2.93 ± 1.7 | 100 |
| 2/rh. 13 (42.2) | 0.45 ± 0.15 | 15 |
| 2/rh. 21 (42.10) | 0.86 ± 0.32 | 29 |
| 2/rh. 22 (42.11) | 0.38 ± 0.18 | 13 |
| 2/rh. 24 (42.13) | 0.3 ± 0.19 | 10 |

The data from both experiments confirmed the superb tropism of clone 44.2 in lung-directed gene transfer.

Interestingly, performance of clone 44.2 in liver and muscle directed gene transfer was also outstanding, close to that of the best liver transducer, AAV8 and the best muscle transducer AAV1, suggesting that this novel AAV has some intriguing biological significance.

To study serological properties of those novel AAVs, pseudotyped AAVGFP vectors were created for immunization of rabbits and in vitro transduction of 84-31 cells in the presence and absence of antisera against different capsids. The data are summarized below:

TABLE 11

| | Cross-NAB assay in 8431 cells and adenovirus (Adv) coinfection Infection in 8431 cells (coinfected with Adv) with: | | | |
|---|---|---|---|---|
| Serum from rabbit immunized with: | $10^9$ GC rh. 13 AAV2/42.2 | $10^9$ GC rh. 21 AAV2/42.10 | $10^9$ GC rh. 22 AAV2/42.11 | $10^{10}$ GC rh. 24 AAV2/42.13 |
| AAV2/1 | 1/20 | 1/20 | 1/20 | No NAB |
| AAV2/2 | 1/640 | 1/1280 | 1/5120 | No NAB |
| AAV2/5 | No NAB | 1/40 | 1/160 | No NAB |
| AAV2/7 | 1/81920 | 1/81920 | 1/40960 | 1/640 |
| AAV2/8 | 1/640 | 1/640 | 1/320 | 1/5120 |
| Ch. 5 AAV2/A3 | 1/20 | 1/160 | 1/640 | 1/640 |
| rh. 8 AAV2/43.25 | 1/20 | 1/20 | 1/20 | 1/320 |

TABLE 11-continued

| | | | | |
|---|---|---|---|---|
| rh. 10 AAV2/44.2 | No NAB | No NAB | No NAB | 1/5120 |
| rh. 13 AAV2/42.2 | 1/5120 | 1/5120 | 1/5120 | No NAB |
| rh. 21 AAV2/42.10 | 1/5120 | 1/10240 | 1/5120 | 1/20 |
| rh. 22 AAV2/42.11 | 1/20480 | 1/20480 | 1/40960 | No NAB |
| rh. 24 AAV2/42.13 | No NAB | 1/20 | 1/20 | 1/5120 |

Cross-NAB assay in 8431 cells and Adv coinfection
Infection in 8431 cells (coinfected with Adv) with:

| Serum from rabbit immunized with: | $10^9$ GC rh. 12 AAV2/42.1B | $10^{10}$ GC ch. 5 AAV2/A3 | $10^{10}$ GC rh. 8 AAV2/43.25 | $10^9$ GC rh. 10 AAV2/44.2 | $10^9$ GC rh. 20 AAV2/42.8.2 |
|---|---|---|---|---|---|
| AAV2/1 | No NAB | 1/20480 | No NAB | 1/80 | ND |
| AAV2/2 | 1/20 | No NAB | No NAB | No NAB | ND |
| AAV2/5 | No NAB | 1/320 | No NAB | No NAB | ND |
| AAV2/7 | 1/2560 | 1/640 | 1/160 | 1/81920 | ND |
| AAV2/8 | 1/10240 | 1/2560 | 1/2560 | 1/81920 | ND |
| ch. 5 AAV2/A3 | 1/1280 | 1/10240 | ND | 1/5120 | 1/320 |
| rh. 8 AAV2/43.25 | 1/1280 | ND | 1/20400 | 1/5120 | 1/2560 |
| rh. 10 AAV2/44.2 | 1/5120 | ND | ND | 1/5120 | 1/5120 |
| rh. 13 AAV2/42.2 | 1/20 | ND | ND | No NAB | 1/320 |
| rh. 21 AAV2/42.10 | 1/20 | ND | ND | 1/40 | 1/80 |
| rh. 22 AAV2/42.11 | No NAB | ND | ND | ND | No NAB |
| rh. 24 AAV2/42.13 | 1/5120 | ND | ND | ND | 1/2560 |

TABLE 12

| | Titer of rabbit sera | | Titer after |
|---|---|---|---|
| | Vector | Titer d21 | Boosting |
| ch. 5 | AAV2/A3 | 1/10,240 | 1/40,960 |
| rh. 8 | AAV2/43.25 | 1/20,400 | 1/163,840 |
| rh. 10 | AAV2/44.2 | 1/10,240 | 1/527,680 |
| rh. 13 | AAV2/42.2 | 1/5,120 | 1/20,960 |
| rh. 21 | AAV2/42.10 | 1/20,400 | 1/81,920 |
| rh. 22 | AAV2/42.11 | 1/40,960 | ND |
| rh. 24 | AAV2/42.13 | 1/5,120 | ND |

TABLE 13 a. Infection in 8431 cells (coinfected with Adv) with GFP

| | $10^9$ GC/well AAV2/1 | $10^9$ GC/well AAV2/2 | $10^9$ GC/well AAV2/5 | $10^9$ GC/well AAV2/7 | $10^9$ GC/well AAV2/8 | $10^9$ GC/well ch. 5 AAV2/A3 |
|---|---|---|---|---|---|---|
| # GFU/ field | 128 | >200 | 95 | 56 | 13 | 1 |
| | 83 | >200 | 65 | 54 | 11 | 1 | b. Infection in 8431 cells (coinfected with Adv) with GFP

| | $10^9$ GC/well rh. 8 AAV2/43.25 | $10^9$ GC/well rh. 10 AAV2/44.2 | $10^9$ GC/well rh. 13 AAV2/42.2 | $10^9$ GC/well rh. 21 AAV2/42.10 | $10^9$ GC/well rh. 22 AAV2/42.11 | $10^9$ GC/well rh. 24 AAV2/42.13 | $10^9$ GC/well rh. 12 AAV2/42.1B |
|---|---|---|---|---|---|---|---|
| # GFU/ field | 3 | 13 | 54 | 62 | 10 | 3 | 18 |
| | 2 | 12 | 71 | 60 | 14 | 2 | 20 |
| | | | 48 | 47 | 16 | 3 | 12 |

Example 10—Mouse Model of Familial Hypercholesterolemia

The following experiment demonstrates that the AAV2/7 construct of the invention delivers the LDL receptor and express LDL receptor in an amount sufficient to reduce the levels of plasma cholesterol and triglycerides in animal models of familial hypercholesterolemia.

A. Vector Construction

AAV vectors packaged with AAV7 or AAV8 capsid proteins were constructed using a pseudotyping strategy [Hildinger M, et al., J. Virol 2001; 75:6199-6203]. Recombinant AAV genomes with AAV2 inverted terminal repeats (ITR) were packaged by triple transfection of 293 cells with the cis-plasmid, the adenovirus helper plasmid and a chimeric packaging construct, a fusion of the capsids of the novel AAV serotypes with the rep gene of AAV2. The chimeric packaging plasmid was constructed as previously described [Hildinger et al, cited above]. The recombinant vectors were purified by the standard $CsCl_2$ sedimentation method. To determine the yield TaqMan (Applied Biosystems) analysis was performed using probes and primers targeting the SV40 poly(A) region of the vectors [Gao G P, et al., Hum Gene Ther. 2000 Oct. 10; 11(15):2079-91]. The resulting vectors express the transgene under the control of the human thyroid hormone binding globulin gene promoter (TBG).

B. Animals

LDL receptor deficient mice on the C57Bl/6 background were purchased from the Jackson Laboratory (Bar Harbor, Me., USA) and maintained as a breeding colony. Mice were given unrestricted access to water and obtained a high fat Western Diet (high % cholesterol) starting three weeks prior to vector injection. At day −7 as well at day 0, blood was obtained via retroorbital bleeds and the lipid profile evaluated. The mice were randomly divided into seven groups. The vector was injected via an intraportal injection as previously described ([Chen S J et al., Mol Therapy 2000; 2(3), 256-261]. Briefly, the mice were anaesthetized with ketamine and xylazine. A laparotomy was performed and the portal vein exposed. Using a 30 g needle the appropriate dose of vector diluted in 100 ul PBS was directly injected into the portal vein. Pressure was applied to the injection site to ensure a stop of the bleeding. The skin wound was closed and draped and the mice carefully monitored for the following day. Weekly bleeds were performed starting at day 14 after liver directed gene transfer to measure blood lipids. Two animals of each group were sacrificed at the time points week 6 and week 12 after vector injection to examine atherosclerotic plaque size as well as receptor expression. The remaining mice were sacrificed at week 20 for plaque measurement and determination of transgene expression.

TABLE 14

|  | Vector | dose | n |
|---|---|---|---|
| Group 1 | AAV2/7-TBG-hLDLr | $1 \times 10^{12}$ gc | 12 |
| Group 2 | AAV2/7-TBG-hLDLr | $3 \times 10^{11}$ gc | 12 |
| Group 3 | AAV2/7-TBG-hLDLr | $1 \times 10^{11}$ gc | 12 |
| Group 4 | AAV2/8-TBG-hLDLr | $1 \times 10^{12}$ gc | 12 |
| Group 5 | AAV2/8-TBG-hLDLr | $3 \times 10^{11}$ gc | 12 |
| Group 6 | AAV2/8-TBG-hLDLr | $1 \times 10^{11}$ gc | 12 |
| Group 7 | AAV2/7-TBG-LacZ | $1 \times 10^{11}$ gc | 16 |

C. Serum Lipoprotein and Liver Function Analysis

Blood samples were obtained from the retroorbital plexus after a 6 hour fasting period. The serum was separated from the plasma by centrifugation. The amount of plasma lipoproteins and liver transaminases in the serum were detected using an automatized clinical chemistry analyzer (ACE, Schiapparelli Biosystems, Alpha Wassermann)

D. Detection of Transgene Expression

LDL receptor expression was evaluated by immunofluorescence staining and Western blotting. For Western Blot frozen liver tissue was homogenized with lysis buffer (20 mM Tris, pH7.4, 130 mM NaCl, 1% Triton X 100, proteinase inhibitor (complete, EDTA-free, Roche, Mannheim, Germany). Protein concentration was determined using the Micro BCA Protein Assay Reagent Kit (Pierce, Rockford, Ill.). 40 µg of protein was resolved on 4-15% Tris-HCl Ready Gels (Biorad, Hercules, Calif.) and transferred to a nitrocellulose membrane (Invitrogen,). To generate Anti-hLDL receptor antibodies a rabbit was injected intravenously with an AdhLDLr prep ($1 \times 10^{13}$ GC). Four weeks later the rabbit serum was obtained and used for Western Blot. A 1:100 dilution of the serum was used as a primary antibody followed by a HRP-conjugated anti-rabbit IgG and ECL chemiluminescent detection (ECL Western Blot Detection Kit, Amersham, Arlington Heights, Ill.).

E. Immunocytochemistry

For determination of LDL receptor expression in frozen liver sections immunohistochemistry analyses were performed. 10 um cryostat sections were either fixed in acetone for 5 minutes, or unfixed. Blocking was obtained via a 1 hour incubation period with 10% of goat serum. Sections were then incubated for one hour with the primary antibody at room temperature. A rabbit polyclonal antibody anti-human LDL (Biomedical Technologies Inc., Stoughton, Mass.) was used diluted accordingly to the instructions of the manufacturer. The sections were washed with PBS, and incubated with 1:100 diluted fluorescein goat anti-rabbit IgG (Sigma, St Louis, Mo.). Specimens were finally examined under fluorescence microscope Nikon Microphot-FXA. In all cases, each incubation was followed by extensive washing with PBS. Negative controls consisted of preincubation with PBS, omission of the primary antibody, and substitution of the primary antibody by an isotype-matched non-immune control antibody. The three types of controls mentioned above were performed for each experiment on the same day.

F. Gene Transfer Efficiency

Liver tissue was obtained after sacrificing the mice at the designated time points. The tissue was shock frozen in liquid nitrogen and stored at −80° C. until further processing. DNA was extracted from the liver tissue using a QIAamp DNA Mini Kit (QIAGEN GmbH, Germany) according to the manufacturers protocol. Genome copies of AAV vectors in the liver tissue were evaluated using Taqman analysis using probes and primers against the SV40 poly(A) tail as described above.

G. Atherosclerotic Plaque Measurement

For the quantification of the atherosclerotic plaques in the mouse aorta the mice were anaesthetized (10% ketamine and xylazine, ip), the chest opened and the arterial system perfused with ice-cold phosphate buffered saline through the left ventricle. The aorta was then carefully harvested, slit down along the ventral midline from the aortic arch down to the femoral arteries and fixed in formalin. The lipid-rich atherosclerotic plaques were stained with Sudan IV (Sigma, Germany) and the aorta pinned out flat on a black wax surface. The image was captured with a Sony DXC-960 MD color video camera. The area of the plaque as well as of the complete aortic surface was determined using Phase 3 Imaging Systems (Media Cybernetics).

H. Clearance of $I^{125}$ LDL

Two animals per experimental group were tested. A bolus of $I^{125}$-labeled LDL (generously provided by Dan Rader, U Penn) was infused slowly through the tail vein over a period of 30 sec (1,000,000 counts of $[I^{125}]$-LDL diluted in 100 µl sterile PBS/animal). At time points 3 min, 30 min, 1.5 hr, 3 hr, 6 hr after injection a blood sample was obtained via the retro-orbital plexus. The plasma was separated off from the whole blood and 10 µl plasma counted in the gamma counter. Finally the fractional catabolic rate was calculated from the lipoprotein clearance data.

I. Evaluation of Liver Lipid Accumulation

Oil Red Staining of frozen liver sections was performed to determine lipid accumulation. The frozen liver sections were briefly rinsed in distilled water followed by a 2 minute incubation in absolute propylene glycol. The sections were then stained in oil red solution (0.5% in propylene glycol) for 16 hours followed by counterstaining with Mayer's hematoxylin solution for 30 seconds and mounting in warmed glycerin jelly solution.

For quantification of the liver cholesterol and triglyceride content liver sections were homogenized and incubated in chloroform/methanol (2:1) overnight. After adding of 0.05%

H2504 and centrifugation for 10 minutes, the lower layer of each sample was collected, divided in two aliquots and dried under nitrogen. For the cholesterol measurement the dried lipids of the first aliquot were dissolved in 1% Triton X-100 in chloroform. Once dissolved, the solution was dried under nitrogen. After dissolving the lipids in ddH$_2$O and incubation for 30 minutes at 3TC the total cholesterol concentration was measured using a Total Cholesterol Kit (Wako Diagnostics). For the second aliquot the dried lipids were dissolved in alcoholic KOH and incubated at 60° C. for 30 minutes. Then 1M MgCl2 was added, followed by incubation on ice for 10 minutes and centrifugation at 14,000 rpm for 30 minutes. The supernatant was finally evaluated for triglycerides (Wako Diagnostics).

All of the vectors pseudotyped in an AAV2/8 or AAV2/7 capsid lowered total cholesterol, LDL and triglycerides as compared to the control. These test vectors also corrected phenotype of hypercholesterolemia in a dose-dependent manner. A reduction in plaque area for the AAV2/8 and AAV2/7 mice was observed in treated mice at the first test (2 months), and the effect was observed to persist over the length of the experiment (6 months).

Example 10—Functional Factor IX Expression and Correction of Hemophilia

A. Knock-Out Mice

Functional canine factor IX (FIX) expression was assessed in hemophilia B mice. Vectors with capsids of AAV1, AAV2, AAV5, AAV7 or AAV8 were constructed to deliver AAV2 5' ITR-liver-specific promoter [LSP]-canine FIX-woodchuck hepatitis post-regulatory element (WPRE)-AAV2 3' ITR. The vectors were constructed as described in Wang et al, 2000, *Molecular Therapy* 2: 154-158), using the appropriate capsids.

Knock-out mice were generated as described in Wang et al, 1997. *Proc. Natl. Acad. Sci. USA* 94: 11563-11566. This model closely mimic the phenotypes of hemophilia Bin human.

Vectors of different serotypes (AAV1, AAV2, AAV5, AAV7 and AAV8) were delivered as a single intraportal injection into the liver of adult hemophiliac C57Bl/6 mice in a dose of 1×10$^{11}$ GC/mouse for the five different serotypes and one group received an AAV8 vector at a lower dose, 1×10$^{10}$ GC/mouse. Control group was injected with 1×10$^{11}$ GC of AAV2/8 TBG LacZ3. Each group contains 5-10 male and female mice. Mice were bled bi-weekly after vector administration.

1. ELISA

The canine FIX concentration in the mouse plasma was determined by an ELISA assay specific for canine factor IX, performed essentially as described by Axelrod et al, 1990, *Proc. Natl. Acad Sci. USA,* 87:5173-5177 with modifications. Sheep anti-canine factor IX (Enzyme Research Laboratories) was used as primary antibody and rabbit anti-canine factor IX ((Enzyme Research Laboratories) was used as secondary antibody. Beginning at two weeks following injection, increased plasma levels of cFIX were detected for all test vectors. The increased levels were sustained at therapeutic levels throughout the length of the experiment, i.e., to 12 weeks. Therapeutic levels are considered to be 5% of normal levels, i.e., at about 250 ng/mL.

The highest levels of expression were observed for the AAV2/8 (at 10") and AAV2/7 constructs, with sustained superphysiology levels cFIX levels (ten-fold higher than the normal level). Expression levels for AAV2/8 (10$^{11}$) were approximately 10 fold higher than those observed for AAV2/2 and AAV2/8 (10$^{10}$). The lowest expression levels, although still above the therapeutic range, were observed for AAV2/5.

2. In Vitro Activated Partial Thromboplastin Time (aPTT) Assay

Functional factor IX activity in plasma of the FIX knock-out mice was determined by an in vitro activated partial thromboplastin time (aPTT) assay—Mouse blood samples were collected from the retro-orbital plexus into 1/10 volume of citrate buffer. The aPTT assay was performed as described by Wang et al, 1997, *Proc. Natl. Acad. Sci. USA* 94: 11563-11566.

Clotting times by aPTT on plasma samples of all vector injected mice were within the normal range (approximately 60 sec) when measured at two weeks post-injection, and sustained clotting times in the normal or shorter than normal range throughout the study period (12 weeks).

Lowest sustained clotting times were observed in the animals receiving AAV2/8 (10$^{11}$) and AAV2/7. By week 12, AAV2/2 also induced clotting times similar to those for AAV2/8 and AAV2/7. However, this lowered clotting time was not observed for AAV2/2 until week 12, whereas lowered clotting times (in the 25-40 sec range) were observed for AAV2/8 and AAV2/7 beginning at week two.

Immuno-histochemistry staining on the liver tissues harvested from some of the treated mice is currently being performed. About 70-80% of hepatocytes are stained positive for canine FIX in the mouse injected with AAV2/8.cFIX vector.

B. Hemophilia B Dogs

Dogs that have a point mutation in the catalytic domain of the F.IX gene, which, based on modeling studies, appears to render the protein unstable, suffer from hemophilia B [Evans et al, 1989, Proc. Natl. Acad. Sci. USA, 86:10095-10099). A colony of such dogs has been maintained for more than two decades at the University of North Carolina, Chapel Hill. The homeostatic parameters of these dogs are well described and include the absence of plasma F.IX antigen, whole blood clotting times in excess of 60 minutes, whereas normal dogs are 6-8 minutes, and prolonged activated partial thromboplastin time of 50-80 seconds, whereas normal dogs are 13-28 seconds. These dogs experience recurrent spontaneous hemorrhages. Typically, significant bleeding episodes are successfully managed by the single intravenous infusion of 10 ml/kg of normal canine plasma; occasionally, repeat infusions are required to control bleeding.

Four dogs are injected intraportally with AAV.cFIX according to the schedule below. A first dog receives a single injection with AAV2/2.cFIX at a dose of 3.7×10$^{11}$ genome copies (GC)/kg. A second dog receives a first injection of AAV2/2.cFIX (2.8×10$^{11}$ GC/kg), followed by a second injection with AAV2/7.cFIX (2.3×10$^{13}$ GC/kg) at day 1180. A third dog receives a single injection with AAV2/2.cFIX at a dose of 4.6×10$^{12}$ GC/kg. The fourth dog receives an injection with AAV2/2.cFIX (2.8×10$^{12}$ GC/kg) and an injection at day 995 with AAV2/7.cFIX (5×10$^{12}$ GC/kg).

The abdomen of hemophilia dogs are aseptically and surgically opened under general anesthesia and a single infusion of vector is administered into the portal vein. The animals are protected from hemorrhage in the pen-operative period by intravenous administration of normal canine plasma. The dog is sedated, intubated to induce general anesthesia, and the abdomen shaved and prepped. After the abdomen is opened, the spleen is moved into the operative field. The splenic vein is located and a suture is loosely placed proximal to a small distal incision in the vein. A needle is rapidly inserted into the vein, then the suture is loosened and a 5 F cannula is threaded to an intravenous location near the portal vein threaded to an intravenous location near the portal vein bifurcation. After hemostasis is secured and the catheter balloon inflated, approximately 5.0 ml of vector diluted in PBS is infused into the portal vein over a 5 minute interval. The vector infusion is followed by a 5.0 ml infusion of saline. The balloon is then deflated, the callula removed and venous hemostasis is secured. The spleen is then replaced, bleeding vessels are cauterized and the operative wound is closed. The animal is extubated having tolerated the surgical procedure well. Blood samples are analyzed as described. [Wang et al, 2000, *Molecular Therapy* 2: 154-158]

Results showing correction or partial correction are anticipated for AAV2/7.

All publications cited in this specification and priority applications, including U.S. patent application Ser. No. 15/584,674, U.S. patent application Ser. No. 14/956,934, U.S. patent application Ser. No. 13/633,971, U.S. patent application Ser. No. 12/962,793, U.S. patent application Ser. No. 10/291,583, and U.S. Provisional Patent Application Nos. 60/386,675, 60/377,066, 60/341,117, and 60/350,607, are incorporated herein by reference. While the invention has been described with reference to particularly preferred embodiments, it will be appreciated that modifications can be made without departing from the spirit of the invention. Such modifications are intended to fall within the scope of the claims.

SEQUENCE LISTING

```
<160> NUMBER OF SEQ ID NOS: 120

<210> SEQ ID NO 1
<211> LENGTH: 4721
<212> TYPE: DNA
<213> ORGANISM: Unknown
<220> FEATURE:
<223> OTHER INFORMATION: adeno-associated virus serotype 7

<400> SEQUENCE: 1
ttggccactc cctctatgcg cgctcgctcg ctcggtgggg cctgcggacc aaaggtccgc      60
agacggcaga gctctgctct gccggcccca ccgagcgagc gagcgcgcat agagggagtg     120
gccaactcca tcactagggg taccgcgaag cgcctccac  gctgccgcgt cagcgctgac     180
gtaaatcacg tcataggga gtggtcctgt attagctgtc acgtgagtgc ttttgcgaca      240
ttttgcgaca ccacgtggcc atttgaggta tatatggccg agtgagcgag caggatctcc     300
attttgaccg cgaaatttga acgagcagca gccatgccgg gtttctacga gatcgtgatc     360
aaggtgccga gcgacctgga cgagcacctg ccgggcattt ctgactcgtt tgtgaactgg     420
gtggccgaga aggaatggga gctgccccg  gattctgaca tggatctgaa tctgatcgag     480
caggcacccc tgaccgtggc cgagaagctg cagcgcgact tcctggtcca atggcgccgc     540
gtgagtaagg ccccggaggc cctgttcttt gttcagttcg agaagggcga gagctacttc     600
caccttcacg ttctggtgga ccacggggt gtcaagtcca tggtgctagg ccgcttcctg      660
agtcagattc gggagaagct ggtccagacc atctaccgcg gggtcgagcc cacgctgccc     720
aactggttcg cggtgaccaa gacgcgtaat ggcgccggcg gggggaacaa ggtggtggac     780
gagtgctaca tccccaacta cctcctgccc aagacccagc ccgagctgca gtgggcgtgg     840
actaacatgg aggagtatat aagcgcgtgt ttgaacctgg ccgaacgcaa acggctcgtg     900
gcgcagcacc tgacccacgt cagccagacg caggagcaga acaaggagaa tctgaacccc     960
aattctgacg cgcccgtgat caggtcaaaa acctccgcgc gctacatgga gctggtcggg    1020
tggctggtgg accggggcat cacctccgag aagcagtgga tccaggagga ccaggcctcg    1080
tacatctcct tcaacgccgc ctccaactcg cggtcccaga tcaaggccgc gctggacaat    1140
gccggcaaga tcatggcgct gaccaaatcc gcgcccgact acctggtggg gccctcgctg    1200
cccgcggaca ttaaaaccaa ccgcatctac cgcatcctgg agctgaacgg gtacgatcct    1260
gcctacgccg gctccgtctt tctcggctgg gcccagaaaa agttcgggaa gcgcaacacc    1320
```

```
atctggctgt ttgggcccgc caccaccggc aagaccaaca ttgcggaagc catcgcccac   1380
gccgtgccct tctacggctg cgtcaactgg accaatgaga ctttcccctt caacgattgc   1440
gtcgacaaga tggtgatctg gtgggaggag ggcaagatga cggccaaggt cgtggagtcc   1500
gccaaggcca ttctcggcgg cagcaaggtg cgcgtggacc aaaagtgcaa gtcgtccgcc   1560
cagatcgacc ccaccccgt gatcgtcacc tccaacacca acatgtgcgc cgtgattgac   1620
gggaacagca ccaccttcga gcaccagcag ccgttgcagg accggatgtt caaatttgaa   1680
ctcacccgcc gtctggagca cgactttggc aaggtgacga agcaggaagt caaagagttc   1740
ttccgctggg ccagtgatca cgtgaccgag gtggcgcatg agttctacgt cagaaagggc   1800
ggagccagca aaagacccgc ccccgatgac gcggatataa gcgagcccaa gcgggcctgc   1860
ccctcagtcg cggatccatc gacgtcagac gcggaaggag ctccggtgga ctttgccgac   1920
aggtaccaaa acaaatgttc tcgtcacgcg ggcatgattc agatgctgtt tccctgcaaa   1980
acgtgcgaga gaatgaatca gaatttcaac atttgcttca cacacggggt cagagactgt   2040
ttagagtgtt tccccggcgt gtcagaatct caaccggtcg tcagaaaaaa gacgtatcgg   2100
aaactctgcg cgattcatca tctgctgggg cgggcgcccg agattgcttg ctcggcctgc   2160
gacctggtca acgtggacct ggacgactgc gtttctgagc aataaatgac ttaaaccagg   2220
tatggctgcc gatggttatc ttccagattg gctcgaggac aacctctctg agggcattcg   2280
cgagtggtgg gacctgaaac ctggagcccc gaaacccaaa gccaaccagc aaaagcagga   2340
caacggccgg ggtctggtgc ttcctggcta caagtacctc ggacccttca acggactcga   2400 caaggggggag cccgtcaacg cggcggacgc agcggccctc gagcacgaca aggcctacga   2460
ccagcagctc aaagcgggtg acaatccgta cctgcggtat aaccacgccg acgccgagtt   2520
tcaggagcgt ctgcaagaag atacgtcatt tgggggcaac ctcgggcgag cagtcttcca   2580
ggccaagaag cggttctcg aacctctcgg tctggttgag gaaggcgcta agacggctcc   2640
tgcaaagaag agaccggtag agccgtcacc tcagcgttcc cccgactcct ccacgggcat   2700
cggcaagaaa ggccagcagc cgccagaaaa gagactcaat ttcggtcaga ctggcgactc   2760
agagtcagtc cccgaccctc aacctctcgg agaacctcca gcagcgccct ctagtgtggg   2820
atctggtaca gtggctgcag gcggtggcgc accaatggca gacaataacg aaggtgccga   2880
cggagtgggt aatgcctcag gaaattggca ttgcgattcc acatggctgg gcgacagagt   2940
cattaccacc agcacccgaa cctgggccct gcccacctac aacaaccacc tctacaagca   3000
aatctccagt gaaactgcag gtagtaccaa cgacaacacc tacttcggct acagcacccc   3060 ctggggtat tttgacttta acagattcca ctgccacttc tcaccacgtg actggcagcg   3120
actcatcaac aacaactggg gattccggcc caagaagctg cggttcaagc tcttcaacat   3180
ccaggtcaag gaggtcacga cgaatgacgg cgttacgacc atcgctaata accttaccag   3240
cacgattcag gtattctcgg actcggaata ccagctgccg tacgtcctcg gctctgcgca   3300
ccagggctgc ctgcctccgt tcccggcgga cgtcttcatg attcctcagt acggctacct   3360
gactctcaac aatggcagtc agtctgtggg acgttcctcc ttctactgcc tggagtactt   3420
cccctctcag atgctgagaa cgggcaacaa ctttgagttc agctacagct cgaggacgt   3480 gcctttccac agcagctacg cacacagcca gagcctggac cggctgatga atcccctcat   3540
cgaccagtac ttgtactacc tggccagaac acagagtaac ccaggaggca cagctggcaa   3600
tcgggaactg cagttttacc agggcggcc ttcaactatg ccgaacaag ccaagaattg   3660
```

```
gttacctgga ccttgcttcc ggcaacaaag agtctccaaa acgctggatc aaaacaacaa    3720
cagcaacttt gcttggactg gtgccaccaa atatcacctg aacggcagaa actcgttggt    3780
taatcccggc gtcgccatgg caactcacaa ggacgacgag gaccgctttt tcccatccag    3840
cggagtcctg attttggaa aaactggagc aactaacaaa actacattgg aaaatgtgtt    3900
aatgacaaat gaagaagaaa ttcgtcctac taatcctgta gccacggaag aatacgggat    3960
agtcagcagc aacttacaag cggctaatac tgcagcccag acacaagttg tcaacaacca    4020
gggagcctta cctggcatgg tctggcagaa ccgggacgtg tacctgcagg gtcccatctg    4080
ggccaagatt cctcacacgg atggcaactt tcacccgtct cctttgatgg gcggctttgg    4140
acttaaacat ccgcctcctc agatcctgat caagaacact cccgttcccg ctaatcctcc    4200
ggaggtgttt actcctgcca gtttgcttc gttcatcaca cagtacagca ccggacaagt    4260
cagcgtggaa atcgagtggg agctgcagaa ggaaaacagc aagcgctgga accccggagat    4320 tcagtacacc tccaactttg aaaagcagag tggtgtggac tttgccgttg acagccaggg    4380
tgtttactct gagcctcgcc ctattggcac tcgttacctc acccgtaatc tgtaattgca    4440
tgttaatcaa taaaccggtt gattcgtttc agttgaactt tggtctcctg tgcttcttat    4500
cttatcggtt tccatagcaa ctggttacac attaactgct tgggtgcgct tcacgataag    4560
aacactgacg tcaccgcggt acccctagtg atggagttgg ccactccctc tatgcgcgct    4620
cgctcgctcg gtggggcctg cggaccaaag gtccgcagac ggcagagctc tgctctgccg    4680
gccccaccga gcgagcgagc gcgcatagag ggagtggcca a                         4721
```

<210> SEQ ID NO 2
<211> LENGTH: 737
<212> TYPE: PRT
<213> ORGANISM: Unknown
<220> FEATURE:
<223> OTHER INFORMATION: capsid protein of adeno-associated virus serotpye 7

<400> SEQUENCE: 2

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Ala Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175
```

```
Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
            195                 200                 205

Gly Ala Pro Met Ala Asp Asn Asn Glu Gly Ala Asp Gly Val Gly Asn
            210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
            245                 250                 255

Leu Tyr Lys Gln Ile Ser Ser Glu Thr Ala Gly Ser Thr Asn Asp Asn
            260                 265                 270

Thr Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
            290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
            325                 330                 335

Asn Leu Thr Ser Thr Ile Gln Val Phe Ser Asp Ser Glu Tyr Gln Leu
            340                 345                 350

Pro Tyr Val Leu Gly Ser Ala His Gln Gly Cys Leu Pro Pro Phe Pro
            355                 360                 365

Ala Asp Val Phe Met Ile Pro Gln Tyr Gly Tyr Leu Thr Leu Asn Asn
            370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
            405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
            435                 440                 445

Arg Thr Gln Ser Asn Pro Gly Gly Thr Ala Gly Asn Arg Glu Leu Gln
            450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
            485                 490                 495

Gln Asn Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
            515                 520                 525

His Lys Asp Asp Glu Asp Arg Phe Phe Pro Ser Ser Gly Val Leu Ile
            530                 535                 540

Phe Gly Lys Thr Gly Ala Thr Asn Lys Thr Thr Leu Glu Asn Val Leu
545                 550                 555                 560

Met Thr Asn Glu Glu Ile Arg Pro Thr Asn Pro Val Ala Thr Glu
            565                 570                 575

Glu Tyr Gly Ile Val Ser Ser Asn Leu Gln Ala Ala Asn Thr Ala Ala
            580                 585                 590
```

-continued

```
Gln Thr Gln Val Val Asn Asn Gln Gly Ala Leu Pro Gly Met Val Trp
            595                 600                 605

Gln Asn Arg Asp Val Tyr Leu Gln Gly Pro Ile Trp Ala Lys Ile Pro
610                 615                 620

His Thr Asp Gly Asn Phe His Pro Ser Pro Leu Met Gly Gly Phe Gly
625                 630                 635                 640

Leu Lys His Pro Pro Gln Ile Leu Ile Lys Asn Thr Pro Val Pro
            645                 650                 655

Ala Asn Pro Pro Glu Val Phe Thr Pro Ala Lys Phe Ala Ser Phe Ile
            660                 665                 670

Thr Gln Tyr Ser Thr Gly Gln Val Ser Val Glu Ile Glu Trp Glu Leu
            675                 680                 685

Gln Lys Glu Asn Ser Lys Arg Trp Asn Pro Glu Ile Gln Tyr Thr Ser
690                 695                 700

Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
            725                 730                 735

Leu

<210> SEQ ID NO 3
<211> LENGTH: 623
<212> TYPE: PRT
<213> ORGANISM: Unknown
<220> FEATURE:
<223> OTHER INFORMATION: rep protein of adeno-associated virus serotype
      7

<400> SEQUENCE: 3

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Val Leu Val Glu
                85                  90                  95

Thr Thr Gly Val Lys Ser Met Val Leu Gly Arg Phe Leu Ser Gln Ile
            100                 105                 110

Arg Glu Lys Leu Val Gln Thr Ile Tyr Arg Gly Val Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Leu Asn
        195                 200                 205
```

```
Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ala Leu Thr Lys Ser Ala Pro Asp Tyr Leu Val Gly Pro Ser
        275                 280                 285

Leu Pro Ala Asp Ile Lys Thr Asn Arg Ile Tyr Arg Ile Leu Glu Leu
290                 295                 300

Asn Gly Tyr Asp Pro Ala Tyr Ala Gly Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Glu His Asp Phe Gly Lys Val Thr Lys Gln
450                 455                 460

Glu Val Lys Glu Phe Phe Arg Trp Ala Ser Asp His Val Thr Glu Val
465                 470                 475                 480

Ala His Glu Phe Tyr Val Arg Lys Gly Gly Ala Ser Lys Arg Pro Ala
                485                 490                 495

Pro Asp Asp Ala Asp Ile Ser Glu Pro Lys Arg Ala Cys Pro Ser Val
            500                 505                 510

Ala Asp Pro Ser Thr Ser Asp Ala Glu Gly Ala Pro Val Asp Phe Ala
        515                 520                 525

Asp Arg Tyr Gln Asn Lys Cys Ser Arg His Ala Gly Met Ile Gln Met
530                 535                 540

Leu Phe Pro Cys Lys Thr Cys Glu Arg Met Asn Gln Asn Phe Asn Ile
545                 550                 555                 560

Cys Phe Thr His Gly Val Arg Asp Cys Leu Glu Cys Phe Pro Gly Val
                565                 570                 575

Ser Glu Ser Gln Pro Val Val Arg Lys Thr Tyr Arg Lys Leu Cys
            580                 585                 590

Ala Ile His His Leu Leu Gly Arg Ala Pro Glu Ile Ala Cys Ser Ala
        595                 600                 605

Cys Asp Leu Val Asn Val Asp Leu Asp Asp Cys Val Ser Glu Gln
610                 615                 620
```

<210> SEQ ID NO 4
<211> LENGTH: 4393
<212> TYPE: DNA
<213> ORGANISM: Unknown
<220> FEATURE:
<223> OTHER INFORMATION: adeno-associated virus serotype 8

<400> SEQUENCE: 4

| | | | | | | |
|---|---|---|---|---|---|---|
| cagagaggga | gtggccaact | ccatcactag | gggtagcgcg | aagcgcctcc | cacgctgccg | 60 |
| cgtcagcgct | gacgtaaatt | acgtcatagg | ggagtggtcc | tgtattagct | gtcacgtgag | 120 |
| tgcttttgcg | gcattttgcg | acaccacgtg | gccatttgag | gtatatatgg | ccgagtgagc | 180 |
| gagcaggatc | tccattttga | ccgcgaaatt | tgaacgagca | gcagccatgc | cgggcttcta | 240 |
| cgagatcgtg | atcaaggtgc | cgagcgacct | ggacgagcac | ctgccgggca | tttctgactc | 300 |
| gtttgtgaac | tgggtggccg | agaaggaatg | ggagctgccc | ccggattctg | acatggatcg | 360 |
| gaatctgatc | gagcaggcac | ccctgaccgt | ggccgagaag | ctgcagcgcg | acttcctggt | 420 |
| ccaatggcgc | cgcgtgagta | aggccccgga | ggccctcttc | tttgttcagt | tcgagaaggg | 480 |
| cgagagctac | tttcacctgc | acgttctggt | cgagaccacg | ggggtcaagt | ccatggtgct | 540 |
| aggccgcttc | ctgagtcaga | ttcgggaaaa | gcttggtcca | gaccatctac | ccgcggggtc | 600 |
| gagccccacc | ttgcccaact | ggttcgcggt | gaccaaagac | gcggtaatgg | cgccggcggg | 660 |
| ggggaacaag | gtggtggacg | agtgctacat | ccccaactac | ctcctgccca | agactcagcc | 720 |
| cgagctgcag | tgggcgtgga | ctaacatgga | ggagtatata | agcgcgtgct | tgaacctggc | 780 |
| cgagcgcaaa | cggctcgtgg | cgcagcacct | gacccacgtc | agccagacgc | aggagcagaa | 840 |
| caaggagaat | ctgaacccca | attctgacgc | gcccgtgatc | aggtcaaaaa | cctccgcgcg | 900 |
| ctatatggag | ctggtcgggt | ggctggtgga | ccggggcatc | acctccgaga | agcagtggat | 960 |
| ccaggaggac | caggcctcgt | acatctcctt | caacgccgcc | tccaactcgc | ggtcccagat | 1020 |
| caaggccgcg | ctggacaatg | ccggcaagat | catggcgctg | accaaatccg | cgcccgacta | 1080 |
| cctggtgggg | ccctcgctgc | ccgcggacat | tacccagaac | cgcatctacc | gcatcctcgc | 1140 |
| tctcaacggc | tacgaccctg | cctacgccgc | ctccgtcttt | ctcggctggg | ctcagaaaaa | 1200 |
| gttcgggaaa | cgcaacacca | tctggctgtt | tgggcccgcc | accaccggca | agaccaacat | 1260 |
| tgcggaagcc | atcgcccacg | ccgtgccctt | ctacggctgc | gtcaactgga | ccaatgagaa | 1320 |
| cttccccttc | aatgattgcg | tcgacaagat | ggtgatctgg | tgggaggagg | caagatgac | 1380 |
| ggccaaggtc | gtggagtccg | ccaaggccat | tctcggcggc | agcaaggtgc | gcgtggacca | 1440 |
| aaagtgcaag | tcgtccgccc | agatcgaccc | caccccgtg | atcgtcacct | ccaacaccaa | 1500 |
| catgtgcgcc | gtgattgacg | ggaacagcac | caccttcgag | caccagcagc | ctctccagga | 1560 |
| ccggatgttt | aagttcgaac | tcacccgcgc | tctggagcac | gactttggca | aggtgacaaa | 1620 |
| gcaggaagtc | aaagagttct | tccgctgggc | cagtgatcac | gtgaccgagg | tggcgcatga | 1680 |
| gttttacgtc | agaaagggcg | gagccagcaa | aagacccgcc | cccgatgacg | cggataaaag | 1740 |
| cgagcccaag | cgggcctgcc | cctcagtcgc | ggatccatcg | acgtcagacg | cggaaggagc | 1800 |
| tccggtggac | tttgccgaca | ggtaccaaaa | caaatgttct | cgtcacgcgg | gcatgcttca | 1860 |
| gatgctgttt | ccctgcaaaa | cgtgcgagag | aatgaatcag | aatttcaaca | tttgcttcac | 1920 |
| acacggggtc | agagactgct | cagagtgttt | ccccggcgtg | tcagaatctc | aaccggtcgt | 1980 |
| cagaaagagg | acgtatcgga | aactctgtgc | gattcatcat | ctgctgggc | gggctcccga | 2040 |
| gattgcttgc | tcggcctgcg | atctggtcaa | cgtggacctg | gatgactgtg | tttctgagca | 2100 |

```
ataaatgact taaaccaggt atggctgccg atggttatct tccagattgg ctcgaggaca    2160
acctctctga gggcattcgc gagtggtggg cgctgaaacc tggagccccg aagcccaaag    2220
ccaaccagca aaagcaggac gacggccggg gtctggtgct tcctggctac aagtacctcg    2280
gacccttcaa cggactcgac aaggggagc ccgtcaacgc ggcggacgca gcggccctcg    2340
agcacgacaa ggcctacgac cagcagctgc aggcgggtga caatccgtac ctgcggtata    2400
accacgccga cgccgagttt caggagcgtc tgcaagaaga tacgtctttt gggggcaacc    2460
tcgggcgagc agtcttccag gccaagaagc gggttctcga acctctcggt ctggttgagg    2520
aaggcgctaa gacggctcct ggaaagaaga gaccggtaga gccatcaccc cagcgttctc    2580
cagactcctc tacgggcatc ggcaagaaag gccaacagcc cgccagaaaa agactcaatt    2640
ttggtcagac tggcgactca gagtcagttc cagaccctca acctctcgga gaacctccag    2700
cagcgccctc tggtgtggga cctaatacaa tggctgcagg cggtggcgca ccaatggcag    2760
acaataacga aggcgccgac ggagtgggta gttcctcggg aaattggcat tgcgattcca    2820
catggctggg cgacagagtc atcaccacca gcacccgaac ctgggccctg cccacctaca    2880
acaaccacct ctacaagcaa atctccaacg ggacatcggg aggagccacc aacgacaaca    2940
cctacttcgg ctacagcacc ccctgggggt attttgactt taacagattc cactgccact    3000
tttcaccacg tgactggcag cgactcatca caacaactg gggattccgg cccaagagac    3060
tcagcttcaa gctcttcaac atccaggtca aggaggtcac gcagaatgaa ggcaccaaga    3120
ccatcgccaa taacctcacc agcaccatcc aggtgtttac ggactcggag taccagctgc    3180
cgtacgttct cggctctgcc caccaggget gcctgcctcc gttcccggcg gacgtgttca    3240
tgattcccca gtacggctac ctaacactca caacggtag tcaggccgtg ggacgctcct    3300
ccttctactg cctggaatac tttccttcgc agatgctgag aaccggcaac aacttccagt    3360
ttacttacac cttcgaggac gtgcctttcc acagcagcta cgcccacagc cagagcttgg    3420
accggctgat gaatcctctg attgaccagt acctgtacta cttgtctcgg actcaaacaa    3480
caggaggcac ggcaaatacg cagactctgg gcttcagcca aggtgggcct aatacaatgg    3540
ccaatcaggc aaagaactgg ctgccaggac cctgttaccg ccaacaacgc gtctcaacga    3600
caaccgggca aaacaacaat agcaactttg cctggactgc tgggaccaaa taccatctga    3660
atggaagaaa ttcattggct aatcctggca tcgctatggc aacacacaaa gacgacgagg    3720
agcgttttt tcccagtaac gggatcctga tttttggcaa acaaatgct gccagagaca    3780
atgcggatta cagcgatgtc atgctcacca gcgaggaaga aatcaaaacc actaaccctg    3840
tggctacaga ggaatacggt atcgtggcag ataacttgca gcagcaaaac acggctcctc    3900
aaattggaac tgtcaacagc caggggggcct tacccggtat ggtctggcag aaccgggacg    3960
tgtacctgca gggtcccatc tgggccaaga ttcctcacac ggacggcaac ttccacccgt    4020
ctccgctgat gggcggcttt ggcctgaaac atcctccgcc tcagatcctg atcaagaaca    4080
cgcctgtacc tgcggatcct ccgaccacct tcaaccagtc aaagctgaac tctttcatca    4140
cgcaatacag caccggacag gtcagcgtgg aaattgaatg ggagctgcag aaggaaaaca    4200
gcaagcgctg gaaccccgag atccagtaca cctccaacta ctacaaatct acaagtgtgg    4260
actttgctgt taatacagaa ggcgtgtact ctgaaccccg ccccattggc acccgttacc    4320
tcaccccgtaa tctgtaattg cctgttaatc aataaaccgg ttgattcgtt tcagttgaac    4380
tttggtctct gcg                                                      4393
```

```
<210> SEQ ID NO 5
<211> LENGTH: 4385
<212> TYPE: DNA
<213> ORGANISM: Unknown
<220> FEATURE:
<223> OTHER INFORMATION: adeno-associated virus serotype 9

<400> SEQUENCE: 5
cagagaggga gtggccaact ccatcactag gggtaatcgc gaagcgcctc ccacgctgcc      60
gcgtcagcgc tgacgtagat tacgtcatag gggagtggtc ctgtattagc tgtcacgtga     120
gtgcttttgc gacatttttgc gacaccacat ggccatttga ggtatatatg gccgagtgag    180
cgagcaggat ctccattttg accgcgaaat ttgaacgagc agcagccatg ccgggcttct     240
acgagattgt gatcaaggtg ccgagcgacc tggacgagca cctgccgggc atttctgact     300
cttttgtgaa ctgggtggcc gagaaggaat gggagctgcc cccggattct gacatggatc     360
ggaatctgat cgagcaggca ccctgaccg tggccgagaa gctgcagcgc gacttcctgg     420
tccaatggcg ccgcgtgagt aaggcccggg aggccctctt ctttgttcag ttcgagaagg     480
gcgagagcta ctttcacctg cacgttctgg tcgagaccac gggggtcaag tccatggtgc     540
taggccgctt cctgagtcag attcgggaga agctggtcca gaccatctac cgcgggatcg     600 agccgacccct gcccaactgg ttcgcggtga ccaagacgcg taatggcgcc ggcggggga     660 acaaggtggt ggacgagtgc tacatcccca actacctcct gcccaagact cagcccgagc     720
tgcagtgggc gtggactaac atggaggagt atataagcgc gtgcttgaac ctggccgagc     780
gcaaacggct cgtggcgcag cacctgaccc acgtcagcca gacgcaggag cagaacaagg     840
agaatctgaa ccccaattct gacgcgcccg tgatcaggtc aaaaacctcc gcgcgctaca     900
tggagctggt cgggtggctg gtggaccggg gcatcacctc cgagaagcag tggatccagg     960
aggaccaggc ctcgtacatc tccttcaacg ccgcctccaa ctcgcggtcc cagatcaagg    1020
ccgcgctgga caatgccggc aagatcatgg cgctgaccaa atccgcgccc gactacctgg    1080
taggcccttc acttccggtg acattacgc agaaccgcat ctaccgcatc ctgcagctca    1140
acggctacga ccctgcctac gccggctccg tctttctcgg ctgggcacaa aagaagttcg    1200
ggaaacgcaa caccatctgg ctgtttgggc cggccaccg gggaaagacc aacatcgcag    1260
aagccattgc ccacgccgtg cccttctacg gctgcgtcaa ctggaccaat gagaactttc    1320
ccttcaacga ttgcgtcgac aagatggtga tctggtggga ggagggcaag atgacggcca    1380
aggtcgtgga gtccgccaag gccattctcg gcggcagcaa ggtgcgcgtg gaccaaaagt    1440
gcaagtcgtc cgcccagatc gaccccactc ccgtgatcgt cacctccaac accaacatgt    1500
gcgccgtgat tgacgggaac agcaccacct tcgagcacca gcagcctctc caggaccgga    1560
tgtttaagtt cgaactcacc cgccgtctgg agcacgactt tggcaaggtg acaaagcagg    1620
aagtcaaaga gttcttccgc tgggccagtg atcacgtgac cgaggtggcg catgagtttt    1680
acgtcagaaa gggcggagcc agcaaaagac ccgccccga tgacgcggat aaaagcgagc    1740
ccaagcgggc ctgcccctca gtcgcggatc catcgacgtc agacgcggaa ggagctccgg    1800 tggacttttgc cgacaggtac caaaacaaat gttctcgtca cgcggcgatg cttcagatgc    1860
tgcttccctg caaaacgtgc gagagaatga atcagaattt caacatttgc ttcacacacg    1920
gggtcagaga ctgctcagag tgttttcccg gcgtgtcaga atctcaaccg gtcgtcagaa    1980
agaggacgta tcgaaactc tgtgcgattc atcatctgct ggggcgggct cccgagattg    2040
cttgctcggc ctgcgatctg gtcaacgtgg acctggatga ctgtgtttct gagcaataaa    2100
```

```
tgacttaaac caggtatggc tgccgatggt tatcttccag attggctcga ggacaacctc   2160
tctgagggca ttcgcgagtg gtgggcgctg aaacctggag ccccgaagcc caaagccaac   2220
cagcaaaagc aggacgacgg ccggggtctg gtgcttcctg gctacaagta cctcggaccc   2280
ttcaacggac tcgacaaggg ggagcccgtc aacgcggcgg acgcagcggc cctcgagcac   2340
ggcaaggcct acgaccagca gctgcaggcg ggtgacaatc cgtacctgcg gtataaccac   2400
gccgacgccg agtttcagga gcgtctgcaa aagatacgt cttttggggg caacctcggg   2460
cgagcagtct tccaggccaa gaagcgggtt ctcgaacctc tcggtctggt tgaggaaggc   2520
gctaagacgg ctcctggaaa gaagagaccg gtagagccat cacccagcg ttctccagac   2580
tcctctacgg gcatcggcaa gaaaggccaa cagcccgcca gaaaaagact caattttggt   2640
cagactggcg actcagagtc agttccagac cctcaacctc tcggagaacc tccagcagcg   2700
ccctctggtg tgggacctaa tacaatggct gcaggcggtg gcgcaccaat ggcagacaat   2760
aacgaaggcg ccgacggagt gggtaattcc tcgggaaatt ggcattgcga ttccacatgg   2820
ctgggggaca gagtcatcac caccagcacc cgaacctggg cattgccac ctacaacaac   2880
cacctctaca gcaaatctc caatggaaca tcgggaggaa gcaccaacga caacacctac   2940
tttggctaca gcacccctg ggggtatttt gacttcaaca gattccactg ccacttctca   3000
ccacgtgact ggcagcgact catcaacaac aactggggat ccggccaaa gagactcaac   3060
ttcaagctgt tcaacatcca ggtcaaggag gttacgacga acgaaggcac caagaccatc   3120
gccaataacc ttaccagcac cgtccaggtc tttacggact cggagtacca gctaccgtac   3180
gtcctaggct ctgcccacca aggatgcctg ccaccgtttc ctgcagacgt cttcatggtt   3240
cctcagtacg gctacctgac gctcaacaat ggaagtcaag cgttaggacg ttcttctttc   3300
tactgtctgg aatacttccc ttctcagatg ctgagaaccg gcaacaactt tcagttcagc   3360
tacactttcg aggacgtgcc tttccacagc agctacgcac acagccagag tctagatcga   3420
ctgatgaacc ccctcatcga ccagtaccta tactacctgg tcagaacaca gacaactgga   3480
actggggaa ctcaaacttt ggcattcagc caagcaggcc ctagctcaat ggccaatcag   3540
gctagaaact gggtacccgg gccttgctac cgtcagcagc gcgtctccac aaccaccaac   3600
caaaataaca acagcaactt gcgtggacg ggagctgcta aattcaagct gaacgggaga   3660
gactcgctaa tgaatcctgg cgtggctatg gcatcgcaca aagacgacga ggaccgcttc   3720
tttccatcaa gtggcgttct catatttggc aagcaaggag ccgggaacga tggagtcgac   3780
tacagccagg tgctgattac agatgaggaa gaaattaaag ccaccaaccc tgtagccaca   3840
gaggaatacg gagcagtggc catcaacaac caggccgcta acacgcaggc gcaaactgga   3900
cttgtgcata accaggggagt tattcctggt atggtctggc agaaccggga cgtgtacctg   3960
cagggcccta tttgggctaa aatacctcac acagatggca actttcaccc gtctcctctg   4020
atgggtggat ttggactgaa acacccacct ccacagattc taattaaaaa tacaccagtg   4080
ccggcagatc ctcctcttac cttcaatcaa gccaagctga actctttcat cacgcagtac   4140
agcacgggac aagtcagcgt ggaaatcgag tgggagctgc agaaagaaaa cagcaagcgc   4200
tggaatccag agatccagta tacttcaaac tactacaaat ctacaaatgt ggactttgct   4260
gtcaataccα aaggtgttta ctctgagcct cgccccattg gtactcgtta cctcacccgt   4320
aatttgtaat tgcctgttaa tcaataaacc ggttaattcg tttcagttga actttggtct   4380
ctgcg                                                              4385
```

<210> SEQ ID NO 6
<211> LENGTH: 4718
<212> TYPE: DNA
<213> ORGANISM: Unknown
<220> FEATURE:
<223> OTHER INFORMATION: adeno-associated virus serotype 1

<400> SEQUENCE: 6

```
ttgcccactc cctctctgcg cgctcgctcg ctcggtgggg cctgcggacc aaaggtccgc      60
agacggcaga gctctgctct gccggcccca ccgagcgagc gagcgcgcag agagggagtg     120
ggcaactcca tcactagggg taatcgcgaa gcgcctccca cgctgccgcg tcagcgctga     180
cgtaaattac gtcataggg agtggtcctg tattagctgt cacgtgagtg cttttgcgac      240
attttgcgac accacgtggc catttagggt atatatggcc gagtgagcga gcaggatctc     300
cattttgacc gcgaaatttg aacgagcagc agccatgccg ggcttctacg agatcgtgat     360
caaggtgccg agcgacctgg acgagcacct gccgggcatt tctgactcgt tgtgagctg      420 ggtggccgag aaggaatggg agctgccccc ggattctgac atggatctga atctgattga     480
gcaggcaccc ctgaccgtgg ccgagaagct gcagcgcgac ttcctggtcc aatggcgccg     540
cgtgagtaag gccccggagg ccctcttctt tgttcagttc gagaagggcg agtcctactt     600
ccacctccat attctggtgg agaccacggg ggtcaaatcc atggtgctgg ccgcttcct      660 gagtcagatt agggacaagc tggtgcagac catctaccgc gggatcgagc cgaccctgcc     720
caactggttc gcggtgacca gacgcgtaa tggcgccgga gggggaaca aggtggtgga      780 cgagtgctac atccccaact acctcctgcc caagactcag cccgagctgc agtgggcgtg     840
gactaacatg gaggagtata taagcgcctg tttgaacctg gccgagcgca aacggctcgt     900
ggcgcagcac ctgacccacg tcagccagac ccaggagcag aacaaggaga atctgaaccc     960
caattctgac gcgcctgtca tccggtcaaa aacctccgcg cgctacatgg agctggtcgg    1020
gtggctggtg gaccggggca tcacctccga gaagcagtgg atccaggagg accaggcctc    1080
gtacatctcc ttcaacgccg cttccaactc gcggtcccag atcaaggccg ctctggacaa    1140
tgccggcaag atcatggcgc tgaccaaatc cgcgcccgac tacctggtag gccccgctcc    1200
gcccgcggac attaaaacca accgcatcta ccgcatcctg gagctgaacg gctacgaacc    1260
tgcctacgcc ggctccgtct ttctcggctg ggcccagaaa aggttcggga agcgcaacac    1320
catctggctg tttgggccgg ccaccacggg caagaccaac atcgcggaag ccatcgccca    1380
cgccgtgccc ttctacggct gcgtcaactg gaccaatgag aactttccct tcaatgattg    1440
cgtcgacaag atggtgatct ggtgggagga gggcaagatg acggccaagg tcgtggagtc    1500
cgccaaggcc attctcggcg gcagcaaggt gcgcgtggac caaaagtgca gtcgtccgc     1560 ccagatcgac cccaccccg tgatcgtcac ctccaacacc aacatgtgcg ccgtgattga    1620
cgggaacagc accaccttcg agcaccagca gccgttgcag gaccggatgt tcaaatttga    1680
actcacccgc cgtctggagc atgactttgg caaggtgaca aagcaggaag tcaaagagtt    1740
cttccgctgg gcgcaggatc acgtgaccga ggtggcgcat gagttctacg tcagaaaggg    1800
tggagccaac aaaagacccg ccccgatga cgccggataaa agcgagccca gcgggcctg     1860 cccctcagtc gcggatccat cgacgtcaga gcgcgaagga ctccggtgg actttgccga    1920 caggtaccaa aacaaatgtt ctcgtcacgc gggcatgctt cagatgctgt ttccctgcaa    1980
gacatgcgag agaatgaatc agaatttcaa catttgcttc acgcacggga cgagagactg    2040
ttcagagtgc ttccccggcg tgtcagaatc tcaaccggtc gtcagaaaga ggacgtatcg    2100
```

```
gaaactctgt gccattcatc atctgctggg gcgggctccc gagattgctt gctcggcctg    2160
cgatctggtc aacgtggacc tggatgactg tgtttctgag caataaatga cttaaaccag    2220
gtatggctgc cgatggttat cttccagatt ggctcgagga caacctctct gagggcattc    2280
gcgagtggtg ggacttgaaa cctggagccc cgaagcccaa agccaaccag caaaagcagg    2340
acgacggccg gggtctggtg cttcctggct acaagtacct cggacccttc aacggactcg    2400 acaagggga  gcccgtcaac gcggcggacg cagcggccct cgagcacgac aaggcctacg    2460
accagcagct caaagcgggt gacaatccgt acctgcggta taaccacgcc gacgccgagt    2520
ttcaggagcg tctgcaagaa gatacgtctt tgggggcaa  cctcgggcga gcagtcttcc    2580
aggccaagaa gcgggttctc gaacctctcg gtctggttga ggaaggcgct aagacggctc    2640
ctggaaagaa acgtccggta gagcagtcgc acaagagcc  agactcctcc tcgggcatcg    2700
gcaagacagg ccagcagccc gctaaaaaga gactcaattt tggtcagact ggcgactcag    2760
agtcagtccc cgatccacaa cctctcggag aacctccagc aaccccgct  gctgtgggac    2820 ctactacaat ggcttcaggc ggtggcgcac caatggcaga caataacgaa ggcgccgacg    2880
gagtgggtaa tgcctcagga aattggcatt gcgattccac atggctgggc gacagagtca    2940
tcaccaccag caccccgcacc tgggccttgc ccacctacaa taaccacctc tacaagcaaa    3000
tctccagtgc ttcaacgggg gccagcaacg acaaccacta cttcggctac agcaccccct    3060
gggggtattt tgatttcaac agattccact gccacttttc accacgtgac tggcagcgac    3120
tcatcaacaa caattgggga ttccggccca agagactcaa cttcaaactc ttcaacatcc    3180
aagtcaagga ggtcacgacg aatgatggcg tcacaaccat cgctaataac cttaccagca    3240
cggttcaagt cttctcggac tcggagtacc agcttccgta cgtcctcggc tctgcgcacc    3300
agggctgcct ccctccgttc ccggcggacg tgttcatgat tccgcaatac ggctacctga    3360
cgctcaacaa tggcagccaa gccgtgggac gttcatcctt ttactgcctg gaatatttcc    3420
cttctcagat gctgagaacg ggcaacaact ttacccttcag ctacaccttt gaggaagtgc    3480 cttttccacag cagctacgcg cacagccaga gcctggaccg gctgatgaat cctctcatcg    3540
accaatacct gtattacctg aacagaactc aaaatcagtc cggaagtgcc caaaacaagg    3600
acttgctgtt tagccgtggg tctccagctg gcatgtctgt tcagcccaaa actggctac    3660 ctggaccctg ttatcggcag cagcgcgttt ctaaaacaaa aacagacaac aacaacagca    3720
attttacctg gactggtgct tcaaaatata acctcaatgg gcgtgaatcc atcatcaacc    3780
ctggcactgc tatggcctca cacaaagacg acgaagacaa gttctttccc atgagcggtg    3840
tcatgatttt tggaaaagag agcgccggag cttcaaacac tgcattggac aatgtcatga    3900
ttacagacga agaggaaatt aaagccacta accctgtggc caccgaaaga tttgggaccg    3960
tggcagtcaa tttccagagc agcagcacag accctgcgac cggagatgtg catgctatgg    4020
gagcattacc tggcatggtg tggcaagata gagacgtgta cctgcagggt cccatttggg    4080
ccaaaattcc tcacacagat ggacactttc acccgtctcc tcttatgggc ggctttggac    4140
tcaagaaccc gcctcctcag atcctcatca aaaacacgcc tgttcctgcg aatcctccgg    4200
cggagttttc agctacaaag tttgcttcat tcatcaccca atactccaca ggacaagtga    4260
gtgtggaaat tgaatgggag ctgcagaaag aaaacagcaa gcgctggaat cccgaagtgc    4320
agtacacatc caattatgca aaatctgcca acgttgattt tactgtggac aacaatggac    4380
tttatactga gcctcgcccc attggcaccc gttaccttac ccgtcccctg taattacgtg    4440
ttaatcaata aaccggttga ttcgtttcag ttgaactttg gtctcctgtc cttcttatct    4500
```

-continued

| | |
|---|---|
| tatcggttac catggttata gcttacacat taactgcttg gttgcgcttc gcgataaaag | 4560 |
| acttacgtca tcgggttacc cctagtgatg gagttgccca ctccctctct gcgcgctcgc | 4620 |
| tcgctcggtg gggcctgcgg accaaaggtc cgcagacggc agagctctgc tctgccggcc | 4680 |
| ccaccgagcg agcgagcgcg cagagaggga gtgggcaa | 4718 |

<210> SEQ ID NO 7
<211> LENGTH: 4675
<212> TYPE: DNA
<213> ORGANISM: adeno-associated virus 2

<400> SEQUENCE: 7

| | |
|---|---|
| ttggccactc cctctctgcg cgctcgctcg ctcactgagg ccgggcgacc aaaggtcgcc | 60 |
| cgacgcccgg gctttgcccg gcggcctca gtgagcgagc gagcgcgcag agagggagtg | 120 |
| gccaactcca tcactagggg ttcctggagg ggtggagtcg tgacgtgaat tacgtcatag | 180 |
| ggttagggag gtcctgtatt agaggtcacg tgagtgtttt gcgacatttt gcgacaccat | 240 |
| gtggtcacgc tgggtattta agcccgagtg agcacgcagg gtctccattt tgaagcggga | 300 |
| ggtttgaacg cgcagccgcc atgccggggt tttacgagat tgtgattaag gtccccagcg | 360 |
| accttgacgg gcatctgccc ggcatttctg acagctttgt gaactgggtg gccgagaagg | 420 |
| aatgggagtt gccgccagat tctgacatgg atctgaatct gattgagcag caccccctga | 480 |
| ccgtggccga aagctgcag cgcgactttc tgacggaatg gcgccgtgtg agtaaggccc | 540 |
| cggaggccct tttctttgtg caatttgaga agggagagag ctacttccac atgcacgtgc | 600 |
| tcgtggaaac caccggggtg aaatccatgg ttttgggacg tttcctgagt cagattcgcg | 660 |
| aaaaactgat tcagagaatt taccgcggga tcgagccgac tttgccaaac tggttcgcgg | 720 |
| tcacaaagac cagaaatggc gccggaggcg gaacaaggt ggtggatgag tgctacatcc | 780 |
| ccaattactt gctccccaaa acccagcctg agctccagtg gcgtggact aatatggaac | 840 |
| agtatttaag cgcctgtttg aatctcacgg agcgtaaacg gttggtggcg cagcatctga | 900 |
| cgcacgtgtc gcagacgcag gagcagaaca aagagaatca gaatcccaat tctgatgcgc | 960 |
| cggtgatcag atcaaaaact tcagccaggt acatggagct ggtcgggtgg ctcgtggaca | 1020 |
| agggattac ctcggagaag cagtggatcc aggaggacca ggcctcatac atctccttca | 1080 |
| atgcggcctc caactcgcgg tcccaaatca aggctgcctt ggacaatgcg ggaaagatta | 1140 |
| tgagcctgac taaaaccgcc cccgactacc tggtgggcca gcagcccgtg gaggacattt | 1200 |
| ccagcaatcg gatttataaa attttggaac taaacgggta cgatcccaa tatgcggctt | 1260 |
| ccgtctttct gggatgggcc acgaaaaagt tcggcaagag gaacaccatc tggctgtttg | 1320 |
| ggcctgcaac taccgggaag accaacatcg cggaggccat agcccacact gtgcccttct | 1380 |
| acgggtgcgt aaactggacc aatgagaact ttccccttca cgactgtgtc gacaagatgg | 1440 |
| tgatctggtg ggaggagggg aagatgaccg ccaaggtcgt ggagtcggcc aaagccattc | 1500 |
| tcggaggaag caaggtgcgc gtggaccaga atgcaagtc ctcggcccag atagacccga | 1560 |
| ctcccgtgat cgtcacctcc aacaccaaca tgtgcgccgt gattgacggg aactcaacga | 1620 |
| ccttcgaaca ccagcagccg ttgcaagacc ggatgttcaa atttgaactc acccgccgtc | 1680 |
| tggatcatga ctttgggaag gtcaccaagc aggaagtcaa agactttttc cggtgggcaa | 1740 |
| aggatcacgt ggttgaggtg gagcatgaat tctacgtcaa aaagggtgga gccaagaaaa | 1800 |
| gacccgcccc cagtgacgca gatataagtg agcccaaacg ggtgcgcgag tcagttgcgc | 1860 |

-continued

```
agccatcgac gtcagacgcg gaagcttcga tcaactacgc agacaggtac caaaacaaat      1920
gttctcgtca cgtgggcatg aatctgatgc tgtttccctg cagacaatgc gagagaatga      1980
atcagaattc aaatatctgc ttcactcacg gacagaaaga ctgtttagag tgctttcccg      2040
tgtcagaatc tcaacccgtt tctgtcgtca aaaaggcgta tcagaaactg tgctacattc      2100
atcatatcat gggaaaggtg ccagacgctt gcactgcctg cgatctggtc aatgtggatt      2160
tggatgactg catctttgaa caataaatga tttaaatcag gtatggctgc cgatggttat      2220
cttccagatt ggctcgagga cactctctct gaaggaataa gacagtggtg gaagctcaaa      2280
cctggcccac caccaccaaa gcccgcagag cggcataagg acgacagcag gggtcttgtg      2340
cttcctgggt acaagtacct cggacccttc aacggactcg acaagggaga gccggtcaac      2400
gaggcagacg ccgcggccct cgagcacgta caaagcctac gaccggcagc tcgacagcgg      2460
agacaacccg tacctcaagt acaaccacgc cgacgcggag tttcaggagc gccttaaaga      2520
agatacgtct tttgggggca acctcggacg agcagtcttc caggcgaaaa agagggttct      2580
tgaacctctg ggcctggttg aggaacctgt taagacggct ccgggaaaaa agaggccggt      2640
agagcactct cctgtggagc cagactcctc ctcgggaacc ggaaaggcgg gccagcagcc      2700
tgcaagaaaa agattgaatt ttggtcagac tggagacgca gactcagtac ctgaccccca      2760
gcctctcgga cagccaccag cagcccctc tggtctggga actaatacga tggctacagg      2820
cagtggcgca ccaatggcag acaataacga gggcgccgac ggagtgggta attcctccgg      2880
aaattggcat tgcgattcca catggatggg cgacagagtc atcaccacca gcacccgaac      2940
ctgggccctg cccacctaca caaccaccct ctacaaacaa atttccagcc aatcaggagc      3000
ctcgaacgac aatcactact ttggctacag cacccccttgg gggtatttttg acttcaacag      3060
attccactgc cacttttcac cacgtgactg gcaaagactc atcaacaaca actgggggatt      3120
ccgacccaag agactcaact tcaagctctt taacattcaa gtcaaagagg tcacgcagaa      3180
tgacggtacg acgacgattg ccaataacct taccagcacg gttcaggtgt ttactgactc      3240
ggagtaccag ctcccgtacg tcctcggctc ggcgcatcaa ggatgcctcc cgccgttccc      3300
agcagacgtc ttcatggtgc cacagtatgg atacctcacc ctgaacaacg ggagtcaggc      3360
agtaggacgc tcttcatttt actgcctgga gtactttcct tctcagatgc tgcgtaccgg      3420
aaacaacttt accttcagct cacacttttga ggacgttcct ttccacagca gctacgctca      3480
cagccagagt ctggaccgtc tcatgaatcc tctcatcgac cagtacctgt attacttgag      3540
cagaacaaac actccaagtg gaaccaccac gcagtcaagg cttcagtttt ctcaggccgg      3600
agcgagtgac attcgggacc agtctaggaa ctggcttcct ggaccctgtt accgccagca      3660
gcgagtatca aagacatctg cggataacaa caacagtgaa tactcgtgga ctggagctac      3720
caagtaccac ctcaatggca gagactctct ggtgaatccg gccatggcaa gccacaagga      3780
cgatgaagaa aagttttttc ctcagagcgg ggttctcatc tttgggaagc aaggctcaga      3840
gaaaacaaat gtgaacattg aaaaggtcat gattacagac gaagaggaaa tcggaacaac      3900
caatcccgtg gctacggagc agtatggttc tgtatctacc aacctccaga gaggcaacag      3960
acaagcagct accgcagatg tcaacacaca aggcgttctt ccaggcatgg tctggcagga      4020
cagagatgtg taccttcagg ggcccatctg ggcaaagatt ccacacacgg acggacattt      4080
tcacccctct cccctcatgg gtggattcgg acttaaacac cctcctccac agattctcat      4140
caagaacacc ccggtacctg cgaatccttc gaccaccttc agtgcggcaa agtttgcttc      4200
cttcatcaca cagtactcca cgggacacgg tcagcgtgga gatcgagtgg gagctgcaga      4260
```

```
aggaaaacag caaacgctgg aatcccgaaa ttcagtacac ttccaactac aacaagtctg   4320
ttaatcgtgg acttaccgtg gatactaatg gcgtgtattc agagcctcgc cccattggca   4380
ccagatacct gactcgtaat ctgtaattgc ttgttaatca ataaaccgtt taattcgttt   4440
cagttgaact ttggtctctg cgtatttctt tcttatctag tttccatggc tacgtagata   4500
agtagcatgg cgggttaatc attaactaca aggaacccct agtgatggag ttggccactc   4560
cctctctgcg cgctcgctcg ctcactgagg ccgggcgacc aaaggtcgcc cgacgcccgg   4620
gctttgcccg gcggcctca gtgagcgagc gagcgcgcag agagggagtg gccaa         4675
```

<210> SEQ ID NO 8
<211> LENGTH: 4726
<212> TYPE: DNA
<213> ORGANISM: adeno-associated virus 3

<400> SEQUENCE: 8

```
ttggccactc cctctatgcg cactcgctcg ctcggtgggg cctggcgacc aaaggtcgcc     60
agacggacgt gctttgcacg tccggcccca ccgagcgagc gagtgcgcat agagggagtg    120
gccaactcca tcactagagg tatggcagtg acgtaacgcg aagcgcgcga agcgagacca    180
cgcctaccag ctgcgtcagc agtcaggtga ccctttttgcg acagtttgcg acaccacgtg    240
gccgctgagg gtatatattc tcgagtgagc gaaccaggag ctccattttg accgcgaaat    300
ttgaacgagc agcagccatg ccgggggttct acgagattgt cctgaaggtc ccgagtgacc    360
tggacgagcg cctgccgggc atttctaact cgtttgttaa ctgggtggcc gagaaggaat    420
gggacgtgcc gccggattct gacatggatc cgaatctgat tgagcaggca cccctgaccg    480
tggccgaaaa gcttcagcgc gagttcctgg tggagtggcg ccgcgtgagt aaggcccgg    540 aggccctctt ttttgtccag ttcgaaaagg gggagaccta cttccacctg cacgtgctga    600
ttgagaccat cggggtcaaa tccatggtgg tcggccgcta cgtgagccag attaaagaga    660
agctggtgac ccgcatctac cgcggggtcg agccgcagct tccgaactgg ttcgcggtga    720
ccaaaacgcg aaatggcgcc gggggcggga caaggtggt ggacgactgc tacatcccca    780
actacctgct ccccaagacc cagccgagc tccagtgggg gtggactaac atggaccagt    840
atttaagcgc ctgtttgaat ctcgcggagc gtaaacggct ggtggcgcag catctgacgc    900
acgtgtcgca gacgcaggag cagaacaaag agaatcagaa ccccaattct gacgcgccgg    960
tcatcaggtc aaaaacctca gccaggtaca tggagctggt cgggtggctg gtggaccgcg   1020
ggatcacgtc agaaaagcaa tggattcagg aggaccaggc ctcgtacatc tccttcaacg   1080
ccgcctccaa ctcgcggtcc cagatcaagg ccgcgctgga caatgcctcc aagatcatga   1140
gcctgacaaa acggctccg gactacctgg tgggcagcaa cccgccggag gacattacca   1200
aaaatcggat ctaccaaatc ctggagctga acgggtacga tccgcagtac gcggcctccg   1260
tcttcctggg ctgggcgcaa aagaagttcg gaagaggaa caccatctgg ctctttgggc   1320
cggccacgac gggtaaaacc aacatcgcgg aagccatcgc ccacgccgtg ccctctacg   1380 gctgcgtaaa ctggaccaat gagaactttc ccttcaacga ttgcgtcgac aagatggtga   1440
tctggtggga ggagggcaag atgacggcca aggtcgtgga gagcgccaag gccattctgg   1500
gcggaagcaa ggtgcgcgtg gaccaaaagt gcaagtcatc ggcccagatc gaacccactc   1560
ccgtgatcgt cacctccaac accaacatgt gcgccgtgat tgacgggaac agcaccacct   1620
tcgagcatca gcagccgctg caggaccgga tgtttgaatt tgaacttacc cgccgtttgg   1680
```

```
accatgactt tgggaaggtc accaaacagg aagtaaagga ctttttccgg tgggcttccg    1740
atcacgtgac tgacgtggct catgagttct acgtcagaaa gggtggagct aagaaacgcc    1800
ccgcctccaa tgacgcggat gtaagcgagc caaaacggga gtgcacgtca cttgcgcagc    1860
cgacaacgtc agacgcggaa gcaccggcgg actacgcgga caggtaccaa acaaatgtt    1920 ctcgtcacgt gggcatgaat ctgatgcttt ttccctgtaa acatgcgag agaatgaatc     1980 aaatttccaa tgtctgtttt acgcatggtc aaagagactg tggggaatgc ttccctggaa    2040
tgtcagaatc tcaacccgtt tctgtcgtca aaagaagac ttatcagaaa ctgtgtccaa     2100
ttcatcatat cctgggaagg gcacccgaga ttgcctgttc ggcctgcgat ttggccaatg    2160
tggacttgga tgactgtgtt tctgagcaat aaatgactta accaggtat ggctgctgac     2220 ggttatcttc cagattggct cgaggacaac ctttctgaag gcattcgtga gtggtgggct    2280
ctgaaacctg gagtccctca acccaaagcg aaccaacaac accaggacaa ccgtcggggt    2340
cttgtgcttc cgggttacaa atacctcgga cccggtaacg gactcgacaa aggagagccg    2400
gtcaacgagg cggacgcggc agccctcgaa cacgacaaag cttacgacca gcagctcaag    2460
gccggtgaca acccgtacct caagtacaac cacgccgacg ccgagtttca ggagcgtctt    2520
caagaagata cgtctttgg gggcaacctt ggcagagcag tcttccaggc caaaaagagg     2580
atccttgagc ctcttggtct ggttgaggaa gcagctaaaa cggctcctgg aaagaagggg    2640
gctgtagatc agtctcctca ggaaccggac tcatcatctg tgttggcaa atcgggcaaa     2700 cagcctgcca gaaaaagact aaatttcggt cagactggag actcagagtc agtcccagac    2760
cctcaacctc tcggagaacc accagcagcc cccacaagtt tgggatctaa tacaatggct    2820
tcaggcggtg gcgcaccaat ggcagacaat aacgagggtg ccgatggagt gggtaattcc    2880
tcaggaaatt ggcattgcga ttcccaatgg ctgggcgaca gagtcatcac caccagcacc    2940
agaacctggg ccctgcccac ttacaacaac catctctaca agcaaatctc cagccaatca    3000
ggagcttcaa cgacaacca ctactttggc tacagcaccc cttgggggta ttttgacttt     3060
aacagattcc actgccactt ctcaccacgt gactggcagc gactcattaa caacaactgg    3120
ggattccggc ccaagaaact cagcttcaag ctcttcaaca tccaagttag aggggtcacg    3180
cagaacgatg gcacgacgac tattgccaat aaccttacca gcacggttca agtgtttacg    3240
gactcggagt atcagctccc gtacgtgctc gggtcggcgc accaaggctg tctcccgccg    3300
tttccagcgg acgtcttcat ggtccctcag tatggatacc tcaccctgaa caacggaagt    3360
caagcggtgg gacgctcatc ctttactgc ctggagtact tcccttcgca gatgctaagg     3420
actggaaata acttccaatt cagctatacc ttcgaggatg tacctttca cagcagctac      3480 gctcacagcc agagtttgga tcgcttgatg aatcctctta ttgatcagta tctgtactac    3540
ctgaacagaa cgcaaggaac aacctctgga caaccaacc aatcacggct gcttttagc     3600 caggctgggc ctcagtctat gtcttttcag gccagaaatt ggctacctgg gccctgctac    3660
cggcaacaga gactttcaaa gactgctaac gacaacaaca cagtaacttt ccttggaca     3720 gcggccagca aatatcatct caatggccgc gactcgctgg tgaatccagg accagctatg    3780
gccagtcaca aggacgatga agaaaatt ttccctatgc acggcaatct aatatttggc       3840
aaagaaggga caacggcaag taacgcagaa ttagataatg taatgattac ggatgaagaa    3900
gagattcgta ccaccaatcc tgtggcaaca gagcagtatg gaactgtggc aaataacttg    3960
cagagctcaa atacagctcc cacgactgga actgtcaatc atcaggggc cttacctggc     4020 atggtgtggc aagatcgtga cgtgtacctt caaggaccta tctgggcaaa gattcctcac    4080
```

```
acggatggac actttcatcc ttctcctctg atgggaggct ttggactgaa acatccgcct    4140
cctcaaatca tgatcaaaaa tactccggta ccggcaaatc ctccgacgac tttcagcccg    4200
gccaagtttg cttcatttat cactcagtac tccactggac aggtcagcgt ggaaattgag    4260
tgggagctac agaaagaaaa cagcaaacgt tggaatccag agattcagta cacttccaac    4320
tacaacaagt ctgttaatgt ggactttact gtagacacta atggtgttta tagtgaacct    4380
cgccctattg gaacccggta tctcacacga aacttgtgaa tcctggttaa tcaataaacc    4440
gtttaattcg tttcagttga actttggctc ttgtgcactt ctttatcttt atcttgtttc    4500
catggctact gcgtagataa gcagcggcct gcggcgcttg cgcttcgcgg tttacaactg    4560
ctggttaata tttaactctc gccatacctc tagtgatgga gttggccact ccctctatgc    4620
gcactcgctc gctcggtggg gcctggcgac caaaggtcgc cagacggacg tgctttgcac    4680
gtccggcccc accgagcgag cgagtgcgca tagagggagt ggccaa                   4726
```

<210> SEQ ID NO 9
<211> LENGTH: 3098
<212> TYPE: DNA
<213> ORGANISM: Unknown
<220> FEATURE:
<223> OTHER INFORMATION: AAV serotype, clone 42.2

<400> SEQUENCE: 9

```
gaattcgccc tttctacggc tgcgtcaact ggaccaatga gaactttccc ttcaacgatt      60
gcgtcgacaa gatggtgatc tggtgggagg agggcaagat gacggccaag gtcgtggagt     120
ccgccaaggc cattctcggc ggcagcaagg tgcgcgtgga ccaaaagtgc aagtcttccg     180
cccagatcga tcccaccccc gtgatcgtca cttccaacac caacatgtgc gctgtgattg     240
acgggaacag caccaccttc gagcaccagc agccgttaca agaccggatg ttcaaatttg     300
aactcacccg ccgtctggag cacgactttg gcaaggtgac aaagcaggaa gtcaaagagt     360
tcttccgctg ggcgcaggat cacgtgaccg aggtggcgca tgagttctac gtcagaaagg     420
gtggagccaa caagagaccc gcccccgatg acgcggataa aagcgagccc aagcgggcct     480 gccccctcagt cgcggatcca tcgacgtcag acgcggaagg agctccggtg gactttgccg     540
acaggtacca aaacaaatgt tctcgtcacg cgggcatgct tcagatgctg tttccctgca     600
agacatgcga gagaatgaat cagaatttca acatttgctt cacgcacggg accagagact     660
gttcagaatg tttccccggc gtgtcagaat ctcaaccggt cgtcagaaag aggacgtatc     720
ggaaactctg tgccattcat catctgctgg ggcgggctcc cgagattgct tgctcggcct     780
gcgatctggt caacgtggac ctggatgacc gtgtttctga gcaataaatg acttaaacca     840
ggtatggctg ccgatggtta tcttccagat tggctcgagg acaacctctc tgagggcatt     900
cgcgagtggt gggacttgaa acctggagcc ccgaaaccca agccaaccag gcaaaagcag     960
gacgacggcc ggggtctggt gcttcctggc tacaagtacc tcggaccctt caacggactc    1020
gacaagggag agccggtcaa cgaggcagac gccgcggccc tcgagcacga caaggcctac    1080
gacaagcagc tcgagcaggg ggacaacccg tacctcaagt acaaccacgc cgacgccgag    1140
tttcaggagc gtcttcaaga agatacgtct ttgggggca acctcgggcg agcagtcttc    1200
caggccaaga agcgggttct cgaacctctc ggtctggttg aggaaggcgc taagacggct    1260
cctggaaaga agagacccat agaatccccc gactcctcca cgggcatcgg caagaaaggc    1320
cagcagcccg ctaaaaagaa gctcaacttt gggcagactg gcgactcaga gtcagtgccc    1380
```

-continued

| | |
|---|---|
| gaccccaac ctctcggaga acctcccgcc gcgccctcag gtctgggatc tggtacaatg | 1440 |
| gctgcaggcg gtggcgcacc aatggcagac aataacgaag cgccgacgg agtgggtaat | 1500 |
| gcctccggaa attggcattg cgattccaca tggctgggcg acagagtcat caccaccagc | 1560 |
| acccgcacct gggccctgcc cacctacaac aaccacctct acaagcagat atcaagtcag | 1620 |
| agcggggcta ccaacgacaa ccacttcttc ggctacagca ccccctgggg ctattttgac | 1680 |
| ttcaacagat tccactgcca cttctcacca cgtgactggc agcgactcat caacaacaac | 1740 |
| tggggattcc ggcccagaaa gctgcggttc aagttgttca acatccaggt caaggaggtc | 1800 |
| acgacgaacg acggcgttac gaccatcgct aataaccta ccagcacgat tcaggtcttc | 1860 |
| tcggactcgg agtaccaact gccgtacgtc ctcggctctg cgcaccaggg ctgcctccct | 1920 |
| ccgttccctg cggacgtgtt catgattcct cagtacggat atctgactct aaacaacggc | 1980 |
| agtcagtctg tgggacgttc ctccttctac tgcctggagt actttccttc tcagatgctg | 2040 |
| agaacgggca ataactttga attcagctac acctttgagg aagtgccttt ccacagcagc | 2100 |
| tatgcgcaca gccagagcct ggaccggctg atgaatcccc tcatcgacca gtacctgtac | 2160 |
| tacctggccc ggacccagag cactacgggg tccacaaggg agctgcagtt ccatcaggct | 2220 |
| gggcccaaca ccatggccga gcaatcaaag aactggctgc ccggaccctg ttatcggcag | 2280 |
| cagagactgt caaaaacat agacagcaac aacaacagta actttgcctg gaccggggcc | 2340 |
| actaaatacc atctgaatgg tagaaaattca ttaaccaacc cggcgtagc catggccacc | 2400 |
| aacaaggacg acgaggacca gttctttccc atcaacggag tgctggtttt tggcgaaacg | 2460 |
| ggggctgcca acaagacaac gctggaaaac gtgctaatga ccagcgagga ggagatcaaa | 2520 |
| accaccaatc ccgtggctac agaagaatac ggtgtggtct ccagcaacct gcaatcgtct | 2580 |
| acggccggac cccagacaca gactgtcaac agccaggggg ctctgcccgg catggtctgg | 2640 |
| cagaaccggg acgtgtacct gcagggtccc atctgggcca aaattcctca cacggacggc | 2700 |
| aactttcacc cgtctcccct gatgggcgga tttggactca acacccgcc tcctcaaatt | 2760 |
| ctcatcaaaa acaccccggt acctgctaat cctccagagg tgtttactcc tgccaagttt | 2820 |
| gcctcattta tcacgcagta cagcaccggc caggtcagcg tggagatcga gtgggaactg | 2880 |
| cagaaagaaa acagcaaacg ctggaatcca gagattcagt acacctcaaa ttatgccaag | 2940 |
| tctaataatg tggaatttgc tgtcaacaac gaagggggttt atactgagcc tcgccccatt | 3000 |
| ggcacccgtt acctcacccg taacctgtaa ttgcctgtta atcaataaac cggttaattc | 3060 |
| gtttcagttg aactttggtc tctgcgaagg gcgaattc | 3098 |

<210> SEQ ID NO 10
<211> LENGTH: 3098
<212> TYPE: DNA
<213> ORGANISM: Unknown
<220> FEATURE:
<223> OTHER INFORMATION: AAV serotype, clone 16.3

<400> SEQUENCE: 10

| | |
|---|---|
| gaattcgccc ttcgcagaga ccaaagttca actgaaacga atcaaccggt ttattgatta | 60 |
| acaagtaatt acaggttacg ggtgaggtaa cgggtgccaa tggggcgagg ctcagtataa | 120 |
| accccttcgt tgttgacagc aaattccaca ttattagact tggcataatt tgaggtgtac | 180 |
| tgaatctctg gattccagcg tttgctgttt tctttctgca gttcccactc gatctccacg | 240 |
| ctgacctggc cggtgctgta ctgcgtgata aatgaggcaa actaggcagg agtaaacacc | 300 |
| cctggaggat tagcaggtac cggggtgttt ttgatgagaa tttgaggagg cgggtgtttg | 360 |

```
agtccaaatc cgcccatcag gggagacggg tgaaagttgc cgtccgtgtg aggaattttg      420
gcccagatgg gaccctgcag gtacacgtcc cggttctgcc agaccatgcc gggcagagcc      480
ccctggctgt tgacagtctg tgtctggggt ccggccgtag acgattgcag gttgctggag      540
accacaccgt attcttctgt agccacggga ttggtggttt tgatctcctc ctcgctggtc      600
attagcacgt tttccagcgt tgtcttgttg gcagccccg ttttgccaaa aaccagcact       660
ccgttgatgg gaaagaactg gccctcgtcg tccttgttgg tggccatggc tacgcccggg      720
ttggttaatg aatttctacc attcagatgg tatttagtgg ccccggtcca ggcaaagtta     780
ctgttgttgt tgctgtctat gttttttgac agtctctgct gccgataaca gggtccgggc      840
agccagttct ttgattgctc ggccatggtg ttgggcccag cctgatggaa ctgcagctcc      900
cttgtggacc ccgtagtgct ctgggtccgg gccaggtagt acaggtactg gtcgatgagg      960
ggattcatca gccggtccag gctctggctg tgcgcatagc tgctgtggaa aggcacttcc     1020
tcaaaggtgt agctgaattc aaagttattg cccgttctca gcatctgaga aggaaagtac     1080
tccaggcagt agaaggagga acgtcccata gactgactgc cgttgtttag agtcagatat     1140
ccgtactgag gaatcatgaa cacgtccgca gggaacggag ggaggcagcc ctggtgcgca     1200
gagccgagga cgtacggcag ttggtactcc gagtccgaga agacctgaat cgtgctggta     1260
aggttattag cgatggtcgt aacgccgtcg ttcgtcgtga cctccttgac ctggatgttg     1320
aacaacttga accgcagctt tctgggccgg aatccccagt tgttgttgat gagtcgctgc     1380
cagtcacgtg gtgagaagtg gcagtggaat ctgttgaagt caaaatagcc caggggggtg    1440
ctgtagccga agaagtggtt gtcgttggta gccccgctct gacttgatat ctgcttgtag     1500
aggtggttgt tgtaggtggg cagggcccag gtgcgggtgc tggtggtgat gactctgtcg     1560
cccagccatg tggaatcgca atgccaattt ccggaggcat acccactcc gtcggcgcct     1620 tcgttattgt ctgccattgg tgcgccaccg cctgcagcca ttgtaccaga tcccagacct     1680
gagggcgcgg cgggaggttc tccgagaggt tgggggtcgg gcactgactc tgagtcgcca     1740
gtctgcccaa agttgagctt cttttagcg ggctgctggc cttcttgcc gatgcccgtg      1800 gaggagtcgg gggattctat gggtctcttc tttccaggag ccgtcttagc gccttcctca     1860
accagaccga gaggttcgag aacccgcttc ttggcctgga agactgctcg cccgaggttg     1920
cccccaaaag acgtatcttc ttgaagacgc tcctgaaact cagcgtcggc gtggttgtac     1980
ttgaggtacg ggttgtcccc ctgctcgagc tgcttgtcgt aggccttgtc gtgctcgagg     2040
gccgcggcgt ctgcctcgtt gaccggctct cccttgtcga gtccgttgaa gggtccgagg     2100
tacttgtagc caggaagcac cagacccggg ccgtcgtcct gcttttgctg gttggctttg     2160
ggtttcgggg ctccaggttt caagtccac cactcgcgaa tgccctcaga gaggttgtcc     2220
tcgagccaat ctggaagata accatcggca gccatacctg gtttaagtca tttattgctc     2280
agaaacacag tcatccaggt ccacgttgac cagatcgcag gccgagcaag caatctcggg    2340
agcccgcccc agcagatgat gaatggcaca gagtttccga tacgtcctct ttctgacgac     2400
cggttgagat tctgacacgc cggggaaaca ttctgaacag tctctggtcc cgtgcgtgaa     2460
gcaaatgttg aaattctgat tcattctctc gcatgtcttg cagggaaaca gcatctgaag     2520
catgcccgcg tgacgagaac atttgttttg gtacctgtcg gcaaagtcca ccggagctcc     2580
ttccgcgtct gacgtcgatg gatccgcgac tgaggggcag gcccgcttgg gctcgctttt     2640
atccgcgtca tcggggggcgg gcctcttgtt ggctccaccc tttctgacgt agaactcatg     2700
```

```
cgccacctcg gtcacgtgat cctgcgccca gcggaagaac tctttgactt cctgctttgt    2760
caccttgcca aagtcctgct ccagacggcg ggtgagttca aatttgaaca tccggtcttg    2820
taacggctgc tggtgctcga aggtggtgct gttcccgtca atcacggcgc acatgttggt    2880
gttggaagtg acgatcacgg gggtgggatc gatctgggcg gacgacttgc acttttggtc    2940
cacgcgcacc ttgctgccgc cgagaatggc cttggcggac tccacgacct tggccgtcat    3000
cttgccctcc tcccaccaga tcaccatctt gtcgacgcaa tcgttgaagg gaaagttctc    3060
attggtccag ttgacgcagc cgtagaaagg gcgaattc                            3098
```

<210> SEQ ID NO 11
<211> LENGTH: 3121
<212> TYPE: DNA
<213> ORGANISM: Unknown
<220> FEATURE:
<223> OTHER INFORMATION: AAV serotype, clone 29.3

<400> SEQUENCE: 11

```
gaattcgccc ttcgcagaga ccaaagttca actgaaacga atcaaccggt ttattgatta      60
acaagcaatt acagattacg ggtgaggtaa cgggtgccga tggggcgagg ctcagaataa     120
gtgccatctg tgttaacagc aaagtccaca tttgtagatt tgtagtagtt ggaagtgtat     180
tgaatctctg ggttccagcg tttgctgttt tctttctgca gctcccattc aatttccacg     240
ctgacctgtc cggtgctgta ctgcgtgatg aacgacgcca gcttagcttg actgaaggta     300
gttggaggat ccgcgggaac aggtgtattc ttaatcagga tctgaggagg cgggtgtttc     360
agtccaaagc cccccatcag cggcgaggga tgaaagtttc cgtccgtgtg aggaatcttg     420
gcccagatag gaccctgcag gtacacgtcc cggttctgcc agaccatgcc aggtaaggct     480
ccttgactgt tgacggcccc tacaatagga gcggcgtttt gctgttgcag ttatcggcc      540 accacgccgt actgttctgt ggccactggg ttggtggttt taatttcttc ctcactggtt     600
agcataacgc tgctatagtc cacgttgcct tttccagctc cctgtttccc aaacattaag    660
actccgctgg acggaaaaaa tcgctcttcg tcgtccttgt gggttgccat agcgacaccg    720
ggatttacca gagagtctct gccattcaga tgatacttgg tggcaccggt ccaggcaaag    780
ttgctgttgt tattttgcga cagtgtcgtg agacgcgtt gctgccggta gcagggcccg     840
ggtagccagt ttttggcctg agccgacatg ttattaggcc cggcctgaga aaatagcaac    900
tgctgagttc ctgcggtacc tcccgtggac tgagtccgag acaggtagta caggtactgg    960
tcgatgaggg ggttcatcag ccggtccagg cttggctgt gcgcgtagct gctgtgaaaa    1020
ggcacgtcct caaactggta gctgaactca agttgttgc ccgttctcag catttgagaa    1080
ggaaagtact ccaggcagta gaaggaggaa cggcccacgg cctgactgcc attgttcaga    1140
gtcaggtacc cgtactgagg aatcatgaag acgtccgccg ggaacggagg caggcagccc    1200
tggcgcgcag agccgaggac gtacgggagc tggtattccg agtccgtaaa gacctgaatc    1260
gtgctggtaa ggttattggc gatggtcttg gtgccttcat tctgcgtgac ctccttgacc    1320
tggatgttga agagcttgaa gttgagtctc ttgggccgga atcccagtt gttgttgatg     1380 agtcgctgcc agtcacgtgg tgagaagtgg cagtggaatc tgttaaagtc aaaatacccc    1440 caggggtgc tgtagccgaa gtaggtgttg tcgttggtgc ttcctcccga agtccgttg      1500 gagatttgct tgtagaggtg gttgttgtag gtgggagggg cccaggttcg ggtgctggtg    1560
gtgatgactc tgtcgcccag ccatgtgaa tcgcaatgcc aatttcctga ggaactaccc    1620
actccgtcgg cgccttcgtt attgtctgcc attggagcgc caccgcctgc agccattgta    1680
```

```
ccagatccca gaccagaggg gcctgcgggg ggttctccga ttggttgagg gtcgggcact    1740
gactctgagt cgccagtctg cccaaagttg agtctctttt tcgcgggctg ctggccttc    1800 ttgccgatgc ccgtagtgga gtctggagaa cgctggggtg atggctctac cggtctcttc    1860
tttccaggag ccgtcttagc gccttcctca accagaccga gaggttcgag aacccgcttc    1920
ttggcctgga agactgctcg tccgaggttg cccccaaaag acgtatcttc ttgcagacgc    1980
tcctgaaact cggcgtcggc gtggttatac cgcaggtacg gattgtcacc cgctttgagc    2040
tgctggtcgt aggccttgtc gtgctcgagg gccgctgcgt ccgccgcgtt gacgggctcc    2100
cccttgtcga gtccgttgaa gggtccgagg tacttgtagc caggaagcac cagacccggg    2160
ccgtcgtcct gcttttgctg gttggctttg gcttcggggg ctccaggttt cagcgcccac    2220
cactcgcgaa tgccctcaga gaggttgtcc tcgagccaat ctggaagata accatcggca    2280
gccatacctg atctaaatca tttattgttc aaagatgcag tcatccaaat ccacattgac    2340
cagatcgcag gcagtgcaag cgtctggcac ctttcccatg atatgatgaa tgtagcacag    2400
tttctgatac gccttttttga cgacagaaac gggttgagat tctgacacgg gaaagcactc    2460
taaacagtct ttctgtccgt gagtgaagca gatatttgaa ttctgattca ttctctcgca    2520
ttgtctgcag ggaaacagca tcagattcat gcccacgtga cgagaacatt tgttttggta    2580
cctgtccgcg tagttgatcg aagcttccgc gtctgacgtc gatggctgcg caactgactc    2640
gcgcacccgt ttgggctcac ttatatctgc gtcactgggg gcgggtcttt tcttggctcc    2700
accctttttg acgtagaatt catgctccac ctcaaccacg tgatcctttg cccaccggaa    2760
aaagtctttg acttcctgct tggtgacctt cccaaagtca tgatccagac ggcgggtgag    2820 ttcaaattg aacatccggt cttgcaacgg ctgctggtgt tcgaaggtcg ttgagttccc    2880
gtcaatcacg gcgcacatgt tggtgttgga ggtgacgatc acgggagtcg ggtctatctg    2940
ggccgaggac ttgcatttct ggtccacgcg cacctttgctt cctccagaa tggctttggc    3000 cgactccacg accttggcgg tcatcttccc ctcctcccac cagatcacca tcttgtcgac    3060
acagtcgttg aagggaaagt tctcattggt ccagttgacg cagccgtaga agggcgaatt    3120
c                                                                   3121
```

<210> SEQ ID NO 12
<211> LENGTH: 3121
<212> TYPE: DNA
<213> ORGANISM: Unknown
<220> FEATURE:
<223> OTHER INFORMATION: AAV serotype, clone 29.4

<400> SEQUENCE: 12

```
gaattcgccc ttctacggct gcgtcaactg gaccaatgag aactttccct tcaacgactg     60
tgtcgacaag atggtgatct ggtgggagga ggggaagatg accgccaagg tcgtggagtc    120
ggccaaagcc attctcggag gaagcaaggt gcgcgtggac cagaaatgca agtcctcggc    180
ccagatagac ccgactcccg tgatcgtcac ctccaacacc aacatgtgcg ccgtgattga    240
cgggaactca cgaccttcg aacaccagca gccgttgcaa gaccggatgt tcaaatttga    300
actcacccgc cgtctggatc atgactttgg gaaggtcacc aagcaggaag tcaaagactt    360
tttccggtgg gcaaaggatc acgtggttga ggtggagcac gaattctacg tcaaaaaggg    420
tggagccaag aaaagacccg cccccagtga cgcagatata agtgagccca acgggtgcg    480 cgagtcagtt gcgcagccat cgacgtcaga cgcggaagct tcgatcaact acgcagacag    540
```

```
gtaccaaaac aaatgttctc gtcacgcggg catgaatctg atgctgtttc cctgcagaca    600
atgcgagaga atgaatcaga attcaaatat ctgcttcact cacggacaga aagactgttt    660
agagtgcttt cccgtgtcag aatctcaacc cgtttctgtc gtcaaaaagg cgtatcagaa    720
actgtgctac attcatcata tcatgggaaa ggtgccagac gcttgcactg cctgcgatct    780
ggtcgatgtg gatttggatg actgcatctt tgaacaataa atgatttaaa tcaggtatgg    840
ctgccgatgg ttatcttcca gattggctcg aggacaacct ctctgagggc attgcgagt     900 ggtgggcgct gaaacctgga gccccgaagc ccaaagccaa ccagcaaaag caggacggcg    960
gccggggtct ggtgcttcct ggctacaagt acctcggacc cttcaacgga ctcgacaagg   1020
gggagcccgt caacgcggcg gacgcagcgg ccctcgagca cgacaaggcc tacgaccagc   1080
agctcaaagc gggtgacaat ccgtacctgc ggtataacca cgccgacgcc gagtttcagg   1140
agcgtctgca agaagatacg tcttttgggg caacctcgg gcgagcagtc ttccaggcca    1200
agaagcgggt tctcgaacct ctcggtctgg ttgaggaagg cgctaagacg gctcctggaa   1260
agaagagacc ggtagagcca tcaccccagc gttctccaga ctcctctacg ggcatcggca   1320
agaaaggcca gcagcccgcg aaaaagagac tcaactttgg gcagactggc gactcagagt   1380
cagtgcccga ccctcaacca atcggagaac ccccgcagg ccctctggt ctgggatctg     1440 gtacaatggc tgcaggcggt ggcgctccaa tggcagacaa taacgaaggc gccgacggag   1500
tgggtagttc ctcaggaaat tggcattgcg attccacatg gctgggcgac tgagtcatca   1560
ccaccagcac ccgaacctgg gccctcccca cctacaacaa ccacctctac aagcaaatct   1620
ccaacgggac ttcggggaga agcaccaacg acaaccta cttcggctac agcaccccct    1680
gggggtattt tgactttaac agattccact gccacttctc accacgtgac tggcagcgac   1740
tcatcaacaa caactgggga ttccggccca agagactcaa cttcaagctc ttcaacatcc   1800
aggtcaagga ggtcacgcag aatgaaggca ccaagaccat cgccaataac cttaccagca   1860
cgattcaggt ctttacggac tcggaatacc agctcccgta cgtcctcggc tctgcgcacc   1920
agggctgcct gcctccgttc ccggcggacg tcttcatgat tcctcagtac gggtacctga   1980
ctctgaacaa tggcagtcag gccgtgggcc gttcctcctt ctactgcctg gagtactttc   2040
cttctcaaat gctgagaacg ggcaacaact ttgagttcag ctaccagttt gaggacgtgc   2100
cttttcacag cagctacgcg cacagccaaa gcctggaccg gctgatgaac cccctcatcg   2160
accagtacct gtactacctg tctcggactc agtccacggg aggtaccgca ggaactcagc   2220
agttgctatt ttctcaggcc gggcctaata acatgtcggc tcaggccaaa aactggctac   2280
ccgggccctg ctaccggcag taacgcgtct ccacgacact gtcgcaaaat aacaacagca   2340
actttgtctg gaccggtgcc accaagtatc atctgaatgg cagagactct ctggtagatc   2400
ccggtgtcgc tatggcaacc cacaaggacg acgaagagcg attttttccg tccagcggag   2460
tcataatgtt tgggaaacag ggagctgaa aagacaacgt ggactatagc agcgtcatgc    2520
taaccagtga ggaagaaatt aaaaccacca acccagtggc cacagaacag tacggcgtgg   2580
tggccgataa cctgcaacag caaaacgccg ctcctattgt aggggccgtc aacagtcaag   2640
gagccttacc tggcatggtc tggcagaacc gggacgtgta cctgcagggt cctacctggg   2700
ccaagattcc tcacacggac ggaaactttc atccctcgcc gctgatggga ggctttggac   2760
tgaaacaccc gcctcctcag atcctgatta agaatacacc tgttcccgcg gatcctccaa   2820
ctaccttcag tcaagctaag ctggcgtcgt tcatcacgca gtacagcacc ggacaggtca   2880
gcgtggaaat tgaatgggag ctgcaggaag aaaacagcaa acgctggaac ccagagattc   2940
```

-continued

| | |
|---|---|
| aatacacttc caactactac aaatctacaa atgtggactt tgctgttaac acagatggca | 3000 |
| cttattctga gcctcgcccc atcggcaccc gttacctcac ccgtaatctg taattgcttg | 3060 |
| ttaatcaata aaccggttga ttcgtttcag ttgaactttg gtctctgcga agggcgaatt | 3120 |
| c | 3121 |

<210> SEQ ID NO 13
<211> LENGTH: 3121
<212> TYPE: DNA
<213> ORGANISM: Unknown
<220> FEATURE:
<223> OTHER INFORMATION: AAV serotype, clone 29.5

<400> SEQUENCE: 13

| | |
|---|---|
| gaattcgccc ttcgcgagac caaagttcaa ctgaaacgaa tcaaccggtt tattgattaa | 60 |
| caagcaatta cagattacgg gtgaggtaac gggtgccgat ggggcgaggc tcagaataag | 120 |
| tgccatctgt gttaacagca aagtccacat ttgtagattt gtagtagttg gaagtgtatt | 180 |
| gaatctctgg gttccagcgt ttgctgtttt ctttctgcag ctcccattca atttccacgc | 240 |
| tgacctgtcc ggtgctgtac tgcgtgatga acgacgccag cttagcttga ctgaaggtag | 300 |
| ttggaggatc cgcgggaaca ggtgtattct taatcaggat ctgaggaggc gggtgtttca | 360 |
| gtccaaagcc tcccatcagc ggcgagggat gaaagtttcc gtccgtgtga ggaatcttgg | 420 |
| cccagatagg accctgcagg tacacgtccc ggttctgcca gaccatgcca ggtaaggctc | 480 |
| cttgactgtt gacggcccct acaataggag cggcgttttg ctgttgcagg ttatcggcca | 540 |
| ccacgccgta ctgttctgtg gccactgggt tggtggtttt aatttcttcc tcactggtta | 600 |
| gcataacgct gctatagtcc acgttgtctt ttccagctcc ctgtttccca aacattaaga | 660 |
| ctccgctgga cggaaaaaat cgctcttcgt cgtccttgtg ggttgccata gcgacaccgg | 720 |
| gatttaccag agagtctctg ccattcagat gatacttggt ggcaccggtc caggcaaagt | 780 |
| tgctgttgtc atttttgcgac agtgtcgtgg agacgcgttg ctgccggtag cagggcccgg | 840 |
| gtagccagtt tttggcctga ccgacatgt tattaggccc ggcctgagaa aatagcaact | 900 |
| gctgagttcc tgcggtacct cccgtggact gagtccgaga caggtagtac aggtactggt | 960 |
| cgatgagggg gttcatcagc cggtccaggc tttggctgtg cgcgtagctg ctgtgaaaag | 1020 |
| gcacgtcctc aaactggtag ctgaactcaa agttgttgcc cgttctcagc atttgagaag | 1080 |
| gaaagtactc caggcagtag aaggaggaac ggcccacggc ctgactgcca ttgttcagag | 1140 |
| tcaggtaccc gtactgagga atcatgaaga cgtccgccgg gaacggaggc aggcagccct | 1200 |
| ggtgcgcaga gccgaggacg tacgggagct ggtattccga gtccgtaaag acctgaatcg | 1260 |
| tgctggtaag gttattggcg atggtcttgg tgccttcatt ctgcgtgacc tccttgacct | 1320 |
| ggatgttgaa gagcttgaag ttgaggctct gggccggaa tccccagttg ttgttgatga | 1380 |
| gtcgctgcca gtcacgtggt gagaagtggc agtggaatct gttaaagtca aaataccccc | 1440 |
| aggggggtgct gtagccgaag taggtgttgt cgttggtgct tcctcccgaa gtcccgttgg | 1500 |
| agatttgctt gtagaggtgg ttgttgtagg tggggagggc ccaggttcgg gtgctggtgg | 1560 |
| tgatgactcc gtcgcccagc catgtggaat cgcaatgcca atttcctgag gaactaccca | 1620 |
| ctccgtcggc gccttcgtta ttgtctgcca ttggagcgcc accgcctgca gccattgtac | 1680 |
| cagatcccag accagagggg cctgcggggg gttctccgat tggttgaggg tcggcactg | 1740 |
| actctgagtc gccagtctgc ccaaagttga gtctcttttt cgcgggctgc tggcctttct | 1800 |

-continued

```
tgccgatgcc cgtagaggag tctggagaac gctggggtga tggctctacc ggtctcttct    1860
ttccaggagc cgtcttagcg ccttcctcaa ccagaccgag aggttcgaga acccgcttct    1920
tggcctggaa gactgctcgc ccgaggttgc ccccaaaaga cgtatcttct tgcagacgct    1980
cctgaaactc ggcgtcggcg tggttatacc gcaggtacgg attgtcaccc gctttgagct    2040
gctggtcgta ggccttgtcg tgctcgaggg ccgctgcgtc cgccgcgttg acgggctccc    2100
ccttgtcgag tccgttgaag ggtccgaggt acttgtagcc aggaagcacc agaccccggc    2160
cgtcgtcctg cttttgctgg ttggctttgg gcttcggggc tccaggtttc agcgcccacc    2220
actcgcgaat gccctcagag aggttgtcct cgagccaatc tggaagataa ccatcggcag    2280
ccatacctga tttaaatcat ttattgttca agatgcagt catccaaatc cacattgacc     2340
agatcgcagg cagtgcaagc gtctggcacc tttcccatga tatgatgaat gtagcacagt    2400
ttctgatacg cctttttgac gacagaaacg ggttgagatt ctgacacggg aaagcactct    2460
aaacagtctt tctgtccgtg agtgaagcag atatttgaat tctgattcat tctctcgcat    2520
tgtctgcagg gaaacagcat cagattcatg cccacgtgac gagaacattt gttttggtac    2580
ctgtctgcgt agttgatcga agcttccgcg tctgacgtcg atggctgcgc aactgactcg    2640
cgcacccgtt tgggctcact tatatctgcg tcactggggg cgggtctttt cttggctcca    2700 cccttttga cgtagaattc atgctccacc tcaaccacgt gatcctttgc ccaccggaaa     2760
aagtctttga cttcctgctt ggtgaccttc ccaaagtcat gatccagacg gcgggtgagt    2820
tcaaatttga acatccggtc ttgcaacggc tgctggtgtt cgaaggtcgt tgagttcccg    2880
tcaatcacgg cgcacatgtt ggtgttggag gtgacgatca cggagtcgg gtctatctgg     2940 gccgaggact tgcatttctg gtccacgcgc accttgcttc ctccgagaat ggctttggcc    3000
gactccacga ccttggcggt catcttcccc tcctcccacc agatcaccat cttgtcgaca    3060
cagtcgttga agggaaagtt ctcattggtc cagttgacgc agccgtagaa agggcgaatt    3120
c                                                                   3121
```

<210> SEQ ID NO 14
<211> LENGTH: 3131
<212> TYPE: DNA
<213> ORGANISM: Unknown
<220> FEATURE:
<223> OTHER INFORMATION: AAV serotype, clone 1-3

<400> SEQUENCE: 14

```
gcggccgcga attcgccctt ggctgcgtca actggaccaa tgagaacttt cccttcaatg     60
attgcgtcga caagatggtg atctggtggg aggagggcaa gatgacggcc aaggtcgtgg    120
agtccgccaa ggccattctc ggcggcagca aggtgcgcgt ggaccaaaag tgcaagtcgt    180
ccgcccagat cgaccccacc cccgtgatcg tcacctccaa caccaacatg tgcgccgtga    240
ttgacgggaa cagcaccacc ttcgagcacc agcagcctct ccaggaccgg atgtttaagt    300
tcgaactcac ccgccgtctg gagcacgact ttggcaaggt gacaaagcag gaagtcaaag    360
agttcttccg ctgggccagt gatcacgtga ccgaggtggc gcatgagttt acgtcagaa    420 agggcggagc cagcaaaaga cccgcccccg atgacgcgga taaagcgag cccaagcggg     480 cctgccctc agtcgcggat ccatcgacgt cagacgcgga aggagctccg gtggactttg    540
ccgacaggta ccaaaacaaa tgttctcgtc acgcgggcat gcttcagatg ctgtttccct    600
gcaaaacgtg cgagagaatg aatcggaatt tcaacatttg cttcacacac ggggtcagag    660
actgctcaga gtgtttcccc ggcgtgtcag aatctcaacc ggtcgtcaga aagaggacgt    720
```

```
atcggaaact ccgtgcgatt catcatctgc tggggcgggc tcccgagatt gcttgctcgg      780
cctgcgatct ggtcaacgtg gacctggatg actgtgtttc tgagcaataa atgacttaaa      840
ccaggtatgg ctgccgatgg ttatcttcca gattggctcg aggacaacct ctctgagggc      900
attcgcgagt ggtgggcgct gaaacctgga gccccgaagc caaagccaa ccagcaaaag       960 caggacgacg gccggggtct ggtgcttcct ggctacaagt acctcggacc cttcaacgga     1020
ctcgacaagg gggagcccgt caacgcggcg gacgcagcgg ccctcgagca cgacaaggct     1080
tacgaccagc agctgcaggc gggtgacaat ccgtacctgc ggtataacca cgccgacgcc     1140
gagtttcagg agcgtctgca agaagatacg tcttttgggg caacctcgg gcgagcagtc      1200 ttccaggcca agaagcgggt tctcgaacct ctcggtctgg ttgaggaagg cgctaagacg     1260
gctcctggaa agaagagacc ggtagagcca tcaccccagc gttctccaga ctcctctacg     1320
ggcatcggca agaaaggcca acagcccgcc agaaaaagac tcaattttgg tcagactggc     1380
gactcagagt cagttccaga ccctcaacct ctcggagaac ctccagcagc gccctctggt     1440
gtgggaccta atacaatggc tgcaggcggt ggcgcaccaa tggcagacaa taacgaaggc     1500
gccgacggag tgggtagttc ctcgggaaat tggcattgcg attccacatg gctgggcgac     1560
agagtcatca ccaccagcac ccgaacctgg gccctgccca cctacaacaa ccacctctac     1620
aagcaaatct ccaacgggac atcggggagg accaccaacg acaacaccta cttcggctac     1680 agcacccct gggggtattt tgactttaac agattccact gccaccttc accacgtgac       1740 tggcagcgac tcatcaacaa caactgggga ttccgaccca agagactcag cttcaagctc     1800
ttcaacatcc aggtcaagga ggtcacgcag aatgaaggca ccaagaccat cgccaataac     1860
ctcaccagca ccatccaggt gtttacggac tcggagtacc agctgccgta cgttctcggc     1920
tctgtccacc agggctgcct gcctccgttc ccggcggacg tgttcatgat tccccagtac     1980
ggctacctaa cactcaacaa cggtagtcag gccgtgggac gctcctcctt ctactgcctg     2040
gaatactttc cttcgcagat gctgagaacc ggcaacaact tccagtttac ttacaccttc     2100
gaggacgtgc ctttccacag cagctacgcc cacagctaga gcttggaccg gctgatgaat     2160
cctctgattg accagtacct gtactacttg tctcggactc aaacaacagg aggcacggca     2220
aatacgcaga ctctgggctt cagccaaggt gggcctaata caatggccaa tcaggcaaag     2280
aactggctgc caggaccctg ttaccgccaa caacgcgtct caacgacaac cgggcaaaac     2340
aacaatagca actttgcctg gactgctggg accaaatacc atctgaatgg aagaaattca     2400
ttggctaatc ctggcatcgc tatggcaaca cacaaagacg acgaggagcg ttttttccc      2460 agtaacggga tcctgatttt tggcaaacaa aatgctgcca gagacaatgc ggattacagc     2520
gatgtcatgc tcaccagcga ggaagaaatc aaaaccacta ccctgtggc tacagaggaa      2580 tacggtatcg tggcagataa cttgcagcag caaaacacgg ctcctcaaat tggaactgtc     2640
aacagccagg gggccttacc cggtatggtc tggcagaacc gggacgtgta cctgcagggt     2700
cccatctggg ccaagattcc tcacacggac ggcaacttcc accgtctcc gctgatgggc      2760 ggctttggcc tgaaacatcc tccgcctcag atcctgatca agaacacgcc tgtacctgcg     2820
gatcctccga ccaccttcaa ccagtcaaag ctgaactctt tcatcacgca atacagcacc     2880
ggacaggtca gcgtggaaat tgaatgggag ctgcagaagg aaaacagcaa gcgctggaac     2940
cccgagatcc agtacacctc caactactac aaatctataa gtgtggactt tgctgttaat     3000
acagaaggcg tgtactctga accccgcccc attggcaccc gttacctcac ccgtaatctg     3060
```

```
taattgcctg ttaatcaata aaccggttga ttcgtttcag ttgaactttg gtctctgcga    3120
agggcgaatt c                                                         3131

<210> SEQ ID NO 15
<211> LENGTH: 3127
<212> TYPE: DNA
<213> ORGANISM: Unknown
<220> FEATURE:
<223> OTHER INFORMATION: AAV serotype, clone 13-3b

<400> SEQUENCE: 15
gcggccgcga attcgccctt cgcagagacc aaagttcaac tgaaacgaat caaccggttt      60
attgattaac atgcaattac agattacggg tgaggtaacg agtgccaata gggcgaggct     120
cagagtaaac accctggctg tcaacggcaa agtccacacc agtctgcttt tcaaagttgg     180
aggtgtactg aatctccggg tcccagcgct tgctgttttc cttctgcagc tcccactcga     240
tttccacgct gacttgtccg gtgctgtact gtgtgatgaa cgaagcaaac ttggcaggag     300
taaacacctc cggaggatta gcgggaacgg gagtgttctt gatcaggatc tgaggaggcg     360
gatgtttaag tccaaagccg cccatcaaag gagacgggtg aaagttgcca tccgtgtgag     420
gaatcttggc ccagatggga ccctgcaggt acacgtcccg gttctgccag accatgccag     480
gtaaggctcc ctggttgttg acaacttgtg tctgggctgc agtattagcc gcttgtaagt     540
tgctgctgac tatcccgtat tcttccgtgg ctacaggatt agtaggacga atttcttctt     600
catttgtcat taacacattt tccaatgtag ttttgttagt tgctccagtt tttccaaaaa     660
tcaggactcc gctggatggg aaaaagcggt cctcgtcgtc cttgtgagtt gccatggcga     720
cgccgggatt aaccaacgag tttctgccgt tcaggtgata tttggtggca ccagtccaag     780
caaagttgct gttgttgttt tgatccagcg ttttggagac cctttgttgc cggaagcagg     840
gtccaggtaa ccaattcttg gcttgttcgg ccatagttga aggcccgccc tggtaaaact     900
gcagttcccg attgccagct gtgcctcctg ggtcactctg tgttctggcc aggtagtaca     960
agtactggtc gatgagggga ttcatcagcc ggtccaggct ctggctgtgt gcgtagctgc    1020
tgtggaaagg cacgtcctcg aagctgtagc tgaactcaaa gttgttgccc gttctcagca    1080
tctgagaggg gaagtactcc aggcagtaga aggaggaacg tcccacagac tgactgccat    1140
tgttgagagt caggtagccg tactgaggaa tcatgaagac gtccgccggg aacggaggca    1200
ggcagccctg gtgcgcagag ccgaggacgt acggcagctg gtattccgag tccgagaata    1260
cctgaatcgt gctggtaagg ttattagcga tggtcgtaac gccgtcattc gtcgtgacct    1320
ccttgacctg gatgttgaag agcttgaacc gcagcttctt gggccggaat ccccagttgt    1380
tgttgatgag tcgctgccag tcacgtggtg agaagtggca gtggaatctg ttaaagtcaa    1440
aataccccca gggggtgctg tagccgaagt aggtgttgtc gttggtacta cctgcagttt    1500
cactggagat ttgctcgtag aggtggttgt tgtaggtggg cagggcccag gttcgggtgc    1560
tggtggtaat gactctgtcg cccagccatg tggaatcgca atgccaattt cctgaggcat    1620
tacccactcc gtcggcacct tcgttattgt ctgccattgg tgcgccaccg cctgcagcca    1680
ctgtaccaga tcccacacta gagggcgctg ctggaggttc tccgagaggt tgagggtcgg    1740
ggactgactc tgagtcgcca gtctgaccga aattgagtct ctttctggcg ggctgctggc    1800
ccttcttgcc gatgcccgtg gaggagtcgg gggaacgctg aggtgacggc tctaccggtc    1860
tcttctttgc aggagccgtc ttagcgcctt cctcaaccag accgagaggt tcgagaaccc    1920
gcttcttggc ctggaagact gctcgcccga ggttgccccc aaatgacgta tcttcttgca    1980
```

```
gacgctcctg aaactcggcg tcggcgtggt tataccgcag gtacgggttg tcacccgcat    2040
tgagctgctg gtcgtaggcc ttgtcgtgct cgagggccgc tgcgtccgcc gcgttgacgg    2100
gctccccctt gtcgagtccg ttgaagggtc cgaggtactt gtagccagga agcaccagac    2160
cccggccgtt gtcctgcttt tgctggttgg ctttgggttt cggggctcca ggtttcaggt    2220
cccaccactc gcgaatgccc tcagagaggt tgtcctcgag ccaatctgga agataaccat    2280
cggcagccat acctgattta aatcatttat tgttcaaaga tgcagtcatc caaatccaca    2340
ttgaccagat cgcaggcagt gcaagcgtct ggcacctttc ccatgatatg atgaatgtag    2400
cacagtttct gatacgcctt tttgacgaca gaaacgggtt tagattctga cacgggaaag    2460
cactctaaac agtctttctg tccgtgagtg aagcagatat ttgaattctg attcattctc    2520
tcgcattgtc tgcagggaaa cagcatcaga ttcatgccca cgtgacgaga catttgttt     2580 tggtacctgt ctgcgtagtt gatcgaagct tccgcgtctg acgtcgatgg ctgcgcaact    2640
gactcgcgca cccgtttggg ctcacttata tctgcgtcac tggggcgggt tcttttcttg    2700
gctccaccct ttttgacgta gaattcatgc tccacctcaa ccacgtaatc ctttgcccac    2760
cggaaaaagt ctttgacttc ctgcttggtg accttcccaa agtcatgatc cagacggcgg    2820
gtgagttcaa atttgaacat ccggtcttgc aacggctgct ggtgttcgaa ggtcgttgag    2880
ttcccgtcga tcacgcgcca catgttggtg ttggagatga cgatcgcggg agtcgggtct    2940
atctgggccg aggacttgca tttctggtcc acgcgcacct tgcttcctcc gagaatggct    3000
ttggccgact ccacgacctt ggcggtcatc ttcccctcct cccaccagat caccatcttg    3060
tcgacacagt cgttgaaggg aaagttctca ttggtccagt tgacgcagcc gtagaaaggg    3120
cgaattc                                                              3127

<210> SEQ ID NO 16
<211> LENGTH: 3106
<212> TYPE: DNA
<213> ORGANISM: Unknown
<220> FEATURE:
<223> OTHER INFORMATION: AAV serotype, clone 24-1

<400> SEQUENCE: 16
gcggccgcga attcgccctt cgcagagacc aaagttcaac tgaaacgaat caaccggttt      60
attgattaac aagtaattac aggttacggg tgaggtaacg ggtgccaatg gggcgaggct     120
cagtataaac cccttcgttg ttgacagcaa attccacatt attagacttg cataatttg      180 aggtgtactg aatctctgga ttccagcgtt tgctgttttc tttctgcagt cccactcga      240 tctccacgct gacctggccg gtgctgtact gcgtgataaa tgaggcaaac ttggcaggag     300
taaacacctc tggaggatta gcaggtaccg gggtgttttt tgatgagaatt tgaggaggcg    360 ggtgtttgag tccaaatccg cccatcaggg gagacgggtg aaagttgccg tccgtgtgag    420
gaattttggc ccagatggga ccctgcaggc acacgtcccg gttctgccag accatgccgg     480
gcagagcccc ctggctgttg acagtctgtg tctggggtcc ggccgtagac gattgcaggt    540
tgctggagac cacaccgtat tcttctgtag ccacgggatt ggtggttttg atctcctcct    600
cgctggtcat tagcacgttt tccagcgttg tcttgttggc agccccgtt ttgccaaaaa      660 ccagcactcc gttgatggga aagaactggt cctcgtcgtc cttgttggtg gccatggcta    720 cgccccgggtt ggttaatgaa tttctaccat tcagatggta tttagtggcc ccggtccagg    780
caaagttact gttgttgttg ctgtctatgt tttttgacag tctctgctgc cgataacagg    840
```

```
gtccgggcag ccagttcttt gattgctcgg ccatggtgtt gggcccagcc tgatggaact    900
gcagctccct tgtggacccc gtagtgctct gggtccgggc caggtagtac aggtactggt    960
cgatgagggg attcatcagc cggtctaggc tctggctgtg cacatagctg ctgtggaaag   1020
gcacttcctc aaaggtgtag ctgaattcaa agttattgcc cgttctcagc atctgagaag   1080
gaaagtactc caggcagtag aaggaggaac gtcccacaga ctgactgccg ttgtttagag   1140
tcagatatcc gtactgagga atcatgaaca cgtccgcagg gaacggaggg aggcagccct   1200
ggtgcgcaga gccgaggacg tacggcagtt ggtactccga gtccgagaag acctgaatcg   1260
tgctggtaag gttattagcg atggtcgtaa cgccgtcgtt cgtcgtgacc tccttgacct   1320
ggatgttgaa caacttgaac cgcagctttc tgggccggaa tccccagttg ttgttgatga   1380
gtcgctgcca gtcacgtggt gagaagtggc agtggaatct gttgaagtca aaatagcccc   1440
aggggtgct gtagctgaag aagtggttgt cgttggtagc cccgctctga cttgatatct   1500
gcttgtagag gtggttgttg taggtgggca gggcccaggt gcgggtgctg gtggtgatga   1560
ctctgtcgcc cagccatgtg aatcgcaat gccaatttcc ggaggcatta cccactccgt   1620
cggcgccttc gttattgtct gccattggtg cgccaccgcc tgcagccatt gtaccagatc   1680
ccagacctga gggcgcggcg ggaggttctc cgagaggttg ggggtcgggc actgactctg   1740
agtcgccagt ctgcccaaag ttgagcttct ttttagcggg ctgctggcct ttcttgccga   1800
tgcccgtgga ggagtcgggg gattctatgg gtctcttctt tccaggagcc gtcttagcga   1860
cttcctcaac cagaccgaga ggttcgagaa cccgcttctt ggcctggaag actgctcgcc   1920
cgaggttgcc cccaaaagac gtatcttctt gaagacgctc ctgaaactcg gcgtcggcgt   1980
ggttgtactt gaggtacggg ttgtcccct gctcgagctg cttgtcgtag gccttgtcgt   2040
gctcgagggc cgcggcgtct gcctcgttga ccggctctcc cttgtcgagt ccgttgaagg   2100
gtctgaggta cttgtagcca ggaagcacca ccccggcc gtcgtcctgc ttttgctggt   2160
tggctttggg tttcggggct ccaggtttca agtcccacca ctcgcgaatg ccctcagaga   2220
ggttgtcctc gagccaatct ggaagataac catcggcagc catacctggt ttaagtcatt   2280
tattgctcag aaacacagtc atccaggtcc acgttgacca gatcgcaggc cgagcaagca   2340
atctcgggag cccgcccag cagatgatga atggcacaga gtttccgata cgtcctcttt   2400
ctgacgaccg gttgagattc tgacacgccg gggaaacatt ctgaacagtc tctggtcccg   2460
tgcgtgaagc aaatgttgaa attctgattc actctctcgc atgtcttgca gggaaacagc   2520
atctgaagca tgcccgcgtg acgagaacat ttgttttggt acctgtcggc aaagtccacc   2580
ggagctcctt ccgcgtctga cgtcgatgga ttcgcgactg aggggcaggc ccgcttgggc   2640
tcgcttttat ccgcgtcatc gggggcgggt ctcttgttgg ccccacccct tctgacgtag   2700
aacccatgcg ccacctcggt cacgtgatcc tgcgcccagc ggaagaacct tttgacttcc   2760
tgctttgtca ccttgccaaa gttatgctcc agacggcggg tgggttcaaa tttgaacatc   2820
cggtcctgca acgctgctg gtgctcgaag gtggcgctgt tcccgtcaat cacggcgcac   2880
atgttggtgt tggaggtgac ggtcacgggg gtggggtcga tctgggcgga cgacttgcac   2940
ttttggtcca cgcgcacctt gctgccgccg agaatggcct tggcggactc cacgaccttg   3000
gccgtcatct tgccctcctc ccaccagatc accatcttgt cggcgcaatc gttgaaggga   3060
aagttctcat tggtccagtt gacgcagccg tagaaagggc gaattc              3106

<210> SEQ ID NO 17
<211> LENGTH: 3102
```

<212> TYPE: DNA
<213> ORGANISM: Unknown
<220> FEATURE:
<223> OTHER INFORMATION: AAV serotype, clone 27-3

<400> SEQUENCE: 17

```
gcggccgcga attcgccctt cgcagagacc aaagttcaac tgaaacgaat caaccggttt      60
attgattaac aagtaattac aggttacggg tgaggtaacg ggtgccaatg gggcgaggct     120
cagtataaac cccttcgttg ttgacagcaa attccacatt attagacttg cataatttg     180
aggtgtactg aatctctgga ttccagcgtt tgctgttttc tttctgcagt tcccactcga     240
tctccacgct gacctggccg gtgctgtact gcgtgataaa tgaggcaaac ttggcaggag     300
taaacacctc tggaggatta gcaggtaccg gggtgttttt gatgagaatt tgaggaggcg     360
ggtgtttgag tccaaatccg cccatcaggg gagacgggtg aaagttgccg tccgtgtgag     420
gaatttcggc ccagatggga ccctgcaggt acacgtcccg gttctgccag accatgccgg     480
gcagagcccc ctggctgttg acagtctgtg tccggggtcc ggccgtagac gattgcaggt     540
tgctggagac cacaccgtat tcttctgtag ccacgggatt ggtggttttg atctcctcct     600
cgctggtcat tagcacgttt tccagcgttg tcttgttggc agccccgtt ttgccaaaaa     660
ccagcactcc gttgatggga aggaactggt cctcgtcgtc cttgttggtg gccatggcta     720
cgcccgggtt ggttaatgaa tttctaccat tcagatggta tttagtgcc ccggtccagg     780
caaagttact gttgttgttg ctgtctatgt tttttgacag tctctgctgc cgataacagg     840
gtccgggcag ccagttcttt gattgctcgg ccacggtgtt gggcccagcc tgatggaact     900
gcagctccct tgtggacccc gtagtgctct gggtccgggc caggtagtac aggtactggt     960
cgatgagggg attcatcagc cggtccaggc tctggctgtg cgcatagctg ctgtggaaag    1020
gcacttcctc aaaggtgtag ctgaattcaa agttattgcc cgttctcagc atctgagaag    1080
gaaagtactc caggcagcag aaggaggaac gtcccacaga ctgactgccg ttgtttagag    1140
tcagatatcc gtactgagga atcatgaaca cgtccgcagg gaacggaggg aggcagccct    1200
ggtgcgcaga gccgaggacg tacgcagtt ggtactccga gtccgagaag acctgaatcg    1260
tgctggtaag gttattagcg atggtcgtaa cgccgtcgtt cgtcgtgacc tccttgacct    1320
ggatgttgaa caacttgaac cgcagctttc tgggccggaa tccccagttg ttgttgatga    1380
gtcgctgcca gtcacgtggt gagaagtggc agtggaatct gttgaagtca aaatagcccc    1440
agggggtgct gtagccgaag aagtggttgt cgttggtagc cccgctctga cttgatatct    1500
gcttgtagag gtgttgttg taggtgggca gggcccaggt gcgggtgctg gtggtgatga    1560
ctctgtcgcc cagccatgtg gaatcgcaat gccaatttcc ggaggcatta cccactccgt    1620
cggcgccttc gttattgtct gccattggtg cgccaccgcc tgcagccatt gtaccagatc    1680
ccagacctga gggcgcggcg ggaggttctc cgagaggttg gggtcgggc actgactctg    1740
agtcgccagt ctgcccaaag ttgagcttct ttttagcggg ctgctggcct ttcttgccga    1800
tgcccgtgga ggagtcgggg gattctatgg gtctcttctt tccggaagcc gtcttagcgc    1860
cttcctcaac cagaccgaga ggttcgagaa cccgcttctt ggcctggaag actgctcgcc    1920
cgaggttgcc cccaaaagac gtatcttctt gaagacgctc tgaaactcg gcgtcggcgt    1980
ggttgtactt gaggtacggg ttgtcccccct gctcgagctg cttgtcgtag gccttgtcgt    2040
gctcgagggc cgcggcgtct gcctcgttga ccggctctcc cttgtcgagt ccgttgaagg    2100
gtccgaggta cttgtagcca ggaagcacca gaccccggcc gtcgtcctgc ttttgctggt    2160
```

```
tggctttggg tttcggggct ccaggtttca agtcccacca ctcgcgaatg ccctcagaga    2220
ggttgtcctc gagccaatct ggaagataac catcggcagc catacctggt ttaagtcatt    2280
tattgctcag aaacacagtc atccaggtcc acgttgacca gatcgcaggc cgagcaagca    2340
atctcgggag cccgcccag cagatgatga atggcacaga gtttccgata cgtcctcttt     2400
ctgacgaccg gttgagattc tgacacgccg gggaaacatt ctgaacagtc tctggtcccg    2460
tgcgtgaagc aaatgttgaa attctgattc attctctcgc atgtcttgca gggaaacagc    2520
atctgaagca tgcccgcgtg acgagaacat tgttttggt acctgtcggc aaagtccacc     2580
ggagctcctt ccgcgtctga cgtcgatgga tccgcgactg aggggcaagc ccgcttgggc    2640
tcgcttttat ccgcgtcatc gggggcgggt ctcttgttgg ctccacccttt tctgacgtag   2700 aactcatgcg ccacctcggt cacgtgatcc tgcgcccagc ggaagaactc tttgacttcc    2760
tgctttgtca ccttgccaaa gtcatgctcc agacggcggg tgagttcaaa tttgaacatc    2820
cggtcttgta acggctgctg gtgctcgaag gtggtgctgt tcccgtcaat cacggcgcac    2880
atgttggtgt tggaagtgac gatcacgggg gtgggatcga tctgggcgga cgacttgcac    2940 tttttggtcca cgcgcacctt gctgccgccg agaatggcct tggcggactc cacgaccttg    3000
gccgtcatct tgccctcctc ccaccagatc accatcttgt cgacgcaatc gttgaaggga    3060
aagttctcat tggtccagtt gacgcagccg aagggcgaat tc                      3102
```

<210> SEQ ID NO 18
<211> LENGTH: 3106
<212> TYPE: DNA
<213> ORGANISM: Unknown
<220> FEATURE:
<223> OTHER INFORMATION: AAV serotype, clone 7-2

<400> SEQUENCE: 18

```
gcggccgcga attcgccctt cgcagagacc aaagttcaac tgaaacgaat cagccggttt      60
attgattaac aagtaattac aggttacggg tgaggtaacg ggtgccaatg gggcgaggct     120
cagtataaac cccttcgttg ttgacagcaa attccacatt attagacttg cataatttg      180 aggtgtactg aatctctgga ttccagcgtt tgctgtttcc tttctgcagt cccactcga     240 tctccacgct gacctggccg gtgctgtact gcgtgataaa tgaggcaaac ttggcaggag    300
taaacacctc tggaggatta gcaggtaccg gggtgttttt gatgagaatt tgaggaggcg    360
ggtgtttgag tccaaatccg cccatcaggg gagacgggtg aaagttgccg tccgtgtgag    420
gaattttggc ccagatggga ccctgcaggt acacgtcccg gttctgccag accatgccgg    480
gcagagcccc ctggctgttg acagtctgtg tctggggtcc ggccgtagac gattgcaggt    540
tgctggagac cacaccgtat tcttctgtag ccacgggatt ggtggttttg atctcctcct    600
cgctggtcat tagcacgttt tccagcgttg tcttgttggc agccccgtt ttgccaaaaa     660 ccagcactcc gttgatggga aagaactggt cctcgtcgtc cttgttggtg gccatggcta    720
cgcccgggtt ggttaatgaa tttctaccat tcagatggta tttagtggcc ccggtccagg    780
caaagttact gttgttgttg ctgtctatgt ttttttgacag tctctgctgc cgataacagg    840
gtccgggcag ccagttcttt gattgctcgg ccatggtgtt gggcccagcc tgatggaact    900
gcagctccct tgtggacccc gtagtgctct gggtccgggc caggtagtac aggtactggt    960
cgatgagggg attcatcagc cggtccaggc tctggctgtg cgcatagctg ctgtggaaag   1020
gcacttcctc aaaggtgtag ctgaattcaa agttatcgcc cgttctcagc atctgagaag   1080
gaaagtactc caggcagtag aaggaggaac gtcccacaga ctgactgccg ttgtttagag   1140
```

| | |
|---|---|
| tcagatatcc gtactgagga atcatgaaca cgtccgcagg gaacggaggg aggcagccct | 1200 |
| ggtgcgcaga gccgaggacg tacggcagtt ggtactccga gtccgagaag acctgaatcg | 1260 |
| tgctggtaag gttattagcg atggtcgtaa cgccgtcgtt cgtcgtgacc tccttgacct | 1320 |
| ggatgttgaa caacttgaac cgcagctttc tgggccggaa tccccagttg ttgttgatga | 1380 |
| gtcgctgcca gtcacgtggt gagaagtggc agtggaatct gttgaagtca aaatagcccc | 1440 |
| aggggggtgct gtagccgaag aagtggttgt cgttggtagc cccgctctga cttgatatct | 1500 |
| gcttgtagag gtggttgttg taggtgggca gggcccaggt gcgggtgctg gtggtgatga | 1560 |
| ctctgtcgcc cagccatgtg gaatcgcaat gccaatttcc ggaggcatta cccactccgt | 1620 |
| cggcgccttc gttattgtct gccattggtg cgccaccgcc tgcagccatt gtaccagatc | 1680 |
| ccagacctga gggcgcggcg ggaggttctc cgagaggttg ggggtcgggc actgactctg | 1740 |
| agtcgccagt ctgcccaaag ttgagcttct ttttagcggg cggctggccg ttcttgccga | 1800 |
| tgcccgtgga ggagtcgggg gattctatgg gtctcttctt tccaggagcc gtcttagcgc | 1860 |
| cttcctcaac cagaccgaga ggttcgagaa cccgcttctt ggcctggaag actgctcgcc | 1920 |
| cgaggttgcc cccaaaagac gtatcttctt gaagacgctc ctgaaactcg gcgtcggcgt | 1980 |
| ggttgtactt gaggtacggg ttgtcccccct gctcgagctg cttgtcgtag gccttgtcgt | 2040 |
| gctcgagggc cgcggcgtct gcctcgttga ccggctctcc cttgtcgagt ccgttgaagg | 2100 |
| gtccgaggta cctgtagcca ggaagcacca gaccccggcc gtcgtcctgc ttttgctggt | 2160 |
| tggctttggg tttcggggct ccaggtttca agtcccacca ctcgcgaatg ccctcagaga | 2220 |
| ggttgccctc gagccaatct ggaagataac catcggcagc catacctggt ttaagtcatt | 2280 |
| tattgctcag aaacacagtc atccaggtcc acgttggcca gatcgcaggc cgagcaagca | 2340 |
| atctcgggag cccgccccag cagatgatga atggcacaga gtttccgata cgtcctcttt | 2400 |
| ctgacgaccg gttgagattc tgacacgccg gggaaacatt ctgaacagtc tctggtcccg | 2460 |
| tgcgtgaagc aaatgttgaa attctgattc attctctcgc atgtcttgca ggggaacagc | 2520 |
| atctgaagca tgcccgcgtg acgagaacat ttgttttggt acctgtcggc aaagtccacc | 2580 |
| ggagctcctt ccgcgtctga cgtcgatgga tccgcgactg aggggcaggc ccgcttgggc | 2640 |
| tcgcttttat ccgcgtcatc gggggcgggt ctcttgttgg ctccaccctt tctgacgtag | 2700 |
| aactcatacg ccacctcggt cacgtgatcc tgcgcccagc ggaagaactc tttgacttcc | 2760 |
| tgctttgtca ccttgccaaa gtcatgctcc agacggcggg tgagttcaaa tttgaacatc | 2820 |
| cggtcttgta acggctgctg gtgctcgaag gtggtgctgt tccgtcaat cacggcgcac | 2880 |
| atgttggtgt tggaagtgac gatcacgggg gtgggatcga tctgggcgga cgacttgcac | 2940 |
| ttttggtcca cgcgcacctt gctgccgccg agaatggcct tggcggactc cacgaccttg | 3000 |
| gccgtcatcc tgccctcctc ccaccagatc accatcttgt cgacgcaatc gttgaaggga | 3060 |
| aagttctcat tggtccagtt gacgcagccg tagaaagggc gaattc | 3106 |

<210> SEQ ID NO 19
<211> LENGTH: 3105
<212> TYPE: DNA
<213> ORGANISM: Unknown
<220> FEATURE:
<223> OTHER INFORMATION: AAV serotype, clone C1

<400> SEQUENCE: 19

| | |
|---|---|
| gaattcgccc ttgctgcgtc aactggacca atgagaactt tcccttcaac gattgcgtcg | 60 |

-continued

```
acaagatggt gatctggtgg gaggagggca agatgaccgc caaggtcgtg gagtccgcca    120
aggccattct gggcggaagc aaggtgcgcg tggaccaaaa gtgcaagtca tcggcccaga    180
tcgaccccac gcccgtgatc gtcacctcca acaccaacat gtgcgccgtg atcgacggga    240
acagcaccac cttcgagcac cagcagccgc tgcaggaccg catgttcaag ttcgagctca    300
cccgccgtct ggagcacgac tttggcaagg tgaccaagca ggaagtcaaa gagttcttcc    360
gctgggctca ggatcacgtg actgaggtgg cgcatgagtt ctacgtcaga aagggcggag    420
ccaccaaaag acccgccccc agtgacgcgg atataagcga gcccaagcgg gcctgcccct    480
cagttgcgga gccatcgacg tcagacgcgg aagcaccggt ggactttgcg gacaggtacc    540
aaaacaaatg ttctcgtcac gcgggcatgc ttcagatgct gtttccctgc aagacatgcg    600
agagaatgaa tcagaatttc aacgtctgct tcacgcacgg ggtcagagac tgctcagagt    660
gcttccccgg cgcgtcagaa tctcaacccg tcgtcagaaa aaagacgtat cagaaactgt    720
gcgcgattca tcatctgctg gggcgggcac ccgagattgc gtgttcggcc cgcgatctcg    780
tcaacgtgga cttggatgac tgtgtttctg agcaataaat gacttaaacc aggtatggct    840
gctgacggtt atcttccaga ttggctcgag acaacctctc tgagggcat tcgcgagtgg    900 tgggacctga acctggagc ccccaagccc aaggccaacc agcagaagca ggacgacggc    960
cggggtctgg tgcttcctgg ctacaagtac ctcggaccct tcaacggact cgacaagggg   1020
gagcccgtca acgcggcgga cgcagcgcc ctcgagcacg acaaggccta cgaccagcag   1080
ctcaaagcgg gtgacaatcc gtacctgcgg tataaccacg ccgacgccga gtttcaggag   1140
cgtctgcaag aagatcgtc ttttgggggc aacctcgggc gagcagtctt ccaggccaag   1200
aagagggtac tcgaacctct gggcctggtt gaagaaggtg ctaagacggc tcctggaaag   1260
aagagaccgt tagagtcacc acaagagccc gactcctcct caggaatcgg caaaaaggc   1320 aaacaaccag ccaaaaagag actcaacttt gaagaggaca ctggagccgg agacggaccc   1380
cctgaaggat cagataccag cgccatgtct tcagacattg aaatgcgtgc agcaccgggc   1440
ggaaatgctg tcgatgcggg acaaggttcc gatggagtgg gtaatgcctc gggtgattgg   1500
cattgcgatt ccacctggtc tgagggcaag gtcacaacaa cctcgaccag aacctgggtc   1560
ttgcccacct acaacaacca cttgtacctg cggctcggaa caacatcaaa cagcaacacc   1620
tacaacggat tctccacccc ctggggatac tttgacttta acagattcca ctgtcacttc   1680
tcaccacgtg actggcaaag actcatcaac aacaactggg gactacgacc aaaagccatg   1740
cgcgttaaaa tcttcaatat ccaagttaag gaggtcacaa cgtcgaacgg cgagactacg   1800
gtcgctaata accttaccag cacggttcag atatttgcgg actcgtcgta tgagctcccg   1860
tacgtgatgg acgctggaca agagggaagt ctgtctcctt tccccaatga cgtcttcatg   1920
gtgcctcaat atggctactg tggcattgtg actggcgaaa tcagaaccag acggacagaa   1980
aatgctttct actgcctgga gtattttcct tcacaaatgc tgagaactgg caataacttt   2040
gaaatggctt acaactttgg gaaggtgccg ttccactcaa tgtatgctta cagccagagc   2100
ccggacagac tgatgaatcc cctcctggac cagtacctgt ggcacttaca gtcgaccacc   2160
tctggagaga ctctgaatca aggcaatgca gcaaccacat ttggaaaaat caggagtgga   2220
gactttgcct tttacagaaa gaactggctg cctgggcctt gtgttaaaca gcagagactc   2280
tcaaaaactg ccagtcaaaa ttacaagatt cctgccagcg ggggcaacgc tctgttaaag   2340
tatgacaccc actataccct aaacaaccgc tggagcaaca tagcgcctgg acctccaatg   2400
gcaacagctg gaccttcaga tgggactttc agcaacgccc agctcatctt ccctggacca   2460
```

```
tcagtcaccg gaaacacaac aacctcagca acaatctgt tgtttacatc agaagaagaa    2520
attgctgcca ccaacccaag agacacggac atgtttggtc agattgctga caataatcag    2580
aatgctacaa ctgctcccat aaccggcaac gtgactgcta tgggagtgct tcctggcatg    2640
gtgtggcaaa acagagacat ttactaccaa gggccaattt gggccaagat cccacacgcg    2700
gacggacatt ttcatccttc accgctaatt ggcggttttg gactgaaaca tccgcctccc    2760
cagatattta tcaaaaacac ccccgtacct gccaatcctg cgacaacctt cactgcagcc    2820
agagtggact cttcatcac acaatacagc accggccagg tcgctgttca gattgaatgg    2880
gaaatcgaaa aggaacgctc caaacgctgg aatcctgaag tgcagtttac ttcaaactat    2940
gggaaccagt cttctatgtt gtgggctccc gatacaactg gaagtatac agagccgcgg    3000 gttattggct ctcgttattt gactaatcat ttgtaactgc ctagttaatc aataaaccgt    3060
gtgattcgtt tcagttgaac tttggtctct gcgaagggcg aattc                   3105
```

<210> SEQ ID NO 20
<211> LENGTH: 3105
<212> TYPE: DNA
<213> ORGANISM: Unknown
<220> FEATURE:
<223> OTHER INFORMATION: AAV serotype, clone C3

<400> SEQUENCE: 20

```
gaattcgccc ttgctgcgtc aactggacca atgagaactt tcccttcaac gattgcgtcg     60
acaagatggt gatctggtgg gaggagggca agatgaccgc caaggtcgtg gagtccgcca    120
aggccattct gggcggaagc aaggtgcgcg tggaccaaaa gtgcaagtca tcggcccaga    180
tcgaccccac gcccgtgatc gtcacctcca acaccaacat gtgcgccgtg atcgacggga    240
acagcaccac cttcgagcac cagcagccgc tgcaggaccg catgttcaag ttcgagctca    300
cccgccgtct ggagcacgac tttgcaaggt gaccaagca ggaagtcaaa gagttcttcc    360
gctgggctca ggatcacgtg actgaggtgg cgcatgagtt ctacgtcaga aagggcggag    420
ccaccaaaag acccgccccc agtgacgcgc atataagcga gcccaagcgg gcctgcccct    480
cagttgcgga gccatcgacg tcagacgcgg aagcaccggt ggactttgcg gacaggtacc    540
aaaacaaatg ttctcgtcac gcgggcatgc ttcagatgct gttcccctgc aagacatgcg    600
agagaatgaa tcagaatttc aacgtctgct tcacgcacgg ggtcagagac tgctcagagt    660
gcttccccgg cgcgtcagaa tctcaacccg tcgtcagaaa aaagacgtat cagaaactgt    720
gcgcgattca tcatctgctg gggcgggcac ccgagattgc gtgttcggcc tgcgatctcg    780
tcaacgtgga cttggatgac tgtgtttctg agcataaat gacttaaaccc aggtatggct    840 gctgacggtt atcttccaga ttggctcgag acaacctct ctgagggcat cgcgagtgg    900 tgggacctga aacctggagc ccccaagctc aaggccaacc agcagaagca ggacgacggc    960
cggggtctgg tgcttcctgg ctacaagtac ctcggaccct tccacggact cgacaagggg   1020
gagcccgtca acgcggcgga cgcagcggcc ctcgagcacg acaaggccta cgaccagcag   1080
ctcaaagcgg gtgacaatcc gtacctgcgg tataaccacg ccgacgccga gtttcaggag   1140
cgtctgcaag aagatacgtc ttttgggggc aacctcgggc agcagtctt ccaggccaag   1200 aagagggtac tcgaaccact gggcctggtt gaagaaggtg ctaagacggc tcctggaaag   1260
aagagaccgt tagagtcacc acaagagccc gactcctcct caggaatcgg caaaaaggc   1320 aaacaaccag ccaaaaagag actcaacttt gaagaggaca ctgagccgg agacggaccc   1380
```

```
cctgaaggat cagataccag cgccatgtct tcagacattg aaatgcgtgc agcaccgggc    1440
ggaaatgctg tcgatgcggg acaaggttcc gatggagtgg gtaatgcctc gggtgattgg    1500
cattgcgatt ccacctggtc tgagggcaag gtcacaacaa cctcgaccag aacctgggtc    1560
ttgcccacct acaacaacca cttgtacctg cggctcggaa caacatcaaa cagcaacacc    1620
tacaacggat tctccacccc tggggatac tttgactta acagattcca ctgtcacttc    1680
tcaccacgtg actggcaaag actcatcaac aacaactggg gactacgacc aaaagccatg    1740
cgcgttaaaa tcttcaatat ccaagttaag gaggtcacaa cgtcgaacgg cgagactacg    1800
gtcgctaata accttaccag cacggttcag atatttgcgg actcgtcgta tgagctcccg    1860
tacgtgatgg acgctggaca agagggaagt ctgcctcctt tccccaatga cgtcttcatg    1920
gtgcctcaat atggctactg tggcattgtg actggcgaaa atcagaacca gacggacaga    1980
aatgctttct actgcctgga gtattttcct tcacaaatgc tgagaactgg caataacttt    2040
gaaatggctt acaactttga aaggtgccgt ttccactcaa tgtatgctca cagccagagc    2100
ctggacagac tgatgaatcc cctcctggac cagtacctgt ggcacttaca gtcgaccacc    2160
tctggagaga ctctgaatca aggcaatgca gcaaccacat ttggaaaaat caggagtgga    2220
gactttgcct tttacagaaa gaactggctg cctgggcctt gtgttaaaca gcagagattc    2280
tcaaaaactg ccagtcaaaa ttacaagatt cctgccagcg ggggcaacgc tctgttaaag    2340
tatgacaccc actataccit aaacaaccgc tggagcaaca tagcgcctgg acctccaatg    2400
gcaacagctg gaccttcaga tgggactic agcaacgccc agctcatctt ccctggacca    2460
tcagtcaccg gaaacacaac aaacctcagca aacaatctgt tgtttacatc agaaggagaa    2520
attgctgcca ccaacccaag agacacggac atgtttggtc agattgctga caataatcag    2580
aatgctacaa ctgctcccat aaccggcaac gtgactgcta tgggagtgct tcctggcatg    2640
gtgtggcaaa acagagacat ttactaccaa gggccaattt gggccaagat cccacacgcg    2700
gacggacatt ttcatccttc accgctaatt ggcggttttg gactgaaaca tccgcctccc    2760
cagatattta tcaaaaacac ccccgtacct gccaatcctg cgacaacctt cactgcagcc    2820
agagtggact ctttcatcac acaatacagc accggccagg tcgctgttca gattgaatgg    2880
gaaatcgaaa aggaacgctc caaacgccgg aatcctgaag tgcagtttac ttcaaactat    2940
gggaaccagt cttctatgtt gtgggctccc gatacaactg gaagtatac agagccgcgg    3000 gttattggct ctcgttattt gactaatcat ttgtaactgc ctagttaatc aataaaccgt    3060
gtgattcgtt tcagttgaac tttggtctct gcgaagggcg aattc             3105
```

<210> SEQ ID NO 21
<211> LENGTH: 3105
<212> TYPE: DNA
<213> ORGANISM: Unknown
<220> FEATURE:
<223> OTHER INFORMATION: AAV serotype, clone C5

<400> SEQUENCE: 21

```
gaattcgccc ttcgcagaga ccaaagttca actgaaacga atcacacggt ttattgatta     60
actaggcagt tacaaatgat tagtcaaata acgagagcca ataaccccgcg gctctgtata    120 cttcccagtt gtatcgggag cccacaacat agaagactgg ttcccacagt tgaagtaaa    180 ctgcacttca ggattccagc gtttggagcg ttccttttcg atttcccatt caatctgaac    240
agcgacctgg ccgtgctgt attgtgtgat gaaagagtcc actctggctg cagtgaaggt    300
tgtcgcagga taggcaggta cgggggtgtt tttgataaat atctggggag gcggatgttt    360
```

```
cagtccaaaa ccgccaatta gcggtgaagg atgaaaatgt ccgtccgcgt gtgggatctt      420
ggcccaaatt ggcccttggt agtaaatgtc tctgttttgc cacaccatgc caggaagcac      480
tcccatagca gtcacgttgc cggttatggg agcagttgta gcattctgat tattgtcagc      540
aatctgacca aacatgtccg tgtctcttgg gttggtggca gcaatttctt cttctgatgt      600
aaacaacaga ttgtttgctg aggttgttgt gtttccggtg actgatggtc cagggaagat      660
gagctgggcg ttgctgaagt ccccatctga aggtccagct gttgccattg gaggtccagg      720
cgctatgttg ctccagcggt tgtttaaggt atagtgggtg tcatacttta acagagcgtt      780
gcccccgctg gcaggaatct tgtaattttg actggcagtt tttgagaatc tctgctgttt      840
aacacaaggc ccaggcagcc agttcttcct gtaaaaggca aagtctccac tcctgatttt      900
tccaaatgtg gttgctgcat tgccttgatt cagagtctct ccagaggtgg tcgactgtaa      960
gtgccacagg tactggtcca ggaggggatt catcagtccg tccaggctct ggctgtgagc     1020
atacattgag tggaacggca ccttctcaaa gttgtaagcc gtttcaaagt tattgccagt     1080
tctcagcatt tgtgaaggaa aatactccag gcagtagaaa gcatttctgt ccgtctggtt     1140
ctgattttcg ccagtcacaa tgccacagta gccatattga ggcaccatga agacgtcatt     1200
ggggaaagga ggcagacttc cctcttgtcc agcgtccatc acgtacggga gctcatacga     1260
cgagtccgca aatatctgaa ccgtgctggt aaggttatta gcgaccgtag tctcgccgtt     1320
cgacgttgtg acctccttaa cttggatatt gaagatttta acgcgcatgg cttttggtcg     1380
tagtccccag ttgttgttga tgagtctttg ccagtcacgt ggtgagaagt gacagtggaa     1440
tctgttaaag tcaaagtatc cccaggggt ggagaatccg ttgtaggtgt tgctgtttga     1500
tgttgttccg agccgcaggt acaagtggtt gttgtaggtg ggcaagaccc aggttctggt     1560
cgaggttgtt gtgaccttgc cctcagacca ggtggaatcg caatgccaat cacccgaggc     1620 attaccact ccatcggaac cttgtcccgc atcgacagca tttccgcccg gtgctgcacg     1680
catttcaatg tctgaagaca tggcgctggt atctgatcct tcagggggtc cgtctccggc     1740
tccagtgtcc tcttcaaagt tgagtctctt ttttggctggt tgtttgcctt ttttgccgat     1800
tcctgaggag gagtcgggct cttgtggtga ctctaacggt ctcttctttc caggagccgt     1860
cttagcacct tcttcaacca ggcccagagg ttcgagtacc ctcttcttgg cctggaagac     1920
tgctcgcccg aggttgcccc caaaagacgt atcttcttgc agacgctcct gaaactcggc     1980
gtcggcgtgg ttataccgca ggtacggatt gtcacccgct ttgagctgct ggtcgtaggc     2040
cttgtcgtgc tcgagggccg ctgcgtccgc cgcgttgacg ggctcccct tgtcgagtcc     2100 gttgaagggt ccgaggtact cgtagccagg aagcaccaga ccccggccgt cgtcctgctt     2160
ctgctggttg gccttgggct tggggctcc aggtttcagg tcccaccact cgcgaatgcc     2220
ctcagagagg ttgtcctcga gccaatctgg aagataaccg tcagcagcca tacctggttt     2280
aagtcattta ttgctcagaa acacagtcat ccaagtccac gttgacgaga tcgcaggccg     2340
aacacgcaat ctcgggtgcc cgccccagca gatgatgaat cgcgcacagt ttctgatacg     2400 tctttttct gacgacgggt tgagattctg acgcgccggg gaagcactct gagcagtctc     2460
tgaccccgtg cgtgaagcag acgttgaaat tctgattcat tctctcgcat gtcttgcagg     2520
gaaacagcat ctgaagcatg cccgcgtgac gagaacattt gttttggtac ctgtccgcaa     2580
ggtccaccgg tgcttccgcg tctgacgtcg atggctccgc aactgagggg caggcccgct     2640
tgggctcgct tatatccgcg tcactggggg cgggtctttt ggtggctccg cccttctga     2700
```

```
cgtagaactc atgcgccacc tcagtcacgt gatcctgagc ccagcggaag aactctttga      2760
cttcctgctt ggtcaccttg ccaaagtcgt gctccagacg gcgggtgagc tcgaacttga      2820
acatgcggtc ctgcagcggc tgctggtgct cgaaggtggt gctgttcccg tcgatcacgg      2880
cgcacatgtt ggtgttggag gtgacgatca cgggcgtggg gtcgatctgg gccgatgact      2940
tgcacttttg gtccacgcgc accttgcttc cgcccagaat ggccttggcg gactccacga      3000
ccttggcggt catcttgccc tcctcccacc agatcaccat cttgtcgacg caatcgttga      3060
agggaaagtt ctcattggtc cagttgacgc agcaagggcg aattc                     3105

<210> SEQ ID NO 22
<211> LENGTH: 3094
<212> TYPE: DNA
<213> ORGANISM: Unknown
<220> FEATURE:
<223> OTHER INFORMATION: AAV serotype, clone F1

<400> SEQUENCE: 22
gaattcgccc ttgctgcgtc aactggacca agagaacttt cccttcaacg attgcgtcga        60
caagatggtg atctggtggg aggagggcaa gatgacggcc aaggtcgtgg agtccgccaa       120
agccattctg gcggaagca aggtgcgcgt cgaccaaaag tgcaagtcct cggcccagat        180
cgatcccacc cccgtgatcg tcacctccaa caccaacatg tgcgccgtga tcgacgggaa       240
cagcaccacc ttcgagcacc agcagccgtt gcaggaccgg atgttcaaat ttgaactcac       300
ccgccgtctg gaacacgact ttggcaaggt gaccaagcag gaagtcaaag agttcttccg       360
ctgggctagt gatcacgtga ctgaggtgac gcatgagttc tacgtcagaa agggcggagc       420
cagcaaaaga cccgccccg atgacgcgga tataagcgag cccaagcggg cctgtccctc       480
agtcacggac ccatcgacgt cagacgcgga aggagctccg gtggactttg ccgacaggta      540
ccaaaacaaa tgttctcgtc acgcgggcat gcttcagatg ctgtttccct gcaaaacgtg      600
cgagagaatg aatcagaatt tcaacatttg cttcacgcac ggggtcagag actgtttaga      660
atgtttcccc ggcgtgtcag aatctcaacc ggtcgtcaga aaaagacgt atcggaagct       720 gtgtgcgatt catcatctgc tggggcgggc acccgagatt gcttgctcgg cctgcgacct       780
ggtcaacgtg gacctggacg actgtgtttc tgagcaataa atgacttaaa ccgggtatgg      840
ctgccgatgg ttatcttcca gattggctcg aggacaaccct ctctgagggc attcgcgagt      900
ggtgggacct gaaacctgga gccccgaaac ccaaagccaa ccagcaaaag caggacgacg      960 gccgggtct ggtgcttcct ggctacaagt acctcggacc cttcaacgga ctcgacaagg      1020
gggagcccgt caacgcggcg gacgcagcgg ccctcgagca cgacaaggcc tacgaccagc     1080
agctcaaagc gggtgacaat ccgtacctgc ggtataacca cgccgacgcc gagtttcagg     1140
agcgtctgca agaagatacg tcatttgggg gcaacctcgg gcgagcagtc ttccaggcca     1200
agaagcgggt tctcgaacct ctcggtctgg ttgaggaagg cgctaagacg gctcctggaa     1260
agaagagacc catagactct ccagactcct ccacgggcat cggcaaaaaa ggccagcagc     1320
ccgctaaaaa gaagctcaat tttggtcaga ctggcgactc agagtcagtc cccgaccctc     1380
aacctcttgg agaacctcca gcagcgccct ctagtgtggg atctggtaca atggctgcag     1440
gcggtggcgc accaatggca gacaataacg aaggtgccga cggagtgggt aatgcctcag     1500
gaaattggca ttcgattcc acatggctgg gcgacagagt catcaccacc agcaccagaa     1560
cctgggccct ccccacctac aacaaccacc tctacaagca aatctccagc agcagctcag     1620
gagccaccaa tgacaaccac tacttcggct acagcacccc ctgggggtat tttgacttta     1680
```

```
acagattcca ctgccacttc tcaccacgtg actggcagcg actcatcaac aacaactggg      1740
gattccggcc aagaagctg cggttcaagc tcttcaacat ccaggtcaag gaggtcacaa      1800
cgaatgacgg cgtcacgacc atcgctaata accttaccag cacggttcag gtcttctcgg      1860
actcggaata ccagctgccg tacgtcctcg gctctgcgca ccagggctgc ctgcctccgt      1920
tcccggcgga cgtcttcatg attcctcagt acggctacct gactctgaac aacggcagcc      1980
aatcggtggg ccgttcctcc ttctactgcc tggaatattt cccctctcaa atgctgagaa      2040
cgggcaacaa ctttgagttc agttacagct cgaggacgt gcctttccac agcagctacg      2100
cgcacagcca gagcctagac cggctgatga ccctctcat cgaccagtac ctgtactacc      2160
tggcccggac ccagagcacc acgggttcca ccagggaact gcaatttcat caagctgggc      2220
ccaatactat ggccgagcag tcaaagaact ggctgcctgg accctgctat aggcaacagg      2280
gactgtcaaa gaacttggac tttaacaaca acagcaattt tgcctggact gctgccacta      2340
aatatcatct gaatggcaga aactctttga ccaatcctgg cattcccatg caaccaaca      2400 aggatgatga ggaccagttc tttcccatca cgggggtact ggtttttggc aagacgggag      2460
ctgccaacaa aactacgctg gaaaacgttc tgatgaccag cgaggaggag atcaagacca      2520
ctaaccctgt ggctacagaa gaatacggtg tggtctccag caacctgcag ccgtctacag      2580
ccgggcctca atcacagact atcaacagcc agggagcact gcctggcatg gtctggcaga      2640
accgggacgt gtatctgcag ggtcccatct gggccaaaat tcctcacacg gatggcaact      2700
ttcacccgtc tcctctgatg ggcggtttg gactcaaaca cccgcctcca cagatcctga      2760
tcaaaaacac acctgtacct gctaatcctc cggaggtgtt tactcctgcc aagtttgcct      2820
ccttcatcac gcagtacagc accggacaag tcagcgtgga aatcgagtgg gagctgcaga      2880
aagaaaacag caagcgctgg aacccagaaa ttcagtatac ttccaattat gccaagtcta      2940
ataatgttga atttgctgtg aaccctgatg gtgtttatac tgagcctcgc cccattggca      3000
ctcgttacct cccccgtaat ctgtaattgc ttgttaatca ataaaccggt tgattcgttt      3060
cagttgaact ttggtctctg cgaagggcga attc                                 3094
```

<210> SEQ ID NO 23
<211> LENGTH: 3095
<212> TYPE: DNA
<213> ORGANISM: Unknown
<220> FEATURE:
<223> OTHER INFORMATION: AAV serotype, clone F3

<400> SEQUENCE: 23

```
gaattcgccc ttcgcagaga ccaaagttca actgaaacga atcaaccggt ttattgatta       60
acaagcaatt acagattacg ggtgaggtaa cgagtgccaa tggggcgagg ctcagtataa      120
acaccatcag ggttcacagc aaattcaaca ttattagact tggcataatt ggaagtatac      180
tgaatttctg ggttccagcg cttgctgttt tctttctgca gctcccactc gatttccacg      240
ctgacttgtc cggtgctgta ctgcgtgatg aaggaggcaa acttggcagg agtaaacacc      300
tccggaggat tagcaggtac aggtgtgttt ttgatcagga tctgtggagg cgggtgtttg      360
agtccaaaac cgcccatcag aggagacggg tgaaagttgc catccgtgtg aggaattttg      420
gcccagatgg gacctgcag atacacgtcc cggttctgcc agaccatgcc aggcagtgct      480
ccctggctgt tgatagtctg tgattgaggc ccggctgtag acgactgcag gttgctggag      540
accacaccgt attcttctgt agccacaggg ttagtggtct tgatctcctc ctcgctggtc      600
```

```
atcagaacgt tttccagcgt agttttgttg gcagctcccg tcttgccaaa aaccagtacc    660
ccgttgatgg gaaagaactg gtcctcatca tccttgttgg ttgccatggg aatgccagga    720
ttggtcaaag agtttctgcc attcagatga tatttagtgg cagcagtcca ggcaaaattg    780
ctgttgttgt taaagtccaa gttctttgac agtctctgtt gcctatagca gggtccaggc    840
agccagttct ttgactgctc ggccatagta ttgggcccag cttgatgaaa ttgcagttcc    900
ctggtggaac ccgtggtgct ctgggtccgg gccaggtagt acaggtactg gtcgatgaga    960
gggttcatca gccggtctag gctctggctg tgcgcgtagc tgctgtggaa aggcacgtcc   1020
tcgaagctgt aactgaactc aaagttgttg cccgttctca gcatttgaga ggggaaatat   1080
tccaggcagt agaaggagga acggcccacc gattggctgc cgttgtccag agtcaggtag   1140
ccgtactgag gaatcatgaa gacgtccgcc gggaacggag gcaggcagcc ctggtgcgca   1200
gagccgagga cgtacggcag ctggtattcc gagtccgaga agacctgaac cgtgctggta   1260
aggttattag cgatggtcgt gacgccgtca ttcgttgtga cctccttgac ctggatgttg   1320
aggagcttga accgcagctt cttgggccgg aatcccagt tgttgttgat gagtcgctgc   1380
cagtcacgtg gtgagaagtg gcagtggaat ctgttaaagt caaaataccc ccaggggtg   1440 ctgtagccga agtagtggtt gtcattggtg gctcctgagc tgctgctgga gatttgcttg   1500
tagaggtggt tgttgtaggt ggggagggcc caggttctgg tgctggtggt gatgactctg   1560
tcgcccagcc atgtggaatc gcaatgccaa tttcctgagg cattacccac tccgtcggca   1620
ccttcgttat tgtctgccat tggtgcgcca ccgcctgcag ccattgtacc agatcccaca   1680
ctagagggcg ctgctggagg ttctccaaga ggttgagggt cggggactga ctctgagtcg   1740
ccagtctgac caaaattgag cttcttttta gcgggctgct ggcctttttt gccgatgccc   1800
gtggaggagt ctggagagcc tatgggtctc ttctttccag gagccgtctt agccgccttcc   1860 tcaaccagac cgagaggttc gagaacccgc ttcttggcct ggaagactgc tcgcccgagg   1920
ttgcccccaa atgacgtatc ttcttgcaga cgctcctgaa actcggcgtc ggcgtggtta   1980
taccgcaggt acggattgtc acccgctttg agctgctggt cgtaggcctt gtcgtgctcg   2040
agggccgctg cgtccgccgc gttgacgggc tcccccttgt cgagtccgtt gaagggtccg   2100
aggtacttgt agccaggaag caccagaccc cggccgtcgt cctgcttttg ctggttggct   2160
ttgggtttcg gggctccagg tttcaggtcc caccactcgc gaatgccctc agagaggttg   2220
tcctcgagcc aatctggaag ataaccatcg gcagccatac ctggtttaag tcatttattg   2280
ctcagaaaca cagtcgtcca ggtccacgtt gaccaggtcg caggccgagc aagcaatctc   2340
gggtgcccgc cccagcagat gatgaatcgc acacagcttc cgatacgtct ttttctgac   2400 gaccggttga gattctgaca cgccggggaa acattctaaa cagtctctga ccccgtgcgt   2460
gaagcaaatg ttgaaattct gattcattct ctcgcacgtt ttgcagggaa acagcacctg   2520
aagcatgccc gcgtgacgag aacatttgtt ttggtacctg tcggcaaagt ccaccggagc   2580
tccttccgcg tctgacgtcg atgggtccgt gactgaggga cgggcccgct tgggctcgct   2640
tatatccgcg tcatcggggg cgggtctttt gctggctccg cccttctga cgtagaactc    2700 atgcgtcacc tcagtcacgt gatcactagc ccagcggaag aactctttga cttcctgctt   2760
tgtcaccttg ccaaagtcgt gttccagacg gcgggtgagt tcaaatttga acatccggtc   2820
ctgcaacggt tgctggtgct cgaaggtggt gctgttcccg tcgatcacgg cgcacatgtt   2880
ggtgttggag gtgacgatca cggggtggg atcgatctgg gcggacgact tgcacttttg   2940
gtccacgcgc accttgctgc cgccgagaat ggccttggcg gactccacga ccttggccgt   3000
```

| | |
|---|---|
| catcttgccc tcctcccacc agatcaccat cttgtcgacg caatcgttga agggaaagtt | 3060 |
| ctcattggtc cagttgacgc agcaagggcg aattc | 3095 |

<210> SEQ ID NO 24
<211> LENGTH: 3095
<212> TYPE: DNA
<213> ORGANISM: Unknown
<220> FEATURE:
<223> OTHER INFORMATION: AAV serotype, clone F5

<400> SEQUENCE: 24

| | |
|---|---|
| gaattcgccc ttcgcagaga ccaaagttca actgaaacga atcaaccggt ttattgatta | 60 |
| acaagcaatt acagattacg ggtgaggtaa cgagtgccaa tggggcgagg ctcagtataa | 120 |
| acaccatcag ggttcacagc aaattcaaca ttattagact tggcataatt ggaagtatac | 180 |
| tgaatttctg ggttccagcg cttgctgttt tctttctgca gctcccactc gatttccacg | 240 |
| ctgacttgtc cggtgctgta ctgcgtgatg aaggaggcaa acttggcagg agtaaacacc | 300 |
| tccggaggat tagcaggtac aggtgtgttt ttgatcagga tctgtggagg cgggtgttcg | 360 |
| agtccaaaac cgcccatcag aggagacggg tgaaagttgc catccgtgtg aggaattttg | 420 |
| gcccagatgg gaccctgcag atacacgtcc cggttctgcc agaccatgcc aggcagtgct | 480 |
| ccctggctgt tgatagtctg tgattgaggc ccggctgtag acgactgcag gttgctggag | 540 |
| accacaccgt attcttctgt agccacaggg ttagtggtct tgatctcctc ctcgctggtc | 600 |
| atcagaacgt tttccagcgt agttttgttg gcagctcccg tcttgccaaa aaccagtacc | 660 |
| ccgttgatgg gaaagaactg gtcctcatca tccttgttgg ttgccatggg aatgccagga | 720 |
| ttggtcaaag agtttctgcc attcagatga tatttagtgg cagcagtcca ggcaaaattg | 780 |
| ctgttgttgt taaagtccaa gttctttgac agtctctgtt gcctatagca gggtccaggc | 840 |
| agccagttct ttgactgctc ggccatagta ttgggcccag cttgatgaaa ttgcagttcc | 900 |
| ctggtggaac ccgtggtgct ctgggtccgg gccaggtagt acaggtactg gtcgatgaga | 960 |
| gggttcatca gccggtctag gctctggctg tgcgcgtagc tgctgtggaa aggcacgtcc | 1020 |
| tcgaagctgt aactgaactc aaagttgttg cccgttctca gcatttgaga ggggaaatat | 1080 |
| tccaggcagt agaaggagga acggcccacc gattggctgc cgttgttcag agtcaggtag | 1140 |
| ccgtactgag gaatcatgaa gacgtccgcc gggaacggag gcaggcagcc ctggtgcgca | 1200 |
| gagccgagga cgtacggcag ctggtattcc gagtccgaga agacctgaac cgtgctggta | 1260 |
| aggttattag cgatggtcgt gacgccgtca ttcgttgtga cctccttgac ctggatgttg | 1320 |
| aagagcttga accgcagctt cttgggccgg aatccccagt tgttgttgat gagtcgctgc | 1380 |
| cagtcacgtg gtgagaagtg gcagtggaat ctgttaaagt caaataccc ccaggggtg | 1440 |
| ctgtagccga agtagtggtt gtcattggtg gctcctgagc tgctgctgga gatttgcttg | 1500 |
| tagaggtggt tgttgtaggt ggggagggcc caggttctgg tgctggtggt gatgactctg | 1560 |
| tcgcccagcc atgtggaatc gcaatgccaa tttcctgagg cattacccac tccgtcggca | 1620 |
| ccttcgttat tgtctgccgt tggtgcgcca ccgcctgcag ccattgtacc agatcccaca | 1680 |
| ctagagggcg ctgctggagg ttctccaaga ggttgagggt cggggactga ctctgagtcg | 1740 |
| ccagtctgac caaaattgag cttcttttta gcgggctgct ggccttttt gccgatgccc | 1800 |
| gtggaggagt ctgagagtc tatggtctc ttctttccag gagccgtctt agcgccttcc | 1860 |
| tcaaccagac cgagaggttc gagaacccgc ttcttggcct ggaagactgc tcgcccgagg | 1920 |

| | |
|---|---|
| ttgcccccaa atgacgtatc ttcttgcagg cgctcctgaa actcggcgtc ggcgtggtta | 1980 |
| taccgcaggt acggattgtc acccgctttg agctgctggt cgtaggcctt gtcgtgctcg | 2040 |
| agggccgctg cgtccgccgc gttgacgggc tcccccttgt cgagtccgtt gaagggtccg | 2100 |
| aggtacttgt agccaggaag caccagaccc cggccgtcgt cctgcttttg ctggttggct | 2160 |
| ttgggtttcg gggctccagg tttcaggtcc caccactcgc gaatgccctc agagaggttg | 2220 |
| tcctcgagcc aatctggaag ataaccatcg gcagccatac ctggtttaag ccatttattg | 2280 |
| ctcagaaaca cagtcgtcca ggtccacgtt gaccaggtcg caggccgagc aggcaatctc | 2340 |
| gggtgcccgc cccagcagat gatgaatcgc acacagcttc cgatacgtct tttttctgac | 2400 |
| gaccggttga gattctgaca cgccggggaa acattctaaa cagtctctga ccccgtgcgt | 2460 |
| gaagcaaatg ttgaaattct gattcattct ctcgcacgtt ttgcagggaa acagcatctg | 2520 |
| aagcatgccc gcgtggcgag aacatttgtt ttggtacctg tcggcaaagt ccaccggagc | 2580 |
| tccttccgcg tctgacgtcg atgggtccgt gactgaggga caggcccgct gggctcgct | 2640 |
| tatatccgcg tcatcggggg cgggtctttt gctggctccg ccctttctga cgtagaactc | 2700 |
| atgcgtcacc tcagtcacgt gatcactagc ccagcggaag aactctttga cttcctgctt | 2760 |
| tgtcaccttg ccaaagtcgt gttccagacg gcgggtgagt tcaaatttga acatccggtc | 2820 |
| ctgcaacggc tgctggtgct cgaaggtggt gctgttcccg tcgatcacgg cgcgcatgtt | 2880 |
| ggtgttggag gtgacgatca cggggggtggg atcgatctgg gcggacgact tgcacttttg | 2940 |
| gtccacgcgc accttgctgc cgccgagaat ggccttggcg gactccacga ccttggccgt | 3000 |
| catcttgccc tcctcccacc agatcaccat cttgtcgacg caatcgttga agggaaagtt | 3060 |
| ctcattggtc cagttgacgc agcaagggcg aattc | 3095 |

<210> SEQ ID NO 25
<211> LENGTH: 3142
<212> TYPE: DNA
<213> ORGANISM: Unknown
<220> FEATURE:
<223> OTHER INFORMATION: AAV serotype, clone H6

<400> SEQUENCE: 25

| | |
|---|---|
| aaaacgacgg gccagtgatt gtaatacgac tcactatagg gcgaaattga aattagcggc | 60 |
| cgcgaattcg cctttcgcag agaccaaagt tcaactgaaa cgaattaaac ggtttattga | 120 |
| ttaacaagca attacagatt acgagtcagg tatctggtgc caatggggcg aggctctgaa | 180 |
| tacacaccat tagtgtccac agtaaagtcc acattaacag acttgttgta gttggaagtg | 240 |
| tactgaattt cgggattcca gcgtttgctg ttctccttct gcagctccca ctcgatctcc | 300 |
| acgctgacct gtcccgtgga atactgtgtg atgaaagaag caaacttggc agaactgaag | 360 |
| tttgtgggag gattggctgg aacgggagtg ttttgatca tgatctgagg aggcgggtgt | 420 |
| ttgagtccaa aacctcccat cagtggagaa ggatgaaagt gtccatcggt gtgaggaatc | 480 |
| ttggcccaaa tgggtccctg caggtacacg tctcgatcct gccacaccat accaggtaac | 540 |
| gctccttggt gattgacagt tccagtagtt ggaccagtgt tgagttttg caaattattt | 600 |
| gacacagtcc cgtactgctc cgtagccacg ggattggtgg ccctgattc ttcttcatct | 660 |
| gtaatcatga cattttccaa atccgcgtcg ttggcatttg ttccttgttt accaaatatc | 720 |
| agggttccat gcatggggaa aaacttttct tcgtcatcct tgtgactggc catagctggt | 780 |
| cctggattaa ccaacgagtc ccggccattt agatgatact ttgtagctgc agtccaggga | 840 |
| aagttgctgt tgttgttgtc gtttgcctgt tttgacagac gctgctgtct gtagcaaggt | 900 |

-continued

```
ccaggcagcc agttttagc ttgaagagac atgttggttg gtccagcttg gctaaacagt      960
agccgagact gctgaagagt tccactattt gtttgtgtct tgttcagata atacaggtac     1020
tggtcgatca gaggattcat cagccgatcc agactctggc tgtgagcgta gctgctgtgg     1080
aaaggcacgt cttcaaaagt gtagctgaac tgaaagttgt ttccagtacg cagcatctga     1140
gaaggaaagt actccaggca gtaaaaggaa gagcgtccta ccgcctgact ccgttgttc      1200
agggtgaggt atccatactg tgggaccatg aagacgtccg ctggaaacgg cgggaggcat     1260
ccttgatgcg ccgagcccag gacgtacggg agctggtact ccgagtcagt aaacacctga    1320
accgtgctgt taaggttatt ggcaatcgtc gtcgtaccgt cattctgcgt gacctctttg     1380
acttgaatat taaagagctt gaagttgagt cttttgggcc ggaatccccg gttgttgttg    1440
acgagtcttt gccagtcacg tggtgaaaag tggcagtgga atctgttgaa gtcaaaatac     1500
ccccaggggg tgctgtagcc aaagtagtgg ttgtcgttgc tggctcctga ttggctggag    1560
atttgcttgt agaggtggtt gttgtatgtg ggcagggccc aggttcgggt gctggtggtg     1620
atgactctgt cgcccagcca ttgggaatcg caatgccaat ttcctgagga attacccact    1680
ccatcggcac cctcgttatt gtctgccatt ggtgcgccac tgcctgtagc cattgtagta     1740
gatcccagac cagaggggc tgctggtggc tgtccgagag gctgggggtc aggtacggag      1800
tctgcgtctc cagtctgacc aaaatttaat ctttttcttg caggctgctg gcccgctttt    1860
ccggttcccg aggaggagtc tggctccaca ggagagtgct ctaccggcct ctttttttccc    1920
ggagccgtct taacaggctc ctcaaccagg cccagaggtt caagaacccct cttttttcgcc   1980
tggaagactg ctcgtccgag gttgccccca aaagacgtat cttctttaag gcgctcctga    2040
aactctgcgt cggcgtggtt gtacttgagg tacgggttgt ctccgctgtc gagctgccgg    2100
tcgtaggcct tgtcgtgctc gagggccgcg gcgtctgcct cgttgaccgg ctccccttg      2160
tcgagtccgt tgaagggtcc gaggtacttg tacccaggaa gcacaagacc cctgctgtcg    2220
tccttatgcc gctctgcggg cttggtggt ggtgggccag gtttgagctt ccaccactgt      2280
cttattcctt cagagagagt gtcctcgagc caatctggaa gataaccatc ggcagccata    2340
cctgatttaa atcatttatt gttcagagat gcagtcatcc aaatccacat tgaccagatc    2400
gcaggcagtg caagcgtctg gcacctttcc catgatatga tgaatgtagc acagtttctg    2460
atacgccttt ttgacgacag aaacggttg agattctgac acgggaaagc actctaaaca     2520
gtctttctgt ccgtgagtga agcagatatt tgaattctga ttcattctct cgcattgtct    2580
gcagggaaac agcatcagat tcatgcccac gtgacgagaa catttgtttt ggtacctgtc    2640
cgcgtagttg atcgaagctt ccgcgtctga cgtcgatggc tgcgcaactg actcgcgcgc    2700
ccgtttgggc tcactatat ctgcgtcact ggggcgggt ctttctcttag ctccacccctt     2760
tttgacgtag aattcatgct ccacctcaac cacgtgatcc tttgcccacc ggaaaaagtc    2820
tttcacttcc tgcttggtga cctttccaaa gtcatgatcc agacggcggg taagttcaaa    2880
tttgaacatc cggtcttgca acggctgctg gtgctcgaag gtcgttgagt tcccgtcaat    2940
cacggcgcac atgttggtgt tggaggtgac gatcacggga gtcgggtcta tctgggccga    3000
ggacttgcat ttctggtcca cacgcacctt gcttcctcca agaatggctt tggccgactc    3060
cacgaccttg gcggtcatct tcccctcctc ccaccagatc accatcttgt cgacgcaatg    3120
gtaaaaggaa agttctcatt gg                                              3142
```

<210> SEQ ID NO 26

<211> LENGTH: 3075
<212> TYPE: DNA
<213> ORGANISM: Unknown
<220> FEATURE:
<223> OTHER INFORMATION: AAV serotype, clone H2

<400> SEQUENCE: 26

```
tgagaacttt cctttcaacg attgcgtcgg acaagatggt gatctggtgg gaggagggga      60
agatgaccgc caaggtcgtg gagtcggcca aagccattct tggaggaagc aaggtgcgtg     120
tggaccagaa atgcaagtcc tcggcccaga tagacccgac tcccgtgatc gtcacctcca     180
acaccaacat gtgcgccgtg attgacggga actcaacgac cttcgagcac cagcagccgt     240
tgcaagaccg gatgttcaaa tttgaactta cccgccgtct ggatcatgac tttggaaagg     300
tcaccaagca ggaagtgaaa gactttttcc ggtgggcaaa ggatcacgtg gttgaggtgg     360
agcatgaatt ctacgtcaaa aagggtggag ctaagaaaag acccgccccc agtgacgcag     420
atataagtga gcccaaacgg gcgcgcgagt cagttgcgca gccatcaacg tcagacgcgg     480
aagcttcgat caactacgcg gacaggtacc aaaaacaaat gttctcgtca cgtgggcatg     540
aatctgatgc tgtttccctg cagacaatgc gagagaatga atcagaattc aaatatctgc     600
ttcactcacg gacagaaaga ctgtttagag tgctttcccg tgtcagaatc tcaacccgtt     660
tctgtcgtca aaaaggcgta tcagaaactg tgctacattc atcatatcat gggaaggtg     720
ccagacgctt gcactgcctg cgatctggtc aatgtggatt tggatgactg catctctgaa     780
caataaatga tttaaatcag gtatggctgc cgatggttat cctccagatt ggctcgagga     840
cactctctct gaagggataa acagtggtg gaagctcaaa cctggcccac caccaccaaa     900
gcccgcagag cggcataagg acgacagcag gggtcttgtg cttcctgggt acaagtacct     960
cggacccttc aacggactcg acaaggggga gccggtcaac gaggcagacg ccgcggccct    1020
cgagcacgac aaggcctacg accggcagct cgacagcgga gacaaccccgt acctcaagta    1080
caaccacgcc gacgcagagt ttcaggagcg ccttaaagaa gatacgtctt ttgggggcaa    1140
cctcggacga gcagtcttcc aggcgaaaaa gagggttctt gaacctctgg gcctggttga    1200
ggaacctgtt aagacggctc cgggaaaaaa gaggccggta gagcactctc ctgtggagcc    1260
agactcctcc tcgggaaccg aaaagcgggc cagcggcct gcaagaaaaa gattaaattt    1320
tggtcagact ggagacgcag actccgtacc tgaccccag cctctcggac agccaccagc    1380
agccccctct ggtctgggat ctactacaat ggctacaggc agtggcgcac caatggcaga    1440
caataacgag ggtgccgatg gagtgggtaa ttcctcagga aattggcatt gcgattccca    1500
atggctgggc gacagagtca tcaccaccag cacccgaacc tgggccctgc ccacatacaa    1560
caaccacctc tacaagcaaa tctccagcca atcaggagcc agcaacgaca ccactactt    1620
tggctacagc accccctggg ggtattttga cttcaacaga ttccactgcc acttttcacc    1680
acgtgactgg caaagactca tcaacaacaa ctgggggattc cggccaaaa gactcaactt    1740
caagctcttt aatattcaag tcaaagaggt cacgcagaat gacggtacga cgacgattgc    1800
caataacctt accagcacgg ttcaggtgtt tactgactcg gagtaccagc tcccgtacgt    1860
cctgggctcg gcgcatcaag gatgcctccc gccgtttcca gcggacgtct tcatggtccc    1920
acagtatgga tacctcaccc tgaacaacgg gagtcaggcg gtaggacgct cttccttta    1980
ctgcctggag tactttcctt ctcagatgct gcgtactgga aacaactttc agttcagcta    2040
cacttttgaa gacgtgcctt tccacagcag ctacgctcac agccagagtc tggatcggct    2100
gatgaatcct ctgatcgacc agtacctgta ttatctgaac aagacacaaa caaatagtgg    2160
```

```
aactcttcag cagtctcggc tactgtttag ccaagctgga ccaaccaaca tgtctcttca    2220
agctaaaaac tggctgcctg gaccttgcta cagacagcag cgtctgtcaa aacaggcaaa    2280
cgacaacaac aacagcaact ttccctggac tgcagctaca agtatcatc taaatggccg     2340 ggactcgttg gttaatccag gaccagctat ggccagtcac aaggatgacg aagaaaagtt    2400
tttccccatg catggaaccc tgatatttgg taaacaagga acaaatgcca acgacgcgga    2460
tttgaaaaat gtcatgatta cagatgaaga agaaatcagg gccaccaatc ccgtggctac    2520
ggagcagtac gggactgtgt caaataattt gcaaaactca acactggtc caactactgg     2580 aactgtcaat cgccaaggag cgttacctgg tatggtgtgg caggatcgag acgtgtacct    2640
gcagggaccc atttgggcca agattcctca caccgatgga cactttcatc cttctccact    2700
gatgggaggt tttggactca acacccgcc tcctcagatc atgatcaaaa acactcccgt     2760
tccagccaat cctcccacaa acttcagttc tgccaagttt gcttctttca tcacacagta    2820
ttccacggga caggtcagcg tggagatcga gtgggagctg cagaaggaga acagcaaacg    2880
ctggaatccc gaaattcagt acacttccaa ctacaacaag tctgttaatg tggactttac    2940
tgtggacact aatggtgtgt attcagagcc tcgcccatt ggcaccagat acctgactcg     3000
taatctgtaa ttgcttgtta atcaataaac cgtttaattc gtttcagttg aactttggtc    3060
tctgcgaagg gcgaa                                                     3075

<210> SEQ ID NO 27
<211> LENGTH: 3128
<212> TYPE: DNA
<213> ORGANISM: Unknown
<220> FEATURE:
<223> OTHER INFORMATION: AAV serotype, clone 42.8

<400> SEQUENCE: 27
gaattcgccc tttctacggc tgcgtcaact ggaccaatga gaactttccc ttcaacgatt      60
gcgtcgacaa gatggtgatc tggtggagg agggcaagat gacggccaag gtcgtggagt      120
ccgccaaggc cattctcggc ggcagcaagg tgcgcgtgga ccaaaagtgc aagtcttccg     180
cccagatcga tcccaccccc gtgatcgtca cttccaacac caacatgtgc gccgtgattg     240
acgggaacag caccaccttc gagcaccagc agccgttaca agaccggatg ttcaaatttg     300
aactcacccg ccgtctggag cacgactttg gcaaggtgac aaagcaggaa gtcaaagagt     360
tcttccgctg gcgcaggat cacgtgaccg aggtggcgca tgagttctac gtcagaaagg      420
gtggagccaa caagagaccc gcccccgatg acgcggataa aagcgagccc aagcgggcct    480
gcccctcagt cgcggatcca tcgacgtcag acgcggaagg agctccggtg gactttgccg    540
acaggtacca aaacaaatgt tctcgtcacg cgggcatgct tcagatgctg tttccctgca    600
agacatgcga gagaatgaat cagaatttca acatttgctt cacgcacggg accagagact    660
gttcagaatg tttccccgc gtgtcagaat ctcaaccgt cgtcagaaag aggacgtatc     720
ggaaactctg tgccattcat catctgctag gcgggctcc cgagattgct tgctcggcct     780
gcgatctggt caacgtggac ctggatgact gtgtttctga gcaataaatg acttaaacca    840
ggtatggctg ccgatggtta tcttccagat tggctcgagg acaacctctc tgagggcatt    900
cgcgagtggt gggacttgaa acctggagcc ccgaaaccca agccaacca gcaaaagcag     960 gacgacggcc ggggtctggt gcttcctggc tacaagtacc tcggacccct caacggactc    1020 gacaagggg agcccgtcaa cgcggcggac gcagcggccc tcgagcacga caaggcctac    1080
```

-continued

```
gaccagcagc tcaaagcggg tgacaatccg tacctgcggt ataaccacgc cgacgccgag   1140
tttcaggagc gtctgcaaga agatacgtct tttgggggca acctcgggcg agcagtcttc   1200
caggccaaga agcgggttct cgaacctctc ggtctggttg aggaaggcgc taagacggct   1260
cctggaaaga agagaccggt agagccatca ccccagcgtt ctccagactc ctctacgggc   1320
atcggcaaga caggccagca gcccgcgaaa aagagactca actttgggca gactggcgac   1380
tcagagtcag tgcccgaccc tcaaccaatc ggagaacccc ccgcaggccc ctctggtctg   1440
ggatctggta caatggctgc aggcggtggc gctccaatgg cagacaataa cgaaggcgcc   1500
gacggagtgg gtagttcctc aggaaattgg cattgcgatt ccacatggct gggcgacaga   1560
gtcatcacca ccagcacccg aacctgggcc ctccccacct acaacaacca cctctacaag   1620
caaatctcca acgggacatc gggaggaagc accaacgaca acacctactt cggctacagc   1680



acccccctggg ggtattttga ctttaacaga ttccactgcc acttctcacc acgtgactgg   1740
cagcgactca tcaacaacaa ctggggattc cggcccaaga gactcaactt caagctcttc   1800
aacatccagg tcaaggaggt cacgcagaat gaaggcacca agaccatcgc caataacctt   1860
accagcacga ttcaggtctt tacggactcg gaataccagc tcccgtacgt cctcggctct   1920
gcgcaccagg gctgcctgcc tccgttcccg gcggacgtct tcatgattcc tcagtacggg   1980
tacctgactc tgaacaacgg cagtcaggcc gtgggccgtt cctccttcta ctgcctggag   2040
tactttcctt ctcaaatgct gagaacgggc aacaactttg agttcagcta ccagtttgag   2100
gacgtgcctt ttcacagcag ctacgcgcac agccaaagcc tggaccggct gatgaacccc   2160
ctcatcgacc agtacctgta ctacctgtct cggactcagt ccacgggagg taccgcagga   2220
actcagcagt tgctattttc tcaggccggg cctaataaca tgtcggctca ggccaaaaac   2280
tggctacccg ggccctgcta ccggcagcaa cgcgtctcca cgacactgtc gcaaaataac   2340
aacagcaact ttgcttggac cggtgccacc aagtatcatc tgaatggcag agactctctg   2400
gtaaatcccg gtgtcgctat ggcaacgcac aaggacgacg aagagcgatt ttttccatcc   2460
agcggagtct tgatgtttgg gaaacaggga gctggaaaag acaacgtgga ctatagcagc   2520
gttatgctaa ccagtgagga agaaatcaaa accaccaacc cagtggccac agaacagtac   2580
ggcgtggtgg ccgataacct gcaacagcaa aacgccgctc ctattgtagg ggccgtcaac   2640
agtcaaggag ccttacctgg catggtctgg cagaaccggg acgtgtacct gcagggtcct   2700
atctgggcca agattcctca cacggacggc aactttcatc cttcgccgct gatgggaggc   2760
tttggactga aacacccgcc tcctcagatc ctgattaaga atacacctgt tcccgcggat   2820
cctccaacta ccttcagtca agccaagctg gcgtcgttca tcacgcagta cagcaccgga   2880
caggtcagcg tggaaattga atgggagctg cagaaagaga acagcaagcg ctggaaccca   2940
gagattcagt atacttccaa ctactacaaa tctacaaatg tggactttgc tgtcaatact   3000
gagggtactt attcagagcc tcgccccatt ggcacccgtt acctcacccg taacctgtaa   3060
ttgcctgtta atcaataaac cggctaattc gtttcagttg aactttggtc tctgcgaagg   3120
gcgaattc                                                            3128
```

<210> SEQ ID NO 28
<211> LENGTH: 3128
<212> TYPE: DNA
<213> ORGANISM: Unknown
<220> FEATURE:
<223> OTHER INFORMATION: AAV serotype, clone 42.15

<400> SEQUENCE: 28

-continued

```
gaattcgccc tttctacggc tgcgtcaact ggaccaatga gaactttccc ttcaacgatt      60
gcgtcgacaa gatggtgatc tggtgggagg agggcaagat gacggccaag gtcgtggagt     120
ccgccaaggc cattctcggc ggcagcaagg tgcgcgtgga ccaaaagtgc aagtcgtccg     180
cccagatcga ccccaccccc gtgatcgtca cctccaacac caacatgtgc gccgtgattg     240
acgggaacag caccaccttc gagcaccagc agccgttgca ggaccggatg ttcaaatttg     300
aactcacccg ccgtctggag catgactttg gcaaggtgac aaagcaggaa gtcaaagagt     360
tcttccgctg ggcgcaggat cacgtgaccg aggtggcgca tgagttctac gtcagaaagg     420
gtggagccaa caagagaccc gcccccgatg acgcggataa aagcgagccc aagcgggcct     480
gcccctcagt cgcggatcca tcgacgtcag acgcggaagg agctccggtg gactttgccg     540
acaggtacca aaacaaatgt tctcgtcacg cgggcatgct tcagatgctg tttccctgca     600
agacatgcga gagaatgaat cagaatttca acatttgctt cacgcgcggg accagagact     660
gttcagaatg tttcccgggc gtgtcagaat ctcaaccggt cgtcagaaag aggacgtatc     720
ggaaactctg tgccattcat catctgctgg ggcgggctcc cgagattgct tgctcggcct     780
gcgatctggt caacgtggac ctggatgact gtgtttctga gcaataaatg acttaaacca     840
ggtatggctg ccgatggtta tcttccagat tggctcgagg acaacctctc tgagggcatt     900
cgcgagtggg gggacttgaa acctggagcc cgaaaaccca agccaaccca gcaaaagcag     960
gacgacggcc ggggtctggt gcttcctggc tacaagtacc tcggacccct caacggactc    1020
gacaagggga agcccgtcaa cgcggcggac gcagcggccc tcgagcacga caaggcctac    1080
gaccagcagc tcaaagcggg tgacaatccg tacctgcggt ataaccacgc cgacgccgag    1140
tttcaggagc gtctgcaaga agatacgtct tttgggggca acctcgggcg agcagtcttc    1200
caggccaaga agcgggttct cgaacctctc ggtctggttg aggaaggcgc taagacggct    1260
cctggaaaga gagaccggt agagccatca ccccagcgtt ctccagactc ctctacgggc    1320
atcggcaaga caggccagca gcccgcgaaa aagagactca actttgggca gactggcgac    1380
tcagagtcag tgcccgaccc tcaaccaatc ggagaacccc cgcaggccc ctctggtctg    1440 ggatctggta caatggctgc aggcggtggc gctccaatgg cagacaataa cgaaggcgcc    1500 gacgagtgg gtagttcctc aggaaattgg cattgcgatt ccacatggct gggcgacaga    1560
gtcatcacca ccagcacccg aacctgggcc ctccccacct acaacaacca cctctacaag    1620
caaatctcca acgggacatc gggaggaagc accaacgaca cacctactt cggctacagc    1680 accccctggg ggtattttga ctttaacaga ttccactgcc acttctcacc acgtgactgg    1740
cagcgactca tcaacaacaa ctggggattc cggcccaaga gactcaactt caagctcttc    1800
aacatccagg tcaaggaggt cacgcagaat gaaggcacca gaccatcgc caataacctt    1860 accagcacga ttcaggtctt tacggactcg aataccagc tcccgtacgt cctcggctct    1920
gcgcaccagg gctgcccgcc tccgttcccg cggacgtct tcatgattcc tcagtacggg    1980
tacctgactc tgaacaacgg cagtcaggcc gtgggccgtt cctccttcta ctgcctggag    2040
tactttcctt ctcaaatgcg gagaacgggc aacaactttg agttcagcta ccagtttgag    2100
gacgtgcctt ttcacagcag ctacgcgcat agccaaagcc tggaccggct gatgaacccc    2160
ctcatcgacc agtacctgta ctacctgtct cggactcagt ccacgggagg taccgcagga    2220
actcagcagt tgctattttc tcaggccggg cctaataaca gtcggctca ggccaaaaac    2280 tggctacccg ggcctgcta ccggcagcaa cgcgtctcca cgacactgtc gcaaaataac    2340
```

```
aacagcaact tgcttggac cggtgccacc aagtatcatc tgaatggcag agactctctg    2400
gtaaatcccg gtgtcgctat ggcaacgcac aaggacgacg aagagcgatt ttttccatcc    2460
agcggagtct tgatgtttgg gaaacaggga gctggaaaag acaacgtgga ctatagcagc    2520
gttatgctaa ccagtgagga agaaatcaaa accaccaacc cagtggccac agaacagtac    2580
ggcgtggtgg ccgataacct gcaacagcaa aacgccgctc ctattgtagg ggccgtcaac    2640
agtcaaggag ccttacctgg catggtctgg cagaaccggg acgtgtacct gcagggtcct    2700
atctgggcca agattcctca cacggacggc aactttcatc cttcgccgct gatgggaggc    2760
tttggactga acacccgcc tcctcagatc ctgattaaga atacacctgt tcccgcggat    2820
cctccaacta ccttcagtca agccaagctg gcgtcgttca tcacgcagta cagcaccgga    2880
caggtcagcg tggaaattga atgggagctg cagaaagaga acagcaagcg ctggaaccca    2940
gagattcagt atacttccaa ctactacaaa tctacaaatg tggactttgc tgtcaatact    3000
gagggtactt attcagagcc tcgccccatt ggcacccgtt acctcacccg taacctgtaa    3060
ttgcctgtta atcaataaac cggttaattc gtttcagttg aactttggtc tctgcgaagg    3120
gcgaattc                                                              3128

<210> SEQ ID NO 29
<211> LENGTH: 3197
<212> TYPE: DNA
<213> ORGANISM: Unknown
<220> FEATURE:
<223> OTHER INFORMATION: AAV serotype. clone 42.5b

<400> SEQUENCE: 29
gaattcgccc tttctacggc tgcgtcaact ggaccaatga gaactttccc ttcaacgatt      60
gcgtcgacaa gatggtgatc tggtgggagg agggcaagat gacggccaag gtcgtggagt    120
ccgccaaggc cattctcggc ggcagcaagg tgcgcgtgga ccaaaagtgc aagtcgtccg    180
cccagatcga ccccacccc gtgatcgtca cctccaacac caacatgtgc gccgtgattg    240
acgggaacag caccaccttc gagcaccagc agccgttaca agaccggatg ttcaaatttg    300
aactcacccg ccgtctggag cacgactttg gcaaggtgac aaagcaggaa gtcaaagagt    360
tcttccgctg ggcgcaggat cacgtgaccg aggtggcgca tgagttctac gtcagaaagg    420
gtggagccaa caagagaccc gcccccgatg acgcggataa aagcgagccc aagcgggcct    480
gcccctcagt cgcggatcca tcgacgtcag acgcggaagg agctccggtg gactttgccg    540
acaggtacca aaacaaatgt tctcgtcacg cgggcatgct tcagatgctg tttccctgca    600
agacatgcga gagaatgaat cagaatttca acatttgctt cacgcacggg accagagact    660
gttcagaatg tttccccggc gtgtcagaat ctcaaccggt cgtcagaaag aggacgtatc    720
ggaaactctg tgccattcat catctgctgg ggcgggctcc cgagattgct tgctcggcct    780
gcgatctggt caacgtggac ctggatgact gtgtttctga gcaataaatg acttaaacca    840
ggtatggctg ccgatggtta tcttccagat tggctcgagg acaacctctc tgagggcatt    900
cgcgagtggt gggacttgaa acctggagcc ccgaaaccca agccaaccag caaaagcag    960 gacgacggcc ggggtctggt gcttcctggc tacaagtacc tcggacccctt caacggactc   1020 gacaagggag agccggtcaa cgaggcagac gccgcggccc tcgagcacga caaggcctac   1080
gacaagcagc tcgagcaggg ggacaacccg tacctcaagt acaaccacgc cgacgccgag   1140
tttcaggagc gtcttcaaga agatacgtct tttgggggca acctcgggcg agcagtcttc   1200
caggccaaga gcgggttct cgaacctctc ggtctggttg aggaaggcgc taagacggct   1260
```

```
cctggaaaga agagaccggt agagccatca ccccagcgtt ctccagactc ctctacgggc    1320
atcggcaaga caggccagca gcccgcgaaa aagagactca actttgggca gactggcgac    1380
tcagagtcag tgcccgaccc tcaaccaatc ggagaacccc ccgcaggccc ctctggtctg    1440
ggatctggta caatggctgc aggcggtggc gctccaatgg cagacaataa cgaaggcgcc    1500
gacggagtgg gtagttcctc aggaaattgg cattgcgatt ccacatggct gggcgacaga    1560
gtcatcacca ccagcacccg aacctgggcc ctccccacct acaacaacca cctctacaag    1620
caaatctcca acgggacatc gggaggaagc accaacgaca cacctactt cggctacagc    1680
accccctggg ggtattttga ctttaacaga ttccactgcc acttctcacc acgtgactgg    1740
cagcgactca tcaacaacaa ctggggattc cggcccaaga gactcaactt caagctcttc    1800
aacatccagg tcaaggaggt cacgcagaat gaaggcacca gaccatcgc caataacctt    1860
accagcacga ttcaggtctt tacggactcg aataccagc tcccgtacgt cctcggctct    1920
gcgcaccagg gctgcctgcc tccgttcccg gcggacgtct tcatgattcc tcagtacggg    1980
tacctgactc tgaacaacgg cagtcaggcc gtgggccgtt cctccttcta ctgcctggag    2040
tactttcctt ctcaaatgct gagaacgggc aacaactttg agttcagcta ccagtttgag    2100
gacgtgcctt ttcacagcag ctacgcgcac agccaaagcc tggaccggct gatgaacccc    2160
ctcatcgacc agtacctgta ctacctgtct cggactcagt ccacggggag gtaccgcagga    2220
actcagcagt tgctatttc tcaggccggg cctaataaca tgtcggctca ggccaaaaac    2280
tggctacccg gcccctgcta ccggcagcaa cgcgtctcca cgacactgtc gcaaaataac    2340
aacagcaact ttgcttggac cggtgccacc aagtatcatc tgaatggcag agactctctg    2400
gtaaatcccg tgtcgctat ggcaacgcac aaggacgacg aagagcgatt ttttccatcc    2460
agcggagtct tgatgtttgg gaaacaggga gctggaaaag caacgtgga ctatagcagc    2520
gttatgctaa ccagtgagga gaaaatcaaa accaccaacc cagtggccac agaacagtac    2580
ggcgtggtgg ccgataacct gcaacagcaa acgccgctc ctattgtagg ggccgtcaac    2640
agtcaaggag ccttacctgg catggtctgg cagaaccggg acgtgtacct gcagggtcct    2700
atctgggcca agattcctca cacggacggc aactttcatc cttcgccgct gatgggaggc    2760
tttggactga aacacccgcc tcctcagatc ctgattaaga atacacctgt tccgcgggat    2820
cctccaacta ccttcagtca agccaagctg gcgtcgttca tcacgcagta cagcaccgga    2880
caggtcagcg tggaaattga atgggagctg cagaaagaga acagcaagcg ctggaaccca    2940
gagattcagt atacttccaa ctactacaaa tctacaaatg tggactttgc tgtcaatact    3000
gagggtactt attcagagcc tcgccccatt ggcacccgtt acctcacccg taacctgtaa    3060
ttgcctgtta atcaataaac cggttaattc gtttcagttg aactttggtc tctgcgaagg    3120
gcgaattcgt ttaaacctgc aggactagtc cctttagtga gggttaattc tgagcttggc    3180
gtaatcatgg gtcatag                                                  3197
```

<210> SEQ ID NO 30
<211> LENGTH: 2501
<212> TYPE: DNA
<213> ORGANISM: Unknown
<220> FEATURE:
<223> OTHER INFORMATION: AAV serotype, clone 42.1b

<400> SEQUENCE: 30

```
gaattcgccc ttggctgcgt caactggacc aatgagaact ttcccttcaa cgattgcgtc    60
```

| | |
|---|---|
| gacaagatgg tgatctggtg ggaggagggc aagatgacgg ccaaggtcgt ggagtccgcc | 120 |
| aaggccattc atcatctgct ggggcgggct cccgagattg cttgctcggc ctgcgatctg | 180 |
| gtcaacgtgg acctggatga ctgtgtttct gagcaataaa tgacttaaac caggtatggc | 240 |
| tgccgatggt tatcttccag attggctcga ggacaacctc tctgagggca ttcgcgagtg | 300 |
| gtgggacttg agacctggag ccccgaaacc caaagccaac cagcaaaagc aggacgacgg | 360 |
| ccggggtctg gtgcttcctg ctacaagta cctcggaccc ttcaacggac tcgacaaggg | 420 |
| agagccggtc aacgaggcag acgccgcggc cctcgagcac gacaaggcct acgacaagca | 480 |
| gctcgagcag ggggacaacc cgtacctcaa gtacaaccac gccgacgccg agtttcagga | 540 |
| gcgtcttcaa gaagatacgt cttttggggg caacctcggg cgagcagtct tccaggccaa | 600 |
| gaagcgggtt ctcgaacctc tcggtctggt tgaggaaggc gctaagacgg ctcctggaaa | 660 |
| gaagagaccc atagaatccc ccgactcctc cacgggcatc ggcaagaaag gccagcagcc | 720 |
| cgctaaaaag agactcaact ttgggcagac tggcgactca gagtcagtgc ccgaccctca | 780 |
| accaatcgga gaacccccg caggcccctc tggtctggga tctggcacaa tggctgcagg | 840 |
| cggtggcgct ccaatggcag acaataacga aggcgccgac ggagtgggta gttcctcagg | 900 |
| aaattggcat tgcgattcca catggctggg cgacagagtc atcaccacca gcacccgaac | 960 |
| ctgggccctc cccacctaca caaccacct ctacaagcaa atctccaacg ggacatcggg | 1020 |
| aggaagcacc aacgacaaca cctacttcgg ctacagcacc ccctgggggt attttgactt | 1080 |
| taacagattc cactgccact tctcaccacg tgactggcag cgactcatca acaacaactg | 1140 |
| gggattccgg cccaagagac tcaacttcaa gctcttcaac atccaggtca aggaggtcac | 1200 |
| gcagaatgaa ggcaccaaga ccatcgccaa taaccttacc agcacgattc aggtctttac | 1260 |
| ggactcggaa taccagctcc cgtacgtcct cggctctgcg caccagggct gcctgcctcc | 1320 |
| gttcccggcg gacgtcttca tgattcctca gtacgggtac ctgactctga acaacggcag | 1380 |
| tcaggccgtg ggccgttcct ccttctactg cctggagtac tttccttctc aaatgctgag | 1440 |
| aacgggcaac aactttgagt tcagctacca gtttgaggac gtgccttttc acagcagcta | 1500 |
| tgcgcacagc caaagcctgg accggctgat gaaccccctc atcgaccagt acctgtacta | 1560 |
| cctgtctcgg actcagtcca cgggaggtac cgcaggaact cagcagttgc tattttctca | 1620 |
| ggccgggcct aataacatgt cggctcaggc caaaaactgg ctacccggc cctgctaccg | 1680 |
| gcagcaacgc gtctccacga cagtgtcgca aaataacaac agcaactttg cttggaccgg | 1740 |
| tgccaccaag tatcatctga atggcagaga ctctctggta aatcccggtg tcgctatggc | 1800 |
| aacgcacaag ggcgacgaag agcgattttt tccatccagc ggagtcttga tgtttgggaa | 1860 |
| acagggagct ggaaaagaca acgtagacta tagcagcgtt atgctaacca gtgaggaaga | 1920 |
| aatcaaaacc accaacccag tggccacaga acagtacggc gtggtggccg ataacctgca | 1980 |
| acagcaaaac gccgctccta ttgtaggggc cgtcaacagt caaggagcct acctggcat | 2040 |
| ggtctggcag aaccgggacg tgtacctgca gggtcctatc tgggccaaga ttcctcacac | 2100 |
| ggacggcaac tttcatcctt cgccgctgat gggaggcttt ggactgaaac cccgcctcc | 2160 |
| tcagatcctg attaagaata cacctgttcc cgcggatcct ccaactacct tcagtcaagc | 2220 |
| caagctggcg tcgttcatca cgcagtacag caccggacag gtcagcgtgg aaattgaatg | 2280 |
| ggagctgcag aaagagaaca gcaagcgctg gaacccagag attcagtata cttccaacta | 2340 |
| ctacaaatct acaaatgtgg actttgctgt caatactgag ggtacttatt cagagcctcg | 2400 |
| ccccattggc acccgttacc tcacccgtaa cctgtaattg cctgttaatc aataaaccgg | 2460 |

```
ttgattcgtt tcagttgaac tttggtctca agggcgaatt c          2501
```

<210> SEQ ID NO 31
<211> LENGTH: 3113
<212> TYPE: DNA
<213> ORGANISM: Unknown
<220> FEATURE:
<223> OTHER INFORMATION: AAV serotype, clone 42.13

<400> SEQUENCE: 31

```
gaattcgccc tttctacggc tgcgtcaact ggaccaatga aactttccc ttcaacgatt   60
gcgtcgacaa gatggtgatc tggtgggagg agggcaagat gacggccaag gtcgtggagt  120
ccgccaaggc cattctcggc ggcagcaagg tgcgcgtgga ccaaaagtgc aagtcgtccg  180
cccagatcga tcccaccccc gtgatcgtca cttccaacac caacatgtgc gccgtgattg  240
acgggaacag caccaccttc gagcaccagc agccgttaca agaccggatg ttcaaatttg  300
aactcacccg ccgtctggag catgactttg gcaaggtgac aaagcaggaa gtcaaagagt  360
tcttccgctg ggcgcaggat cacgtgaccg aggtggcgca tgagttctac gtcagaaagg  420
gtggagccaa caagagaccc gcccccgatg acgcggataa aagcgagccc aagcgggcct  480
gccctcagt cgcggatcca tcgacgtcag acgcggaagg agctccggtg gactttgccg  540
acaggtacca aaacaaatgt tctcgtcacg cgggcatgct tcagatgctg tttccctgca  600
agacatgcga gagaatgaat cagaatttca acatttgctt cacgcacggg accagagact  660
gttcagaatg tttccccggc gtgtcagaat ctcaaccggt cgtcagaaag aggacgtatc  720
ggaaactctg tgccattcat catctgctgg ggcgggctcc cgagattgct tgctcggcct  780
gcgatctggt caacgtggac ctggatgact gtgtttctga gcaataaatg acttaaacca  840
ggtatggctg ccgatggtta tcttccagat tggctcgagg acaacctctc tgagggcatt  900
cgcgagtggt gggacttgaa acctggagcc ccgaaaccca agccaaccca gcaaaagcag  960
gacgacggcc ggggtctggt gcttcctggc tacaagtacc tcggacccct caacggactc 1020
gacaaggggg agcccgtcaa cgcggcggac gcagcggccc tcgagcacga caaggcctac 1080
gaccagcagc tcaaagcggg tgacaatccg tacctgcggt ataaccacgc cgacgccgag 1140
tttcaggagc gtcttcaaga agatacgtct tttgggggca acctcggcg agcagtcttc 1200
caggccaaga agcgggttct cgaacctctc ggtctggttg aggaaggcgc taagacggct 1260
cctggaaaga gagacccat agaatccccc gactcctcca cgggcatcgg caagaaaggc 1320
cagcagcccg ctaaaaagaa gctcaacttt ggcagactg cgactcaga gtcagtgccc 1380
gaccctcaac caatcggaga accccccgca ggcccctctg gtctgggatc tggtacaatg 1440
gctgcaggcg gtggcgctcc aatggcagac aataacgaag cgccgacgg agtgggtagt 1500
tcctcaggaa attggcattg cgattccaca tggctgggcg acagagtcat caccaccagc 1560
acccgaacct gggcccctcc cacctacaac aaccacctct acaagcaaat ctccaacggg 1620
acatcgggag gaagcaccaa cgacaacacc tacttcggct acagcacccc ctgggggtat 1680
tttgactta acagattcca ctgccacttc tcaccacgtg actggcagcg actcatcaac 1740
aacaactggg gattccggcc caagagactc aacttcaagc tcttcaacat ccaggtcaag 1800
gaggtcacgc agaatgaagg caccaagacc atcgccaata accttaccag cacgattcag 1860
gtctttacgg actcggaata ccagctcccg tacgtcctcg gctctgcgca ccagggctgc 1920
ctgcctccgt tcccggcgga cgtcttcatg attcctcagt acgggtacct gactctgaac 1980
```

```
aacggcagtc aggccgtggg ccgttcctcc ttctactgcc tggagtactt tccttctcaa   2040
atgctgagaa cgggcaacaa ctttgagttc agctaccagt ttgaggacgt gccttttcac   2100
agcagctatg cgcacagcca agcctggac cggctgatga accccctcat cgaccagtac    2160
ctgtactacc tgtctcggac tcagtccacg ggaggtaccg caggaactca gcagttgcta   2220
ttttctcagg ccgggcctaa taacatgtcg gctcaggcca aaaactggct acccgggccc   2280
tgctaccggc agcaacgcgt ctccacgaca gtgtcgcaaa ataacaacag caactttgct   2340
tggaccggtg ccaccaagta tcatctgaat ggcagagact ctctggtaaa tcccggtgtc   2400
gctatggcaa cgcacaaggg cgacgaagag cgattttttc catccagcgg agtcttgatg   2460
tttgggaaac agggagctgg aaaagacaac gtggactata gcagcgttat gctaaccagt   2520
gaggaagaaa tcaaaaccac caacccagtg gccacagaac agtacggcgt ggtggccgat   2580
aacctgcaac agcaaaacgc cgctcctatt gtaggggccg tcaacagtca aggagcctta   2640
cctggcatgg tctggcagaa ccgggacgtg tacctgcagg gtcctatctg ggccaagatt   2700
cctcacacgg acggcaactt tcatccttcg ccgctgatgg gaggctttgg actgaaacac   2760
ccgcctcctc agatcctgat taagaataca cctgttcccg cggatcctcc aactaccttc   2820
agtcaagcca agctggcgtc gttcatcacg cagtacagca ccggacaggt cagcgtggaa   2880
attgaatggg agctgcagaa agagaacagc aagcgctgga acccagagat tcagtatact   2940
tccaactact acaaatctac aaatgtggac tttgctgtca atactgaggg tacttattca   3000
gagcctcgcc ccattggcac ccgttacctc acccgtagcc tgtaattgcc tgttaatcaa   3060
taaaccggtt gattcgtttc agttgaactt tggtctctgc gaagggcgaa ttc           3113
```

<210> SEQ ID NO 32
<211> LENGTH: 3113
<212> TYPE: DNA
<213> ORGANISM: Unknown
<220> FEATURE:
<223> OTHER INFORMATION: AAV serotype, clone 42.3a

<400> SEQUENCE: 32

```
gaattcgccc tttctacggc tgcgtcaact ggaccaatga gaactttccc ttcaacgatt    60
gcgtcgacaa gatggtgatc tggtgggagg agggcaagat gacggccaag gtcgtggagt   120
ccgccaaggc cattctcggc ggcagcaagg tgcgcgtgga ccaaaagtgc aagtcgtccg   180
cccagatcga tcccaccccc gtgatcgtca cttccaacac caacatgtgc gccgtgattg   240
acggaaacag caccaccttc gagcaccagc agccgttaca agaccggatg ttcaaatttg   300
aactcacccg ccgtctggag catgactttg gcaaggtgac aaagcaggaa gtcaaagagt   360
tcttccgctg ggcgcaggat cacgtgaccg aggtggcgca tgagttctac gtcagaaagg   420
gtggagccaa caagagaccc gccccgatg acgcggataa aagcgagccc aagcgggcct   480 gccctcagt cgcggatcca tcgacgtcag acgcggaagg agctccggtg gactttgccg   540
acaggtacca aaacaaatgt tctcgtcacg cgggcatgct tcagatgctg cttccctgca   600
agacatgcga gagaatgaat cagaatttca gcatttgctt cacgcacggg accagagact   660
gttcagaatg tttccccggc gtgtcagaat ctcaaccggt cgtcagaaag aggacgtatc   720
ggaaactctg tgccattcat catctgctgg ggcgggctcc cgagattgct tgctcggcct   780
gcgatctggt caacgtggac ctggatgact gtgtttctga gcaataaatg acttaaacca   840
ggtatggctc cgatggtca tcttccagat tggctcgagg acaacctctc tgagggcatt   900
cgcgagtggt gggacttgaa acctggagcc ccgaaaccca agccaaccca gcaaaagcag   960
```

```
gacgacggcc ggggtctggt gcttcctggc tacaagtacc tcggacccct caacggactc    1020 gacaagggg  agcccgtcaa cgcggcggac gcagcggccc tcgagcacga caaggcctac    1080
gaccagcagc tcaaagcggg tgacaatccg tacctgcggt ataaccacgc cgacgccgag    1140
tttcaggagc gtcttcaaga agatacgtct tttgggggca acctcgggcg agcagtcttc    1200
caggccaaga agcgggttct cgaacctctc ggtctggttg aggaaggcgc taagacggct    1260
cctggaaaga agagacccat agaatccccc gactcctcca cgggcatcgg caagaaaggc    1320
cagcagcccg ctaaaaagaa gctcaacttt gggcagactg gcgactcaga gtcagtgccc    1380
gaccctcaac caatcggaga accccccgca ggccctctg  gtctgggatc tggtacaatg    1440
gctgcaggcg gtggcgctcc aatggcagac aataacgaag gcgccgacgg agtgggtagt    1500
tcctcaggaa attggcattg cgattccaca tagctgggcg acagagtcat caccaccagc    1560
acccgaacct gggccctccc cacctacaac aaccacctct acaagcaaat ctccaacggg    1620
acatcgggag gaagcaccaa cgacaacacc tacttcggct acagcacccc ctgggggtat    1680 tttgactta  acagattcca ctgccacttc tcaccacgtg actggcagcg actcatcaac    1740
aacagctggg gattccggcc caagagactc aacttcaagc tcttcaacat ccaggtcaag    1800
gaggtcacgc agaatgaagg caccaagacc atcgccaata accttaccag cacgattcag    1860
gtctttacgg actcggaata ccagctcccg tacgtcctcg gctctgcgca ccagggctgc    1920
ctgcctccgt tcccggcgga cgtcttcatg attcctcagt acgggtacct gactctgaac    1980
aacggcagtc aggccgtggg ccgttcctcc ttctactgcc tggagtactt tccttctcaa    2040
atgctgagaa cgggcaacaa ctttgagttc agctaccagt ttgaggacgt gccttttcac    2100
agcagctacg cgcacagcca aagcctggac cggctgatga accccctcat cgaccagtac    2160
ctgtactacc tgtctcggac tcagtccacg ggaggtaccg caggaactca gcagttgcta    2220
ttttctcagg ccgggcctaa taacatgtcg gctcaggcca aaaactggct acccgggccc    2280
tgctaccggc agcaacgcgt ctccacgaca ctgtcgcaaa ataacaacag caactttgct    2340
tggaccggtg ccaccaagta tcatctgaat ggcagagact ctctggtaaa tcccggtgtc    2400
gctatggcaa cgcacaagga cgacgaagag cgatttttc  catccagcgg agtcttgatg    2460
tttgggaaac agggagctgg aaaagacaac gtggactata gcagcgttat gctaaccagt    2520
gaggaagaaa tcaaaaccac caacccagtg gccacagaac agtacggcgt ggtggccgat    2580
aacctgcaac agcaaaacgc cgctcctatt gtaggggccg tcaacagtca aggagcctta    2640
cctggcatgt tctggcagaa ccgggacgtg tacctgcagg gtcctatctg gccaagatt    2700 cctcacacgg acggcaactt tcatccttcg ccgctgatgg gaggctttgg actgaaacac    2760
ccgcctcctc agatcctgat taagaataca cctgttcccg cggatcctcc aactaccttc    2820
agtcaagcca agctggcgtc gttcatcacg cagtacagca ccggacaggt cagcgtggaa    2880
attgaatggg agctgcagaa agagaacagc aagcgctgga acccagagat tcagtatact    2940
tccaactact acaaatctac aaatgtggac tttgctgtca atactgaggg tacttattca    3000
gagcctcgcc ccattggcac ccgttacctc acccgtaacc tgtaattgcc tgttaatcaa    3060
taaaccggtt aattcgtttc agttgaactt tggtctctgc gaagggcgaa ttc           3113
```

<210> SEQ ID NO 33  
<211> LENGTH: 2504  
<212> TYPE: DNA  
<213> ORGANISM: Unknown  
<220> FEATURE:

<223> OTHER INFORMATION: AAV serotype, clone 42.4

<400> SEQUENCE: 33

```
gaattcgccc tttctacggc tgcgtcaact ggaccaatga gaactttccc ttcaacgatt    60
gcgtcgacaa gatggtgatc tggtgggagg agggcaagat gacggccaag gtcgtggagt   120
ccgccaaggc cattcatcat ctgctggggc gggctcccga gattgcttgc tcggcctgcg   180
atctggtcaa cgtggacctg gatgactgtg tttctgagca taaatgact taaaccaggt    240
atggctgccg atggttatct tccagattgg ctcgaggaca acctctctga gggcattcgc   300
gagtggtggg acttgaaacc tggagccccg aaacccaaag ccaaccagca aaagcaggac   360
gacggccggg gtctggtgct tcctggctac aagtacctcg gacccttcaa cggactcgac   420
aagggagagc cggtcaacga ggcagacgcc gcggccctcg agcacgacaa ggcctacgac   480
aagcagctcg agcaggggga caacccgtac ctcaagtaca ccacgccga cgccgagttt   540
caggagcgtc ttcaagaaga tacgtctttt ggggggcaacc tcgggcgagc agtcttccag   600
gccaagaagc gggttctcga acctctcggt ctggttgagg aaggcgctaa gacggctcct   660
ggaaagaaga gacccataga atcccccgac tcctccacgg gcatcggcaa gaaaggccag   720
cagcccgcta aaaagaagct caactttggg cagactggcg actcagagtc agtgcccgac   780
cctcaaccaa tcggagaacc ccccgcaggc ccctctggtc tgggatctgg tacaatggct   840
gcaggcggtg gcgctccaat ggcagacaat aacgaaggcg ccgacggagt gggtaatgcc   900
tccggaaatt ggcattgcga ttccacatgg ctgggcgaca gagtcatcac caccagcacc   960
cgcacctggg ccctgcccac ctacaacaac cacctctaca agcagatatc aagtcagagc  1020
ggggctacca cgacaaccca cttcttcggc tacagcaccc cctggggcta ttttgacttc  1080
aacagattcc actgccactt ctcatcacgt gactggcagc gactcatcaa caacaactgg  1140
ggattccggc caagagact caacttcaag ctcttcaaca tccaggtcaa ggaggtcacg   1200
cagaatgaag gcaccaagac catcgccaat aaccttacca gcacgattca ggtctttacg  1260
gactcggaat accggctccc gtacgtcctc ggctctgcgc accagggctg cctgcctccg  1320
ttcccggcgg acgtcttcat gattcctcag tacgggtacc tgactctgaa caacggcagt  1380
caggccgtgg gccgttcctc cttctactgc ctggagtact tccttctca aatgctgaga  1440
acgggcaaca actttgagtt cagctaccag tttgaggacg tgccttttca cagcagctac   1500
gcgcacagcc aaagcctgga ccggctgatg aacccccctca tcgaccagta cctgtactac  1560
ctgtctcgga ctcagtccac gggaggtacc gcaggaactc agcagttgct attttctcag  1620
gccgggccta ataacatgtc ggctcaggcc aaaaactggc tacccgggcc ctgctaccgg  1680
cagcaacgcg tctccacgac actgtcgcaa aataacaaca gcaactttgc cttggaccggt  1740
gccaccaagt atcatctgaa tggcagagac tctctggtaa atcccggtgt cgctatggca  1800
acgcacaagg acgacgaaga gcgatttttt ccatccagcg gagtcttgat gtttgggaaa  1860
cagggagctg gaaaagacaa cgtggactat agcagcgtta tgctaaccag tgaggaagaa  1920
atcaaaacca ccaacccagt ggccacagaa cagtacggcg tggtggccga taacctgcaa  1980
cagcaaaacg ccgctcctat tgtaggggcc gtcaacagtc aaggagcctt acctggcatg  2040
gtctggcaga accgggacgt gtacctgcag ggtcctatct gggccaagat tcctcacacg  2100
gacggcaact tcatccttc gccgctgatg ggaggctttg gactgaaaca cccgcctcct  2160
cagatcctga ttaagaatac acctgttccc gcggatcctc caactacctt cagtcaagcc  2220
aagccggcgt cgttcatcac gcagtacagc accggacagg tcagcgtgga aattgaatgg  2280
```

-continued

| | |
|---|---|
| gagctgcaga aagagaacag caagcgctgg aacccagaga ttcagtatac ttccaactac | 2340 |
| tacaaatcta caaatgtgga ctttgctgtc aatactgagg gtacttattc agagcctcgc | 2400 |
| cccattggca cccgttacct cacccgtaac ctgtaattgc ctgttaatca ataaaccggt | 2460 |
| taattcgttt cagttgaact ttggtctctg cgaagggcga attc | 2504 |

<210> SEQ ID NO 34
<211> LENGTH: 3106
<212> TYPE: DNA
<213> ORGANISM: Unknown
<220> FEATURE:
<223> OTHER INFORMATION: AAV serotype, clone 42.5a

<400> SEQUENCE: 34

| | |
|---|---|
| gaattcgccc ttctacggct gcgtcaactg gaccaatgag aactttccct tcaacgattg | 60 |
| cgtcgacaag atggtgatct ggtgggagga gggcaagatg acggccaagg tcgtggagtc | 120 |
| cgccaaggcc attctcggcg gcagcaaggt gcgcgtggac caaaagtgca agtcgtccgc | 180 |
| ccagatcgac cccacccccg tgatcgtcac ctccaacacc aacatgtgcg ccgtgattga | 240 |
| cgggaacagc accaccttcg agcaccagca gccgttgcag gaccggatgt tcaaatttga | 300 |
| actcacccgc cgtctggagc atgactttgg caaggcgaca aagcaggaag tcaaagagtt | 360 |
| cttccgctgg gcgcaggatc acgtgaccga ggtggcgcat gagttctacg tcagaaaggg | 420 |
| tggagccaac aagagacccg ccccgatga cgcggataaa gcgagccca gcgggcccg | 480 |
| cccctcagtc gcggatccat cgacgtcaga cgcggaagga gctccggtgg actttgccga | 540 |
| caggtaccaa aacaaatgtt ctcgtcacgc gggcatgctt cagatgctgt ttccctgcaa | 600 |
| aacatgcgag agaatgaatc agaatttcaa catttgcttc acgcacggga ccagagactg | 660 |
| ttcagaatgt ttccccggcg tgtcagaatc tcaaccggtc gtcagaaaga ggacgtatcg | 720 |
| gaaactctgt gccattcatc atctgctggg gcgggctccc gagattgctt gctcggcctg | 780 |
| cgatctggtc aacgtggacc tggatgactg tgtttctgag caataaatga cttaaaccag | 840 |
| gtatggctgc cgatggttat cttccagatt ggctcgagga caacctctct gagggcattc | 900 |
| gcgagtggtg ggacttgaaa cctggagccc cgaaacccaa agccaaccag caaaagcagg | 960 |
| acgacggccg ggtctggtg cttcctggct acaagtacct cggacccttc aacggactcg | 1020 |
| acaagggaga gccggtcaac gaggcagacg ccgcggccct cgagcacgac aaggcctacg | 1080 |
| acaagcagct cgagcagggg gacaacccgt acctcaagta caaccacgcc gacgccgagt | 1140 |
| ttcaggagcg tcttcaagaa gatacgtctt ttggggcaa cctcgggcga gcagtcttcc | 1200 |
| gggccaagaa gcgggttctc gaacctctcg gtctggttga ggaaggcgct aagacggctc | 1260 |
| ctggaaagaa gagacccata gaatccccg actcctccac gggcatcggc aagaaaggcc | 1320 |
| agcagcccgc taaaaagaag ctcaactttg gcagactgg cgactcagag tcagtgcccg | 1380 |
| accccaacc tctcggagaa cctcccgccg cgcctcagg tctgggatct ggtacaatgg | 1440 |
| ctgcaggcgg tggcgcacca atggcagaca ataacgaagg cgccgacgga gtgggtaatg | 1500 |
| cctccggaaa ttggcattgc gattccacat ggctgggcga cagagtcatc accaccagca | 1560 |
| cccgcacctg ggcctgccc acctacaaca accacctcta caagcagata tcaagtcaga | 1620 |
| gcggggctac caacgacaac cacttcttcg gctacagcac ccctgggc tattttgact | 1680 |
| tcaacagatt ccactgccac ttctcaccac gtgactggca gcgactcatc aacaacaacc | 1740 |
| ggggattccg gcccagaaag ctgcggttca agttgttcaa catccaggtc aaggaggtca | 1800 |

| | |
|---|---|
| cgacgaacga cggcgttacg accatcgcta ataaccttac cagcacgatt caggtcttct | 1860 |
| cggactcgga gtaccaactg ccgtacgtcc tcggctctgc gcaccagggc tgcctccctc | 1920 |
| cgttccctgc ggacgtgttc atgattcctc agtacggata tctgactcta acaacggca | 1980 |
| gtcagtctgt gggacgttcc tccttctact gcctggagta cttccttct cagatgctga | 2040 |
| gaacgggcaa taactttgaa ttcagctacc agtttgagga cgtgcccttt cacagcagct | 2100 |
| acgcgcacag ccaaagcctg gaccggctga tgaaccccct catcgaccag tacctgtact | 2160 |
| acctgtctcg gactcagtcc acgggaggta ccgcaggaac tcagcagttg ctattttctc | 2220 |
| aggccgggcc taataacatg tcggctcagg ccaaaaactg gctacccggg ccctgctacc | 2280 |
| ggcagcaacg cgtctccacg acactgtcgc aaaataacaa cagcaacttt gcttggaccg | 2340 |
| gtgccaccaa gtatcatctg aatggcagag actctctggt aaatcccggt gtcgctatgg | 2400 |
| caacgcacaa ggacgacgaa gagcgatttt ttccatccag cggagtcttg atgtttggga | 2460 |
| aacagggagc tggaaaagac aacgtggact atagcagcgt tatgctaacc agtgaggaag | 2520 |
| aaatcaaaac caccaaccca gtggccacag aacagtacgg cgtggtggcc gataacctgc | 2580 |
| aacagcaaaa cgccgctcct attgtagggg ccgtcaacag tcaaggagcc ttacctggca | 2640 |
| tggcctggca gaaccgggac gtgtacctgc agggtcctat ctgggccaag attcctcaca | 2700 |
| cggacggcaa ctttcatcct tcgccgctga tgggaggctt tggactgaaa cacccgcctc | 2760 |
| ctcagatcct gattaagaat acacctgttc ccgcggatcc tccaactacc ttcagtcaag | 2820 |
| ccaagctggc gtcgttcatc acgcagtaca gcaccggaca ggtcagcgtg gaaattgaat | 2880 |
| gggagctgca gaaagagaac agcaagcgct ggaacccaga gattcagtat acttccaact | 2940 |
| actacaaatc tacaaatgtg gactttgctg tcaatactga gggtacttat tcagagcctc | 3000 |
| gccccattgg caccgttac ctcacccgta acctgtaatt gcctgttaat caataaaccg | 3060 |
| gttaattcgt ttcagttgaa ctttggtctc tgcgaagggc gaattc | 3106 |

<210> SEQ ID NO 35
<211> LENGTH: 2489
<212> TYPE: DNA
<213> ORGANISM: Unknown
<220> FEATURE:
<223> OTHER INFORMATION: AAV serotype, clone 42.10

<400> SEQUENCE: 35

| | |
|---|---|
| gaattcgccc tttctacggc tgcgtcaact ggaccaatga gaactttccc ttcaacgatt | 60 |
| gcgtcgacaa gatggtgatc tggtgggagg agggcaagat gacggccaag gtcgtgaagt | 120 |
| ccgccaaggc cattcatcat ctgctggggc gggctcccga gattgcttgc tcggcctgcg | 180 |
| atctggtcaa cgtggacctg gatgactgtg tttctgagca ataaatgact taaaccaggt | 240 |
| atggctgccg atggttatct tccagattgg ctcgaggaca acctctctga gggcattcgc | 300 |
| gagtggtggg acttgaaacc tggagccccg aaacccaaag ccaaccagca aaagcaggac | 360 |
| gacggccggg gtctggtgct tcctggctac aagtacctcg gacccttcaa cggactcgac | 420 |
| aagggagagc cggtcaacga ggcagacgcc gcggccctcg agcacgacaa ggcctacgac | 480 |
| aagcagctcg agcagggga caacccgtac ctcaagtaca accacgccga cgccgagttt | 540 |
| caggagcgtc ttcaagaaga tacgtctttt gggggcaacc tcgggcgagc agtcttccag | 600 |
| gccaagaagc gggttctcga acctctcggt ctggttgagg aaggcgctaa gacggctcct | 660 |
| ggaaagaaga gacccataga atcccccgac tcctccacgg gcatcggcag gaaaggccag | 720 |
| cagcccgcta aaaagaagct caactttggg cagactggcg actcagagtc agtgcccgac | 780 |

```
cctcaaccaa tcggagaacc ccccgcaggc ccctctggtc tgggatctgg tacaatggct      840
gcaggcggtg gcgctccaat ggcagacaat aacgaaggcg ccgacggagt gggtaatgcc      900
tccggaaatt ggcattgcga ttccacatgg ctgggcgaca gagtcatcac caccagcacc      960
cgcacctggg ccctgcccac ctacaacaac cacctctaca agcagatatc aagtcagagc     1020
ggggctacca acgacaacca cttcttcggc tacagcaccc cctggggcta ttttgacttc     1080
aacagattcc actgccactt ctcaccacgt gactggcagc gactcatcaa caacaactgg     1140
ggattccggc cagaaagct gcggttcaag ttgttcaaca tccaggtcaa ggaggtcacg      1200
acgaacgacg gcgttacgac catcgccaat aaccttacca gcacgattca ggtcttctcg     1260
gactcggagt accaactgcc gtacgtcctc ggctctgcgc accagggctg cctccctccg     1320
ttccctgcgg acgtgttcat gattcctcag tacggatatc tgactctaaa caacggcagt     1380
cagtctgtgg acgttcctc cttctactgc ctggagtact ttccttctca gatgctgaga      1440
acgggcaata actttgaatt cagctacacc tttgaggaag tgccttttca cagcagctat     1500
gcgcacagcc agagcctgga ccggctgatg aatcccctca tcgaccagta cctgtactac     1560
ctggcccgga cccagagcac tacggggtcc acaagggagc tgcagttcca tcaggctggg     1620
cccaacacca tggccgagca atcaaagaac tggctgcccg gaccctgtta tcggcagcag     1680
agactgtcaa aaacataga cagcaacaac aacagtaact ttgcctggac cggggccact     1740
aaataccatc tgaatggtag aaattcatta accaacccgg gcgtagccat ggccaccaac     1800
aaggacgacg aggaccagtt cttccatc aacggagtgc tggttttgg caaaacgggg       1860 gctgccaaca agacaacgct ggaaaacgtg ctaatgacca gcgaggagga gatcaaaacc     1920
accaatcccg tggctacaga agaatacggt gtggtctcca gcaacctgca atcgtctacg     1980
gccggacccc agacacagac tgtcaacagc caggggctc tgcccggcat ggtctggcag     2040
aaccgggacg tgtacctgca gggtcccatc tgggccaaaa ttcctcacac ggacggcaac     2100
tttcacccgt ctccctgat gggcggattt ggactcaaac cccgcctcc tcaaattctc      2160 atcaaaaaca ccccggtacc tgctaatcct ccagaggtgt ttactcctgc caagtttgcc     2220
tcatttatca cgcagtacag caccggccag gtcagcgtgg agatcgagtg gaactgcaga     2280
aaagaaaaca gcaaacgctg gaatccagag attcagtaca cctcaaatta tgccaagtct     2340
aataatgtgg aatttgctgt caacaacgaa ggggtttata ctgagcctcg ccccattggc     2400
acccgttacc tcacccgtaa cctgtaattg cctgttaatc aataaaccgg ttaattcgtt     2460
tcagttgaac tttggtcaag ggcgaattc                                      2489

<210> SEQ ID NO 36
<211> LENGTH: 2495
<212> TYPE: DNA
<213> ORGANISM: Unknown
<220> FEATURE:
<223> OTHER INFORMATION: AAV serotype, clone 42.3b

<400> SEQUENCE: 36
gaattcgccc tttctacggc tgcgtcaact agaccaatga gaactttccc ttcaacgatt       60
gcgtcgacaa gatggtgatc tggtgggagg agggcaagat gacggccaag gtcgtggagt      120
ccgccaaggc cattcatcat ctgctggggc gggctcccga gattgcttgc tcggcctgcg      180
atctggtcaa cgtggacctg gatgactgtg tttctgagca ataaatgact taaaccaggt      240
atggctgccg atggttatct tccagattgg ctcgaggaca acctctctga gggcattcgc      300
```

```
gagtggtggg acttgaaacc tggagccccg aaacccaaag ccaaccagca aaagcaggac        360
gacggccggg gtctggtgct tcctggctac aagtacctcg gacccttcaa cggactcgac        420
aagggagagc cggtcaacga ggcagacgcc gcggccctcg agcacgacaa ggcctacgac        480
aagcagctcg agcaggggga caacccgtac ctcaagtaca ccacgccga cgccgagttt         540 caggagcgtc ttcaagaaga tacgtctttt gggggcaacc tcgggcgagc agtcttccag        600
gccaagaagc gggttctcga acctctcggt ctggttgagg aaggcgctaa gacggctcct        660
ggaaagaaga gacccataga atccccgac tcctccacgg gcatcggcaa gaaaggccag         720
cagcccgcta aaagaagct caactttggg cagactggcg actcagagtc agtgcccgac         780
cctcaaccaa tcggagaacc ccccgcaggc ccctctggtc tgggatctgg tacaatggct        840
gcaggcggtg gcgctccaat ggcagacaat aacgaaggcg ccgacggagt gggtaatgcc        900
tccggaaatt ggcattgcga ttccacatgg ctgggcgaca gagtcatcac caccagcacc        960
cgcacctggg ccctgccac ctacaacaac cacctctaca agcagatatc aagtcagagc        1020
ggggctacca acgacaacca cttcttcggc tacagcaccc cctggggcta ttttgacttc        1080
aacagattcc actgccactt ctcaccacgt gactggcagc gactcatcaa caacaactgg        1140
ggattccggc ccagaaagct gcggttcaag ttgttcaaca tccaggtcaa ggaggtcacg        1200
acgaacgacg gcgttacgac catcgctaat aaccttacca gcacgattca ggtcttctcg        1260
gactcggagt accaactgcc gtacgtcctc ggctctgcgc accagggctg cctccctccg        1320
ttccctgcgg acgtgttcat gattcctcag tacggatatc tgactctaaa caacggcagt        1380
cagtctgtgg gacgttcctc cttctactgc ctggagtact tccttctca gatgctgaga         1440 acgggcaata actttgaatt cagctacacc tttgaggaag tgccttttcca cagcagctat       1500 gcgcacagcc agagcctgga ccggctgatg aatcccctca tcgaccagta cctgtactac        1560
ctggcccgga cccagagcac tacggggtcc acaagggagc tgcagttcca tcaggctggg        1620
cccaacacca tggccgagca atcaaagaac tggctgcccg gaccctgtta tcggcagcag        1680
agactgtcaa aaacatag a cagcaacaac accagtaact ttgcctggac cggggccact         1740
aaataccatc tgaatggtag aaattcatta accaacccgg gcgtagccat ggccaccaac        1800
aaggacgacg aggaccagtt cttttcccatc aacggagtgc tggtttttgg caaaacgggg       1860
gctgccaaca gacaacgct ggaaaacgtg ctaatgacca gcgaggagga gatcaaaacc         1920
accaatcccg tggctacaga acagtacggt gtggtctcca gcaacctgca atcgtctacg        1980
gccgaccccc agacacagac tgtcaacagc cagggggctc tgcccggcat ggtctggcag        2040
aaccgggacg tgtacctgca gggtcccatc tgggccaaaa ttcctcacac ggacggcaac        2100
tttcacccgt ctccctgat gggcggattt ggactcaaac acccgcctcc tcaaattctc         2160
atcaaaaaca ccccggtacc tgctaatcct ccagaggtgt ttactcctgc caagtttgcc        2220
tcatttatca cgcagtacag caccggccag gtcagcgtgg agatcgagtg ggaactgcag        2280
aaagaaaaca gcaaacgctg gaatccagag attcagtaca cctcaaatta tgccaagtct        2340
aataatgtgg aatttgctgt caacaacgaa ggggtttata ctgagcctcg ccccattggc        2400
acccgttacc tcaccccgtaa cctgtaattg cctgttaatc aataaaccgg ttaattcgtt       2460
tcagttgaac tttggtctct gcgaagggcg aattc                                  2495
```

<210> SEQ ID NO 37
<211> LENGTH: 3098
<212> TYPE: DNA
<213> ORGANISM: Unknown

<220> FEATURE:
<223> OTHER INFORMATION: AAV serotype, clone 42.11

<400> SEQUENCE: 37

```
gaattcgccc tttctacggc tgcgtcaact ggaccaatga gaactttccc ttcaacgatt    60
gcgtcgacaa gatggtgatc tggtgggagg agggcaagat gacggccaag gtcgtggagt   120
ccgccaaggc cattctcggc ggcagcaagg tgcgcgtgga ccaaaagtgc aagtcttccg   180
cccagatcga tcccaccccc gtgatcgtca cttccaacac caacatgtgc gccgtgattg   240
acgggaacag caccaccttc gagcaccagc agccgttaca agaccggatg ttcaaatttg   300
aactcacccg ccgtctggag cacgactttg caaggtgac aaagcaggaa gtcaaagagt    360
tcttccgctg ggcgcaggat cacgtgaccg aggtggcgca tgagttctac gtcagaaagg   420
gtggagccaa caagagaccc gcccccgatg acgcggataa aagcgagccc aagcgggcct   480
gcccctcagt cgcggatcca tcgacgtcag acgcggaagg agctccggtg actttgccg    540
acaggtacca aaacaaatgt tctcgtcacg cgggcatgct tcagatgctg tttccctgca   600
agacatgcga gagaatgaat cagaatttca acatttgctt cacgcacggg accggagact   660
gttcagaatt tttccccggc gtgtcagaat ctcaaccggt cgtcagaaag aggacgtatc   720
ggaaactctg tgccattcat catctgctgg ggcgggctcc cgagattgct tgctcggcct   780
gcgatctggt caacgtggac ctggatgact gtgtttctga gcaataaatg acttaaacca   840
ggtatggctg ccgatggtta tcttccagat tggctcgagg acaacctctc tgagggcatt   900
cgcgagtggt gggacttgaa acctggagcc ccgaaaccca agccaaacca gcaaaagcag   960
gacgacggcc ggggtctggt gcttcctggc tacaagtacc tcggacccctt caacggactc  1020
gacaagggag agccggtcaa cgcggcggac gcagcggccc tcgagcacga caaggcctac  1080
gaccagcagc tcaaagcggg tgacaatccg tacctgcggt ataaccacgc cgacgccgag  1140
tttcaggagc gtcttcaaga agatacgtct tttgggggca acctcgggcg agcagtcttc  1200
caggccaaga agcgggttct cgaacctctc ggtctggttg aggaaggcgc taagacggct  1260
cctggaaaga gagacccat agaatccccc gactcctcca cgggcatcgg caagaaaggc  1320
cagcagcccg ctaaaaagaa gctcaacttt gggcagactg gcgactcaga gtcagtgccc  1380
gaccctcaac caatcggaga accccccgca ggcccctctg gtctgggatc tggtacaatg   1440
gctgcaggcg gtggcgctcc aatggcagac aataacgaag cgccgacgg agtgggtaat  1500
gcctccggaa attggcattg cgattccaca tggctgggcg acagagtcat caccaccagc  1560
acccgcacct gggcctgcc cacctacaac aaccacctct acaagcagat atcaagtcag  1620
agcggggcta ccaacgacaa ccacttcttc ggctacagca cccctgggg ctattttgac  1680
ttcaacagat ccactgcca cttctcacca cgtgactggc agcgactcat caacaacaac  1740
tggggattcc ggcccagaaa gctgcggttc aagttgttca acatccaggt caaggaggtc   1800
acgacgaacg acggcgttac gaccatcgct aataacctta ccagcacgat tcaggtcttc   1860
tcggactcgg agtaccaact gccgtacgtc ctcggctctg cgcaccaggg ctgcctccct   1920
ccgttcctg cggacgtgtt catgattcct cagtacggat atctgactct aaacaacggc   1980
agtcagtctg tgggacgttc ctccttctac tgcctggagt actttccttc tcagatgctg   2040
agaacgggca ataactttga attcagctac acctttgagg aagtgccttt ccacagcagc   2100
tatgcgcaca gccagagcct ggaccggctg atgaatcccc tcatcgacca gtacctgtac   2160
tacctggccc ggaccagag cactacgggg tccacaaggg agctgcagtt ccatcaggct   2220
```

```
gggcccaaca ccatggccga gcaatcaaag aactggctgc ccggaccctg ttatcggcgg    2280
cagagactgt caaaagacat agacagcaac aacaacagta actttgcctg gaccggggcc    2340
actaaatacc atctgaatgg tagaaattca ttaaccaacc cgggcgtagc catggccacc    2400
aacaaggacg acgaggacca gttctttccc atcaacggag tgctggtttt tggcaaaacg    2460
ggggctgcca acaagacaac gctggaaaac gtgctaatga ccagcgagga ggagatcaaa    2520
accaccaatc ccgtggctac agaagaatac ggtgtggtct ccagcaacct gcaatcgtct    2580
acggccggac cccagacaca gactgtcaac agccaggggg ctctgcccgg catggtctgg    2640
cagaaccggg acgtgtacct gcagggtccc atctgggcca aaattcctca cacggacggc    2700
aactttcacc cgtctcccct gatgggcgga tttggactca acacccgcc tcctcaaatt    2760 ctcatcaaaa acaccccggt acctgctaat cctccagagg tgtttactcc tgccaagttt    2820
gcctcattta tcacgcagta cagcaccggc caggtcagcg tggagatcga gtgggaactg    2880
cagaaagaga cagcaaacg ctggaatcca gagattcagt acacctcaaa ttatgccaag    2940
tctaataatg tggaatttgc tgtcaacaac gaaggggttt atactgagcc tcgccccatt    3000
ggcacccgtt acctcacccg taacctgtaa ttacttgtta atcaataaac cggttgattc    3060
gtttcagttg aactttggtc tctgcgaagg gcgaattc                            3098

<210> SEQ ID NO 38
<211> LENGTH: 3276
<212> TYPE: DNA
<213> ORGANISM: Unknown
<220> FEATURE:
<223> OTHER INFORMATION: AAV serotype, clone 42.6a

<400> SEQUENCE: 38
gaattcgccc ttcgcagaga ccaaagttca actgaaacga attaaccggt ttattgatta      60
acaggcaatt acaggttacg ggtgaggtaa cgggtgccaa tggggcgagg ctcagtataa     120 acccccttcgt tgttgacagc aaattccaca ttattagact tggcataatt tgaggtgtac    180
tgaatctctg gattccagcg tttgctgttt tctttctgca gttcccactc gatctccacg     240
ctgacctggc cggtgctgta ctgcgtgata aatgaggcaa acttggcagg agtaaacacc     300
tctggaggat tagcaggtac cggggtgttt ttgatgagaa tttgaggagg cgggtgtttg     360
agtccaaatc cgtccatcag gggagacggg tgaaagttgc cgtccgtgtg aggaattttg     420
gcccagatgg gaccctgcag gtacacgtcc cggttctgcc agaccatgcc gggcagagcc     480
ccctggctgt tgacagtctg tgtctggggt ccggccgtag acgattgcag gttgctggag     540
accacaccgt attcttctgt agccacggga ttggtggttt tgatctcctc ctcgctggtc     600
attagcacgt tttccagcgt tgtcttgttg gcagccccg ttttgccaaa accagcacct     660
ccgttgatgg gaaagaactg gtcctcgtcg tccttgttgg tggccatggc tacgcccggg    720
ttggttaatg aatttctacc attcagatgg tatttagtgg ccccggtcca ggcaaagtta    780
ctgttgttgt tgctgtctat gtttttttgac agtctctgct gccgataaca gggtccgggc    840
agccagttct tgattgctc ggccatggtg ttgggcccag cctgatggaa ctgcagctcc    900
cttgtggacc ccgtagtgct ctgggtccgg gccaggtagt acaggtactg gtcgatgagg   960
ggattcatca gccggtccag gctctggcta tgcgcatagc tgctgtggaa aggcacttcc    1020
tcaaaggtgt agctgaattc aaagttattg cccgttctca gcatctgaga aggaaagtac   1080
tccaggcagt agaggagga acgtcccaca gactgactgc cgttgtttag agtcagatat    1140
ccgtactgag gaatcatgaa cacgtccgca gggaacggag ggaggcagcc ctggtgcgca   1200
```

```
gagccgagga cgtacggcag ttggtactcc gagtccgaga agacctgaat cgtgctggta    1260
aggttattag cgatggtcgt aacgccgtcg tccgtcgtga cctccttgac ctggatgttg    1320
aacaacttga accgcagctt tctgggccgg aatccccagt tgttgttgat gagtcgctgc    1380
cagtcacgtg gtgagaagtg gcagtggaat ctgttaaagt caaaataccc ccaggggtg     1440
ctgtagccga agtaggtgtt gtcgttggtg cttcctcccg atgtcccgtt ggagatttgc    1500
ttgtagaggt ggttgttgta ggtggggagg gcccaggttc gggtgctggt ggtgatgact    1560
ctgtcgccca gccatgtgga atcgcaatgc caatttcctg aggaactacc cactccgtcg    1620
gcgccttcgt tattgtctgc cattggagcg ccaccgcctg cagccattgt accagatccc    1680
agaccagagg ggcctgcggg gggttctccg attggttgag ggtcgggcac tgactctgag    1740
tcgccagtct gcccaaagtt gagtctcttt ttcgcgggct gctggcctgt cttgccgatg    1800
cccgtagagg agtctggaga acgctggggt gatggctcta ccggtctctt ctttccagga    1860
gccgtcttag cgccttcctc aaccagaccg agaggttcga gaacccgctt cttggcctgg    1920
aagactgctc gcccgaggtt gcccccaaaa gacgtatctt cttgaagacg ctcctgaaac    1980
tcggcgtcgg cgtggttgta cttgaggtac ggggttgtccc cctgctcgag ctgcttgtcg    2040
taggccttgt cgtgctcgag ggccgcggcg tctgcctcgt tgaccggctc tcccttgtcg    2100
agtccgttga agggtccgag gtacttgtag ccaggaagca ccagaccccg gccgtcgtcc    2160
tgcttttgct ggttggcttt gggtttcggg gctccaggtt tcaagtccca ccactcgcga    2220
atgccctcag agaggttgtc ctcgagccaa tctggaagat aaccatcggc agccataccet   2280
ggtttaagtc atttattgct cagaaacaca gtcatccagg tccacgttga ccagatcgca    2340
ggccgagcaa gcaatctcgg gagcccgccc cagcagatga tgaatggcac agagtttccg    2400
atacgtcctc tttctgacga ccggttgaga ttctgacacg ccggggaaac attctgaaca    2460
gtctctggtc ccgtgcgtga agcaaatgtt gaaattctga ttcattctct cgcatgtctt    2520
gcagggaaac agcatctgaa gcatgcccgc gtgacgagaa cacttgtttt ggtacctgtc    2580
ggcaaagtcc accggagctc cttccgcgtc tgacgtcgat ggatgcaaaa tgtcgcaaaa    2640
gcactcacgt gacagctaat acaggaccac tccectatga cgtgatttac gtcagcgcta    2700
tgcccgcgtg acgagaacat tgttttggt acctgtcggc aaagtccacc ggagctcctt    2760
ccgcgtctga cgtcgatgga tccgcgactg aggggcaggc ccgcttgggc tcgcttttat    2820
ccgcgtcatc gggggcgggt ctcttgttgg ctccacccct tctgacgtag aactcatgcg    2880
ccacctcggt cacgtgatcc tgcgcccagc ggaagaactc tttgacttcc tgctttgtca    2940
ccttgccaaa gtcatgctcc agacggcggg tgagttcaaa tttgaacatc cggtcctgca    3000
acggctgctg gtgctcgaag gtggtgctgt tcccgtcaat cacggcgcac atgttggtgt    3060
tggaagtgac gatcacgggg gtgggatcga tctgggcgga agacttgcac ttttggtcca    3120
cgcgcacctt gctgccgccg agaatggcct tggcggactc cacgaccttg gccgtcatct    3180
tgccctcctc ccaccagatc accatcttgt cgacgcaatc gttgaaggga aagttctcat    3240
tggtccagtt gacgcagccg tagaaagggc gaattc    3276
```

<210> SEQ ID NO 39
<211> LENGTH: 3084
<212> TYPE: DNA
<213> ORGANISM: Unknown
<220> FEATURE:
<223> OTHER INFORMATION: AAV serotype, clone 43.1

<400> SEQUENCE: 39

```
gaattcgccc tttctacggc tgcatcaact ggaccaatga aactttccc ttcaacgatt      60
gcgtcgacaa gatggtgatc tggtgggagg agggcaagat gacggccaag gtcgtggagt     120
ccgccaaggc cattctcggc ggcagcaagg tgcgcgtgga ccaaaagtgc aagtcgtccg     180
cccagatcga ccccaccccc gtgatcgtca cctccaacac caacatgtgc gccgtgattg     240
acgggaacag caccaccttc gagcaccagc agccgttgca ggaccggatg ttcaagttcg     300
aactcacccg ccgtctggag cacgactttg gcaaggtgac caagcaggaa gtcaaagagt     360
tcttccgctg ggcgcaggat cacgtgaccg aggtggcgca tgagttctac gtcagaaagg     420
gcggagccag caaaagaccc gccccgatg acgcggatat aagcgagccc aagcgggcct      480
gcccctcagt cgcggatcca tcgacgtcag acgcggaagg agctccggtg gactttgccg     540
acaggtacca aaacaaatgt tctcgtcacg cgggcatgct tcagatgctg tttcctgca      600
aaacgtgcga gaaatgaat cagaatttca catttgctt cacgcacggg gtcagagact       660
gctcagaatg tttccccggt gcatcagaat ctcaaccggt cgtcagaaaa aaacgtatc      720
agaaactgtg tgccattcat catctgctgg ggcgggcacc cgagattgct tgctcggcct     780
gcgatctggt caacgtggac ctggacgact gtgtttctga gcaataaatg acttaaacca     840
ggtatggctg ccgatggtta tcttccagat tggcttgagg acaacctctc tgagggcatt     900
cgcgagtggt gggacctgaa acctggagcc ccgaaaccca agccaaccca gcaaaagcag     960
gacgacggcc ggggtctggt gcttcctggc tacaagtacc tcggacccctt caacggactc    1020
gacaaggggg agcccgtcaa cgcggcggac gcagcggccc tcgagcacga caaggcctac    1080
gaccagcagc tcaaagcggg tgacaatccg tacctgcggt ataaccacgc cgacgccgag    1140
tttcaggagc gtctgcaaga agatacgtct tttgggggca acctcgggcg agcagtcttc    1200
caggccaaga agcgggttct cgaacctctc ggtctggttg aggaaggcgc taagacggct    1260
cctgaaaaga agagaccggt agagccatca cctcagcgtt ccccgactc ctccacgggc     1320
atcggcaaga aaggccacca gcccgcgaga aagagactga actttgggca gactggcgac    1380
tcggagtcag tccccgaccc tcaaccaatc ggagaaccac cagcaggccc ctctggtctg    1440
ggatctggta caatggctgc aggcggtggc gctccaatgg cagacaataa cgaaggcgcc    1500
gacgagtgg gtagttcctc aggaaattgg cattgcgatt ccacatggct gggcgacaga     1560
gtcatcacca ccagcacccg aacctgggcc ctgcccacct acaacaacca tctctacaag    1620
caaatctcca cgggacatc gggaggaagc actaacgaca cacctactt tggctacagc      1680
acccccctggg ggtattttga cttcaacaga ttccactgcc acttctcacc acgtgactgg    1740
cagcgactca tcaacaataa ctggggattc cggcccaaga gactcaactt caagctcttc    1800
aacatccagg tcaaggaggt cacgcagaat gaaggcacca agaccatcgc caataacctt    1860
accagcacga ttcaggtgtt tacgactcg gaataccagc tcccgtacgt ccccggctct     1920
gcgcaccagg gctgcctccc tccgttcccg gcggacgtct tcatgattcc tcagtacggg    1980
tatctgaccc taaacaatgg cagtcaggct gtgggccgtt cctccttcta ctgcctggaa    2040
tacttcccctt ctcaaatgct gaggacgggc aacaactttg aattcagcta caccttcgag    2100
gacgtgcctt tccacagcag ctacgcgcac agccagagcc tggaccggct gatgaaccct    2160
ctcatcgacc agtacctgta ttacttatcc agaactcagt ccacaggagg aactcaaggt    2220
actcagcaat tgttattttc tcaagccggg cccgcaaaca tgtcggctca ggccaagaac    2280
tggctacctg gaccgtgtta ccgtcagcaa cgagtttcca cgacactgtc gcaaaacaac    2340
```

```
aacagcaatt ttgcttggac cggtgccacc aagtatcacc tgaatggcag agactccctg    2400
gttaatcccg gcgttgccat ggctacccac aaggacgacg aggagcgctt cttcccgtca    2460
agcggagttc taatgtttgg caagcagggg gctggaaaag acaatgtgga ctacagcagc    2520
gtgatgctca ccagcgaaga agaaattaaa actactaacc cagtggctac agagcagtat    2580
ggtgtggtgg cagacaacct gcagcagacc aacggagctc ccattgtggg aactgtcaac    2640 agccagggg ccttacctgg tatggtctgg caaaaccggg acgtgtacct gcagggcccc    2700
atctgggcca aaattcctca cacggacggc aactttcatc cttcgccgct gatgggaggc    2760
tttggactga acacccgcc tcctcagatc ctggtgaaaa acactcctgt tcctgcggat    2820
cctccgacca ccttcagcca ggccaagctg gcttcttta tcacgcagta cagcaccgga    2880
caggtcagcg tggaaatcga atgggagctg cagaaagaaa acagcaagcg ctggaaccca    2940
gagattcagt atacttccaa ctactacaaa tctacaaatg tggactttgc tgtcaatact    3000
gagggtactt attcagagcc tcgccccatt ggcactcgtt atctcacccg taatctgtaa    3060
ttgcttgtta atcaataaac cggt                                          3084
```

<210> SEQ ID NO 40
<211> LENGTH: 2370
<212> TYPE: DNA
<213> ORGANISM: Unknown
<220> FEATURE:
<223> OTHER INFORMATION: AAV serotype, clone 43.5

<400> SEQUENCE: 40

```
gaattcgccc tttctacggc tgcgtcaact ggaccaatga gaactttccc ttcaacgatt     60
gcgtcgacaa gatggtgatc tggtgggagg agggcaagat gacggccaag gtcgtggagt    120
ccgccaaggc cattctcggc ggcagcaagg tgcgcgtgga ccaaaagtgc aagtcgtccg    180
cccagatcga cccccacccc gtgatcgtca cctccaacac caacatgtgc gccgtgattg    240
acgggaacag caccacccttc gagcaccagc agccgttgca ggaccggatg ttcaagttcg    300
aactcacccg ccgtctggag cacgactttg gcaaggtgac caagcaggaa gtcaaagagt    360
tcttccgctg ggcgcaggat cacgtgaccg aggtggcgca tgagttctac gtcagaaagg    420
gcggagccag caaaagaccc gccccgatg acgcggatat aagcgagccc aagcgggcct    480 gccctcagt cgcggatcca tcgacgtcag acgcggaagg agctccggtg actttgccg    540 acaggtacca aaacaaatgt tctcgtcacg cgggcatgct tcagacgctg tttccctgca    600
aaacgtgcga gagaatgaat cagaatttca acatttgctt cacgcacggg gtcagagact    660
gctcagaatg tttccccggt gcatcagaat ctcaaccggt cgtcagaaaa aaaacgtatc    720
agaaactgtg tgccattcat catctgctgg ggcgggcacc cgagattgct tgctcggcct    780
gcgatctggt caacgtggac ctggacgact gtgtttctga gcaataaatg acttaaacca    840
ggtatggctg ccgatggtta tcttccagat tggcttgagg acaacctctc tgagggcatt    900
cgcgagtggt gggacctgaa acctggagcc ccgaaaccca agccaaccca gcaaaagcag    960
gacgacggcc ggggtctggt gcttcctggc tacaagtacc tcggacccctt caacggactc    1020 gacaaggggg agcccgtcaa cgcggcggac gcagcggccc tcgagcacga caaggcctac    1080
gaccagcagc tcaaagcggg tgacaatccg tacctgcggt ataaccacgc cgacgccgag    1140
tttcaggagc gtctgcaaga agatacgtct tttgggggca acctcggcg agcagtcttc    1200 caggccaaga agcgggttct cgaacctctc ggtctggttg aggaaggcgc taagacggct    1260
```

```
cctggaaaga agagaccggt agagccatca cctcagcgtt cccccgactc ctccacgggc    1320
atcggcaaga aaggccacca gcccgcgaga aagagactga actttgggca gactggcgac    1380
tcggagtcag tccccgaccc tcaaccaatc ggagaaccac cagcaggccc tctggtctg     1440 ggatctggta caatggctgc aggcggtggc gctccaatgg cagacaataa cgaaggcgcc    1500
gacggagtgg gtagttcctc aggaaattgg cattgcgatt ccacatggct gggcgacaga    1560
gtcatcacca ccagcacccg aacctgggcc ctgcccacct acaacaacca tctctacaag    1620
caaatctcca acgggacatc gggaggaagc actaacgaca cacctactt tggctacagc     1680 accccctggg ggtattttga cttcaacaga ttccactgcc acttctcacc acgtgactgg    1740
cagcgactca tcaacaataa ctggggattc cggcccaaga gactcaactt caagctcttc    1800
aacatccagg tcaaggaggt cacgcagaat gaaggcacca gaccatcgc caataacctt     1860 accagcacga ttcaggtgtt tacggactcg aataccagc tcccgtacgt cctcggctct     1920
gcgcaccagg gctgcctccc tccgttcccg gcggacgtct tcatgattcc tcagtacggg    1980
tatctgaccc taaacaatgg cagtcaggct gtgggccgtt cctccttcta ctgcctggaa    2040
tacttccctt ctcaaatgct gaggacgggc aacaactttg aattcagcta caccttcgag    2100
gacgtgcctt tccacagcag ctacgcgcac agccagagcc tggaccggct gatgaaccct    2160
ctcatcgacc agtacctgta ttacttatcc agaactcagt ccacaggagg aactcaaggt    2220
actcagcaat tgttatttc tcaagccggg cccgcaaaca tgtyggctca ggccaagaac    2280
tggctacctg gaccgtgtta ccgtcagcaa cgagtttcca cgacactgtc gcaaaacaac    2340
aacagcaatt ttgctggacc ggtgccacca                                     2370
```

<210> SEQ ID NO 41
<211> LENGTH: 3123
<212> TYPE: DNA
<213> ORGANISM: Unknown
<220> FEATURE:
<223> OTHER INFORMATION: AAV serotype, clone 43.12

<400> SEQUENCE: 41

```
gaattcgccc ttggctgcgt caactggacc aatgagaact ttcccttcaa cgattgcgtc      60
gacaagatgg tgatctggtg ggaggagggc aagatgacgg ccaaggtcgt ggagtccgcc     120
aaggccattc tcggcggcag caaggtgcgc gtggaccaaa agtgcaagtc gtccgcccag     180 atcgaccccca cccccgtgat cgtcacctcc aacaccaaca tgtgcgccgt gattgacggg    240
aacagcacca ccttcgagca ccagcagccg ttgcaggacc ggatgttcaa gttcgaactc    300
acccgccgtc tggagcacga ctttggcaag gtgaccaagc aggaagtcaa agagttcttc    360
cgctgggcgc aggatcacgt gaccgaggtg gcgcatgagt tctacgtcag aaagggcgga    420
gccagcaaaa gacccgcccc cgatgacgcg gatataagcg agcccaagcg ggcctgcccc    480
tcagtcgcgg atcatcgac gtcagacgcg gaaggagctc cggtggactt tgccgacagg    540
taccaaaaca aatgttctcg tcacgcgggc atgctccaga tgctgtttcc ctgcaaaacg    600
tgcgagagaa tgaatcagaa tttcaacatt tgcttcacgc acgggtcag agactgctca    660 gaatgtttcc ccgtgcatc agaatctcaa ccggtcgtca gaaaaaaaac gtatcagaaa     720
ctgtgtgcca ttcatcatct gctggggcgg gcacccgaga ttgcttgctc ggcctgcgat    780
ctggtcaacg tggacctgga cgactgtgtt tctgagcaat aaatgactta aaccaggtat    840
ggctgccgat ggttatcttc cagattggct tgaggacaac ctctctgagg gcattcgcga    900
gtggtgggac ctgaaacctg gagccccgaa acccaaagcc aaccagcaaa agcaggacga    960
```

```
cggccggggt ctggtgcttc ctggctacaa gtacctcgga cccttcaacg gactcgacaa    1020 ggggagccc  gtcaacgcgg cggacgcagc ggccctcgag cacgacaagg cctacgacca    1080
gcagctcaaa gcgggtgaca atccgtacct gcggtataac cacgccgacg ccgagtttca    1140
ggagcgtctg caagaagata cgtcttttgg gggcaacctc gggcgagcag tcttccaggc    1200
caagaagcgg gttctcgaac ctctcggtct ggttgaggaa ggcgctaaga cggctcctgg    1260
aaagaagaga ccgtagagc  catcacctca gcgttccccc gactcctcca cgggcatcgg    1320
caagaaaggc caccagcccg cgagaaagag actgaacttt gggcagactg cgactcgga    1380 gtcagtcccc gaccctcaac caatcggaga accaccagca ggcccctctg gtctgggatc    1440
tggtacaatg gctgcaggcg gtggcgctcc aatggcagac aataacgaag gcgccgacgg    1500
agtgggtagt tcctcaggaa attggcattg cgattccaca tggctgggcg acagagtcat    1560
caccaccagc acccgaacct gggccctgcc cacctacaac aaccatctct acaagcaaat    1620
ctccaacggg acatcgggag gaagcactaa cgacaacacc tactttggct acagcacccc    1680
ctgggggtat tttgacttca acagattcca ctgccacttc tcaccacgtg actggcagcg    1740
actcatcaac aataactggg gattccggcc caagagactc aacttcaagc tcttcaacat    1800
ccaggtcaag gaggtcacgc agaatgaagg caccaagacc atcgccaata accttaccag    1860
cacgattcag gtgtttacgg actcggaata ccagctcccg tacgtcctcg gctctgcgca    1920
ccagggctgc ctccctccgt tcccggcgga cgtcttcatg attcctcagt acgggtatct    1980
gaccctaaac aatggcagtc aggctgtggg ccgttcctcc ttctactgcc tggaatactt    2040
cccttctcaa atgctgagga cgggcaacaa ctttgaattc agctacacct tcgaggacgt    2100 gccttccac  agcagctacg cgcacagcca gagcctggac cggctgatga accctctcat    2160
cgaccagtac ctgtattact tatccagaac tcagtccaca ggaggaactc aaggtactca    2220
gcaattgtta ttttctcaag ccgggcccgc aaacatgtcg gctcaggcca gaactggct     2280 acctggaccg tgttaccgtc agcaacgagt ttccacgaca ctgtcgcaaa caacaacag    2340 caattttgct tggaccggtg ccaccaagta tcacctgaat ggcagagact ccctggttaa    2400
tcccggcgtt gccatggcta cccacaagga cgacgaggag cgcttcttcc cgtcaagcgg    2460
agttctaatg tttggcaagc agggggctgg aaaagacaat gtggactaca gcagcgtgat    2520
gctcaccagc gaagaagaaa ttaaaactac taacccagtg gctacagagc agtatggtgt    2580
ggtggcagac aacctgcagc agaccaacgg agctcccatt gtgggaactg tcaacagcca    2640
gggggcctta cctggtatgg tctggcaaaa ccggacgtg  tacctgcagg gccccatctg    2700
ggccaaaatt cctcacacgg acggcaactt tcatccttcg ccgctgatgg gaggctttgg    2760
actgaaacac ccgcctcctc agatcctggt gaaaaacact cctgttcctg cggatcctcc    2820
gaccaccttc agccaggcca agctggcttc ttttatcacg cagtacagca ccggacaggt    2880
cagcgtggaa atcgaatggg agctgcagaa agaaaacagc aagcgctgga acccagagat    2940
tcagtatact tccaactact acaaatctac aaatgtggac tttgctgtca atactgaggg    3000
tacttattca gagcctcgcc ccattggcac tcgttatctc acccgtaatc tgtaattgct    3060
tgttaatcaa taaaccggtt aattcgtttc agttgaactt tggtctctgc gaagggcgaa    3120
ttc                                                                 3123

<210> SEQ ID NO 42
<211> LENGTH: 3122
<212> TYPE: DNA
```

<213> ORGANISM: Unknown
<220> FEATURE:
<223> OTHER INFORMATION: AAV serotype, clone 43.20

<400> SEQUENCE: 42

```
gaattcgccc tttctacggc tgcgtcaact ggaccaatga aactttccc ttcaacgatt      60
gcgtcgacaa gatggtgatc tggtgggagg agggcaagat gacggccaag gtcgtggagt    120
ccgccaaggc cattctcggc ggcagcaagg tgcgtgtgga ccaaaagtgc aagtcttccg    180
cccagatcga tcccacccccc gtgatcgtca cctccaacac caacatgtgc gccgtgattg    240
acgggaacag cgccaccttc gagcaccagc agccgttgca ggaccggatg ttcaaatttg    300
aactcacccg ccgtctggag catgactttg gcaaggtgac gaagcaggaa gtcaaagagt    360
tcttccgctg ggcgcaggat cacgtgaccg aggtggcgca tgagttccac gtcagaaagg    420
gtggagccaa caagagaccc gcccccgatg acgcggatat aagcgagccc aagcgggcct    480
gccctcagt cgcggatcca tcgacgtcag acgcggaagg agctccggtg gactttgccg    540
acaggtacca aaacaaatgt tctcgtcacg cgggcatgct tcagatgctg tttccctgca    600
agacatgcga gagaatgaat cagaatttca acatttgctt cacgcacggg accagagact    660
gttcagaatg tttccccggc gtgtcagaat ctcaaccggt cgtcagaaag aggacgtatc    720
ggaaactctg tgcgattcat catctgctgg ggcgggctcc cgagattgct tgctcggcct    780
gcgatctggt caacgtggac ctggatgact gtgtttctga gcaataaatg acttaaacca    840
ggtatggctg ccgatggtta tcttccagat tggctcgagg acaacctctc tgagggcatt    900
cgcgagtggt gggacttgaa acctggagcc ccgaaaccca agccaaccac gcaaaagcag    960
gacgacggcc ggggtctggt gcttcctggc tacaagtacc tcggaccctt caacggactc   1020
gacaagggg agcccgtcaa cgcggcggac gcagcggccc tcgagcacga caaagcctac   1080
gaccagcagc tcaaagcggg tgacaatccg tacctgcggt ataatcacgc cgacgccgag   1140
tttcaggagc gtctgcaaga agatacgtct tttgggggca acctcgggcg agcagtcttc   1200
caggccaaga agcgggttct cgaacctctc ggtctggttg aggaaggcgc taagacggct   1260
cctggaaaga agagactggt agagcagtcg ccacaagagc cagactcctc ctcgggcatc   1320
ggcaagacag gccagcagcc cgctaaaaag agactcaatt ttggtcagac tggcgactca   1380
gagtcagtcc ccgacccaca acctctcgga gaacctccag cagcccctc aggtctggga   1440
cctaatacaa tggcttcagg cggtggcgct ccaatggcag acaataacga aggcgccgac   1500
ggagtgggta attcctcggg aaattggcat tgcgattcca catggctggg ggacagagtc   1560
atcaccacca gcacccgaac ctgggccctg cccacctaca acaaccacct ctacaagcaa   1620
atctccaacg gcacctcggg aggaagcacc aacgacaaca cctatttgg ctacagcacc   1680
ccctggggt attttgactt caacagattc cactgtcact tttcaccacg tgactggcaa   1740
cgactcatca caacaattg gggattccgg cccaaaagac tcaacttcaa gctgttcaac   1800
atccaggtca aggaagtcac gacgaacgaa ggcaccaaga ccatcgccaa taatctcacc   1860
agcaccgtgc aggtctttac ggactcggag taccagttac cgtacgtgct aggatccgct   1920
caccagggat gtctgcctcc gttccgcgcg gacgtcttca cggttcctca gtacggctat   1980
ttaactttaa acaatggaag ccaagccctg ggacgttcct ccttctactg tctggagtat   2040
ttcccatcgc agatgctgag aaccggcaac aactttcagt tcagctacac cttcgaggac   2100
gtgccttttcc acagcagcta cgcgcacagc cagagcctgg acaggctgat gaatcccctc   2160
atcgaccagt acctgtacta cctggtcaga acgcaaacga ctggaactgg agggacgcag   2220
```

| | |
|---|---|
| actctggcat tcagccaagc gggtcctagc tcaatggcca accaggctag aaattgggtg | 2280 |
| cccggacctt gctaccggca gcagcgcgtc tccacgacaa ccaaccagaa caacaacagc | 2340 |
| aactttgcct ggacgggagc tgccaagttt aagctgaacg gccgagactc tctaatgaat | 2400 |
| ccgggcgtgg caatggcttc ccacaaggat gacgacgacc gcttcttccc ttcgagcggg | 2460 |
| gtcctgattt ttggcaagca aggagccggg aacgatggag tggattacag ccaagtgctg | 2520 |
| attacagatg aggaagaaat caaggctacc aaccccgtgg ccacagaaga atatggagca | 2580 |
| gtggccatca acaaccaggc cgccaatacg caggcgcaga ccggactcgt gcacaaccag | 2640 |
| ggggtgattc ccgcatggt gtggcagaat agagacgtgt acctgcaggg tcccatctgg | 2700 |
| gccaaaattc ctcacacgga cggcaacttt caccgtctc ccctgatggg cggctttgga | 2760 |
| ctgaagcacc cgcctcctca aattctcatc aagaacacac cggttccagc ggacccgccg | 2820 |
| cttaccttca accaggccaa gctgaactct ttcatcacgc agtacagcac cggacaggtc | 2880 |
| agcgtggaaa tcgagtggga gctgcagaaa gaaaacagca aacgctggaa tccagagatt | 2940 |
| caatacactt ccaactacta caaatctaca aatgtggact tgctgtcaa cacggaagga | 3000 |
| gtttatagcg agcctcgccc cattggcacc cgttacctca cccgcaacct gtaattacat | 3060 |
| gttaatcaat aaaccggtta attcgtttca gttgaacttt ggtctctgcg aagggcgaat | 3120 |
| tc | 3122 |

<210> SEQ ID NO 43
<211> LENGTH: 3117
<212> TYPE: DNA
<213> ORGANISM: Unknown
<220> FEATURE:
<223> OTHER INFORMATION: AAV serotype, clone 43.21

<400> SEQUENCE: 43

| | |
|---|---|
| gaattcgccc ttggctgcgt caactggacc aatgagaact ttcccttcaa cgattgcgtc | 60 |
| gacaagatgg tgatctggtg ggaggagggc aagatgacgg ccaaggtcgt ggagtccgcc | 120 |
| aaggccattc tcggcggcag caaggtgcgt gtggaccaaa agtgcaagtc ttccgcccag | 180 |
| atcgatccca cccccgtgat cgtcacctcc aacaccaaca tgtgcgccgt gattgacggg | 240 |
| aacagcacca ccttcgagca ccagcagccc ttgcaggacc ggatgttcaa atttgaactc | 300 |
| acccgccgtc tggagcatga ctttggcaag gtgacgaagc aggaagtcaa agagttcttc | 360 |
| cgctgggcgc aggatcacgt gaccgaggtg cgcatgagt ccacgtcag aaagggtgga | 420 |
| gccaacaaga gacccgcccc cgatgacgcg gatataagcg agcccaagcg ggcctgcccc | 480 |
| tcagtcgcgg atccatcgac gtcagacgcg gaaggagctc cggtggactt gccgacagg | 540 |
| taccaaaaca aatgttctcg tcacgcgggc atgcttcaga tgctgtttcc ctgcaagaca | 600 |
| tgcgagagaa tgaatcagaa tttcaacatt gcttcacgc acgggaccag agactgttca | 660 |
| gaatgtttcc ccgcgtgtc agaatctcaa ccggtcgtca gaaagaggac gtatcggaaa | 720 |
| ctctgtgcga ttcatcatct gctggggcgg gctcccgaga ttgcttgctc ggcctgcgat | 780 |
| ctggtcaacg tggacctgga tgactgtgtt tctgagcaat aaatgactta aaccaggtat | 840 |
| ggctgccgat ggttatcttc cagattggct cgaggacaac ctctctgagg gcattcgcga | 900 |
| gtggtgggac ttgaaacctg gagccccgaa acccaaagcc aaccagcaaa agcaggacga | 960 |
| cggccggggg ctggtgcttc ctggctacaa gtacctcgga cccttcaacg gactcgacaa | 1020 |
| gggggagccc gtcaacgcgg cggacgcagc ggccctcgag cacgacaaag cctacgacca | 1080 |

```
gcagctcaaa gcgggtgaca atccgtacct gcggtataat cacgccgacg ccgagtttca   1140
ggagcgtctg caagaagata cgtcttttgg gggcaacctc gggcgagcag tcttccaggc   1200
caagaagcgg gttctcgaac ctctcggtct ggttgaggaa ggcgctaaga cggctcctgg   1260
aaagaagaga ccggtagagc agtcgccaca agagccagac tcctcctcgg gcatcggcaa   1320
gacaggccag cagcccgcta aaagagact caattttggt cagactggcg actcagagtc   1380
agtccccgac ccacaacctc tcggagaacc tccagcagcc ccctcaggtc tgggacctaa   1440
tacaatggct tcaggcggtg gcgctccaat ggcagacaat aacgaaggcg ccgacggagt   1500
gggtaattcc tcgggaaatt ggcattgcga ttccacatgg ctgggggaca gagtcatcac   1560
caccagcacc cgaacctggg ccctgcccac ctacaacaac cacctctaca gcaaatctc   1620
caacggcacc tcgggaggaa gcaccaacga caacacctat tttggctaca gcacccctg   1680
ggggtatttt gacttcaaca gattccactg tcacttttca ccacgtgact ggcaacgact   1740
catcaacaac aattgggat tccggcccaa aagactcaac ttcaagctgt caacatcca   1800
ggtcaaggaa gtcacgacga acgaaggcac caagaccatc gccaataatc tcaccagcac   1860
cgtgcgggtc tttacggact cggagtacca gttaccgtac gtgctaggat ccgctcacca   1920
gggatgtctg cctccgttcc cggcggacgt cttcatggtt cctcagtacg ctatttaac   1980
tttaaacaat ggaagccaag ccctgggacg ttcctccttc tactgtctgg agtatttccc   2040
atcgcagatg ctgagaaccg gcaacaactt tcagttcagc tacaccttcg aggacgtgcc   2100
tttccacagc agctacgcgc acagccagag cctggacagg ctgatgaatc ccctcatcga   2160
ccagtacctg tactcctgg tcagaacgca aacgactgga actggaggga cgcagactct   2220
ggcattcagc caagcgggtc ctagctcaat ggccaaccag gctagaaatt gggtgcccgg   2280
accttgctac cggcagcagc gcgtctccac gacaaccaac cagagcaaca acagcaactt   2340
tgcctggacg ggagctgcca gtttaagct gaacggccga gactctctaa tgaatccggg   2400
cgtggcaatg gcttcccaca aggatgacga cgaccgcttc ttccctcga gcggggtcct   2460
gattttggc aagcaaggag ccgggaacga tggagtggat tacagccaag tgctgattac   2520
agatgaggaa gaaatcaagg ctaccaaccc cgtggccaca gaagaatatg agcagtggc   2580
catcaacaac caggccgcca atcgcaggc gcagaccgga ctcgtgcaca accaggggt   2640
gattcccggc atggtgtggc agaatagaga cgtgtacctg cagggtccca tctgggccaa   2700
aattcctcac acggacggca actttcaccc gtctcccctg atgggcggct ttggactgaa   2760
gcacccgcct cctcaaattc tcatcaagaa cacaccggtt ccagcggacc cgccgcttac   2820
cttcaaccag gccaagctga actctttcat cacgcagtac agcaccggac aggtcagcgt   2880
ggaaatcgag tgggagctgc agaaagaaaa cagcaaacgc tggaatccag agattcaata   2940
cacttccaac tactacaaat ctacaaatgt ggactttgct gtcaacacgg aaggagttta   3000
tagcgagcct cgccccattg gcacccgtta cctcacccgc aacctgtaat tacatgttaa   3060
tcaataaacc ggttaattcg tttcagttga actttggtct ctgcgaaggg cgaattc      3117
```

<210> SEQ ID NO 44
<211> LENGTH: 3121
<212> TYPE: DNA
<213> ORGANISM: Unknown
<220> FEATURE:
<223> OTHER INFORMATION: AAV serotype, clone 43.23

<400> SEQUENCE: 44

```
gaattcgccc ttctacggct gcgtcaactg gaccaatgag aactttccct tcaacgattg     60
```

```
cgtcgacaag atggtgatct ggtgggagga gggcaagatg acggccaagg tcgtggagtc    120
cgccaaggcc attctcggcg gcagcaaggt gcgtgtggac caaaagtgca agtcttccgc    180
ccagatcgat cccaccccg tgatcgtcac ctccaacacc aacatgtgcg ccgtgattga    240
cgggaacagc accaccttcg agcaccagca gccgttgcag gaccggatgt tcaaatttga    300
actcacccgc cgtctggagc atgactttgg caaggtgacg aagcaggaag tcaaagagtt    360
cttccgctgg gcgcaggatc acgtgaccga ggtggcgcat gagttccacg tcagaaaggg    420
tggcgccaac aagagacccg ccccgatga cgcggatata agcgagccca gcgggcctg    480 cccctcagtc gcggatccat cgacgtcaga gcggaagga gctccggtgg actttgccga    540
caggtaccaa acaaatgtt ctcgtcacgc gggcatgctt cagatgctgt ttccctgcaa    600
gacatgcgag agaatgaatc agaatttcaa catttgcttc acgcacggga ccagagactg    660
ttcagaatgt tccccggcg tgtcagaatc tcaaccggtc gtcagaaaga ggacgtatcg    720
gaaactctgt gcgattcatc atctgctggg gcgggctccc gagattgctt gctcggcctg    780
cgatctggtc aacgtggacc tggatgactg tgtttctgag caataaatga cttaaaccag    840
gtatggctgc cgatggttat cttccagatt ggctcgagga caacctctct gagggcattc    900
gcgagtggtg ggacttgaaa cctggagccc cgaaacccaa agccaaccag caaaagcagg    960
acgacggccg gggtctggtg cttcctggct acaagtacct cggacccttc aacggactcg    1020
acaaggggga gcccgtcaac gcggcggacg cagcggccct cgagcacgac aaagcctacg    1080
accagcagct caaagcgggt gacaatccgt acctgcggta taatcacgcc gacgccgagt    1140 tcaggagcg tctgcaagaa gatacgtcct ttggggggcaa cctcgggcga gcagtcttcc    1200
aggccaagaa gcgggttctc gaacctctcg gtctggttga ggaaggcgct aagacggctc    1260
ctggaaagaa gagaccggta gagcagtcgc cacaagagcc agactcctcc tcgggcatcg    1320
gcaagacagg ccagcagccc gctaaaaaga gactcaattt tggtcagact ggcgactcag    1380
agtcagtccc cgacccacaa cctctcggag aacctccagc agcccctca ggtctgggac    1440 ctaatacaat ggcttcaggc ggtggcgctc caatggcaga caataacgaa ggcgccgacg    1500
gagtgggtaa ttcctcggga aattggcatt gcgattccac atggctgggg gacagagtca    1560
tcaccaccag cacccgaacc tgggccctgc ccacctacaa caaccacctc tacagcaaa    1620 tctccaacgg cacctcggga ggaagcacca acgacaacac ctatttggc tacagcaccc    1680 cctgggggta ttttgacttc aacagattcc actgtcactt ttcaccacgt gactggcaac    1740
gactcatcaa caacaattgg ggattccggc caaaagact caacttcaag ctgttcaaca    1800
tccaggtcaa ggaagtcacg acgaacgaag gcaccaagac catcgccaat aatctcacca    1860
gcaccgtgca ggtctttacg gacttggagt accagttacc gtacgtgcta ggatccgctc    1920
accagggatg tctgcctccg ttcccggcgg acgtcttcat ggttcctcag tacggctatt    1980
taactttaaa caatggaagc caagccctgg acgttcctc cttctactgt ctggagtatt    2040
tcccatcgca gatgccgaga accggcaaca actttcagtt cagctacacc ttcgaggacg    2100
tgcctttcca cagcagctac gcgcacagcc agagcctgga caggctgatg aatcccctca    2160
tcgaccagta cctgtactac ctggtcagaa cgcaaacgac tggaactgga gggacgcaga    2220
ctctggcatt cagccaagcg gtcctagct caatggccaa ccaggctaga aattgggtgc    2280
ccggaccttg ctaccggcag cagcgcgtct ccacgacaac caaccagaac aacaacagca    2340
actttgcctg gacgggagct gccaagttta agctgaacgg ccgagactct ctaatgaatc    2400
```

```
cgggcgtggc aatggcttcc cacaaggatg acgacgaccg cttcttccct tcgagcgggg    2460
tcctgatttt tggcaagcaa ggagccggga acgatggagt ggattacagc caagtgctga    2520
ttacagatga ggaagaaatc aaggctacca accccgtggc cacagaagaa tatggagcag    2580
tggccatcaa caaccaggcc gccaatacgc aggcgcagac cggactcgtg cacaaccagg    2640
gggtgattcc cggcatggtg tggcagaata gagacgtgta cctgcagggt cccatctggg    2700
ccaaaattcc tcacacggac ggcaactttc acccgtctcc cctgatgggc ggctttggac    2760
tgaagcaccc gcctcctcaa attctcatca agaacacacc ggttccagcg acccgccgc    2820 ttaccttcaa ccaggccaag ctgaactctt tcatcacgca gtacagcacc ggacaggtca    2880
gcgtggaaat cgagtgggag ctgcagaaag aaaacagcaa acgctggaat ccagagattc    2940
aatacacttc caactactac aaatctacaa atgtggactt tgctgtcaac acggaaggag    3000
tttatagcga gcctcgcccc attggcaccc gttacctcac ccgcaacctg taattacatg    3060
ttaatcaata aaccggttaa ttcgtttcag ttgaactttg gtctctgcga agggcgaatt    3120
c                                                                     3121
```

<210> SEQ ID NO 45
<211> LENGTH: 3122
<212> TYPE: DNA
<213> ORGANISM: Unknown
<220> FEATURE:
<223> OTHER INFORMATION: AAV serotype, clone 43.25

<400> SEQUENCE: 45

```
gaattcgccc tttctacggc tgcgtcaact ggaccaatga gaactttccc ttcaacgatt     60
gcgtcgacaa gatggtgatc tggtgggagg agggcaagat gacggccaag gtcgtggagt    120
ccgccaaggc cattctcggc ggcagcaagg tgcgtgtgga ccaaaagtgc aagtcttccg    180
cccagatcga tcccaccccc gtgatcgtca cctccaacac caacatgtgc gccgtgattg    240
acgggaacag caccaccttc gagcaccagc agccgttgca ggaccggatg ttcaaatttg    300
aactcacccg ccgtctggag catgactttg gcaaggtgac gaagcaggaa gtcaaagggt    360
tcttccgctg ggcgcaggat cacgtgaccg aggtggcgca tgagttccac gtgcgagccc    420
aagcgggcct gcccctcagt cgcggatcca tcgacgtcag accagaaagg gtggagccaa    480
caagagaccc gccccgatg acgcggatat aagcggaagg agctccggtg gactttgccg    540
acaggtacca aaacaaatgt tctcgtcacg cgggcatgct tcagatgctg tttccctgca    600
agacatgcga gagaatgaat cagaatttca acatttgctt cacgcacggg accagagact    660
gttcagaatg tttccccggc gtgtcagaat ctcaaccggt cgtcagaaag aggacgtatc    720
ggaaactctg tgcgattcat catctgctgg ggcgggctcc cgagattgct tgctcggcct    780
gcgatctggt caacgtggac ctggatgact gtgtttctga gcaataaatg acttaaacca    840
ggtatggctg ccgatggtta tcttccagat tggctcgagg acaacctctc tgagggcatt    900
cgcgagtggt gggacttgaa acctggagcc ccgaaaccca agccaaccag caaaagcag    960 gacgacggcc ggggtctggt gcttcctggc tacaagtacc tcggaccctt caacggactc   1020
gacaaggggg agcccgtcaa cgcggcggac gcagcggccc tcgagcacga caaagcctac   1080
gaccagcagc tcaaagcggg tgacaatccg tacctgcggt ataatcacgc cgacgccgag   1140
tttcaggagg tctgcaaga agatacgtct tttgggggca acctcggcg agcagtcttc   1200 caggccaaga gcgggttct cgaacctctc ggtctggttg aggaaggcgc taagacggct   1260
cctggaaaga agagaccggt agagcagtcg ccacaagagc cagactcctc ctcgggcatc   1320
```

```
ggcaagacag gccagcagcc cgctaaaaag agactcaatt ttggtcagac tggcgactca    1380
gagtcagtcc ccgacccaca acctctcgga gaacctccag cagccccctc aggtctggga    1440
cctaatacaa tggcttcagg cggtggcgct ccaatggcag acaataacga aggcgccgac    1500
ggagtgggta attcctcggg aaattggcat tgcgattcca catggctggg ggacagagtc    1560
atcaccacca gcacccgaac ctgggccctg cccacctaca acaaccacct ctacaagcaa    1620
atctccaacg gcacctcggg aggaagcacc aacgacaaca cctatttggg ctacagcacc    1680
ccctgggggt attttgactt caacagattc cactgtcact tttcaccacg tgactggcaa    1740
cgactcatca caacaattgg ggattccggg cccaaaagac tcaacttcaa gctgttcaac    1800
atccaggtca aggaagtcac gacgaacgaa ggcaccaaga ccatcgccaa taatctcacc    1860
agcaccgtgc aggtctttac ggactcggag taccagttac cgtacgtgct aggatccgct    1920
caccagggat gtctgcctcc gttccggcg gacgtcttca tggttcctca gtacggctat    1980
ttaactttaa acaatggaag ccaagccctg gacgttcct ccttctactg tctggagtat    2040
ttcccatcgc agatgctgag aaccggcaac aactttcagt tcagctacac cttcgaggac    2100 gtgccttttcc acagcagcta cgcgcacagc cagagcctgg acaggctgat gaatcccctc    2160
atcgaccagt acctgtacta cctggtcaga acgcaaacga ctggaactgg agggacgcag    2220
actctggcat tcagccaagc gggtcctagc tcaatggcca accaggctag aaattgggtg    2280
cccggacctt gctaccggca gcagcgcgtc tccacgacaa ccaaccagaa caacaacagc    2340
aactttgcct ggacgggagc tgccaagttt aagctgaacg gccgagactc tctaatgaat    2400
ccgggcgtgg caatggcttc ccacaaggat gacgacgacc gcttcttccc ttcgagcggg    2460
gtcctgattt ttggcaagca aggagccggg aacgatggag tggattacag ccaagtgctg    2520
attacagatg aggaagaaat caaggctacc aaccccgtgg ccacagaaga atatgagca    2580 gtggccatca caaccaggc cgccaatacg caggcgcaga ccggactcgt gcacaaccag    2640
ggggtgattc ccggcatggt gtggcagaat agagacgtgt acctgcaggg tcccatctgg    2700
gccaaaattc ctcacacgga cggcaacttt caccgtctc ccctgatggg cggctttgga    2760
ctgaagcacc cgcctcctca aattctcatc aagaacacac cggttccagc ggacccgccg    2820
cttaccttca accaggccaa gctgaactct ttcatcacgc agtacagcac cggacaggtc    2880
agcgtggaaa tcgagtggga gctgcagaaa gaaaacagca acgctggaa tccagagatt    2940 caatacactt ccaactacta caaatctaca aatgtggact tgctgtcaa cacggagggg    3000 gtttatagcg agcctcgccc cattggcacc cgttacctca cccgcaacct gtaattacat    3060
gttaatcaat aaaccggtta attcgtttca gttgaacttt ggtctctgcg aagggcgaat    3120
tc                                                                  3122
```

<210> SEQ ID NO 46
<211> LENGTH: 3128
<212> TYPE: DNA
<213> ORGANISM: Unknown
<220> FEATURE:
<223> OTHER INFORMATION: AAV serotype, clone 44.1

<400> SEQUENCE: 46

```
gaattcgccc tttctacggc tgcgtcaact ggaccaatga gaactttccc ttcaacgatt     60
gcgtcgacaa gatgttgatc tggtgggagg agggcaagat gacggccaag gtcgtggagt    120
ccgccaaggc cattctcggc ggcagcaaag tgcgcgtgga ccaaaagtgc aagccgtccg    180
```

```
cccagatcga ccccaccccc gtgatcgtca cctccaacac caacatgtgc gccgtgattg      240
acgggaacag caccaccttc gagcaccagc agccgttgcg ggaccggatg ttcaagtttg      300
aactcacccg ccgtctggag cacgactttg gcaaggtgac aaagcaggaa gtcagagagt      360
tcttccgctg ggcgcaggat cacgtgaccg aggtggcgca cgagttctac gtcagaaagg      420
gtggagccaa caagagaccc gcccccgatg acgcggataa aagcgagccc aagcgggcct      480
gcccctcagt cgcggatcca tcgacgtcag acgcggaagg agctccggtg gactttgccg      540
acaggtacca aaacaaatgt tctcgtcacg cgggcatgct tcagatgctg tttccctgca      600
aaacatgcga gagaatgaat cagaatttca acatttgctt cacgcacggg accagagact      660
gttcagaatg tttccccggc gtgtcagaat ctcaaccggt cgtcagaaaa aagacgtatc      720
ggaaactctg tgcgattcat catctgctgg ggcgggcacc cgagattgct tgctcggcct      780
gcgatctggt caacgtggac ctagatgact gtgtttctga gcaataaatg acttaaacca      840
ggtatggctg ccgatggtta tcttccagat tggctcgagg acaacctctc tgagggcatt      900
cgcgagtggt gggacttgaa acctggagcc ccgaaaccca agccaaacca gcaaaagcag      960
gacgacggcc ggggtctggt gcttcctggc tacaagtacc tcggacccct caacggactc     1020
gacaaggggg agcccgtcaa cgcggcggac gcagcggccc tcgagcacga caaggcctac     1080
gaccagcagc tcaaagcggg tgacaatccg tacctgcggt ataaccacgc cgacgccgag     1140
tttcaggagc gtctgcaaga agatacgtct tttgggggca acctcgggcg agcagtcttc     1200
caggccaaga gcgggttctc gaacctctcg gtctggttg aggaaggcgc taagacggct     1260
cctgaaagaa agagaccggt agagccatca ccccagcgtt ctccagactc ctctacgggc     1320
atcggcaaga aaggccagca gcccgcgaaa aagagactca actttgggca gactggcgac     1380
tcagagtcag tgcccgaccc tcaaccaatc ggagaacccc ccgcaggccc ctctggtctg     1440
ggatctggta caatggctgc aggcggtggc gctccaatgg cagacaataa cgaaggcgcc     1500
gacggagtgg gtagttcctc aggaaattgg cattgcgatt ccacatggct gggcgacaga     1560
gtcatcacca ccagcacccg aacctgggcc ctccccacct acaacaacca cctctacaag     1620
caaatctcca acgggacttc gggaggaagc accaacgaca caccttactt cggctacagc     1680
accccctggg ggtattttga ctttaacaga ttccactgcc acttctcacc acgtgactgg     1740
cagcgactca tcaacaacaa ctgggggatt cggcccaaga gactcaactt caagctcttc     1800
aacatccagg tcaaggaggt cacgcagaat gaaggcacca gaccatcgc caataacctt     1860 accagcacga ttcaggtctt tacgactcg gaataccagc tcccgtacgt cctcggctct     1920
gcgcaccagg gctgcctgcc tccgttcccg gcggacgtct tcatgattcc tcagtacggg     1980
tacctgactc tgaacaatgg cagtcaggcc gtgggccgtt cctccttcta ctgcctggag     2040
tactttcctt ctcaaatgct gagaacgggc aacaactttg agttcagcta ccagtttgag     2100
gacgtgcctt ttcacagcag ctacgcgcac agccaaagcc tggaccggct gatgaacccc     2160
ctcatcgacc agtacctgta ctacctgtct cggactcagt ccacgggagg taccgcagga     2220
actcagcagt tgctatttc tcaggccggg cctaataaca tgtcggctca ggccaaaaac     2280
tggctacccg gccctgcta ccggcagcaa cgcgtctcca cgacactgtc gcaaaataac     2340
aacagcaact gtaaatcccg tgtcgctat ggcaacccac aaggacgacg aagagcgatt     2400
ttgcctggac cggtgccacc aagtatcatc tgaatggcag agactctctg ttttccgtcc     2460
agcggagtct taatgtttgg gaaacaggga gctggaaaag caacgtggca ctatagcagc     2520
gttatgctaa ccagtgagga agaaattaaa accaccaacc cagtggccac ggaacagtac     2580
```

-continued

```
ggcgtggtgg ccgataacct gcaacagcaa aacgccgctc ctattgtagg ggccgtcaac      2640
agtcaaggag ccttacctgg catggtctgg cagaaccggg acgtgtacct gcagggtcct      2700
atctgggcca agattcctca cacggacgga aactttcatc cctcgccgct gatgggaggc      2760
tttggactga aacacccgcc tcctcagatc ctgattaaga atacacctgt tcccgcggat      2820
cctccaacta ccttcagtca agctaagctg gcgtcgttca tcacgcagta cagcaccgga      2880
caggtcagcg tggaaattga atgggagctg cagaaagaaa acagcaaacg ctggaaccca      2940
gagattcaat acacttccaa ctactacaaa tctacaaatg tggacttcgc tgttaacaca      3000
gatggcactt attctgagcc tcgccccatt ggcacccgtt acctcacccg taatctgtaa      3060
ttgctcgtta atcaataaac cggttgattc gtttcagttg aactttggtc tctgcgaagg      3120
gcgaattc                                                              3128
```

<210> SEQ ID NO 47
<211> LENGTH: 3128
<212> TYPE: DNA
<213> ORGANISM: Unknown
<220> FEATURE:
<223> OTHER INFORMATION: AAV serotype, clone 44.5

<400> SEQUENCE: 47

```
gaattcgccc tttctacggc tgcgtcaact ggaccaatga gaactttccc ttcaacgatt        60
gcgtcgacaa gatggtgatc tggtgggagg agggcaagat gacggccaag gtcgtggagt       120
ccgccaaggc cattctcggc ggcagcaaag tgcgcgtgga ccaaaagtgc aagtcgtccg       180
cccagatcga ccccaccccc gtgatcgtca cctccaacac caacatgtgc gccgtgattg       240
acggaaacag caccaccttc gagcaccagc agccgttgca ggaccggatg ttcaagtttg       300
aactcacccg ccgtctggag cacgactttg gcaaggtgac aaagcaggaa gtcagagagt       360
tcttccgctg ggcgcaggat cacgtgaccg aggtggcgca cgagttctac gtcagaaagg       420
gtggagccaa caagagaccc gcccccgatg acgcggataa aagcgagccc aagcgggcct       480
gccccctcag tcgcggatcc tcgacgtcag acgcggaagg agctccggtg gactttgccg       540
acaggtacca aaacaaatgt tctcgtcacg cgggcatgct tcagatgctg tttccctgca       600
aaacatgcga gagaatgaat cagaatttca catttgctt cacgcacggg accagagact       660
gttcagaatg tttccccggc gtgtcagaat ctcaaccggt tgtcagaaaa aagacgtatc       720
ggaaactctg tgcgattcat catctgctgg ggcgggcacc cgagattgct tgctcggcct       780
gcgatctggt caacgtggac ctagatgact gtgtttctga gcaataaatg acttaaacca       840
ggtatggctg ccgatggtta tcttccagat tggctcgagg acaacctctc tgagggcatt       900
cgcgagtggt gggacttgaa acctggagcc ccgaaaccca agccaaccca gcaaaagcag       960
gacgacggcc ggggtctggt gcttcctggc tacaagtacc tcggacccct caacggactc      1020 gacaagggg agcccgtcaa gcggcggac gcagcggccc tcgagcacga caaggcctac      1080
gaccagcagc tcaaagcggg tgacaatccg tacctgcggt ataaccacgc cgacgccgag      1140
tttcaggagc gtctgcaaga agatacgtct tttgggggca acctcgggcg agcagtcttc      1200
caggccaaga agcgggttct cgaacctctc ggtctggttg aggaaggcgc taagacggct      1260
cctggaaaga gagaccggt agagccatca ccccagcgtt ctccagactc ctctacgggc      1320
atcggcaaga aggccagca gcccgcgaaa aagagactca actttgggca gactggcgac      1380
tcagagtcag tgcccgaccc tcaaccaatc ggagaacccc ccgcaggccc ctctggtctg      1440
```

```
ggatctggta caatggctgc aggcggtggc gctccaatgg cagacaataa cgaaggcgcc   1500
gacggagtgg gtagttcctc aggaaattgg cattgcgatt ccacatggct gggcgacaga   1560
gtcatcacca ccagcacccg aacctgggcc ctccccacct acaacaacca cctctacaag   1620
caaatctcca acgggacttc gggaggaagc accaacgaca cacctactt cggctacagc    1680 accccctggg ggtattttga ctttaacaga ttccactgcc acttctcacc acgtgactgg   1740
cagcgactca tcaacaacaa ctggggattc cggcccaaga gacccaactt caagctcttc   1800
aacatccagg tcaaggaggt cacgcagaat gaaggcacca agaccatcgc caataacctt   1860
accagcacga ttcaggtctt tacgactcg gaataccagc tcccgtacgt cctcggctct     1920
gcgcaccagg gctgcctgcc tccgttcccg gcggacgtct tcatgattcc tcagtacggg   1980
tacctgactc tgaacaatgg cagtcaggcc gtgggccgtt cctccttcta ctgcctggag   2040
tactttcctt ctcaaatgct gagaacgggc aacaactttg agttcagcta ccagtttgag   2100
gacgtgcctt ttcacagcag ctacgcgcac agccaaagcc tggaccggct gatgaacccc   2160
ctcatcgacc agtacctgta ctacctgtct cggactcagt ccacgggagg taccgcagga   2220
actcagcagt tgctattttc tcaggccggg cctaataaca tgtcggctca ggccaaaaac   2280
tggctacccg ggcctgcta ccggcagcaa cgcgtctcca cgacactgtc gcaaaataac    2340
aacagcaact tgcctggac cggtgccacc aagtatcatc tgaatggcag agactctctg    2400
gtaaatcccg tgtcgctat ggcaacccac aaggacgacg aagagcgatt ttttccgtcc     2460
agcggagtct taatgtttgg gaaacaggga gctggaaaag acaacgtgga ctatagcagc    2520
gttatgctaa ccagtgagga agaaattaaa accaccaacc cagtggccac agaacagtac   2580
ggcgtggtgg ccgataacct gcaacagcaa acgccgctc ctattgtagg ggccgtcaac     2640
agtcaaggag ccttacctgg catggtctgg cagaaccggg acgtgtacct gcagggtcct   2700
atctgggcca agattcctca cacggacgga aactttcatc cctcgccgct gatgggaggc   2760
tttggactga aacacccgcc tcctcagatc ctgattaaga atacacctgt tcccgcggat   2820
cctccaacta ccttcagtca agctaagctg gcgtcgttca tcacgcagta cagcaccgga   2880
caggtcagcg tggaaattga atgggagctg cagaaagaaa acagcaaacg ctggaaccca   2940
gagattcaat acacttccaa ctactacaaa tctacaaatg tggactttgc tgttaacaca   3000
gatggcactt attctgagcc tcgccccatt ggcacccgtt acctcacccg taatctgtaa   3060
ttgcttgtta atcaataaac cggttgattc gtttcagttg aactttggtc tctgcgaagg   3120
gcgaattc                                                           3128

<210> SEQ ID NO 48
<211> LENGTH: 1933
<212> TYPE: DNA
<213> ORGANISM: Unknown
<220> FEATURE:
<223> OTHER INFORMATION: AAV serotype, clone 223.10
<220> FEATURE:
<221> NAME/KEY: misc_feature
<222> LOCATION: (1302)..(1302)
<223> OTHER INFORMATION: can be a, c, g or t

<400> SEQUENCE: 48
caaggcctac gaccagcagc tcaaagcggg tgacaatccg tacctgcggt ataaccacgc     60
cgacgccgag tttcaggagc gtcttcaaga agatacgtct tttggggca acctcggcg      120 agcagtcttc caggccaaaa agcgggttct cgaacctctt ggtctggttg agacgccagc   180
taagacggca cctggaaaga agcgaccggt agactcgcca gactccaccct cgggcatcgg    240
```

```
caagaaaggc cagcagcccg cgaaaaagag actcaacttt gggcagactg gcgactcaga      300
gtcagtcccc gaccctcaac caatcggaga accaccagca ggcccctctg gtctgggatc      360
tggtacaatg gctgcaggcg gtggcgcacc aatggctgac aataacgagg gcgccgacgg      420
agtgggtaat gcctcaggaa attggcattg cgattccaca tggctgggcg acagagtcat      480
caccaccagc acccgaacct gggccctgcc cacctacaac aaccacctct acaagcaaat      540
ctccagtcag tcagcaggga gcaccaacga taacgtctat ttcggctaca gcacccctg      600 ggggtatttt gacttcaaca gattccattg ccacttctca ccacgtgact ggcagcgact      660
tatcaacaac aactggggat tccggcccaa gaagctcaac ttcaagctct caacatcca      720 ggtcaaggag gtcacgacga atgacggtgt cacaaccatc gctaataacc ttaccagcac      780
ggttcaggtc ttttcggact cggaatatca actgccgtac gtcctcggct ccgcgcacca      840
gggctgcctg cctccgttcc cggcagacgt gttcatgatt ccgcagtacg gatacctgac      900
tctgaacaat ggcagccaat cggtaggcc ttcctccttc tactgcctgg agtactttcc      960
ttctcagatg ctgagaacgg gcaacaactt cacctttagc tacaccttcg aggacgtgcc     1020
tttccacagc agctacgcgc acagccgag tctggaccgg ctgatgaatc ccctcatcga     1080
ccagtacctg tactacttgg ccagaacaca gagcaacgca ggaggtactg ctggcaatcg     1140
ggaactgcag ttttatcagg gcggacctac caccatggcc gaacaagcaa agaactggct     1200
gcccggacct tgcttccggc aacagagagt atccaagacg ctggatcaaa ataacaacag     1260
caactttgcc tggactggtg ccacaaaata ccatttaaat gnaagaaatt cattggttaa     1320
tcccggtgtc gccatggcaa cccacaagga cgacgaggaa cgcttcttcc cttcgagcgg     1380
agttctaatt tttggcaaaa ctggagcagc taataaaact acattagaaa acgtgctcat     1440
gacaaatgaa gaagaaattc gtcctaccaa cccggtagct accgaggaat acgggattgt     1500
aagcagcaac ttgcaggcgg ctagcaccgc agcccagaca caagttgtta acaaccaggg     1560
agccttacct ggcatggtct ggcagaaccg ggacgtgtac ctgcaaggtc ccatttgggc     1620
caagattcct cacacggacg gcaactttca cccgtctcct ctaatgggtg gctttggact     1680
gaaacacccg cctccccaga tcctgatcaa aaacacaccg gtacctgcta atcctccaga     1740
agtgtttact cctgccaagt ttgcttcctt catcacgcag tacagcaccg gcaagtcag      1800 cgttgagatc gagtgggagc tgcagaaaga gaacagcaag cgctggaacc cagagattca     1860
gtacacctcc aactttgaca aacagactgg agtggacttt gctgttgaca gccagggtgt     1920
ttactctgag cct                                                        1933
```

<210> SEQ ID NO 49
<211> LENGTH: 1933
<212> TYPE: DNA
<213> ORGANISM: Unknown
<220> FEATURE:
<223> OTHER INFORMATION: AAV serotype, clone 223.2

<400> SEQUENCE: 49

```
caaggcctac gaccagcagc tcaaagcggg tgacaatccg tacctgcggt ataaccacgc       60
cgacgccgag tttcaggagt gtcttcaaga agatacgtct tttggggca acctcgggcg      120 agcagtcttc caggccaaaa agcgggttct cgaacctctt ggtctggttg agacgccagc      180
taagacggca cctggaaaga gcgaccggt agactcgcca gactccacct cgggcatcgg      240
caagaaaggc cagcagcccg cgaaaaagag actcaacttt gggcagactg gcgactcaga      300
```

-continued

```
gtcagtcccc gaccctcaac caatcggaga accaccagca ggcccctctg gtctgggatc    360
tggtacaatg gttgcaggcg gtggcgcacc aatggctgac aataacgagg gcgccgacgg    420
agtgggtaat gcctcaggaa attggcattg cgattccaca tggctgggcg acagagtcat    480
caccaccagc acccgaacct gggccctgcc cacctacaac aaccacctct acaagcaaat    540
ctccagtcag tcagcaggga gcaccaacga taacgtctat ttcggctaca gcacccctg     600
ggggtatttt gacttcaaca gattccattg ccacttctca ccacgtgact ggcagcgact    660
tatcaacaac aactggggat ccggcccaa gaagctcaac ttcaagctct tcaacatcca     720
ggtcaaggag gtcacgacga atgacggtgt cacaaccatc gctaataacc ttaccagcac    780
ggttcaggtc ttttcggact cggaatatca actgccgtac gtcctcggct ccgcgcacca    840
gggctgcctg cctccgttcc cggcagacgt gttcatgatt ccgcagtacg atacctgac     900
tctgaacaat ggcagccaat cggtaggccg ttcctccttc tactgcctgg agtactttcc    960
ttctcagatg ctgagaacgg caacaactt caccttagc tacaccttcg aggacgtgcc     1020
tttccacagc agctacgcgc acagccagag tctggaccgg ctgatgaatc ccctcatcga   1080
ccagtacctg tactacttgg ccagaacaca gagcaacgca ggaggtactg ctggcaatcg   1140
ggaactgcag ttttatcagg gcggacctac caccatggcc gaacaagcaa gaactggct    1200
gcccggacct tgcttccggc aacagagagt atccaagacg ctggatcaaa ataacaacag   1260
caactttgcc tggactggtg ccacaaaata ccatttaaat ggaagaaatt cattggttaa   1320
tcccggtgtc gccatggcaa cccacaagga cgacgaggaa cgcttctccc cttcgagcgg   1380
agttctaatt tttggcaaaa ctggagcagc taataaaact acattagaaa acgtgctcat   1440
gacaaatgaa gaagaaattc gtcctaccaa cccggtagct accgaggaat acgggattgt   1500
aagcagcaac ttgcaggcgg ctagcaccgc agcccagaca caagttgtta caaccagggg   1560
agccttacct ggcatggtct ggcagaaccg ggacgtgtac ctgcaaggtc ccatttgggc   1620
caagattcct cacacggacg gcaactttca cccgtctcct ctaatgggtg ctttggact    1680
gaaacacccg cctccccaga tcctgatcaa aaacacgccg gtacctgcta atcctccaga   1740
agtgttact cctgccaagt ttgcttcctt catcacgcag tacagcaccg gcaagtcag     1800
cgttgagatc gagtgggagc tgcagaaaga gaacagcaag cgctggaacc cagagattca   1860
gtacacctcc aactttgaca aacagactgg agtggacttt gctgttgaca gccagggtgt   1920
tactctgag cct                                                      1933
```

<210> SEQ ID NO 50
<211> LENGTH: 1933
<212> TYPE: DNA
<213> ORGANISM: Unknown
<220> FEATURE:
<223> OTHER INFORMATION: AAV serotype, clone 223.4

<400> SEQUENCE: 50

```
caaggcctac gaccagcagc tcaaagcggg tgacaatccg tacctgcggt ataaccacgc     60
cgacgccgag tttcaggagc gtcttcaaga agatacgtct tttgggggca acctcgggcg    120
agcagtcttc caggccaaaa agcgggttct cgaacctctt ggtctggttg agacgccagc    180
taagacggca cctggaaaga gcgaccggt agactcgcca gactccacct cgggcatcgg    240
caagaaaggc cagcagcccg cgaaaaagag actcaacttt gggcagactg gcgactcaga    300
gccagtcccc gaccctcaac caatcggaga accaccagca ggcccctctg gtctgggatc    360
tggtacaatg gctgcaggcg gtggcgcacc aatggctgac aataacgagg gcgccgacgg    420
```

```
agtgggtaat gcctcaggaa attggcattg cgattccaca cggctgggcg acagagtcat      480
caccaccagc acccgaacct gggccctgcc cacctacaac aaccacctct acaagcaaat      540
ctccagtcag tcagcaggga gcaccaacga taacgtctat ttcggctaca gcaccccctg      600
ggggtatttt gacttcaaca gattccattg ccacttctca ccacgtgact ggcagcgact      660
tatcaacaac aactggggat tccggcccaa gaagctcaac ttcaagctct tcaacatcca      720
ggtcaaggag gtcacgacga tgacggcgt cacaaccatc gctaataacc ttaccagcac      780
ggttcaggtc ttttcggact cggaatatca actgccgtac gtcctcggct ccgcgcacca      840
gggctgcctg cctccgttcc cggcagacgt gttcatgatt ccgcagtacg atacctgac      900 tctgaacaat ggcagccaat cggtaggccg ttcctccttc tactgcctgg agtactttcc      960
ttctcagatg ctgagaacgg gcaacaactt cacctttagc tacaccttcg aggacgtgcc     1020
tttccacagc agctacgcgc acagccagag tctgggccgg ctgatgaatc ccctcatcga     1080
ccagtacctg tactacttgg ccagaacaca gagcaacgca ggaggtactg ctggcaatcg     1140
ggaactgcag ttttatcagg gcggacctac caccatggcc gaacaagcaa agaactggct     1200
gcccggacct tgcttccggc aacagagagt atccaagacg ctggatcaaa ataacaacag     1260
caactttgcc tggactggtg ccacaaaata ccatttaaat ggaagaaatt cattggttaa     1320
tcccggtgtc gccatggcaa cccacaagga cgacgaggaa cgcttcttcc cttgagcgg     1380 agttctaatt tttggcaaaa ctggagcagc taataaaact acattagaaa acgtgctcat     1440
gacaaatgaa gaagaaattc gtcctaccaa cccggtagct accgaggaat acggattgt      1500 aagcagcaac ttgcaggcgg ctagcaccgc agcccagaca caagttgtta acaaccaggg     1560
agccttacct ggcatggtct ggcagaaccg ggacgtgtac ctgcaaggtc ccatttgggc     1620
caagattcct cacacggacg gcaactttca cccgtctcct ctaatgggtg ctttggact      1680 gaaacacccg cctcccccaga tcctgatcaa aaacacaccg gtacctgcta atcctccaga     1740
agtgtttact cctgccaagt tgcttcctt catcacgcag tacagcaccg ggcaagtcag      1800
cgttgagatc gaatgggagc tgcagaaaga gaacagcaag cgctggaacc cagagattca     1860
gtacacctcc aactttgaca aacagactgg agtggacttt gctgttgaca gccagggtgt     1920
ttactctgag cct                                                        1933
```

<210> SEQ ID NO 51
<211> LENGTH: 1933
<212> TYPE: DNA
<213> ORGANISM: Unknown
<220> FEATURE:
<223> OTHER INFORMATION: AAV serotype, clone 223.5

<400> SEQUENCE: 51

```
caaggcctac gaccagcagc tcaaagcggg tgacaatccg tacctgcggt ataaccacgc       60
cgacgccgag tttcaggagc gtcttcaaga agatacgtct tttggggggca acctcgggcg     120 agcagtcttc caggccaaaa agcgggttct cgaacctctt ggtctggttg agacgccagc     180
taagacggca cctggaaaga gcgaccggt agactcgcca gactccacct cgggcatcgg     240
caagaaaggc cagcagcccg cgaaaaagag actcaacttt gggcagactg gcgactcaga     300
gccagtcccc gaccctcaac caatcggaga accaccagca ggcccctctg gtctgggatc     360
tggtacaatg gctgcaggcg gtggcgcacc aatggctgac aataacgagg gcgccgacgg     420
agtgggtaat gcctcaggaa attggcattg cgattccaca cggctgggcg acagagtcat     480
```

```
caccaccagc acccgaacct gggccctgcc cacctacaac aaccacctct acaagcaaat    540
ctccagtcag tcagcaggga gcaccaacga taacgtctat ttcggctaca gcaccccctg    600
ggggtatttt gacttcaaca gattccattg ccacttctca ccacgtgact ggcagcgact    660
tatcaacaac aactggggat tccggcccaa gaagctcaac ttcaagctct tcaacatcca    720
ggtcaaggag gtcacgacga atgacggcgt cacaaccatc gctaataacc ttaccagcac    780
ggttcaggtc ttttcggact cggaatatca actgccgtac gtcctcggct ccgcgcacca    840
gggctgcctg cctccgttcc cggcagacgt gttcatgatt ccgcagtacg gatacctgac    900
tctgaacaat ggcagccaat cggtaggccg ttcctccttc tactgcctgg agtactttcc    960
ttctcagatg ctgagaacgg gcaacaactt cacctttagc tacaccttcg aggacgtgcc   1020
tttccacagc agctacgcgc acagccagag tctgggccgg ctgatgaatc ccctcatcga   1080
ccagtacctg tactacttgg ccagaacaca gagcaacgca ggaggtactg ctggcaatcg   1140
ggaactgcag ttttatcagg gcggacctac caccatggcc gaacaagcaa agaactggct   1200
gcccggacct tgcttccggc aacagagagt atccaagacg ctggatcaaa ataacaacag   1260
caactttgcc tggactggtg ccacaaaata ccatttaaat ggaagaaatt cattggttaa   1320
tcccggtgtc gccatggcaa cccacaagga cgacgaggaa cgcttcttcc cttcgagcgg   1380
agttctaatt tttggcaaaa ctggagcagc taataaaact acattagaaa acgtgctcat   1440
gacaaatgaa gaagaaattc gtcctaccaa cccggtagct accgaggaat acgggattgt   1500
aagcagcaac ttgcaggcgg ctagcaccgc agcccagaca caagttgtta acaaccaggg   1560
agccttacct ggcatggtct ggcagaaccg ggacgtgtac ctgcaaggtc ccatttgggc   1620
caagattcct cacacggacg gcaactttca cccgtctcct ctaatgggtg ctttggact    1680
gaaacacccg cctccccaga tcctgatcaa aaacacaccg gtacctgcta atcctccaga   1740
agtgtttact cctgccaagt ttgcttcctt catcacgcag tacagcaccg ggcaagtcag   1800
cgttgagatc gaatgggagc tgcagaaaga gaacagcaag cgctggaacc cagagattca   1860
gtacacctcc aactttgaca acagactggg agtggacttt gctgttgaca gccagggtgt   1920
ttactctgag cct                                                      1933
```

<210> SEQ ID NO 52
<211> LENGTH: 1933
<212> TYPE: DNA
<213> ORGANISM: Unknown
<220> FEATURE:
<223> OTHER INFORMATION: AAV serotype, clone 223.6

<400> SEQUENCE: 52

```
caaggcctac gaccagcagc tcaaagcggg tgacaatccg tacctgcggt ataaccacgc     60
cgacgccgag tttcaggagc gtcttcaaga agatacgtct tttggggca acctcgggcg    120
agcagtcttc caggccaaaa agcgggttct cgaacctctt ggtctggttg agacgccagc    180
taagacggca cctggaaaga gcgaccggt agactcgcca gactccacct cgggcatcgg    240
caagaaaggc cagcagcccg cgaaaaagag actcaacttt gggcagactg gcgactcaga    300
gtcagtcccc gaccctcaac caatcggaga accaccagca ggcccctctg gtctgggatc    360
tggtacaatg gctgcaggcg gtggcgcacc aatggctgac aatagcgagg gcgccgacgg    420
agtgggtaat gcctcaggaa attggcattg cgattccaca tggctgggcg acagagtcat    480
caccaccagc acccgaacct gggccctgcc cacctacaac aaccacctct acaagcaaat    540
ctccagtcag tcagcaggga gcaccaacga taacgtctat ttcggctaca gcaccccctg    600
```

```
ggggtatttt gacttcaaca gattccattg ccacttctca ccacgtgact ggcagcgact      660
tatcaacaac aactggggat tccggcccaa gaagctcaac ttcaagctct tcaacatcca      720
ggtcaaggag gtcacgacga atgacggtgt cacaaccatc gctaataacc ttaccagcac      780
ggttcaggtc ttttcggact cggaatatca actgccgtac gtcctcggct ccgcgcacca      840
gggctgcctg cctccgttcc cggcagacgt gttcatgatt ccgcagtacg atacctgac      900 tctgaacaat ggcagccaat cggtaggccg ttcctccttc tactgcctgg agtactttcc      960
ttctcagatg ctgagaacgg gcaacaactt cacctttagc tacaccttcg aggacgtgcc     1020
tttccacagc agctacgcgc acagccagag tctggaccgg ctgatgaatc ccctcatcga     1080
ccagtacctg tactacttgg ccagaacaca gagcaacgca ggaggtactg ctggcaatcg     1140
ggaactgcag ttttatcagg gcggacctac caccatggcc gaacaagcaa gaactggct      1200 gcccggacct tgcttccggc aacagagagt atccaagacg ctggatcaaa ataacaacag     1260
caactttgcc tggactggtg ccacaaaata ccatttaaat ggaagaaatt cattggttaa     1320
tcccggtgtc gccatggcaa cccacaagga cgacgaggaa cgcttcttcc cttcgagcgg     1380
agttctaatt tttggcaaaa ctggagcagc taataaaact acattagaaa acgtgctcat     1440
gacaaatgaa gaagaaattc gtcctaccaa cccggtagct accgaggaat acgggattgt     1500
aagcagcaac ttgcaggcgg ctagcaccgc agcccagaca caagttgtta acaaccaggg     1560
agccttacct ggcatggtct ggcagaaccg ggacgtgtac ctgcaaggtc ccatttgggc     1620
caagattcct cacacggacg gcaactttca cccgtctcct ctaatgggtg ctttggact      1680 gaaacacccg cctccccaga tcctgatcaa aaacacaccg gtacctgcta atcctccaga     1740
agtgtttact cctgccaagc ttgcttcctt catcacgcag tacagcaccg gcaagtcag      1800 cgttgagatc gagtgggagc tgcagaaaga gaacagcaag cgctggaacc cagagattca     1860
gtacaccTcc aactttgaca aacagactgg agtggacttt gctgttgaca gccagggtgt     1920
ttactctgag cct                                                         1933
```

<210> SEQ ID NO 53
<211> LENGTH: 1933
<212> TYPE: DNA
<213> ORGANISM: Unknown
<220> FEATURE:
<223> OTHER INFORMATION: AAV serotype, clone 223.7

<400> SEQUENCE: 53

```
caaggcctac gaccagcagc tcaaagcggg tgacaatccg tacctgcggt ataaccacgc       60
cgacgccgag tttcaggagc gtcttcaaga agatacgtct tttgggggca acctcgggcg      120
agcagtcttc caggccaaaa agcgggttct cgaacctctt ggtctggttg agacgccagc      180
taagacggca cctggaaaga agcgaccggt agactcgcca gactccacct cgggcatcgg      240
caagaaaggc cagcagcccg cgaaaaagag actcaacttt gggcagactg gcgactcaga      300
gtcagtcccc gaccctcaac caatcggaga accaccagca ggcccctctg gtctgggatc      360
tggtacaatg gctgcaggcg gtggcgcacc aatggctgac aataacgagg gcgccgacgg      420
agtgggtaat gcctcaggaa attggcattg cgattccaca tggctgggcg acagagtcat      480
caccaccagc acccgaacct gggcctgcc cacctacaac aaccacctct acaagcaaat      540
ctccagtcag tcagcaggga gcaccaacga taacgtctat ttcggctaca gcacccctg     600 ggggtatttt gacttcaaca gattccattg ccacttctca ccacgtgact ggcagcgact      660
```

| | |
|---|---:|
| tatcaacaac aactggggat tccggcccaa gaagctcaac ttcaagctct tcaacatcca | 720 |
| ggtcaaggag gtcacgacga atgacggcgt cacaaccatc gctaataacc ttaccagcac | 780 |
| ggttcaggtc ttttcggacc cggaatatca actgccgtac gtcctcggct ccgcgcacca | 840 |
| gggctgcctg cctccgttcc cggcagacgt gttcatgatt ccgcagtacg gatacctgac | 900 |
| tctgaacaat ggcagccaat cggtaggccg ttcctccttc tactgcctgg agtactttcc | 960 |
| ttctcagatg ctgagaacgg gcaacaactt cacctttagc tacaccttcg aggacgtgcc | 1020 |
| tttccacagc agctacgcgc acagccagag tctggaccgg ctgatgaatc ccctcatcga | 1080 |
| ccagtacctg tactacttgg ccagaacaca gagcaacgca ggaggtactg ctggcaatcg | 1140 |
| ggaactgcag ttttatcagg gcggacctac caccatggcc gaacaagcaa agaactggct | 1200 |
| gcccggacct tgcttccggc aacagagagt atccaagacg ctggatcaaa ataacaacag | 1260 |
| caactttgcc tggactggtg ccacaaaata ccatttaaat ggaagaaatt cattggttaa | 1320 |
| tcccggtgtc gccatggcaa cccacaagga cgacgaggaa cgcttcttcc cttcgagcgg | 1380 |
| agttctaatt tttggcaaaa ctggagcagc taataaaact acattagaaa acgtgctcat | 1440 |
| gacaaatgaa gaagaaattc gtcctaccaa cccggtagct accgaggaat acggggattgt | 1500 |
| aagcagcaac ttgcaggcgg ctagcaccgc agcccagaca caagttgtta acaaccaggg | 1560 |
| agccttacct ggcatggtct ggcagaaccg ggacgtgtac ctgcaaggtc ccatttgggc | 1620 |
| caagattcct cacacggacg gcaactttca cccgtctcct ctaatgggtg gctttggact | 1680 |
| gaaacacccg cctccccaga tcctgatcaa aaacacaccg gtacctgcta atcctccaga | 1740 |
| agtgttact cctgccaaga ttgcttcctt catcacgcag tacagcaccg ggcaagtcag | 1800 |
| cgttgagatc gagtgggagc tgcagaaaga aacagcaag cgctggaacc cagagattca | 1860 |
| gtacaccctcc aactttgaca aacagactgg agtggacttt gctgttgaca gccagggtgt | 1920 |
| ttactctgag cct | 1933 |

<210> SEQ ID NO 54
<211> LENGTH: 3123
<212> TYPE: DNA
<213> ORGANISM: Unknown
<220> FEATURE:
<223> OTHER INFORMATION: AAV serotype, clone A3.4

<400> SEQUENCE: 54

| | |
|---|---:|
| gaattcgccc tttctacggc tgcgtcaact ggaccaatga aaactttccc ttcaacgatt | 60 |
| gcgtcgacaa gatggtgatc tggtggggag agggaaagat gaccgccaag gtcgtggaat | 120 |
| ctgccaaagc cattctgggt ggaagcaagg ttcgtgtgga ccagaaatgc aagtcttcgg | 180 |
| cccagatcga cccggactcc gtgattgtca cctctaacac caacatgtgc gccgtgattg | 240 |
| acggaaactc gaccaccttc gagcaccagc agccgttgca agaccggatg ttcaaatttg | 300 |
| aacttacccg ccgtttggat catgactttg ggaaggtcac caagcaggaa gtcaaagact | 360 |
| ttttccggtg ggctcaagat cacgtgactg aggtggagca tgagttctac gtcaaaaagg | 420 |
| gtggagccaa gaaaaggccc gccccccgatg atgtatatat aaatgagccc aagcgggcgc | 480 |
| gcgagtcagt tgcgcagcca tcgacgtcag acgcggaagc ttcgataaac tacgcgggca | 540 |
| ggtaccaaaa caaatgttct cgtcacgtgg gcatgaatct gatgctgttt ccctgtcgac | 600 |
| aatgcgaaag aatgaatcag aattcaaata tctgcttcac acacgggcaa aaagactgtt | 660 |
| tggaatgctt tcccgtgtca gaatctcaac ccgtttctgt cgtcagaaaa acgtatcaga | 720 |
| aactttgtta cattcatcat atcatgggaa aagaaccaga cgcctgcact gcctgcgacc | 780 |

```
tggtaaatgt ggacttggat gactgtattt ctgagcaata aatgacttaa atcaggtatg    840
gctgctgacg gttatcttcc agattggctc gaggacactc tctctgaagg aatcagacag    900
tggtggaagc tcaaacctgg cccaccaccg ccgaaaccta accaacaaca ccgggacgac    960
agtagggtc ttgtgcttcc tgggtacaag tacctcggac ccttcaacgg actcgacaaa   1020
ggagagccgg tcaacgaggc agacgccgcg ccctcgagc acgacaaagc ctacgaccac   1080
cagctcaagc aaggggacaa cccgtacctc aaatacaacc acgcggacgc tgaatttcag   1140
gagcgtcttc aagaagatac gtctttcggg ggcaacctcg ggcgagcagt cttccaggcc   1200
aaaaagaggg tactcgagcc tcttggtctg gttgaggaag ctgttaagac ggctcctgga   1260
aaaaagagac ctatagagca gtctcctgca gaaccggact cttcctcggg catcggcgaa   1320
tcaggccagc agcccgctaa gaaaagactc aattttggtc agactggcga cacagagtca   1380
gtcccagacc ctcaaccaat cggagaaccc cccgcagccc cctctggtgt gggatctaat   1440
acaatggctt caggcggtgg ggcaccaatg gcagacgata cgaaggcgc cgacggagtg   1500
ggtaattcct cgggaaattg gcattgcgat tccacatgga tgggcgacag agttatcacc   1560
accagcacaa gaacctgggc cctccccacc tacaataatc acctctacaa gcaaatctcc   1620
agcgaatcgg gagccaccaa cgacaaccac tacttcggct acagcacccc ctgggggtat   1680
tttgacttta acagattcca ctgtcacttc tcaccacgtg actggcagcg actcatcaac   1740
aacaactggg gatttagacc caagaaactc aatttcaagc tcttcaacat ccaagtcaag   1800
gaggtcacgc agaatgatgg aaccacgacc atcgccaata accttaccag cacggtgcag   1860
gtcttcacag actctgagta ccagctgccc tacgtcctcg gttcggctca ccagggctgc   1920
cttccgccgt tcccagcaga cgtcttcatg attcctcagt acggctactt gactctgaac   1980
aatggcagcc aagcggtagg acgttcttca ttctactgtc tagagtattt tccctctcag   2040
atgctgagga cgggaaacaa cttcaccttc agctacactt ttgaagacgt gccttttcac   2100
agcagctacg cgcacagcca gagtctggat cggctgatga atcctctcat tgaccagtac   2160
ctgtattacc tgagcaaaac tcagggtaca agtggaacaa cgcagcaatc gagactgcag   2220
ttcagccaag ctgggcctag ctccatggct cagcaggcca aaaactggct accgggaccc   2280
agctaccgac agcagcgaat gtctaagacg gctaatgaca caacaacag tgaatttgct   2340
tggactgcag ccaccaaata ttacctgaat ggaagaaatt ctctggtcaa tcccgggccc   2400
ccaatggcca gtcacaagga cgatgaggaa aagtatttcc ccatgcacgg aaatctcatc   2460
tttgaaaaac aaggcacagg aactaccaat gtggacattg aatcagtgct tattacagac   2520
gaagaagaaa tcagaacaac taatcctgtg gctacagaac aatacggaca ggttgccacc   2580
aaccatcaga gtcaggacac cacagcttcc tatggaagtg tggacagcca gggaatctta   2640
cctggaatgg tgtggcagga ccgcgatgtc tatcttcaag gtcccatttg ggccaaaact   2700
cctcacacga cggacactt tcatccttct ccgctcatgg aggctttgg actgaaacac   2760
cctcctcccc agatcctgat caaaaacaca cctgtgccag cgaatcccgc gaccactttc   2820
actcctggaa agtttgcttc gttcattacc cagtattcca ccggacaggt cagcgtggaa   2880
atagagtggg agctgcagaa agaaaacagc aaacgctgga acccagaaat tcagtacacc   2940
tccaactaca acaagtcggt gaatgtggag tttaccgtgg acgcaaacgg tgtttattct   3000
gaaccccgcc ctattggcac tcgttacctt acccggaact tgtaatttcc tgttaatgaa   3060
taaaccgatt tatgcgtttc agttgaactt tggtctctgc gaagggcgaa ttcgcggccg   3120
```

```
<210> SEQ ID NO 55
<211> LENGTH: 3113
<212> TYPE: DNA
<213> ORGANISM: Unknown
<220> FEATURE:
<223> OTHER INFORMATION: AAV serotype, clone A3.5

<400> SEQUENCE: 55
```

| | |
|---|---:|
| cta | 3123 |
| gaattcgccc tttctacggc tgcgtcaact ggaccaatga aaactttccc ttcaacgatt | 60 |
| gcgtcgacaa gatggtgatc tggtgggagg agggaaagat gaccgccaag gtcgtggaat | 120 |
| ctgccaaagc cattctgggt ggaagcaagg ttcgtgtgga ccagaaatgc aagtcttcgg | 180 |
| cccagatcga cccgactccg gtgattgtca cctctaacac caacatgtgc gccgtgattg | 240 |
| acggaaactc gaccaccttc gagcaccagc agccgttgca agaccggatg ttcaaatttg | 300 |
| aacttaccct ccgtttggat catgactttg gaaggtcac caagcaggaa gtcaaagact | 360 |
| tttccggtg ggctcaagat cacgtgactg aggtggagca tgagttctac gtcaaaaagg | 420 |
| gtggagccaa gaaaaggccc gcccccgatg atgtatatat aaatgagccc aagcgggcgc | 480 |
| gcgagtcagt tgcgcagcca tcgacgtcag acgcggaagc ttcgataaac tacgcggaca | 540 |
| ggtaccaaaa caaatgttct cgtcacgtgg gcatgaatct gatgctgttt ccctgtcgac | 600 |
| aatgcgaaag aatgaatcag aattcaaata tctgcttcac acacgggcaa aaagactgtt | 660 |
| tggaatgctt tccgtgtca gaatctcaac ccgttcctgt cgtcagaaaa acgtatcaga | 720 |
| aactttgtta cattcatcat atcatgggaa aagtaccaga cgcctgcact gcctgcgacc | 780 |
| tggtaaatgt ggacttggat gactgtattt ctgagcaata aatgacttaa atcaggtatg | 840 |
| gctgctgacg gttatcttcc agattggctc gaggacactc tctctgaagg aatcagacag | 900 |
| tggtggaagc tcaaacctgg cccaccaccg ccgaaaccta accaacaaca ccgggacgac | 960 |
| agtaggggtc ttgtgcttcc tgggtacaag tacctcggac ccttcaacgg actcgacaaa | 1020 |
| ggagagccgg tcaacgaggc agacgccgcg gccctcgagc acgacaaagc ctacgaccac | 1080 |
| cagctcaagc aaggggacaa cccgtacctc aaatacaacc acgcggacgc tgaatttcag | 1140 |
| gagcgtcttc aagaagatac gtctttcggg ggcaacctcg ggcgagcagt cttccaggcc | 1200 |
| aaaaagaggg tactcgagcc tcttggtctg gttgaggaag ctgttaagac ggctcctgga | 1260 |
| aaaaagagac ctatagagca gtctcctgca gaaccggact cttcctcggg catcggcaaa | 1320 |
| tcaggccagc agcccgctaa gaaaagactc aattttggtc agactggcga cacagagtca | 1380 |
| gtcccagacc ctcaaccaat cggagaaccc cccgcagccc cctctggtgt gggatctaat | 1440 |
| acaatggctt caggcggtgg ggcaccaatg gcagacaata acgaaggcgc cgacggagtg | 1500 |
| ggtaattcct cgggaaattg gcattgcgat tccacatgga tgggcgacag agttatcacc | 1560 |
| accagcacaa gaacctgggc cctccccacc tacaataatc acctctacaa gcaaatctcc | 1620 |
| agcgaatcgg gagccaccaa cgacaaccac tacttcggct acagcacccc ctgggggtat | 1680 |
| tttgacttta acagattcca ctgtcacttc tcaccacgtg actggcagcg actcatcaat | 1740 |
| aacaactggg gatttagacc caagaaactc aatttcaagc tcttcaacat ccaagtcaag | 1800 |
| gaggtcacgc agaatgatgg aaccacgacc atcgccaata accttaccag cacggtgcag | 1860 |
| gtcttcacag actctgagta ccagctgccc tacgtcctcg gttcggctca ccagggctgc | 1920 |
| cttccgccgt tccagcagag cgtcttcatg attcctcagt acggctactt gactctgaac | 1980 |
| aatggcagcc aagcggtagg acgttcttca ttctactgtc tagagtattt tccctctcag | 2040 |

| | | | | | |
|---|---|---|---|---|---|
| atgctgagga | cgggaaacaa | cttcaccttc | agctacactt | ttgaagacgt | gcctttccac | 2100 |
| agcagctacg | cgcacagcca | gagtctggat | cggctgatga | atcctctcat | tgaccagtac | 2160 |
| ctgtattacc | tgagcaaaac | tcagggtaca | agtggaacaa | cgcagcaatc | gagactgcag | 2220 |
| ttcaaccaag | ctgggcctag | ctccatggct | cagcaggcca | aaaactggct | accgggaccc | 2280 |
| agctaccgac | agcagcgaat | gtctaagacg | gctaatgaca | acaacaacag | tgaatttgct | 2340 |
| tggactgcag | ccaccaaata | ttacccgaat | ggaagaaatt | ctctggtcaa | tcccgggccc | 2400 |
| ccaatggcca | gtcacaagga | cgatgaggaa | aagtatttcc | ccatgcacgg | aaatctcatc | 2460 |
| tttggaaaac | aaggcacagg | aactaccaat | gtggacattg | aatcagtgct | tattacagac | 2520 |
| gaagaagaaa | tcagaacgac | taatcctgtg | gctacagaac | aatacggaca | ggttgccacc | 2580 |
| aaccgtcaga | gtcagaacac | cacagcttcc | tatggaagtg | tggacagcca | gggaatctta | 2640 |
| cctggaatgg | tgtggcagga | ccgcgatgtc | tatcttcaag | gtcccatttg | gccaaaaact | 2700 |
| cctcacacgg | acgacactt | tcatccttct | ccgctcatgg | gaggctttgg | actgaaacac | 2760 |
| cctcctcccc | agatcctgat | caaaaacaca | cctgtgccag | cgaatcccgc | gaccactttc | 2820 |
| actcctggaa | agtttgcttc | gttcattacc | cagtattcca | ccggacaggt | cagcgtggaa | 2880 |
| atagagtggg | agctgcagaa | agaaaacagc | aaacgctgga | acccggaaat | tcagtacacc | 2940 |
| tccaactaca | acaagtcggt | gaatgtggag | tttaccgtgg | acgcaaacgg | tgtttattct | 3000 |
| gaaccccgcc | ctattggcac | tcgttacctt | acccggaact | tgtaatttcc | tgttaatgaa | 3060 |
| taaaccgatt | tatgcgtttc | agttgaactt | tggtctctgc | gaagggcgaa | ttc | 3113 |

<210> SEQ ID NO 56
<211> LENGTH: 3122
<212> TYPE: DNA
<213> ORGANISM: Unknown
<220> FEATURE:
<223> OTHER INFORMATION: AAV serotype, clone A3.7

<400> SEQUENCE: 56

| | | | | | |
|---|---|---|---|---|---|
| agcggccgcg | aattcgccct | ttctacggct | gcgtcaactg | gaccaatgaa | aactttccct | 60 |
| tcaacgattg | cgtcgacaag | atggtgatct | ggtgggagga | gggaaagatg | accgccaagg | 120 |
| tcgtggaatc | tgccaaagcc | attctgggtg | gaagcaaggt | tcgtgtggac | cagaaatgca | 180 |
| ggtcttcggc | ccagatcgac | ccgactccgg | tgattgtcac | ctctaacacc | aacatgtgcg | 240 |
| ccgtgattga | cggaaactcg | accaccttcg | agcaccagca | gccgttgcaa | gaccggatgt | 300 |
| tcaaatttga | acttacccgc | cgtttggatc | atgactttgg | gaaggtcacc | aagcaggaag | 360 |
| tcaaagactt | tttccggtgg | gctcaagatc | acgtgactga | ggtggagcat | gagttctacg | 420 |
| tcaaaaaggg | tggagccaag | aaaaggcccg | cccccgatga | tgtatatata | aatgagccca | 480 |
| agcgggcgcg | cgagtcagtt | gcgcagccat | cgacgtcaga | cgcggaagct | tcgataaact | 540 |
| acgcggacag | gtaccaaaac | aaatgttctc | gtcacgtggg | catgaatctg | atgctgtttc | 600 |
| cctgtcgaca | atgcgaaaga | atgaatcaga | attcaaatat | ctgcttcaca | cacggcaaa | 660 |
| aagactgttt | ggaatgcttt | ccgtgtcag | aatctcaacc | cgtttctgtc | gtcagaaaaa | 720 |
| cgtatcagaa | actttgttac | attcatcata | tcatgggaaa | agtaccagac | gcctgcactg | 780 |
| cctgcgacct | ggtaaatgtg | gacttggatg | actgtatttc | tgagcaataa | atgacttaaa | 840 |
| tcaggtatgg | ctgctgacgg | ttatcttcca | gattggctcg | aggacactct | ctctgaagga | 900 |
| atcagacagt | ggtggaagct | caaacctggc | ccaccaccgc | cgaaacctaa | ccaacaacac | 960 |

```
cgggacgaca gtaggggtct tgtgcttcct gggtacaagt acctcggacc cttcaacgga    1020
ctcgacaaag gagagccggt caacgaggca gacgccgcgg ccctcgagca cgacaaagcc    1080
tacgaccacc agctcaagca aggggacaac ccgtacctca aatacaacca cgcggacgct    1140
gaatttcagg agcgtcttca agaagatacg tctttcgggg caacctcgg gcgagcagtc     1200 ttccaggcca aaagagggt actcgagcct cttggtctgg ttgaggaagc tgttaagacg     1260
gctcctggaa aaagagacc tatagagcag tctcctgcag aaccggactc ttcctcgggc    1320
atcggcaaat caggccagca gcccgctaag aaaagactca attttggtca gactggcgac    1380
acagagtcag tcccagaccc tcaaccaatc ggagaacccc ccgcagcccc ctctggtgtg    1440
ggatctaata caatggcttc aggcggtggg gcaccaatgg cagacaataa cgaaggcgcc    1500
gacggagtgg gtaattcctc gggaaattgg cattgcgatt ccacatggat gggcgacaga    1560
gttatcacca ccagcacaag aacctgggcc ctccccacct acaataatcg cctctacaag    1620
caaatctcca gcgaatcggg agccaccaac gacaaccact acttcggcta cagcaccccc    1680
tgggggtatt ttgactttaa cagattccac tgtcacttct caccacgtga ctggcagcga    1740
ctcatcaaca caactgggg atttagaccc aagaaactca atttcaagct cttcaacatc     1800
caagtcaagg aggtcacgca gaatgatgga accacgacca tcgccaataa ccttaccagc    1860
acggtgcagg tcttcacaga ctctgagtac cagctgcccct acgtcctcgg ttcggctcac    1920
cagggctgcc ttccgccgtt cccagcagac gtcttcatga ttcctcagta cggctacttg    1980
actctgaaca atggcagcca agcggtagga cgttcttcat tctactgtct agagtatttt    2040
ccctctcaga tgctgaggac gggaaacaac ttcaccttca gctacacttt tgaagacgtg    2100
cctttccaca gcagctacgc gcacagccag agtctggatc ggctgatgaa tcctctcatt    2160
gaccagtacc tgtattacct gagcaaaact cagggtacaa gtggaacaac gcagcaatcg    2220
agactgcagt tcagccaagc tgggcctagc tccatggctc agcaggccaa aaactggcta    2280
ccgggaccca gctaccgaca gcagcgaatg tctaagacgg ctaatgacaa caacaacagt    2340
gaatttgctt ggactgcagc caccaaatat acctgaatg gaagaaattc tctggtcaat    2400
cccgggcccc caatggccag tcacaaggac gatgaggaaa agtatttccc catgcacgga    2460
aatctcatct ttggaaaaca aggcacagga actaccaatg tggacattga atcagtgctt    2520
attacagacg aagaagaaat cagaacaact aatcctgtgg ctacagaaca atacggacag    2580
gttgccacca ccatcagag tcagaacacc acagcttcct atggaagtgt ggacagccag    2640
ggaatcttac ctgaatggt gtggcaggac gcgatgtct atcttcaagg tcccatttgg    2700
gccaaaactc ctcacacgga cggacacttt catccttctc cgctcatggg aggctttgga    2760
ctgaaacacc ctcctcccca gatcctgatc aaaaacacac ctgtgccagc gaatcccgcg    2820
accactttca ctcctggaaa gtttgcttcg ttcattaccc agtattccac cggacaggtc    2880
agcgtggaaa tagagtggga gctgcagaaa gaaaacagca aacgctggaa cccagaaatt    2940
cagtacacct ccaactacaa caagtcggtg aatgtggagt ttaccgtgga cgcaaacggt    3000
gtttattctg aaccccgccc tattggcact cgttacctta cccggaactt gtaatttcct    3060
gttaatgaat aaaccgattt atgcgtttca gttgaacttt ggtctctgcg aagggcgaat    3120
tc                                                                 3122
```

<210> SEQ ID NO 57
<211> LENGTH: 3123
<212> TYPE: DNA
<213> ORGANISM: Unknown

<220> FEATURE:
<223> OTHER INFORMATION: AAV serotype, clone A3.3

<400> SEQUENCE: 57

```
gaattcgccc tttctacggc tgcgtcaact ggaccaatga aaactttccc ttcaacgatt    60
gcgtcgacaa gatggtgatc tggtgggagg agggaaagat gaccgccaag gtcgtggaat   120
ctgccaaagc cattctgggt ggaggcaagg ttcgtgtgga ccagaaatgc aagtcttcgg   180
cccagatcga cccgactccg gtgattgtca cctctaacac caacatgtgc gccgtgattg   240
acggaaactc gaccaccttc gagcaccagc agccgttgca agaccggatg ttcaaatttg   300
aacttacccg ccgtttggat catgactttg gaaggtcac caagcaggaa gtcaaagact   360
ttttccggtg ggctcaagat cacgtgactg aggtggagca tgagttctac gtcaaaaagg   420
gtggagccaa gaaaaggccc gcccccgatg atgtatatat aaatgagccc aagcgggcgc   480
gcgagtcagt tgcgcagcca tcgacgtcag acgcggaagc ttcgataaac tacgcggaca   540
ggtaccaaaa caaatgttct cgtcacgtgg gcatgaatct gatgctgttt ccctgtcgac   600
aatgcgaaag aatgaatcag aattcaaata tctgcttcac acacgggcaa aaagactgtt   660
tggaatgctt tcccgtgtca gaatctcaac ccgtttctgt cgtcagaaaa acgtatcaga   720
aactttgtta cattcatcat atcatgggaa aagtaccaga cgcctgcact gcctgcgacc   780
tggtaaatgt ggacttggat gactgtattt ctgagcaata aatgacttaa atcaggtatg   840
gctgctgacg gttatcttcc agattggctc gaggacactc tctctgaagg aatcagacag   900
tggtggaagc tcaaacctgg cccaccaccg ccgaaaccta accaacaaca ccgggacgac   960
agtaggggtc ttgtgcttcc tgggtacaag tacctcggac ccttcaacgg actcgacaaa  1020
ggagagccgg tcaacgaggc agacgccgcg gccctcgagc acgacaaagc ctacgaccac  1080
cagctcaagc aaggggacaa cccgtacctc aaatacaacc acgcggacgc tgaatttcag  1140
gagcgtcttc aagaagatac gtctttcggg ggcaacctcg ggcgagcagt cttccaggcc  1200
aaaaagaggg tactcgagcc tcttggtctg gttgaggaag ctgttaagac ggctcctgga  1260
aaaaagagac ctatagagca gtctcctgca gaaccggact cttcctcggg catcggcaaa  1320
tcaggccagc agcccgctaa gaaaagactc aattttggtc agactggcga cacagagtca  1380
gtcccaggcc ctcaaccaat cggagaaccc cccgcagccc cctctggtgt gggatctaat  1440
acaatggctt caggcggtgg ggcaccaatg cagacaata cgaaggcgc cgacggagtg  1500
ggtaattcct cgggaaattg gcattgcgat tccacatgga tgggcgacag agttatcacc  1560
accagcacaa gaacctgggc cctccccacc tacaataatc acctctacaa gcaaatctcc  1620
agcgaatcgg gagccaccaa cgacaaccac tacttcggct acagcacccc ctgggggtat  1680
tttgacttta acagattcca ctgtcacttc tcaccacgtg actggcagcg actcatcaac  1740
aacaactggg gatttagacc caagaaactc aatttcaagc tcttcaacat ccaagtcaag  1800
gaggtcacgc agaatgatgg aaccacgacc atcgccaata accttaccag cgcggtgcag  1860
gtcttcacag actctgagta ccagctgccc tacgtcctcg gttcggctca ccagggctgc  1920
cttccgccgt tcccagcaga cgtcttcatg attcctcagt acggctactt gactctgaac  1980
aatggcagcc aagcggtagg acgttcttca ttctactgtc tagagtattt tccctctcag  2040
atgctgagga cggaaacaa cttcaccttc agctacactt ttgaagacgt gcctttccac  2100
agcagctacg cgcacagcca gagtctggat cggctgatga atcctctcat tgaccagtac  2160
ctgtattacc tgagcaaaac tcagggtaca agtggaacaa cgcagcaatc gagactgcag  2220
```

```
ttcagccaag ctgggcctag ctccatggct cagcaggcca aaaactggct accgggaccc    2280
agctaccgac agcagcgaat gtctaagacg gctaatgaca acaacaacag tgaatttgct    2340
tggactgcag ccaccaaata ttacctgaat ggaagaaatt ctctggtcaa tcccgggccc    2400
ccagtggcca gtcacaagga cgatgaggaa aagtatttcc ccatgcacgg aaatctcatc    2460
tttggaaaac aaggcacagg aactaccaat gtggacattg aatcagtgct tattacagac    2520
gaagaagaaa tcagaacaac taatcctgtg gctacagaac aatacggaca ggttgccacc    2580
aaccatcaga gtcagaacac cacagcttcc tatggaagtg tggacagcca gggaatctta    2640
cctggaatgg tgtggcagga ccgcgatgtc tatcttcaag gtcccatttg gccaaaaact    2700
cctcacacgg acggacactt tcatccttct ccgctcatgg gaggctttgg actgaaacac    2760
cctcctcccc agatcctgat caaaaacaca cctgtgccag cgaatcccgc gaccactttc    2820
actcctggaa agtttgcttc gttcattacc cagtattcca cctgacaggt cagcgtggaa    2880
atagagtggg agctgcagaa agaaaacagc aaacgctgga acccagaaat tcagtacacc    2940
tccaactaca acaagtcggt gaatgtggag tttaccgtgg acgcaaacgg tgtttattct    3000
gaacccccgc ctattggcac tcgttacctt acccggaact tgtaatttcc tgttaatgaa    3060
taagccgatt tatgcgtttc agttgaactt tggtctctgc gaagggcgaa ttcgtttaaa    3120
cct                                                                  3123
```

<210> SEQ ID NO 58
<211> LENGTH: 2969
<212> TYPE: DNA
<213> ORGANISM: Unknown
<220> FEATURE:
<223> OTHER INFORMATION: AAV serotype, clone 42.12

<400> SEQUENCE: 58

```
gaattcgccc tttctacggc tgcgtcaact ggaccaatga gaactttccc ttcaacgatt      60
gcgtcgacaa gatggtgatc tggtgggagg agggcaagat gacggccaag gtcgtggagt    120
ccgccaaggc cattctcggc ggcagcaagg tgcgcgtgga ccaaaagtgc aagtcgtccg    180
cccagatcga ccccaccccc gtgatcgtca cctccaacac caacatgtgc gccgtgattg    240
acgggaacag caccaccttc gagcaccagc agccgttaca agaccggatg ttcaaatttg    300
aactcacccg ccgtctggag cacgactttg gcaaggtgac aaagcaggaa gtcaaagagt    360
tcttccgctg ggcgcaggat cacgtgaccg aggtggcgca tgagttctac gtcagaaagg    420
gtggagccaa caagagaccc gcccccgatg acgcggataa agcgagccca agcgggcct    480 gcccctcagt cgcggatcca tcgacgtcag acgcggaagg agctccggtg gactttgccg    540
acaggtacca aaacaaatgt tctcgtcacg cgggcatgct tcagatgctg tttccctgca    600
agacatgcga gagaatgaat cagaatttca acatttgctt cacgcacggg accagagact    660
gttcagaatg ttttccccggc gtgtcagaat ctcaaccggt cgtcagaaag aggacgtatc    720
ggaaactctg tgccattcat catctgctgg ggcgggctcc cgagattgct tgctcggcct    780
gcgatctggt caacgtggac ctggatgact gtgtttctga gcaataaatg acttaaacca    840
ggtatggctg ccgatggtta tcttccagat tggctcgagg acaacctctc tgagggcatc    900
cgcgagtggt gggacttgaa acctggagcc ccgaaaccca agccaaccca gcaaaagcag    960
gacgacggcc ggggtctggt gcttcctggc tacaagtacc tcggacccct caacggactc    1020
gacaagggag agccggtcaa cgaggcagac gccgcggccc tcgagcacga caaggcctac    1080
gacaagcagc tcgagcaggg ggacaacccg tacctcaagt acaaccacgc cgacgccgag    1140
```

```
tttcaggagc gtcttcaaga agatacgtct tttgggggca acctcgggcg agcagtcttc    1200
caggccaaga agcgggttct cgaacctctc ggtctggttg aggaaggcgc taagacggct    1260
cctggaaaga agagaccggt agagccatca ccccagcgtt ctccagactc ctctacgggc    1320
atcggcaaga caggccagca gcccgcgaaa aagagactca actttgggca gactggcgac    1380
tcagagtcag tgcccgaccc tcaaccaatc ggagaacccc cgcaggccc ctctggtctg    1440 ggatctggta caatggctgc aggcggtggc gctccaatgg cagacaataa cgaaggcgcc    1500
gacggagtgg gtagttcctc aggaaattgg cattgcgatt ccacatggct gggcgacaga    1560
gtcatcacca ccagcacccg aacctgggcc ctccccacct acaacaacca cctctacaag    1620
caaatctcca acgggacatc gggaggaagc accaacgaca cacctactt cggctacagc    1680 acccctggg ggtattttga ctttaacaga ttccactgcc acttctcacc acgtgactgg    1740
cagcgactca tcaacaacaa ctggggattc cggcccaaga gactcaactt caagctcttc    1800
aacatccagg tcaaggaggt cacgcagaat gaaggcacca gaccatcgc caataaccctt    1860 accagcacga ttcaggtctt tacggactcg gaataccagc tcccgtacgt cctcggctct    1920
gcgcaccagg gctgcctgcc tccgttcccg gcggacgtct tcatgattcc tcagtacggg    1980
tacctgactc tgaacaacgg cagtcaggcc gtgggccgtt cctccttcta ctgcctggag    2040
tactttcctt ctcaaatgct gagaacgggc aacaactttg agttcagcta ccagtttgag    2100
gacgtgcctt ttcacagcag ctacgcgcac agccaaagcc tggaccggct gacgaacccc    2160
ctcatcgacc agtacctgta ctacctggcc cggacccaga gcactacggg gtccacaagg    2220
gggctgcagt tccatcaggc tgggcccaac accatggccg agcaatcaaa gaactggctg    2280
cccgacccct gttatcggca gcagagactg tcaaaaaaca tagacagcaa caacaacagt    2340
aactttgcct ggaccggggc cactaaatac catctgaatg gtagaaattc attaaccaac    2400
ccgggcgtag ccatggccac caacaaggac gacgaggacc agttctttcc catcaacgga    2460
gtgctggttt ttggcaaaac gggggctgcc aacaagacaa cgctggaaaa cgtgctaatg    2520
accagcgagg aggagatcaa aaccaccaat cccgtggcta cagaagaata cggtgtggtc    2580
tccagcaacc tgcaatcgtc tacggccgga ccccagacac agactgtcaa cagccagggg    2640
gctctgcccg gcatggtctg gcagaaccgg gacgtgtacc tgcagggtcc catctgggcc    2700
aaaattcctc acacggacgg caactttcac ccgtctcccc tgatgggcgg atttggactc    2760
aaacacccgc ctcctcaaat tctcatcaag tatacttcca actactacaa atctacaaat    2820
gtggactttg ctgtcaatac tgagggtact tattcagagc ctcgccccat ggcacccgt    2880 tacctcaccc gtaacctgta attgcctgtt aatcaataaa ccggttaatt cgtttcagtt    2940
gaactttggt ctctgcgaag ggcgaattc                                      2969
```

<210> SEQ ID NO 59
<211> LENGTH: 3129
<212> TYPE: DNA
<213> ORGANISM: Unknown
<220> FEATURE:
<223> OTHER INFORMATION: AAV serotype, clone 44.2

<400> SEQUENCE: 59

```
gaattcgccc tttctacggc tgcgtcaact ggaccaatga gaactttccc ttcaacgatt     60
gcgtcgacaa gatggtgatc tggtgggagg agggcaagat gacggccaag gtcgtggagt    120
ccgccaaggc cattctcggc ggcagcaaag tgcgcgtgga ccaaaagtgc aagtcgtccg    180
```

-continued

| | | | | |
|---|---|---|---|---|
| cccagatcga | ccccacccc | gtgatcgtca | cctccaacac | caacatgtgc gccgtgattg | 240 |
| acgggaacag | caccaccttc | gagcaccagc | agccgttgca | ggaccggatg ttcaagtttg | 300 |
| aactcacccg | ccgtctggag | cacgactttg | gcaaggtgac | aaagcaggaa gtcagagagt | 360 |
| tcttccgctg | ggcgcaggat | cacgtgaccg | aggtggcgca | cgagttctac gtcagaaagg | 420 |
| gtggagccaa | caagagaccc | gccccgatg | acgcggataa | aagcgagccc aagcgggcct | 480 |
| gccctcagt | cgcggatcca | tcgacgtcag | acgcggaagg | agctccggtg gactttgccg | 540 |
| acaggtacca | aaacaaatgt | tctcgtcacg | cgggcatgct | tcagatgctg tttccctgca | 600 |
| aaacatgcga | gagaatgaat | cagaatttca | acatttgctt | cacgcacggg accagagact | 660 |
| gttcagaatg | tttccccggc | gtgtcagaat | ctcaaccggt | cgtcagaaaa aagacgtatc | 720 |
| ggaaactctg | tgcgattcat | catctgctgg | gggcgggcac | ccgagattgc ttgctcggcc | 780 |
| tgcgatctgg | tcaacgtgga | cctagatgac | tgtgtttctg | agcaataaat gacttaaacc | 840 |
| aggtatggct | gccgatggtt | atcttccaga | ttggctcgag | gacaacctct ctgagggcat | 900 |
| tcgcgagtgg | tgggacttga | aacctggagc | cccgaaaccc | aaagccaacc agcaaaagca | 960 |
| ggacgacggc | cggggtctgg | tgcttcctgg | ctacaagtac | ctcggaccct tcaacggact | 1020 |
| cgacaagggg | gagcccgtca | acgcggcgga | cgcagcggcc | ctcgagcacg acaaggccta | 1080 |
| cgaccagcag | ctcaaagcgg | gtgacaatcc | gtacctgcgg | tataaccacg ccgacgccga | 1140 |
| gtttcaggag | cgtctgcaag | aagatacgtc | ttttggggc | aacctcgggc gagcagtctt | 1200 |
| ccaggccaag | aagcgggttc | tcgaacctct | cggtctggtt | gaggaaggcg ctaagacggc | 1260 |
| tcctggaaaa | aagagaccgg | tagagccatc | accccagcgt | tctccagact cctctacggg | 1320 |
| catcggcaag | aaaggccagc | agcccgcgaa | aaagagactc | aactttgggc agactggcga | 1380 |
| ctcagagtca | gtgcccgacc | ctcaaccaat | cggagaaccc | cccgcaggcc cctctggtct | 1440 |
| gggatctggt | acaatggctg | caggcggtgg | cgctccaatg | gcagacaata cgaaggcgc | 1500 |
| cgacggagtg | ggtagttcct | caggaaattg | gcattgcgat | tccacatggc tgggcgacag | 1560 |
| agtcatcacc | accagcaccc | gaacctgggc | cctccccacc | tacaacaacc acctctacaa | 1620 |
| gcaaatctcc | aacgggactt | cgggaggaag | caccaacgac | aacacctact cggctacag | 1680 |
| cacccctgg | gggtattttg | actttaacag | attccactgc | cacttctcac cacgtgactg | 1740 |
| gcagcgactc | atcaacaaca | ctgggggatt | ccggcccaag | agactcaact tcaagctctt | 1800 |
| caacatccag | gtcaaggagg | tcacgcagaa | tgaaggcacc | aagaccatcg ccaataacct | 1860 |
| taccagcacg | attcaggtct | ttacggactc | ggaataccag | ctcccgtacg tcctcggctc | 1920 |
| tgcgcaccag | ggctgcctgc | ctccgttccc | ggcggacgtc | ttcatgattc ctcagtacgg | 1980 |
| gtacctgact | ctgaacaatg | gcagtcaggc | cgtgggccgt | tcctccttct actgcctgga | 2040 |
| gtactttcct | tctcaaatgc | tgagaacggg | caacaacttt | gagttcagct accagtttga | 2100 |
| ggacgtgcct | tttcacagca | gctacgcgca | cagccaaagc | ctggaccggc tgatgaaccc | 2160 |
| cctcatcgac | cagtacctgt | actacctgtc | tcggactcag | tccacgggag gtaccgcagg | 2220 |
| aactcagcag | ttgctatttt | ctcaggccgg | gcctaataac | atgtcggctc aggccaaaaa | 2280 |
| ctggctaccc | gggccctgct | accggcagca | acgcgtctcc | acgacactgt cgcaaaataa | 2340 |
| caacagcaac | tttgcctgga | ccggtgccac | caagtatcat | ctgaatggca gagactctct | 2400 |
| ggtaaatccc | ggtgtcgcta | tggcaaccca | caaggacgac | gaagagcgat tttttccgtc | 2460 |
| cagcggagtc | ttaatgtttg | ggaaacaggg | agctggaaaa | gacaacgtgg actatagcag | 2520 |
| cgttatgcta | accagtgagg | aagaaattaa | aaccaccaac | ccagtggcca cagaacagta | 2580 |

-continued

```
cggcgtggtg gccgataacc tgcaacagca aaacgccgct cctattgtag gggccgtcaa    2640
cagtcaagga gccttacctg gcatggtctg gcagaaccgg gacgtgtacc tgcagggtcc    2700
tatctgggcc aagattcctc acacggacgg aaactttcat ccctcgccgc tgatgggagg    2760
ctttggactg aaacacccgc ctcctcagat cctgattaag aatacacctg ttcccgcgga    2820
tcctccaact accttcagtc aagctaagct ggcgtcgttc atcacgcagt acagcaccgg    2880
acaggtcagc gtggaaattg aatgggagct gcagaaagaa aacagcaaac gctggaaccc    2940
agagattcaa tacacttcca actactacaa atctacaaat gtggactttg ctgttaacac    3000
agatggcact tattctgagc ctcgccccat cggcacccgt acctcaccc gtaatctgta    3060 attgcttgtt aatcaataaa ccggttgatt cgtttcagtt gaactttggt ctctgcgaag    3120
ggcgaattc                                                            3129
```

<210> SEQ ID NO 60
<211> LENGTH: 733
<212> TYPE: PRT
<213> ORGANISM: Unknown
<220> FEATURE:
<223> OTHER INFORMATION: capsid protein of AAV serotype, clone C1VP1

<400> SEQUENCE: 60

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Leu Glu Ser Pro Gln Glu Pro Asp Ser Ser Ser Gly Ile Gly Lys
145                 150                 155                 160

Lys Gly Lys Gln Pro Ala Lys Lys Arg Leu Asn Phe Glu Glu Asp Thr
                165                 170                 175

Gly Ala Gly Asp Gly Pro Pro Glu Gly Ser Asp Thr Ser Ala Met Ser
            180                 185                 190

Ser Asp Ile Glu Met Arg Ala Ala Pro Gly Gly Asn Ala Val Asp Ala
        195                 200                 205

Gly Gln Gly Ser Asp Gly Val Gly Asn Ala Ser Gly Asp Trp His Cys
    210                 215                 220

Asp Ser Thr Trp Ser Glu Gly Lys Val Thr Thr Thr Ser Thr Arg Thr
225                 230                 235                 240

Trp Val Leu Pro Thr Tyr Asn Asn His Leu Tyr Leu Arg Leu Gly Thr
                245                 250                 255
```

```
Thr Ser Asn Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
        275                 280                 285

Arg Leu Ile Asn Asn Asn Trp Gly Leu Arg Pro Lys Ala Met Arg Val
        290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Ser Pro Phe Pro Asn Asp Val Phe Met Val Pro Gln Tyr Gly Tyr
            355                 360                 365

Cys Gly Ile Val Thr Gly Glu Asn Gln Asn Gln Thr Asp Arg Asn Ala
    370                 375                 380

Phe Tyr Cys Leu Glu Tyr Phe Pro Ser Gln Met Leu Arg Thr Gly Asn
385                 390                 395                 400

Asn Phe Glu Met Ala Tyr Asn Phe Gly Lys Val Pro Phe His Ser Met
                405                 410                 415

Tyr Ala Tyr Ser Gln Ser Pro Asp Arg Leu Met Asn Pro Leu Leu Asp
            420                 425                 430

Gln Tyr Leu Trp His Leu Gln Ser Thr Thr Ser Gly Glu Thr Leu Asn
            435                 440                 445

Gln Gly Asn Ala Ala Thr Thr Phe Gly Lys Ile Arg Ser Gly Asp Phe
    450                 455                 460

Ala Phe Tyr Arg Lys Asn Trp Leu Pro Gly Pro Cys Val Lys Gln Gln
465                 470                 475                 480

Arg Leu Ser Lys Thr Ala Ser Gln Asn Tyr Lys Ile Pro Ala Ser Gly
                485                 490                 495

Gly Asn Ala Leu Leu Lys Tyr Asp Thr His Tyr Thr Leu Asn Asn Arg
            500                 505                 510

Trp Ser Asn Ile Ala Pro Gly Pro Pro Met Ala Thr Ala Gly Pro Ser
    515                 520                 525

Asp Gly Asp Phe Ser Asn Ala Gln Leu Ile Phe Pro Gly Pro Ser Val
    530                 535                 540

Thr Gly Asn Thr Thr Thr Ser Ala Asn Asn Leu Leu Phe Thr Ser Glu
545                 550                 555                 560

Glu Glu Ile Ala Ala Thr Asn Pro Arg Asp Thr Asp Met Phe Gly Gln
                565                 570                 575

Ile Ala Asp Asn Asn Gln Asn Ala Thr Thr Ala Pro Ile Thr Gly Asn
            580                 585                 590

Val Thr Ala Met Gly Val Leu Pro Gly Met Val Trp Gln Asn Arg Asp
            595                 600                 605

Ile Tyr Tyr Gln Gly Pro Ile Trp Ala Lys Ile Pro His Ala Asp Gly
            610                 615                 620

His Phe His Pro Ser Pro Leu Ile Gly Gly Phe Gly Leu Lys His Pro
625                 630                 635                 640

Pro Pro Gln Ile Phe Ile Lys Asn Thr Pro Val Pro Ala Asn Pro Ala
                645                 650                 655

Thr Thr Phe Thr Ala Ala Arg Val Asp Ser Phe Ile Thr Gln Tyr Ser
            660                 665                 670

Thr Gly Gln Val Ala Val Gln Ile Glu Trp Glu Ile Glu Lys Glu Arg
```

```
                675                 680                 685
Ser Lys Arg Trp Asn Pro Glu Val Gln Phe Thr Ser Asn Tyr Gly Asn
        690                 695                 700

Gln Ser Ser Met Leu Trp Ala Pro Asp Thr Thr Gly Lys Tyr Thr Glu
705                 710                 715                 720

Pro Arg Val Ile Gly Ser Arg Tyr Leu Thr Asn His Leu
            725                 730

<210> SEQ ID NO 61
<211> LENGTH: 733
<212> TYPE: PRT
<213> ORGANISM: Unknown
<220> FEATURE:
<223> OTHER INFORMATION: capsid protein of AAV serotype, clone C2VP1

<400> SEQUENCE: 61

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Leu
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe His Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Leu Glu Ser Pro Gln Glu Pro Asp Ser Ser Ser Gly Ile Gly Lys
145                 150                 155                 160

Lys Gly Lys Gln Pro Ala Lys Lys Arg Leu Asn Phe Glu Glu Asp Thr
                165                 170                 175

Gly Ala Gly Asp Gly Pro Pro Glu Gly Ser Asp Thr Ser Ala Met Ser
            180                 185                 190

Ser Asp Ile Glu Met Arg Ala Ala Pro Gly Gly Asn Ala Val Asp Ala
        195                 200                 205

Gly Gln Gly Ser Asp Gly Val Gly Asn Ala Ser Gly Asp Trp His Cys
    210                 215                 220

Asp Ser Thr Trp Ser Glu Gly Lys Val Thr Thr Thr Ser Thr Arg Thr
225                 230                 235                 240

Trp Val Leu Pro Thr Tyr Asn Asn His Leu Tyr Leu Arg Leu Gly Thr
                245                 250                 255

Thr Ser Asn Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
        275                 280                 285

Arg Leu Ile Asn Asn Asn Trp Gly Leu Arg Pro Lys Ala Met Arg Val
    290                 295                 300

Lys Ile Phe Asn Ile Gln Val Lys Glu Val Thr Thr Ser Asn Gly Glu
```

-continued

```
305                 310                 315                 320
Thr Thr Val Ala Asn Asn Leu Thr Ser Thr Val Gln Ile Phe Ala Asp
                325                 330                 335
Ser Ser Tyr Glu Leu Pro Tyr Val Met Asp Ala Gly Gln Glu Gly Ser
                340                 345                 350
Leu Pro Pro Phe Pro Asn Asp Val Phe Met Val Pro Gln Tyr Gly Tyr
                355                 360                 365
Cys Gly Ile Val Thr Gly Glu Asn Gln Asn Gln Thr Asp Arg Asn Ala
370                 375                 380
Phe Tyr Cys Leu Glu Tyr Phe Pro Ser Gln Met Leu Arg Thr Gly Asn
385                 390                 395                 400
Asn Phe Glu Met Ala Tyr Asn Phe Glu Lys Val Pro Phe His Ser Met
                405                 410                 415
Tyr Ala His Ser Gln Ser Leu Asp Arg Leu Met Asn Pro Leu Leu Asp
                420                 425                 430
Gln Tyr Leu Trp His Leu Gln Ser Thr Thr Ser Gly Glu Thr Leu Asn
                435                 440                 445
Gln Gly Asn Ala Ala Thr Thr Phe Gly Lys Ile Arg Ser Gly Asp Phe
450                 455                 460
Ala Phe Tyr Arg Lys Asn Trp Leu Pro Gly Pro Cys Val Lys Gln Gln
465                 470                 475                 480
Arg Phe Ser Lys Thr Ala Ser Gln Asn Tyr Lys Ile Pro Ala Ser Gly
                485                 490                 495
Gly Asn Ala Leu Leu Lys Tyr Asp Thr His Tyr Thr Leu Asn Asn Arg
                500                 505                 510
Trp Ser Asn Ile Ala Pro Gly Pro Pro Met Ala Thr Ala Gly Pro Ser
                515                 520                 525
Asp Gly Asp Phe Ser Asn Ala Gln Leu Ile Phe Pro Gly Pro Ser Val
                530                 535                 540
Thr Gly Asn Thr Thr Thr Ser Ala Asn Asn Leu Leu Phe Thr Ser Glu
545                 550                 555                 560
Gly Glu Ile Ala Ala Thr Asn Pro Arg Asp Thr Asp Met Phe Gly Gln
                565                 570                 575
Ile Ala Asp Asn Asn Gln Asn Ala Thr Thr Ala Pro Ile Thr Gly Asn
                580                 585                 590
Val Thr Ala Met Gly Val Leu Pro Gly Met Val Trp Gln Asn Arg Asp
                595                 600                 605
Ile Tyr Tyr Gln Gly Pro Ile Trp Ala Lys Ile Pro His Ala Asp Gly
                610                 615                 620
His Phe His Pro Ser Pro Leu Ile Gly Gly Phe Gly Leu Lys His Pro
625                 630                 635                 640
Pro Pro Gln Ile Phe Ile Lys Asn Thr Pro Val Pro Ala Asn Pro Ala
                645                 650                 655
Thr Thr Phe Thr Ala Ala Arg Val Asp Ser Phe Ile Thr Gln Tyr Ser
                660                 665                 670
Thr Gly Gln Val Ala Val Gln Ile Glu Trp Glu Ile Glu Lys Glu Arg
                675                 680                 685
Ser Lys Arg Arg Asn Pro Glu Val Gln Phe Thr Ser Asn Tyr Gly Asn
                690                 695                 700
Gln Ser Ser Met Leu Trp Ala Pro Asp Thr Thr Gly Lys Tyr Thr Glu
705                 710                 715                 720
Pro Arg Val Ile Gly Ser Arg Tyr Leu Thr Asn His Leu
                725                 730
```

```
<210> SEQ ID NO 62
<211> LENGTH: 733
<212> TYPE: PRT
<213> ORGANISM: Unknown
<220> FEATURE:
<223> OTHER INFORMATION: capsid protein of AAV serotype, clone C5VP1[@0002]

<400> SEQUENCE: 62
```

| | | | | | | | | | | | | | | |
|---|---|---|---|---|---|---|---|---|---|---|---|---|---|---|
| Met | Ala | Ala | Asp | Gly | Tyr | Leu | Pro | Asp | Trp | Leu | Glu | Asp | Asn | Leu | Ser |
| 1 | | | | 5 | | | | | 10 | | | | | 15 | |
| Glu | Gly | Ile | Arg | Glu | Trp | Trp | Asp | Leu | Lys | Pro | Gly | Ala | Pro | Lys | Pro |
| | | | | 20 | | | | | 25 | | | | | 30 | |
| Lys | Ala | Asn | Gln | Gln | Lys | Gln | Asp | Asp | Gly | Arg | Gly | Leu | Val | Leu | Pro |
| | | | 35 | | | | | 40 | | | | | 45 | | |
| Gly | Tyr | Glu | Tyr | Leu | Gly | Pro | Phe | Asn | Gly | Leu | Asp | Lys | Gly | Glu | Pro |
| | 50 | | | | | 55 | | | | | 60 | | | | |
| Val | Asn | Ala | Ala | Asp | Ala | Ala | Ala | Leu | Glu | His | Asp | Lys | Ala | Tyr | Asp |
| 65 | | | | | 70 | | | | | 75 | | | | | 80 |
| Gln | Gln | Leu | Lys | Ala | Gly | Asp | Asn | Pro | Tyr | Leu | Arg | Tyr | Asn | His | Ala |
| | | | | 85 | | | | | 90 | | | | | 95 | |
| Asp | Ala | Glu | Phe | Gln | Glu | Arg | Leu | Gln | Glu | Asp | Thr | Ser | Phe | Gly | Gly |
| | | | | 100 | | | | | 105 | | | | | 110 | |
| Asn | Leu | Gly | Arg | Ala | Val | Phe | Gln | Ala | Lys | Lys | Arg | Val | Leu | Glu | Pro |
| | | | 115 | | | | | 120 | | | | | 125 | | |
| Leu | Gly | Leu | Val | Glu | Glu | Gly | Ala | Lys | Thr | Ala | Pro | Gly | Lys | Lys | Arg |
| | 130 | | | | | 135 | | | | | 140 | | | | |
| Pro | Leu | Glu | Ser | Pro | Gln | Glu | Pro | Asp | Ser | Ser | Ser | Gly | Ile | Gly | Lys |
| 145 | | | | | 150 | | | | | 155 | | | | | 160 |
| Lys | Gly | Lys | Gln | Pro | Ala | Lys | Lys | Arg | Leu | Asn | Phe | Glu | Glu | Asp | Thr |
| | | | | 165 | | | | | 170 | | | | | 175 | |
| Gly | Ala | Gly | Asp | Gly | Pro | Pro | Glu | Gly | Ser | Asp | Thr | Ser | Ala | Met | Ser |
| | | | 180 | | | | | 185 | | | | | 190 | | |
| Ser | Asp | Ile | Glu | Met | Arg | Ala | Ala | Pro | Gly | Gly | Asn | Ala | Val | Asp | Ala |
| | | | | 195 | | | | | 200 | | | | | 205 | |
| Gly | Gln | Gly | Ser | Asp | Gly | Val | Gly | Asn | Ala | Ser | Gly | Asp | Trp | His | Cys |
| | 210 | | | | | 215 | | | | | 220 | | | | |
| Asp | Ser | Thr | Trp | Ser | Glu | Gly | Lys | Val | Thr | Thr | Thr | Ser | Thr | Arg | Thr |
| 225 | | | | | 230 | | | | | 235 | | | | | 240 |
| Trp | Val | Leu | Pro | Thr | Tyr | Asn | Asn | His | Leu | Tyr | Leu | Arg | Leu | Gly | Thr |
| | | | | 245 | | | | | 250 | | | | | 255 | |
| Thr | Ser | Asn | Ser | Asn | Thr | Tyr | Asn | Gly | Phe | Ser | Thr | Pro | Trp | Gly | Tyr |
| | | | 260 | | | | | 265 | | | | | 270 | | |
| Phe | Asp | Phe | Asn | Arg | Phe | His | Cys | His | Phe | Ser | Pro | Arg | Asp | Trp | Gln |
| | | | | 275 | | | | | 280 | | | | | 285 | |
| Arg | Leu | Ile | Asn | Asn | Asn | Trp | Gly | Leu | Arg | Pro | Lys | Ala | Met | Arg | Val |
| | | 290 | | | | | 295 | | | | | 300 | | | |
| Lys | Ile | Phe | Asn | Ile | Gln | Val | Lys | Glu | Val | Thr | Thr | Ser | Asn | Gly | Glu |
| 305 | | | | | 310 | | | | | 315 | | | | | 320 |
| Thr | Thr | Val | Ala | Asn | Asn | Leu | Thr | Ser | Thr | Val | Gln | Ile | Phe | Ala | Asp |
| | | | | 325 | | | | | 330 | | | | | 335 | |
| Ser | Ser | Tyr | Glu | Leu | Pro | Tyr | Val | Met | Asp | Ala | Gly | Gln | Glu | Gly | Ser |
| | | | | 340 | | | | | 345 | | | | | 350 | |
| Leu | Pro | Pro | Phe | Pro | Asn | Asp | Val | Phe | Met | Val | Pro | Gln | Tyr | Gly | Tyr |
| | | | 355 | | | | | 360 | | | | | 365 | | |

Cys Gly Ile Val Thr Gly Glu Asn Gln Asn Gln Thr Asp Arg Asn Ala
            370                 375                 380

Phe Tyr Cys Leu Glu Tyr Phe Pro Ser Gln Met Leu Arg Thr Gly Asn
385                 390                 395                 400

Asn Phe Glu Thr Ala Tyr Asn Phe Glu Lys Val Pro Phe His Ser Met
                405                 410                 415

Tyr Ala His Ser Gln Ser Leu Asp Gly Leu Met Asn Pro Leu Leu Asp
            420                 425                 430

Gln Tyr Leu Trp His Leu Gln Ser Thr Thr Ser Gly Glu Thr Leu Asn
            435                 440                 445

Gln Gly Asn Ala Ala Thr Thr Phe Gly Lys Ile Arg Ser Gly Asp Phe
450                 455                 460

Ala Phe Tyr Arg Lys Asn Trp Leu Pro Gly Pro Cys Val Lys Gln Gln
465                 470                 475                 480

Arg Phe Ser Lys Thr Ala Ser Gln Asn Tyr Lys Ile Pro Ala Ser Gly
                485                 490                 495

Gly Asn Ala Leu Leu Lys Tyr Asp Thr His Tyr Thr Leu Asn Asn Arg
            500                 505                 510

Trp Ser Asn Ile Ala Pro Gly Pro Pro Met Ala Thr Ala Gly Pro Ser
            515                 520                 525

Asp Gly Asp Phe Ser Asn Ala Gln Leu Ile Phe Pro Gly Pro Ser Val
530                 535                 540

Thr Gly Asn Thr Thr Thr Ser Ala Asn Asn Leu Leu Phe Thr Ser Glu
545                 550                 555                 560

Glu Glu Ile Ala Ala Thr Asn Pro Arg Asp Thr Asp Met Phe Gly Gln
                565                 570                 575

Ile Ala Asp Asn Asn Gln Asn Ala Thr Thr Ala Pro Ile Thr Gly Asn
            580                 585                 590

Val Thr Ala Met Gly Val Leu Pro Gly Met Val Trp Gln Asn Arg Asp
            595                 600                 605

Ile Tyr Tyr Gln Gly Pro Ile Trp Ala Lys Ile Pro His Ala Asp Gly
610                 615                 620

His Phe His Pro Ser Pro Leu Ile Gly Gly Phe Gly Leu Lys His Pro
625                 630                 635                 640

Pro Pro Gln Ile Phe Ile Lys Asn Thr Pro Val Pro Ala Tyr Pro Ala
                645                 650                 655

Thr Thr Phe Thr Ala Ala Arg Val Asp Ser Phe Ile Thr Gln Tyr Ser
            660                 665                 670

Thr Gly Gln Val Ala Val Gln Ile Glu Trp Glu Ile Glu Lys Glu Arg
            675                 680                 685

Ser Lys Arg Trp Asn Pro Glu Val Gln Phe Thr Ser Asn Cys Gly Asn
690                 695                 700

Gln Ser Ser Met Leu Trp Ala Pro Asp Thr Thr Gly Lys Tyr Thr Glu
705                 710                 715                 720

Pro Arg Val Ile Gly Ser Arg Tyr Leu Thr Asn His Leu
                725                 730

<210> SEQ ID NO 63
<211> LENGTH: 734
<212> TYPE: PRT
<213> ORGANISM: Unknown
<220> FEATURE:
<223> OTHER INFORMATION: capsid protein of AAV serotype, clone AAV4VP1

<400> SEQUENCE: 63

```
Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
            20                  25                  30

Ala Asn Gln Gln His Gln Asp Asn Ala Arg Gly Leu Val Leu Pro Gly
            35                  40                  45

Tyr Lys Tyr Leu Gly Pro Gly Asn Gly Leu Asp Lys Gly Glu Pro Val
        50                  55                  60

Asn Ala Ala Asp Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp
                85                  90                  95

Ala Glu Phe Gln Gln Arg Leu Gln Gly Asp Thr Ser Phe Gly Gly Asn
            100                 105                 110

Leu Gly Arg Ala Val Phe Gln Ala Lys Lys Arg Val Leu Glu Pro Leu
        115                 120                 125

Gly Leu Val Glu Gln Ala Gly Glu Thr Ala Pro Gly Lys Lys Arg Pro
    130                 135                 140

Leu Ile Glu Ser Pro Gln Gln Pro Asp Ser Ser Thr Gly Ile Gly Lys
145                 150                 155                 160

Lys Gly Lys Gln Pro Ala Lys Lys Leu Val Phe Glu Asp Glu Thr
                165                 170                 175

Gly Ala Gly Asp Gly Pro Pro Glu Gly Ser Thr Ser Gly Ala Met Ser
                180                 185                 190

Asp Asp Ser Glu Met Arg Ala Ala Gly Gly Ala Ala Val Glu Gly
            195                 200                 205

Gly Gln Gly Ala Asp Gly Val Gly Asn Ala Ser Gly Asp Trp His Cys
        210                 215                 220

Asp Ser Thr Trp Ser Glu Gly His Val Thr Thr Thr Ser Thr Arg Thr
225                 230                 235                 240

Trp Val Leu Pro Thr Tyr Asn Asn His Leu Tyr Lys Arg Leu Gly Glu
                245                 250                 255

Ser Leu Gln Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
        275                 280                 285

Arg Leu Ile Asn Asn Asn Trp Gly Met Arg Pro Lys Ala Met Arg Val
    290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
        355                 360                 365

Cys Gly Leu Val Thr Gly Asn Thr Ser Gln Gln Gln Thr Asp Arg Asn
    370                 375                 380

Ala Phe Tyr Cys Leu Glu Tyr Phe Pro Ser Gln Met Leu Arg Thr Gly
385                 390                 395                 400

Asn Asn Phe Glu Ile Thr Tyr Ser Phe Glu Lys Val Pro Phe His Ser
                405                 410                 415
```

```
Met Tyr Ala His Ser Gln Ser Leu Asp Arg Leu Met Asn Pro Leu Ile
            420                 425                 430

Asp Gln Tyr Leu Trp Gly Leu Gln Ser Thr Thr Thr Gly Thr Thr Leu
            435                 440                 445

Asn Ala Gly Thr Ala Thr Thr Asn Phe Thr Lys Leu Arg Pro Thr Asn
450                 455                 460

Phe Ser Asn Phe Lys Lys Asn Trp Leu Pro Gly Pro Ser Ile Lys Gln
465                 470                 475                 480

Gln Gly Phe Ser Lys Thr Ala Asn Gln Asn Tyr Lys Ile Pro Ala Thr
                485                 490                 495

Gly Ser Asp Ser Leu Ile Lys Tyr Glu Thr His Ser Thr Leu Asp Gly
            500                 505                 510

Arg Trp Ser Ala Leu Thr Pro Gly Pro Pro Met Ala Thr Ala Gly Pro
            515                 520                 525

Ala Asp Ser Lys Phe Ser Asn Ser Gln Leu Ile Phe Ala Gly Pro Lys
530                 535                 540

Gln Asn Gly Asn Thr Ala Thr Val Pro Gly Thr Leu Ile Phe Thr Ser
545                 550                 555                 560

Glu Glu Glu Leu Ala Ala Thr Asn Ala Thr Asp Thr Asp Met Trp Gly
                565                 570                 575

Asn Leu Pro Gly Gly Asp Gln Ser Asn Ser Asn Leu Pro Thr Val Asp
            580                 585                 590

Arg Leu Thr Ala Leu Gly Ala Val Pro Gly Met Val Trp Gln Asn Arg
            595                 600                 605

Asp Ile Tyr Tyr Gln Gly Pro Ile Trp Ala Lys Ile Pro His Thr Asp
610                 615                 620

Gly His Phe His Pro Ser Pro Leu Ile Gly Gly Phe Gly Leu Lys His
625                 630                 635                 640

Pro Pro Pro Gln Ile Phe Ile Lys Asn Thr Pro Val Pro Ala Asn Pro
                645                 650                 655

Ala Thr Thr Phe Ser Ser Thr Pro Val Asn Ser Phe Ile Thr Gln Tyr
            660                 665                 670

Ser Thr Gly Gln Val Ser Val Gln Ile Asp Trp Glu Ile Gln Lys Glu
            675                 680                 685

Arg Ser Lys Arg Trp Asn Pro Glu Val Gln Phe Thr Ser Asn Tyr Gly
690                 695                 700

Gln Gln Asn Ser Leu Leu Trp Ala Pro Asp Ala Ala Gly Lys Tyr Thr
705                 710                 715                 720

Glu Pro Arg Ala Ile Gly Thr Arg Tyr Leu Thr His His Leu
                725                 730

<210> SEQ ID NO 64
<211> LENGTH: 736
<212> TYPE: PRT
<213> ORGANISM: Unknown
<220> FEATURE:
<223> OTHER INFORMATION: capsid protein of AAV serotype, clone AAV1

<400> SEQUENCE: 64

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45
```

Gly Tyr Lys Tyr Leu Gly Pro Phe Asn Gly Leu Asp Lys Gly Glu Pro
 50                  55                  60

Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
             100                 105                 110

Asn Leu Gly Arg Ala Val Phe Gln Ala Lys Lys Arg Val Leu Glu Pro
         115                 120                 125

Leu Gly Leu Val Glu Glu Gly Ala Lys Thr Ala Pro Gly Lys Lys Arg
     130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                 165                 170                 175

Gly Asp Ser Glu Ser Val Pro Asp Pro Gln Pro Leu Gly Glu Pro Pro
             180                 185                 190

Ala Thr Pro Ala Ala Val Gly Pro Thr Thr Met Ala Ser Gly Gly Gly
         195                 200                 205

Ala Pro Met Ala Asp Asn Asn Glu Gly Ala Asp Gly Val Gly Asn Ala
     210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                 245                 250                 255

Tyr Lys Gln Ile Ser Ser Ala Ser Thr Gly Ala Ser Asn Asp Asn His
             260                 265                 270

Tyr Phe Gly Tyr Ser Thr Pro Trp Gly Tyr Phe Asp Phe Asn Arg Phe
         275                 280                 285

His Cys His Phe Ser Pro Arg Asp Trp Gln Arg Leu Ile Asn Asn Asn
     290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                 325                 330                 335

Leu Thr Ser Thr Val Gln Val Phe Ser Asp Ser Glu Tyr Gln Leu Pro
             340                 345                 350

Tyr Val Leu Gly Ser Ala His Gln Gly Cys Leu Pro Pro Phe Pro Ala
         355                 360                 365

Asp Val Phe Met Ile Pro Gln Tyr Gly Tyr Leu Thr Leu Asn Asn Gly
     370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                 405                 410                 415

Glu Glu Val Pro Phe His Ser Ser Tyr Ala His Ser Gln Ser Leu Asp
             420                 425                 430

Arg Leu Met Asn Pro Leu Ile Asp Gln Tyr Leu Tyr Tyr Leu Asn Arg
         435                 440                 445

Thr Gln Asn Gln Ser Gly Ser Ala Gln Asn Lys Asp Leu Leu Phe Ser
     450                 455                 460

Arg Gly Ser Pro Ala Gly Met Ser Val Gln Pro Lys Asn Trp Leu Pro

```
                465                 470                 475                 480
Gly Pro Cys Tyr Arg Gln Gln Arg Val Ser Lys Thr Lys Thr Asp Asn
                    485                 490                 495

Asn Asn Ser Asn Phe Thr Trp Thr Gly Ala Ser Lys Tyr Asn Leu Asn
                500                 505                 510

Gly Arg Glu Ser Ile Ile Asn Pro Gly Thr Ala Met Ala Ser His Lys
            515                 520                 525

Asp Asp Glu Asp Lys Phe Phe Pro Met Ser Gly Val Met Ile Phe Gly
        530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
                    580                 585                 590

Thr Gly Asp Val His Ala Met Gly Ala Leu Pro Gly Met Val Trp Gln
                595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                    645                 650                 655

Asn Pro Pro Ala Glu Phe Ser Ala Thr Lys Phe Ala Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
        690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                    725                 730                 735

<210> SEQ ID NO 65
<211> LENGTH: 736
<212> TYPE: PRT
<213> ORGANISM: Unknown
<220> FEATURE:
<223> OTHER INFORMATION: capsid protein of  AAV serotype, clone AAV6VP1

<400> SEQUENCE: 65

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
```

```
            100                 105                 110
Asn Leu Gly Arg Ala Val Phe Gln Ala Lys Lys Arg Val Leu Glu Pro
            115                 120                 125

Phe Gly Leu Val Glu Glu Gly Ala Lys Thr Ala Pro Gly Lys Lys Arg
            130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                    165                 170                 175

Gly Asp Ser Glu Ser Val Pro Asp Pro Gln Pro Leu Gly Glu Pro Pro
                    180                 185                 190

Ala Thr Pro Ala Ala Val Gly Pro Thr Thr Met Ala Ser Gly Gly Gly
                    195                 200                 205

Ala Pro Met Ala Asp Asn Asn Glu Gly Ala Asp Gly Val Gly Asn Ala
            210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                    245                 250                 255

Tyr Lys Gln Ile Ser Ser Ala Ser Thr Gly Ala Ser Asn Asp Asn His
                    260                 265                 270

Tyr Phe Gly Tyr Ser Thr Pro Trp Gly Tyr Phe Asp Phe Asn Arg Phe
                    275                 280                 285

His Cys His Phe Ser Pro Arg Asp Trp Gln Arg Leu Ile Asn Asn Asn
            290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                    325                 330                 335

Leu Thr Ser Thr Val Gln Val Phe Ser Asp Ser Glu Tyr Gln Leu Pro
                    340                 345                 350

Tyr Val Leu Gly Ser Ala His Gln Gly Cys Leu Pro Pro Phe Pro Ala
                    355                 360                 365

Asp Val Phe Met Ile Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                    405                 410                 415

Glu Asp Val Pro Phe His Ser Ser Tyr Ala His Ser Gln Ser Leu Asp
                    420                 425                 430

Arg Leu Met Asn Pro Leu Ile Asp Gln Tyr Leu Tyr Tyr Leu Asn Arg
                    435                 440                 445

Thr Gln Asn Gln Ser Gly Ser Ala Gln Asn Lys Asp Leu Leu Phe Ser
                    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                    485                 490                 495

Asn Asn Ser Asn Phe Thr Trp Thr Gly Ala Ser Lys Tyr Asn Leu Asn
                    500                 505                 510

Gly Arg Glu Ser Ile Ile Asn Pro Gly Thr Ala Met Ala Ser His Lys
                    515                 520                 525
```

```
Asp Asp Lys Asp Lys Phe Phe Pro Met Ser Gly Val Met Ile Phe Gly
            530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Thr Asp Pro Ala
            580                 585                 590

Thr Gly Asp Val His Val Met Gly Ala Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys His Pro Pro Gln Ile Leu Ile Lys Asn Thr Pro Val Pro Ala
            645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 66
<211> LENGTH: 735
<212> TYPE: PRT
<213> ORGANISM: Unknown
<220> FEATURE:
<223> OTHER INFORMATION: capsid protein of AAV serotype, clone A3.3

<400> SEQUENCE: 66

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
                20                  25                  30

Lys Pro Asn Gln Gln His Arg Asp Asp Ser Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Glu Ala Asp Ala Ala Leu Glu His Asp Lys Ala Tyr Asp
65                  70                  75                  80

His Gln Leu Lys Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Val Lys Thr Ala Pro Gly Lys Lys Arg
    130                 135                 140

Pro Ile Glu Gln Ser Pro Ala Glu Pro Asp Ser Ser Ser Gly Ile Gly
145                 150                 155                 160
```

```
Lys Ser Gly Gln Gln Pro Ala Lys Lys Arg Leu Asn Phe Gly Gln Thr
            165                 170                 175
Gly Asp Thr Glu Ser Val Pro Gly Pro Gln Pro Ile Gly Glu Pro Pro
        180                 185                 190
Ala Ala Pro Ser Gly Val Gly Ser Asn Thr Met Ala Ser Gly Gly Gly
            195                 200                 205
Ala Pro Met Ala Asp Asn Asn Glu Gly Ala Asp Gly Val Gly Asn Ser
210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Glu Ser Gly Ala Thr Asn Asp Asn His Tyr
                260                 265                 270
Phe Gly Tyr Ser Thr Pro Trp Gly Tyr Phe Asp Phe Asn Arg Phe His
            275                 280                 285
Cys His Phe Ser Pro Arg Asp Trp Gln Arg Leu Ile Asn Asn Asn Trp
        290                 295                 300
Gly Phe Arg Pro Lys Lys Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Ala Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
            355                 360                 365
Val Phe Met Ile Pro Gln Tyr Gly Tyr Leu Thr Leu Asn Asn Gly Ser
        370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Ser Lys Thr
        435                 440                 445
Gln Gly Thr Ser Gly Thr Thr Gln Gln Ser Arg Leu Gln Phe Ser Gln
            450                 455                 460
Ala Gly Pro Ser Ser Met Ala Gln Ala Lys Asn Trp Leu Pro Gly
465                 470                 475                 480
Pro Ser Tyr Arg Gln Gln Arg Met Ser Lys Thr Ala Asn Asp Asn Asn
                485                 490                 495
Asn Ser Glu Phe Ala Trp Thr Ala Ala Thr Lys Tyr Tyr Leu Asn Gly
            500                 505                 510
Arg Asn Ser Leu Val Asn Pro Gly Pro Val Ala Ser His Lys Asp
        515                 520                 525
Asp Glu Glu Lys Tyr Phe Pro Met His Gly Asn Leu Ile Phe Gly Lys
530                 535                 540
Gln Gly Thr Gly Thr Thr Asn Val Asp Ile Glu Ser Val Leu Ile Thr
545                 550                 555                 560
Asp Glu Glu Glu Ile Arg Thr Thr Asn Pro Val Ala Thr Glu Gln Tyr
                565                 570                 575
```

-continued

```
Gly Gln Val Ala Thr Asn His Gln Ser Gln Asn Thr Ala Ser Tyr
            580                 585                 590

Gly Ser Val Asp Ser Gln Gly Ile Leu Pro Gly Met Val Trp Gln Asp
        595                 600                 605

Arg Asp Val Tyr Leu Gln Gly Pro Ile Trp Ala Lys Thr Pro His Thr
610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
            645                 650                 655

Pro Ala Thr Thr Phe Thr Pro Gly Lys Phe Ala Ser Phe Ile Thr Gln
            660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
            690                 695                 700

Asn Lys Ser Val Asn Val Glu Phe Thr Val Asp Ala Asn Gly Val Tyr
705                 710                 715                 720

Ser Glu Pro Arg Pro Ile Gly Thr Arg Tyr Leu Thr Arg Asn Leu
            725                 730                 735

<210> SEQ ID NO 67
<211> LENGTH: 735
<212> TYPE: PRT
<213> ORGANISM: Unknown
<220> FEATURE:
<223> OTHER INFORMATION: capsid protein of AAV serotype, clone A3.7

<400> SEQUENCE: 67

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Asn Gln Gln His Arg Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

His Gln Leu Lys Gln Gly Asp Asn Pro Tyr Leu Lys Tyr Asn His Ala
            85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Val Lys Thr Ala Pro Gly Lys Lys Arg
    130                 135                 140

Pro Ile Glu Gln Ser Pro Ala Glu Pro Asp Ser Ser Ser Gly Ile Gly
145                 150                 155                 160

Lys Ser Gly Gln Gln Pro Ala Lys Lys Arg Leu Asn Phe Gly Gln Thr
            165                 170                 175

Gly Asp Thr Glu Ser Val Pro Asp Pro Gln Pro Ile Gly Glu Pro Pro
            180                 185                 190

Ala Ala Pro Ser Gly Val Gly Ser Asn Thr Met Ala Ser Gly Gly Gly
        195                 200                 205
```

Ala Pro Met Ala Asp Asn Asn Glu Gly Ala Asp Gly Val Gly Asn Ser
210             215                 220

Ser Gly Asn Trp His Cys Asp Ser Thr Trp Met Gly Asp Arg Val Ile
225             230                 235                 240

Thr Thr Ser Thr Arg Thr Trp Ala Leu Pro Thr Tyr Asn Asn Arg Leu
            245                 250                 255

Tyr Lys Gln Ile Ser Ser Glu Ser Gly Ala Thr Asn Asp Asn His Tyr
                260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
290                 295                 300

Gly Phe Arg Pro Lys Lys Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
            355                 360                 365

Val Phe Met Ile Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Lys Thr
            435                 440                 445

Gln Gly Thr Ser Gly Thr Thr Gln Gln Ser Arg Leu Gln Phe Ser Gln
    450                 455                 460

Ala Gly Pro Ser Ser Met Ala Gln Gln Ala Lys Asn Trp Leu Pro Gly
465                 470                 475                 480

Pro Ser Tyr Arg Gln Gln Arg Met Ser Lys Thr Ala Asn Asp Asn Asn
                485                 490                 495

Asn Ser Glu Phe Ala Trp Thr Ala Ala Thr Lys Tyr Tyr Leu Asn Gly
            500                 505                 510

Arg Asn Ser Leu Val Asn Pro Gly Pro Pro Met Ala Ser His Lys Asp
            515                 520                 525

Asp Glu Glu Lys Tyr Phe Pro Met His Gly Asn Leu Ile Phe Gly Lys
530                 535                 540

Gln Gly Thr Gly Thr Thr Asn Val Asp Ile Glu Ser Val Leu Ile Thr
545                 550                 555                 560

Asp Glu Glu Glu Ile Arg Thr Thr Asn Pro Val Ala Thr Glu Gln Tyr
                565                 570                 575

Gly Gln Val Ala Thr Asn His Gln Ser Gln Asn Thr Thr Ala Ser Tyr
            580                 585                 590

Gly Ser Val Asp Ser Gln Gly Ile Leu Pro Gly Met Val Trp Gln Asp
            595                 600                 605

Arg Asp Val Tyr Leu Gln Gly Pro Ile Trp Ala Lys Thr Pro His Thr
610                 615                 620

Asp Gly His Phe His Pro Ser Pro Leu Met Gly Gly Phe Gly Leu Lys

His Pro Pro Gln Ile Leu Ile Lys Asn Thr Pro Val Pro Ala Asn
625                 630                 635                 640

Pro Ala Thr Thr Phe Thr Pro Gly Lys Phe Ala Ser Phe Ile Thr Gln
            645                 650                 655

Tyr Ser Thr Gly Gln Val Ser Val Glu Ile Glu Trp Glu Leu Gln Lys
        660                 665                 670

Glu Asn Ser Lys Arg Trp Asn Pro Glu Ile Gln Tyr Thr Ser Asn Tyr
    690                 695                 700

Asn Lys Ser Val Asn Val Glu Phe Thr Val Asp Ala Asn Gly Val Tyr
705                 710                 715                 720

Ser Glu Pro Arg Pro Ile Gly Thr Arg Tyr Leu Thr Arg Asn Leu
            725                 730                 735

<210> SEQ ID NO 68
<211> LENGTH: 735
<212> TYPE: PRT
<213> ORGANISM: Unknown
<220> FEATURE:
<223> OTHER INFORMATION: capsid protein of AAV serotype, clone A3.4

<400> SEQUENCE: 68

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Asn Gln Gln His Arg Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

His Gln Leu Lys Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Val Lys Thr Ala Pro Gly Lys Lys Arg
130                 135                 140

Pro Ile Glu Gln Ser Pro Ala Glu Pro Asp Ser Ser Ser Gly Ile Gly
145                 150                 155                 160

Glu Ser Gly Gln Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Asn Thr Met Ala Ser Gly Gly Gly
        195                 200                 205

Ala Pro Met Ala Asp Asp Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Glu Ser Gly Ala Thr Asn Asp Asn His Tyr

```
              260                 265                 270
Phe Gly Tyr Ser Thr Pro Trp Gly Tyr Phe Asp Phe Asn Arg Phe His
            275                 280                 285
Cys His Phe Ser Pro Arg Asp Trp Gln Arg Leu Ile Asn Asn Asn Trp
            290                 295                 300
Gly Phe Arg Pro Lys Lys Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
            355                 360                 365
Val Phe Met Ile Pro Gln Tyr Gly Tyr Leu Thr Leu Asn Asn Gly Ser
            370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Ser Lys Thr
            435                 440                 445
Gln Gly Thr Ser Gly Thr Thr Gln Gln Ser Arg Leu Gln Phe Ser Gln
450                 455                 460
Ala Gly Pro Ser Ser Met Ala Gln Gln Ala Lys Asn Trp Leu Pro Gly
465                 470                 475                 480
Pro Ser Tyr Arg Gln Gln Arg Met Ser Lys Thr Ala Asn Asp Asn Asn
                485                 490                 495
Asn Ser Glu Phe Ala Trp Thr Ala Ala Thr Lys Tyr Tyr Leu Asn Gly
            500                 505                 510
Arg Asn Ser Leu Val Asn Pro Gly Pro Pro Met Ala Ser His Lys Asp
            515                 520                 525
Asp Glu Glu Lys Tyr Phe Pro Met His Gly Asn Leu Ile Phe Gly Lys
            530                 535                 540
Gln Gly Thr Gly Thr Thr Asn Val Asp Ile Glu Ser Val Leu Ile Thr
545                 550                 555                 560
Asp Glu Glu Glu Ile Arg Thr Thr Asn Pro Val Ala Thr Glu Gln Tyr
                565                 570                 575
Gly Gln Val Ala Thr Asn His Gln Ser Gln Asp Thr Thr Ala Ser Tyr
            580                 585                 590
Gly Ser Val Asp Ser Gln Gly Ile Leu Pro Gly Met Val Trp Gln Asp
            595                 600                 605
Arg Asp Val Tyr Leu Gln Gly Pro Ile Trp Ala Lys Thr Pro His Thr
            610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                645                 650                 655
Pro Ala Thr Thr Phe Thr Pro Gly Lys Phe Ala Ser Phe Ile Thr Gln
            660                 665                 670
Tyr Ser Thr Gly Gln Val Ser Val Glu Ile Glu Trp Glu Leu Gln Lys
            675                 680                 685
```

```
Glu Asn Ser Lys Arg Trp Asn Pro Glu Ile Gln Tyr Thr Ser Asn Tyr
    690                 695                 700

Asn Lys Ser Val Asn Val Glu Phe Thr Val Asp Ala Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 69
<211> LENGTH: 735
<212> TYPE: PRT
<213> ORGANISM: Unknown
<220> FEATURE:
<223> OTHER INFORMATION: capsid protein of AAV serotype, clone A3.5

<400> SEQUENCE: 69

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Asn Gln Gln His Arg Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

His Gln Leu Lys Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Val Lys Thr Ala Pro Gly Lys Lys Arg
    130                 135                 140

Pro Ile Glu Gln Ser Pro Ala Glu Pro Asp Ser Ser Ser Gly Ile Gly
145                 150                 155                 160

Lys Ser Gly Gln Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Glu Ser Gly Ala Thr Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Asn Phe Lys Leu Phe Asn Ile Gln Val
305                 310                 315                 320
```

```
Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Ile Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Lys Thr
        435                 440                 445

Gln Gly Thr Ser Gly Thr Thr Gln Gln Ser Arg Leu Gln Phe Asn Gln
    450                 455                 460

Ala Gly Pro Ser Ser Met Ala Gln Gln Ala Lys Asn Trp Leu Pro Gly
465                 470                 475                 480

Pro Ser Tyr Arg Gln Gln Arg Met Ser Lys Thr Ala Asn Asp Asn Asn
                485                 490                 495

Asn Ser Glu Phe Ala Trp Thr Ala Ala Thr Lys Tyr Tyr Pro Asn Gly
            500                 505                 510

Arg Asn Ser Leu Val Asn Pro Gly Pro Pro Met Ala Ser His Lys Asp
        515                 520                 525

Asp Glu Glu Lys Tyr Phe Pro Met His Gly Asn Leu Ile Phe Gly Lys
    530                 535                 540

Gln Gly Thr Gly Thr Thr Asn Val Asp Ile Glu Ser Val Leu Ile Thr
545                 550                 555                 560

Asp Glu Glu Glu Ile Arg Thr Thr Asn Pro Val Ala Thr Glu Gln Tyr
                565                 570                 575

Gly Gln Val Ala Thr Asn Arg Gln Ser Gln Asn Thr Thr Ala Ser Tyr
            580                 585                 590

Gly Ser Val Asp Ser Gln Gly Ile Leu Pro Gly Met Val Trp Gln Asp
        595                 600                 605

Arg Asp Val Tyr Leu Gln Gly Pro Ile Trp Ala Lys Thr Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ala Thr Thr Phe Thr Pro Gly Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Glu Phe Thr Val Asp Ala Asn Gly Val Tyr
705                 710                 715                 720

Ser Glu Pro Arg Pro Ile Gly Thr Arg Tyr Leu Thr Arg Asn Leu
                725                 730                 735
```

```
<210> SEQ ID NO 70
<211> LENGTH: 735
<212> TYPE: PRT
<213> ORGANISM: Unknown
<220> FEATURE:
<223> OTHER INFORMATION: capsid protein of AAV serotype, clone AAV2

<400> SEQUENCE: 70
```

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

```
Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
                435                 440                 445

Asn Thr Pro Ser Gly Thr Thr Thr Gln Ser Arg Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
                500                 505                 510

Arg Asp Ser Leu Val Asn Pro Gly Pro Ala Met Ala Ser His Lys Asp
                515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
                580                 585                 590

Ala Asp Val Asn Thr Gln Gly Val Leu Pro Gly Met Val Trp Gln Asp
                595                 600                 605

Arg Asp Val Tyr Leu Gln Gly Pro Ile Trp Ala Lys Ile Pro His Thr
                610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
                660                 665                 670

Tyr Ser Thr Gly Gln Val Ser Val Glu Ile Glu Trp Glu Leu Gln Lys
                675                 680                 685

Glu Asn Ser Lys Arg Trp Asn Pro Glu Ile Gln Tyr Thr Ser Asn Tyr
                690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 71
<211> LENGTH: 736
<212> TYPE: PRT
<213> ORGANISM: Unknown
<220> FEATURE:
<223> OTHER INFORMATION: capsid protein of AAV serotype, clone AAV3

<400> SEQUENCE: 71
```

-continued

```
Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Val Pro Gln Pro
            20                  25                  30
Lys Ala Asn Gln Gln His Gln Asp Asn Arg Arg Gly Leu Val Leu Pro
            35                  40                  45
Gly Tyr Lys Tyr Leu Gly Pro Gly Asn Gly Leu Asp Lys Gly Glu Pro
50                  55                  60
Val Asn Glu Ala Asp Ala Ala Leu Glu His Asp Lys Ala Tyr Asp
65                  70                  75                  80
Gln Gln Leu Lys Ala Gly Asp Asn Pro Tyr Leu Lys Tyr Asn His Ala
            85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Ile Leu Glu Pro
            115                 120                 125
Leu Gly Leu Val Glu Glu Ala Ala Lys Thr Ala Pro Gly Lys Lys Gly
            130                 135                 140
Ala Val Asp Gln Ser Pro Gln Glu Pro Asp Ser Ser Ser Gly Val Gly
145                 150                 155                 160
Lys Ser Gly Lys Gln Pro Ala Arg Lys Arg Leu Asn Phe Gly Gln Thr
            165                 170                 175
Gly Asp Ser Glu Ser Val Pro Asp Pro Gln Pro Leu Gly Glu Pro Pro
            180                 185                 190
Ala Ala Pro Thr Ser Leu Gly Ser Asn Thr Met Ala Ser Gly Gly Gly
            195                 200                 205
Ala Pro Met Ala Asp Asn Asn Glu Gly Ala Asp Gly Val Gly Asn Ser
            210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
            245                 250                 255
Tyr Lys Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
            275                 280                 285
Cys His Phe Ser Pro Arg Asp Trp Gln Arg Leu Ile Asn Asn Asn Trp
            290                 295                 300
Gly Phe Arg Pro Lys Lys Leu Ser Phe Lys Leu Phe Asn Ile Gln Val
305                 310                 315                 320
Arg Gly Val Thr Gln Asn Asp Gly Thr Thr Thr Ile Ala Asn Asn Leu
            325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
            355                 360                 365
Val Phe Met Val Pro Gln Tyr Gly Tyr Leu Thr Leu Asn Asn Gly Ser
            370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Gln Phe Ser Tyr Thr Phe Glu
            405                 410                 415
Asp Val Pro Phe His Ser Ser Tyr Ala His Ser Gln Ser Leu Asp Arg
```

```
            420                 425                 430
Leu Met Asn Pro Leu Ile Asp Gln Tyr Leu Tyr Tyr Leu Asn Arg Thr
            435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Gly Thr Val Asn His Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 72
<211> LENGTH: 737
<212> TYPE: PRT
<213> ORGANISM: Unknown
<220> FEATURE:
<223> OTHER INFORMATION: capsid protein of AAV serotype, clone 3.3bVP1

<400> SEQUENCE: 72

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asn Gly Arg Gly Leu Val Leu Pro
            35                  40                  45

Gly Tyr Lys Tyr Leu Gly Pro Phe Asn Gly Leu Asp Lys Gly Glu Pro
```

```
            50                  55                  60
Val Asn Ala Ala Asp Ala Ala Leu Glu His Asp Lys Ala Tyr Asp
 65                  70                  75                  80

Gln Gln Leu Asn Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Glu Gly Ala Lys Thr Ala Pro Ala Lys Lys Arg
            130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
                180                 185                 190

Pro Ala Ala Pro Ser Ser Val Gly Ser Gly Thr Val Ala Ala Gly Gly
                195                 200                 205

Gly Ala Pro Met Ala Asp Asn Asn Glu Gly Ala Asp Gly Val Gly Asn
210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Glu Gln Ile Ser Ser Glu Thr Ala Gly Ser Thr Asn Asp Asn
                260                 265                 270

Thr Tyr Phe Gly Tyr Ser Thr Pro Trp Gly Tyr Phe Asp Phe Asn Arg
                275                 280                 285

Phe His Cys His Phe Ser Pro Arg Asp Trp Gln Arg Leu Ile Asn Asn
                290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Ile Gln Val Phe Ser Asp Ser Glu Tyr Gln Leu
                340                 345                 350

Pro Tyr Val Leu Gly Ser Ala His Gln Gly Cys Leu Pro Pro Phe Pro
                355                 360                 365

Ala Asp Val Phe Met Ile Pro Gln Tyr Gly Tyr Leu Thr Leu Asn Asn
370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
                405                 410                 415

Phe Glu Asp Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ala
                435                 440                 445

Arg Thr Gln Ser Asp Pro Gly Gly Thr Ala Gly Asn Arg Glu Leu Gln
                450                 455                 460

Phe Tyr Gln Gly Gly Pro Ser Thr Met Ala Glu Gln Ala Lys Asn Trp
465                 470                 475                 480
```

Leu Pro Gly Pro Cys Phe Arg Gln Gln Arg Val Ser Lys Thr Leu Asp
                485                 490                 495

Gln Asn Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
            515                 520                 525

His Lys Asp Asp Glu Asp Arg Phe Phe Pro Ser Ser Gly Val Leu Ile
        530                 535                 540

Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
                565                 570                 575

Glu Tyr Gly Ile Val Ser Ser Asn Leu Gln Ala Ala Asn Thr Ala Ala
                580                 585                 590

Gln Thr Gln Val Val Asn Asn Gln Gly Ala Leu Pro Gly Met Val Trp
            595                 600                 605

Gln Asn Arg Asp Val Tyr Leu Gln Gly Pro Ile Trp Ala Lys Ile Pro
        610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Glu Val Phe Thr Pro Ala Lys Phe Ala Ser Phe Ile
                660                 665                 670

Thr Gln Tyr Ser Thr Gly Gln Val Ser Val Glu Ile Glu Trp Glu Leu
            675                 680                 685

Gln Lys Glu Asn Ser Lys Arg Trp Asp Pro Glu Ile Gln Tyr Thr Ser
        690                 695                 700

Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 73
<211> LENGTH: 644
<212> TYPE: PRT
<213> ORGANISM: Unknown
<220> FEATURE:
<223> OTHER INFORMATION: capsid protein of AAV serotype, clone 223-4

<400> SEQUENCE: 73

Lys Ala Tyr Asp Gln Gln Leu Lys Ala Gly Asp Asn Pro Tyr Leu Arg
1               5                   10                  15

Tyr Asn His Ala Asp Ala Glu Phe Gln Glu Arg Leu Gln Glu Asp Thr
                20                  25                  30

Ser Phe Gly Gly Asn Leu Gly Arg Ala Val Phe Gln Ala Lys Lys Arg
            35                  40                  45

Val Leu Glu Pro Leu Gly Leu Val Glu Thr Pro Ala Lys Thr Ala Pro
        50                  55                  60

Gly Lys Lys Arg Pro Val Asp Ser Pro Asp Ser Thr Ser Gly Ile Gly
65                  70                  75                  80

Lys Lys Gly Gln Gln Pro Ala Lys Lys Arg Leu Asn Phe Gly Gln Thr
                85                  90                  95

```
Gly Asp Ser Glu Pro Val Pro Asp Pro Gln Pro Ile Gly Glu Pro Pro
                100                 105                 110

Ala Gly Pro Ser Gly Leu Gly Ser Gly Thr Met Ala Ala Gly Gly Gly
        115                 120                 125

Ala Pro Met Ala Asp Asn Asn Glu Gly Ala Asp Gly Val Gly Asn Ala
    130                 135                 140

Ser Gly Asn Trp His Cys Asp Ser Thr Arg Leu Gly Asp Arg Val Ile
145                 150                 155                 160

Thr Thr Ser Thr Arg Thr Trp Ala Leu Pro Thr Tyr Asn Asn His Leu
                165                 170                 175

Tyr Lys Gln Ile Ser Ser Gln Ser Ala Gly Ser Thr Asn Asp Asn Val
            180                 185                 190

Tyr Phe Gly Tyr Ser Thr Pro Trp Gly Tyr Phe Asp Phe Asn Arg Phe
        195                 200                 205

His Cys His Phe Ser Pro Arg Asp Trp Gln Arg Leu Ile Asn Asn Asn
    210                 215                 220

Trp Gly Phe Arg Pro Lys Lys Leu Asn Phe Lys Leu Phe Asn Ile Gln
225                 230                 235                 240

Val Lys Glu Val Thr Thr Asn Asp Gly Val Thr Thr Ile Ala Asn Asn
                245                 250                 255

Leu Thr Ser Thr Val Gln Val Phe Ser Asp Ser Glu Tyr Gln Leu Pro
            260                 265                 270

Tyr Val Leu Gly Ser Ala His Gln Gly Cys Leu Pro Pro Phe Pro Ala
        275                 280                 285

Asp Val Phe Met Ile Pro Gln Tyr Gly Tyr Leu Thr Leu Asn Asn Gly
    290                 295                 300

Ser Gln Ser Val Gly Arg Ser Ser Phe Tyr Cys Leu Glu Tyr Phe Pro
305                 310                 315                 320

Ser Gln Met Leu Arg Thr Gly Asn Asn Phe Thr Phe Ser Tyr Thr Phe
                325                 330                 335

Glu Asp Val Pro Phe His Ser Ser Tyr Ala His Ser Gln Ser Leu Gly
            340                 345                 350

Arg Leu Met Asn Pro Leu Ile Asp Gln Tyr Leu Tyr Tyr Leu Ala Arg
        355                 360                 365

Thr Gln Ser Asn Ala Gly Gly Thr Ala Gly Asn Arg Glu Leu Gln Phe
    370                 375                 380

Tyr Gln Gly Gly Pro Thr Thr Met Ala Glu Gln Ala Lys Asn Trp Leu
385                 390                 395                 400

Pro Gly Pro Cys Phe Arg Gln Gln Arg Val Ser Lys Thr Leu Asp Gln
                405                 410                 415

Asn Asn Asn Ser Asn Phe Ala Trp Thr Gly Ala Thr Lys Tyr His Leu
            420                 425                 430

Asn Gly Arg Asn Ser Leu Val Asn Pro Gly Val Ala Met Ala Thr His
        435                 440                 445

Lys Asp Asp Glu Glu Arg Phe Phe Pro Ser Ser Gly Val Leu Ile Phe
    450                 455                 460

Gly Lys Thr Gly Ala Ala Asn Lys Thr Thr Leu Glu Asn Val Leu Met
465                 470                 475                 480

Thr Asn Glu Glu Glu Ile Arg Pro Thr Asn Pro Val Ala Thr Glu Glu
                485                 490                 495

Tyr Gly Ile Val Ser Ser Asn Leu Gln Ala Ala Ser Thr Ala Ala Gln
            500                 505                 510

Thr Gln Val Val Asn Asn Gln Gly Ala Leu Pro Gly Met Val Trp Gln
```

|   |   |   | 515 |   |   |   | 520 |   |   |   | 525 |   |   |

Asn Arg Asp Val Tyr Leu Gln Gly Pro Ile Trp Ala Lys Ile Pro His
    530                 535                 540

Thr Asp Gly Asn Phe His Pro Ser Pro Leu Met Gly Gly Phe Gly Leu
545                 550                 555                 560

Lys His Pro Pro Gln Ile Leu Ile Lys Asn Thr Pro Val Pro Ala
                565                 570                 575

Asn Pro Pro Glu Val Phe Thr Pro Ala Lys Phe Ala Ser Phe Ile Thr
            580                 585                 590

Gln Tyr Ser Thr Gly Gln Val Ser Val Glu Ile Glu Trp Glu Leu Gln
                595                 600                 605

Lys Glu Asn Ser Lys Arg Trp Asn Pro Glu Ile Gln Tyr Thr Ser Asn
    610                 615                 620

Phe Asp Lys Gln Thr Gly Val Asp Phe Ala Val Asp Ser Gln Gly Val
625                 630                 635                 640

Tyr Ser Glu Pro

<210> SEQ ID NO 74
<211> LENGTH: 644
<212> TYPE: PRT
<213> ORGANISM: Unknown
<220> FEATURE:
<223> OTHER INFORMATION: capsid protein of AAV serotype, clone 223-5

<400> SEQUENCE: 74

Lys Ala Tyr Asp Gln Gln Leu Lys Ala Gly Asp Asn Pro Tyr Leu Arg
1               5                   10                  15

Tyr Asn His Ala Asp Ala Glu Phe Gln Glu Arg Leu Gln Glu Asp Thr
            20                  25                  30

Ser Phe Gly Gly Asn Leu Gly Arg Ala Val Phe Gln Ala Lys Lys Arg
        35                  40                  45

Val Leu Glu Pro Leu Gly Leu Val Glu Thr Pro Ala Lys Thr Ala Pro
    50                  55                  60

Gly Lys Lys Arg Pro Val Asp Ser Pro Asp Ser Thr Ser Gly Ile Gly
65                  70                  75                  80

Lys Lys Gly Gln Gln Pro Ala Lys Lys Arg Leu Asn Phe Gly Gln Thr
                85                  90                  95

Gly Asp Ser Glu Pro Val Pro Asp Pro Gln Pro Ile Gly Glu Pro Pro
            100                 105                 110

Ala Gly Pro Ser Gly Leu Gly Ser Gly Thr Met Ala Ala Gly Gly Gly
        115                 120                 125

Ala Pro Met Ala Asp Asn Asn Glu Gly Ala Asp Gly Val Gly Asn Ala
    130                 135                 140

Ser Gly Asn Trp His Cys Asp Ser Thr Arg Leu Gly Asp Arg Val Ile
145                 150                 155                 160

Thr Thr Ser Thr Arg Thr Trp Ala Leu Pro Thr Tyr Asn Asn His Leu
                165                 170                 175

Tyr Lys Gln Ile Ser Ser Gln Ser Ala Gly Ser Thr Asn Asp Asn Val
            180                 185                 190

Tyr Phe Gly Tyr Ser Thr Pro Trp Gly Tyr Phe Asp Phe Asn Arg Phe
        195                 200                 205

His Cys His Phe Ser Pro Arg Asp Trp Gln Arg Leu Ile Asn Asn Asn
    210                 215                 220

Trp Gly Phe Arg Pro Lys Lys Leu Asn Phe Lys Leu Phe Asn Ile Gln
225                 230                 235                 240

-continued

Val Lys Glu Val Thr Thr Asn Asp Gly Val Thr Thr Ile Ala Asn Asn
            245                 250                 255

Leu Thr Ser Thr Val Gln Val Phe Ser Asp Ser Glu Tyr Gln Leu Pro
            260                 265                 270

Tyr Val Leu Gly Ser Ala His Gln Gly Cys Leu Pro Pro Phe Pro Ala
            275                 280                 285

Asp Val Phe Met Ile Pro Gln Tyr Gly Tyr Leu Thr Leu Asn Asn Gly
            290                 295                 300

Ser Gln Ser Val Gly Arg Ser Ser Phe Tyr Cys Leu Glu Tyr Phe Pro
305                 310                 315                 320

Ser Gln Met Leu Arg Thr Gly Asn Asn Phe Thr Phe Ser Tyr Thr Phe
            325                 330                 335

Glu Asp Val Pro Phe His Ser Ser Tyr Ala His Ser Gln Ser Leu Gly
            340                 345                 350

Arg Leu Met Asn Pro Leu Ile Asp Gln Tyr Leu Tyr Tyr Leu Ala Arg
            355                 360                 365

Thr Gln Ser Asn Ala Gly Gly Thr Ala Gly Asn Arg Glu Leu Gln Phe
            370                 375                 380

Tyr Gln Gly Gly Pro Thr Thr Met Ala Glu Gln Ala Lys Asn Trp Leu
385                 390                 395                 400

Pro Gly Pro Cys Phe Arg Gln Gln Arg Val Ser Lys Thr Leu Asp Gln
            405                 410                 415

Asn Asn Asn Ser Asn Phe Ala Trp Thr Gly Ala Thr Lys Tyr His Leu
            420                 425                 430

Asn Gly Arg Asn Ser Leu Val Asn Pro Gly Val Ala Met Ala Thr His
            435                 440                 445

Lys Asp Asp Glu Glu Arg Phe Phe Pro Ser Ser Gly Val Leu Ile Phe
450                 455                 460

Gly Lys Thr Gly Ala Ala Asn Lys Thr Thr Leu Glu Asn Val Leu Met
465                 470                 475                 480

Thr Asn Glu Glu Glu Ile Arg Pro Thr Asn Pro Val Ala Thr Glu Glu
            485                 490                 495

Tyr Gly Ile Val Ser Ser Asn Leu Gln Ala Ala Ser Thr Ala Ala Gln
            500                 505                 510

Thr Gln Val Val Asn Asn Gln Gly Ala Leu Pro Gly Met Val Trp Gln
            515                 520                 525

Asn Arg Asp Val Tyr Leu Gln Gly Pro Ile Trp Ala Lys Ile Pro His
530                 535                 540

Thr Asp Gly Asn Phe His Pro Ser Pro Leu Met Gly Gly Phe Gly Leu
545                 550                 555                 560

Lys His Pro Pro Pro Gln Ile Leu Ile Lys Asn Thr Pro Val Pro Ala
            565                 570                 575

Asn Pro Pro Glu Val Phe Thr Pro Ala Lys Phe Ala Ser Phe Ile Thr
            580                 585                 590

Gln Tyr Ser Thr Gly Gln Val Ser Val Glu Ile Glu Trp Glu Leu Gln
            595                 600                 605

Lys Glu Asn Ser Lys Arg Trp Asn Pro Glu Ile Gln Tyr Thr Ser Asn
            610                 615                 620

Phe Asp Lys Gln Thr Gly Val Asp Phe Ala Val Asp Ser Gln Gly Val
625                 630                 635                 640

Tyr Ser Glu Pro

<210> SEQ ID NO 75
<211> LENGTH: 644
<212> TYPE: PRT
<213> ORGANISM: Unknown
<220> FEATURE:
<223> OTHER INFORMATION: capsid protein of AAV serotype, clone 223-10
<220> FEATURE:
<221> NAME/KEY: MISC_FEATURE
<222> LOCATION: (434)..(434)
<223> OTHER INFORMATION: can be any amino acid

<400> SEQUENCE: 75

```
Lys Ala Tyr Asp Gln Gln Leu Lys Ala Gly Asp Asn Pro Tyr Leu Arg
  1               5                  10                  15
Tyr Asn His Ala Asp Ala Glu Phe Gln Glu Arg Leu Gln Glu Asp Thr
                 20                  25                  30
Ser Phe Gly Gly Asn Leu Gly Arg Ala Val Phe Gln Ala Lys Lys Arg
             35                  40                  45
Val Leu Glu Pro Leu Gly Leu Val Glu Thr Pro Ala Lys Thr Ala Pro
 50                  55                  60
Gly Lys Lys Arg Pro Val Asp Ser Pro Asp Ser Thr Ser Gly Ile Gly
 65                  70                  75                  80
Lys Lys Gly Gln Gln Pro Ala Lys Lys Arg Leu Asn Phe Gly Gln Thr
                 85                  90                  95
Gly Asp Ser Glu Ser Val Pro Asp Pro Gln Pro Ile Gly Glu Pro Pro
                100                 105                 110
Ala Gly Pro Ser Gly Leu Gly Ser Gly Thr Met Ala Ala Gly Gly Gly
            115                 120                 125
Ala Pro Met Ala Asp Asn Asn Glu Gly Ala Asp Gly Val Gly Asn Ala
130                 135                 140
Ser Gly Asn Trp His Cys Asp Ser Thr Trp Leu Gly Asp Arg Val Ile
145                 150                 155                 160
Thr Thr Ser Thr Arg Thr Trp Ala Leu Pro Thr Tyr Asn Asn His Leu
                165                 170                 175
Tyr Lys Gln Ile Ser Ser Gln Ser Ala Gly Ser Thr Asn Asp Asn Val
                180                 185                 190
Tyr Phe Gly Tyr Ser Thr Pro Trp Gly Tyr Phe Asp Phe Asn Arg Phe
            195                 200                 205
His Cys His Phe Ser Pro Arg Asp Trp Gln Arg Leu Ile Asn Asn Asn
        210                 215                 220
Trp Gly Phe Arg Pro Lys Lys Leu Asn Phe Lys Leu Phe Asn Ile Gln
225                 230                 235                 240
Val Lys Glu Val Thr Thr Asn Asp Gly Val Thr Thr Ile Ala Asn Asn
                245                 250                 255
Leu Thr Ser Thr Val Gln Val Phe Ser Asp Ser Glu Tyr Gln Leu Pro
                260                 265                 270
Tyr Val Leu Gly Ser Ala His Gln Gly Cys Leu Pro Pro Phe Pro Ala
            275                 280                 285
Asp Val Phe Met Ile Pro Gln Tyr Gly Tyr Leu Thr Leu Asn Asn Gly
        290                 295                 300
Ser Gln Ser Val Gly Arg Ser Ser Phe Tyr Cys Leu Glu Tyr Phe Pro
305                 310                 315                 320
Ser Gln Met Leu Arg Thr Gly Asn Asn Phe Thr Phe Ser Tyr Thr Phe
                325                 330                 335
Glu Asp Val Pro Phe His Ser Ser Tyr Ala His Ser Gln Ser Leu Asp
                340                 345                 350
```

Arg Leu Met Asn Pro Leu Ile Asp Gln Tyr Leu Tyr Leu Ala Arg
        355                 360                 365

Thr Gln Ser Asn Ala Gly Gly Thr Ala Gly Asn Arg Glu Leu Gln Phe
    370                 375                 380

Tyr Gln Gly Gly Pro Thr Thr Met Ala Glu Gln Ala Lys Asn Trp Leu
385                 390                 395                 400

Pro Gly Pro Cys Phe Arg Gln Gln Arg Val Ser Lys Thr Leu Asp Gln
                405                 410                 415

Asn Asn Asn Ser Asn Phe Ala Trp Thr Gly Ala Thr Lys Tyr His Leu
            420                 425                 430

Asn Xaa Arg Asn Ser Leu Val Asn Pro Gly Val Ala Met Ala Thr His
    435                 440                 445

Lys Asp Asp Glu Glu Arg Phe Phe Pro Ser Ser Gly Val Leu Ile Phe
450                 455                 460

Gly Lys Thr Gly Ala Ala Asn Lys Thr Thr Leu Glu Asn Val Leu Met
465                 470                 475                 480

Thr Asn Glu Glu Glu Ile Arg Pro Thr Asn Pro Val Ala Thr Glu Glu
                485                 490                 495

Tyr Gly Ile Val Ser Ser Asn Leu Gln Ala Ala Ser Thr Ala Ala Gln
            500                 505                 510

Thr Gln Val Val Asn Asn Gln Gly Ala Leu Pro Gly Met Val Trp Gln
    515                 520                 525

Asn Arg Asp Val Tyr Leu Gln Gly Pro Ile Trp Ala Lys Ile Pro His
530                 535                 540

Thr Asp Gly Asn Phe His Pro Ser Pro Leu Met Gly Gly Phe Gly Leu
545                 550                 555                 560

Lys His Pro Pro Pro Gln Ile Leu Ile Lys Asn Thr Pro Val Pro Ala
                565                 570                 575

Asn Pro Pro Glu Val Phe Thr Pro Ala Lys Phe Ala Ser Phe Ile Thr
            580                 585                 590

Gln Tyr Ser Thr Gly Gln Val Ser Val Glu Ile Glu Trp Glu Leu Gln
    595                 600                 605

Lys Glu Asn Ser Lys Arg Trp Asn Pro Glu Ile Gln Tyr Thr Ser Asn
610                 615                 620

Phe Asp Lys Gln Thr Gly Val Asp Phe Ala Val Asp Ser Gln Gly Val
625                 630                 635                 640

Tyr Ser Glu Pro

<210> SEQ ID NO 76
<211> LENGTH: 644
<212> TYPE: PRT
<213> ORGANISM: Unknown
<220> FEATURE:
<223> OTHER INFORMATION: capsid protein of AAV serotype, clone 223-2

<400> SEQUENCE: 76

Lys Ala Tyr Asp Gln Gln Leu Lys Ala Gly Asp Asn Pro Tyr Leu Arg
1               5                   10                  15

Tyr Asn His Ala Asp Ala Glu Phe Gln Glu Cys Leu Gln Glu Asp Thr
            20                  25                  30

Ser Phe Gly Gly Asn Leu Gly Arg Ala Val Phe Gln Ala Lys Lys Arg
        35                  40                  45

Val Leu Glu Pro Leu Gly Leu Val Glu Thr Pro Ala Lys Thr Ala Pro
    50                  55                  60

Gly Lys Lys Arg Pro Val Asp Ser Pro Asp Ser Thr Ser Gly Ile Gly

```
                65                  70                  75                  80
           Lys Lys Gly Gln Gln Pro Ala Lys Lys Arg Leu Asn Phe Gly Gln Thr
                            85                  90                  95
           Gly Asp Ser Glu Ser Val Pro Asp Pro Gln Pro Ile Gly Glu Pro Pro
                            100                 105                 110
           Ala Gly Pro Ser Gly Leu Gly Ser Gly Thr Met Val Ala Gly Gly Gly
                            115                 120                 125
           Ala Pro Met Ala Asp Asn Asn Glu Gly Ala Asp Gly Val Gly Asn Ala
                            130                 135                 140
           Ser Gly Asn Trp His Cys Asp Ser Thr Trp Leu Gly Asp Arg Val Ile
           145                 150                 155                 160
           Thr Thr Ser Thr Arg Thr Trp Ala Leu Pro Thr Tyr Asn Asn His Leu
                            165                 170                 175
           Tyr Lys Gln Ile Ser Ser Gln Ser Ala Gly Ser Thr Asn Asp Asn Val
                            180                 185                 190
           Tyr Phe Gly Tyr Ser Thr Pro Trp Gly Tyr Phe Asp Phe Asn Arg Phe
                            195                 200                 205
           His Cys His Phe Ser Pro Arg Asp Trp Gln Arg Leu Ile Asn Asn Asn
                            210                 215                 220
           Trp Gly Phe Arg Pro Lys Lys Leu Asn Phe Lys Leu Phe Asn Ile Gln
           225                 230                 235                 240
           Val Lys Glu Val Thr Thr Asn Asp Gly Val Thr Thr Ile Ala Asn Asn
                            245                 250                 255
           Leu Thr Ser Thr Val Gln Val Phe Ser Asp Ser Glu Tyr Gln Leu Pro
                            260                 265                 270
           Tyr Val Leu Gly Ser Ala His Gln Gly Cys Leu Pro Pro Phe Pro Ala
                            275                 280                 285
           Asp Val Phe Met Ile Pro Gln Tyr Gly Tyr Leu Thr Leu Asn Asn Gly
                            290                 295                 300
           Ser Gln Ser Val Gly Arg Ser Ser Phe Tyr Cys Leu Glu Tyr Phe Pro
           305                 310                 315                 320
           Ser Gln Met Leu Arg Thr Gly Asn Asn Phe Thr Phe Ser Tyr Thr Phe
                            325                 330                 335
           Glu Asp Val Pro Phe His Ser Ser Tyr Ala His Ser Gln Ser Leu Asp
                            340                 345                 350
           Arg Leu Met Asn Pro Leu Ile Asp Gln Tyr Leu Tyr Tyr Leu Ala Arg
                            355                 360                 365
           Thr Gln Ser Asn Ala Gly Gly Thr Ala Gly Asn Arg Glu Leu Gln Phe
                            370                 375                 380
           Tyr Gln Gly Gly Pro Thr Thr Met Ala Glu Gln Ala Lys Asn Trp Leu
           385                 390                 395                 400
           Pro Gly Pro Cys Phe Arg Gln Gln Arg Val Ser Lys Thr Leu Asp Gln
                            405                 410                 415
           Asn Asn Asn Ser Asn Phe Ala Trp Thr Gly Ala Thr Lys Tyr His Leu
                            420                 425                 430
           Asn Gly Arg Asn Ser Leu Val Asn Pro Gly Val Ala Met Ala Thr His
                            435                 440                 445
           Lys Asp Asp Glu Glu Arg Phe Ser Pro Ser Ser Gly Val Leu Ile Phe
                            450                 455                 460
           Gly Lys Thr Gly Ala Ala Asn Lys Thr Thr Leu Glu Asn Val Leu Met
           465                 470                 475                 480
           Thr Asn Glu Glu Glu Ile Arg Pro Thr Asn Pro Val Ala Thr Glu Glu
                            485                 490                 495
```

```
Tyr Gly Ile Val Ser Ser Asn Leu Gln Ala Ala Ser Thr Ala Ala Gln
            500                 505                 510

Thr Gln Val Val Asn Asn Gln Gly Ala Leu Pro Gly Met Val Trp Gln
        515                 520                 525

Asn Arg Asp Val Tyr Leu Gln Gly Pro Ile Trp Ala Lys Ile Pro His
530                 535                 540

Thr Asp Gly Asn Phe His Pro Ser Pro Leu Met Gly Gly Phe Gly Leu
545                 550                 555                 560

Lys His Pro Pro Gln Ile Leu Ile Lys Asn Thr Pro Val Pro Ala
                565                 570                 575

Asn Pro Pro Glu Val Phe Thr Pro Ala Lys Phe Ala Ser Phe Ile Thr
            580                 585                 590

Gln Tyr Ser Thr Gly Gln Val Ser Val Glu Ile Glu Trp Glu Leu Gln
        595                 600                 605

Lys Glu Asn Ser Lys Arg Trp Asn Pro Glu Ile Gln Tyr Thr Ser Asn
610                 615                 620

Phe Asp Lys Gln Thr Gly Val Asp Phe Ala Val Asp Ser Gln Gly Val
625                 630                 635                 640

Tyr Ser Glu Pro

<210> SEQ ID NO 77
<211> LENGTH: 644
<212> TYPE: PRT
<213> ORGANISM: Unknown
<220> FEATURE:
<223> OTHER INFORMATION: capsid protein of AAV serotype, clone 223-7

<400> SEQUENCE: 77

Lys Ala Tyr Asp Gln Gln Leu Lys Ala Gly Asp Asn Pro Tyr Leu Arg
1               5                   10                  15

Tyr Asn His Ala Asp Ala Glu Phe Gln Glu Arg Leu Gln Glu Asp Thr
            20                  25                  30

Ser Phe Gly Gly Asn Leu Gly Arg Ala Val Phe Gln Ala Lys Lys Arg
        35                  40                  45

Val Leu Glu Pro Leu Gly Leu Val Glu Thr Pro Ala Lys Thr Ala Pro
    50                  55                  60

Gly Lys Lys Arg Pro Val Asp Ser Pro Asp Ser Thr Ser Gly Ile Gly
65                  70                  75                  80

Lys Lys Gly Gln Gln Pro Ala Lys Lys Arg Leu Asn Phe Gly Gln Thr
                85                  90                  95

Gly Asp Ser Glu Ser Val Pro Asp Pro Gln Pro Ile Gly Glu Pro Pro
            100                 105                 110

Ala Gly Pro Ser Gly Leu Gly Ser Gly Thr Met Ala Ala Gly Gly Gly
        115                 120                 125

Ala Pro Met Ala Asp Asn Asn Glu Gly Ala Asp Gly Val Gly Asn Ala
    130                 135                 140

Ser Gly Asn Trp His Cys Asp Ser Thr Trp Leu Gly Asp Arg Val Ile
145                 150                 155                 160

Thr Thr Ser Thr Arg Thr Trp Ala Leu Pro Thr Tyr Asn Asn His Leu
                165                 170                 175

Tyr Lys Gln Ile Ser Ser Gln Ser Ala Gly Ser Thr Asn Asp Asn Val
            180                 185                 190

Tyr Phe Gly Tyr Ser Thr Pro Trp Gly Tyr Phe Asp Phe Asn Arg Phe
        195                 200                 205
```

His Cys His Phe Ser Pro Arg Asp Trp Gln Arg Leu Ile Asn Asn Asn
    210                 215                 220

Trp Gly Phe Arg Pro Lys Lys Leu Asn Phe Lys Leu Phe Asn Ile Gln
225                 230                 235                 240

Val Lys Glu Val Thr Thr Asn Asp Gly Val Thr Thr Ile Ala Asn Asn
                245                 250                 255

Leu Thr Ser Thr Val Gln Val Phe Ser Asp Pro Glu Tyr Gln Leu Pro
                260                 265                 270

Tyr Val Leu Gly Ser Ala His Gln Gly Cys Leu Pro Pro Phe Pro Ala
            275                 280                 285

Asp Val Phe Met Ile Pro Gln Tyr Gly Tyr Leu Thr Leu Asn Asn Gly
        290                 295                 300

Ser Gln Ser Val Gly Arg Ser Ser Phe Tyr Cys Leu Glu Tyr Phe Pro
305                 310                 315                 320

Ser Gln Met Leu Arg Thr Gly Asn Asn Phe Thr Phe Ser Tyr Thr Phe
                325                 330                 335

Glu Asp Val Pro Phe His Ser Ser Tyr Ala His Ser Gln Ser Leu Asp
                340                 345                 350

Arg Leu Met Asn Pro Leu Ile Asp Gln Tyr Leu Tyr Tyr Leu Ala Arg
            355                 360                 365

Thr Gln Ser Asn Ala Gly Gly Thr Ala Gly Asn Arg Glu Leu Gln Phe
        370                 375                 380

Tyr Gln Gly Gly Pro Thr Thr Met Ala Glu Gln Ala Lys Asn Trp Leu
385                 390                 395                 400

Pro Gly Pro Cys Phe Arg Gln Gln Arg Val Ser Lys Thr Leu Asp Gln
                405                 410                 415

Asn Asn Asn Ser Asn Phe Ala Trp Thr Gly Ala Thr Lys Tyr His Leu
                420                 425                 430

Asn Gly Arg Asn Ser Leu Val Asn Pro Gly Val Ala Met Ala Thr His
            435                 440                 445

Lys Asp Asp Glu Glu Arg Phe Phe Pro Ser Ser Gly Val Leu Ile Phe
        450                 455                 460

Gly Lys Thr Gly Ala Ala Asn Lys Thr Thr Leu Glu Asn Val Leu Met
465                 470                 475                 480

Thr Asn Glu Glu Glu Ile Arg Pro Thr Asn Pro Val Ala Thr Glu Glu
                485                 490                 495

Tyr Gly Ile Val Ser Ser Asn Leu Gln Ala Ala Ser Thr Ala Ala Gln
            500                 505                 510

Thr Gln Val Val Asn Asn Gln Gly Ala Leu Pro Gly Met Val Trp Gln
        515                 520                 525

Asn Arg Asp Val Tyr Leu Gln Gly Pro Ile Trp Ala Lys Ile Pro His
530                 535                 540

Thr Asp Gly Asn Phe His Pro Ser Pro Leu Met Gly Gly Phe Gly Leu
545                 550                 555                 560

Lys His Pro Pro Pro Gln Ile Leu Ile Lys Asn Thr Pro Val Pro Ala
                565                 570                 575

Asn Pro Pro Glu Val Phe Thr Pro Ala Lys Ile Ala Ser Phe Ile Thr
            580                 585                 590

Gln Tyr Ser Thr Gly Gln Val Ser Val Glu Ile Glu Trp Glu Leu Gln
        595                 600                 605

Lys Glu Asn Ser Lys Arg Trp Asn Pro Glu Ile Gln Tyr Thr Ser Asn
610                 615                 620

Phe Asp Lys Gln Thr Gly Val Asp Phe Ala Val Asp Ser Gln Gly Val

```
                625                 630                 635                 640

Tyr Ser Glu Pro

<210> SEQ ID NO 78
<211> LENGTH: 644
<212> TYPE: PRT
<213> ORGANISM: Unknown
<220> FEATURE:
<223> OTHER INFORMATION: capsid protein of AAV serotype, clone 223-6

<400> SEQUENCE: 78

Lys Ala Tyr Asp Gln Gln Leu Lys Ala Gly Asp Asn Pro Tyr Leu Arg
1               5                   10                  15

Tyr Asn His Ala Asp Ala Glu Phe Gln Glu Arg Leu Gln Glu Asp Thr
            20                  25                  30

Ser Phe Gly Gly Asn Leu Gly Arg Ala Val Phe Gln Ala Lys Lys Arg
        35                  40                  45

Val Leu Glu Pro Leu Gly Leu Val Glu Thr Pro Ala Lys Thr Ala Pro
    50                  55                  60

Gly Lys Lys Arg Pro Val Asp Ser Pro Asp Ser Thr Ser Gly Ile Gly
65                  70                  75                  80

Lys Lys Gly Gln Gln Pro Ala Lys Lys Arg Leu Asn Phe Gly Gln Thr
                85                  90                  95

Gly Asp Ser Glu Ser Val Pro Asp Pro Gln Pro Ile Gly Glu Pro Pro
            100                 105                 110

Ala Gly Pro Ser Gly Leu Gly Ser Gly Thr Met Ala Ala Gly Gly Gly
        115                 120                 125

Ala Pro Met Ala Asp Asn Ser Glu Gly Ala Asp Gly Val Gly Asn Ala
    130                 135                 140

Ser Gly Asn Trp His Cys Asp Ser Thr Trp Leu Gly Asp Arg Val Ile
145                 150                 155                 160

Thr Thr Ser Thr Arg Thr Trp Ala Leu Pro Thr Tyr Asn Asn His Leu
                165                 170                 175

Tyr Lys Gln Ile Ser Ser Gln Ser Ala Gly Ser Thr Asn Asp Asn Val
            180                 185                 190

Tyr Phe Gly Tyr Ser Thr Pro Trp Gly Tyr Phe Asp Phe Asn Arg Phe
        195                 200                 205

His Cys His Phe Ser Pro Arg Asp Trp Gln Arg Leu Ile Asn Asn Asn
    210                 215                 220

Trp Gly Phe Arg Pro Lys Lys Leu Asn Phe Lys Leu Phe Asn Ile Gln
225                 230                 235                 240

Val Lys Glu Val Thr Thr Asn Asp Gly Val Thr Thr Ile Ala Asn Asn
                245                 250                 255

Leu Thr Ser Thr Val Gln Val Phe Ser Asp Ser Glu Tyr Gln Leu Pro
            260                 265                 270

Tyr Val Leu Gly Ser Ala His Gln Gly Cys Leu Pro Pro Phe Pro Ala
        275                 280                 285

Asp Val Phe Met Ile Pro Gln Tyr Gly Tyr Leu Thr Leu Asn Asn Gly
    290                 295                 300

Ser Gln Ser Val Gly Arg Ser Ser Phe Tyr Cys Leu Glu Tyr Phe Pro
305                 310                 315                 320

Ser Gln Met Leu Arg Thr Gly Asn Asn Phe Thr Phe Ser Tyr Thr Phe
                325                 330                 335

Glu Asp Val Pro Phe His Ser Ser Tyr Ala His Ser Gln Ser Leu Asp
            340                 345                 350
```

-continued

```
Arg Leu Met Asn Pro Leu Ile Asp Gln Tyr Leu Tyr Tyr Leu Ala Arg
        355                 360                 365

Thr Gln Ser Asn Ala Gly Gly Thr Ala Gly Asn Arg Glu Leu Gln Phe
    370                 375                 380

Tyr Gln Gly Gly Pro Thr Thr Met Ala Glu Gln Ala Lys Asn Trp Leu
385                 390                 395                 400

Pro Gly Pro Cys Phe Arg Gln Gln Arg Val Ser Lys Thr Leu Asp Gln
                405                 410                 415

Asn Asn Asn Ser Asn Phe Ala Trp Thr Gly Ala Thr Lys Tyr His Leu
            420                 425                 430

Asn Gly Arg Asn Ser Leu Val Asn Pro Gly Val Ala Met Ala Thr His
        435                 440                 445

Lys Asp Asp Glu Glu Arg Phe Phe Pro Ser Ser Gly Val Leu Ile Phe
    450                 455                 460

Gly Lys Thr Gly Ala Ala Asn Lys Thr Thr Leu Glu Asn Val Leu Met
465                 470                 475                 480

Thr Asn Glu Glu Glu Ile Arg Pro Thr Asn Pro Val Ala Thr Glu Glu
                485                 490                 495

Tyr Gly Ile Val Ser Ser Asn Leu Gln Ala Ala Ser Thr Ala Ala Gln
            500                 505                 510

Thr Gln Val Val Asn Asn Gln Gly Ala Leu Pro Gly Met Val Trp Gln
        515                 520                 525

Asn Arg Asp Val Tyr Leu Gln Gly Pro Ile Trp Ala Lys Ile Pro His
    530                 535                 540

Thr Asp Gly Asn Phe His Pro Ser Pro Leu Met Gly Gly Phe Gly Leu
545                 550                 555                 560

Lys His Pro Pro Pro Gln Ile Leu Ile Lys Asn Thr Pro Val Pro Ala
                565                 570                 575

Asn Pro Pro Glu Val Phe Thr Pro Ala Lys Leu Ala Ser Phe Ile Thr
            580                 585                 590

Gln Tyr Ser Thr Gly Gln Val Ser Val Glu Ile Glu Trp Glu Leu Gln
        595                 600                 605

Lys Glu Asn Ser Lys Arg Trp Asn Pro Glu Ile Gln Tyr Thr Ser Asn
    610                 615                 620

Phe Asp Lys Gln Thr Gly Val Asp Phe Ala Val Asp Ser Gln Gly Val
625                 630                 635                 640

Tyr Ser Glu Pro

<210> SEQ ID NO 79
<211> LENGTH: 738
<212> TYPE: PRT
<213> ORGANISM: Unknown
<220> FEATURE:
<223> OTHER INFORMATION: capsid protein of AAV serotype, clone 44.1

<400> SEQUENCE: 79

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60
```

```
Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Arg Tyr Asn His Ala
             85                  90                  95

Asp Ala Glu Phe Gln Glu Arg Leu Gln Glu Asp Thr Ser Phe Gly Gly
        100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
```

```
            485                 490                 495
Gln Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
        530                 535                 540

Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
        610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 80
<211> LENGTH: 738
<212> TYPE: PRT
<213> ORGANISM: Unknown
<220> FEATURE:
<223> OTHER INFORMATION: capsid protein of AAV serotype, clone 44.5

<400> SEQUENCE: 80

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110
```

```
Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
                180                 185                 190

Pro Ala Gly Pro Ser Gly Leu Gly Ser Gly Thr Met Ala Ala Gly Gly
            195                 200                 205

Gly Ala Pro Met Ala Asp Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
        260                 265                 270

Asn Thr Tyr Phe Gly Tyr Ser Thr Pro Trp Gly Tyr Phe Asp Phe Asn
    275                 280                 285

Arg Phe His Cys His Phe Ser Pro Arg Asp Trp Gln Arg Leu Ile Asn
290                 295                 300

Asn Asn Trp Gly Phe Arg Pro Lys Arg Pro Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
        340                 345                 350

Leu Pro Tyr Val Leu Gly Ser Ala His Gln Gly Cys Leu Pro Pro Phe
    355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
        420                 425                 430

Leu Asp Arg Leu Met Asn Pro Leu Ile Asp Gln Tyr Leu Tyr Tyr Leu
    435                 440                 445

Ser Arg Thr Gln Ser Thr Gly Gly Thr Ala Gly Thr Gln Gln Leu Leu
450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
        500                 505                 510

Leu Asn Gly Arg Asp Ser Leu Val Asn Pro Gly Val Ala Met Ala Thr
    515                 520                 525
```

```
His Lys Asp Asp Glu Glu Arg Phe Phe Pro Ser Ser Gly Val Leu Met
        530                 535                 540

Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
            580                 585                 590

Pro Ile Val Gly Ala Val Asn Ser Gln Gly Ala Leu Pro Gly Met Val
            595                 600                 605

Trp Gln Asn Arg Asp Val Tyr Leu Gln Gly Pro Ile Trp Ala Lys Ile
        610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 81
<211> LENGTH: 738
<212> TYPE: PRT
<213> ORGANISM: Unknown
<220> FEATURE:
<223> OTHER INFORMATION: capsid protein of  AAV serotype, clone 44.2

<400> SEQUENCE: 81

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
```

-continued

```
         145                 150                 155                 160
Gly Lys Lys Gly Gln Gln Pro Ala Lys Lys Arg Leu Asn Phe Gly Gln
                    165                 170                 175
Thr Gly Asp Ser Glu Ser Val Pro Asp Pro Gln Pro Ile Gly Glu Pro
            180                 185                 190
Pro Ala Gly Pro Ser Gly Leu Gly Ser Gly Thr Met Ala Ala Gly Gly
                195                 200                 205
Gly Ala Pro Met Ala Asp Asn Asn Glu Gly Ala Asp Gly Val Gly Ser
        210                 215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Asn Gly Thr Ser Gly Gly Ser Thr Asn Asp
                260                 265                 270
Asn Thr Tyr Phe Gly Tyr Ser Thr Pro Trp Gly Tyr Phe Asp Phe Asn
                275                 280                 285
Arg Phe His Cys His Phe Ser Pro Arg Asp Trp Gln Arg Leu Ile Asn
        290                 295                 300
Asn Asn Trp Gly Phe Arg Pro Lys Arg Leu Asn Phe Lys Leu Phe Asn
305                 310                 315                 320
Ile Gln Val Lys Glu Val Thr Gln Asn Glu Gly Thr Lys Thr Ile Ala
                325                 330                 335
Asn Asn Leu Thr Ser Thr Ile Gln Val Phe Thr Asp Ser Glu Tyr Gln
                340                 345                 350
Leu Pro Tyr Val Leu Gly Ser Ala His Gln Gly Cys Leu Pro Pro Phe
                355                 360                 365
Pro Ala Asp Val Phe Met Ile Pro Gln Tyr Gly Tyr Leu Thr Leu Asn
        370                 375                 380
Asn Gly Ser Gln Ala Val Gly Arg Ser Ser Phe Tyr Cys Leu Glu Tyr
385                 390                 395                 400
Phe Pro Ser Gln Met Leu Arg Thr Gly Asn Asn Phe Glu Phe Ser Tyr
                405                 410                 415
Gln Phe Glu Asp Val Pro Phe His Ser Ser Tyr Ala His Ser Gln Ser
                420                 425                 430
Leu Asp Arg Leu Met Asn Pro Leu Ile Asp Gln Tyr Leu Tyr Tyr Leu
                435                 440                 445
Ser Arg Thr Gln Ser Thr Gly Gly Thr Ala Gly Thr Gln Gln Leu Leu
450                 455                 460
Phe Ser Gln Ala Gly Pro Asn Asn Met Ser Ala Gln Ala Lys Asn Trp
465                 470                 475                 480
Leu Pro Gly Pro Cys Tyr Arg Gln Gln Arg Val Ser Thr Thr Leu Ser
                485                 490                 495
Gln Asn Asn Asn Ser Asn Phe Ala Trp Thr Gly Ala Thr Lys Tyr His
                500                 505                 510
Leu Asn Gly Arg Asp Ser Leu Val Asn Pro Gly Val Ala Met Ala Thr
            515                 520                 525
His Lys Asp Asp Glu Glu Arg Phe Phe Pro Ser Ser Gly Val Leu Met
        530                 535                 540
Phe Gly Lys Gln Gly Ala Gly Lys Asp Asn Val Asp Tyr Ser Ser Val
545                 550                 555                 560
Met Leu Thr Ser Glu Glu Glu Ile Lys Thr Thr Asn Pro Val Ala Thr
                565                 570                 575
```

-continued

Glu Gln Tyr Gly Val Ala Asp Asn Leu Gln Gln Asn Ala Ala
              580                 585                 590

Pro Ile Val Gly Ala Val Asn Ser Gln Gly Ala Leu Pro Gly Met Val
              595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
              645                 650                 655

Pro Ala Asp Pro Pro Thr Thr Phe Ser Gln Ala Lys Leu Ala Ser Phe
              660                 665                 670

Ile Thr Gln Tyr Ser Thr Gly Gln Val Ser Val Glu Ile Glu Trp Glu
              675                 680                 685

Leu Gln Lys Glu Asn Ser Lys Arg Trp Asn Pro Glu Ile Gln Tyr Thr
              690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
              725                 730                 735

Asn Leu

<210> SEQ ID NO 82
<211> LENGTH: 738
<212> TYPE: PRT
<213> ORGANISM: Unknown
<220> FEATURE:
<223> OTHER INFORMATION: capsid protein of AAV serotype, clone 29.3VP1

<400> SEQUENCE: 82

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
              20                  25                  30

Lys Ala Asn Gln Gln Lys Gln Asp Asp Gly Arg Gly Leu Val Leu Pro
          35                  40                  45

Gly Tyr Lys Tyr Leu Gly Pro Phe Asn Gly Leu Asp Lys Gly Glu Pro
      50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
              85                  90                  95

Asp Ala Glu Phe Gln Glu Arg Leu Gln Glu Asp Thr Ser Phe Gly Gly
              100                 105                 110

Asn Leu Gly Arg Ala Val Phe Gln Ala Lys Lys Arg Val Leu Glu Pro
          115                 120                 125

Leu Gly Leu Val Glu Glu Gly Ala Lys Thr Ala Pro Gly Lys Lys Arg
      130                 135                 140

Pro Val Glu Pro Ser Pro Gln Arg Ser Pro Asp Ser Thr Thr Gly Ile
145                 150                 155                 160

Gly Lys Lys Gly Gln Gln Pro Ala Lys Lys Arg Leu Asn Phe Gly Gln
              165                 170                 175

Thr Gly Asp Ser Glu Ser Val Pro Asp Pro Gln Pro Ile Gly Glu Pro
              180                 185                 190

-continued

```
Pro Ala Gly Pro Ser Gly Leu Gly Ser Gly Thr Met Ala Gly Gly
            195                 200                 205
Gly Ala Pro Met Ala Asp Asn Asn Glu Gly Ala Asp Gly Val Gly Ser
210             215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Asn Gly Thr Ser Gly Gly Ser Thr Asn Asp
            260                 265                 270
Asn Thr Tyr Phe Gly Tyr Ser Thr Pro Trp Gly Tyr Phe Asp Phe Asn
        275                 280                 285
Arg Phe His Cys His Phe Ser Pro Arg Asp Trp Gln Arg Leu Ile Asn
    290                 295                 300
Asn Asn Trp Gly Phe Arg Pro Lys Arg Leu Asn Phe Lys Leu Phe Asn
305                 310                 315                 320
Ile Gln Val Lys Glu Val Thr Gln Asn Glu Gly Thr Lys Thr Ile Ala
                325                 330                 335
Asn Asn Leu Thr Ser Thr Ile Gln Val Phe Thr Asp Ser Glu Tyr Gln
            340                 345                 350
Leu Pro Tyr Val Leu Gly Ser Ala Arg Gln Gly Cys Leu Pro Pro Phe
        355                 360                 365
Pro Ala Asp Val Phe Met Ile Pro Gln Tyr Gly Tyr Leu Thr Leu Asn
    370                 375                 380
Asn Gly Ser Gln Ala Val Gly Arg Ser Ser Phe Tyr Cys Leu Glu Tyr
385                 390                 395                 400
Phe Pro Ser Gln Met Leu Arg Thr Gly Asn Asn Phe Glu Phe Ser Tyr
                405                 410                 415
Gln Phe Glu Asp Val Pro Phe His Ser Ser Tyr Ala His Ser Gln Ser
            420                 425                 430
Leu Asp Arg Leu Met Asn Pro Leu Ile Asp Gln Tyr Leu Tyr Tyr Leu
        435                 440                 445
Ser Arg Thr Gln Ser Thr Gly Gly Thr Ala Gly Thr Gln Gln Leu Leu
    450                 455                 460
Phe Ser Gln Ala Gly Pro Asn Asn Met Ser Ala Gln Ala Lys Asn Trp
465                 470                 475                 480
Leu Pro Gly Pro Cys Tyr Arg Gln Gln Arg Val Ser Thr Thr Leu Ser
                485                 490                 495
Gln Asn Asn Asn Ser Asn Phe Ala Trp Thr Gly Ala Thr Lys Tyr His
            500                 505                 510
Leu Asn Gly Arg Asp Ser Leu Val Asn Pro Gly Val Ala Met Ala Thr
        515                 520                 525
His Lys Asp Asp Glu Glu Arg Phe Phe Pro Ser Ser Gly Val Leu Met
    530                 535                 540
Phe Gly Lys Gln Gly Ala Gly Lys Gly Asn Val Asp Tyr Ser Ser Val
545                 550                 555                 560
Met Leu Thr Ser Glu Glu Glu Ile Lys Thr Thr Asn Pro Val Ala Thr
                565                 570                 575
Glu Gln Tyr Gly Val Val Ala Asp Asn Leu Gln Gln Asn Ala Ala
            580                 585                 590
Pro Ile Val Gly Ala Val Asn Ser Gln Gly Ala Leu Pro Gly Met Val
        595                 600                 605
Trp Gln Asn Arg Asp Val Tyr Leu Gln Gly Pro Ile Trp Ala Lys Ile
```

```
                610                 615                 620
Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
            690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 83
<211> LENGTH: 738
<212> TYPE: PRT
<213> ORGANISM: Unknown
<220> FEATURE:
<223> OTHER INFORMATION: capsid protein of AAV serotype, clone 29.5VP1

<400> SEQUENCE: 83

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Gly Val
225                 230                 235                 240
```

```
Ile Thr Thr Ser Thr Arg Thr Trp Ala Leu Pro Thr Tyr Asn Asn His
            245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
            290                 295                 300

Asn Asn Trp Gly Phe Arg Pro Lys Ser Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
                340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
            370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
            435                 440                 445

Ser Arg Thr Gln Ser Thr Gly Gly Thr Ala Gly Thr Gln Gln Leu Leu
            450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asp Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
            580                 585                 590

Pro Ile Val Gly Ala Val Asn Ser Gln Gly Ala Leu Pro Gly Met Val
            595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655
```

```
Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 84
<211> LENGTH: 738
<212> TYPE: PRT
<213> ORGANISM: Unknown
<220> FEATURE:
<223> OTHER INFORMATION: capsid protein of AAV serotype, clone 42.15

<400> SEQUENCE: 84

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Thr Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
```

-continued

```
                275                 280                 285
Arg Phe His Cys His Phe Ser Pro Arg Asp Trp Gln Arg Leu Ile Asn
290                 295                 300
Asn Asn Trp Gly Phe Arg Pro Lys Arg Leu Asn Phe Lys Leu Phe Asn
305                 310                 315                 320
Ile Gln Val Lys Glu Val Thr Gln Asn Glu Gly Thr Lys Thr Ile Ala
                325                 330                 335
Asn Asn Leu Thr Ser Thr Ile Gln Val Phe Thr Asp Ser Glu Tyr Gln
                340                 345                 350
Leu Pro Tyr Val Leu Gly Ser Ala His Gln Gly Cys Pro Pro Pro Phe
                355                 360                 365
Pro Ala Asp Val Phe Met Ile Pro Gln Tyr Gly Tyr Leu Thr Leu Asn
370                 375                 380
Asn Gly Ser Gln Ala Val Gly Arg Ser Ser Phe Tyr Cys Leu Glu Tyr
385                 390                 395                 400
Phe Pro Ser Gln Met Arg Arg Thr Gly Asn Asn Phe Glu Phe Ser Tyr
                405                 410                 415
Gln Phe Glu Asp Val Pro Phe His Ser Ser Tyr Ala His Ser Gln Ser
                420                 425                 430
Leu Asp Arg Leu Met Asn Pro Leu Ile Asp Gln Tyr Leu Tyr Tyr Leu
                435                 440                 445
Ser Arg Thr Gln Ser Thr Gly Gly Thr Ala Gly Thr Gln Gln Leu Leu
450                 455                 460
Phe Ser Gln Ala Gly Pro Asn Asn Met Ser Ala Gln Ala Lys Asn Trp
465                 470                 475                 480
Leu Pro Gly Pro Cys Tyr Arg Gln Gln Arg Val Ser Thr Thr Leu Ser
                485                 490                 495
Gln Asn Asn Asn Ser Asn Phe Ala Trp Thr Gly Ala Thr Lys Tyr His
                500                 505                 510
Leu Asn Gly Arg Asp Ser Leu Val Asn Pro Gly Val Ala Met Ala Thr
                515                 520                 525
His Lys Asp Asp Glu Glu Arg Phe Phe Pro Ser Ser Gly Val Leu Met
530                 535                 540
Phe Gly Lys Gln Gly Ala Gly Lys Asp Asn Val Asp Tyr Ser Ser Val
545                 550                 555                 560
Met Leu Thr Ser Glu Glu Ile Lys Thr Thr Asn Pro Val Ala Thr
                565                 570                 575
Glu Gln Tyr Gly Val Val Ala Asp Asn Leu Gln Gln Gln Asn Ala Ala
                580                 585                 590
Pro Ile Val Gly Ala Val Asn Ser Gln Gly Ala Leu Pro Gly Met Val
                595                 600                 605
Trp Gln Asn Arg Asp Val Tyr Leu Gln Gly Pro Ile Trp Ala Lys Ile
                610                 615                 620
Pro His Thr Asp Gly Asn Phe His Pro Ser Pro Leu Met Gly Gly Phe
625                 630                 635                 640
Gly Leu Lys His Pro Pro Pro Gln Ile Leu Ile Lys Asn Thr Pro Val
                645                 650                 655
Pro Ala Asp Pro Pro Thr Thr Phe Ser Gln Ala Lys Leu Ala Ser Phe
                660                 665                 670
Ile Thr Gln Tyr Ser Thr Gly Gln Val Ser Val Glu Ile Glu Trp Glu
                675                 680                 685
Leu Gln Lys Glu Asn Ser Lys Arg Trp Asn Pro Glu Ile Gln Tyr Thr
690                 695                 700
```

```
Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
            725                 730                 735

Asn Leu

<210> SEQ ID NO 85
<211> LENGTH: 738
<212> TYPE: PRT
<213> ORGANISM: Unknown
<220> FEATURE:
<223> OTHER INFORMATION: capsid protein of AAV serotype, clone 42.8

<400> SEQUENCE: 85

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Thr Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
290                 295                 300

Asn Asn Trp Gly Phe Arg Pro Lys Arg Leu Asn Phe Lys Leu Phe Asn
305                 310                 315                 320
```

```
Ile Gln Val Lys Glu Val Thr Gln Asn Glu Gly Thr Lys Thr Ile Ala
                325                 330                 335

Asn Asn Leu Thr Ser Thr Ile Val Phe Thr Asp Ser Glu Tyr Gln
            340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
            435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
            530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
            580                 585                 590

Pro Ile Val Gly Ala Val Asn Ser Gln Gly Ala Leu Pro Gly Met Val
            595                 600                 605

Trp Gln Asn Arg Asp Val Tyr Leu Gln Gly Pro Ile Trp Ala Lys Ile
            610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
            690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu
```

<210> SEQ ID NO 86
<211> LENGTH: 733
<212> TYPE: PRT
<213> ORGANISM: Unknown
<220> FEATURE:
<223> OTHER INFORMATION: capsid protein of AAV serotype, clone 42.13

<400> SEQUENCE: 86

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Ile Gly Glu Pro Pro Ala Gly Pro Ser
            180                 185                 190

Gly Leu Gly Ser Gly Thr Met Ala Ala Gly Gly Gly Ala Pro Met Ala
        195                 200                 205

Asp Asn Asn Glu Gly Ala Asp Gly Val Gly Ser Ser Ser Gly Asn Trp
    210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Asn Gly Thr Ser Gly Gly Ser Thr Asn Asp Asn Thr Tyr Phe Gly
            260                 265                 270

Tyr Ser Thr Pro Trp Gly Tyr Phe Asp Phe Asn Arg Phe His Cys His
        275                 280                 285

Phe Ser Pro Arg Asp Trp Gln Arg Leu Ile Asn Asn Asn Trp Gly Phe
    290                 295                 300

Arg Pro Lys Arg Leu Asn Phe Lys Leu Phe Asn Ile Gln Val Lys Glu
305                 310                 315                 320

Val Thr Gln Asn Glu Gly Thr Lys Thr Ile Ala Asn Asn Leu Thr Ser
                325                 330                 335

Thr Ile Gln Val Phe Thr Asp Ser Glu Tyr Gln Leu Pro Tyr Val Leu
            340                 345                 350

Gly Ser Ala His Gln Gly Cys Leu Pro Pro Phe Pro Ala Asp Val Phe
        355                 360                 365

Met Ile Pro Gln Tyr Gly Tyr Leu Thr Leu Asn Asn Gly Ser Gln Ala
370                 375                 380

Val Gly Arg Ser Ser Phe Tyr Cys Leu Glu Tyr Phe Pro Ser Gln Met
385                 390                 395                 400

Leu Arg Thr Gly Asn Asn Phe Glu Phe Ser Tyr Gln Phe Glu Asp Val
                405                 410                 415

Pro Phe His Ser Ser Tyr Ala His Ser Gln Ser Leu Asp Arg Leu Met
                420                 425                 430

Asn Pro Leu Ile Asp Gln Tyr Leu Tyr Tyr Leu Ser Arg Thr Gln Ser
                435                 440                 445

Thr Gly Gly Thr Ala Gly Thr Gln Gln Leu Leu Phe Ser Gln Ala Gly
450                 455                 460

Pro Asn Asn Met Ser Ala Gln Ala Lys Asn Trp Leu Pro Gly Pro Cys
465                 470                 475                 480

Tyr Arg Gln Gln Arg Val Ser Thr Thr Val Ser Gln Asn Asn Asn Ser
                485                 490                 495

Asn Phe Ala Trp Thr Gly Ala Thr Lys Tyr His Leu Asn Gly Arg Asp
                500                 505                 510

Ser Leu Val Asn Pro Gly Val Ala Met Ala Thr His Lys Gly Asp Glu
                515                 520                 525

Glu Arg Phe Phe Pro Ser Ser Gly Val Leu Met Phe Gly Lys Gln Gly
530                 535                 540

Ala Gly Lys Asp Asn Val Asp Tyr Ser Ser Val Met Leu Thr Ser Glu
545                 550                 555                 560

Glu Glu Ile Lys Thr Thr Asn Pro Val Ala Thr Glu Gln Tyr Gly Val
                565                 570                 575

Val Ala Asp Asn Leu Gln Gln Gln Asn Ala Ala Pro Ile Val Gly Ala
                580                 585                 590

Val Asn Ser Gln Gly Ala Leu Pro Gly Met Val Trp Gln Asn Arg Asp
                595                 600                 605

Val Tyr Leu Gln Gly Pro Ile Trp Ala Lys Ile Pro His Thr Asp Gly
                610                 615                 620

Asn Phe His Pro Ser Pro Leu Met Gly Gly Phe Gly Leu Lys His Pro
625                 630                 635                 640

Pro Pro Gln Ile Leu Ile Lys Asn Thr Pro Val Pro Ala Asp Pro Pro
                645                 650                 655

Thr Thr Phe Ser Gln Ala Lys Leu Ala Ser Phe Ile Thr Gln Tyr Ser
                660                 665                 670

Thr Gly Gln Val Ser Val Glu Ile Glu Trp Glu Leu Gln Lys Glu Asn
                675                 680                 685

Ser Lys Arg Trp Asn Pro Glu Ile Gln Tyr Thr Ser Asn Tyr Tyr Lys
                690                 695                 700

Ser Thr Asn Val Asp Phe Ala Val Asn Thr Glu Gly Thr Tyr Ser Glu
705                 710                 715                 720

Pro Arg Pro Ile Gly Thr Arg Tyr Leu Thr Arg Ser Leu
                725                 730

<210> SEQ ID NO 87
<211> LENGTH: 733
<212> TYPE: PRT
<213> ORGANISM: Unknown
<220> FEATURE:
<223> OTHER INFORMATION: capsid protein of AAV serotype, clone 42.3A

<400> SEQUENCE: 87

```
Met Ala Ala Asp Gly His Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
                35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65              70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Glu Gly Ala Lys Thr Ala Pro Gly Lys Lys Arg
    130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Ile Gly Glu Pro Pro Ala Gly Pro Ser
                180                 185                 190

Gly Leu Gly Ser Gly Thr Met Ala Ala Gly Gly Gly Ala Pro Met Ala
    195                 200                 205

Asp Asn Asn Glu Gly Ala Asp Gly Val Gly Ser Ser Ser Gly Asn Trp
210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Asn Gly Thr Ser Gly Gly Ser Thr Asn Asp Asn Thr Tyr Phe Gly
                260                 265                 270

Tyr Ser Thr Pro Trp Gly Tyr Phe Asp Phe Asn Arg Phe His Cys His
    275                 280                 285

Phe Ser Pro Arg Asp Trp Gln Arg Leu Ile Asn Asn Ser Trp Gly Phe
    290                 295                 300

Arg Pro Lys Arg Leu Asn Phe Lys Leu Phe Asn Ile Gln Val Lys Glu
305                 310                 315                 320

Val Thr Gln Asn Glu Gly Thr Lys Thr Ile Ala Asn Asn Leu Thr Ser
                325                 330                 335

Thr Ile Gln Val Phe Thr Asp Ser Glu Tyr Gln Leu Pro Tyr Val Leu
                340                 345                 350

Gly Ser Ala His Gln Gly Cys Leu Pro Pro Phe Pro Ala Asp Val Phe
                355                 360                 365

Met Ile Pro Gln Tyr Gly Tyr Leu Thr Leu Asn Asn Gly Ser Gln Ala
                370                 375                 380

Val Gly Arg Ser Ser Phe Tyr Cys Leu Glu Tyr Phe Pro Ser Gln Met
385                 390                 395                 400

Leu Arg Thr Gly Asn Asn Phe Glu Phe Ser Tyr Gln Phe Glu Asp Val
                405                 410                 415
```

```
Pro Phe His Ser Ser Tyr Ala His Ser Gln Ser Leu Asp Arg Leu Met
            420                 425                 430

Asn Pro Leu Ile Asp Gln Tyr Leu Tyr Tyr Leu Ser Arg Thr Gln Ser
            435                 440                 445

Thr Gly Gly Thr Ala Gly Thr Gln Gln Leu Leu Phe Ser Gln Ala Gly
        450                 455                 460

Pro Asn Asn Met Ser Ala Gln Ala Lys Asn Trp Leu Pro Gly Pro Cys
465                 470                 475                 480

Tyr Arg Gln Gln Arg Val Ser Thr Thr Leu Ser Gln Asn Asn Asn Ser
                485                 490                 495

Asn Phe Ala Trp Thr Gly Ala Thr Lys Tyr His Leu Asn Gly Arg Asp
            500                 505                 510

Ser Leu Val Asn Pro Gly Val Ala Met Ala Thr His Lys Asp Asp Glu
            515                 520                 525

Glu Arg Phe Phe Pro Ser Ser Gly Val Leu Met Phe Gly Lys Gln Gly
            530                 535                 540

Ala Gly Lys Asp Asn Val Asp Tyr Ser Ser Val Met Leu Thr Ser Glu
545                 550                 555                 560

Glu Glu Ile Lys Thr Thr Asn Pro Val Ala Thr Glu Gln Tyr Gly Val
                565                 570                 575

Val Ala Asp Asn Leu Gln Gln Gln Asn Ala Ala Pro Ile Val Gly Ala
            580                 585                 590

Val Asn Ser Gln Gly Ala Leu Pro Gly Met Val Trp Gln Asn Arg Asp
            595                 600                 605

Val Tyr Leu Gln Gly Pro Ile Trp Ala Lys Ile Pro His Thr Asp Gly
            610                 615                 620

Asn Phe His Pro Ser Pro Leu Met Gly Gly Phe Gly Leu Lys His Pro
625                 630                 635                 640

Pro Pro Gln Ile Leu Ile Lys Asn Thr Pro Val Pro Ala Asp Pro Pro
                645                 650                 655

Thr Thr Phe Ser Gln Ala Lys Leu Ala Ser Phe Ile Thr Gln Tyr Ser
            660                 665                 670

Thr Gly Gln Val Ser Val Glu Ile Glu Trp Glu Leu Gln Lys Glu Asn
        675                 680                 685

Ser Lys Arg Trp Asn Pro Glu Ile Gln Tyr Thr Ser Asn Tyr Tyr Lys
        690                 695                 700

Ser Thr Asn Val Asp Phe Ala Val Asn Thr Glu Gly Thr Tyr Ser Glu
705                 710                 715                 720

Pro Arg Pro Ile Gly Thr Arg Tyr Leu Thr Arg Asn Leu
                725                 730

<210> SEQ ID NO 88
<211> LENGTH: 731
<212> TYPE: PRT
<213> ORGANISM: Unknown
<220> FEATURE:
<223> OTHER INFORMATION: capsid protein of AAV serotype, clone 42.4

<400> SEQUENCE: 88

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45
```

```
Gly Tyr Lys Tyr Leu Gly Pro Phe Asn Gly Leu Asp Lys Gly Glu Pro
         50                  55                  60

Val Asn Glu Ala Asp Ala Ala Leu Glu His Asp Lys Ala Tyr Asp
 65                  70                  75                  80

Lys Gln Leu Glu Gln Gly Asp Asn Pro Tyr Leu Lys Tyr Asn His Ala
                     85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Ile Gly Glu Pro Ala Gly Pro Ser
                180                 185                 190

Gly Leu Gly Ser Gly Thr Met Ala Ala Gly Gly Ala Pro Met Ala
            195                 200                 205

Asp Asn Asn Glu Gly Ala Asp Gly Val Gly Asn Ala Ser Gly Asn Trp
            210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Gln Ser Gly Ala Thr Asn Asp Asn His Phe Phe Gly Tyr Ser
                260                 265                 270

Thr Pro Trp Gly Tyr Phe Asp Phe Asn Arg Phe His Cys His Phe Ser
            275                 280                 285

Ser Arg Asp Trp Gln Arg Leu Ile Asn Asn Asn Trp Gly Phe Arg Pro
            290                 295                 300

Lys Arg Leu Asn Phe Lys Leu Phe Asn Ile Gln Val Lys Glu Val Thr
305                 310                 315                 320

Gln Asn Glu Gly Thr Lys Thr Ile Ala Asn Asn Leu Thr Ser Thr Ile
                325                 330                 335

Gln Val Phe Thr Asp Ser Glu Tyr Arg Leu Pro Tyr Val Leu Gly Ser
            340                 345                 350

Ala His Gln Gly Cys Leu Pro Pro Phe Pro Ala Asp Val Phe Met Ile
            355                 360                 365

Pro Gln Tyr Gly Tyr Leu Thr Leu Asn Asn Gly Ser Gln Ala Val Gly
370                 375                 380

Arg Ser Ser Phe Tyr Cys Leu Glu Tyr Phe Pro Ser Gln Met Leu Arg
385                 390                 395                 400

Thr Gly Asn Asn Phe Glu Phe Ser Tyr Gln Phe Glu Asp Val Pro Phe
                405                 410                 415

His Ser Ser Tyr Ala His Ser Gln Ser Leu Asp Arg Leu Met Asn Pro
                420                 425                 430

Leu Ile Asp Gln Tyr Leu Tyr Leu Ser Arg Thr Gln Ser Thr Gly
            435                 440                 445

Gly Thr Ala Gly Thr Gln Gln Leu Leu Phe Ser Gln Ala Gly Pro Asn
450                 455                 460

Asn Met Ser Ala Gln Ala Lys Asn Trp Leu Pro Gly Pro Cys Tyr Arg
```

```
            465                 470                 475                 480
    Gln Gln Arg Val Ser Thr Thr Leu Ser Gln Asn Asn Asn Ser Asn Phe
                        485                 490                 495

Ala Trp Thr Gly Ala Thr Lys Tyr His Leu Asn Gly Arg Asp Ser Leu
                        500                 505                 510

Val Asn Pro Gly Val Ala Met Ala Thr His Lys Asp Asp Glu Glu Arg
                        515                 520                 525

Phe Phe Pro Ser Ser Gly Val Leu Met Phe Gly Lys Gln Gly Ala Gly
                        530                 535                 540

Lys Asp Asn Val Asp Tyr Ser Ser Val Met Leu Thr Ser Glu Glu Glu
    545                 550                 555                 560

Ile Lys Thr Thr Asn Pro Val Ala Thr Glu Gln Tyr Gly Val Val Ala
                        565                 570                 575

Asp Asn Leu Gln Gln Gln Asn Ala Ala Pro Ile Val Gly Ala Val Asn
                        580                 585                 590

Ser Gln Gly Ala Leu Pro Gly Met Val Trp Gln Asn Arg Asp Val Tyr
                        595                 600                 605

Leu Gln Gly Pro Ile Trp Ala Lys Ile Pro His Thr Asp Gly Asn Phe
                        610                 615                 620

His Pro Ser Pro Leu Met Gly Gly Phe Gly Leu Lys His Pro Pro Pro
    625                 630                 635                 640

Gln Ile Leu Ile Lys Asn Thr Pro Val Pro Ala Asp Pro Pro Thr Thr
                        645                 650                 655

Phe Ser Gln Ala Lys Pro Ala Ser Phe Ile Thr Gln Tyr Ser Thr Gly
                        660                 665                 670

Gln Val Ser Val Glu Ile Glu Trp Glu Leu Gln Lys Glu Asn Ser Lys
                        675                 680                 685

Arg Trp Asn Pro Glu Ile Gln Tyr Thr Ser Asn Tyr Tyr Lys Ser Thr
                        690                 695                 700

Asn Val Asp Phe Ala Val Asn Thr Glu Gly Thr Tyr Ser Glu Pro Arg
    705                 710                 715                 720

Pro Ile Gly Thr Arg Tyr Leu Thr Arg Asn Leu
                        725                 730

<210> SEQ ID NO 89
<211> LENGTH: 731
<212> TYPE: PRT
<213> ORGANISM: Unknown
<220> FEATURE:
<223> OTHER INFORMATION: capsid protein of AAV serotype, clone 42.5A

<400> SEQUENCE: 89

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Glu Ala Asp Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
```

```
                    100                 105                 110
Asn Leu Gly Arg Ala Val Phe Arg Ala Lys Lys Arg Val Leu Glu Pro
            115                 120                 125
Leu Gly Leu Val Glu Glu Gly Ala Lys Thr Ala Pro Gly Lys Lys Arg
            130                 135                 140
Pro Ile Glu Ser Pro Asp Ser Ser Thr Gly Ile Gly Lys Lys Gly Gln
145                 150                 155                 160
Gln Pro Ala Lys Lys Leu Asn Phe Gly Gln Thr Gly Asp Ser Glu
                165                 170                 175
Ser Val Pro Asp Pro Gln Pro Leu Gly Glu Pro Ala Ala Pro Ser
                180                 185                 190
Gly Leu Gly Ser Gly Thr Met Ala Ala Gly Gly Ala Pro Met Ala
            195                 200                 205
Asp Asn Asn Glu Gly Ala Asp Gly Val Gly Asn Ala Ser Gly Asn Trp
            210                 215                 220
His Cys Asp Ser Thr Trp Leu Gly Asp Arg Val Ile Thr Thr Ser Thr
225                 230                 235                 240
Arg Thr Trp Ala Leu Pro Thr Tyr Asn Asn His Leu Tyr Lys Gln Ile
                245                 250                 255
Ser Ser Gln Ser Gly Ala Thr Asn Asp Asn His Phe Phe Gly Tyr Ser
            260                 265                 270
Thr Pro Trp Gly Tyr Phe Asp Phe Asn Arg Phe His Cys His Phe Ser
            275                 280                 285
Pro Arg Asp Trp Gln Arg Leu Ile Asn Asn Arg Gly Phe Arg Pro
            290                 295                 300
Arg Lys Leu Arg Phe Lys Leu Phe Asn Ile Gln Val Lys Glu Val Thr
305                 310                 315                 320
Thr Asn Asp Gly Val Thr Thr Ile Ala Asn Asn Leu Thr Ser Thr Ile
                325                 330                 335
Gln Val Phe Ser Asp Ser Glu Tyr Gln Leu Pro Tyr Val Leu Gly Ser
            340                 345                 350
Ala His Gln Gly Cys Leu Pro Pro Phe Pro Ala Asp Val Phe Met Ile
            355                 360                 365
Pro Gln Tyr Gly Tyr Leu Thr Leu Asn Asn Gly Ser Gln Ser Val Gly
            370                 375                 380
Arg Ser Ser Phe Tyr Cys Leu Glu Tyr Phe Pro Ser Gln Met Leu Arg
385                 390                 395                 400
Thr Gly Asn Asn Phe Glu Phe Ser Tyr Gln Phe Glu Asp Val Pro Phe
                405                 410                 415
His Ser Ser Tyr Ala His Ser Gln Ser Leu Asp Arg Leu Met Asn Pro
                420                 425                 430
Leu Ile Asp Gln Tyr Leu Tyr Tyr Leu Ser Arg Thr Gln Ser Thr Gly
            435                 440                 445
Gly Thr Ala Gly Thr Gln Gln Leu Leu Phe Ser Gln Ala Gly Pro Asn
            450                 455                 460
Asn Met Ser Ala Gln Ala Lys Asn Trp Leu Pro Gly Pro Cys Tyr Arg
465                 470                 475                 480
Gln Gln Arg Val Ser Thr Thr Leu Ser Gln Asn Asn Asn Ser Asn Phe
                485                 490                 495
Ala Trp Thr Gly Ala Thr Lys Tyr His Leu Asn Gly Arg Asp Ser Leu
            500                 505                 510
Val Asn Pro Gly Val Ala Met Ala Thr His Lys Asp Asp Glu Glu Arg
            515                 520                 525
```

```
Phe Phe Pro Ser Ser Gly Val Leu Met Phe Gly Lys Gln Gly Ala Gly
        530                 535                 540
Lys Asp Asn Val Asp Tyr Ser Ser Val Met Leu Thr Ser Glu Glu Glu
545                 550                 555                 560
Ile Lys Thr Thr Asn Pro Val Ala Thr Glu Gln Tyr Gly Val Val Ala
                565                 570                 575
Asp Asn Leu Gln Gln Gln Asn Ala Ala Pro Ile Val Gly Ala Val Asn
            580                 585                 590
Ser Gln Gly Ala Leu Pro Gly Met Ala Trp Gln Asn Arg Asp Val Tyr
        595                 600                 605
Leu Gln Gly Pro Ile Trp Ala Lys Ile Pro His Thr Asp Gly Asn Phe
    610                 615                 620
His Pro Ser Pro Leu Met Gly Gly Phe Gly Leu Lys His Pro Pro Pro
625                 630                 635                 640
Gln Ile Leu Ile Lys Asn Thr Pro Val Pro Ala Asp Pro Pro Thr Thr
                645                 650                 655
Phe Ser Gln Ala Lys Leu Ala Ser Phe Ile Thr Gln Tyr Ser Thr Gly
            660                 665                 670
Gln Val Ser Val Glu Ile Glu Trp Glu Leu Gln Lys Glu Asn Ser Lys
        675                 680                 685
Arg Trp Asn Pro Glu Ile Gln Tyr Thr Ser Asn Tyr Tyr Lys Ser Thr
    690                 695                 700
Asn Val Asp Phe Ala Val Asn Thr Glu Gly Thr Tyr Ser Glu Pro Arg
705                 710                 715                 720
Pro Ile Gly Thr Arg Tyr Leu Thr Arg Asn Leu
                725                 730

<210> SEQ ID NO 90
<211> LENGTH: 733
<212> TYPE: PRT
<213> ORGANISM: Unknown
<220> FEATURE:
<223> OTHER INFORMATION: capsid protein of AAV serotype, clone 42.1B

<400> SEQUENCE: 90

Met Ala Ala Asp Gly Tyr Leu Pro Asp Trp Leu Glu Asp Asn Leu Ser
1               5                   10                  15
Glu Gly Ile Arg Glu Trp Trp Asp Leu Arg Pro Gly Ala Pro Lys Pro
            20                  25                  30
Lys Ala Asn Gln Gln Lys Gln Asp Asp Gly Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Glu Ala Asp Ala Ala Ala Leu Glu His Asp Lys Ala Tyr Asp
65                  70                  75                  80
Lys Gln Leu Glu Gln Gly Asp Asn Pro Tyr Leu Lys Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Gly Ala Lys Thr Ala Pro Gly Lys Lys Arg
    130                 135                 140
Pro Ile Glu Ser Pro Asp Ser Ser Thr Gly Ile Gly Lys Lys Gly Gln
145                 150                 155                 160
```

```
Gln Pro Ala Lys Lys Arg Leu Asn Phe Gly Gln Thr Gly Asp Ser Glu
            165                 170                 175

Ser Val Pro Asp Pro Gln Pro Ile Gly Glu Pro Ala Gly Pro Ser
        180                 185                 190

Gly Leu Gly Ser Gly Thr Met Ala Ala Gly Gly Ala Pro Met Ala
            195                 200             205

Asp Asn Asn Glu Gly Ala Asp Gly Val Gly Ser Ser Gly Asn Trp
        210                 215                 220

His Cys Asp Ser Thr Trp Leu Gly Asp Arg Val Ile Thr Ser Thr
225             230                 235                 240

Arg Thr Trp Ala Leu Pro Thr Tyr Asn Asn His Leu Tyr Lys Gln Ile
                245                 250                 255

Ser Asn Gly Thr Ser Gly Gly Ser Thr Asn Asp Asn Thr Tyr Phe Gly
            260                 265                 270

Tyr Ser Thr Pro Trp Gly Tyr Phe Asp Phe Asn Arg Phe His Cys His
        275                 280                 285

Phe Ser Pro Arg Asp Trp Gln Arg Leu Ile Asn Asn Asn Trp Gly Phe
    290                 295                 300

Arg Pro Lys Arg Leu Asn Phe Lys Leu Phe Asn Ile Gln Val Lys Glu
305                 310                 315                 320

Val Thr Gln Asn Glu Gly Thr Lys Thr Ile Ala Asn Asn Leu Thr Ser
                325                 330                 335

Thr Ile Gln Val Phe Thr Asp Ser Glu Tyr Gln Leu Pro Tyr Val Leu
                340                 345                 350

Gly Ser Ala His Gln Gly Cys Leu Pro Pro Phe Pro Ala Asp Val Phe
            355                 360                 365

Met Ile Pro Gln Tyr Gly Tyr Leu Thr Leu Asn Asn Gly Ser Gln Ala
        370                 375                 380

Val Gly Arg Ser Ser Phe Tyr Cys Leu Glu Tyr Phe Pro Ser Gln Met
385                 390                 395                 400

Leu Arg Thr Gly Asn Asn Phe Glu Phe Ser Tyr Gln Phe Glu Asp Val
                405                 410                 415

Pro Phe His Ser Ser Tyr Ala His Ser Gln Ser Leu Asp Arg Leu Met
            420                 425                 430

Asn Pro Leu Ile Asp Gln Tyr Leu Tyr Tyr Leu Ser Arg Thr Gln Ser
        435                 440                 445

Thr Gly Gly Thr Ala Gly Thr Gln Gln Leu Leu Phe Ser Gln Ala Gly
    450                 455                 460

Pro Asn Asn Met Ser Ala Gln Ala Lys Asn Trp Leu Pro Gly Pro Cys
465                 470                 475                 480

Tyr Arg Gln Gln Arg Val Ser Thr Thr Val Ser Gln Asn Asn Asn Ser
                485                 490                 495

Asn Phe Ala Trp Thr Gly Ala Thr Lys Tyr His Leu Asn Gly Arg Asp
            500                 505                 510

Ser Leu Val Asn Pro Gly Val Ala Met Ala Thr His Lys Gly Asp Glu
        515                 520                 525

Glu Arg Phe Phe Pro Ser Ser Gly Val Leu Met Phe Gly Lys Gln Gly
    530                 535                 540

Ala Gly Lys Asp Asn Val Asp Tyr Ser Ser Val Met Leu Thr Ser Glu
545                 550                 555                 560

Glu Glu Ile Lys Thr Thr Asn Pro Val Ala Thr Glu Gln Tyr Gly Val
                565                 570                 575
```

-continued

Val Ala Asp Asn Leu Gln Gln Gln Asn Ala Ala Pro Ile Val Gly Ala
              580                 585                 590

Val Asn Ser Gln Gly Ala Leu Pro Gly Met Val Trp Gln Asn Arg Asp
        595                 600                 605

Val Tyr Leu Gln Gly Pro Ile Trp Ala Lys Ile Pro His Thr Asp Gly
    610                 615                 620

Asn Phe His Pro Ser Pro Leu Met Gly Gly Phe Gly Leu Lys His Pro
625                 630                 635                 640

Pro Pro Gln Ile Leu Ile Lys Asn Thr Pro Val Pro Ala Asp Pro Pro
                645                 650                 655

Thr Thr Phe Ser Gln Ala Lys Leu Ala Ser Phe Ile Thr Gln Tyr Ser
            660                 665                 670

Thr Gly Gln Val Ser Val Glu Ile Glu Trp Glu Leu Gln Lys Glu Asn
        675                 680                 685

Ser Lys Arg Trp Asn Pro Glu Ile Gln Tyr Thr Ser Asn Tyr Tyr Lys
    690                 695                 700

Ser Thr Asn Val Asp Phe Ala Val Asn Thr Glu Gly Thr Tyr Ser Glu
705                 710                 715                 720

Pro Arg Pro Ile Gly Thr Arg Tyr Leu Thr Arg Asn Leu
                725                 730

<210> SEQ ID NO 91
<211> LENGTH: 738
<212> TYPE: PRT
<213> ORGANISM: Unknown
<220> FEATURE:
<223> OTHER INFORMATION: capsid protein of AAV serotype, clone 42.5B

<400> SEQUENCE: 91

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Glu Ala Asp Ala Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Thr Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Ser Thr Asn Asp
        260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
        290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
        340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
            450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe

-continued

```
            625                 630                 635                 640
Gly Leu Lys His Pro Pro Gln Ile Leu Ile Lys Asn Thr Pro Val
                    645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu
```

<210> SEQ ID NO 92
<211> LENGTH: 738
<212> TYPE: PRT
<213> ORGANISM: Unknown
<220> FEATURE:
<223> OTHER INFORMATION: capsid protein of AAV serotype, clone 43.1

<400> SEQUENCE: 92

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly His Gln Pro Ala Arg Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255
```

-continued

Leu Tyr Lys Gln Ile Ser Asn Gly Thr Ser Gly Ser Thr Asn Asp
            260                 265             270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Pro Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Gln Gly Thr Gln Gln Leu Leu
    450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Thr Asn Gly Ala
            580                 585                 590

Pro Ile Val Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Val Lys Asn Thr Pro Val
                645                 650                 655

Pro Ala Asp Pro Pro Thr Thr Phe Ser Gln Ala Lys Leu Ala Ser Phe
            660                 665                 670

```
Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu
```

<210> SEQ ID NO 93
<211> LENGTH: 738
<212> TYPE: PRT
<213> ORGANISM: Unknown
<220> FEATURE:
<223> OTHER INFORMATION: capsid protein of AAV serotype, clone 43.12

<400> SEQUENCE: 93

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly His Gln Pro Ala Arg Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
```

```
               290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
                340                 345                 350

Leu Pro Tyr Val Leu Gly Ser Ala His Gln Gly Cys Leu Pro Pro Phe
                355                 360                 365

Pro Ala Asp Val Phe Met Ile Pro Gln Tyr Gly Tyr Leu Thr Leu Asn
                370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
                435                 440                 445

Ser Arg Thr Gln Ser Thr Gly Gly Thr Gln Gly Thr Gln Gln Leu Leu
                450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
                500                 505                 510

Leu Asn Gly Arg Asp Ser Leu Val Asn Pro Gly Val Ala Met Ala Thr
                515                 520                 525

His Lys Asp Asp Glu Glu Arg Phe Phe Pro Ser Ser Gly Val Leu Met
                530                 535                 540

Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Thr Asn Gly Ala
                580                 585                 590

Pro Ile Val Gly Thr Val Asn Ser Gln Gly Ala Leu Pro Gly Met Val
                595                 600                 605

Trp Gln Asn Arg Asp Val Tyr Leu Gln Gly Pro Ile Trp Ala Lys Ile
                610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Val Lys Asn Thr Pro Val
                645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
                675                 680                 685

Leu Gln Lys Glu Asn Ser Lys Arg Trp Asn Pro Glu Ile Gln Tyr Thr
                690                 695                 700

Ser Asn Tyr Tyr Lys Ser Thr Asn Val Asp Phe Ala Val Asn Thr Glu
705                 710                 715                 720
```

```
Gly Thr Tyr Ser Glu Pro Arg Pro Ile Gly Thr Arg Tyr Leu Thr Arg
                725                 730                 735

Asn Leu

<210> SEQ ID NO 94
<211> LENGTH: 738
<212> TYPE: PRT
<213> ORGANISM: Unknown
<220> FEATURE:
<223> OTHER INFORMATION: capsid protein of AAV serotype, clone 43.5

<400> SEQUENCE: 94

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Lys Gly His Gln Pro Ala Arg Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335
```

```
Asn Asn Leu Thr Ser Thr Ile Gln Val Phe Thr Asp Ser Glu Tyr Gln
                340                 345                 350

Leu Pro Tyr Val Leu Gly Ser Ala His Gln Gly Cys Leu Pro Pro Phe
    355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
            435                 440                 445

Ser Arg Thr Gln Ser Thr Gly Gly Thr Gln Gly Thr Gln Gln Leu Leu
        450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
530                 535                 540

Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Thr Asn Gly Ala
                580                 585                 590

Pro Ile Val Gly Thr Val Asn Ser Gln Gly Ala Leu Pro Gly Met Val
            595                 600                 605

Trp Gln Asn Arg Asp Val Tyr Leu Gln Gly Pro Ile Trp Ala Lys Ile
        610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Val Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 95
```

<211> LENGTH: 738
<212> TYPE: PRT
<213> ORGANISM: Unknown
<220> FEATURE:
<223> OTHER INFORMATION: capsid protein of AAV serotype, clone AAV8

<400> SEQUENCE: 95

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380
```

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
            405                 410                 415

Thr Phe Glu Asp Val Pro Phe His Ser Ser Tyr Ala His Ser Gln Ser
        420                 425                 430

Leu Asp Arg Leu Met Asn Pro Leu Ile Asp Gln Tyr Leu Tyr Tyr Leu
    435                 440                 445

Ser Arg Thr Gln Thr Thr Gly Gly Thr Ala Asn Thr Gln Thr Leu Gly
450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
            485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Ile Lys Thr Thr Asn Pro Val Ala Thr
            565                 570                 575

Glu Glu Tyr Gly Ile Val Ala Asp Asn Leu Gln Gln Asn Thr Ala
            580                 585                 590

Pro Gln Ile Gly Thr Val Asn Ser Gln Gly Ala Leu Pro Gly Met Val
    595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
            645                 650                 655

Pro Ala Asp Pro Pro Thr Thr Phe Asn Gln Ser Lys Leu Asn Ser Phe
        660                 665                 670

Ile Thr Gln Tyr Ser Thr Gly Gln Val Ser Val Glu Ile Glu Trp Glu
    675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
            725                 730                 735

Asn Leu

<210> SEQ ID NO 96
<211> LENGTH: 736
<212> TYPE: PRT
<213> ORGANISM: Unknown
<220> FEATURE:
<223> OTHER INFORMATION: capsid protein of AAV serotype, clone 43.21

<400> SEQUENCE: 96

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Leu Gly Pro Asn Thr Met Ala Ser Gly Gly Gly
            195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ser Thr Asn Asp Asn
            260                 265                 270

Thr Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Glu Gly Thr Lys Thr Ile Ala Asn
                325                 330                 335

Asn Leu Thr Ser Thr Val Arg Val Phe Thr Asp Ser Glu Tyr Gln Leu
            340                 345                 350

Pro Tyr Val Leu Gly Ser Ala His Gln Gly Cys Leu Pro Pro Phe Pro
            355                 360                 365

Ala Asp Val Phe Met Val Pro Gln Tyr Gly Tyr Leu Thr Leu Asn Asn
            370                 375                 380

Gly Ser Gln Ala Leu Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Thr
                405                 410                 415

Phe Glu Asp Val Pro Phe His Ser Ser Tyr Ala His Ser Gln Ser Leu
```

```
              420                 425                 430
Asp Arg Leu Met Asn Pro Leu Ile Asp Gln Tyr Leu Tyr Tyr Leu Val
            435                 440                 445

Arg Thr Gln Thr Thr Gly Thr Gly Gly Thr Gln Thr Leu Ala Phe Ser
        450                 455                 460

Gln Ala Gly Pro Ser Ser Met Ala Asn Gln Ala Arg Asn Trp Val Pro
465                 470                 475                 480

Gly Pro Cys Tyr Arg Gln Gln Arg Val Ser Thr Thr Thr Asn Gln Ser
                485                 490                 495

Asn Asn Ser Asn Phe Ala Trp Thr Gly Ala Ala Lys Phe Lys Leu Asn
            500                 505                 510

Gly Arg Asp Ser Leu Met Asn Pro Gly Val Ala Met Ala Ser His Lys
        515                 520                 525

Asp Asp Asp Asp Arg Phe Phe Pro Ser Ser Gly Val Leu Ile Phe Gly
    530                 535                 540

Lys Gln Gly Ala Gly Asn Asp Gly Val Asp Tyr Ser Gln Val Leu Ile
545                 550                 555                 560

Thr Asp Glu Glu Glu Ile Lys Ala Thr Asn Pro Val Ala Thr Glu Glu
                565                 570                 575

Tyr Gly Ala Val Ala Ile Asn Asn Gln Ala Ala Asn Thr Gln Ala Gln
            580                 585                 590

Thr Gly Leu Val His Asn Gln Gly Val Ile Pro Gly Met Val Trp Gln
        595                 600                 605

Asn Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asp Pro Pro Leu Thr Phe Asn Gln Ala Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Thr Asn Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 97
<211> LENGTH: 736
<212> TYPE: PRT
<213> ORGANISM: Unknown
<220> FEATURE:
<223> OTHER INFORMATION: capsid protein of AAV serotype, clone 43.25

<400> SEQUENCE: 97

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
```

```
            50                  55                  60
Val Asn Ala Ala Asp Ala Ala Leu Glu His Asp Lys Ala Tyr Asp
 65                  70                  75                  80
Gln Gln Leu Lys Ala Gly Asp Asn Pro Tyr Leu Arg Tyr Asn His Ala
                 85                  90                  95
Asp Ala Glu Phe Gln Glu Arg Leu Gln Glu Asp Thr Ser Phe Gly Gly
                100                 105                 110
Asn Leu Gly Arg Ala Val Phe Gln Ala Lys Lys Arg Val Leu Glu Pro
                115                 120                 125
Leu Gly Leu Val Glu Glu Gly Ala Lys Thr Ala Pro Gly Lys Lys Arg
            130                 135                 140
Pro Val Glu Gln Ser Pro Gln Glu Pro Asp Ser Ser Ser Gly Ile Gly
145                 150                 155                 160
Lys Thr Gly Gln Gln Pro Ala Lys Lys Arg Leu Asn Phe Gly Gln Thr
                165                 170                 175
Gly Asp Ser Glu Ser Val Pro Asp Pro Gln Pro Leu Gly Glu Pro Pro
                180                 185                 190
Ala Ala Pro Ser Gly Leu Gly Pro Asn Thr Met Ala Ser Gly Gly Gly
                195                 200                 205
Ala Pro Met Ala Asp Asn Asn Glu Gly Ala Asp Gly Val Gly Asn Ser
            210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Gly Thr Ser Gly Gly Ser Thr Asn Asp Asn
                260                 265                 270
Thr Tyr Phe Gly Tyr Ser Thr Pro Trp Gly Tyr Phe Asp Phe Asn Arg
                275                 280                 285
Phe His Cys His Phe Ser Pro Arg Asp Trp Gln Arg Leu Ile Asn Asn
            290                 295                 300
Asn Trp Gly Phe Arg Pro Lys Arg Leu Asn Phe Lys Leu Phe Asn Ile
305                 310                 315                 320
Gln Val Lys Glu Val Thr Thr Asn Glu Gly Thr Lys Thr Ile Ala Asn
                325                 330                 335
Asn Leu Thr Ser Thr Val Gln Val Phe Thr Asp Ser Glu Tyr Gln Leu
                340                 345                 350
Pro Tyr Val Leu Gly Ser Ala His Gln Gly Cys Leu Pro Pro Phe Pro
                355                 360                 365
Ala Asp Val Phe Met Val Pro Gln Tyr Gly Tyr Leu Thr Leu Asn Asn
            370                 375                 380
Gly Ser Gln Ala Leu Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Thr
                405                 410                 415
Phe Glu Asp Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Val
            435                 440                 445
Arg Thr Gln Thr Thr Gly Thr Gly Thr Gln Thr Leu Ala Phe Ser
            450                 455                 460
Gln Ala Gly Pro Ser Ser Met Ala Asn Gln Ala Arg Asn Trp Val Pro
465                 470                 475                 480
```

```
Gly Pro Cys Tyr Arg Gln Gln Arg Val Ser Thr Thr Thr Asn Gln Asn
                485                 490                 495

Asn Asn Ser Asn Phe Ala Trp Thr Gly Ala Ala Lys Phe Lys Leu Asn
            500                 505                 510

Gly Arg Asp Ser Leu Met Asn Pro Gly Val Ala Met Ala Ser His Lys
        515                 520                 525

Asp Asp Asp Asp Arg Phe Phe Pro Ser Ser Gly Val Leu Ile Phe Gly
    530                 535                 540

Lys Gln Gly Ala Gly Asn Asp Gly Val Asp Tyr Ser Gln Val Leu Ile
545                 550                 555                 560

Thr Asp Glu Glu Glu Ile Lys Ala Thr Asn Pro Val Ala Thr Glu Glu
                565                 570                 575

Tyr Gly Ala Val Ala Ile Asn Asn Gln Ala Ala Asn Thr Gln Ala Gln
            580                 585                 590

Thr Gly Leu Val His Asn Gln Gly Val Ile Pro Gly Met Val Trp Gln
        595                 600                 605

Asn Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asp Pro Pro Leu Thr Phe Asn Gln Ala Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Thr Asn Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 98
<211> LENGTH: 736
<212> TYPE: PRT
<213> ORGANISM: Unknown
<220> FEATURE:
<223> OTHER INFORMATION: capsid protein of AAV serotype, clone 43.23

<400> SEQUENCE: 98

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110
```

-continued

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
        130                 135                 140

Pro Val Glu Gln Ser Pro Gln Glu Pro Asp Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Leu Gly Pro Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Ser Thr Asn Asp Asn
            260                 265                 270

Thr Tyr Phe Gly Tyr Ser Thr Pro Trp Gly Tyr Phe Asp Phe Asn Arg
    275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Glu Gly Thr Lys Thr Ile Ala Asn
                325                 330                 335

Asn Leu Thr Ser Thr Val Gln Val Phe Thr Asp Leu Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Val Pro Gln Tyr Gly Tyr Leu Thr Leu Asn Asn
    370                 375                 380

Gly Ser Gln Ala Leu Gly Arg Ser Ser Phe Tyr Cys Leu Glu Tyr Phe
385                 390                 395                 400

Pro Ser Gln Met Pro Arg Thr Gly Asn Asn Phe Gln Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Val
        435                 440                 445

Arg Thr Gln Thr Thr Gly Thr Gly Thr Gln Thr Leu Ala Phe Ser
    450                 455                 460

Gln Ala Gly Pro Ser Ser Met Ala Asn Gln Ala Arg Asn Trp Val Pro
465                 470                 475                 480

Gly Pro Cys Tyr Arg Gln Gln Arg Val Ser Thr Thr Thr Asn Gln Asn
                485                 490                 495

Asn Asn Ser Asn Phe Ala Trp Thr Gly Ala Ala Lys Phe Lys Leu Asn
            500                 505                 510

Gly Arg Asp Ser Leu Met Asn Pro Gly Val Ala Met Ala Ser His Lys
        515                 520                 525

Asp Asp Asp Asp Arg Phe Phe Pro Ser Ser Gly Val Leu Ile Phe Gly
530                535                540

Lys Gln Gly Ala Gly Asn Asp Gly Val Asp Tyr Ser Gln Val Leu Ile
545                550                555                560

Thr Asp Glu Glu Glu Ile Lys Ala Thr Asn Pro Val Ala Thr Glu Glu
                565                570                575

Tyr Gly Ala Val Ala Ile Asn Asn Gln Ala Ala Asn Thr Gln Ala Gln
                580                585                590

Thr Gly Leu Val His Asn Gln Gly Val Ile Pro Gly Met Val Trp Gln
                595                600                605

Asn Arg Asp Val Tyr Leu Gln Gly Pro Ile Trp Ala Lys Ile Pro His
610                615                620

Thr Asp Gly Asn Phe His Pro Ser Pro Leu Met Gly Gly Phe Gly Leu
625                630                635                640

Lys His Pro Pro Pro Gln Ile Leu Ile Lys Asn Thr Pro Val Pro Ala
                645                650                655

Asp Pro Pro Leu Thr Phe Asn Gln Ala Lys Leu Asn Ser Phe Ile Thr
                660                665                670

Gln Tyr Ser Thr Gly Gln Val Ser Val Glu Ile Glu Trp Glu Leu Gln
                675                680                685

Lys Glu Asn Ser Lys Arg Trp Asn Pro Glu Ile Gln Tyr Thr Ser Asn
690                695                700

Tyr Tyr Lys Ser Thr Asn Val Asp Phe Ala Val Asn Thr Glu Gly Val
705                710                715                720

Tyr Ser Glu Pro Arg Pro Ile Gly Thr Arg Tyr Leu Thr Arg Asn Leu
                725                730                735

<210> SEQ ID NO 99
<211> LENGTH: 736
<212> TYPE: PRT
<213> ORGANISM: Unknown
<220> FEATURE:
<223> OTHER INFORMATION: capsid protein of AAV serotype, clone 43.20

<400> SEQUENCE: 99

Met Ala Ala Asp Gly Tyr Leu Pro Asp Trp Leu Glu Asp Asn Leu Ser
1                5                10                15

Glu Gly Ile Arg Glu Trp Trp Asp Leu Lys Pro Gly Ala Pro Lys Pro
                20                25                30

Lys Ala Asn Gln Gln Lys Gln Asp Asp Gly Arg Gly Leu Val Leu Pro
                35                40                45

Gly Tyr Lys Tyr Leu Gly Pro Phe Asn Gly Leu Asp Lys Gly Glu Pro
                50                55                60

Val Asn Ala Ala Asp Ala Ala Leu Glu His Asp Lys Ala Tyr Asp
65                70                75                80

Gln Gln Leu Lys Ala Gly Asp Asn Pro Tyr Leu Arg Tyr Asn His Ala
                85                90                95

Asp Ala Glu Phe Gln Glu Arg Leu Gln Glu Asp Thr Ser Phe Gly Gly
                100                105                110

Asn Leu Gly Arg Ala Val Phe Gln Ala Lys Lys Arg Val Leu Glu Pro
                115                120                125

Leu Gly Leu Val Glu Glu Gly Ala Lys Thr Ala Pro Gly Lys Lys Arg
                130                135                140

Leu Val Glu Gln Ser Pro Gln Glu Pro Asp Ser Ser Ser Gly Ile Gly
145                150                155                160

-continued

Lys Thr Gly Gln Gln Pro Ala Lys Lys Arg Leu Asn Phe Gly Gln Thr
            165                 170                 175
Gly Asp Ser Glu Ser Val Pro Asp Pro Gln Pro Leu Gly Glu Pro Pro
        180                 185                 190
Ala Ala Pro Ser Gly Leu Gly Pro Asn Thr Met Ala Ser Gly Gly Gly
        195                 200                 205
Ala Pro Met Ala Asp Asn Asn Glu Gly Ala Asp Gly Val Gly Asn Ser
        210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
            245                 250                 255
Tyr Lys Gln Ile Ser Asn Gly Thr Ser Gly Gly Ser Thr Asn Asp Asn
            260                 265                 270
Thr Tyr Phe Gly Tyr Ser Thr Pro Trp Gly Tyr Phe Asp Phe Asn Arg
        275                 280                 285
Phe His Cys His Phe Ser Pro Arg Asp Trp Gln Arg Leu Ile Asn Asn
        290                 295                 300
Asn Trp Gly Phe Arg Pro Lys Arg Leu Asn Phe Lys Leu Phe Asn Ile
305                 310                 315                 320
Gln Val Lys Glu Val Thr Thr Asn Glu Gly Thr Lys Thr Ile Ala Asn
            325                 330                 335
Asn Leu Thr Ser Thr Val Gln Val Phe Thr Asp Ser Glu Tyr Gln Leu
            340                 345                 350
Pro Tyr Val Leu Gly Ser Ala His Gln Gly Cys Leu Pro Pro Phe Pro
        355                 360                 365
Ala Asp Val Phe Thr Val Pro Gln Tyr Gly Tyr Leu Thr Leu Asn Asn
        370                 375                 380
Gly Ser Gln Ala Leu Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Thr
            405                 410                 415
Phe Glu Asp Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Val
        435                 440                 445
Arg Thr Gln Thr Thr Gly Thr Gly Thr Gln Thr Leu Ala Phe Ser
        450                 455                 460
Gln Ala Gly Pro Ser Ser Met Ala Asn Gln Ala Arg Asn Trp Val Pro
465                 470                 475                 480
Gly Pro Cys Tyr Arg Gln Gln Arg Val Ser Thr Thr Thr Asn Gln Asn
            485                 490                 495
Asn Asn Ser Asn Phe Ala Trp Thr Gly Ala Ala Lys Phe Lys Leu Asn
            500                 505                 510
Gly Arg Asp Ser Leu Met Asn Pro Gly Val Ala Met Ala Ser His Lys
        515                 520                 525
Asp Asp Asp Asp Arg Phe Phe Pro Ser Ser Gly Val Leu Ile Phe Gly
        530                 535                 540
Lys Gln Gly Ala Gly Asn Asp Gly Val Asp Tyr Ser Gln Val Leu Ile
545                 550                 555                 560
Thr Asp Glu Glu Glu Ile Lys Ala Thr Asn Pro Val Ala Thr Glu Glu
            565                 570                 575
Tyr Gly Ala Val Ala Ile Asn Asn Gln Ala Ala Asn Thr Gln Ala Gln

```
                580                 585                 590
Thr Gly Leu Val His Asn Gln Gly Val Ile Pro Gly Met Val Trp Gln
                    595                 600                 605

Asn Arg Asp Val Tyr Leu Gln Gly Pro Ile Trp Ala Lys Ile Pro His
                    610                 615                 620

Thr Asp Gly Asn Phe His Pro Ser Pro Leu Met Gly Gly Phe Gly Leu
625                 630                 635                 640

Lys His Pro Pro Gln Ile Leu Ile Lys Asn Thr Pro Val Pro Ala
                    645                 650                 655

Asp Pro Pro Leu Thr Phe Asn Gln Ala Lys Leu Asn Ser Phe Ile Thr
                660                 665                 670

Gln Tyr Ser Thr Gly Gln Val Ser Val Glu Ile Glu Trp Glu Leu Gln
                675                 680                 685

Lys Glu Asn Ser Lys Arg Trp Asn Pro Glu Ile Gln Tyr Thr Ser Asn
                690                 695                 700

Tyr Tyr Lys Ser Thr Asn Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
                    725                 730                 735

<210> SEQ ID NO 100
<211> LENGTH: 736
<212> TYPE: PRT
<213> ORGANISM: Unknown
<220> FEATURE:
<223> OTHER INFORMATION: capsid protein of AAV serotype, clone AAV9

<400> SEQUENCE: 100

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Val Glu Gln Ser Pro Gln Glu Pro Asp Ser Ser Ser Gly Ile Gly
145                 150                 155                 160

Lys Ser Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Glu Ala Pro Ser Gly Leu Gly Pro Asn Thr Met Ala Ser Gly Gly Gly
        195                 200                 205

Ala Pro Met Ala Asp Asn Asn Glu Gly Ala Asp Gly Val Gly Asn Ser
```

```
                    210                 215                 220
Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                    245                 250                 255

Tyr Lys Gln Ile Ser Asn Gly Thr Ser Gly Gly Ser Thr Asn Asp Asn
                260                 265                 270

Thr Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Glu Gly Thr Lys Thr Ile Ala Asn
                325                 330                 335

Asn Leu Thr Ser Thr Val Gln Val Phe Thr Asp Ser Glu Tyr Gln Leu
                340                 345                 350

Pro Tyr Val Leu Gly Ser Ala His Gln Gly Cys Leu Pro Pro Phe Pro
            355                 360                 365

Ala Asp Val Phe Met Val Pro Gln Tyr Gly Tyr Leu Thr Leu Asn Asn
        370                 375                 380

Gly Ser Gln Ala Leu Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Thr
                405                 410                 415

Phe Glu Asp Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Val
            435                 440                 445

Arg Thr Gln Thr Thr Gly Thr Gly Gly Thr Gln Thr Leu Ala Phe Ser
        450                 455                 460

Gln Ala Gly Pro Ser Ser Met Ala Asn Gln Ala Arg Asn Trp Val Pro
465                 470                 475                 480

Gly Pro Cys Tyr Arg Gln Gln Arg Val Ser Thr Thr Thr Asn Gln Asn
                485                 490                 495

Asn Asn Ser Asn Phe Ala Trp Thr Gly Ala Ala Lys Phe Lys Leu Asn
                500                 505                 510

Gly Arg Asp Ser Leu Met Asn Pro Gly Val Ala Met Ala Ser His Lys
            515                 520                 525

Asp Asp Glu Asp Arg Phe Phe Pro Ser Ser Gly Val Leu Ile Phe Gly
        530                 535                 540

Lys Gln Gly Ala Gly Asn Asp Gly Val Asp Tyr Ser Gln Val Leu Ile
545                 550                 555                 560

Thr Asp Glu Glu Glu Ile Lys Ala Thr Asn Pro Val Ala Thr Glu Glu
                565                 570                 575

Tyr Gly Ala Val Ala Ile Asn Asn Gln Ala Ala Asn Thr Gln Ala Gln
                580                 585                 590

Thr Gly Leu Val His Asn Gln Gly Val Ile Pro Gly Met Val Trp Gln
            595                 600                 605

Asn Arg Asp Val Tyr Leu Gln Gly Pro Ile Trp Ala Lys Ile Pro His
        610                 615                 620

Thr Asp Gly Asn Phe His Pro Ser Pro Leu Met Gly Gly Phe Gly Leu
625                 630                 635                 640
```

-continued

```
Lys His Pro Pro Gln Ile Leu Ile Lys Asn Thr Pro Val Pro Ala
                645                 650                 655

Asp Pro Pro Leu Thr Phe Asn Gln Ala Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
690                 695                 700

Tyr Tyr Lys Ser Thr Asn Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 101
<211> LENGTH: 728
<212> TYPE: PRT
<213> ORGANISM: Unknown
<220> FEATURE:
<223> OTHER INFORMATION: capsid protein of AAV serotype, clone 24.1

<400> SEQUENCE: 101

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Arg Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Val Ala Lys Thr Ala Pro Gly Lys Lys Arg
    130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Leu Gly Glu Pro Ala Ala Pro Ser
            180                 185                 190

Gly Leu Gly Ser Gly Thr Met Ala Ala Gly Gly Ala Pro Met Ala
        195                 200                 205

Asp Asn Asn Glu Gly Ala Asp Gly Val Gly Asn Ala Ser Gly Asn Trp
    210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Gln Ser Gly Ala Thr Asn Asp Asn His Phe Phe Ser Tyr Ser
            260                 265                 270
```

-continued

```
Thr Pro Trp Gly Tyr Phe Asp Phe Asn Arg Phe His Cys His Phe Ser
    275                 280                 285
Pro Arg Asp Trp Gln Arg Leu Ile Asn Asn Asn Trp Gly Phe Arg Pro
290                 295                 300
Arg Lys Leu Arg Phe Lys Leu Phe Asn Ile Gln Val Lys Glu Val Thr
305                 310                 315                 320
Thr Asn Asp Gly Val Thr Thr Ile Ala Asn Asn Leu Thr Ser Thr Ile
                325                 330                 335
Gln Val Phe Ser Asp Ser Glu Tyr Gln Leu Pro Tyr Val Leu Gly Ser
                340                 345                 350
Ala His Gln Gly Cys Leu Pro Pro Phe Pro Ala Asp Val Phe Met Ile
                355                 360                 365
Pro Gln Tyr Gly Tyr Leu Thr Leu Asn Asn Gly Ser Gln Ser Val Gly
        370                 375                 380
Arg Ser Ser Phe Tyr Cys Leu Glu Tyr Phe Pro Ser Gln Met Leu Arg
385                 390                 395                 400
Thr Gly Asn Asn Phe Glu Phe Ser Tyr Thr Phe Glu Glu Val Pro Phe
                    405                 410                 415
His Ser Ser Tyr Val His Ser Gln Ser Leu Asp Arg Leu Met Asn Pro
                420                 425                 430
Leu Ile Asp Gln Tyr Leu Tyr Tyr Leu Ala Arg Thr Gln Ser Thr Thr
                435                 440                 445
Gly Ser Thr Arg Glu Leu Gln Phe His Gln Ala Gly Pro Asn Thr Met
        450                 455                 460
Ala Glu Gln Ser Lys Asn Trp Leu Pro Gly Pro Cys Tyr Arg Gln Gln
465                 470                 475                 480
Arg Leu Ser Lys Asn Ile Asp Ser Asn Asn Asn Ser Asn Phe Ala Trp
                    485                 490                 495
Thr Gly Ala Thr Lys Tyr His Leu Asn Gly Arg Asn Ser Leu Thr Asn
                500                 505                 510
Pro Gly Val Ala Met Ala Thr Asn Lys Asp Asp Glu Asp Gln Phe Phe
        515                 520                 525
Pro Ile Asn Gly Val Leu Val Phe Gly Lys Thr Gly Ala Ala Asn Lys
    530                 535                 540
Thr Thr Leu Glu Asn Val Leu Met Thr Ser Glu Glu Ile Lys Thr
545                 550                 555                 560
Thr Asn Pro Val Ala Thr Glu Glu Tyr Gly Val Val Ser Ser Asn Leu
                565                 570                 575
Gln Ser Ser Thr Ala Gly Pro Gln Thr Gln Thr Val Asn Ser Gln Gly
                580                 585                 590
Ala Leu Pro Gly Met Val Trp Gln Asn Arg Asp Val Cys Leu Gln Gly
            595                 600                 605
Pro Ile Trp Ala Lys Ile Pro His Thr Asp Gly Asn Phe His Pro Ser
    610                 615                 620
Pro Leu Met Gly Gly Phe Gly Leu Lys His Pro Pro Gln Ile Leu
625                 630                 635                 640
Ile Lys Asn Thr Pro Val Pro Ala Asn Pro Glu Val Phe Thr Pro
                645                 650                 655
Ala Lys Phe Ala Ser Phe Ile Thr Gln Tyr Ser Thr Gly Gln Val Ser
                660                 665                 670
Val Glu Ile Glu Trp Glu Leu Gln Lys Glu Asn Ser Lys Arg Trp Asn
                675                 680                 685
```

Pro Glu Ile Gln Tyr Thr Ser Asn Tyr Ala Lys Ser Asn Asn Val Glu
    690                 695                 700

Phe Ala Val Asn Glu Gly Val Tyr Thr Glu Pro Arg Pro Ile Gly
705                 710                 715                 720

Thr Arg Tyr Leu Thr Arg Asn Leu
                725

<210> SEQ ID NO 102
<211> LENGTH: 728
<212> TYPE: PRT
<213> ORGANISM: Unknown
<220> FEATURE:
<223> OTHER INFORMATION: capsid protein of AAV serotype, clone 42.2REAL

<400> SEQUENCE: 102

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Leu Gly Glu Pro Pro Ala Ala Pro Ser
            180                 185                 190

Gly Leu Gly Ser Gly Thr Met Ala Ala Gly Gly Gly Ala Pro Met Ala
        195                 200                 205

Asp Asn Asn Glu Gly Ala Asp Gly Val Gly Asn Ala Ser Gly Asn Trp
    210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Gln Ser Gly Ala Thr Asn Asp Asn His Phe Phe Gly Tyr Ser
            260                 265                 270

Thr Pro Trp Gly Tyr Phe Asp Phe Asn Arg Phe His Cys His Phe Ser
        275                 280                 285

Pro Arg Asp Trp Gln Arg Leu Ile Asn Asn Asn Trp Gly Phe Arg Pro
    290                 295                 300

Arg Lys Leu Arg Phe Lys Leu Phe Asn Ile Gln Val Lys Glu Val Thr
305                 310                 315                 320

-continued

```
Thr Asn Asp Gly Val Thr Thr Ile Ala Asn Asn Leu Thr Ser Thr Ile
                325                 330                 335
Gln Val Phe Ser Asp Ser Glu Tyr Gln Leu Pro Tyr Val Leu Gly Ser
            340                 345                 350
Ala His Gln Gly Cys Leu Pro Pro Phe Pro Ala Asp Val Phe Met Ile
        355                 360                 365
Pro Gln Tyr Gly Tyr Leu Thr Leu Asn Asn Gly Ser Gln Ser Val Gly
    370                 375                 380
Arg Ser Ser Phe Tyr Cys Leu Glu Tyr Phe Pro Ser Gln Met Leu Arg
385                 390                 395                 400
Thr Gly Asn Asn Phe Glu Phe Ser Tyr Thr Phe Glu Glu Val Pro Phe
                405                 410                 415
His Ser Ser Tyr Ala His Ser Gln Ser Leu Asp Arg Leu Met Asn Pro
            420                 425                 430
Leu Ile Asp Gln Tyr Leu Tyr Tyr Leu Ala Arg Thr Gln Ser Thr Thr
        435                 440                 445
Gly Ser Thr Arg Glu Leu Gln Phe His Gln Ala Gly Pro Asn Thr Met
    450                 455                 460
Ala Glu Gln Ser Lys Asn Trp Leu Pro Gly Pro Cys Tyr Arg Gln Gln
465                 470                 475                 480
Arg Leu Ser Lys Asn Ile Asp Ser Asn Asn Ser Asn Phe Ala Trp
                485                 490                 495
Thr Gly Ala Thr Lys Tyr His Leu Asn Gly Arg Asn Ser Leu Thr Asn
            500                 505                 510
Pro Gly Val Ala Met Ala Thr Asn Lys Asp Asp Glu Asp Gln Phe Phe
        515                 520                 525
Pro Ile Asn Gly Val Leu Val Phe Gly Glu Thr Gly Ala Ala Asn Lys
    530                 535                 540
Thr Thr Leu Glu Asn Val Leu Met Thr Ser Glu Glu Ile Lys Thr
545                 550                 555                 560
Thr Asn Pro Val Ala Thr Glu Glu Tyr Gly Val Val Ser Ser Asn Leu
                565                 570                 575
Gln Ser Ser Thr Ala Gly Pro Gln Thr Gln Thr Val Asn Ser Gln Gly
            580                 585                 590
Ala Leu Pro Gly Met Val Trp Gln Asn Arg Asp Val Tyr Leu Gln Gly
        595                 600                 605
Pro Ile Trp Ala Lys Ile Pro His Thr Asp Gly Asn Phe His Pro Ser
    610                 615                 620
Pro Leu Met Gly Gly Phe Gly Leu Lys His Pro Pro Gln Ile Leu
625                 630                 635                 640
Ile Lys Asn Thr Pro Val Pro Ala Asn Pro Pro Glu Val Phe Thr Pro
                645                 650                 655
Ala Lys Phe Ala Ser Phe Ile Thr Gln Tyr Ser Thr Gly Gln Val Ser
            660                 665                 670
Val Glu Ile Glu Trp Glu Leu Gln Lys Glu Asn Ser Lys Arg Trp Asn
        675                 680                 685
Pro Glu Ile Gln Tyr Thr Ser Asn Tyr Ala Lys Ser Asn Asn Val Glu
    690                 695                 700
Phe Ala Val Asn Asn Glu Gly Val Tyr Thr Glu Pro Arg Pro Ile Gly
705                 710                 715                 720
Thr Arg Tyr Leu Thr Arg Asn Leu
                725
```

```
<210> SEQ ID NO 103
<211> LENGTH: 728
<212> TYPE: PRT
<213> ORGANISM: Unknown
<220> FEATURE:
<223> OTHER INFORMATION: capsid protein of AAV serotype, clone 7.2VP1

<400> SEQUENCE: 103
```

| | | | | | | | | | | | | | | |
|---|---|---|---|---|---|---|---|---|---|---|---|---|---|---|
| Met | Ala | Ala | Asp | Gly | Tyr | Leu | Pro | Asp | Trp | Leu | Glu | Gly | Asn | Leu | Ser |
| 1 | | | | 5 | | | | | 10 | | | | | 15 | |
| Glu | Gly | Ile | Arg | Glu | Trp | Trp | Asp | Leu | Lys | Pro | Gly | Ala | Pro | Lys | Pro |
| | | | 20 | | | | | 25 | | | | | 30 | | |
| Lys | Ala | Asn | Gln | Gln | Lys | Gln | Asp | Asp | Gly | Arg | Gly | Leu | Val | Leu | Pro |
| | | 35 | | | | | 40 | | | | | 45 | | | |
| Gly | Tyr | Arg | Tyr | Leu | Gly | Pro | Phe | Asn | Gly | Leu | Asp | Lys | Gly | Glu | Pro |
| 50 | | | | | 55 | | | | | 60 | | | | | |
| Val | Asn | Glu | Ala | Asp | Ala | Ala | Leu | Glu | His | Asp | Lys | Ala | Tyr | Asp |
| 65 | | | | 70 | | | | | 75 | | | | | 80 |
| Lys | Gln | Leu | Glu | Gln | Gly | Asp | Asn | Pro | Tyr | Leu | Lys | Tyr | Asn | His | Ala |
| | | | | 85 | | | | | 90 | | | | | 95 | |
| Asp | Ala | Glu | Phe | Gln | Glu | Arg | Leu | Gln | Glu | Asp | Thr | Ser | Phe | Gly | Gly |
| | | | 100 | | | | | 105 | | | | | 110 | | |
| Asn | Leu | Gly | Arg | Ala | Val | Phe | Gln | Ala | Lys | Lys | Arg | Val | Leu | Glu | Pro |
| | | 115 | | | | | 120 | | | | | 125 | | | |
| Leu | Gly | Leu | Val | Glu | Glu | Gly | Ala | Lys | Thr | Ala | Pro | Gly | Lys | Lys | Arg |
| 130 | | | | | 135 | | | | | 140 | | | | | |
| Pro | Ile | Glu | Ser | Pro | Asp | Ser | Ser | Thr | Gly | Ile | Gly | Lys | Asn | Gly | Gln |
| 145 | | | | | 150 | | | | | 155 | | | | | 160 |
| Pro | Pro | Ala | Lys | Lys | Lys | Leu | Asn | Phe | Gly | Gln | Thr | Gly | Asp | Ser | Glu |
| | | | | 165 | | | | | 170 | | | | | 175 | |
| Ser | Val | Pro | Asp | Pro | Gln | Pro | Leu | Gly | Glu | Pro | Pro | Ala | Ala | Pro | Ser |
| | | | 180 | | | | | 185 | | | | | 190 | | |
| Gly | Leu | Gly | Ser | Gly | Thr | Met | Ala | Ala | Gly | Gly | Gly | Ala | Pro | Met | Ala |
| | | 195 | | | | | 200 | | | | | 205 | | | |
| Asp | Asn | Asn | Glu | Gly | Ala | Asp | Gly | Val | Gly | Asn | Ala | Ser | Gly | Asn | Trp |
| 210 | | | | | 215 | | | | | 220 | | | | | |
| His | Cys | Asp | Ser | Thr | Trp | Leu | Gly | Asp | Arg | Val | Ile | Thr | Thr | Ser | Thr |
| 225 | | | | | 230 | | | | | 235 | | | | | 240 |
| Arg | Thr | Trp | Ala | Leu | Pro | Thr | Tyr | Asn | Asn | His | Leu | Tyr | Lys | Gln | Ile |
| | | | | 245 | | | | | 250 | | | | | 255 | |
| Ser | Ser | Gln | Ser | Gly | Ala | Thr | Asn | Asp | Asn | His | Phe | Phe | Gly | Tyr | Ser |
| | | | 260 | | | | | 265 | | | | | 270 | | |
| Thr | Pro | Trp | Gly | Tyr | Phe | Asp | Phe | Asn | Arg | Phe | His | Cys | His | Phe | Ser |
| | | 275 | | | | | 280 | | | | | 285 | | | |
| Pro | Arg | Asp | Trp | Gln | Arg | Leu | Ile | Asn | Asn | Asn | Trp | Gly | Phe | Arg | Pro |
| | 290 | | | | | 295 | | | | | 300 | | | | |
| Arg | Lys | Leu | Arg | Phe | Lys | Leu | Phe | Asn | Ile | Gln | Val | Lys | Glu | Val | Thr |
| 305 | | | | | 310 | | | | | 315 | | | | | 320 |
| Thr | Asn | Asp | Gly | Val | Thr | Thr | Ile | Ala | Asn | Asn | Leu | Thr | Ser | Thr | Ile |
| | | | | 325 | | | | | 330 | | | | | 335 | |
| Gln | Val | Phe | Ser | Asp | Ser | Glu | Tyr | Gln | Leu | Pro | Tyr | Val | Leu | Gly | Ser |
| | | | 340 | | | | | 345 | | | | | 350 | | |
| Ala | His | Gln | Gly | Cys | Leu | Pro | Pro | Phe | Pro | Ala | Asp | Val | Phe | Met | Ile |
| | | 355 | | | | | 360 | | | | | 365 | | | |
| Pro | Gln | Tyr | Gly | Tyr | Leu | Thr | Leu | Asn | Asn | Gly | Ser | Gln | Ser | Val | Gly |

```
                    370                 375                 380
Arg Ser Ser Phe Tyr Cys Leu Glu Tyr Phe Pro Ser Gln Met Leu Arg
385                 390                 395                 400

Thr Gly Asp Asn Phe Glu Phe Ser Tyr Thr Phe Glu Glu Val Pro Phe
                405                 410                 415

His Ser Ser Tyr Ala His Ser Gln Ser Leu Asp Arg Leu Met Asn Pro
                420                 425                 430

Leu Ile Asp Gln Tyr Leu Tyr Tyr Leu Ala Arg Thr Gln Ser Thr Thr
                435                 440                 445

Gly Ser Thr Arg Glu Leu Gln Phe His Gln Ala Gly Pro Asn Thr Met
450                 455                 460

Ala Glu Gln Ser Lys Asn Trp Leu Pro Gly Pro Cys Tyr Arg Gln Gln
465                 470                 475                 480

Arg Leu Ser Lys Asn Ile Asp Ser Asn Asn Ser Asn Phe Ala Trp
                485                 490                 495

Thr Gly Ala Thr Lys Tyr His Leu Asn Gly Arg Asn Ser Leu Thr Asn
                500                 505                 510

Pro Gly Val Ala Met Ala Thr Asn Lys Asp Asp Glu Asp Gln Phe Phe
                515                 520                 525

Pro Ile Asn Gly Val Leu Val Phe Gly Lys Thr Gly Ala Ala Asn Lys
                530                 535                 540

Thr Thr Leu Glu Asn Val Leu Met Thr Ser Glu Glu Ile Lys Thr
545                 550                 555                 560

Thr Asn Pro Val Ala Thr Glu Glu Tyr Gly Val Val Ser Ser Asn Leu
                565                 570                 575

Gln Ser Ser Thr Ala Gly Pro Gln Thr Gln Thr Val Asn Ser Gln Gly
                580                 585                 590

Ala Leu Pro Gly Met Val Trp Gln Asn Arg Asp Val Tyr Leu Gln Gly
                595                 600                 605

Pro Ile Trp Ala Lys Ile Pro His Thr Asp Gly Asn Phe His Pro Ser
610                 615                 620

Pro Leu Met Gly Gly Phe Gly Leu Lys His Pro Pro Gln Ile Leu
625                 630                 635                 640

Ile Lys Asn Thr Pro Val Pro Ala Asn Pro Pro Glu Val Phe Thr Pro
                645                 650                 655

Ala Lys Phe Ala Ser Phe Ile Thr Gln Tyr Ser Thr Gly Gln Val Ser
                660                 665                 670

Val Glu Ile Glu Trp Glu Leu Gln Lys Glu Asn Ser Lys Arg Trp Asn
                675                 680                 685

Pro Glu Ile Gln Tyr Thr Ser Asn Tyr Ala Lys Ser Asn Asn Val Glu
                690                 695                 700

Phe Ala Val Asn Asn Glu Gly Val Tyr Thr Glu Pro Arg Pro Ile Gly
705                 710                 715                 720

Thr Arg Tyr Leu Thr Arg Asn Leu
                725

<210> SEQ ID NO 104
<211> LENGTH: 728
<212> TYPE: PRT
<213> ORGANISM: Unknown
<220> FEATURE:
<223> OTHER INFORMATION: capsid protein of AAV serotype, clone 27.3VP1

<400> SEQUENCE: 104

Met Ala Ala Asp Gly Tyr Leu Pro Asp Trp Leu Glu Asp Asn Leu Ser
```

```
1               5                   10                  15
Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
                35                  40                  45

Gly Tyr Lys Tyr Leu Gly Pro Phe Asn Gly Leu Asp Lys Gly Glu Pro
        50                  55                  60

Val Asn Glu Ala Asp Ala Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Glu Gly Ala Lys Thr Ala Ser Gly Lys Lys Arg
                130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Leu Gly Glu Pro Ala Ala Pro Ser
                180                 185                 190

Gly Leu Gly Ser Gly Thr Met Ala Ala Gly Gly Ala Pro Met Ala
                195                 200                 205

Asp Asn Asn Glu Gly Ala Asp Gly Val Gly Asn Ala Ser Gly Asn Trp
                210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Gln Ser Gly Ala Thr Asn Asp Asn His Phe Gly Tyr Ser
                260                 265                 270

Thr Pro Trp Gly Tyr Phe Asp Phe Asn Arg Phe His Cys His Phe Ser
                275                 280                 285

Pro Arg Asp Trp Gln Arg Leu Ile Asn Asn Asn Trp Gly Phe Arg Pro
                290                 295                 300

Arg Lys Leu Arg Phe Lys Leu Phe Asn Ile Gln Val Lys Glu Val Thr
305                 310                 315                 320

Thr Asn Asp Gly Val Thr Thr Ile Ala Asn Asn Leu Thr Ser Thr Ile
                325                 330                 335

Gln Val Phe Ser Asp Ser Glu Tyr Gln Leu Pro Tyr Val Leu Gly Ser
                340                 345                 350

Ala His Gln Gly Cys Leu Pro Pro Phe Pro Ala Asp Val Phe Met Ile
                355                 360                 365

Pro Gln Tyr Gly Tyr Leu Thr Leu Asn Asn Gly Ser Gln Ser Val Gly
                370                 375                 380

Arg Ser Ser Phe Cys Cys Leu Glu Tyr Phe Pro Ser Gln Met Leu Arg
385                 390                 395                 400

Thr Gly Asn Asn Phe Glu Phe Ser Tyr Thr Phe Glu Glu Val Pro Phe
                405                 410                 415

His Ser Ser Tyr Ala His Ser Gln Ser Leu Asp Arg Leu Met Asn Pro
                420                 425                 430
```

```
Leu Ile Asp Gln Tyr Leu Tyr Tyr Leu Ala Arg Thr Gln Ser Thr Thr
            435                 440                 445

Gly Ser Thr Arg Glu Leu Gln Phe His Gln Ala Gly Pro Asn Thr Val
        450                 455                 460

Ala Glu Gln Ser Lys Asn Trp Leu Pro Gly Pro Cys Tyr Arg Gln Gln
465                 470                 475                 480

Arg Leu Ser Lys Asn Ile Asp Ser Asn Asn Ser Asn Phe Ala Trp
            485                 490                 495

Thr Gly Ala Thr Lys Tyr His Leu Asn Gly Arg Asn Ser Leu Thr Asn
        500                 505                 510

Pro Gly Val Ala Met Ala Thr Asn Lys Asp Asp Glu Asp Gln Phe Leu
            515                 520                 525

Pro Ile Asn Gly Val Leu Val Phe Gly Lys Thr Gly Ala Ala Asn Lys
        530                 535                 540

Thr Thr Leu Glu Asn Val Leu Met Thr Ser Glu Glu Ile Lys Thr
545                 550                 555                 560

Thr Asn Pro Val Ala Thr Glu Glu Tyr Gly Val Val Ser Ser Asn Leu
            565                 570                 575

Gln Ser Ser Thr Ala Gly Pro Arg Thr Gln Thr Val Asn Ser Gln Gly
        580                 585                 590

Ala Leu Pro Gly Met Val Trp Gln Asn Arg Asp Val Tyr Leu Gln Gly
            595                 600                 605

Pro Ile Trp Ala Glu Ile Pro His Thr Asp Gly Asn Phe His Pro Ser
610                 615                 620

Pro Leu Met Gly Gly Phe Gly Leu Lys His Pro Pro Gln Ile Leu
625                 630                 635                 640

Ile Lys Asn Thr Pro Val Pro Ala Asn Pro Pro Glu Val Phe Thr Pro
            645                 650                 655

Ala Lys Phe Ala Ser Phe Ile Thr Gln Tyr Ser Thr Gly Gln Val Ser
        660                 665                 670

Val Glu Ile Glu Trp Glu Leu Gln Lys Glu Asn Ser Lys Arg Trp Asn
            675                 680                 685

Pro Glu Ile Gln Tyr Thr Ser Asn Tyr Ala Lys Ser Asn Asn Val Glu
        690                 695                 700

Phe Ala Val Asn Asn Glu Gly Val Tyr Thr Glu Pro Arg Pro Ile Gly
705                 710                 715                 720

Thr Arg Tyr Leu Thr Arg Asn Leu
            725

<210> SEQ ID NO 105
<211> LENGTH: 728
<212> TYPE: PRT
<213> ORGANISM: Unknown
<220> FEATURE:
<223> OTHER INFORMATION: capsid protein of AAV serotype, clone 16.3VP1

<400> SEQUENCE: 105

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60
```

```
Val Asn Glu Ala Asp Ala Ala Leu Glu His Asp Lys Ala Tyr Asp
 65                  70                  75                  80

Lys Gln Leu Glu Gln Gly Asp Asn Pro Tyr Leu Lys Tyr Asn His Ala
                 85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Leu Gly Glu Pro Pro Ala Ala Pro Ser
            180                 185                 190

Gly Leu Gly Ser Gly Thr Met Ala Ala Gly Gly Ala Pro Met Ala
        195                 200                 205

Asp Asn Asn Glu Gly Ala Asp Gly Val Gly Asn Ala Ser Gly Asn Trp
210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Gln Ser Gly Ala Thr Asn Asp Asn His Phe Phe Gly Tyr Ser
            260                 265                 270

Thr Pro Trp Gly Tyr Phe Asp Phe Asn Arg Phe His Cys His Phe Ser
        275                 280                 285

Pro Arg Asp Trp Gln Arg Leu Ile Asn Asn Asn Trp Gly Phe Arg Pro
290                 295                 300

Arg Lys Leu Arg Phe Lys Leu Phe Asn Ile Gln Val Lys Glu Val Thr
305                 310                 315                 320

Thr Asn Asp Gly Val Thr Thr Ile Ala Asn Asn Leu Thr Ser Thr Ile
                325                 330                 335

Gln Val Phe Ser Asp Ser Glu Tyr Gln Leu Pro Tyr Val Leu Gly Ser
            340                 345                 350

Ala His Gln Gly Cys Leu Pro Pro Phe Pro Ala Asp Val Phe Met Ile
        355                 360                 365

Pro Gln Tyr Gly Tyr Leu Thr Leu Asn Asn Gly Ser Gln Ser Met Gly
370                 375                 380

Arg Ser Ser Phe Tyr Cys Leu Glu Tyr Phe Pro Ser Gln Met Leu Arg
385                 390                 395                 400

Thr Gly Asn Asn Phe Glu Phe Ser Tyr Thr Phe Glu Glu Val Pro Phe
                405                 410                 415

His Ser Ser Tyr Ala His Ser Gln Ser Leu Asp Arg Leu Met Asn Pro
            420                 425                 430

Leu Ile Asp Gln Tyr Leu Tyr Tyr Leu Ala Arg Thr Gln Ser Thr Thr
        435                 440                 445

Gly Ser Thr Arg Glu Leu Gln Phe His Gln Ala Gly Pro Asn Thr Met
    450                 455                 460

Ala Glu Gln Ser Lys Asn Trp Leu Pro Gly Pro Cys Tyr Arg Gln Gln
465                 470                 475                 480
```

Arg Leu Ser Lys Asn Ile Asp Ser Asn Asn Ser Asn Phe Ala Trp
            485                 490                 495

Thr Gly Ala Thr Lys Tyr His Leu Asn Gly Arg Asn Ser Leu Thr Asn
        500                 505                 510

Pro Gly Val Ala Met Ala Thr Asn Lys Asp Asp Glu Gly Gln Phe Phe
        515                 520                 525

Pro Ile Asn Gly Val Leu Val Phe Gly Lys Thr Gly Ala Ala Asn Lys
        530                 535                 540

Thr Thr Leu Glu Asn Val Leu Met Thr Ser Glu Glu Ile Lys Thr
545                 550                 555                 560

Thr Asn Pro Val Ala Thr Glu Glu Tyr Gly Val Val Ser Ser Asn Leu
                565                 570                 575

Gln Ser Ser Thr Ala Gly Pro Gln Thr Gln Thr Val Asn Ser Gln Gly
            580                 585                 590

Ala Leu Pro Gly Met Val Trp Gln Asn Arg Asp Val Tyr Leu Gln Gly
            595                 600                 605

Pro Ile Trp Ala Lys Ile Pro His Thr Asp Gly Asn Phe His Pro Ser
        610                 615                 620

Pro Leu Met Gly Gly Phe Gly Leu Lys His Pro Pro Gln Ile Leu
625                 630                 635                 640

Ile Lys Asn Thr Pro Val Pro Ala Asn Pro Pro Gly Val Phe Thr Pro
                645                 650                 655

Ala Leu Phe Ala Ser Phe Ile Thr Gln Tyr Ser Thr Gly Gln Val Ser
            660                 665                 670

Val Glu Ile Glu Trp Glu Leu Gln Lys Glu Asn Ser Lys Arg Trp Asn
            675                 680                 685

Pro Glu Ile Gln Tyr Thr Ser Asn Tyr Ala Lys Ser Asn Asn Val Glu
        690                 695                 700

Phe Ala Val Asn Asn Glu Gly Val Tyr Thr Glu Pro Arg Pro Ile Gly
705                 710                 715                 720

Thr Arg Tyr Leu Thr Arg Asn Leu
                725

<210> SEQ ID NO 106
<211> LENGTH: 728
<212> TYPE: PRT
<213> ORGANISM: Unknown
<220> FEATURE:
<223> OTHER INFORMATION: capsid protein of AAV serotype, clone 42.10

<400> SEQUENCE: 106

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

```
Asn Leu Gly Arg Ala Val Phe Gln Ala Lys Lys Arg Val Leu Glu Pro
            115                 120                 125
Leu Gly Leu Val Glu Glu Gly Ala Lys Thr Ala Pro Gly Lys Lys Arg
        130                 135                 140
Pro Ile Glu Ser Pro Asp Ser Ser Thr Gly Ile Gly Arg Lys Gly Gln
145                 150                 155                 160
Gln Pro Ala Lys Lys Lys Leu Asn Phe Gly Gln Thr Gly Asp Ser Glu
                165                 170                 175
Ser Val Pro Asp Pro Gln Pro Ile Gly Glu Pro Ala Gly Pro Ser
            180                 185                 190
Gly Leu Gly Ser Gly Thr Met Ala Ala Gly Gly Ala Pro Met Ala
        195                 200                 205
Asp Asn Glu Gly Ala Asp Gly Val Gly Asn Ala Ser Gly Asn Trp
210                 215                 220
His Cys Asp Ser Thr Trp Leu Gly Asp Arg Val Ile Thr Ser Thr
225                 230                 235                 240
Arg Thr Trp Ala Leu Pro Thr Tyr Asn Asn His Leu Tyr Lys Gln Ile
                245                 250                 255
Ser Ser Gln Ser Gly Ala Thr Asn Asp Asn His Phe Phe Gly Tyr Ser
            260                 265                 270
Thr Pro Trp Gly Tyr Phe Asp Phe Asn Arg Phe His Cys His Phe Ser
        275                 280                 285
Pro Arg Asp Trp Gln Arg Leu Ile Asn Asn Asn Trp Gly Phe Arg Pro
        290                 295                 300
Arg Lys Leu Arg Phe Lys Leu Phe Asn Ile Gln Val Lys Glu Val Thr
305                 310                 315                 320
Thr Asn Asp Gly Val Thr Thr Ile Ala Asn Asn Leu Thr Ser Thr Ile
                325                 330                 335
Gln Val Phe Ser Asp Ser Glu Tyr Gln Leu Pro Tyr Val Leu Gly Ser
            340                 345                 350
Ala His Gln Gly Cys Leu Pro Pro Phe Pro Ala Asp Val Phe Met Ile
        355                 360                 365
Pro Gln Tyr Gly Tyr Leu Thr Leu Asn Asn Gly Ser Gln Ser Val Gly
    370                 375                 380
Arg Ser Ser Phe Tyr Cys Leu Glu Tyr Phe Pro Ser Gln Met Leu Arg
385                 390                 395                 400
Thr Gly Asn Asn Phe Glu Phe Ser Tyr Thr Phe Glu Glu Val Pro Phe
                405                 410                 415
His Ser Ser Tyr Ala His Ser Gln Ser Leu Asp Arg Leu Met Asn Pro
            420                 425                 430
Leu Ile Asp Gln Tyr Leu Tyr Tyr Leu Ala Arg Thr Gln Ser Thr Thr
        435                 440                 445
Gly Ser Thr Arg Glu Leu Gln Phe His Gln Ala Gly Pro Asn Thr Met
    450                 455                 460
Ala Glu Gln Ser Lys Asn Trp Leu Pro Gly Pro Cys Tyr Arg Gln Gln
465                 470                 475                 480
Arg Leu Ser Lys Asn Ile Asp Ser Asn Asn Ser Asn Phe Ala Trp
                485                 490                 495
Thr Gly Ala Thr Lys Tyr His Leu Asn Gly Arg Asn Ser Leu Thr Asn
            500                 505                 510
Pro Gly Val Ala Met Ala Thr Asn Lys Asp Asp Glu Asp Gln Phe Phe
        515                 520                 525
Pro Ile Asn Gly Val Leu Val Phe Gly Lys Thr Gly Ala Ala Asn Lys
```

```
                530                 535                 540
Thr Thr Leu Glu Asn Val Leu Met Thr Ser Glu Glu Ile Lys Thr
545                 550                 555                 560

Thr Asn Pro Val Ala Thr Glu Glu Tyr Gly Val Val Ser Ser Asn Leu
                565                 570                 575

Gln Ser Ser Thr Ala Gly Pro Gln Thr Gln Thr Val Asn Ser Gln Gly
            580                 585                 590

Ala Leu Pro Gly Met Val Trp Gln Asn Arg Asp Val Tyr Leu Gln Gly
            595                 600                 605

Pro Ile Trp Ala Lys Ile Pro His Thr Asp Gly Asn Phe His Pro Ser
610                 615                 620

Pro Leu Met Gly Gly Phe Gly Leu Lys His Pro Pro Gln Ile Leu
625                 630                 635                 640

Ile Lys Asn Thr Pro Val Pro Ala Asn Pro Pro Glu Val Phe Thr Pro
                645                 650                 655

Ala Lys Phe Ala Ser Phe Ile Thr Gln Tyr Ser Thr Gly Gln Val Ser
            660                 665                 670

Val Glu Ile Glu Trp Glu Leu Gln Lys Glu Asn Ser Lys Arg Trp Asn
            675                 680                 685

Pro Glu Ile Gln Tyr Thr Ser Asn Tyr Ala Lys Ser Asn Asn Val Glu
            690                 695                 700

Phe Ala Val Asn Asn Glu Gly Val Tyr Thr Glu Pro Arg Pro Ile Gly
705                 710                 715                 720

Thr Arg Tyr Leu Thr Arg Asn Leu
                725

<210> SEQ ID NO 107
<211> LENGTH: 728
<212> TYPE: PRT
<213> ORGANISM: Unknown
<220> FEATURE:
<223> OTHER INFORMATION: capsid protein of AAV serotype, clone 42.3B

<400> SEQUENCE: 107

Met Ala Ala Asp Gly Tyr Leu Pro Asp Trp Leu Glu Asp Asn Leu Ser
1                   5                  10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
50                  55                  60

Val Asn Glu Ala Asp Ala Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
        130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
```

```
              165                 170                 175
Ser Val Pro Asp Pro Gln Pro Ile Gly Glu Pro Pro Ala Gly Pro Ser
             180                 185                 190
Gly Leu Gly Ser Gly Thr Met Ala Ala Gly Gly Ala Pro Met Ala
             195                 200                 205
Asp Asn Asn Glu Gly Ala Asp Gly Val Gly Asn Ala Ser Gly Asn Trp
             210                 215                 220
His Cys Asp Ser Thr Trp Leu Gly Asp Arg Val Ile Thr Thr Ser Thr
225                  230                 235                 240
Arg Thr Trp Ala Leu Pro Thr Tyr Asn His Leu Tyr Lys Gln Ile
             245                 250                 255
Ser Ser Gln Ser Gly Ala Thr Asn Asp Asn His Phe Phe Gly Tyr Ser
             260                 265                 270
Thr Pro Trp Gly Tyr Phe Asp Phe Asn Arg Phe His Cys His Phe Ser
             275                 280                 285
Pro Arg Asp Trp Gln Arg Leu Ile Asn Asn Trp Gly Phe Arg Pro
             290                 295                 300
Arg Lys Leu Arg Phe Lys Leu Phe Asn Ile Gln Val Lys Glu Val Thr
305                  310                 315                 320
Thr Asn Asp Gly Val Thr Thr Ile Ala Asn Asn Leu Thr Ser Thr Ile
             325                 330                 335
Gln Val Phe Ser Asp Ser Glu Tyr Gln Leu Pro Tyr Val Leu Gly Ser
             340                 345                 350
Ala His Gln Gly Cys Leu Pro Pro Phe Pro Ala Asp Val Phe Met Ile
             355                 360                 365
Pro Gln Tyr Gly Tyr Leu Thr Leu Asn Asn Gly Ser Gln Ser Val Gly
             370                 375                 380
Arg Ser Ser Phe Tyr Cys Leu Glu Tyr Phe Pro Ser Gln Met Leu Arg
385                  390                 395                 400
Thr Gly Asn Asn Phe Glu Phe Ser Tyr Thr Phe Glu Glu Val Pro Phe
             405                 410                 415
His Ser Ser Tyr Ala His Ser Gln Ser Leu Asp Arg Leu Met Asn Pro
             420                 425                 430
Leu Ile Asp Gln Tyr Leu Tyr Tyr Leu Ala Arg Thr Gln Ser Thr Thr
             435                 440                 445
Gly Ser Thr Arg Glu Leu Gln Phe His Gln Ala Gly Pro Asn Thr Met
             450                 455                 460
Ala Glu Gln Ser Lys Asn Trp Leu Pro Gly Pro Cys Tyr Arg Gln Gln
465                  470                 475                 480
Arg Leu Ser Lys Asn Ile Asp Ser Asn Asn Thr Ser Asn Phe Ala Trp
             485                 490                 495
Thr Gly Ala Thr Lys Tyr His Leu Asn Gly Arg Asn Ser Leu Thr Asn
             500                 505                 510
Pro Gly Val Ala Met Ala Thr Asn Lys Asp Asp Glu Asp Gln Phe Phe
             515                 520                 525
Pro Ile Asn Gly Val Leu Val Phe Gly Lys Thr Gly Ala Ala Asn Lys
             530                 535                 540
Thr Thr Leu Glu Asn Val Leu Met Thr Ser Glu Glu Ile Lys Thr
545                  550                 555                 560
Thr Asn Pro Val Ala Thr Glu Gln Tyr Gly Val Val Ser Ser Asn Leu
             565                 570                 575
Gln Ser Ser Thr Ala Gly Pro Gln Thr Gln Thr Val Asn Ser Gln Gly
             580                 585                 590
```

```
Ala Leu Pro Gly Met Val Trp Gln Asn Arg Asp Val Tyr Leu Gln Gly
            595                 600                 605

Pro Ile Trp Ala Lys Ile Pro His Thr Asp Gly Asn Phe His Pro Ser
610                 615                 620

Pro Leu Met Gly Gly Phe Gly Leu Lys His Pro Pro Gln Ile Leu
625                 630                 635                 640

Ile Lys Asn Thr Pro Val Pro Ala Asn Pro Pro Glu Val Phe Thr Pro
            645                 650                 655

Ala Lys Phe Ala Ser Phe Ile Thr Gln Tyr Ser Thr Gly Gln Val Ser
            660                 665                 670

Val Glu Ile Glu Trp Glu Leu Gln Lys Glu Asn Ser Lys Arg Trp Asn
            675                 680                 685

Pro Glu Ile Gln Tyr Thr Ser Asn Tyr Ala Lys Ser Asn Asn Val Glu
            690                 695                 700

Phe Ala Val Asn Asn Glu Gly Val Tyr Thr Glu Pro Arg Pro Ile Gly
705                 710                 715                 720

Thr Arg Tyr Leu Thr Arg Asn Leu
            725

<210> SEQ ID NO 108
<211> LENGTH: 728
<212> TYPE: PRT
<213> ORGANISM: Unknown
<220> FEATURE:
<223> OTHER INFORMATION: capsid protein of AAV serotype, clone 42.11

<400> SEQUENCE: 108

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Ile Glu Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Ile Gly Glu Pro Pro Ala Gly Pro Ser
            180                 185                 190

Gly Leu Gly Ser Gly Thr Met Ala Ala Gly Gly Ala Pro Met Ala
        195                 200                 205

Asp Asn Asn Glu Gly Ala Asp Gly Val Gly Asn Ala Ser Gly Asn Trp
    210                 215                 220
```

```
His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
            245                 250                 255

Ser Ser Gln Ser Gly Ala Thr Asn Asp Asn His Phe Phe Gly Tyr Ser
        260                 265                 270

Thr Pro Trp Gly Tyr Phe Asp Phe Asn Arg Phe His Cys His Phe Ser
    275                 280                 285

Pro Arg Asp Trp Gln Arg Leu Ile Asn Asn Asn Trp Gly Phe Arg Pro
290                 295                 300

Arg Lys Leu Arg Phe Lys Leu Phe Asn Ile Gln Val Lys Glu Val Thr
305                 310                 315                 320

Thr Asn Asp Gly Val Thr Thr Ile Ala Asn Asn Leu Thr Ser Thr Ile
                325                 330                 335

Gln Val Phe Ser Asp Ser Glu Tyr Gln Leu Pro Tyr Val Leu Gly Ser
            340                 345                 350

Ala His Gln Gly Cys Leu Pro Pro Phe Pro Ala Asp Val Phe Met Ile
        355                 360                 365

Pro Gln Tyr Gly Tyr Leu Thr Leu Asn Asn Gly Ser Gln Ser Val Gly
    370                 375                 380

Arg Ser Ser Phe Tyr Cys Leu Glu Tyr Phe Pro Ser Gln Met Leu Arg
385                 390                 395                 400

Thr Gly Asn Asn Phe Glu Phe Ser Tyr Thr Phe Glu Glu Val Pro Phe
                405                 410                 415

His Ser Ser Tyr Ala His Ser Gln Ser Leu Asp Arg Leu Met Asn Pro
            420                 425                 430

Leu Ile Asp Gln Tyr Leu Tyr Tyr Leu Ala Arg Thr Gln Ser Thr Thr
        435                 440                 445

Gly Ser Thr Arg Glu Leu Gln Phe His Gln Ala Gly Pro Asn Thr Met
450                 455                 460

Ala Glu Gln Ser Lys Asn Trp Leu Pro Gly Pro Cys Tyr Arg Arg Gln
465                 470                 475                 480

Arg Leu Ser Lys Asp Ile Asp Ser Asn Asn Ser Asn Phe Ala Trp
                485                 490                 495

Thr Gly Ala Thr Lys Tyr His Leu Asn Gly Arg Asn Ser Leu Thr Asn
            500                 505                 510

Pro Gly Val Ala Met Ala Thr Asn Lys Asp Asp Glu Asp Gln Phe Phe
        515                 520                 525

Pro Ile Asn Gly Val Leu Val Phe Gly Lys Thr Gly Ala Ala Asn Lys
    530                 535                 540

Thr Thr Leu Glu Asn Val Leu Met Thr Ser Glu Glu Ile Lys Thr
545                 550                 555                 560

Thr Asn Pro Val Ala Thr Glu Glu Tyr Gly Val Val Ser Ser Asn Leu
                565                 570                 575

Gln Ser Ser Thr Ala Gly Pro Gln Thr Gln Thr Val Asn Ser Gln Gly
            580                 585                 590

Ala Leu Pro Gly Met Val Trp Gln Asn Arg Asp Val Tyr Leu Gln Gly
        595                 600                 605

Pro Ile Trp Ala Lys Ile Pro His Thr Asp Gly Asn Phe His Pro Ser
    610                 615                 620

Pro Leu Met Gly Gly Phe Gly Leu Lys His Pro Pro Gln Ile Leu
625                 630                 635                 640
```

```
Ile Lys Asn Thr Pro Val Pro Ala Asn Pro Glu Val Phe Thr Pro
                645                 650                 655

Ala Lys Phe Ala Ser Phe Ile Thr Gln Tyr Ser Thr Gly Gln Val Ser
        660                 665                 670

Val Glu Ile Glu Trp Glu Leu Gln Lys Glu Asn Ser Lys Arg Trp Asn
            675                 680                 685

Pro Glu Ile Gln Tyr Thr Ser Asn Tyr Ala Lys Ser Asn Asn Val Glu
        690                 695                 700

Phe Ala Val Asn Asn Glu Gly Val Tyr Thr Glu Pro Arg Pro Ile Gly
705                 710                 715                 720

Thr Arg Tyr Leu Thr Arg Asn Leu
                725

<210> SEQ ID NO 109
<211> LENGTH: 729
<212> TYPE: PRT
<213> ORGANISM: Unknown
<220> FEATURE:
<223> OTHER INFORMATION: capsid protein of AAV serotype, clone F1VP1

<400> SEQUENCE: 109

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Ile Asp Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Leu Gly Glu Pro Pro Ala Ala Pro Ser
            180                 185                 190

Ser Val Gly Ser Gly Thr Met Ala Ala Gly Gly Gly Ala Pro Met Ala
        195                 200                 205

Asp Asn Asn Glu Gly Ala Asp Gly Val Gly Asn Ala Ser Gly Asn Trp
210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Ser Ser Gly Ala Thr Asn Asp Asn His Tyr Phe Gly Tyr
            260                 265                 270
```

-continued

```
Ser Thr Pro Trp Gly Tyr Phe Asp Phe Asn Arg Phe His Cys His Phe
            275                 280                 285

Ser Pro Arg Asp Trp Gln Arg Leu Ile Asn Asn Asn Trp Gly Phe Arg
            290                 295                 300

Pro Lys Lys Leu Arg Phe Lys Leu Phe Asn Ile Gln Val Lys Glu Val
305                 310                 315                 320

Thr Thr Asn Asp Gly Val Thr Ile Ala Asn Asn Leu Thr Ser Thr
                    325                 330                 335

Val Gln Val Phe Ser Asp Ser Glu Tyr Gln Leu Pro Tyr Val Leu Gly
                    340                 345                 350

Ser Ala His Gln Gly Cys Leu Pro Pro Phe Pro Ala Asp Val Phe Met
            355                 360                 365

Ile Pro Gln Tyr Gly Tyr Leu Thr Leu Asn Asn Gly Ser Gln Ser Val
370                 375                 380

Gly Arg Ser Ser Phe Tyr Cys Leu Glu Tyr Phe Pro Ser Gln Met Leu
385                 390                 395                 400

Arg Thr Gly Asn Asn Phe Glu Phe Ser Tyr Ser Phe Glu Asp Val Pro
                    405                 410                 415

Phe His Ser Ser Tyr Ala His Ser Gln Ser Leu Asp Arg Leu Met Asn
            420                 425                 430

Pro Leu Ile Asp Gln Tyr Leu Tyr Tyr Leu Ala Arg Thr Gln Ser Thr
            435                 440                 445

Thr Gly Ser Thr Arg Glu Leu Gln Phe His Gln Ala Gly Pro Asn Thr
            450                 455                 460

Met Ala Glu Gln Ser Lys Asn Trp Leu Pro Gly Pro Cys Tyr Arg Gln
465                 470                 475                 480

Gln Gly Leu Ser Lys Asn Leu Asp Phe Asn Asn Asn Ser Asn Phe Ala
                    485                 490                 495

Trp Thr Ala Ala Thr Lys Tyr His Leu Asn Gly Arg Asn Ser Leu Thr
            500                 505                 510

Asn Pro Gly Ile Pro Met Ala Thr Asn Lys Asp Asp Glu Asp Gln Phe
            515                 520                 525

Phe Pro Ile Asn Gly Val Leu Val Phe Gly Lys Thr Gly Ala Ala Asn
530                 535                 540

Lys Thr Thr Leu Glu Asn Val Leu Met Thr Ser Glu Glu Ile Lys
545                 550                 555                 560

Thr Thr Asn Pro Val Ala Thr Glu Glu Tyr Gly Val Val Ser Ser Asn
                    565                 570                 575

Leu Gln Pro Ser Thr Ala Gly Pro Gln Ser Gln Thr Ile Asn Ser Gln
            580                 585                 590

Gly Ala Leu Pro Gly Met Val Trp Gln Asn Arg Asp Val Tyr Leu Gln
            595                 600                 605

Gly Pro Ile Trp Ala Lys Ile Pro His Thr Asp Gly Asn Phe His Pro
610                 615                 620

Ser Pro Leu Met Gly Gly Phe Gly Leu Lys His Pro Pro Gln Ile
625                 630                 635                 640

Leu Ile Lys Asn Thr Pro Val Pro Ala Asn Pro Glu Val Phe Thr
                    645                 650                 655

Pro Ala Lys Phe Ala Ser Phe Ile Thr Gln Tyr Ser Thr Gly Gln Val
            660                 665                 670

Ser Val Glu Ile Glu Trp Glu Leu Gln Lys Glu Asn Ser Lys Arg Trp
            675                 680                 685

Asn Pro Glu Ile Gln Tyr Thr Ser Asn Tyr Ala Lys Ser Asn Asn Val
```

```
                690              695              700
Glu Phe Ala Val Asn Pro Asp Gly Val Tyr Thr Glu Pro Arg Pro Ile
705              710              715              720

Gly Thr Arg Tyr Leu Pro Arg Asn Leu
                725
```

<210> SEQ ID NO 110
<211> LENGTH: 729
<212> TYPE: PRT
<213> ORGANISM: Unknown
<220> FEATURE:
<223> OTHER INFORMATION: capsid protein of AAV serotype, clone F5VP1[@0003]

<400> SEQUENCE: 110

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Ile Asp Ser Pro Asp Ser Ser Thr Gly Ile Gly Lys Lys Gly Gln
145                 150                 155                 160

Gln Pro Ala Lys Lys Lys Leu Asn Phe Gly Gln Thr Gly Asp Ser Glu
                165                 170                 175

Ser Val Pro Asp Pro Gln Pro Leu Gly Glu Pro Pro Ala Ala Pro Ser
            180                 185                 190

Ser Val Gly Ser Gly Thr Met Ala Ala Gly Gly Gly Ala Pro Thr Ala
        195                 200                 205

Asp Asn Asn Glu Gly Ala Asp Gly Val Gly Asn Ala Ser Gly Asn Trp
210                 215                 220

His Cys Asp Ser Thr Trp Leu Gly Asp Arg Val Ile Thr Thr Ser Thr
225                 230                 235                 240

Arg Thr Trp Ala Leu Pro Thr Tyr Asn Asn His Leu Tyr Lys Gln Ile
                245                 250                 255

Ser Ser Ser Ser Ser Gly Ala Thr Asn Asp Asn His Tyr Phe Gly Tyr
            260                 265                 270

Ser Thr Pro Trp Gly Tyr Phe Asp Phe Asn Arg Phe His Cys His Phe
        275                 280                 285

Ser Pro Arg Asp Trp Gln Arg Leu Ile Asn Asn Asn Trp Gly Phe Arg
290                 295                 300

Pro Lys Lys Leu Arg Phe Lys Leu Phe Asn Ile Gln Val Lys Glu Val
305                 310                 315                 320

Thr Thr Asn Asp Gly Val Thr Thr Ile Ala Asn Asn Leu Thr Ser Thr
```

-continued

```
                325                 330                 335
Val Gln Val Phe Ser Asp Ser Glu Tyr Gln Leu Pro Tyr Val Leu Gly
            340                 345                 350

Ser Ala His Gln Gly Cys Leu Pro Pro Phe Pro Ala Asp Val Phe Met
            355                 360                 365

Ile Pro Gln Tyr Gly Tyr Leu Thr Leu Asn Asn Gly Ser Gln Ser Val
            370                 375                 380

Gly Arg Ser Ser Phe Tyr Cys Leu Glu Tyr Phe Pro Ser Gln Met Leu
385                 390                 395                 400

Arg Thr Gly Asn Asn Phe Glu Phe Ser Tyr Ser Phe Glu Asp Val Pro
                405                 410                 415

Phe His Ser Ser Tyr Ala His Ser Gln Ser Leu Asp Arg Leu Met Asn
                420                 425                 430

Pro Leu Ile Asp Gln Tyr Leu Tyr Tyr Leu Ala Arg Thr Gln Ser Thr
            435                 440                 445

Thr Gly Ser Thr Arg Glu Leu Gln Phe His Gln Ala Gly Pro Asn Thr
            450                 455                 460

Met Ala Glu Gln Ser Lys Asn Trp Leu Pro Gly Pro Cys Tyr Arg Gln
465                 470                 475                 480

Gln Arg Leu Ser Lys Asn Leu Asp Phe Asn Asn Ser Asn Phe Ala
                485                 490                 495

Trp Thr Ala Ala Thr Lys Tyr His Leu Asn Gly Arg Asn Ser Leu Thr
            500                 505                 510

Asn Pro Gly Ile Pro Met Ala Thr Asn Lys Asp Asp Glu Asp Gln Phe
            515                 520                 525

Phe Pro Ile Asn Gly Val Leu Val Phe Gly Lys Thr Gly Ala Ala Asn
            530                 535                 540

Lys Thr Thr Leu Glu Asn Val Leu Met Thr Ser Glu Glu Ile Lys
545                 550                 555                 560

Thr Thr Asn Pro Val Ala Thr Glu Glu Tyr Gly Val Val Ser Ser Asn
                565                 570                 575

Leu Gln Ser Ser Thr Ala Gly Pro Gln Ser Gln Thr Ile Asn Ser Gln
            580                 585                 590

Gly Ala Leu Pro Gly Met Val Trp Gln Asn Arg Asp Val Tyr Leu Gln
            595                 600                 605

Gly Pro Ile Trp Ala Lys Ile Pro His Thr Asp Gly Asn Phe His Pro
            610                 615                 620

Ser Pro Leu Met Gly Gly Phe Gly Leu Glu His Pro Pro Gln Ile
625                 630                 635                 640

Leu Ile Lys Asn Thr Pro Val Pro Ala Asn Pro Glu Val Phe Thr
                645                 650                 655

Pro Ala Lys Phe Ala Ser Phe Ile Thr Gln Tyr Ser Thr Gly Gln Val
            660                 665                 670

Ser Val Glu Ile Glu Trp Glu Leu Gln Lys Glu Asn Ser Lys Arg Trp
            675                 680                 685

Asn Pro Glu Ile Gln Tyr Thr Ser Asn Tyr Ala Lys Ser Asn Asn Val
            690                 695                 700

Glu Phe Ala Val Asn Pro Asp Gly Val Tyr Thr Glu Pro Arg Pro Ile
705                 710                 715                 720

Gly Thr Arg Tyr Leu Thr Arg Asn Leu
            725
```

<210> SEQ ID NO 111

```
<211> LENGTH: 729
<212> TYPE: PRT
<213> ORGANISM: Unknown
<220> FEATURE:
<223> OTHER INFORMATION: capsid protein of AAV serotype, clone F3VP1

<400> SEQUENCE: 111
```

| | | | | | | | | | | | | | | |
|---|---|---|---|---|---|---|---|---|---|---|---|---|---|---|
| Met | Ala | Ala | Asp | Gly | Tyr | Leu | Pro | Asp | Trp | Leu | Glu | Asp | Asn | Leu | Ser |
| 1 | | | | 5 | | | | | 10 | | | | | 15 | |
| Glu | Gly | Ile | Arg | Glu | Trp | Trp | Asp | Leu | Lys | Pro | Gly | Ala | Pro | Lys | Pro |
| | | | 20 | | | | | 25 | | | | | 30 | | |
| Lys | Ala | Asn | Gln | Gln | Lys | Gln | Asp | Asp | Gly | Arg | Gly | Leu | Val | Leu | Pro |
| | | 35 | | | | | 40 | | | | | 45 | | | |
| Gly | Tyr | Lys | Tyr | Leu | Gly | Pro | Phe | Asn | Gly | Leu | Asp | Lys | Gly | Glu | Pro |
| | 50 | | | | | 55 | | | | | 60 | | | | |
| Val | Asn | Ala | Ala | Asp | Ala | Ala | Leu | Glu | His | Asp | Lys | Ala | Tyr | Asp |
| 65 | | | | | 70 | | | | | 75 | | | | | 80 |
| Gln | Gln | Leu | Lys | Ala | Gly | Asp | Asn | Pro | Tyr | Leu | Arg | Tyr | Asn | His | Ala |
| | | | | 85 | | | | | 90 | | | | | 95 | |
| Asp | Ala | Glu | Phe | Gln | Glu | Arg | Leu | Gln | Glu | Asp | Thr | Ser | Phe | Gly | Gly |
| | | | 100 | | | | | 105 | | | | | 110 | | |
| Asn | Leu | Gly | Arg | Ala | Val | Phe | Gln | Ala | Lys | Lys | Arg | Val | Leu | Glu | Pro |
| | | 115 | | | | | 120 | | | | | 125 | | | |
| Leu | Gly | Leu | Val | Glu | Glu | Gly | Ala | Lys | Thr | Ala | Pro | Gly | Lys | Lys | Arg |
| 130 | | | | | 135 | | | | | 140 | | | | | |
| Pro | Ile | Gly | Ser | Pro | Asp | Ser | Ser | Thr | Gly | Ile | Gly | Lys | Lys | Gly | Gln |
| 145 | | | | 150 | | | | | 155 | | | | | 160 | |
| Gln | Pro | Ala | Lys | Lys | Lys | Leu | Asn | Phe | Gly | Gln | Thr | Gly | Asp | Ser | Glu |
| | | | | 165 | | | | | 170 | | | | | 175 | |
| Ser | Val | Pro | Asp | Pro | Gln | Pro | Leu | Gly | Glu | Pro | Pro | Ala | Ala | Pro | Ser |
| | | | 180 | | | | | 185 | | | | | 190 | | |
| Ser | Val | Gly | Ser | Gly | Thr | Met | Ala | Ala | Gly | Gly | Gly | Ala | Pro | Met | Ala |
| | | | 195 | | | | | 200 | | | | | 205 | | |
| Asp | Asn | Asn | Glu | Gly | Ala | Asp | Gly | Val | Gly | Asn | Ala | Ser | Gly | Asn | Trp |
| | 210 | | | | | 215 | | | | | 220 | | | | |
| His | Cys | Asp | Ser | Thr | Trp | Leu | Gly | Asp | Arg | Val | Ile | Thr | Thr | Ser | Thr |
| 225 | | | | | 230 | | | | | 235 | | | | | 240 |
| Arg | Thr | Trp | Ala | Leu | Pro | Thr | Tyr | Asn | Asn | His | Leu | Tyr | Lys | Gln | Ile |
| | | | | 245 | | | | | 250 | | | | | 255 | |
| Ser | Ser | Ser | Ser | Ser | Gly | Ala | Thr | Asn | Asp | Asn | His | Tyr | Phe | Gly | Tyr |
| | | | | 260 | | | | | 265 | | | | | 270 | |
| Ser | Thr | Pro | Trp | Gly | Tyr | Phe | Asp | Phe | Asn | Arg | Phe | His | Cys | His | Phe |
| | | 275 | | | | | 280 | | | | | 285 | | | |
| Ser | Pro | Arg | Asp | Trp | Gln | Arg | Leu | Ile | Asn | Asn | Asn | Trp | Gly | Phe | Arg |
| | 290 | | | | | 295 | | | | | 300 | | | | |
| Pro | Lys | Lys | Leu | Arg | Phe | Lys | Leu | Leu | Asn | Ile | Gln | Val | Lys | Glu | Val |
| 305 | | | | | 310 | | | | | 315 | | | | | 320 |
| Thr | Thr | Asn | Asp | Gly | Val | Thr | Thr | Ile | Ala | Asn | Asn | Leu | Thr | Ser | Thr |
| | | | | 325 | | | | | 330 | | | | | 335 | |
| Val | Gln | Val | Phe | Ser | Asp | Ser | Glu | Tyr | Gln | Leu | Pro | Tyr | Val | Leu | Gly |
| | | | 340 | | | | | 345 | | | | | 350 | | |
| Ser | Ala | His | Gln | Gly | Cys | Leu | Pro | Pro | Phe | Pro | Ala | Asp | Val | Phe | Met |
| | | 355 | | | | | 360 | | | | | 365 | | | |
| Ile | Pro | Gln | Tyr | Gly | Tyr | Leu | Thr | Leu | Asp | Asn | Gly | Ser | Gln | Ser | Val |
| 370 | | | | | 375 | | | | | 380 | | | | | |

```
Gly Arg Ser Ser Phe Tyr Cys Leu Glu Tyr Phe Pro Ser Gln Met Leu
385                 390                 395                 400

Arg Thr Gly Asn Asn Phe Glu Phe Ser Tyr Ser Phe Glu Asp Val Pro
            405                 410                 415

Phe His Ser Ser Tyr Ala His Ser Gln Ser Leu Asp Arg Leu Met Asn
        420                 425                 430

Pro Leu Ile Asp Gln Tyr Leu Tyr Leu Ala Arg Thr Gln Ser Thr
            435                 440                 445

Thr Gly Ser Thr Arg Glu Leu Gln Phe His Gln Ala Gly Pro Asn Thr
    450                 455                 460

Met Ala Glu Gln Ser Lys Asn Trp Leu Pro Gly Pro Cys Tyr Arg Gln
465                 470                 475                 480

Gln Arg Leu Ser Lys Asn Leu Asp Phe Asn Asn Ser Asn Phe Ala
            485                 490                 495

Trp Thr Ala Ala Thr Lys Tyr His Leu Asn Gly Arg Asn Ser Leu Thr
        500                 505                 510

Asn Pro Gly Ile Pro Met Ala Thr Asn Lys Asp Asp Glu Asp Gln Phe
        515                 520                 525

Phe Pro Ile Asn Gly Val Leu Val Phe Gly Lys Thr Gly Ala Ala Asn
    530                 535                 540

Lys Thr Thr Leu Glu Asn Val Leu Met Thr Ser Glu Glu Ile Lys
545                 550                 555                 560

Thr Thr Asn Pro Val Ala Thr Glu Glu Tyr Gly Val Val Ser Ser Asn
            565                 570                 575

Leu Gln Ser Ser Thr Ala Gly Pro Gln Ser Gln Thr Ile Asn Ser Gln
        580                 585                 590

Gly Ala Leu Pro Gly Met Val Trp Gln Asn Arg Asp Val Tyr Leu Gln
            595                 600                 605

Gly Pro Ile Trp Ala Lys Ile Pro His Thr Asp Gly Asn Phe His Pro
    610                 615                 620

Ser Pro Leu Met Gly Gly Phe Gly Leu Lys His Pro Pro Gln Ile
625                 630                 635                 640

Leu Ile Lys Asn Thr Pro Val Pro Ala Asn Pro Glu Val Phe Thr
            645                 650                 655

Pro Ala Lys Phe Ala Ser Phe Ile Thr Gln Tyr Ser Thr Gly Gln Val
        660                 665                 670

Ser Val Glu Ile Glu Trp Glu Leu Gln Lys Glu Asn Ser Lys Arg Trp
        675                 680                 685

Asn Pro Glu Ile Gln Tyr Thr Ser Asn Tyr Ala Lys Ser Asn Asn Val
        690                 695                 700

Glu Phe Ala Val Asn Pro Asp Gly Val Tyr Thr Glu Pro Arg Pro Ile
705                 710                 715                 720

Gly Thr Arg Tyr Leu Thr Arg Asn Leu
                725

<210> SEQ ID NO 112
<211> LENGTH: 735
<212> TYPE: PRT
<213> ORGANISM: Unknown
<220> FEATURE:
<223> OTHER INFORMATION: capsid protein of AAV serotype, clone 42.6B

<400> SEQUENCE: 112

Met Ala Ala Asp Gly Tyr Leu Pro Asp Trp Leu Glu Asp Asn Leu Ser
1               5                   10                  15
```

```
Glu Gly Ile Arg Glu Trp Trp Asp Leu Lys Pro Gly Ala Pro Lys Pro
             20                  25                  30

Lys Ala Asn Gln Gln Lys Gln Asp Asp Gly Arg Gly Leu Val Leu Pro
         35                  40                  45

Gly Tyr Lys Tyr Leu Gly Pro Phe Asn Gly Leu Asp Lys Gly Glu Pro
 50                  55                  60

Val Asn Glu Ala Asp Ala Ala Ala Leu Glu His Asp Lys Ala Tyr Asp
 65                  70                  75                  80

Lys Gln Leu Glu Gln Gly Asp Asn Pro Tyr Leu Lys Tyr Asn His Ala
             85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Thr Gly Gln Gln Pro Ala Lys Lys Arg Leu Asn Phe Gly Gln
            165                 170                 175

Thr Gly Asp Ser Glu Ser Val Pro Asp Pro Gln Pro Ile Gly Glu Pro
        180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
        210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
            245                 250                 255

Leu Tyr Lys Gln Ile Ser Asn Gly Thr Ser Gly Gly Ser Thr Asn Asp
        260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
        290                 295                 300

Asn Asn Trp Gly Phe Arg Pro Arg Lys Leu Arg Phe Lys Leu Phe Asn
305                 310                 315                 320

Ile Gln Val Lys Glu Val Thr Thr Asp Asp Gly Val Thr Thr Ile Ala
            325                 330                 335

Asn Asn Leu Thr Ser Thr Ile Gln Val Phe Ser Asp Ser Glu Tyr Gln
        340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
        370                 375                 380

Asn Gly Ser Gln Ser Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
            405                 410                 415

Thr Phe Glu Glu Val Pro Phe His Ser Ser Tyr Ala His Ser Gln Ser
        420                 425                 430
```

```
Leu Asp Arg Leu Met Asn Pro Leu Ile Asp Gln Tyr Leu Tyr Tyr Leu
            435                 440                 445

Ala Arg Thr Gln Ser Thr Thr Gly Ser Thr Arg Glu Leu Gln Phe His
450                 455                 460

Gln Ala Gly Pro Asn Thr Met Ala Glu Gln Ser Lys Asn Trp Leu Pro
465                 470                 475                 480

Gly Pro Cys Tyr Arg Gln Gln Arg Leu Ser Lys Asn Ile Asp Ser Asn
            485                 490                 495

Asn Asn Ser Asn Phe Ala Trp Thr Gly Ala Thr Lys Tyr His Leu Asn
            500                 505                 510

Gly Arg Asn Ser Leu Thr Asn Pro Gly Val Ala Met Ala Thr Asn Lys
            515                 520                 525

Asp Asp Glu Asp Gln Phe Phe Pro Ile Asn Gly Val Leu Val Phe Gly
530                 535                 540

Lys Thr Gly Ala Ala Asn Lys Thr Thr Leu Glu Asn Val Leu Met Thr
545                 550                 555                 560

Ser Glu Glu Glu Ile Lys Thr Thr Asn Pro Val Ala Thr Glu Glu Tyr
                565                 570                 575

Gly Val Val Ser Ser Asn Leu Gln Ser Ser Thr Ala Gly Pro Gln Thr
            580                 585                 590

Gln Thr Val Asn Ser Gln Gly Ala Leu Pro Gly Met Val Trp Gln Asn
            595                 600                 605

Arg Asp Val Tyr Leu Gln Gly Pro Ile Trp Ala Lys Ile Pro His Thr
            610                 615                 620

Asp Gly Asn Phe His Pro Ser Pro Leu Met Asp Gly Phe Gly Leu Lys
625                 630                 635                 640

His Pro Pro Pro Gln Ile Leu Ile Lys Asn Thr Pro Val Pro Ala Asn
            645                 650                 655

Pro Pro Glu Val Phe Thr Pro Ala Lys Phe Ala Ser Phe Ile Thr Gln
            660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
690                 695                 700

Ala Lys Ser Asn Asn Val Glu Phe Ala Val Asn Asn Glu Gly Val Tyr
705                 710                 715                 720

Thr Glu Pro Arg Pro Ile Gly Thr Arg Tyr Leu Thr Arg Asn Leu
                725                 730                 735

<210> SEQ ID NO 113
<211> LENGTH: 685
<212> TYPE: PRT
<213> ORGANISM: Unknown
<220> FEATURE:
<223> OTHER INFORMATION: capsid protein of AAV serotype, clone 42.12

<400> SEQUENCE: 113

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60
```

```
Val Asn Glu Ala Asp Ala Ala Leu Glu His Asp Lys Ala Tyr Asp
 65                  70                  75                  80

Lys Gln Leu Glu Gln Gly Asp Asn Pro Tyr Leu Lys Tyr Asn His Ala
                 85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Thr Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Thr Asn Pro Leu Ile Asp Gln Tyr Leu Tyr Tyr Leu
        435                 440                 445

Ala Arg Thr Gln Ser Thr Thr Gly Ser Thr Arg Gly Leu Gln Phe His
    450                 455                 460

Gln Ala Gly Pro Asn Thr Met Ala Glu Gln Ser Lys Asn Trp Leu Pro
465                 470                 475                 480

Gly Pro Cys Tyr Arg Gln Gln Arg Leu Ser Lys Asn Ile Asp Ser Asn
```

```
                  485                 490                 495
Asn Asn Ser Asn Phe Ala Trp Thr Gly Ala Thr Lys Tyr His Leu Asn
                500                 505                 510

Gly Arg Asn Ser Leu Thr Asn Pro Gly Val Ala Met Ala Thr Asn Lys
                515                 520                 525

Asp Asp Glu Asp Gln Phe Phe Pro Ile Asn Gly Val Leu Val Phe Gly
                530                 535                 540

Lys Thr Gly Ala Ala Asn Lys Thr Thr Leu Glu Asn Val Leu Met Thr
545                 550                 555                 560

Ser Glu Glu Glu Ile Lys Thr Thr Asn Pro Val Ala Thr Glu Glu Tyr
                565                 570                 575

Gly Val Val Ser Ser Asn Leu Gln Ser Ser Thr Ala Gly Pro Gln Thr
                580                 585                 590

Gln Thr Val Asn Ser Gln Gly Ala Leu Pro Gly Met Val Trp Gln Asn
                595                 600                 605

Arg Asp Val Tyr Leu Gln Gly Pro Ile Trp Ala Lys Ile Pro His Thr
                610                 615                 620

Asp Gly Asn Phe His Pro Ser Pro Leu Met Gly Gly Phe Gly Leu Lys
625                 630                 635                 640

His Pro Pro Pro Gln Ile Leu Ile Lys Tyr Thr Ser Asn Tyr Tyr Lys
                645                 650                 655

Ser Thr Asn Val Asp Phe Ala Val Asn Thr Glu Gly Thr Tyr Ser Glu
                660                 665                 670

Pro Arg Pro Ile Gly Thr Arg Tyr Leu Thr Arg Asn Leu
                675                 680                 685

<210> SEQ ID NO 114
<211> LENGTH: 724
<212> TYPE: PRT
<213> ORGANISM: Unknown
<220> FEATURE:
<223> OTHER INFORMATION: capsid protein of AAV serotype, clone AAV5CAP

<400> SEQUENCE: 114

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
                20                  25                  30

Pro Asn Gln Gln His Gln Asp Gln Ala Arg Gly Leu Val Leu Pro Gly
                35                  40                  45

Tyr Asn Tyr Leu Gly Pro Gly Asn Gly Leu Asp Arg Gly Glu Pro Val
                50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
                100                 105                 110

Leu Gly Lys Ala Val Phe Gln Ala Lys Lys Arg Val Leu Glu Pro Phe
                115                 120                 125

Gly Leu Val Glu Glu Gly Ala Lys Thr Ala Pro Thr Gly Lys Arg Ile
                130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
```

```
            165                 170                 175
Gln Leu Gln Ile Pro Ala Gln Pro Ala Ser Ser Leu Gly Ala Asp Thr
            180                 185                 190

Met Ser Ala Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
        210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
                260                 265                 270

Phe Asp Phe Asn Arg Phe His Ser His Trp Ser Pro Arg Asp Trp Gln
            275                 280                 285

Arg Leu Ile Asn Asn Tyr Trp Gly Phe Arg Pro Arg Ser Leu Arg Val
            290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
            355                 360                 365

Ala Thr Leu Asn Arg Asp Asn Thr Glu Asn Pro Thr Glu Arg Ser Ser
        370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
            435                 440                 445

Phe Asn Lys Asn Leu Ala Gly Arg Tyr Ala Asn Thr Tyr Lys Asn Trp
        450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
            515                 520                 525

Phe Asn Ser Gln Pro Ala Asn Pro Gly Thr Thr Ala Thr Tyr Leu Glu
            530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590
```

```
Gly Ser Val Trp Met Glu Arg Asp Val Tyr Leu Gln Gly Pro Ile Trp
        595                 600                 605
Ala Lys Ile Pro Glu Thr Gly Ala His Phe His Pro Ser Pro Ala Met
    610                 615                 620
Gly Gly Phe Gly Leu Lys His Pro Pro Met Met Leu Ile Lys Asn
625                 630                 635                 640
Thr Pro Val Pro Gly Asn Ile Thr Ser Phe Ser Asp Val Pro Val Ser
                645                 650                 655
Ser Phe Ile Thr Gln Tyr Ser Thr Gly Gln Val Thr Val Glu Met Glu
            660                 665                 670
Trp Glu Leu Lys Lys Glu Asn Ser Lys Arg Trp Asn Pro Glu Ile Gln
        675                 680                 685
Tyr Thr Asn Asn Tyr Asn Asp Pro Gln Phe Val Asp Phe Ala Pro Asp
    690                 695                 700
Ser Thr Gly Glu Tyr Arg Thr Thr Arg Pro Ile Gly Thr Arg Tyr Leu
705                 710                 715                 720
Thr Arg Pro Leu

<210> SEQ ID NO 115
<211> LENGTH: 9
<212> TYPE: DNA
<213> ORGANISM: Artificial Sequence
<220> FEATURE:
<223> OTHER INFORMATION: DraIII restriction enzyme site

<400> SEQUENCE: 115 caccacgtc                                                              9

<210> SEQ ID NO 116
<211> LENGTH: 28
<212> TYPE: DNA
<213> ORGANISM: Unknown
<220> FEATURE:
<223> OTHER INFORMATION: AV2cas

<400> SEQUENCE: 116
cgcagagacc aaagttcaac tgaaacga                                         28

<210> SEQ ID NO 117
<211> LENGTH: 255
<212> TYPE: DNA
<213> ORGANISM: Unknown
<220> FEATURE:
<223> OTHER INFORMATION: adeno-associated virus serotype 10

<400> SEQUENCE: 117
ggtaattcct ccggaaattg gcattgcgat tccacatggc tgggcgacag agtcatcacc      60
accagcaccc gaacctgggt cctgcccacc tacaacaacc acatctacaa gcaaatctcc     120
agcgagacag agccaccaa cgacaaccac tacttcggct acagcacccc ctggggggtat     180 tttgacttta acagattcca ctgccacttt tcaccacgtg actggcagcg actcatcaac     240
aacaactggg gattc                                                     255

<210> SEQ ID NO 118
<211> LENGTH: 258
<212> TYPE: DNA
<213> ORGANISM: Unknown
<220> FEATURE:
<223> OTHER INFORMATION: adeno-associated virus serotype 11
```

<400> SEQUENCE: 118

```
ggtaattcct ccggaaattg gcattgcgat tccacatggc tgggcgacag agtcatcacc      60
accagcaccc gaacctgggc cctgccaacc tacaacaacc acctctacaa acaaatctcc     120
agcgcttcaa cggggggccag caacgacaac cactactttg ctacagcac cccctggggg    180
tattttgact ttaacagatt ccactgccac ttctcaccac gtgactggca gcgactcatc    240
aacaacaact ggggattc                                                  258
```

<210> SEQ ID NO 119
<211> LENGTH: 255
<212> TYPE: DNA
<213> ORGANISM: Unknown
<220> FEATURE:
<223> OTHER INFORMATION: adeno-associated virus serotype 12

<400> SEQUENCE: 119

```
ggtaattcct ccggaaattg gcattgcgat tccacatggc tgggcgaccg agtcattacc      60
accagcaccc ggacttgggc cctgcccacc tacaacaacc acctctacaa gcaaatctcc     120
agccaatcgg gtgccaccaa cgacaaccac tacttcggct acagcacccc ttgggggtat    180
tttgatttca acagattcca ctgccatttc tcaccacgtg actggcagcg actcatcaac    240
aacaactggg gattc                                                     255
```

<210> SEQ ID NO 120
<211> LENGTH: 2205
<212> TYPE: DNA
<213> ORGANISM: Unknown
<220> FEATURE:
<223> OTHER INFORMATION: adeno-associated virus serotype, clone A3.1vp1

<400> SEQUENCE: 120

```
atggctgccg atggttatct tccagattgg ctcgaggaca ctctctctga aggaatcaga     60
cagtggtgga agctcaaacc tggcccacca ccgccgaaac ctaaccaaca caccgggac    120
gacagtaggg gtcttgtgct tcctgggtac aagtacctcg gacccttcaa cggactcgac   180
aaaggagagc cggtcaacga ggcagacgcc gcggccctcg agcacgacaa agcctacgac   240
caccagctca agcaagggga caacccgtac ctcaaataca accacgcgga cgctgaattt    300
caggagcgtc ttcaagaaga tacgtctttc ggggggcaacc tcgggcgagc agtcttccag   360
gccaaaaaga gggtactcga gcctcttggt ctggttgagg aagctgttaa gacggctcct   420
ggaaaaaaga gacctataga gcagtctcct gcagaaccgg actcttcctc gggcatcggc   480
aaatcaggcc agcagcccgc taagaaaaga ctcaattttg gtcagactgg cgacacagag   540
tcagtcccag accctcaacc aatcggagaa ccccccgcag cccctctggt gtgggatct   600
aatacaatgg cttcaggcgg tgggcacca atggcagaca ataacgaagg cgccgacgga   660
gtgggtaatt cctcgggaaa ttggcattgc gattccacat ggatgggcga cagagttatc    720
accaccagca caagaacctg ggccctcccc acctacaata tcacctcta caagcaaatc    780
tccagcgaat cggagccac caacgacaac cactacttcg gctacagcac cccctggggg    840
tattttgact ttaacagatt ccactgtcac ttctcaccac gtgactggca gcgactcatc    900
aacaacaact ggggattag acccaagaaa ctcaatttca gctcttcaa catccaagtc    960
aaggaggtca cgcagaatga tggaaccacg accatcgcca ataaccttac agcacggtg   1020
caggtcttca cagactctga gtaccagctg ccctacgtcc tcggtcggc tcaccagggc   1080
tgccttccgc cgttcccagc agacgtcttc atgattcctc agtacggcta cttgactctg   1140
```

```
aacaatggca gccaagcggt aggacgttct tcattctact gtctagagta ttttccctct    1200
cagatgctga ggacgggaaa caacttcacc ttcagctaca cttttgaaga cgtgcctttc    1260
cacagcagct acgcgcacag ccagagtctg gatcggctga tgaatcctct cattgaccag    1320
tacctgtatt acctgagcaa aactcagggt acaagtggaa caacgcagca atcgagactg    1380
cagttcagcc aagctgggcc tagctccatg gctcagcagg ccaaaaactg gctaccggga    1440
cccagctacc gacagcagcg aatgtctaag acggctaatg acaacaacaa cagtgaattt    1500
gcttggactg cagccaccaa atattacctg aatggaagaa attctctggt caatcccggg    1560
cccccaatgg ccagtcacaa ggacgatgag gaaaagtatt tccccatgca cggaaatctc    1620
atctttggaa aacaaggcac aggaactacc aatgtggaca ttgaatcagt gcttattaca    1680
gacgaagaag aaatcagaac aactaatcct gtggctacag aacaatacgg acaggttgcc    1740
accaaccatc agagtcagaa caccacagct tcctatgaa gtgtggacag ccagggaatc    1800
ttacctggaa tggtgtggca ggaccgcgat gtctatcttc aaggtcccat ttgggccaaa    1860
actcctcaca cggacggaca ctttcatcct tctccgctca tgggaggctt tggactgaaa    1920
caccctcctc cccagatcct gatcaaaaac acacctgtgc cagcgaatcc cgcgaccact    1980
ttcactcctg gaaagtttgc ttcgttcatt acccagtatt ccaccggaca ggtcagcgtg    2040
gaaatagagt gggagctgca gaaagaaaac agcaaacgct ggaacccaga aattcagtac    2100
acctccaact acaacaagtc ggtgaatgtg gagtttaccg tggacgcaaa cggtgtttat    2160
tctgaacccc gccctattgg cactcgttac cttacccgga acttg                   2205
```

The invention claimed is:

1. A method of generating a recombinant adeno-associated virus (AAV) comprising culturing a host cell containing: (a) a molecule encoding the AAV vp1 capsid protein having a sequence of amino acids 1 to 738 of SEQ ID NO: 85, or a sequence which is at least 95% identical to the full length of amino acids 1 to 738 of SEQ ID NO: 85; (b) a functional rep gene; (c) a nucleic acid molecule comprising at least one AAV inverted terminal repeat (ITR) and a non-AAV nucleic acid sequence encoding a gene product operably linked to sequences which direct expression of the product in a host cell; and (d) sufficient helper functions to permit packaging of the minigene into the AAV capsid protein under conditions which permit packaging of the minigene into the AAV capsid.

2. The method of claim 1, wherein the sequence of the vp1 protein is at least 97% identical to the full length of amino acids 1 to 738 of SEQ ID NO: 85.

3. The method of claim 1, wherein the sequence of the vp1 protein is at least 99% identical to the full-length of amino acids 1 to 738 of SEQ ID NO: 85.

4. The method of claim 1, wherein the sequence of the vp1 protein is the full-length of amino acids 1 to 738 of SEQ ID NO: 85.

5. The method of claim 1, wherein the gene product is alpha-1 antitrypsin, Factor VIII, Factor IX, ornithine transcarbamylase, glucose-6-phosphatase, phenylalanine hydroxylase, argininosuccinate synthetase, β-glucuronidase (GUSB), or a dystrophin protein.

6. The method of claim 1, wherein the molecule is a nucleic acid molecule comprising nucleotides 844 to 3057 of SEQ ID NO: 27, or a nucleotide sequence at least 99% identical to nucleotides 844 to 3057 of SEQ ID NO: 27.

7. The method of claim 1, wherein the rep gene is from AAV2.

8. A method of generating a recombinant adeno-associated virus (AAV) comprising culturing a host cell containing: (a) a molecule encoding the AAV vp2 capsid protein having a sequence of amino acids 138 to 738 of SEQ ID NO: 85, or a sequence which is at least 95% identical to the full length of amino acids 138 to 738 of SEQ ID NO: 85; (b) a functional rep gene; (c) a nucleic acid molecule comprising at least one AAV inverted terminal repeat (ITR) and a non-AAV nucleic acid sequence encoding a gene product operably linked to sequences which direct expression of the product in a host cell; and (d) sufficient helper functions to permit packaging of the minigene into the AAV capsid protein under conditions which permit packaging of the minigene into the AAV capsid.

9. The method of claim 8, wherein the sequence of the vp2 protein is at least 97% identical to the full length of amino acids 138 to 738 of SEQ ID NO: 85.

10. The method of claim 8, wherein the sequence of the vp2 protein is at least 99% identical to the full-length of amino acids 138 to 738 of SEQ ID NO: 85.

11. The method of claim 8, wherein the sequence of the vp2 protein is the full-length of amino acids 138 to 738 of SEQ ID NO: 85.

12. The method of claim 8, wherein the gene product is alpha-1 antitrypsin, Factor VIII, Factor IX, ornithine transcarbamylase, glucose-6-phosphatase, phenylalanine hydroxylase, argininosuccinate synthetase, β-glucuronidase (GUSB), or a dystrophin protein.

13. The method of claim 8, wherein the molecule is a nucleic acid molecule comprising nucleotides 1255 to 3057 of SEQ ID NO: 27, or a nucleotide sequence at least 99% identical to nucleotides 1255 to 3057 of SEQ ID NO: 27.

14. The method of claim 8, wherein the rep gene is from AAV2.

15. A method of generating a recombinant adeno-associated virus (AAV) comprising culturing a host cell containing: (a) a molecule encoding the AAV vp3 capsid protein having a sequence of amino acids 204 to 738 of SEQ ID NO: 85, or a sequence which is at least 95% identical to the full length of amino acids 204 to 738 of SEQ ID NO: 85; (b) a functional rep gene; (c) a nucleic acid molecule comprising at least one AAV inverted terminal repeat (ITR) and a non-AAV nucleic acid sequence encoding a gene product operably linked to sequences which direct expression of the product in a host cell; and (d) sufficient helper functions to permit packaging of the minigene into the AAV capsid protein under conditions which permit packaging of the minigene into the AAV capsid.

16. The method of claim 15, wherein the sequence of the vp3 protein is at least 97% identical to the full length of amino acids 204 to 738 of SEQ ID NO: 85.

17. The method of claim 15, wherein the sequence of the vp3 protein is at least 99% identical to the full-length of amino acids 204 to 738 of SEQ ID NO: 85.

18. The method of claim 15, wherein the sequence of the vp3 protein is the full-length of amino acids 204 to 738 of SEQ ID NO: 85.

19. The method of claim 15, wherein the gene product is alpha-1 antitrypsin, Factor VIII, Factor IX, ornithine transcarbamylase, glucose-6-phosphatase, phenylalanine hydroxylase, argininosuccinate synthetase, β-glucuronidase (GUSB), or a dystrophin protein.

20. The method of claim 15, wherein the molecule is a nucleic acid molecule comprising nucleotides 1453 to 3057 of SEQ ID NO: 27, or a nucleotide sequence at least 99% identical to nucleotides 1453 to 3057 of SEQ ID NO: 27.

21. The method of claim 15, wherein the rep gene is from AAV2.

\* \* \* \* \*